(12) United States Patent
Lynn et al.

(10) Patent No.: US 12,370,255 B2
(45) Date of Patent: Jul. 29, 2025

(54) PEPTIDE-BASED VACCINES, METHODS OF MANUFACTURING, AND USES THEREOF FOR INDUCING AN IMMUNE RESPONSE

(71) Applicants: Barinthus Biotherapeutics North America, Inc., Germantown, MD (US); The United States of America, as represented by the Secretary, Department of Health and Human Services, Office of Technology Transfer, National Institute of Health, Bethesda, MD (US)

(72) Inventors: Geoffrey Martin Lynn, Baltimore, MD (US); Andrew Scott Ishizuka, Washington, DC (US)

(73) Assignees: BARINTHUS BIOTHERAPEUTICS NORTH AMERICA, INC., Germantown, MD (US); THE UNITED STATES OF AMERICA, AS REPRESENTED BY THE SECRETARY, DEPARTMENT OF HEALTH AND HUMAN SERVICES, OFFICE OF TECHNOLOGY TRANSFER—NATIONAL INSTITUTES OF HEALTH, Bethesda, MD (US)

( * ) Notice: Subject to any disclaimer, the term of this patent is extended or adjusted under 35 U.S.C. 154(b) by 522 days.

(21) Appl. No.: 16/500,762

(22) PCT Filed: Apr. 4, 2018

(86) PCT No.: PCT/US2018/026145
§ 371 (c)(1),
(2) Date: Oct. 3, 2019

(87) PCT Pub. No.: WO2018/187515
PCT Pub. Date: Oct. 11, 2018

(65) Prior Publication Data
US 2020/0054741 A1 Feb. 20, 2020

Related U.S. Application Data

(60) Provisional application No. 62/617,519, filed on Jan. 15, 2018, provisional application No. 62/481,432, filed on Apr. 4, 2017.

(51) Int. Cl.
*A61K 39/385* (2006.01)
*A61K 31/33* (2006.01)
(Continued)

(52) U.S. Cl.
CPC ............ *A61K 39/385* (2013.01); *A61K 31/33* (2013.01); *A61K 31/395* (2013.01); *A61K 31/40* (2013.01);
(Continued)

(58) Field of Classification Search
CPC ........... A61K 2039/55511; A61K 2039/55555; A61K 2039/57; A61K 2039/6093;
(Continued)

(56) References Cited

U.S. PATENT DOCUMENTS 5,312,620 A 5/1994 Ribi
6,573,245 B1 6/2003 Marciani
(Continued)

FOREIGN PATENT DOCUMENTS

CA 2627903 A1 9/2009
EP 0324455 A2 7/1989
(Continued)

OTHER PUBLICATIONS

The Biology Project, "Tyrosine", Department of Biochemistry and Molecular Biophysics, University of Arizona, available online at http://www.biology.arizona.edu/biochemistry/problem_sets/aa/tyrosine.html, 2 pages (2003) (Year: 2003).*

(Continued)

Non-limiting example of a peptide antigen conjugate of Formula V

Primary Examiner — Randall L Beane
(74) Attorney, Agent, or Firm — Goodwin Procter LLP

(57) ABSTRACT

The present disclosure relates to novel peptide-based vaccines, methods of manufacturing the novel peptide-based vaccines and uses thereof for delivering peptide antigens to induce an immune response, and in particular a T cell response to a subject.

1 Claim, 65 Drawing Sheets

Specification includes a Sequence Listing.

(51) Int. Cl.
| | | |
|---|---|---|
| A61K 31/395 | (2006.01) | |
| A61K 31/40 | (2006.01) | |
| A61K 31/435 | (2006.01) | |
| A61K 38/02 | (2006.01) | |
| A61K 38/03 | (2006.01) | |
| A61K 39/00 | (2006.01) | |
| A61K 39/12 | (2006.01) | |
| A61K 39/39 | (2006.01) | |
| C07K 4/00 | (2006.01) | |
| C07K 17/00 | (2006.01) | |
| C07K 17/06 | (2006.01) | |
| C07K 17/08 | (2006.01) | |
| A61K 38/10 | (2006.01) | |
| A61K 38/26 | (2006.01) | |

(52) U.S. Cl.
CPC ............ *A61K 31/435* (2013.01); *A61K 38/02* (2013.01); *A61K 38/03* (2013.01); *A61K 39/0011* (2013.01); *A61K 39/12* (2013.01); *A61K 39/39* (2013.01); *C07K 4/00* (2013.01); *C07K 17/00* (2013.01); *C07K 17/06* (2013.01); *C07K 17/08* (2013.01); *A61K 38/10* (2013.01); *A61K 38/26* (2013.01); *A61K 2039/55555* (2013.01); *A61K 2039/57* (2013.01); *A61K 2039/6093* (2013.01); *A61K 2039/627* (2013.01); *A61K 2039/64* (2013.01); *A61K 2039/70* (2013.01); *C07K 2318/00* (2013.01)

(58) Field of Classification Search
CPC .......... A61K 2039/627; A61K 2039/64; A61K 2039/70; A61K 31/33; A61K 31/395; A61K 31/40; A61K 31/435; A61K 38/02; A61K 38/03; A61K 38/10; A61K 38/26; A61K 39/0011; A61K 39/12; A61K 39/385; A61K 39/39; A61K 47/58; A61K 47/595; A61K 47/6907; C07K 17/00; C07K 17/06; C07K 17/08; C07K 2318/00; C07K 4/00; C07K 2740/16034
See application file for complete search history.

(56) References Cited

U.S. PATENT DOCUMENTS

| | | | | |
|---|---|---|---|---|
| 6,747,137 | B1* | 6/2004 | Weinstock | ............ C12Q 1/6895 |
| | | | | 435/6.13 |
| 6,858,396 | B2* | 2/2005 | Dix | ............ C07C 229/26 |
| | | | | 514/17.7 |
| 9,115,402 | B2 | 8/2015 | Hacohen et al. | |
| 9,120,841 | B2 | 9/2015 | Hauser et al. | |
| 9,682,934 | B2 | 6/2017 | Stafford et al. | |
| 9,962,453 | B2 | 5/2018 | Georges | |
| 11,191,821 | B2* | 12/2021 | Seder | ............ A61K 39/001102 |
| 2004/0057958 | A1 | 3/2004 | Waggoner et al. | |
| 2006/0216702 | A1 | 9/2006 | Compans et al. | |
| 2008/0139481 | A1* | 6/2008 | Dix | ............ A61P 29/02 |
| | | | | 514/12.4 |
| 2008/0160089 | A1 | 7/2008 | Vitiello et al. | |
| 2010/0028381 | A1 | 2/2010 | Gorski et al. | |
| 2010/0129439 | A1 | 5/2010 | Alexis et al. | |
| 2011/0150978 | A1 | 6/2011 | Lee et al. | |
| 2012/0114699 | A1* | 5/2012 | Mistrello | ............ A61P 37/08 |
| | | | | 530/370 |
| 2012/0141409 | A1 | 6/2012 | Seymour et al. | |
| 2013/0237561 | A1 | 9/2013 | Leoni et al. | |
| 2013/0287857 | A1 | 10/2013 | von Andrian et al. | |
| 2013/0330367 | A1 | 12/2013 | Song et al. | |
| 2013/0336996 | A1 | 12/2013 | Vernejoul et al. | |
| 2017/0112923 | A1 | 4/2017 | Seymour et al. | |
| 2017/0224803 | A1* | 8/2017 | Berti | ............ A61K 47/646 |
| 2017/0304420 | A1 | 10/2017 | Fisher et al. | |
| 2019/0060435 | A1 | 2/2019 | Seder et al. | |
| 2021/0000934 | A1 | 1/2021 | Fisher et al. | |
| 2021/0113705 | A1* | 4/2021 | Lynn | ............ A61K 47/595 |
| 2021/0393523 | A1 | 12/2021 | Lynn et al. | |
| 2023/0381112 | A1 | 11/2023 | Lynn et al. | |
| 2024/0269269 | A1 | 8/2024 | Lynn et al. | |
| 2024/0382614 | A1 | 11/2024 | Lynn et al. | |

FOREIGN PATENT DOCUMENTS

| | | | | |
|---|---|---|---|---|
| JP | H10509038 | A | 9/1998 | |
| JP | 2001294636 | A | 10/2001 | |
| JP | 2002526436 | A | 8/2002 | |
| JP | 2005532405 | A | 10/2005 | |
| JP | 2006523185 | A | 10/2006 | |
| JP | 2013544074 | A | 12/2013 | |
| JP | 2014139139 | A | 7/2014 | |
| JP | 2015500229 | A | 1/2015 | |
| KR | 20090002946 | A | 1/2009 | |
| WO | 9322338 | A1 | 11/1993 | |
| WO | 9615249 | A1 | 5/1996 | |
| WO | 1998001558 | A2 | 1/1998 | |
| WO | 1998019710 | A2 | 5/1998 | |
| WO | 0016746 | A2 | 3/2000 | |
| WO | 2000074722 | A2 | 12/2000 | |
| WO | 0118035 | A2 | 3/2001 | |
| WO | 0152614 | A2 | 7/2001 | |
| WO | 02070006 | A2 | 9/2002 | |
| WO | 02094994 | A2 | 11/2002 | |
| WO | 03075956 | A2 | 9/2003 | |
| WO | 2004007525 | A3 | 3/2004 | |
| WO | 2005007789 | A2 | 1/2005 | |
| WO | 2005099752 | A2 | 10/2005 | |
| WO | 2006083874 | A2 | 8/2006 | |
| WO | 2006084319 | A1 | 8/2006 | |
| WO | 2007075502 | A2 | 7/2007 | |
| WO | 2004071457 | A3 | 10/2007 | |
| WO | 2007149802 | A2 | 12/2007 | |
| WO | 2009043165 | A1 | 4/2009 | |
| WO | 2009051837 | A2 | 4/2009 | |
| WO | 2009104001 | A2 | 8/2009 | |
| WO | 2010067041 | A1 | 6/2010 | |
| WO | 2010128303 | A1 | 11/2010 | |
| WO | WO-2011101332 | A1* | 8/2011 | ......... C07K 14/4748 |
| WO | 2011150240 | A1 | 12/2011 | |
| WO | 2012049317 | A3 | 6/2012 | |
| WO | 2012090002 | A1 | 7/2012 | |
| WO | 2012139094 | A3 | 11/2012 | |
| WO | 2013006050 | A9 | 2/2013 | |
| WO | 2013019669 | A2 | 2/2013 | |
| WO | 2013080187 | A1 | 6/2013 | |
| WO | 2013051936 | A9 | 9/2013 | |
| WO | 2013151771 | A1 | 10/2013 | |
| WO | 2013154774 | A1 | 10/2013 | |
| WO | 2014142653 | A1 | 9/2014 | |
| WO | 2015033140 | A1 | 3/2015 | |
| WO | 2015082905 | A1 | 6/2015 | |
| WO | 2015085233 | A1 | 6/2015 | |
| WO | 2016055812 | A1 | 4/2016 | |
| WO | 2016146143 | A1 | 9/2016 | |

(56) References Cited

FOREIGN PATENT DOCUMENTS

| | | |
|---|---|---|
| WO | 2016146260 A1 | 9/2016 |
| WO | 2017044803 A1 | 3/2017 |
| WO | 2017083963 A1 | 5/2017 |
| WO | 2017147597 A1 | 8/2017 |
| WO | 2017157964 A1 | 9/2017 |
| WO | 2017173321 A1 | 10/2017 |
| WO | 2018055060 A1 | 3/2018 |
| WO | 2018148671 A1 | 8/2018 |
| WO | 2018187356 A2 | 10/2018 |
| WO | 2018187515 A1 | 10/2018 |
| WO | 2019126186 A1 | 6/2019 |
| WO | 2019126371 A1 | 6/2019 |
| WO | 2019195626 A1 | 10/2019 |
| WO | 2019204663 A1 | 10/2019 |
| WO | 2019094642 A1 | 11/2019 |
| WO | 2019241306 A2 | 12/2019 |
| WO | 2019246315 A1 | 12/2019 |
| WO | WO-2020190762 A1 * | 9/2020 |
| WO | 2020191305 A3 | 10/2020 |
| WO | 2021156404 A3 | 9/2021 |

OTHER PUBLICATIONS

"Amino acids molecular weights," available online at: http://fortiusbio.com/Aa_MW.html, 2 pages (accessed on Dec. 22, 2021) (Year: 2021).*

U.S. Appl. No. 17/638,576, filed Feb. 2022, Stoidl et al.*

U.S. Appl. No. 17/517,597, filed Nov. 2021, Seder; Robert.*

Yadav et al., Nature 515:572-578 (2014) (Year: 2014).*

Brito et al., J. Controlled Rel. 190:563-579 (2014) (Year: 2014).*

Perrie et al., Intl. J. Pharmaceutics 364:272-280 (2008) (Year: 2008).*

"Amino Acid Structures, Codes, and Reference Information," available online at www.promega.com/resources/tools/amino-acid-chart-amino-acid-structure/, 14 pages (accessed on Apr. 21, 2022) (Year: 2022).*

"Tyrosine", available online at www.russelllab.org/aas/Tyr.html#:~:text=Substitutions%3A%20As%20Tyrosine%20is%20an,position%20on%20the%20benzene%20ring, 2 pages (accessed on Apr. 21, 2022) (Year: 2022).*

Mitsui et al., J. Investigative Dermatol. 126:1804-1812 (2006) (Year: 2006).*

Carr et al., Ind. Eng. Chem. Res. 49:11991-11995 (2010) (Year: 2010).*

"How to Enhance the Solubility of L-Tyrosine in Cell Culture Media Applications," Evonik, available online at https://healthcare.evonik.com/en/biopharma/cell-culture/common-challenges/performance-improvement, 2 pages (accessed on Dec. 1, 2022) (Year: 2022).*

Klein et al., Prot. Eng. Des. Selection 27:325-330 (2014) (Year: 2014).*

"Chemistry of Crosslinking," Thermo Fisher Scientific, available online at www.thermofisher.com/us/en/home/life-science/protein-biology/protein-biology-learning-center/protein-biology-resource-library/pierce-protein-methods/chemistry-crosslinking.html, 10 pages (first available 2015) (Year: 2015).*

Ji et al., Ind. Eng. Chem. Res. 47:6275-6279 (2008) (Year: 2008).*

"Peptide Mimetics" Biosyn, available online at www.biosyn.com/tew/peptide-mimetics.aspx, 7 pages (2012) (Year: 2012).*

Wagner et al., New Naturally Occurring Amino Acids, Anew. Chem. Int. Ed. Engl. 22:816-828 (1983) (Year: 1983).*

Chruszcz et al., Serum albumins-unusual allergens. Biochim Biophys Acta. Dec. 2013;1830(12):5375-81. doi: 10.1016/j.bbagen.2013.06.016. Epub Jun. 26, 2013. PMID: 23811341; PMCID: PMC4419372 (Year: 2013).*

Alexander et al., A Simple Method for Improving Protein Solubility and Long-Term Stability, Journal of the American Chemical Society 2004 126 (29), 8933-8939 DOI: 10.1021/ja049297h (Year: 2004).*

Dehsorkhi et al., Self-assembling amphiphilic peptides. J Pept Sci. Jul. 2014;20(7):453-67. doi: 10.1002/psc.2633. Epub Apr. 13, 2014. PMID: 24729276; PMCID: PMC4237179 (Year: 2014).*

National Center for Biotechnology Information. "PubChem Compound Summary for CID 12391, Pentadecane" PubChem, https://pubchem.ncbi.nlm.nih.gov/compound/Pentadecane. Accessed Oct. 12, 2023 (Year: 2023).*

NCBI Protein database, NCBI Reference Sequence: WP_047111413.1, DNA methyltransferase [Brachyspira hyodysenteriae], earliest reference of 1986, attached as 2 pages, also available at https://www.ncbi.nlm.nih.gov/. Accessed Oct. 12, 2023 (Year: 2023).*

Zang et al., Tunable diblock copolypeptide hydrogel depots for local delivery of hydrophobic molecules in healthy and injured central nervous system, Biomaterials 35 (2014) 1989e2000 (Year: 2014).*

Pina et al., Tryptophan tags and de novo designed complementary affinity ligands for the expression and purification of recombinant proteins, Journal of Chromatography A, 1472 (2016) 55-65 (Year: 2016).*

Fexby et al., Hydrophobic peptide tags as tools in bioseparation, TRENDS in Biotechnology vol. 22 No. Oct. 10, 2004 (Year: 2004).*

Guo et al., Cell-penetrating peptides: Possible transduction mechanisms and therapeutic applications (Review), Biomedical Reports 4: 528-534, 2016 (Year: 2016).*

Collins et al., Self-assembly of peptides into spherical nanoparticles for delivery of hydrophilic moieties to the cytosol. ACS Nano. May 25, 2010;4(5):2856-64. doi: 10.1021/nn901414q. PMID: 20408581 (Year: 2010).*

International Search Report and Written Opinion dated Sep. 24, 2018 and received in PCT/US2018/026145.

Wilson et al., "pH-Responsive Nanoparticle Vaccines for Dual-Delivery of Antigens and Immunostimulatory Oligonucleotides", ACS Nano, vol. 7, No. 5, pp. 3912-3925, (2013).

International Preliminary Report of Patentability mailed Oct. 17, 2019 and received in PCT/US2018/026145.

Fujita et al., "6-(4-Amino-2-butyl-imidazoquinolyl)-norleucine: Toll-like receptor 7 and 8 agonist amino add for self-adjuvanting peptide vaccine," Amino Acids (20(6) 48; 1319-1329, 2016.

Gerster, J. et al., "Synthesis and Structure-Activity-Relationships of 1H-Imidazo[4,5-c]Quinolines that Induce Interferon Production", Journal of Medicinal Chemistry, vol. 48, No. 10, pp. 3481-3491, (2005).

Ghendon Y. et al., "Chitosan as an Adjuvant for Parenterally Administered Inactivated Influenza Vaccines", Arch Virol, vol. 153, pp. 831-837, (2008).

Grela, F. et al., "The TLR7 Agonist R848 Alleviates Allergic Inflammation by Targeting Invariant NKT Cells To Produce IFN-y", The Journal of Immunology, vol. 186, No. 1, pp. 284-290, (2010).

Harris et al., "Rapid and general profiling of protease specificity by using combinatorial fluorogenic substrate libraries," PNAS, Jul. 5, 2000, vol. 97, No. 14, pp. 7754-7759.

Harris et al., "Substrate specificity of the human proteasome," Chemistry & Biology 8 (2001) 1131-1141.

Heuking, S. et al., "Stimulation of Human Macrophages (THP-1) Using Toll-like Receptor-2 (TLR-2) Agonist Decorated Nanocarriers", Journal of Drug Targeting, vol. 17, No. 8, pp. 662-670, (2009).

Heuking, S. et al., "Toll-Like Receptor-2 Agonist Functionalized Biopolymer for Mucosal Vaccination," International Journal of Pharmaceutics, vol. 381, pp. 97-105, (2009).

Huber et al., "Immuno- and Constitutive Proteasome Crystal Structures Reveal Differences in Substrate and Inhibitor Specificity," Cell 148, 727-738, Feb. 17, 2012.

Seder et al., U.S. Appl. No. 16/079,972, filed Aug. 24, 2018.

International Preliminary Examination Report dated Sep. 13, 2011 received in PCT/GB2010/000915.

International Preliminary Report of Patentability and Written Opinion mailed Dec. 3, 2020 and received in PCT/US19/33612.

Pola et al., "Click chemistry as a powerful and chemoselective tool for the attachment of targeting ligands to polymer drug carriers," Polym. Chem., 2014, 5, 1340-1350.

International Search Report and Written Opinion dated Aug. 30, 2019 and received in PCT/US2019/033612.

(56) References Cited

OTHER PUBLICATIONS

International Search Report dated Aug. 19, 2010 received in PCT/GB2010/000915.
Raissi, A. et al., "Enhanced Potency of the Metalloprotease Inhibitor TAPI-2 by Multivalent Display", Bioorganic & Medicinal Chemistry Letters, vol. 24, No. 8, pp. 2002-2007, (2014).
International Search Report, and Written Opinion dated Dec. 5, 2019 and received in PCT/US2019/033612.
Iuurovskii, T., et al., "Artificial Peptide and Carbohydrate Antigens. Immobilization of Haptens and Adjuvant (MDP) on Polyacrylamide", Bioorganicheskaia Khimiia., vol. 12, No. 1, pp. 100-105, (1986).
Rihova, B., et al., "HPMA-Based Biodegradable Hydrogels Containing Different Forms of Doxorubicin -Antitumor Effects and Biocompatibility", Ann. New York Academy Sciences, vol. 831, pp. 57-71, (1997).
Jackson, D. et al., "A Totally Synthetic Vaccine of Generic Structure That Targets Toll-Like Receptor 2 on Dendritic Cells and Promotes Antibody or Cytotoxic T Cell Responses", Proc. Natl. Acad. Sci. USA, vol. 101, No. 43, pp. 15440-15445, (2004).
Joshi, N. et al., "Inflammation Directs Memory Precursor and Short-Lived Effector CD8+ T Cell Fates via the Graded Expression of T-bet Transcription Factor", Immunity, vol. 27, pp. 281-295, (2007).
Moynihan et al., "Eradication of large established tumors in mice by combination immunotherapy that engages innate and adaptive immune responses," Nature Medicine, vol. 22, No. 12, Dec. 2016, pp. 1402-1410.
Kleine, B. et al., "Lipopeptide-Polyoxyethylene Conjugates as Mitogens and Adjuvants", Immunobiol., vol. 190, pp. 53-66, (1994).
Levina, A. et al., "Synthesis of Polyamine-Containing Oligonucleotides", Russian Journal of Bioorganic Chemistry, vol. 34, No. 1, pp. 80-86, (2008).
Liras et al., "Thermo-Responsive Allyl-Functionalized 2-(2-Methoxyethoxy)ethyl Methacrylate-Based Polymers as Versatile Precursors for Smart Polymer Conjugates and Conetworks", Macromolecules, vol. 44, pp. 3739-3745, (2011).
Lynn, G. et al., "In Vivo Characterization of the Physicochemical Properties of Polymer-Linked TLR Agonists that Enhance Vaccine Immunogenicity", Nature Biotechnology, vol. 33, No. 11, pp. 1201-1213, (2015).
Liu et al., "Structure-based programming of lymph-node targeting in molecular vaccines," Nature, vol. 507; Mar. 27, 2014; pp. 519-522 and extended figures, 11 pages.
Maurer, T. et al., "CpG-DNA Aided Cross-Presentation of Soluble Antigens By Dendritic Cells." Eur. J. Immunol., vol. 32, pp. 2356-2364, (2002).
Morelli et al., "Self-Assembled or Mixed Peptide Amphiphile Micelles from Herpes Simplex Virus Glycoproteins as Potential Immunomodulatory Treatment", International Journal of Nanomedicine, pp. 2137-2148, (2014).
Morgan, S. et al., "Evaluation of N -(2-Hydroxypropyl)Methacrylamide Copolymer-Peptide Conjugates as Potential Oral Vaccines. Studies on their Degradation by Isolated Rat Small Intestinal Peptidases and their Uptake by Adult Rat Small Intestinal Tissue in Vitro", International Journal of Pharmaceutics, vol. 128, pp. 99-111, (1996).
Moyle et al., "Self-Adjuvanting Lipopeptide Vaccines," Current Medicinal Chemistry, vol. 15, No. 5, pp. 506-516, 2008).
"Acrylamide", Wikipedia, the Free Encyclopedia, https://en.wikipedia.org/wiki/Acrylamide[Jun. 4, 2016 12:28:13]. (2016).
"Adjuvant Therapy", Wikipedia, the Free Encyclopedia, http://en.wikipedia.org/wiki/Adjuvant_therapy[May 28, 2012; 10:22:52]. (2012).
"CD40—Tumor Necrosis Factor Receptor Superfamily Member 5 Precursor . . . ", UniProtKB—P25942 (TNR5_HUMAN) UniProt P25942—TNR5_HUMAN, http://www.uniprot.org/uniprot/P25942. (1992).
"CD40 (Protein)", Wikipedia, the Free Encyclopedia, https://en.wikipedia.org/w/index.php?title=CD40_(protein)&oldid=742991040, (2016).
"ChitoClear—A Natural and Functional Ingredient for Personal Care Products/ LipoSan—The Natural Way of Weight Loss", Primex—Products: ChitoClear the Purest Chitosan & LipoSan Ultra, http://www.primex.is/Products/, (2013).
"Chitosan", Wikipedia, the Free Encyclopedia, http://en.wikipedia.org/wiki/Chitosan[Aug. 29, 2014 14:50:23], (2014).
"CSF2—Granulocyte-Macrophage Colony-Stimulating Factor Precursor—. . . ", UniProtKB—P04141 (CSF2_HUMAN) UniProt P04141—CSF2_HUMAN, http://www.uniprot.org/uniprot/P04141, (1986).
"Guidelines on Adjuvants in Vaccines for Human Use", EMEA Adjuvants Guidance, The European Medicines Agency Evaluation of Medicines for Human Use, (2005).
"Methacrylamide", Wikipedia, the Free Encyclopedia, https://en.wikipedia.org/wiki/Methacrylamide[Jun. 4, 2016; 11:54:24], (2016).
"Particulate Contamination—Risk Prevention in Infusion Therapy", B. Braun Melsungen AG, No. 6069091, Edition: 03, 2011 ).
"Polyacrylamide" Wikipedia, the Free Encyclopedia, https://en.wikipedia.org/wiki/Polyacrylamide[Jun. 4, 2016 11:51:51], (2016).
'TNFSF4 - Tumor Necrosis Factor Ligand Superfamily Member 4—Homo . . . , UniProtKB—P23510 (TNFL4_HUMAN) UniProt P23510—TNFL4_HUMAN, http://www.uniprot.org/uniprot/P23510, (1991).
"Toll-Like Receptor", Wikipedia, the Free Encyclopedia, http://en.wikipedia.org/wiki/Toll-like_receptor[May 28, 2012; 13:57:51]. (2012).
Arnon, R. et al., "Antiviral Response Elicited by a Completely Synthetic Antigen with Built-in Adjuvanticity", Proc. National Acad. Sci. USA, vol. 77, No. 11, pp. 6769-6772, (1980).
Audibert, F., et al., "Successful Immunization with a Totally Synthetic Diphtheria Vaccine", Proc. Natl. Acad. Sci., vol. 79, pp. 5042-5046, (1982).
Bachmann et al., "Vaccine Delivery: a Matter of Size, Geometry, Kinetics and Molecular Patterns", Nature Reviews Immunology, vol. 10, No. 11, pp. 787-796, (2010).
Barrios et al., "TriVax-HPV: an improved peptide-based therapeutic vaccination strategy against human papillomavirus-induced cancers," Cancer Immunol Immunother (2012) 61:1307-1317.
Basalp, A. et al., "Immune Response to 17[Beta]-Estradiol Involved in Polymer Gels: Antigen Specificity and Affinity of Hybridoma Clones," Hybridoma, vol. 19, No. 6, pp. 495-499, (2000).
Belnoue et al., "Enhancing Antitumor Immune Responses by Optimized Combinations of Cell-penetrating Peptide-based Vaccines and Adjuvants," Molecular Therapy vol. 24 No. 9, 1675-1685, 2016.
Belnoue et al., "Targeting self-and neoepitopes with a modular self-adjuvanting cancer vaccine," JCI Insight. 2019;4(11), pp. 1-17.
Black et al., "Self-Assembled Peptide Amphiphile Micelles Containing a Cytotoxic T-Cell Epitope Promote a Protective Immune Response In Vivo", Advanced Materials, vol. 24, No. 28, p. 3848, (2012).
Bogyo et al., "Substrate binding and sequence preference of the proteasome revealed by active-site-directed affinity probes," Chemistry & Biology Jun. 1998, 5:307-320.
Brito et al., "Designing and Building the Next Generation of Improved Vaccine Adjuvants", Journal of Controlled Release, vol. 190, pp. 563-579, (2014).
Choe et al., "Substrate Profiling of Cysteine Proteases Using a Combinatorial Peptide Library Identifies Functionally Unique Specificities," The Journal of Biological Chemistry vol. 281, No. 18, pp. 12824-12832, May 5, 2006.
Chan et al., "Synthesis and Immunological Characterization of Toll-Like Receptor 7 Agonistic Conjugates," Bioconjugate Chem. 2009, 20, pp. 1194-1200.
Chaudhuri et al., "High-Throughput Biophysical Analysis of Protein Therapeutics to Examine Interrelationships Between Aggregate Formation and Conformational Stability", The AAPS Journal, vol. 16, No. 1, pp. 48-64, (2013).
Chedid, L., et al., "Enhancement of Certain Biological Activities of Muramyl Dipeptide Derivatives After Conjugation to a Multi-Poly(DL-Alanine)-Poly(L-Lysine) Carrier", Proc. Natl. Acad. Sci., vol. 76, No. 12, pp. 6557-6561, (1979).
Cho et al., "BiVax: a peptide/poly-IC subunit vaccine that mimics an acute infection elicits vast and effective anti-tumor CD8 T-cell responses," Cancer Immunol Immunother (2013) 62:787-799.
Etrych, T. et al., "Synthesis of HPMA Copolymers Containing Doxorubicin Bound via a Hydrazone Linkage. Effect of Spacer on

(56) References Cited

OTHER PUBLICATIONS

Drug Release and In Vitro Cytotoxicity", Macromolecular Bioscience, vol. 2, No. 1, pp. 43-52, (2002).
Cristofaro et al., "The Toll-Like Receptors and their Role in Septic Shock", Expert Opinion on Therapeutic Targets, vol. 7, No. 5, pp. 603-612, (2003).
Dane et al., "Big Thinking for Adjuvants. Particles Formed by Polymeric Adjuvants Preferentially Localize to the Lymph Node and Elicit Robust Immunity", Nature Biotechnology, vol. 33, No. 11, pp. 1146-1148, (2015).
Francica et al., "Thermoresponsive Polymer Nanoparticles Co-deliver RSV F Trimers with a TLR-7/8 Adjuvant," Bioconjugate Chem. 2016, 27, 2372-2385.
Dintzis, H. et al., "Molecular Determinants of Immunogenicity: The Immunon Model of Immune Response", Proceedings of the National Academy of Science USA, vol. 73, No. 10, pp. 3671-3675, (1976).
Duncan, R. et al., "Anticancer Agents Coupled to N-(2-Hydroxypropyl)Methacrylamide Copolymers. II. Evaluation of Daunomycin Conjugates in Vivo Against L 1210 Leukaemia", Br. J_ Cancer, vol. 57, pp. 147-156, (1988).
Duncan, R. et al., "Do HPMA Copolymer Conjugates Have a Future as Clinically Useful Nanomedicines? A Critical Overview of Current Status and Future Opportunities", Advanced Drug Delivery Reviews, vol. 62, pp. 272-282, (2010).
Ryu, K. et al., "Stimulation of Innate Immune Cells by Light-Activated TLR7/8 Agonists", Journal of the American Chemical Society, vol. 136, pp. 10823-10825, (2014).
Shakya et al., "Characterization of Chemically Defined Poly-N-Isopropylacrylamide Based Copolymeric Adjuvants", Magazine, vol. 31, pp. 3519-3527 (2013).
Shukla et al., Toward self-adjuvanting subunit vaccines: Model peptide and protein antigens incorporating covalently pound toll-like receptor-7 agonistic imidazoquinolines, Bioorganic & Medicinal Chemistry Letters 21 (2011) 3232-3236.
Subr, V., et al., "Coating of Adenovirus Type 5 With Polymers Containing Quaternary Amines Prevents Binding to Blood Components," Journal of Controlled Release, vol. 135, No. 2, pp. 152-158, (2009).
Tanji, H., et al., "Structural Reorganization of the Toll-Like Receptor 8 Dimer Induced by Agonistic Ligands", Science, vol. 339, No. 6126, pp. 1426-1429, (2013).
Trent et al., "Peptide Amphiphile Micelles Self-Adjuvant Group A Streptococcal Vaccination", The AAPS Journal, vol. 17, No. 2, pp. 380-388, (2014).
Trzcinska et al., "Bioactive Mesoglobules of Poly(di(ethylene glycol) monomethyl ether methacrylate)-Peptide Conjugate", Polymer Chemistry vol. 50, pp. 3104-3115, (2012).
Wu et al., "Immunotherapeutic activity of a conjugate of a Toll-like receptor 7 ligand," PNAS, Mar. 6, 2007, vol. 104, No. 10, pp. 3990-3995.
Zeng et al., "A Modular Approach to Assembly of Totally Synthetic Self-adjuvanting Lipopeptide-based Vaccines Allows Conformational Epitope Building," The Journal of Biological Chemistry vol. 286, No. 15, pp. 12944-12951, Apr. 15, 2011.
Zhu et al., "Albumin/vaccine nanocomplexes that assemble in vivo for combination cancer immunotherapy," Nature Communications, 2017, 8:1954, pp. 1-15.
Zom et al., "Efficient Induction of Antitumor Immunity by Synthetic Toll-like Receptor Ligand-Peptide Conjugates," Cancer Immunol Res; 2(8) Aug. 2014, pp. 756-764.
Wang et al., "Aggregation of Therapeutic Proteins Passage", 5.3.6 Turbidimetry and Nephelometry, pp. 235-237, p. 236, second and third paragraphs, (2010).
Weterings et al., "Synthesis of 2-alkoxy-8-hydroxyadenylpeptides: Towards synthetic epitope-based vaccines," Bioorganic & Medicinal Chemistry Letters 16 (2006) 3258-3261.
Weterings, J. et al., "Synthesis of 2-Alkoxy-8-Hydroxyadenylpeptides: Towards Synthetic Epitope-Based Vaccines." Bioorganic & Medicinal Chemistry Letters, vol. 16, pp. 3258-3261, (2006).

Wille-Reece et al., "Immunization with HIV-1 Gag Protein Conjugated to a TLR7/8 Agonist Results in the Generation of HIV-1 Gag-Specific Th1 and CD8+ T Cell Responses," The Journal of Immunology, 2005, 174: 7676-7683.
Wille-Reece, U. et al., "HIV Gag Protein Conjugated to a Toll-Like Receptor 7/8 Agonist Improves the Magnitude and Quality of Th1 and CD8+ T Cell Responses in Nonhuman Primates." Proc. Natl. Acad. Sci. USA, vol. 102, No. 42, pp. 15190-15194, (2005).
Wille-Reece, U. et al., "Immunization with HIV-1 Gag Protein Conjugated to a TLR7/8 Agonist Results in the Generation of HIV-1 Gag-Specific Th1 and CD8+ T Cell Responses", The Journal of Immunology, vol. 174, pp. 7676-7683, (2005).
Wille-Reece, U. et al., "Toll-Like Receptor Agonists Influence the Magnitude and Quality of Memory T Cell Responses After Prime-Boost Immunization in Nonhuman Primates", The Journal of Experimental Medicine, vol. 203, No. 5, pp. 1249-1258, (2006).
Oradd et al., "Effects of peptide hydrophobicity on its incorporation in phospholipid membrane—an NMR and ellipsometry study," Biochimica et Biophysica Acta 1808 (2011) 244-252.
U.S. Appl. No. 16/907,912, filed Jun. 22, 2020, Polymer Adjuvant, Abandoned.
U.S. Appl. No. 18/970,451, filed Dec. 5, 2024, Polymer Adjuvant, Pending.
U.S. Appl. No. 18/570,579, filed Dec. 14, 2023, Self-Assembing Nanoparticles Based on Amphiphilic Peptides for Drug Delivery Applications, Published as US 2024/0382614 A1.
Hein et al. Click Chemistry, A Powerful Tool for Pharmaceutical Sciences. Pharmaceutical Research. 2008; 25 (10):2216-2230.
Co-pending U.S. Appl. No. 18/970,451, filed Dec. 5, 2024.
U.S. Appl. No. 13/318,844, filed Feb. 21, 2012, Multi-Valent Adjuvant Display, Abandoned.
U.S. Appl. No. 15/299,936, filed Oct. 21, 2016, Multi-Valent Adjuvant Display, Abandoned.
U.S. Appl. No. 15/517,121, filed Apr. 5, 2017, Polymer Adjuvant, Abandoned.
U.S. Appl. No. 16/907,912, filed Jun. 22, 2020, Polymer Adjuvant, Published as US 2021/0000934 A1.
U.S. Appl. No. 17/057,658, filed Nov. 21, 2020, Improved Methods of Manufacturing Peptide-Based Vaccines, Published as US 2021/0113705 A1.
U.S. Appl. No. 17/282,447, filed Apr. 2, 2021, Aromatic Ring Substituted Amphiphilic Polymers as Drug Delivery Systems, Published as US 2021/0393523 A1.
U.S. Appl. No. 17/604,227, filed Oct. 15, 2021, Compositions and Methods of Manufacturing Star Polymers for Ligang Display and/or Drug Delivery, Published as US 2023/0026627 A1.
U.S. Appl. No. 18/277,220, filed Aug. 14, 2023, Self-Assembling Nanoparticles Based on Amphiphilic Peptides, Pending.
U.S. Appl. No. 18/570,579, filed Dec. 14, 2023, Self-Assembling Nanoparticles Based on Amphiphilic Peptides for Drug Delivery Applications, Pending.
U.S. Appl. No. 18/027,346, filed Mar. 20, 2023, Compositions and Methods of Manufacturing Amphiphilic Block, Published as US 2023/0381112 A1.
U.S. Appl. No. 18/032,538, filed Apr. 18, 2023, Star Polymer Drug Conjugates, Published as US 2023/0390406 A1.
U.S. Appl. No. 17/638,576, filed Feb. 25, 2022, Methods for Inducing an Immune Response Against Neoantigens, Published as 202210305099 A1.
U.S. Appl. No. 18/494,491, filed Oct. 25, 2023, Self-Assebling Nanoparticles, Published as US 2024/0269269 A1.
Heuking & Borchard. Toll-like receptor-7 agonist decoration enhances the adjuvanticity of chitosan-DNA nanoparticles. J Pharm Sci. 2012; 101(3):1166-1177.
Luo et al. Synthetic nanovaccines for immunotherapy. J Control Release. 2017;263:200-210.
Segura & Hubbell. Synthesis and in vitro characterization of an ABC triblock copolymer for siRNA delivery. Bioconjug Chem. 2007;18(3):736-745.
Fuks et al. Biohybrid block copolymers: towards functional micelles and vesicles. Chem Soc Rev. 2011;40 (5):2475-2493.
Duong et al. Pronounced peptide selectivity for melanoma through tryptophan end-tagging. Sci Rep. 2016;6:24952.

(56) References Cited

OTHER PUBLICATIONS

Co-pending U.S. Appl. No. 18/277,220, filed Aug. 14, 2023.
Co-pending U.S. Appl. No. 18/570,579, filed Dec. 14, 2023.

* cited by examiner

Example of a reaction between a linker precursor X1 (K') comprising an azide and a linker precursor X2 comprising a DBCO that results in the formation of a triazole Linker (L) that joints the peptide antigen (A) to the Hydrophobic molecule (H).

K' = azido-lysine

Synthesis of Compound 1

(A) HNO$_3$, 75°C, 1h; (B) PhPOCl$_2$, 130°C, 3h; (C) R-NH$_2$, DCM, 70°C, 2h (D) 10% pt/c, EtoAc, 55 psi H$_2$, 2h (E) (i) Valeroyl chloride, THF, RT, 2h (ii) CaO(s), methanol, 100°C; 5h (F) Benzyl-amine, 110°C, 8h (G) 98% H$_2$SO$_4$, 2h

Figure 4

| Vaccine | Sequence<br>A-B2-X1 or A-B2-(L)-H or A-X1 or A-(L)-H | Molecular weight | Particle formation |
|---|---|---|---|
| Irgq LP | KARDETAALLNSAVLGAAPLFVPPAD-K' | 2761.2 | No |
| Irgq Min | AALLNSAVLG-SLVR-K' | 1536.7 | No |
| Irgq LP-W$_3$ | KARDETAALLNSAVLGAAPLFVPPAD-(K'-DBCO)-W$_3$ | 3623.5 | Yes |
| Irgq Min-W$_3$ | AALLNSAVLG-SLVR-(K'-DBCO)-W$_3$ | 2399.0 | Yes |
| Irgq LP-2BXy$_3$ | KARDETAALLNSAVLGAAPLFVPPAD(K'-DBCO)-2BXy$_3$ | 4476.0 | Yes |
| Irgq Min-2BXy$_3$ | AALLNSAVLG-SLVR-(K'-DBCO)-2BXy$_3$ | 3251.5 | Yes |
| Cpne1 LP | DFTGSNGDPSSPYSLHYLSPTGVNEY-K' | 2957.3 | No |
| Cpne1 Min | SSPYSLHYLS-SLVR-K' | 1763.1 | No |
| Cpne1 LP-W$_3$ | DFTGSNGDPSSPYSLHYLSPTGVNEY-(K'-DBCO)-W$_3$ | 3819.7 | No |
| Cpne1 Min-W$_3$ | SSPYSLHYLS-SLVR-(K'-DBCO)-W$_3$ | 2625.4 | Yes |
| Cpne1 LP-2BXy$_3$ | DFTGSNGDPSSPYSLHYLSPTGVNEY-(K'-DBCO)-2BXy$_3$ | 4672.2 | Yes |
| Cpne1 Min-2BXy$_3$ | SSPYSLHYLS-SLVR-(K'-DBCO)-2BXy$_3$ | 3477.9 | Yes |

K' = azido-Lysine (Lys(N3)); DBCO = dibenzocyclooctyne

Figure 7

| Vaccine | Sequence A-B2-(L)-H or A-(L)-H | Molecular weight | Particle formation |
|---|---|---|---|
| M33 LP-2BXy$_5$ | DSGSPFPAAVILRDALHMARGLKYLHQ-(K'-DBCO)-2BXy5 | 5772.97 | Yes |
| M08 LP-2BXy$_5$ | ANFESGKHKYRQTAMFTATMPPAVERL-(K'-DBCO)-2BXy5 | 5890.76 | Yes |
| M27 LP-2BXy$_5$ | REGVELCPGNKYEMRRHGTTHSLVIHD-(K'-DBCO)-2BXy5 | 5944.04 | Yes |
| M47 LP-2BXy$_5$ | GRGHLLGRLAAIVGKQVLLGRKVVVVR-(K'-DBCO)-2BXy5 | 5673.96 | Yes |
| M30 LP-2BXy$_5$ | PSKPSFQEFVDWENVSPELNSTDQPFL-(K'-DBCO)-2BXy5 | 5947.17 | Yes |
| M44 LP-2BXy$_5$ | EFKHIKAFDRTFANNPGPMVVFATPGM-(K'-DBCO)-2BXy5 | 5831.74 | Yes |
| M25 LP-2BXy$_5$ | STANYNTSHLNNDVWQIFENPVDWKEK-(K'-DBCO)-2BXy5 | 6058.97 | Yes |
| M33 Min-2BXy$_5$ | AAVILRDALH-*SLVR*-(K'-DBCO)-2BXy5 | 4342.18 | Yes |
| M08 Min-2BXy$_5$ | QTAMFTATMP-*SLVR*-(K'-DBCO)-2BXy5 | 4362.21 | Yes |
| M27 Min-2BXy$_5$ | LCPGNKYEMR-*SLVR*-(K'-DBCO)-2BXy5 | 4474.34 | Yes |
| M47 Min-2BXy$_5$ | AAIVGKQVLL-*SLVR*-(K'-DBCO)-2BXy5 | 4275.17 | Yes |
| M30 Min-2BXy$_5$ | FQEFVDWENVS-*SLVR*-(K'-DBCO)-2BXy5 | 4663.38 | Yes |
| M33 LP-2B$_5$ | DSGSPFPAAVILRDALHMARGLKYLHQ-(K'-DBCO)-2B5 | 5532.97 | Yes |
| M08 LP-2B$_5$ | ANFESGKHKYRQTAMFTATMPPAVERL-(K'-DBCO)-2B5 | 5650.76 | Yes |
| M27 LP-2B$_5$ | REGVELCPGNKYEMRRHGTTHSLVIHD-(K'-DBCO)-2B5 | 5704.04 | Yes |
| M47 LP-2B$_5$ | GRGHLLGRLAAIVGKQVLLGRKVVVVR-(K'-DBCO)-2B5 | 5433.96 | Yes |
| M30 LP-2B$_5$ | PSKPSFQEFVDWENVSPELNSTDQPFL-(K'-DBCO)-2B5 | 5707.17 | Yes |
| M44 LP-2B$_5$ | EFKHIKAFDRTFANNPGPMVVFATPGM-(K'-DBCO)-2B5 | 5591.74 | Yes |
| M25 LP-2B$_5$ | STANYNTSHLNNDVWQIFENPVDWKEK-(K'-DBCO)-2B5 | 5818.97 | Yes |
| M33 Min-2B$_5$ | AAVILRDALH-*SLVR*-(K'-DBCO)-2B5 | 4102.18 | Yes |
| M08 Min-2B$_5$ | QTAMFTATMP-*SLVR*-(K'-DBCO)-2B5 | 4122.21 | Yes |
| M27 Min-2B$_5$ | LCPGNKYEMR-*SLVR*-(K'-DBCO)-2B5 | 4234.34 | Yes |
| M47 Min-2B$_5$ | AAIVGKQVLL-*SLVR*-(K'-DBCO)-2B5 | 4035.17 | Yes |
| M30 Min-2B$_5$ | FQEFVDWENVS-*SLVR*-(K'-DBCO)-2B5 | 4423.38 | Yes |

K' = azido-Lysine (Lys(N3)); DBCO = dibenzocyclooctyne

Figure 8
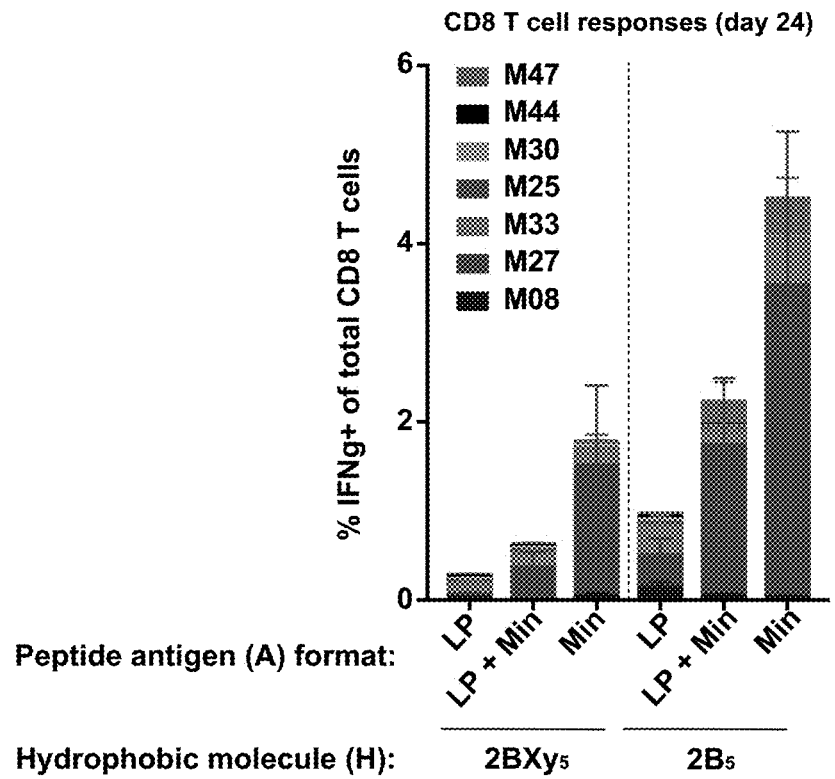
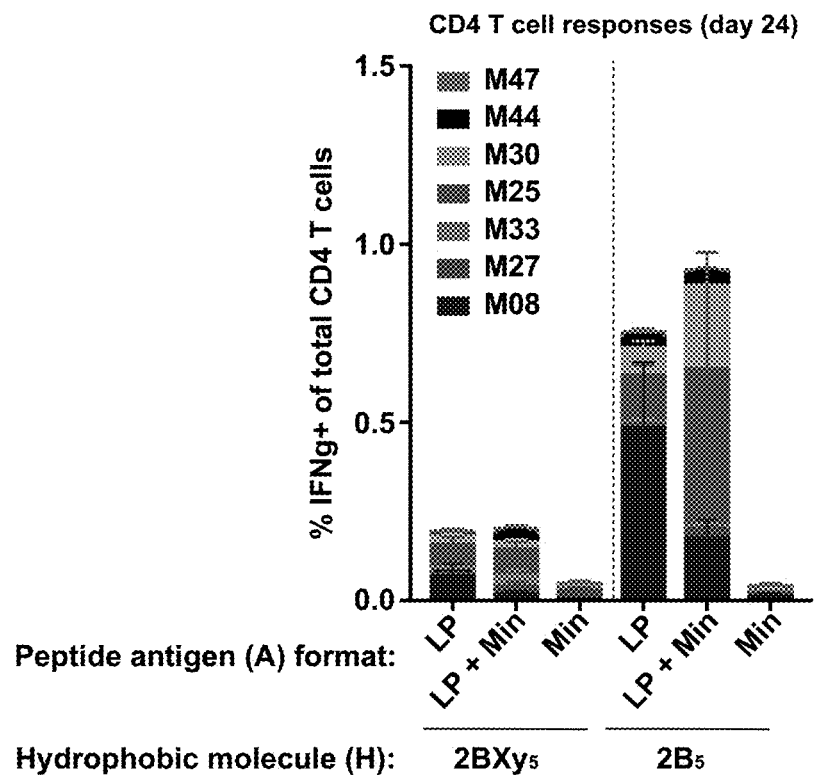

Schematic representation of peptide antigen conjugates of Formula V (referred to as LP-SNP-7/8a or Min-SNP-7/8a) wherein the hydrophobic molecule is a poly(amino acid) linked to TLR-7/8 agonists.

Figure 13

| Sequence<br>C-B1-A-(L)-H or C-B1-A-B2-(L)-H | Cathepsin cleavable N- or C-terminal extensions | | Proteasomal cleavable N- or C-terminal extensions | |
|---|---|---|---|---|
| | N-term | C-term | C-term | N-term |
| KSKSKS-GG-SSPYSLHYL-(K'-DBCO)-2BXy3 | - | - | - | - |
| KSKSKS-GGSLVR-SSPYSLHYL-(K'-DBCO)-2BXy3 | + | - | - | - |
| KSKSKS-GGSLVR-SSPYSLHYL-SLVR-(K'-DBCO)-2BXy3 | + | + | - | - |
| KSKSKS-GGSLVR-SSPYSLHYL-GGSLVR-(K'-DBCO)-2BXy3 | + | + | + | - |
| KSKSKS-GGSLVRYLLL-SSPYSLHYL-(K'-DBCO)-2BXy3 | + | - | - | + |
| KSKSKS-GGSLVRYLLL-SSPYSLHYL-SLVR-(K'-DBCO)-2BXy3 | + | + | - | + |
| KSKSKS-GGSLVRYLLL-SSPYSLHYL-GGSLVR-(K'-DBCO)-2BXy3 | + | + | + | + |
| ESESES-GG-SSPYSLHYL-(K'-DBCO)-2BXy3 | - | - | - | - |
| ESESES-GGSLVR-SSPYSLHYL-(K'-DBCO)-2BXy3 | + | - | - | - |
| ESESES-GGSLVR-SSPYSLHYL-SLVR-(K'-DBCO)-2BXy3 | + | + | - | - |
| ESESES-GGSLVR-SSPYSLHYL-GGSLVR-(K'-DBCO)-2BXy3 | + | + | + | - |
| ESESES-GGSLVRYLLL-SSPYSLHYL-(K'-DBCO)-2BXy3 | + | - | - | + |
| ESESES-GGSLVRYLLL-SSPYSLHYL-SLVR-(K'-DBCO)-2BXy3 | + | + | - | + |
| ESESES-GGSLVRYLLL-SSPYSLHYL-GGSLVR-(K'-DBCO)-2BXy3 | + | + | + | + |
| EKEKEK-GG-SSPYSLHYL-(K'-DBCO)-2BXy3 | - | - | - | - |
| EKEKEK-GGSLVR-SSPYSLHYL-(K'-DBCO)-2BXy3 | + | - | - | - |
| EKEKEK-GGSLVR-SSPYSLHYL-SLVR-(K'-DBCO)-2BXy3 | + | + | - | - |
| EKEKEK-GGSLVR-SSPYSLHYL-GGSLVR-(K'-DBCO)-2BXy3 | + | + | + | - |
| EKEKEK-GGSLVRYLLL-SSPYSLHYL-(K'-DBCO)-2BXy3 | + | - | - | + |
| EKEKEK-GGSLVRYLLL-SSPYSLHYL-SLVR-(K'-DBCO)-2BXy3 | + | + | - | + |
| EKEKEK-GGSLVRYLLL-SSPYSLHYL-GGSLVR-(K'-DBCO)-2BXy3 | + | + | + | + |

K' = azido-Lysine (Lys(N3)); DBCO = dibenzocyclooctyne

Figure 14
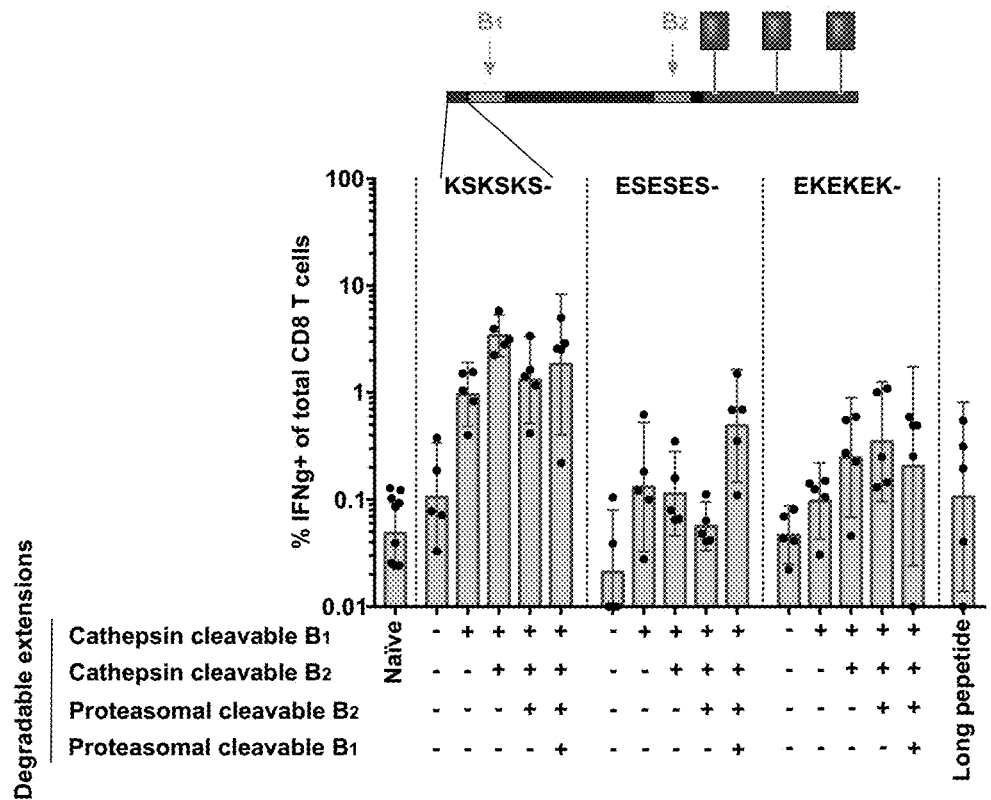
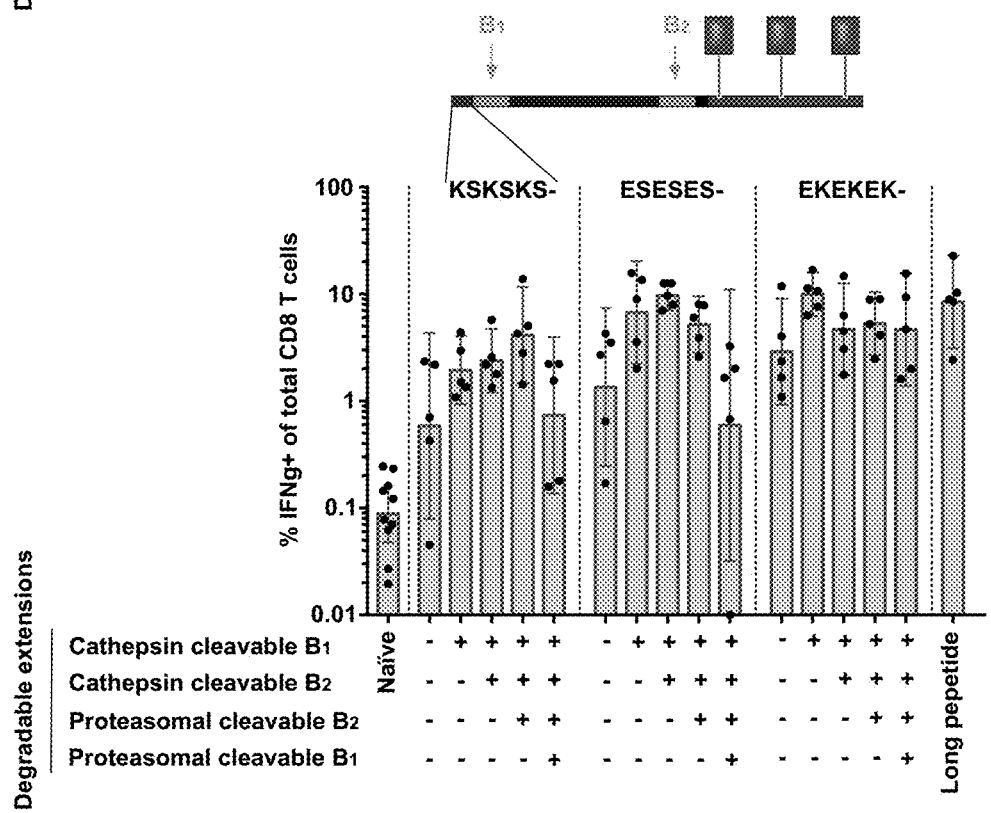

Figure 15

| # | B1 | B2 | Antigen | EC50 | Sequence<br>A or A-(L)-H or A-B2-(L)-H or B1-A-(L)-H or B1-A-B2-(L)-H |
|---|---|---|---|---|---|
| 1 | | | -ASMTNMELM- | 0.05 | ASMTNMELM-(K'-DBCO)-2B3W2 |
| 2 | SLVR | SPVZ | -ASMTNMELM- | 1.54 | SLVR-ASMTNMELM-SPVZ-(K'-DBCO)-2B3W2 |
| 3 | SLVR | R | -ASMTNMELM- | 1.93 | SLVR-ASMTNMELM-R-(K'-DBCO)-2B3W2 |
| 4 | | SLVR | -ASMTNMELM- | 2.26 | ASMTNMELM-SLVR-(K'-DBCO)-2B3W2 |
| 5 | SLVR | | -ASMTNMELM- | 2.50 | SLVR-ASMTNMELM-(K'-DBCO)-2B3W2 |
| 6 | SLVR | GP | -ASMTNMELM- | 3.05 | SLVR-ASMTNMELM-GP-(K'-DBCO)-2B3W2 |
| 7 | SLVR | SPVR | -ASMTNMELM- | 3.16 | SLVR-ASMTNMELM-SPVR-(K'-DBCO)-2B3W2 |
| 8 | SLVR | SLVR | -ASMTNMELM- | 4.80 | SLVR-ASMTNMELM-SLVR-(K'-DBCO)-2B3W2 |
| 9 | SLVR | | -ASMTNMELM- | 7.38 | SLVR-ASMTNMELM-(K'-DBCO)-2B3W2 |
| 10 | SPVR | | -ASMTNMELM- | 7.55 | SPVR-ASMTNMELM-(K'-DBCO)-2B3W2 |
| 11 | ELVR | | -ASMTNMELM- | 8.22 | ELVR-ASMTNMELM-(K'-DBCO)-2B3W2 |
| 12 | SPVR | | -ASMTNMELM- | 9.68 | SPVR-ASMTNMELM-(K'-DBCO)-2B3W2 |
| 13 | ELVL | | -ASMTNMELM- | 12.50 | ELVL-ASMTNMELM-(K'-DBCO)-2B3W2 |
| 14 | ELVZ | | -ASMTNMELM- | 12.85 | ELVZ-ASMTNMELM-(K'-DBCO)-2B3W2 |
| 15 | SLVR | KPLR | -ASMTNMELM- | 12.91 | SLVR-ASMTNMELM-KPLR-(K'-DBCO)-2B3W2 |
| 16 | SLVR | GSG | -ASMTNMELM- | 13.34 | SLVR-ASMTNMELM-GSG-(K'-DBCO)-2B3W2 |
| 17 | EPVZ | | -ASMTNMELM- | 14.55 | EPVZ-ASMTNMELM-(K'-DBCO)-2B3W2 |
| 18 | KPLR | | -ASMTNMELM- | 16.11 | KPLR-ASMTNMELM-(K'-DBCO)-2B3W2 |
| 19 | SLVR | SLVZ | -ASMTNMELM- | 16.18 | SLVR-ASMTNMELM-SLVZ-(K'-DBCO)-2B3W2 |
| 20 | KPLR | | -ASMTNMELM- | 16.98 | KPLR-ASMTNMELM-(K'-DBCO)-2B3W2 |
| 21 | ELVL | | -ASMTNMELM- | 21.98 | ELVL-ASMTNMELM-(K'-DBCO)-2B3W2 |
| 22 | ELVZ | | -ASMTNMELM- | 22.08 | ELVZ-ASMTNMELM-(K'-DBCO)-2B3W2 |
| 23 | RLVS | | -ASMTNMELM- | 29.31 | RLVS-ASMTNMELM-(K'-DBCO)-2B3W2 |
| 24 | EPVZ | | -ASMTNMELM- | 31.77 | EPVZ-ASMTNMELM-(K'-DBCO)-2B3W2 |
| 25 | SLVR | SLVL | -ASMTNMELM- | 39.72 | SLVR-ASMTNMELM-SLVL-(K'-DBCO)-2B3W2 |
| 26 | SLVR | ELVR | -ASMTNMELM- | 39.72 | SLVR-ASMTNMELM-ELVR-(K'-DBCO)-2B3W2 |
| 27 | SLVZ | | -ASMTNMELM- | 45.19 | SLVZ-ASMTNMELM-(K'-DBCO)-2B3W2 |
| 28 | SLVR | EPVZ | -ASMTNMELM- | 52.97 | SLVR-ASMTNMELM-EPVZ-(K'-DBCO)-2B3W2 |
| 29 | SPVZ | | -ASMTNMELM- | 56.62 | SPVZ-ASMTNMELM-(K'-DBCO)-2B3W2 |
| 30 | SLVR | GGSLVZ | -ASMTNMELM- | 78.70 | SLVR-ASMTNMELM-GGSLVZ-(K'-DBCO)-2B3W2 |
| 31 | SLVR | GGGG | -ASMTNMELM- | 114.55 | SLVR-ASMTNMELM-GGGG-(K'-DBCO)-2B3W2 |
| 32 | SLVR | ELVZ | -ASMTNMELM- | 129.42 | SLVR-ASMTNMELM-ELVZ-(K'-DBCO)-2B3W2 |
| 33 | SLVL | | -ASMTNMELM- | 135.52 | SLVL-ASMTNMELM-(K'-DBCO)-2B3W2 |
| 34 | SLVR | GGSLVR | -ASMTNMELM- | 179.89 | SLVR-ASMTNMELM-GGSLVR-(K'-DBCO)-2B3W2 |
| 35 | GGGG | | -ASMTNMELM- | 187.07 | GGGG-ASMTNMELM-(K'-DBCO)-2B3W2 |
| 36 | SLVR | ELVL | -ASMTNMELM- | 212.81 | SLVR-ASMTNMELM-ELVL-(K'-DBCO)-2B3W2 |
| 37 | SLVR | dSLVR | -ASMTNMELM- | 521.19 | SLVR-ASMTNMELM-dSLVR-(K'-DBCO)-2B3W2 |
| 38 | dSLVR | | -ASMTNMELM- | 1927.52 | dSLVR-ASMTNMELM-(K'-DBCO)-2B3W2 |
| 39 | | | | NA | GIPVHLELASMTNRELMSSIVHQQVFPT |
| 40 | | | | NA | SSPYSLHYL |

Z = citrulline; K' = azido-Lysine (Lys(N3)); DBCO = dibenzocyclooctyne;
d = D amino acids

Figure 18

| Sequence<br>C-A-(L)-H or C-B1-A-(L)-H or C-A-B2-(L)-H<br>or C-B1-A-B2-(L)-H | Molecular weight | GRAVY of native antigen | Net charge | Particle size (diameter, nm) |
|---|---|---|---|---|
| Ac-EEE-ELVL-KNHRNRQVI-GGESELVL-(K'-DBCO)-W5 | 4220.83 | -0.68 | -3 | 7.2 |
| Ac-EEE-ELVL-KNHRNRQVI-GGELVL-(K'-DBCO)-W5 | 4004.65 | -0.55 | -2 | 46.9 |
| Ac-SLVL-KNHRNRQVI-GGELVL-(K'-DBCO)-W5 | 3575.26 | 0.03 | 2 | 1624.0 |
| Ac-SLVR-KNHRNRQVI-GGESELVL-(K'-DBCO)-W5 | 3834.49 | -0.55 | 2 | 44.4 |
| Ac-SLVL-KNHRNRQVI-GGSLVL-(K'-DBCO)-W5 | 3533.22 | 0.17 | 3 | 101.7 |
| Ac-SLVL-KNHRNRQVI-GGELVR-(K'-DBCO)-W5 | 3618.30 | -0.39 | 3 | 12.5 |
| Ac-SLVL-KNHRNRQVI-GGSLVR-(K'-DBCO)-W5 | 3576.25 | -0.25 | 4 | 8.9 |
| Ac-SLVR-KNHRNRQVI-GGSLVL-(K'-DBCO)-W5 | 3576.26 | -0.25 | 4 | 11.6 |
| Ac-EK-SLVL-KNHRNRQVI-GGSLVR-(K'-DBCO)-W5 | 3833.53 | -0.56 | 4 | 10.1 |
| Ac-KLVR-KNHRNRQVI-GGELVL-(K'-DBCO)-W5 | 3659.39 | -0.54 | 4 | 12.0 |
| Ac-SLVL-KNHRNRQVI-GGKLVR-(K'-DBCO)-W5 | 3617.35 | -0.41 | 5 | 7.5 |
| Ac-SLVR-KNHRNRQVI-GGSLVR-(K'-DBCO)-W5 | 3619.29 | -0.67 | 5 | 8.7 |
| Ac-KLVR-KNHRNRQVI-GGELVR-(K'-DBCO)-W5 | 3702.41 | -0.96 | 5 | 8.7 |
| Ac-SLVR-KNHRNRQVI-GGKLVR-(K'-DBCO)-W5 | 3660.39 | -0.82 | 6 | 7.8 |
| Ac-KS-KLVR-KNHRNRQVI-GGSLVL-(K'-DBCO)-W5 | 3832.60 | -0.58 | 6 | 9.6 |
| Ac-KE-KLVR-KNHRNRQVI-GGSLVR-(K'-DBCO)-W5 | 3917.67 | -1.08 | 6 | 8.8 |
| Ac-ESES-ELVL-SPERNDWEPL-GGSLVL-(K'-DBCO)-W5 | 4085.62 | -0.39 | -5 | 9.9 |
| Ac-ES-ELVL-SPERNDWEPL-GGSLVL-(K'-DBCO)-W5 | 3869.44 | -0.23 | -4 | 11.8 |
| Ac-E-SLVL-SPERNDWEPL-GGSLVL-(K'-DBCO)-W5 | 3740.31 | -0.09 | -3 | 8.9 |
| Ac-EK-ELVL-SPERNDWEPL-GGSLVL-(K'-DBCO)-W5 | 3910.53 | -0.37 | -3 | 8.9 |
| Ac-SLVL-SPERNDWEPL-GGSLVL-(K'-DBCO)-W5 | 3611.20 | 0.08 | -2 | 72.0 |
| Ac-EK-SLVL-SPERNDWEPL-GGSLVL-(K'-DBCO)-W5 | 3868.49 | -0.25 | -2 | 11.1 |
| Ac-KLVR-SPERNDWEPL-GGKLVR-(K'-DBCO)-W5 | 3779.44 | -1.01 | 2 | 18.2 |
| Ac-KSKS-KLVR-SPERNDWEPL-GGSLVL-(K'-DBCO)-W5 | 4125.83 | -0.77 | 2 | 24.5 |
| Ac-KS-KLVR-SPERNDWEPL-GGKLVR-(K'-DBCO)-W5 | 3994.69 | -1.13 | 3 | 11.0 |
| Ac-KSKS-KLVR-SPERNDWEPL-GGSLVR-(K'-DBCO)-W5 | 4168.86 | -1.10 | 3 | 11.5 |
| Ac-KSKS-KLVR-SPERNDWEPL-GGKLVR-(K'-DBCO)-W5 | 4209.94 | -1.22 | 4 | 8.9 |

K' = azido-Lysine (Lys(N3)); DBCO = dibenzocyclooctyne; Ac = N-terminal acetyl

Figure 18 continued

| Sequence<br>C-A-(L)-H or C-B1-A-(L)-H or C-A-B2-(L)-H<br>or C-B1-A-B2-(L)-H | Molecular weight | GRAVY of native antigen | Net charge | Particle size (diameter, nm) |
|---|---|---|---|---|
| Ac-EEE-ELVL-KNHRNRQVI-GGESELVL-(K'-DBCO)-2B5 | 5401.65 | -0.68 | -3 | 129.6 |
| Ac-EEE-ELVL-KNHRNRQVI-GGELVL-(K'-DBCO)-2B5 | 5185.47 | -0.55 | -2 | 142.6 |
| Ac-SLVL-KNHRNRQVI-GGELVL-(K'-DBCO)-2B5 | 4756.08 | 0.03 | 2 | 126.7 |
| Ac-SLVR-KNHRNRQVI-GGESELVL-(K'-DBCO)-2B5 | 5015.31 | -0.55 | 2 | 28.2 |
| Ac-SLVL-KNHRNRQVI-GGSLVL-(K'-DBCO)-2B5 | 4714.04 | 0.17 | 3 | 28.1 |
| Ac-SLVL-KNHRNRQVI-GGELVR-(K'-DBCO)-2B5 | 4799.12 | -0.39 | 3 | 30.8 |
| Ac-SLVL-KNHRNRQVI-GGSLVR-(K'-DBCO)-2B5 | 4757.07 | -0.25 | 4 | 19.1 |
| Ac-SLVR-KNHRNRQVI-GGSLVL-(K'-DBCO)-2B5 | 4757.08 | -0.25 | 4 | 14.7 |
| Ac-EK-SLVL-KNHRNRQVI-GGSLVR-(K'-DBCO)-2B5 | 5014.35 | -0.56 | 4 | 14.2 |
| Ac-KLVR-KNHRNRQVI-GGELVL-(K'-DBCO)-2B5 | 4840.21 | -0.54 | 4 | 14.3 |
| Ac-SLVL-KNHRNRQVI-GGKLVR-(K'-DBCO)-2B5 | 4798.17 | -0.41 | 5 | 15.3 |
| Ac-SLVR-KNHRNRQVI-GGSLVR-(K'-DBCO)-2B5 | 4800.11 | -0.67 | 5 | 12.6 |
| Ac-KLVR-KNHRNRQVI-GGELVR-(K'-DBCO)-2B5 | 4883.23 | -0.96 | 5 | 13.2 |
| Ac-SLVR-KNHRNRQVI-GGKLVR-(K'-DBCO)-2B5 | 4841.21 | -0.82 | 6 | 16.3 |
| Ac-KS-KLVR-KNHRNRQVI-GGSLVL-(K'-DBCO)-2B5 | 5013.42 | -0.58 | 6 | 19.7 |
| Ac-KE-KLVR-KNHRNRQVI-GGSLVR-(K'-DBCO)-2B5 | 5098.49 | -1.08 | 6 | 18.7 |
| Ac-ESES-ELVL-SPERNDWEPL-GGSLVL-(K'-DBCO)-2B5 | 5266.44 | -0.39 | -5 | 96.3 |
| Ac-ES-ELVL-SPERNDWEPL-GGSLVL-(K'-DBCO)-2B5 | 5050.26 | -0.23 | -4 | 104.4 |
| Ac-E-SLVL-SPERNDWEPL-GGSLVL-(K'-DBCO)-2B5 | 4921.13 | -0.09 | -3 | 107.0 |
| Ac-EK-ELVL-SPERNDWEPL-GGSLVL-(K'-DBCO)-2B5 | 5091.35 | -0.37 | -3 | 109.1 |
| Ac-SLVL-SPERNDWEPL-GGSLVL-(K'-DBCO)-2B5 | 4792.02 | 0.08 | -2 | 1663.0 |
| Ac-EK-SLVL-SPERNDWEPL-GGSLVL-(K'-DBCO)-2B5 | 5049.31 | -0.25 | -2 | 137.4 |
| Ac-KLVR-SPERNDWEPL-GGKLVR-(K'-DBCO)-2B5 | 4960.26 | -1.01 | 2 | 33.4 |
| Ac-KSKS-KLVR-SPERNDWEPL-GGSLVL-(K'-DBCO)-2B5 | 5306.65 | -0.77 | 2 | 14.9 |
| Ac-KS-KLVR-SPERNDWEPL-GGKLVR-(K'-DBCO)-2B5 | 5175.51 | -1.13 | 3 | 20.6 |
| Ac-KSKS-KLVR-SPERNDWEPL-GGSLVR-(K'-DBCO)-2B5 | 5349.68 | -1.10 | 3 | 14.4 |
| Ac-KSKS-KLVR-SPERNDWEPL-GGKLVR-(K'-DBCO)-2B5 | 5390.76 | -1.22 | 4 | 20.2 |

K' = azido-Lysine (Lys(N3)); DBCO = dibenzocyclooctyne; Ac = N-terminal acetyl

Figure 18 continued

| Sequence<br>C-A-(L)-H or C-B1-A-(L)-H or C-A-B2-(L)-H<br>or C-B1-A-B2-(L)-H | Molecular weight | GRAVY of native antigen | Net charge | Particle size (diameter, nm) |
|---|---|---|---|---|
| Ac-KS-KLVR-VVIAIFIIL-GGELVR-(K'-DBCO)-W5 | 3753.67 | 3.87 | 3 | 220.0 |
| Ac-KSKS-KLVR-VVIAIFIIL-GGELVR-(K'-DBCO)-W5 | 3968.91 | 3.87 | 4 | 2329.0 |
| Ac-KSKS-KLVR-VVIAIFIIL-GGSLVR-(K'-DBCO)-W5 | 3926.87 | 3.87 | 5 | 1370.0 |
| Ac-KSKS-KLVR-VVIAIFIIL-GGKLVR-(K'-DBCO)-W5 | 3967.98 | 3.87 | 6 | 43.4 |
| EKE-KLVL-ASMTNMELM-SSGGSLVL-(K'-DBCO)-W5 | 3955.76 | 0.31 | 0 | 1368.0 |
| EK-SLVR-ASMTNMELM-SSGGELVR-(K'-DBCO)-W5 | 3913.64 | 0.31 | 1 | 1518.0 |
| KE-KLVR-ASMTNMELM-SSGGSLVL-(K'-DBCO)-W5 | 3869.67 | 0.31 | 2 | 52.1 |
| KE-KLVR-ASMTNMELM-SSGGELVR-(K'-DBCO)-W5 | 3954.74 | 0.31 | 2 | 19.2 |
| KS-KLVR-ASMTNMELM-SSGGSLVL-(K'-DBCO)-W5 | 3827.63 | 0.31 | 3 | 26.8 |
| KSKS-KLVR-ASMTNMELM-SSGGELVL-(K'-DBCO)-W5 | 4084.93 | 0.31 | 3 | 19.1 |
| KSKS-KLVR-ASMTNMELM-SSGGSLVL-(K'-DBCO)-W5 | 4042.88 | 0.31 | 4 | 10.2 |
| KSKS-KLVR-ASMTNMELM-SSGGELVR-(K'-DBCO)-W5 | 4127.95 | 0.31 | 4 | 8.8 |
| KSKS-KLVR-ASMTNMELM-SSGGSLVR-(K'-DBCO)-W5 | 4085.91 | 0.31 | 5 | 9.0 |
| KSKS-KLVR-ASMTNMELM-SSGGKLVR-(K'-DBCO)-W5 | 4127.02 | 0.31 | 6 | 8.2 |
| Ac-ESESES-ELVL-AKFVAAWTLKAAA-GGESELVL-(K'-DBCO)-W5 | 4665.35 | 0.94 | -4 | 2000 |
| Ac-EKE-KLVL-AKFVAAWTLKAAA-GGSLVL-(K'-DBCO)-W5 | 4144.00 | 0.94 | 2 | 1414.0 |
| Ac-EK-ELVL-AKFVAAWTLKAAA-GGKLVR-(K'-DBCO)-W5 | 4099.96 | 0.94 | 3 | 25.0 |
| Ac-EKE-KLVL-AKFVAAWTLKAAA-GGKLVR-(K'-DBCO)-W5 | 4228.14 | 0.94 | 4 | 6.7 |
| Ac-KE-KLVR-AKFVAAWTLKAAA-GGSLVL-(K'-DBCO)-W5 | 4057.92 | 0.94 | 4 | 41.2 |

K' = azido-Lysine (Lys(N3)); DBCO = dibenzocyclooctyne; Ac = N-terminal acetyl

Figure 18 continued

| Sequence<br>C-A-(L)-H or C-B1-A-(L)-H or C-A-B2-(L)-H<br>or C-B1-A-B2-(L)-H | Molecular weight | GRAVY of native antigen | Net charge | Particle size (diameter, nm) |
|---|---|---|---|---|
| Ac-KS-KLVR-VVIAIFIIL-GGELVR-(K'-DBCO)-2B5 | 4934.49 | 3.87 | 3 | 791.1 |
| Ac-KSKS-KLVR-VVIAIFIIL-GGELVR-(K'-DBCO)-2B5 | 5149.73 | 3.87 | 4 | 981.8 |
| Ac-KSKS-KLVR-VVIAIFIIL-GGSLVL-(K'-DBCO)-2B5 | 5107.69 | 3.87 | 5 | 1338.0 |
| Ac-KSKS-KLVR-VVIAIFIIL-GGKLVR-(K'-DBCO)-2B5 | 5148.80 | 3.87 | 6 | 41.1 |
| EKE-KLVL-ASMTNMELM-SSGGSLVL-(K'-DBCO)-2B5 | 5136.58 | 0.31 | 0 | 1362.0 |
| EK-SLVR-ASMTNMELM-SSGGELVR-(K'-DBCO)-2B5 | 5094.46 | 0.31 | 1 | 1381.0 |
| KE-KLVR-ASMTNMELM-SSGGSLVL-(K'-DBCO)-2B5 | 5050.49 | 0.31 | 2 | 1115.0 |
| KE-KLVR-ASMTNMELM-SSGGELVR-(K'-DBCO)-2B5 | 5135.56 | 0.31 | 2 | 1390.0 |
| KS-KLVR-ASMTNMELM-SSGGSLVL-(K'-DBCO)-2B5 | 5008.45 | 0.31 | 3 | 45.5 |
| KSKS-KLVR-ASMTNMELM-SSGGELVL-(K'-DBCO)-2B5 | 5265.75 | 0.31 | 3 | 603.6 |
| KSKS-KLVR-ASMTNMELM-SSGGSLVL-(K'-DBCO)-2B5 | 5223.70 | 0.31 | 4 | 32.9 |
| KSKS-KLVR-ASMTNMELM-SSGGELVR-(K'-DBCO)-2B5 | 5308.77 | 0.31 | 4 | 13.0 |
| KSKS-KLVR-ASMTNMELM-SSGGSLVR-(K'-DBCO)-2B5 | 5266.73 | 0.31 | 5 | 16.0 |
| KSKS-KLVR-ASMTNMELM-SSGGKLVR-(K'-DBCO)-2B5 | 5307.84 | 0.31 | 6 | 16.4 |
| Ac-ESESES-ELVL-AKFVAAWTLKAAA-GGESELVL-(K'-DBCO)-2B5 | 5846.17 | 0.94 | -4 | 618.5 |
| Ac-EKE-KLVL-AKFVAAWTLKAAA-GGSLVL-(K'-DBCO)-2B5 | 5324.82 | 0.94 | 2 | 88.5 |
| Ac-EK-ELVL-AKFVAAWTLKAAA-GGKLVR-(K'-DBCO)-2B5 | 5280.78 | 0.94 | 3 | 1560.0 |
| Ac-EKE-KLVL-AKFVAAWTLKAAA-GGKLVR-(K'-DBCO)-2B5 | 5408.96 | 0.94 | 4 | 222.8 |
| Ac-KE-KLVR-AKFVAAWTLKAAA-GGSLVL-(K'-DBCO)-2B5 | 5238.74 | 0.94 | 4 | 75.4 |
| ESGSGSGS-SLVR-GRVLELFRAAQLANDVVLQIMELCGATR-(K'-DBCO)-2B5 | 6760.30 | 0.52 | 1 | 2076.0 |
| ESGSGSGS-SLVR-GRVLELFRAAQLANDVVLQIMELCGATR-SGSGS-(K'-DBCO)-2B5 | 7135.63 | 0.52 | 1 | 1725.0 |
| ESGSGSGS-SLVR-GRVLELFRAAQLANDVVLQIMELCGATR-LLLLL-(K'-DBCO)-2B5 | 7326.09 | 0.52 | 1 | 1539.0 |
| EEEEEEEE-SLVR-VLELFRAAQLANDVVLQIMELCGATR-(K'-DBCO)-2B5 | 6931.40 | 0.75 | -7 | 1214.0 |
| RRRRR-KPLR-GRVLELFRAAQLANDVVLQIMELCGATR-LLLLL-(K'-DBCO)-2B5 | 7497.52 | 0.52 | 8 | 24.5 |
| EEEEEEEE-SLVR-GRVLELFRAAQLANDVVLQIMELCGATR-LLLLL-(K'-DBCO)-2B5 | 7710.43 | 0.52 | -6 | 128.1 |

K' = azido-Lysine (Lys(N3)); DBCO = dibenzocyclooctyne; Ac = N-terminal acetyl

Figure 18 continued

| Sequence<br>C-A-(L)-H or C-B1-A-(L)-H or C-A-B2-(L)-H<br>or C-B1-A-B2-(L)-H | Molecular weight | GRAVY of native antigen | Net charge | Particle size (diameter, nm) |
|---|---|---|---|---|
| EKE-KLVL-ASMTNMELM-SSGGSLVL-(K'-DBCO)-2B2W8 | 5358.48 | 0.31 | 0 | 800.3 |
| EK-SLVR-ASMTNMELM-SSGGELVR-(K'-DBCO)-2B2W8 | 5316.36 | 0.31 | 1 | 1042.0 |
| KE-KLVR-ASMTNMELM-SSGGSLVL-(K'-DBCO)-2B2W8 | 5272.39 | 0.31 | 2 | 1146

Figure 18 continued

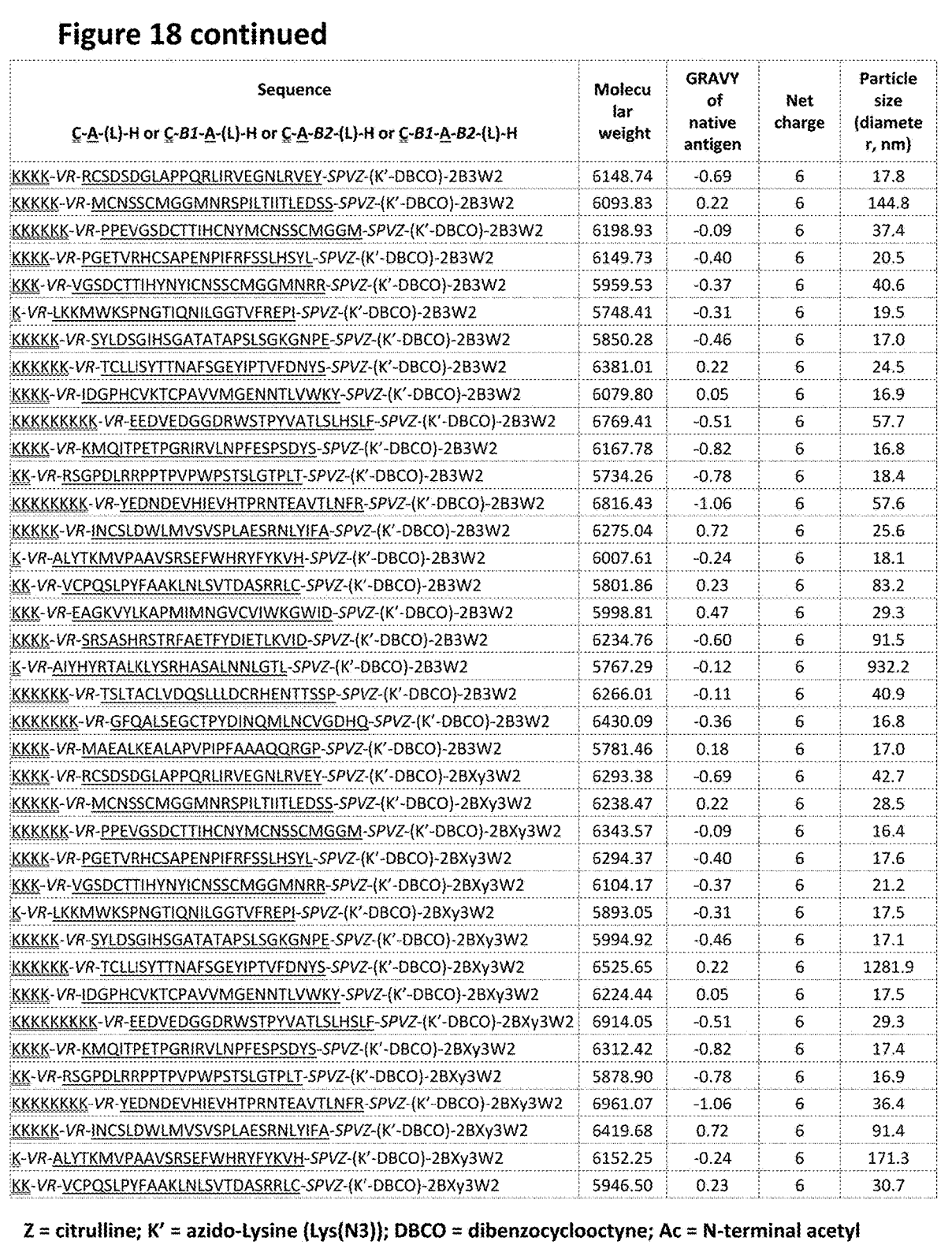

| Sequence<br>C-A-(L)-H or C-B1-A-(L)-H or C-A-B2-(L)-H or C-B1-A-B2-(L)-H | Molecular weight | GRAVY of native antigen | Net charge | Particle size (diameter, nm) |
|---|---|---|---|---|
| KKKK-VR-RCSDSDGLAPPQRLIRVEGNLRVEY-SPVZ-(K'-DBCO)-2B3W2 | 6148.74 | -

Figure 18 continued

| Sequence<br>C-A-(L)-H or C-B1-A-(L)-H or C-A-B2-(L)-H or C-B1-A-B2-(L)-H | GRAVY of native antigen | Net charge | Particle size (diameter, nm) |
|---|---|---|---|
| KKK-VR-EAGKVYLKAPMIMNGVCVIWKGWID-SPVZ-(K'-DBCO)-2BXy3W2 | 0.47 | 6 | 57.3 |
| KKKK-VR-SRSASHRSTRFAETFYDIETLKVID-SPVZ-(K'-DBCO)-2BXy3W2 | -0.60 | 6 | 185.0 |
| K-VR-AIYHYRTALKLYSRHASALNNLGTL-SPVZ-(K'-DBCO)-2BXy3W2 | -0.12 | 6 | 287.9 |
| KKKKKK-VR-TSLTACLVDQSLLLDCRHENTTSSP-SPVZ-(K'-DBCO)-2BXy3W2 | -0.11 | 6 | 60.9 |
| KKKKKKK-VR-GFQALSEGCTPYDINQMLNCVGDHQ-SPVZ-(K'-DBCO)-2BXy3W2 | -0.36 | 6 | 26.8 |
| KKKK-VR-MAEALKEALAPVPIPFAAAQQRGP-SPVZ-(K'-DBCO)-2BXy3W2 | 0.18 | 6 | 54.5 |
| KKKK-VR-GRVLELFRAAQLANDVVLQIMELCGATR-GSGVZ-(K'-DBCO)-2B3W2 | 0.52 | 6 | 33.8 |
| KKKKKK-VR-GIPVHLELASMTNMELMSSIVHQQVFPT-GSGVZ-(K'-DBCO)-2B3W2 | 0.43 | 6 | 177.9 |
| KKKKKKK-VR-EAGQSLVISASIIVFNLLELEGDYR-GSGVZ-(K'-DBCO)-2B3W2 | 0.54 | 6 | 56.0 |
| KKKKK-VR-SKLLSFMAPIDHTTMSDDARTELFRS-GSGVZ-(K'-DBCO)-2B3W2 | -0.31 | 6 | 26.2 |
| KKKKKKK-VR-DFTGSNGDPSSPYSLHYLSPTGVNEY-GSGVZ-(K'-DBCO)-2B3W2 | -0.82 | 6 | 18.4 |
| KKKKK-VR-KARDETAALLNSAVLGAAPLFVPPAD-GSGVZ-(K'-DBCO)-2B3W2 | 0.38 | 6 | 17.8 |
| KKKKKKKK-VR-DIDPSSSVLFEYMEKPDFSLFSP-SPVZ-(K'-DBCO)-2B3W2 | -0.21 | 6 | 20.2 |
| KKKKKKK-VR-SKLLSFMAPIDHTTMSDDARTELFRS-SPVZ-(K'-DBCO)-2B3W2 | -0.31 | 8 | 20.8 |
| KKKKKKKK-VR-GIPVHLELASMTNMELMSSIVHQQVFPT-SPVZ-(K'-DBCO)-2B3W2 | 0.43 | 8 | 20.8 |
| KKKKKKKK-VR-DFTGSNGDPSSPYSLHYLSPTGVNEY-SPVZ-(K'-DBCO)-2B3W2 | -0.82 | 8 | 19.0 |
| KKKKKKKK-VR-EAGQSLVISASIIVFNLLELEGDYR-SPVZ-(K'-DBCO)-2B3W2 | 0.54 | 8 | 20.0 |
| KKKKKKK-VR-KARDETAALLNSAVLGAAPLFVPPAD-SPVZ-(K'-DBCO)-2B3W2 | 0.38 | 8 | 19.4 |
| KKKKKKKKK-VR-DIDPSSSVLFEYMEKPDFSLFSP-SPVZ-(K'-DBCO)-2B3W2 | -0.21 | 8 | 19.8 |
| KKKKKK-VR-GRVLELFRAAQLANDVVLQIMELCGATR-SPVZ-(K'-DBCO)-2B3W2 | 0.52 | 8 | 17.6 |
| KKKKKKKKK-VR-ETLGEISFLLSLDLHFTDGDYSAGD-SPVZ-(K'-DBCO)-2B3W2 | 0.02 | 6 | 79.6 |
| KKKKKKKK-VR-DDEGDYTCQFTHVENGTNYIVTATR-SPVZ-(K'-DBCO)-2B3W2 | -0.90 | 6 | 25.6 |
| KKKKKK-VR-GIPVHLELASMTNMELMSSIVHQQVFPT-SPVZ-(K'-DBCO)-2B3W2 | 0.43 | 6 | 24.3 |
| KKKK-VR-VVDRNPQFLDPVLAYLMKGLCEKPLAS-SPVZ-(K'-DBCO)-2B3W2 | 0.20 | 6 | 17.2 |
| KK-VR-NIEGIDKLTQLKKPFLVNNKINKIENI-SPVZ-(K'-DBCO)-2B3W2 | -0.47 | 6 | 25.1 |
| VR-MAAALTFRRLLTLPRAARGFGVQVS-SPVZ-(K'-DBCO)-2B3W2 | 0.56 | 6 | 48.7 |
| VR-GRGHLLGRLAAIVGKQVLLGRKVVVVR-SPVZ-(K'-DBCO)-2B3W2 | 0.66 | 8 | 46.4 |
| KKK-VR-LKSSPERNDWEPLDKKVDTRKYRAE-SPVZ-(K'-DBCO)-2B3W2 | -1.91 | 6 | 16.2 |
| KKKKKKKKKKK-VR-ETLGEISFLLSLDLHFTDGDYSAGD-SPVZ-(K'-DBCO)-2B3W2 | 0.02 | 8 | 17.2 |
| KKKKKKKKKK-VR-DDEGDYTCQFTHVENGTNYIVTATR-SPVZ-(K'-DBCO)-2B3W2 | -0.90 | 8 | 27.0 |
| KKKKKKKK-VR-GIPVHLELASMTNMELMSSIVHQQVFPT-SPVZ-(K'-DBCO)-2B3W2 | 0.43 | 8 | 22.2 |
| KKKKKK-VR-VVDRNPQFLDPVLAYLMKGLCEKPLAS-SPVZ-(K'-DBCO)-2B3W2 | 0.20 | 8 | 17.0 |
| KKKK-VR-NIEGIDKLTQLKKPFLVNNKINKIENI-SPVZ-(K'-DBCO)-2B3W2 | -0.47 | 8 | 26.4 |
| KK-VR-MAAALTFRRLLTLPRAARGFGVQVS-SPVZ-(K'-DBCO)-2B3W2 | 0.56 | 8 | 102.5 |
| VR-GRGHLLGRLAAIVGKQVLLGRKVVVVR-SPVZ-(K'-DBCO)-2B3W2 | 0.66 | 8 | 43.4 |
| KKKK-VR-LKSSPERNDWEPLDKKVDTRKYRAE-SPVZ-(K'-DBCO)-2B3W2 | -1.91 | 7 | 22.8 |
| KKKKKKKK-VR-QGTDVVIAIFIILAMSFVPASFVVF-SPVZ-(K'-DBCO)-2B3W2 | 2.00 | 9 | 173.0 |
| KD-VR-MAAALTFRRLLTLPRAARGFGVQVS-SPVZ-(K'-DBCO)-2B3W2 | 0.56 | 6 | 18.6 |

Z = citrulline; K' = azido-Lysine (Lys(N3)); DBCO = dibenzocyclooctyne; Ac = N-terminal acetyl

Figure 18 continued

| Sequence<br>C-A-(L)-H or C-B1-A-(L)-H or C-A-B2-(L)-H or C-B1-A-B2-(L)-H | GRAVY of native antigen | Net charge | Particle size (diameter, nm) |
|---|---|---|---|
| KKKKK-VR-LCSEPMFTFVYPTIFPLRETPMAGL-SPVZ-(K'DBCO)-2B3W2 | 0.56 | 6 | 18.4 |
| KD-VR-AWHTNLSRKILRMSPLLAKFHQFLV-SPVZ-(K'-DBCO)-2B3W2 | 0.15 | 6 | 16.4 |
| KKKKK-VR-KGFELLYQPEVVHLYLSLLTESRNF-SPVZ-(K'-DBCO)-2B3W2 | 0.03 | 6 | 18.2 |
| KKK-VR-SFVRQLNMYGFRNVVHIESGIIKQE-SPVZ-(K'-DBCO)-2B3W2 | -0.14 | 6 | 2000.0 |
| KK-VR-MAAALTFRRLLTLPRAARGFGVQVS-SPVZ-(K'-DBCO)-2B3W2 | 0.56 | 8 | 19.4 |
| KKKKKKK-VR-LCSEPMFTFVYPTIFPLRETPMAGL-SPVZ-(K'-DBCO)-2B3W2 | 0.56 | 8 | 17.6 |
| KK-VR-AWHTNLSRKILRMSPLLAKFHQFLV-SPVZ-(K'-DBCO)-2B3W2 | 0.15 | 8 | 17.2 |
| KKKKKKK-VR-KGFELLYQPEVVHLYLSLLTESRNF-SPVZ-(K'-DBCO)-2B3W2 | 0.03 | 8 | 18.0 |
| KKKKK-VR-SFVRQLNMYGFRNVVHIESGIIKQE-SPVZ-(K'-DBCO)-2B3W2 | -0.14 | 8 | 11.4 |
| KKK-VR-LQGDVAFGHSNLFIRSPRTL-SPVZ-(K'-DBCO)-2B3W2 | 0.00 | 6 | 926.4 |
| KKKK-VR-ALEKIAFLPFAYLVDQWRWG-SPVZ-(K'-DBCO)-2B3W2 | 0.36 | 6 | 47.6 |
| KKKKKK-VR-GSSAEESHLSCLNWSTLVPL-SPVZ-(K'-DBCO)-2B3W2 | 0.12 | 6 | 105.6 |
| KKKK-VR-MLWLALGPFCGMENQVLVIR-SPVZ-(K'-DBCO)-2B3W2 | 1.04 | 6 | 592.3 |
| KKKK-VR-TERIYSLFNLSMGKLEKMQE-SPVZ-(K'-DBCO)-2B3W2 | -0.57 | 6 | 2000.0 |
| KKK-VR-ALGLRHLVVVGNHNQVVGLV-SPVZ-(K'-DBCO)-2B3W2 | 0.98 | 6 | 2000.0 |
| KKKKKKK-VR-AELINCQADVSAVDDHGKSA-SPVZ-(K'-DBCO)-2B3W2 | -0.19 | 6 | 71.4 |
| KKKKDK-VR-MAAALLLPLAFTLLSGQ-SPVZ-(K'-DBCO)-2B3W2 | 1.63 | 6 | 21.0 |
| KD-VR-LSGWWLLWKRCNPLATKVKV-SPVZ-(K'-DBCO)-2B3W2 | 0.10 | 6 | 4270.1 |
| KKKKK-VR-SHRNSLDTNLISMLFQNLSE-SPVZ-(K'-DBCO)-2B3W2 | -0.41 | 6 | 102.6 |
| KK-VR-KVGTAWKQVYLFLGVPYAAP-SPVZ-(K'-DBCO)-2B3W2 | 0.45 | 6 | 75.7 |
| KK-VR-IKIVRLTTGSAYQFRVCAEN-SPVZ-(K'-DBCO)-2B3W2 | 0.14 | 6 | 4055.8 |
| KKKKK-VR-LQGDVAFGHSNLFIRSPRTL-SPVZ-(K'-DBCO)-2B3W2 | 0.00 | 8 | 17.6 |
| KKKKKKK-VR-ALEKIAFLPFAYLVDQWRWG-SPVZ-(K'-DBCO)-2B3W2 | 0.36 | 9 | 17.8 |
| KKKKKKKK-VR-GSSAEESHLSCLNWSTLVPL-SPVZ-(K'-DBCO)-2B3W2 | 0.12 | 8 | 16.0 |
| KKKKKKKK-VR-MLWLALGPFCGMENQVLVIR-SPVZ-(K'-DBCO)-2B3W2 | 1.04 | 10 | 14.8 |
| KKKKKK-VR-TERIYSLFNLSMGKLEKMQE-SPVZ-(K'-DBCO)-2B3W2 | -0.57 | 8 | 24.6 |
| KKKKKKK-VR-ALGLRHLVVVGNHNQVVGLV-SPVZ-(K'-DBCO)-2B3W2 | 0.98 | 10 | 38.9 |
| KKKKKKKKK-VR-AELINCQADVSAVDDHGKSA-SPVZ-(K'-DBCO)-2B3W2 | -0.19 | 8 | 18.8 |
| KKKKKKK-VR-MAAALLLPLAFTLLSGQ-SPVZ-(K'-DBCO)-2B3W2 | 1.63 | 10 | 17.2 |
| KK-VR-LSGWWLLWKRCNPLATKVKV-SPVZ-(K'-DBCO)-2B3W2 | 0.10 | 8 | 13.2 |
| KKKKKKK-VR-SHRNSLDTNLISMLFQNLSE-SPVZ-(K'-DBCO)-2B3W2 | -0.41 | 8 | 17.8 |
| KKKKK-VR-KVGTAWKQVYLFLGVPYAAP-SPVZ-(K'-DBCO)-2B3W2 | 0.45 | 9 | 15.8 |
| KKKK-VR-IKIVRLTTGSAYQFRVCAEN-SPVZ-(K'-DBCO)-2B3W2 | 0.14 | 8 | 27.9 |
| KKKK-VR-FVVKAYLPVNESFAFTADLRSNTGGQAG-SLVZ-(K'-DBCO)-2B3W2 | 0.10 | 6 | 278.4 |
| KK-VR-TAKSVMCTYSPPLDKLFCQLAKTCPVQG-SLVZ-(K'-DBCO)-2B3W2 | 0.11 | 6 | 17.9 |
| KK-VR-ANFESGKHKYRQTAMFTATMPPAVERLG-SLVZ-(K'-DBCO)-2B3W2 | -0.63 | 6 | 20.8 |
| KKKK-VR-VVDRNPQFLDPVLAYLMKGLCEKPLASG-SLVZ-(K'-DBCO)-2B3W2 | 0.18 | 6 | 16.2 |
| KKKKKKK-VR-NEVAPLEWLRYFDKKELELMLCGMQEIG-SLVZ-(K'-DBCO)-2B3W2 | -0.23 | 6 | 17.6 |

Z = citrulline; K' = azido-Lysine (Lys(N3)); DBCO = dibenzocyclooctyne; Ac = N-terminal acetyl

Figure 18 continued

| Sequence<br>C-A-(L)-H or C-B1-A-(L)-H or C-A-B2-(L)-H or C-B1-A-B2-(L)-H | GRAVY of native antigen | Net charge | Particle size (diameter, nm) |
|---|---|---|---|
| KKKKKK-VR-SSPDEVALVEGVQSLGFTYLRLKDNYMG-SLVZ-(K'-DBCO)-2B3W2 | -0.13 | 6 | 59.9 |
| KK-VR-PKPDFSQLQRNILPSNPRVTRFHINWDG-SLVZ-(K'-DBCO)-2B3W2 | -1.03 | 6 | 18.0 |
| KKKK-VR-LILISTNGSFIRLLDAFKGVVMHTFGGG-SLVZ-(K'-DBCO)-2B3W2 | 0.91 | 7 | 27.3 |
| KKKKKK-VR-STANYNTSHLNNDVWQIFENPVDWKEKG-SLVZ-(K'-DBCO)-2B3W2 | -1.17 | 6 | 17.6 |
| KK-VR-RVDQKTLHNLLRKVVPSFSAEIERLNQG-SLVZ-(K'-DBCO)-2B3W2 | -0.59 | 6 | 18.8 |
| KKKK-VR-IPSGTTILNCFHDVLSGKLSGGSPGVPG-SLVZ-(K'-DBCO)-2B3W2 | 0.29 | 6 | 94.5 |
| KKK-VR-DSGSPFPAAVILRDALHMARGLKYLHQG-SLVZ-(K'-DBCO)-2B3W2 | -0.05 | 6 | 17.4 |
| KK-VR-HLTQQLDTYILKNVVAFSRTDKYRQLPG-SLVZ-(K'-DBCO)-2B3W2 | -0.56 | 6 | 43.5 |
| KKKK-VR-CGTAFFINFIAIYHHASRAIPFGTMVAG-SLVZ-(K'-DBCO)-2B3W2 | 0.93 | 7 | 2000.0 |
| KKKK-VR-GPDGLALPNNYCDVCLGDSKINKKTGQG-SLVZ-(K'-DBCO)-2B3W2 | -0.62 | 6 | 19.0 |
| KK-VR-ELINFKRKRVAAFQKNLIEMSELEIKHG-SLVZ-(K'-DBCO)-2B3W2 | -0.48 | 6 | 2000.0 |
| KKK-VR-NREKMKGELGMMLILQNVIQKTTTPGEG-SLVZ-(K'-DBCO)-2B3W2 | -0.56 | 6 | 2000.0 |
| KKK-VR-EFKHIKAFDRTFANNPGPMVVFATPGMG-SLVZ-(K'-DBCO)-2B3W2 | -0.13 | 6 | 19.0 |
| KKKKKKKK-VR-NHSGLVTFQAFIDVMSRETTDTDTADQG-SLVZ-(K'-DBCO)-2B3W2 | -0.49 | 6 | 2000.0 |
| D-VR-GRGHLLGRLAAIVGKQVLLGRKVVVVRG-SLVZ-(K'-DBCO)-2B3W2 | 0.62 | 7 | 53.8 |
| KKK-VR-EKFSMDHKTGTIAMQNTTQLRSRYELTG-SLVZ-(K'-DBCO)-2B3W2 | -0.99 | 6 | 2000.0 |
| KKKKK-VR-SGCYFMVAVAHVAAFLLEDRAVCVERFG-SLVZ-(K'-DBCO)-2B3W2 | 0.98 | 6 | 2000.0 |
| KKKK-VR-REGVELCPGNKYEMRRHGTTHSLVIHD-SPVZ-(K'-DBCO)-2B3W2 | -0.96 | 6 | 19.0 |
| KKKKKKKKK-VR-PSKPSFQEFVDWENVSPELNSTDQPFL-SPVZ-(K'-DBCO)-2B3W2 | -0.82 | 8 | 18.0 |
| KKKK-VR-TAKSVMCTYSPPLDKLFCQLAKTCPVQ-SPVZ-(K'-DBCO)-2B3W2 | 0.13 | 8 | 20.4 |
| KKKKKK-VR-VVDRNPQFLDPVLAYLMKGLCEKPLAS-SPVZ-(K'-DBCO)-2B3W2 | 0.20 | 8 | 17.0 |
| KKKKKKKK-VR-SSPDEVALVEGVQSLGFTYLRLKDNYM-SPVZ-(K'-DBCO)-2B3W2 | -0.12 | 8 | 31.1 |
| KKKKKK-VR-IPSGTTILNCFHDVLSGKLSGGSPGVP-SPVZ-(K'-DBCO)-2B3W2 | 0.32 | 8 | 22.6 |
| KKKKK-VR-DSGSPFPAAVILRDALHMARGLKYLHQ-SPVZ-(K'-DBCO)-2B3W2 | -0.03 | 8 | 17.0 |
| KKKKK-VR-NREKMKGELGMMLILQNVIQKTTTPGE-SPVZ-(K'-DBCO)-2B3W2 | -0.57 | 8 | 171.7 |
| KKKKK-VR-EKFSMDHKTGTIAMQNTTQLRSRYELT-SPVZ-(K'-DBCO)-2B3W2 | -1.01 | 8 | 33.4 |
| KKKKKK-VR-REGVELCPGNKYEMRRHGTTHSLVIHD-SPVZ-(K'-DBCO)-2B3W2 | -0.96 | 8 | 21.0 |
| KKKKKKK-VR-YMRTGEGFLCVFAINNTKSFEDIHH-SPVZ-(K'-DBCO)-2B3W2 | -0.20 | 8 | 25.8 |
| KKKKKK-VR-DTKQAQELARSYGIPFIETSAKTRQ-SPVZ-(K'-DBCO)-2B3W2 | -0.95 | 8 | 18.2 |
| KKK-VR-QRVEDAFYTLVREIRQYRLKKISKE-SPVZ-(K'-DBCO)-2B3W2 | -1.01 | 8 | 2000.0 |
| KKKKKKK-VR-MTEYKLVVVGADGVGKSALTIQLIQ-SPVZ-(K'-DBCO)-2B3W2 | 0.65 | 9 | 16.6 |
| KKKK-VR-QACAHFFSLISKANVDVLPRRSLER-SPVZ-(K'-DBCO)-2B3W2 | -0.03 | 8 | 21.6 |
| KKKKKK-VR-YQKACSAFQNVSGLEYFEKIKTFLG-SPVZ-(K'-DBCO)-2B3W2 | -0.16 | 8 | 17.0 |
| KKKKKK-VR-LARQMDLVNEIPFTYEQLSIFKHKL-SPVZ-(K'-DBCO)-2B3W2 | -0.13 | 8 | 24.4 |
| KKKKKK-VR-RLGLGLQGGIPNGYLVLDFNVREA-SPVZ-(K'-DBCO)-2B3W2 | 0.21 | 8 | 17.6 |
| KK-VR-LKVSKGQKMNAQAIALVACYLRGGG-SPVZ-(K'-DBCO)-2B3W2 | 0.22 | 8 | 17.8 |
| KKKKK-VR-LRALSQHNVSMDIATFKRLQVDSLV-SPVZ-(K'-DBCO)-2B3W2 | 0.16 | 8 | 331.7 |
| KKKKKK-VR-LGSCGSPICSRSFLLLLSLGWIPR-SPVZ-(K'-DBCO)-2B3W2 | 1.00 | 10 | 18.0 |

Z = citrulline; K' = azido-Lysine (Lys(N3)); DBCO = dibenzocyclooctyne; Ac = N-terminal acetyl

Figure 18 continued

| Sequence<br>C-A-(L)-H or C-B1-A-(L)-H or C-A-B2-(L)-H or C-B1-A-B2-(L)-H | GRAVY of native antigen | Net charge | Particle size (diameter, nm) |
|---|---|---|---|
| KKKKKKKK-*VR*-LSEDVKSYYTVHLLQLENINTGETRTI-*SPVZ*-(K'-DBCO)-2B3W2 | -0.40 | 8 | 17.8 |
| KK

Figure 23

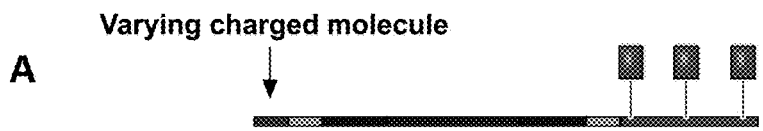

A  Varying charged molecule

| Charge molecule | Sequence (C-*B1*-A-*B2*-(L)-H) |
|---|---|
| Positive | KKKK-*SLVR*-ASMTNMELM-*SLVR*-(K'-DBCO)-2B3W2 |
| Negative | Ac-DDDDDDDDDDDDDD-GIPVHLELASMTNMELMSSIVHQQVFPT-*SPVZ*-(K'-DBCO)-2B3W2 |
| Neutral | HO-PEG24-ASMTNMELM-*GSPVZ*-(K'-DBCO)-2B3W2 |

Z = citrulline; K' = azido-Lysine (Lys(N3)); DBCO = dibenzocyclooctyne; Ac = N-terminal acetyl

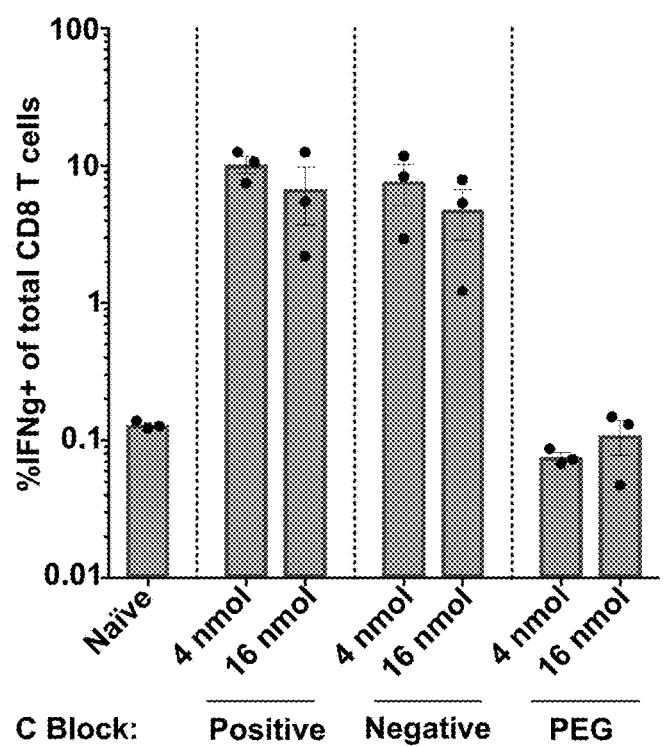

B  Impact of C block composition on CD8 T cell responses (d36)

Figure 25

Adpgk vaccine compositions

| Sequence (C-B1-A-B2-(L)-H) | Particle |
|---|---|
| EK-SLVR-ASMTNMELM-SSGGELVR-(K'-DBCO)-2BXy5 | MP |
| EK-SLVR-ASMTNMELM-SSGGELVR-(K'-DBCO)-2B2W8 | MP |
| EK-SLVR-ASMTNMELM-SSGGELVR-(K'-DBCO)-2B5 | MP |
| EK-SLVR-ASMTNMELM-SSGGELVR-(K'-DBCO)-2B3 | MP |
| EK-SLVR-ASMTNMELM-SSGGELVR-(K'-DBCO)-2B2 | MP |
| EK-SLVR-ASMTNMELM-SSGGELVR-(K'-DBCO)-2B1 | MP |
| KSKS-KLVR-ASMTNMELM-SSGGELVR-(K'-DBCO)-2BXy5 | NP |
| KSKS-KLVR-ASMTNMELM-SSGGELVR-(K'-DBCO)-2B2W8 | NP |
| KSKS-KLVR-ASMTNMELM-SSGGELVR-(K'-DBCO)-2B5 | NP |
| KSKS-KLVR-ASMTNMELM-SSGGELVR-(K'-DBCO)-2B3 | NP |
| KSKS-KLVR-ASMTNMELM-SSGGELVR-(K'-DBCO)-2B2 | NP |
| KSKS-KLVR-ASMTNMELM-SSGGELVR-(K'-DBCO)-2B1 | NP |

MP = microparticle; NP = nanoparticle; K' = azido-Lysine (Lys(N3)); DBCO = dibenzocyclooctyne

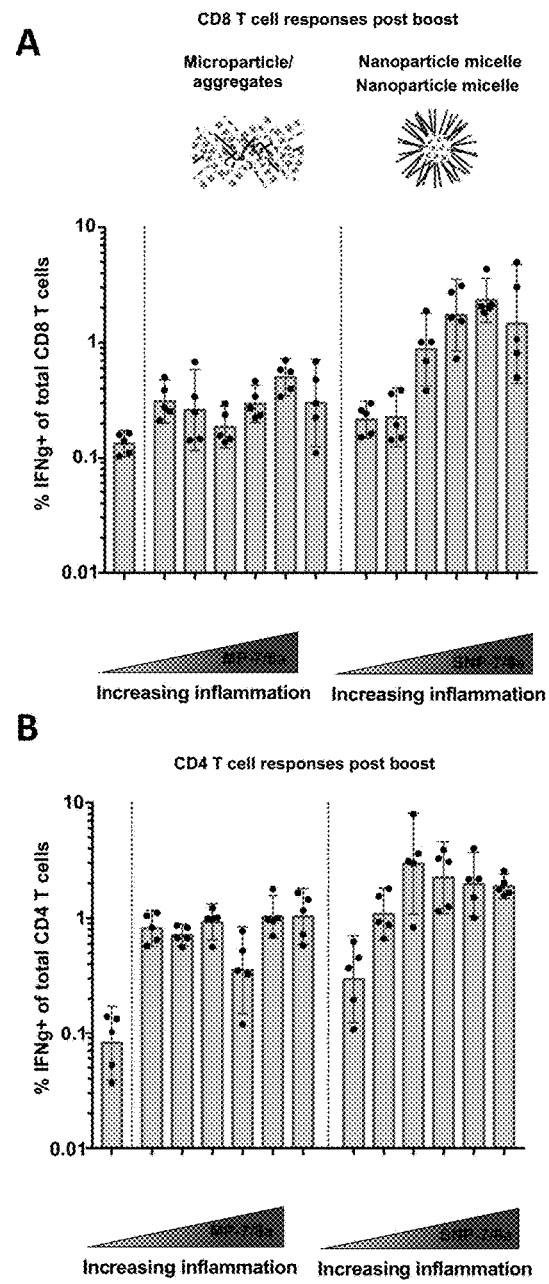

Figure 27

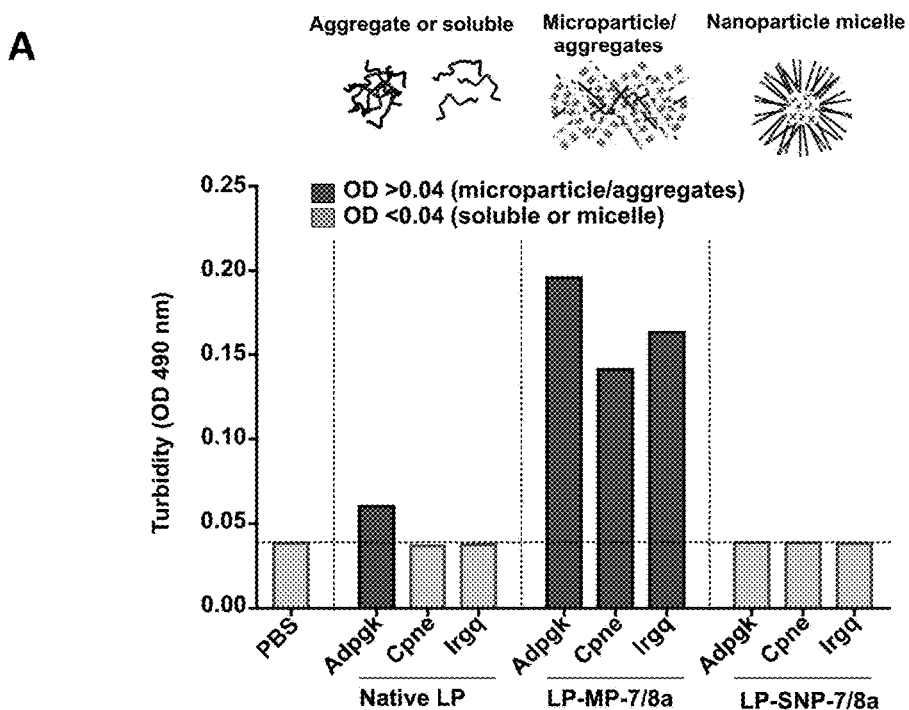

| Vaccine | Sequence (A or A(L)-H or C-B1-A-B2-(L)-H) |
|---|---|
| Adpgk Native LP | GIPVHLELASMTNMELMSSIVHQQVFPT |
| Cpne1 Native LP | DFTGSNGDPSSPYSLHYLSPTGVNEY |
| Irgq Native LP | KARDETAALLNSAVLGAAPLFVPPAD |
| Adpgk LP-MP-7/8 | GIPVHLELASMTNMELMSSIVHQQVFPT-(K'-DBCO)-2B3W2 |
| Cpne1 LP-MP-7/8 | DFTGSNGDPSSPYSLHYLSPTGVNEY-(K'-DBCO)-2B3W2 |
| Irgq LP-MP-7/8 | KARDETAALLNSAVLGAAPLFVPPAD-(K'-DBCO)-2B3W2 |
| Adpgk LP-SNP-7/8a | KKKKKK-VR-GIPVHLELASMTNMELMSSIVHQQVFPT-GSGVZ-(K'-DBCO)-2B3W2 |
| Cpne1 LP-SNP-7/8a | KKKKKKKKK-VR-DFTGSNGDPSSPYSLHYLSPTGVNEY-SPVZ-(K'-DBCO)-2B3W2 |
| Irgq LP-SNP-7/8a | KKKKKKK-VR-KARDETAALLNSAVLGAAPLFVPPAD-SPVZ-(K'-DBCO)-2B3W2 |

Z = citrulline; K' = azido-Lysine (Lys(N3)); DBCO = dibenzocyclooctyne

Figure 27 continued

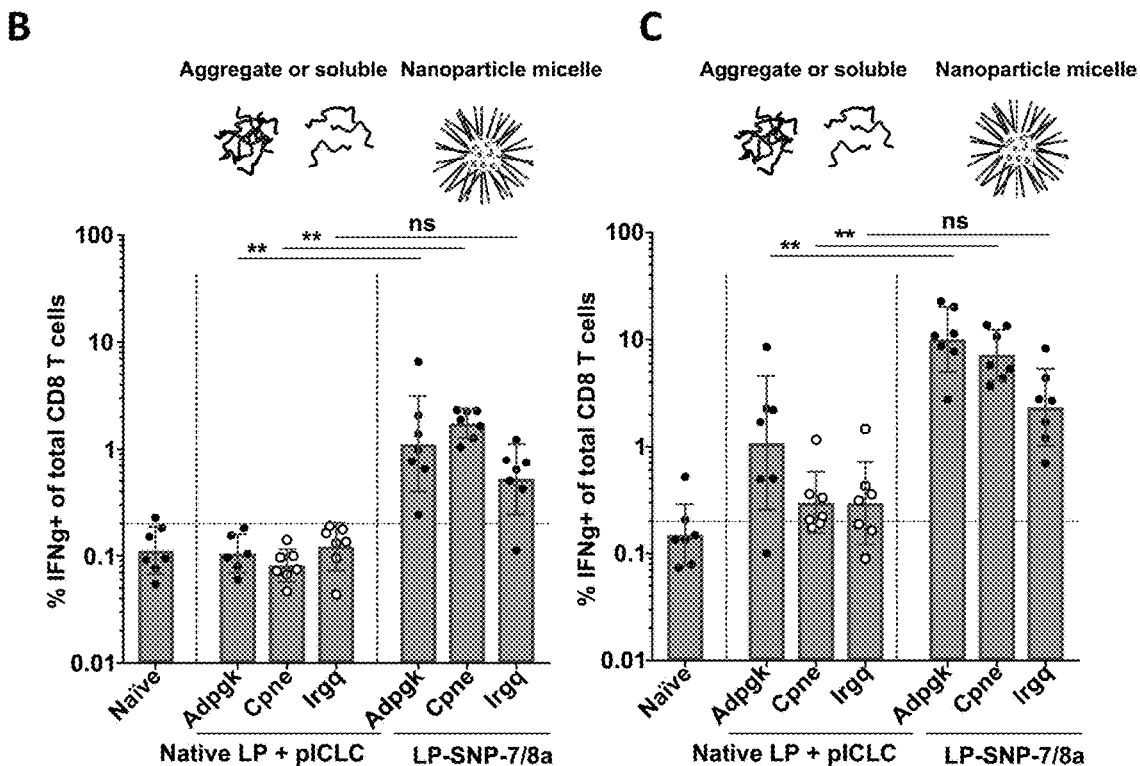

| Vaccine | Sequence (A or A(L)-H or C-B1-A-B2-(L)-H) |
|---|---|
| Adpgk Native LP | GIPVHLELASMTNMELMSSIVHQQVFPT |
| Cpne1 Native LP | DFTGSNGDPSSPYSLHYLSPTGVNEY |
| Irgq Native LP | KARDETAALLNSAVLGAAPLFVPPAD |
| Adpgk LP-MP-7/8 | GIPVHLELASMTNMELMSSIVHQQVFPT-(K'-DBCO)-2B3W2 |
| Cpne1 LP-MP-7/8 | DFTGSNGDPSSPYSLHYLSPTGVNEY-(K'-DBCO)-2B3W2 |
| Irgq LP-MP-7/8 | KARDETAALLNSAVLGAAPLFVPPAD-(K'-DBCO)-2B3W2 |
| Adpgk LP-SNP-7/8a | KKKKKK-*VR*-GIPVHLELASMTNMELMSSIVHQQVFPT-*GSGVZ*-(K'-DBCO)-2B3W2 |
| Cpne1 LP-SNP-7/8a | KKKKKKKKK-*VR*-DFTGSNGDPSSPYSLHYLSPTGVNEY-*SPVZ*-(K'-DBCO)-2B3W2 |
| Irgq LP-SNP-7/8a | KKKKKKK-*VR*-KARDETAALLNSAVLGAAPLFVPPAD-*SPVZ*-(K'-DBCO)-2B3W2 |

Z = citrulline; K' = azido-Lysine (Lys(N3)); DBCO = dibenzocyclooctyne

Figure 27 continued

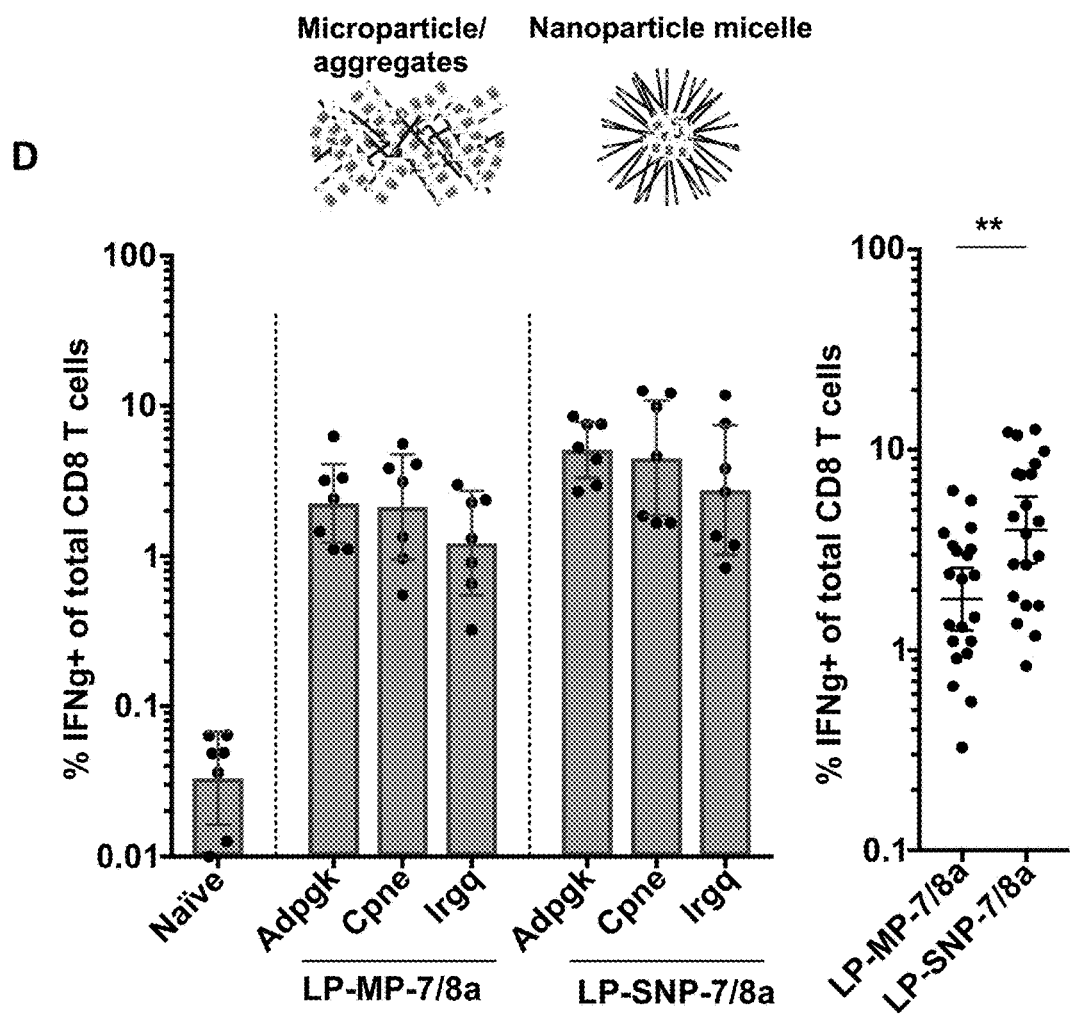

| Vaccine | Sequence (A(L)-H or C-B1-A-B2-(L)-H) |
|---|---|
| Adpgk LP-MP-7/8 | GIPVHLELASMTNMELMSSIVHQQVFPT-(K'-DBCO)-2B3W2 |
| Cpne1 LP-MP-7/8 | DFTGSNGDPSSPYSLHYLSPTGVNEY-(K'-DBCO)-2B3W2 |
| Irgq LP-MP-7/8 | KARDETAALLNSAVLGAAPLFVPPAD-(K'-DBCO)-2B3W2 |
| Adpgk LP-SNP-7/8a | KKKKKK-VR-GIPVHLELASMTNMELMSSIVHQQVFPT-GSGVZ-(K'-DBCO)-2B3W2 |
| Cpne1 LP-SNP-7/8a | KKKKKKKK-VR-DFTGSNGDPSSPYSLHYLSPTGVNEY-SPVZ-(K'-DBCO)-2B3W2 |
| Irgq LP-SNP-7/8a | KKKKKKK-VR-KARDETAALLNSAVLGAAPLFVPPAD-SPVZ-(K'-DBCO)-2B3W2 |

Z = citrulline; K' = azido-Lysine (Lys(N3)); DBCO = dibenzocyclooctyne

| Vaccine | Sequence (C-B1-A-B2-(L)-H) |
|---|---|
| Aatf Min-SNP-7/8a | KKKK-SLVR-MAPIDHTTM-SPVZ-(K'-DBCO)-2B3W2 |
| Adpgk Min-SNP-7/8a | KKKKK-SLVR-ASMTNMELM-SPVZ-(K'-DBCO)-2B3W2 |
| Cpne1 Min-SNP-7/8a | KKKK-SLVR-SSPYSLHYL-SPVZ-(K'-DBCO)-2B3W2 |
| D

Figure 29 continued

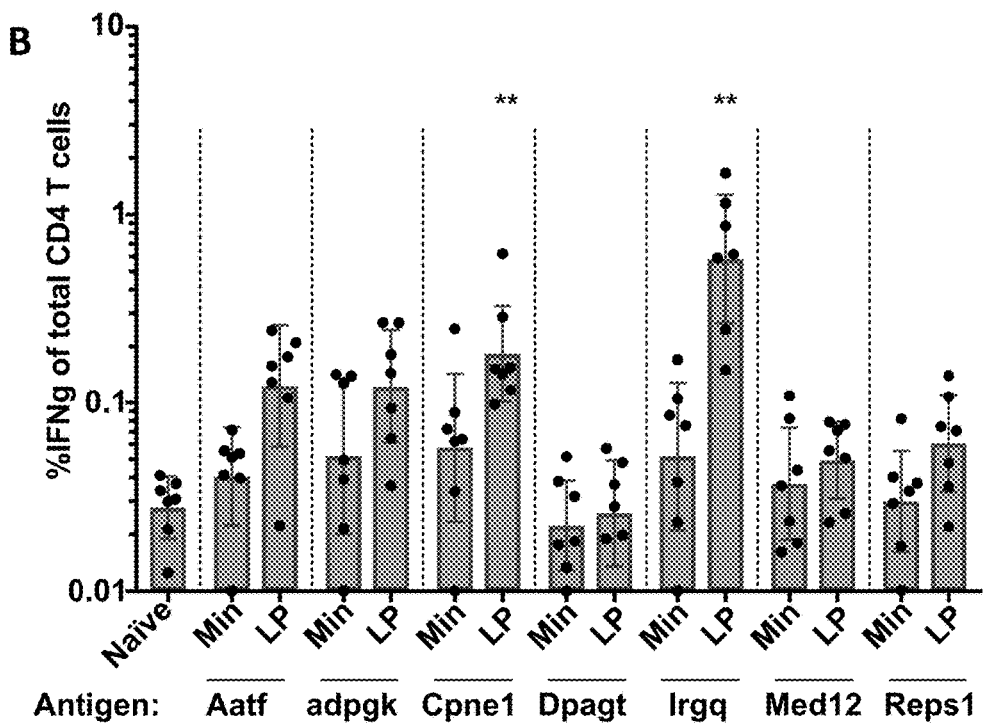

| Vaccine | Sequence (C-B1-A-B2-(L)-H) |
|---|---|
| Aatf Min-SNP-7/8a | KKKK-*SLVR*-MAPIDHTTM-*SPVZ*-(K'-DBCO)-2B3W2 |
| Adpgk Min-SNP-7/8a | KKKKK-*SLVR*-ASMTNMELM-*SPVZ*-(K'-DBCO)-2B3W2 |
| Cpne1 Min-SNP-7/8a | KKKK-*SLVR*-SSPYSLHYL-*SPVZ*-(K'-DBCO)-2B3W2 |
| Dpagt Min-SNP-7/8a | KKKK-*SLVR*-SIIVFNLL-*SPVZ*-(K'-DBCO)-2B3W2 |
| Irgq Min-SNP-7/8a | KKKK-*SLVR*-AALLNSAVL-*SPVZ*-(K'-DBCO)-2B3W2 |
| Med12 Min-SNP-7/8a | KKK-*SLVR*-SSVLFEYM-*SPVZ*-(K'-DBCO)-2B3W2 |
| Reps1 Min-SNP-7/8a | KKKKK-*SLVR*-AQLANDVVL-*SPVZ*-(K'-DBCO)-2B3W2 |
| Aatf LP-SNP-7/8a | KKKKKKK-*VR*-SKLLSFMAPIDHTTMSDDARTELFRS-*SPVZ*-(K'-DBCO)-2B3W2 |
| Adpgk LP-SNP-7/8a | KKKKKK-*VR*-GIPVHLELASMTNMELMSSIVHQQVFPT-*GSGVZ*-(K'-DBCO)-2B3W2 |
| Cpne1 LP-SNP-7/8a | KKKKKKKKK-*VR*-DFTGSNGDPSSPYSLHYLSPTGVNEY-*SPVZ*-(K'-DBCO)-2B3W2 |
| Dpagt LP-SNP-7/8a | KKKKKKK-*VR*-EAGQSLVISASIIVFNLLELEGDYR-*GSGVZ*-(K'-DBCO)-2B3W2 |
| Irgq LP-SNP-7/8a | KKKKKKK-*VR*-KARDETAALLNSAVLGAAPLFVPPAD-*SPVZ*-(K'-DBCO)-2B3W2 |
| Med12 LP-SNP-7/8a | KKKKKKK-*VR*-DIDPSSSVLFEYMEKPDFSLFSP-*SPVZ*-(K'-DBCO)-2B3W2 |
| Reps1 LP-SNP-7/8a | KKKKKK-*VR*-GRVLELFRAAQLANDVVLQIMELCGATR-*SPVZ*-(K'-DBCO)-2B3W2 |

Z = citrulline; K' = azido-Lysine (Lys(N3)); DBCO = dibenzocyclooctyne

Figure 30

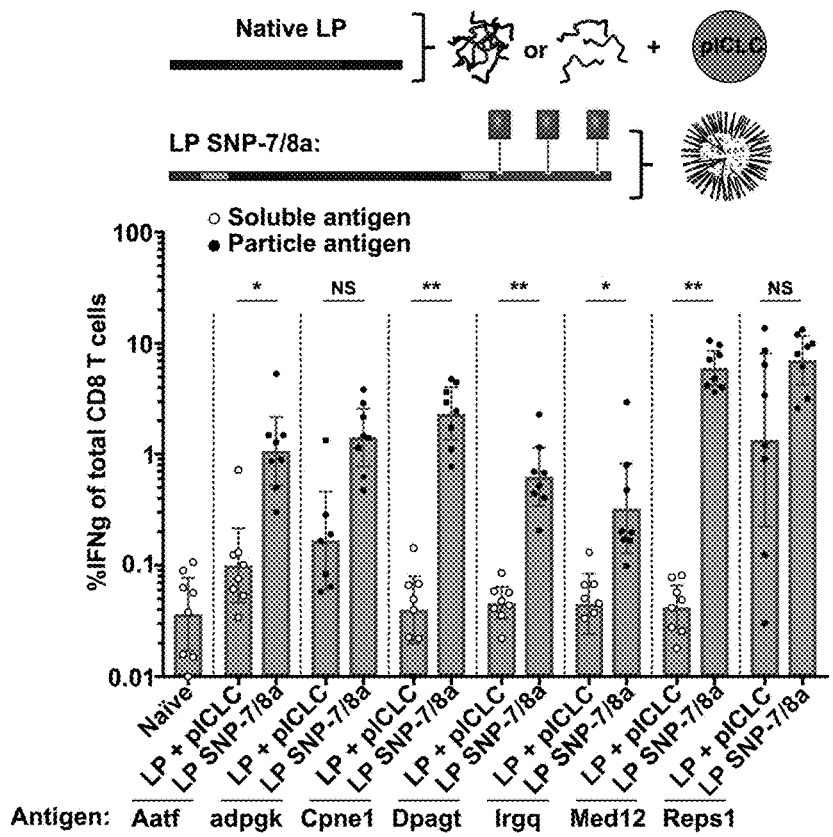

| Vaccine | Sequence (A or C-B1-A-B2-(L)-H) |
|---|---|
| Aatf native LP | SKLLSFMAPIDHTTMSDDARTELFRS |
| Adpgk native LP | GIPVHLELASMTNMELMSSIVHQQVFPT |
| Cpne1 native LP | DFTGSNGDPSSPYSLHYLSPTGVNEY |
| Dpagt native LP | EAGQSLVISASIIVFNLLELEGDYR |
| Irgq native LP | KARDETAALLNSAVLGAAPLFVPPAD |
| Med12 native LP | DIDPSSSVLFEYMEKPDFSLFSP |
| Reps1 native LP | GRVLELFRAAQLANDVVLQIMELCGATR |
| Aatf LP-SNP-7/8a | KKKKKKK-VR-SKLLSFMAPIDHTTMSDDARTELFRS-SPVZ-(K'-DBCO)-2B3W2 |
| Adpgk LP-SNP-7/8a | KKKKKK-VR-GIPVHLELASMTNMELMSSIVHQQVFPT-GSGVZ-(K'-DBCO)-2B3W2 |
| Cpne1 LP-SNP-7/8a | KKKKKKKK-VR-DFTGSNGDPSSPYSLHYLSPTGVNEY-SPVZ-(K'-DBCO)-2B3W2 |
| Dpagt LP-SNP-7/8a | KKKKKKK-VR-EAGQSLVISASIIVFNLLELEGDYR-GSGVZ-(K'-DBCO)-2B3W2 |
| Irgq LP-SNP-7/8a | KKKKKKK-VR-KARDETAALLNSAVLGAAPLFVPPAD-SPVZ-(K'-DBCO)-2B3W2 |
| Med12 LP-SNP-7/8a | KKKKKKKK-VR-DIDPSSSVLFEYMEKPDFSLFSP-SPVZ-(K'-DBCO)-2B3W2 |
| Reps1 LP-SNP-7/8a | KKKKKK-VR-GRVLELFRAAQLANDVVLQIMELCGATR-SPVZ-(K'-DBCO)-2B3W2 |

Z = citrulline; K' = azido-Lysine (Lys(N3)); DBCO = dibenzocyclooctyne

Treatment of established B16.F10 tumor

| Vaccine | Sequence (C-B1-A-B2-(L)-H) |
|---|---|
| Med12 LP-NP-7/8a | KKKKKKKKKK-VR-DIDPSSSVLFEYMEKPDFSLFSP-SPVZ-(K'-DBCO)-2B3W2 |
| M30 LP-NP-7/8a | KKKKKKKKKK-VR-PSKPSFQEFVDWENVSPELNSTDQPFL-SPVZ-(K'-DBCO)-2B3W2 |
| Trp1 LP-NP-7/8a | KK-PLR-TAPDNLGYM-SLVR-(K'-DBCO)-2B3W2 |

Z = citrulline; K' = azido-Lysine (Lys(N3)); DBCO = dibenzocyclooctyne

Treatment of established MC38 tumor

| Vaccine | Sequence (C-B1-A-B2-(L)-H) |
|---|---|
| Adpgk LP-SNP-7/8a | KKKKKK-VR-GIPVHLELASMTNMELMSSIVHQQVFPT-GSGVZ-(K'-DBCO)-2B3W2 |

Z = citrulline; K' = azido-Lysine (Lys(N3)); DBCO = dibenzocyclooctyne

| Vaccine | Sequence (C-B1-A-B2-(L)-H) |
|---|---|
| Med12 LP-SNP-7/8a | KKKKKKKKKK-VR-DIDPSSSVLFEYMEKPDFSLFSP-SPVZ-(K'-DBCO)-2B3W2 |
| Trp1 LP-SNP-7/8a | KK-PLR-TAPDNLGYM-SLVR-(K'-DBCO)-2B3W2 |
| M39 LP-SNP-7/8a | KK-VR-ELINFKRKRVAAFQKNLIEMSELEIKHG-SLVZ-(K'-DBCO)-2B3W2 |

Z = citrulline; K' = azido-Lysine (Lys(N3)); DBCO = dibenzocyclooctyne

| Vaccine | Sequence (C-A-B2-(L)-H or C-B1-A-B2-(L)-H) |
|---|---|
| 1846 | KKK-SLVR-RAHYNIVTF-SPVZ-(K'-DBCO)-2B3W2 |
| 1847 | KKK-RRAHYNIVTF-Z-(K'-DBCO)-2B3W2 |
| 1848 | KKKKK-VR-CKQQLLRREVYDFAFRDLCIVYRDG-SPVZ-(K'-DBCO)-2B3W2 |
| 1849 | KKKKKK-SLVR-EVYDFAFRDL-SPVZ-(K'-DBCO)-2B3W2 |

Z = citrulline; K' = azido-Lysine (Lys(N3)); DBCO = dibenzocyclooctyne

Figure 38

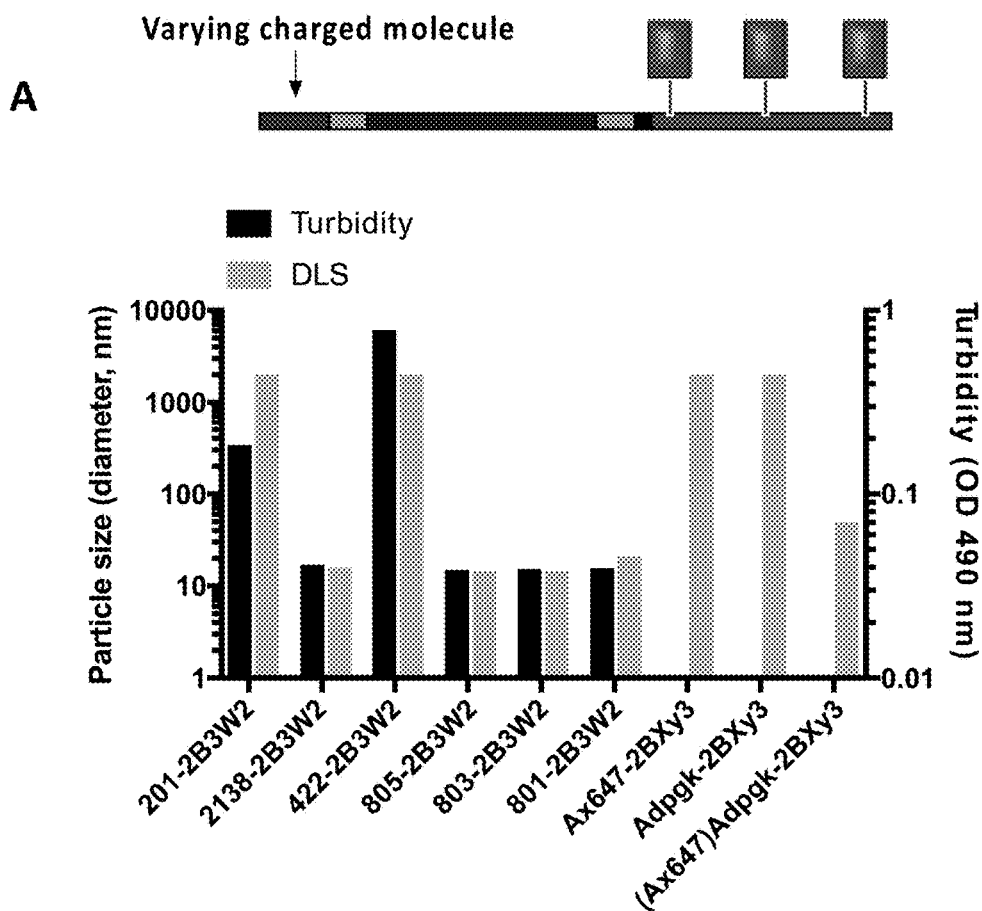

| Antigen conjugate | Sequence (*B1*-A-*B2*-(L)-H or C-*B1*-A-*B2*-(L)-H) | Net charge |
|---|---|---|
| 201-2B₃W₂ | AQLANDVVL-*QSLVR*-(K'-DBCO)-2B3W2 | 1 |
| 2138-2B₃W₂ | K*K*K*K*-*VR*-AQLANDVVL-*SPVZ*-(K'-DBCO)-2B3W2 | 5 |
| 422-2B₃W₂ | SPERNDWEPL-*SLVR*-(K'-DBCO)-2B3W2 | -1 |
| 805-2B₃W₂ | Ac-S'-*SPLZ*-SPERNDWEPL-*GGSPLZ*-(K'-DBCO)-2B3W2 | -4 |
| 803-2B₃W₂ | Ac-S'S'-*PLZ*-SPERNDWEPL-*GGSPLZ*-(K'-DBCO)-2B3W2 | -6 |
| 801-2B₃W₂ | Ac-S'S'S'-*PLZ*-SPERNDWEPL-*GGSPLZ*-(K'-DBCO)-2B3W2 | -8 |
| Ax647-2BXy₃ | Ax647-(K'-DBCO)-2BXy3 | -3 |
| Adpgk-2BXy₃ | ASMTNMELMS-*SLVR*-(K'-DBCO)-2BXy3 | 1 |
| (Ax647)Adpgk-2BXy₃ | Ax647-ASMTNMELMS-*SLVR*-(K'-DBCO)-2BXy3 | -3 |

Ac = N-terminal acetyl; Z = citrulline;
K' = azido-Lysine (Lys(N3)); DBCO = dibenzylcyclooctyne;
S' = phosphoserine; K* = (6-*N*,6-*N*,6-*N*)trimethyllysine
Ax647 = Alexa Fluor® 647

B

Peptide antigen conjugates of Formula V linked to different hydrophobic molecules of Formula II linked to adjuvants of Formula III Adpgk, -1: GIPVHLELASMTNMELMSSIVHQQVFPTGSPVZK'-DBCO-H
Adpgk, +6: KKKKKK-VR-GIPVHLELASMTNMELMSSIVHQQVFPTG-SGVZK'DBCO-H
Adpgk, +9: KKKKKKKKK-VR-GIPVHLELASMTNMELMSSIVHQQVFPT-SPVZK'DBCO-H

Figure 38 continued

D Tetra-alkyl ammonium C block (pH-independent)

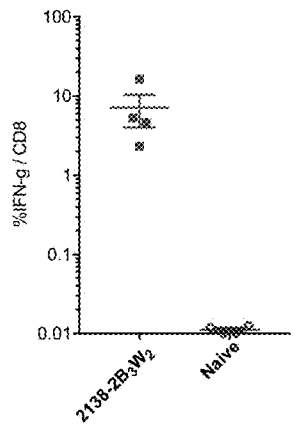

E Phosphoserine C block (negatively-charged)

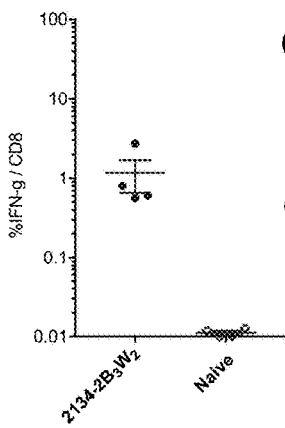

CD8 T cell responses 2 weeks after 2 immunizations using peptide antigen conjugates comprising different charged molecules (C)

F H = 15 amino acids long ($2B_5G_{10}$)

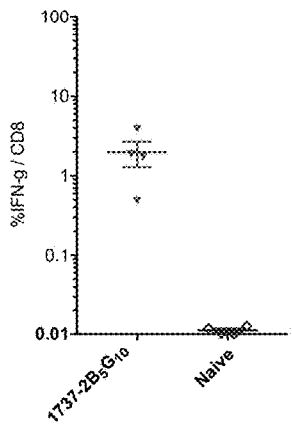

G H = 30 amino acids long $2B_5W_{10}G_{15}$

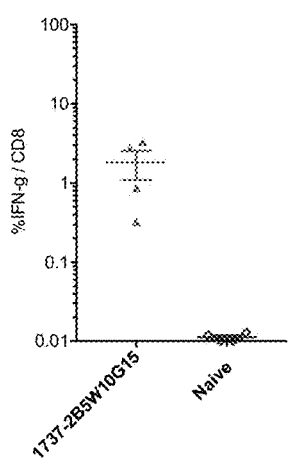

CD8 T cell responses 2 weeks after 2 immunizations using peptide antigen conjugates comprising different hydrophobic molecules (H)

$2138\text{-}2B_3W_2$ = K+K+K+K+-VR-AQLANDVVL-SPVZ-K'-DBCO-$2B_3W_2$ wherein K+ = is a tetra-alkyl ammonium modified amino acid $2134\text{-}2B_3W_2$ = {Acetyl}-S'S'S'-VZ-AQLANDVVL-SPVZ-K'-DBCO-$2B_3W_2$ wherein S' is phosphoserine $1737\text{-}2B_5G_{10}$ = KKKKKKKKK-VR-GIPVHLELASMTNMELMSSIVHQQVFPT-SPVZ-K'-DBCO-$2B_5G_{10}$ wherein $2B_5G_{10}$ = E(2B)GGE(2B)GGE(2B)GGE(2B)GGE(2B)GG $1737\text{-}2B_5W_{10}G_{15}$ = KKKKKKKKK-VR-GIPVHLELASMTNMELMSSIVHQQVFPT-SPVZ-K'-DBCO-$2B_5W_{10}G_{15}$
wherein $2B_5W_{10}G_{15}$ = K(2B)GWGWGK(2B)GWGWGK(2B)GWGWGK(2B)GWGWGK(2B)GWGWG K' = azido-lysine Particle size dependency on net charge of peptide antigen conjugates comprising different H

| Antigen | Sequence (A-X1 or C-B1-A-B2-X1) | Net charge |
|---|---|---|
| Adpgk, -1 | GIPVHLELASMTNMELMSSIVHQQVFPT-K' | -1 |
| Adpgk, +6 | KKKKKK-VR-GIPVHLELASMTNMELMSSIVHQQVFPT-GSGVZ-K' | 6 |
| Adpgk, +9 | KKKKKKKKK-VR-GIPVHLELASMTNMELMSSIVHQQVFPT-SPVZ-K' | 9 |

Z = citrulline; K' = azido-Lysine (Lys(N3)); Ac = N-terminal acetyl

Figure 39 continued
CD8 T cell responses 2 weeks after 2 immunizations using peptide antigen conjugates comprising different PRR agonists
A H carrying TLR-2 agonist
B H carrying TLR-4 agonist
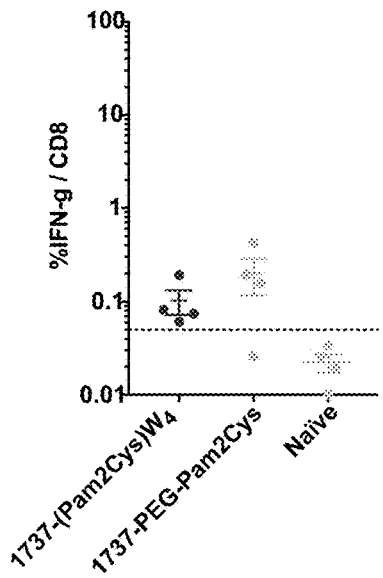
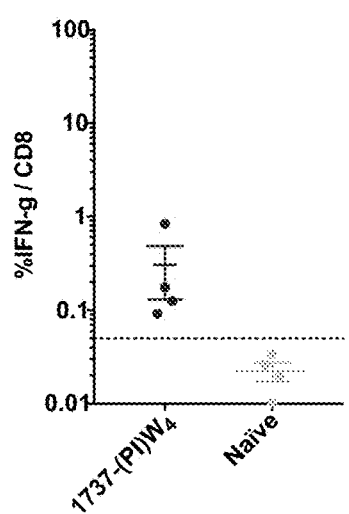
C H linked to a TLR-7 agonist
D H linked to a STING agonist
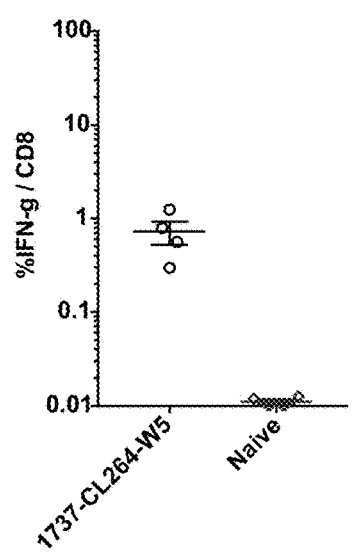
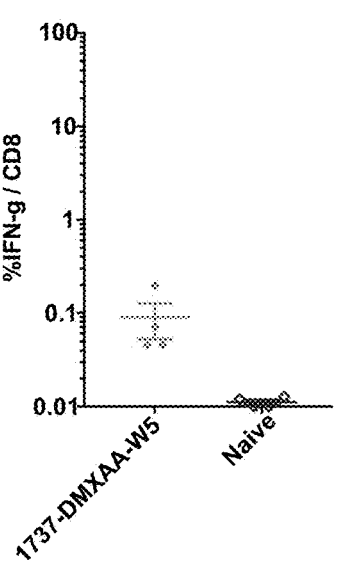
1737 = KKKKKKKKK-VR-GIPVHLELASMTNMELMSSIVHQQVFPT-SPVZ-K'
Where K' = azido-lysine CD8 T cell responses 2 weeks after 2 immunizations using peptide antigen conjugates comprising different Linkers (L)

2143 = Ac-RRRRR-VR-SSPYSLHYL-SPVZ-K(G)-L(amide)-2B$_3$W$_2$

2144 = 2B$_3$W$_2$-L(amide)-RRRRR-VR-SSPYSLHYL-SPVZ

2154 = 2B$_3$W$_2$-L(amide)-VZ-SSPYSLHYL-SPVR-RRRRR

2142 = Ac-KKKKK-VR-SSPYSLHYL-SPVZ-C(G)-L(thioether)-2B$_3$W$_2$

2146 = 2B$_3$W$_2$-L(thioether)-CGGG-RRRR-VR-SSPYSLHYL-SPVZ

1737 = KKKKKKKKK-VR-GIPVHLELASMTNMELMSSIVHQQVFPT-SPVZ-K'-DBCO-H

1908 = KKK-VR-MAAALTFRRLLTLPRAARGFGVQVS-SPVZ-K'-DBCO-H

Where K' = azido-lysine

1737 = KKKKKKKKK-VR-GIPVHLELASMTNMELMSSIVHQQVFPT-SPVZ-K'-DBCO-H

Figure 43

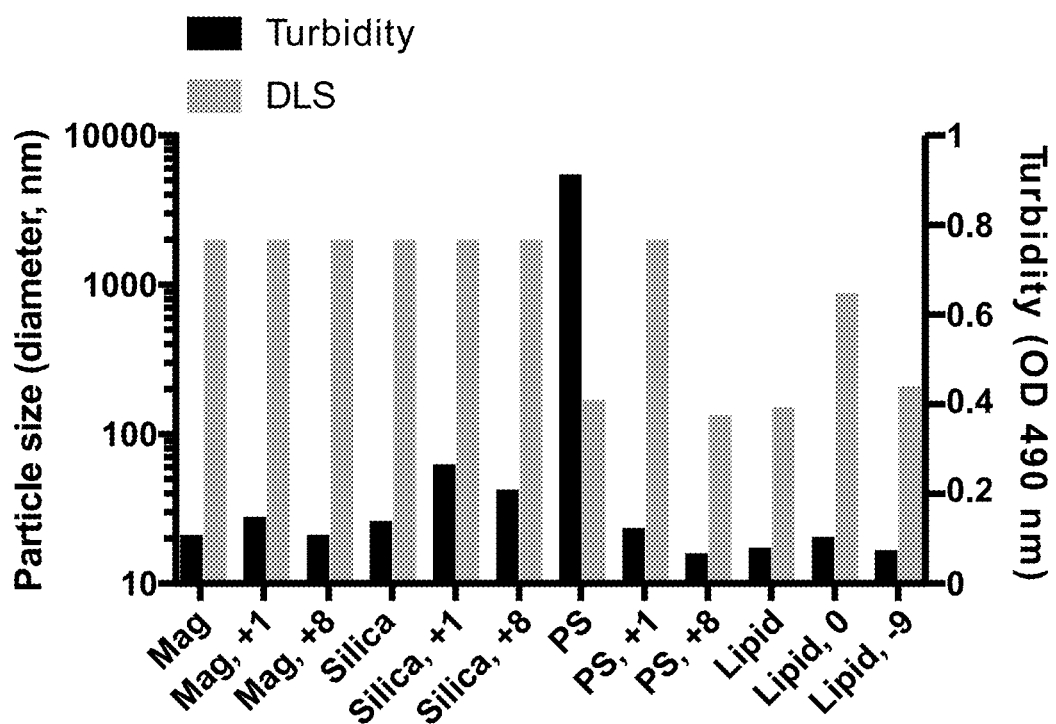

Particle size and stability of peptide antigen conjugates comprising preformed Particles (P)

| Antigen | Sequence (A-X1 or A-B2-X1 or C-B1-A-B2-X1) | Net charge |
|---|---|---|
| 214 | GRVLELFRAAQLANDVVLQIMELCGATR-K' | 1 |
| 1588 | KKKKKK-VR-GRVLELFRAAQLANDVVLQIMELCGATR-SPVZ-K' | 8 |
| 1016 | ASMTNMELM-GSPVZ-K' | 0 |
| 1197 | Ac-DDDDDDDD-SPVZ-ASMTNMELM-SPVZ-K' | -9 |

Z = citrulline; K' = azido-Lysine (Lys(N3)); Ac = N-terminal acetyl

Mag = DBCO functionalized iron oxide nanoparticles (~20 nm)
Silica = DBCO functionalized silica nanoparticles (~ 20 nm)
PS = DBCO functionalized polystyrene nanoparticles (~ 20 nm)
Lipid = DBCO functionalized liposomes (~ 200 nm)

Figure 44

Auto-antigens delivered as peptide antigen conjugates of Formula V assemble into stable nanoparticles

| Antigen conjugate | Sequence (C-B1-A-B2-(L)-H) | Particle size (diameter, nm) | Turbidity (OD 490 nm) |
|---|---|---|---|
| 2081-W$_5$ | KKK-VR-MEVGWYRSPFSRVVHLYRNGK-SPVZ-(K'-DBCO)-W5 | 14.0 | 0.04 |
| 2082-W$_5$ | KKKKKK-VR-GPLGPKGQAGEPGIAGFKGDQGPKGETGPAGPQG-SPVZ-(K'-DBCO)-W5 | 14.4 | 0.04 |
| 2083-W$_5$ | KKKKKK-VR-GEPGIAGFKGDQGPKGETG-SPVZ-(K'-DBCO)-W5 | 15.0 | 0.04 |

Z = citrulline; K' = azido-Lysine (Lys(N3)); DBCO = dibenzylcyclooctyne

AH = 215-2B$_3$W$_2$ = GIPVHLELASMTNMELMSSIVHQQVFPT-K'-DBCO-2B$_3$W$_2$

CA'H = 1200-2B$_3$W$_2$ = KKK-SLVR-AKFVAAWTLKAAA-SPVZ-K'-DBCO-2B$_3$W$_2$

AH = 215-2B$_3$W$_2$ = GIPVHLELASMTNMELMSSIVHQQVFPT-K'-DBCO-2B$_3$W$_2$

CH = 106-2B$_3$W$_2$ = KKKKKKKKKK-K'-DBCO-2B$_3$W$_2$

CH(A) = 761-2B$_3$W$_2$-(220) =

EEEE-2B$_3$W$_2$-(ASMTNMELM-SSLVR-K'-DBCO)

PEPTIDE-BASED VACCINES, METHODS OF MANUFACTURING, AND USES THEREOF FOR INDUCING AN IMMUNE RESPONSE

PRIORITY DOCUMENT

The present application is a § 371 National Stage Application of PCT/US2018/026145 filed on Apr. 4, 2018, which claims priority from U.S. Provisional Patent Application No. 62/481,432, filed on 4 Apr. 2017, and from U.S. Provisional Patent Application No. 62/617,519, filed on 15 Jan. 2018, all of which are titled "PEPTIDE-BASED VACCINES, METHODS OF MANUFACTURING, AND USES THEREOF FOR INDUCING AN IMMUNE RESPONSE", and the contents of each are hereby incorporated by reference in their entirety.

This invention was created in the performance of a Cooperative Research and Development Agreement with the National Institutes of Health, an Agency of the Department of Health and Human Services. The Government of the United States has certain rights in this invention.

SEQUENCE LISTING

The instant application contains a Sequence Listing which has been submitted electronically in ASCII format and is hereby incorporated by reference in its entirety. Said ASCII copy, created on Jun. 7, 2023, is named 2023-06-07_01304-0003-00US_SL.txt and is 293,004 bytes in size.

FIELD OF DISCLOSURE

The present disclosure relates to novel peptide-based vaccines, methods of manufacturing the novel peptide-based vaccines and uses thereof for inducing an immune response, and in particular, a T cell response in a subject. Embodiments of the peptide-based vaccines of the present disclosure may be used for preventing or treating infectious diseases and cancer, as well as for inducing tolerance or modulating immunity for preventing or treating auto-immunity and allergies.

BACKGROUND

Vaccines comprising immunogenic compositions of antigens may be used to induce an immune response in a subject, including for the treatment or prevention of cancers or infectious diseases, or even for inducing tolerance and/or immune suppression for the treatment or prevention of auto-immunity or allergies. The compositions of vaccines for inducing immune responses for the treatment or prevention of cancers and infectious diseases contain antigens and specific types of adjuvants that induce cytotoxic T cell responses and/or antibodies directed to the antigen that mediate pathogen clearance or killing of virally infected or cancerous cells. In contrast, compositions of vaccines for inducing tolerogenic or suppressive responses may contain an antigen and a vehicle (e.g., delivery system such as a particle carrier) and/or immune-suppressive compounds, such as mTOR inhibitors, but will lack specific adjuvants that induce cytotoxic T cells, and may instead induce T cell tolerance or activation of regulatory cells, such as regulatory T cells, that down-regulate or modulate the qualitative characteristics of the response.

There is an increasing recognition that the genetic background, particularly the composition of major histocompatibility complex (MHC) alleles, and environment of a patient can affect their susceptibility to cancer, infectious diseases, autoimmunity and allergies, as well as impact their response to vaccines used to treat such conditions. The continued development of new diagnostic and informatics methods that provide an understanding of the molecular basis of disease has meant that patient specific information is increasingly more available. Thus, there is increasing interest in using information about an individual's genes, proteins, and environment to direct the medical care the individual receives, including the selection of particular immunotherapies, including vaccines to treat or prevent cancer, infectious diseases, autoimmunity and allergies.

In cancer therapy, specific information about an individual's tumor can be used to help diagnose, plan treatment, find out how well treatment is working, or make a prognosis. For example, specific information about an individual's genes, proteins, and environment, can be used to tailor a preventative approach to cancer treatment by developing vaccines based on that information. Vaccines used for the immunological treatment or prevention of certain cancers should induce an immune response against tumor-associated antigens. One preferred immune response is a CD8 T cell response and/or a CD4 T cell response that recognizes a tumor-associated antigen.

Similarly, personalized approaches to treat auto-immunity or allergies is possible through the identification of the specific self-antigens or foreign antigens, respectively, that are the cause of immune-mediated pathology. While some auto-antigens and allergens are known and common across patients, some auto-antigen and allergens may be patient-specific and thus treatment of these patients must be tailored. The antigens identified as the cause of the pathology may be administered in the form of a peptide as a vaccine that is capable of inducing tolerance against the auto-antigens (i.e. self-antigens). Alternatively, the immune response against a foreign antigen that gives rise to allergies may be of a particular type of immune response that results in pathology. Thus, a vaccine against such a foreign antigen may be provided as a peptide-based vaccine to shift the immune response to a qualitatively distinct type of immune response that does not result in pathology.

Role of T Cells in Cancer Treatment or Prevention

T cells are known to mediate tumor regression and improve patient survival as has been shown using immunotherapies based on adoptive T cell therapy and immune checkpoint inhibitors. Several studies in humans have shown that intravenous infusion of a large number of expanded CD8 and/or CD4 T cells that recognize a single tumor-associated antigen can mediate tumor regression and improve survival (see: E. Tran et al., N Engl J Med 375: 2255-2262, 2016; and E. Tran et al., Science 344: 641-645, 2014). Additionally, treatment of certain cancers with drugs that block or reverse T cell suppression, such as monoclonal antibodies that block CTLA-4, PD-1 and/or PD-L1 (so-called 'checkpoint inhibitors') result in tumor regression and improvement in overall survival (see: D. M. Pardoll, Nat Rev Cancer, 12: 252-264, 2012; F. S. Hodi et al., N Engl J Med, 363:711-723, 2010; and, M. Reck et al., N Engl J Med, 375:1823-1833, 2016; J. E. Rosenberg et al., Lancet 387: 1909-1920, 2016). PD-1/PD-L1 is a receptor-ligand pair wherein PD-1 is expressed on T cells and PD-L1 is expressed on cells in the tumor. The PD-1/PD-L1 interaction blocks T cells from performing their effector functions, which otherwise would result in slowed growth or elimination of tumor cells expressing a tumor-associated antigen recognized by the T cell. Blocking the PD-1/PD-L1 interaction with a monoclonal antibody results in cessation of the suppressive signal, thereby releasing T cells to perform an effector function that results in slowed tumor cell growth or tumor cell death (D. M. Pardoll, Nat Rev Cancer, 12: 252-264, 2012.)

The role of T cells in promoting tumor clearance in patients is supported by studies in humans showing that checkpoint inhibitors have higher efficacy (lower mortality) in patients who have a higher level of T cell infiltration present in their tumor biopsy at the time treatment begins (see: J. E. Rosenberg et al., Lancet 387:1909-1920, 2016). Moreover, it has also been shown that checkpoint inhibitors have higher efficacy in patients whose tumors have a higher level of mutations (see: A. Snyder et al., N Engl J Med 371, 2189-2199 2014; and N. A. Rizvi et al., Science, 348:124-128, 2015) presumably because increasing numbers of mutations lead to a greater number of mutant proteins thereby providing a higher number of potential targets for which T cells can recognize the tumor cells and target them for elimination.

However, a major challenge is that many prevalent tumors (for example, prostate, breast, and pancreatic cancers) have low mutational burden (see: T. N. Schumacher, R. D. Schreiber, Science, 348: 69-74, 2015) and patients with these cancers realize little or no benefit from checkpoint inhibitors. Furthermore, even among tumors that have high mutational burden, only a subset of patients benefit from checkpoint inhibitor therapy because the majority of subjects lack the requisite pre-existing tumor-specific T cell response that is required for immunotherapies to mediate an effect.

Vaccines that Target Tumor-Associated Antigens for Cancer Treatment or Prevention Generating immune responses, particularly T cell responses, for cancer treatment or prevention requires the identification of suitable tumor-associated antigens. Tumor-associated antigens include self-antigens, which are present on certain healthy cells but are preferentially expressed by tumor cells; pathogen-derived antigens from oncogenic microbial pathogens; and/or neoantigens, which are aberrant proteins that are specific to tumor cells and are often but not always unique to individual patients.

Suitable self-antigens can be antigens derived from proteins that are no longer expressed in post-partum subjects. For example, suitable self-antigens can include antigens that are preferentially expressed by tumor cells, such as NY-ESO-1 and MAGE-A3 (see: N. N. Hunder et al., N Engl J Med, 358:2698-2703, 2008). Alternatively, self-antigens can include antigens that are expressed in a healthy tissue wherein a T cell response against that healthy tissue is not excessively detrimental to the patient, for example, prostatic acid phosphatase (PAP) (see: P. W. Kantoff et al., N Engl J Med 363:411-422, 2010).

A tumor-associated antigen may be a pathogen-derived antigen, such as a virus or other pathogen that is the underlying driver of the neoplastic process, for example, proteins from human papilloma virus (HPV) (see: G. G. Kenter et al., N Engl J Med, 361:1838-1847, 2009).

Neoantigens are antigens that are the result of mutations that are present only in tumor cells and not normal cells (see: T. N. Schumacher, R. D. Schreiber, Science, 348: 69-74, 2015). Neoantigens may be created by nucleotide polymorphisms that result in non-conservative amino acid changes. Neoantigens may be created by insertions and/or deletions, which can result in peptide antigens containing an insertion or deletion or a frameshift mutation. Neoantigens may be created by the introduction of a stop codon that in its new context is not recognized by the stop codon machinery, resulting in the ribosome skipping the codon and generating a peptide that contains a single amino acid deletion. Neoantigens may be created by mutations at splice sites, which result in incorrectly spliced mRNA transcripts. Neoantigens may be created by inversions and/or chromosomal translocations that result in fusion peptides.

Finally, a tumor-associated antigen may contain novel post-translational modifications of un-mutated or mutant peptides wherein the post-translational modifications are not present in normal tissue.

In summary, a tumor-associated antigen is any antigen that is produced by a neoplastic cell, which upon targeting by a T cell response, ideally results in a meaningful regression of tumor growth, or prevents tumorigenesis, with limited effect on healthy, non-cancerous cells.

Challenges Facing the Vaccine Field

For the treatment of certain cancers, the preferred immune response is a CD8 T cell response (see: E. Tran et al., N Engl J Med 375:2255-2262, 2016) and/or CD4 T cell response (and see: E. Tran et al., Science 344: 641-645, 2014; and N. N. Hunder et al., N Engl J Med, 358:2698-2703, 2008) that recognizes a tumor-associated antigen, which may preferentially be sustained, high magnitude, and highly functional (high quality) (L. Gattinoni et al., Nature Medicine, 17:1290-1297, 2011).

One means of inducing a T cell response against antigens, e.g., tumor-associated antigens, in a subject is through vaccination. There are numerous approaches currently under investigation to induce CD8 and/or CD4 T cell responses against tumor-associated antigens, including DNA/RNA-based, viral vector-based, and peptide-based approaches (for example, see: L. M. Kranz et al., Nature 534, 396-401, 2016; and C. J. Melief, S. H. van der BurgNat Rev Cancer 8:351-360, 2008). A major challenge to generating effective T cell immunity against cancers, however, is that most current vaccine approaches are limited by weak immunogenicity for eliciting CD8 T cell immunity and limited antigenic breadth of responses against most predicted neoantigens (see: S. Kreiter et al., Nature 520, 692-696, 2015).

Much effort to induce anti-tumor T cell immunity has been focused on either using synthetic peptide antigens simply mixed with different immunostimulants and/or vehicles (adjuvants) (see: C. J. Melief, S. H. van der Burg, Nat Rev Cancer 8:351-360, 2008; and M. S. Bijker et al., Eur J Immunol 38, 1033-1042, 2008) or RNA (see: Kranz L M, et al. *Nature* 534(7607):396-401, 2016 and Kreiter S, et al. *Nature* 520(7549):692-696, 2015).

However, a major challenge to generating effective T cell immunity against cancers is that most current vaccine approaches based on peptide antigens or RNA have been hampered by low magnitude and limited antigenic breadth of responses against tumor-associated antigens, including neoantigens. For example, with regard to antigenic breadth, the current gold-standard peptide-based vaccine approaches based on peptide antigens (for example, mixing 25 amino acid synthetic long peptides with the adjuvant polyIC:LC) or RNA induce T cell responses against less than 10% of predicted neoantigens (see: S. Kreiter et al., Nature 520, 692-696, 2015). Thus, improved vaccine approaches, particularly peptide-based vaccine approaches are needed.

A full explanation for the low magnitude and poor antigenic breadth of T cell responses by contemporary vaccine technologies remains to be determined, and thus, an ongoing challenge is that there is currently no consensus around the optimal parameters for delivering peptide antigens to ensure reliable priming of T cell immunity for cancer treatment and prevention, as well for other applications, including for the treatment and prevention of infectious diseases. Similarly, the optimal parameters of peptide-based vaccines for inducing suppression and tolerance remain unknown.

Current Challenges Around Peptide-Based T Cell Vaccines

A major challenge to the development of vaccines for the treatment or prevention or infectious diseases and cancer is that there is presently no consensus concerning how best to construct a peptide-based vaccine to reliably elicit high magnitude T cell immunity against most antigens. Similarly, there is no consensus on how best to construct a peptide-based vaccine for inducing immune tolerance or for shifting immune response from those that induce allergies to an innocuous type of response. For instance, there is still considerable debate as to the optimal peptide antigen length, physical format of peptide antigen delivery (e.g., soluble versus particulate) and type of innate immune stimulation (e.g., adjuvant choice) needed to induce optimal T cell immunity for the treatment or prevention of cancer and infectious diseases, as well as for the treatment or prevention of auto-immunity and allergies. Indeed, the impact of many parameters of peptide-based vaccines, including the influence of amino acids flanking CD4 and CD8 T cell epitopes, linker chemistries used, charge, etc., on immune responses remain largely unexplored. This problem is particularly pronounced when considering that personalized vaccine approaches must be uniquely tailored for each patient and thus universal peptide-based vaccines approaches for reliably eliciting immunity, particularly T cell immunity against patient-specific antigens, are needed.

Another major challenge facing current peptide-based vaccine approaches is that they do not account for the broad range of possible physical and chemical characteristics of peptide antigens. For instance, individualized cancer vaccine approaches will require that from each patient a unique set of peptide antigens is generated that may have a broad range of possible physical and chemical characteristics. With respect to auto-immunity, multiple different antigens may be identified as the cause of pathology. Thus, tolerance-inducing vaccines must contain a set of peptide antigens that are unique to each patient. The problem is that variability in peptide antigen composition can result in some peptide-based antigens that are difficult or impossible to manufacture as the native peptide antigen, which is estimated to be about 10 to 30% of peptide-based antigens of 25 or more amino acids in length. Thus, many antigens cannot be targeted by current vaccine approaches because the native peptide antigen cannot be produced efficiently or isolated following synthesis. Additionally, variability in peptide antigen composition that impacts charge and solubility, which is not controlled for in current peptide-based vaccine approaches, can impact various attributes of the vaccine formulation, including material loading of peptide and/or lead to adverse interactions of a peptide antigen with either other peptide antigens or other components of the vaccine.

Thus, to overcome the limitations of current peptide-based vaccine approaches, novel compositions and methods of manufacturing peptide-based vaccines that (i) account for the variability in the physical and chemical properties of peptide antigens during manufacturing as well as in the vaccine formulation are needed for ensuring optimal delivery of peptide antigens to (ii) reliably induce an immune response, and in particular, a T cell response in a subject, against most antigens. Such vaccines and methods, which account for peptide antigen variability and are therefore generalizable for any peptide antigen, would be particularly useful in the field of personalized cancer treatment, wherein the characteristics of peptide antigens used in a personalized cancer vaccine may vary from patient to patient. However, the applicability of the peptide-based vaccine compositions for any peptide antigen means that the compositions can also be used in other personalized immunological-based treatments, such as for inducing tolerance or for modulating the immune response to allergens for the treatment of auto-immunity and allergies, respectively.

SUMMARY

The present inventors have developed novel compositions and methods of manufacturing peptide-based vaccines that overcome at least one of the limitations of current peptide-based vaccine approaches. The novel peptide-based vaccine compositions and methods of manufacturing disclosed herein account for the variability in the physical and chemical properties of peptide antigens and are therefore generalizable for any peptide antigen. Moreover, the novel peptide-based vaccine compositions disclosed herein ensure optimal delivery of a range of different peptide antigens to induce an immune response in a subject.

The novel compositions disclosed herein relate to immunogenic compositions comprising peptide antigen conjugates. The peptide antigen conjugates comprise a peptide antigen (A) that is linked to either a hydrophobic molecule (H) that forms particles or a pre-formed Particle (P) either directly or indirectly through an optional Linker (L) and/or an optional N- or C-terminal extension (B1 or B2) that is linked to either the N- or C-terminus of the peptide antigen, respectively.

In some embodiments, particles formed by peptide antigen conjugates additionally comprise an optional charged molecule (C). In some embodiment, the charged molecule is linked to the peptide antigen conjugate to stabilize the particles in aqueous conditions. In other embodiments, the charged molecule (C) is provided on a separate molecule and is incorporated into particles formed by the peptide antigen conjugates.

Addition of certain N- and/or C-terminal extensions (B1 and/or B2) and/or charged molecules (C) results in unexpected improvements in peptide-based vaccine manufacturing by solid-phase synthesis as well as improved ease of purification through improved organic solvent solubility, as well as unexpected improvements in control over the size and stability of the particles formed by the peptide antigen conjugates. These compositions exhibit unexpected improvements in T cell immunity and tumor clearance, particularly in regard to the magnitude and breadth of T cells generated against tumor-associated antigens.

Embodiments of the present disclosure include a peptide antigen conjugate comprising: a peptide antigen (A); and either a hydrophobic molecule (H) or a particle (P), wherein the peptide antigen (A) is linked to either the hydrophobic molecule (H) or the particle (P) directly or indirectly via a N-terminal extension (B1) that is linked to the N-terminus of the peptide antigen (A) or a C-terminal extension (B2) that is linked to the C-terminus of the peptide antigen (A). Additional embodiments of the present disclosure include an immunogenic composition comprising the peptide antigen conjugates. Still further embodiments of the present disclosure include a method of treating a patient suffering from a disease comprising administering to the patient suffering from the disease, the peptide antigen conjugate thereof or the immunogenic composition.

In some embodiments, the vaccine used for cancer treatment can be used alone or in combination with other immunotherapies and cancer treatment modalities, including but not limited to chemotherapy, checkpoint inhibitors, radiation, and any other technology used to combat cancer.

Thus, also disclosed herein is a method of treating a patient suffering from a disease comprising administering to the patient suffering from the disease the peptide antigen conjugate or the immunogenic composition of the present disclosure.

Furthermore, disclosed herein is use of the peptide antigen conjugate or the immunogenic composition of the present disclosure in the manufacture of a medicament for the treatment of a disease.

The unexpected findings disclosed herein relate to:
(i) The optimal length of peptide antigens (A) used in cancer vaccines to ensure reliable priming of T cell immunity;
(ii) Use of peptide antigen extension sequences, i.e., N- or C-terminal extensions (B1 and/or B2) and/or optional charged molecules (C) that facilitate manufacturing of peptide-based vaccines;
(iii) How characteristics of the hydrophobic molecule (H) comprising peptide antigen conjugates impacts manufacturability as well as the size and stability of particles, and how these parameters impact biological activity;
(iv) The composition of charged molecules (C) and net charge of peptide antigen conjugates needed to induce and stabilize particles of an optimal size for promoting T cell immunity;
(v) The composition of enzyme degradable peptide sequences that promote efficient processing of minimal epitopes delivered within the context of the peptide antigen conjugate; and/or
(vi) How the potency and qualitative characteristics of Ligands with adjuvant properties (e.g., PRR agonists) delivered on peptide antigen conjugates impart on the breadth, magnitude and quality of T cell responses.

BRIEF DESCRIPTION OF FIGURES

FIG. 2 discloses SEQ ID NOS 188-189, respectively, in order of appearance.

FIG. 4: Molecular weight and hydrodynamic behavior of peptide antigens (A) and peptide antigen conjugates delivering peptide antigens (A) comprised of either synthetic long peptides (SLP or "LP") or minimal ("Min") CD8 T cell epitopes derived from the MC38 tumor cell line. The peptide antigens (A) comprised of LPs were linked to the linker precursor X1, azido-lysine (K') that was either left unlinked or was linked to a hydrophobic molecule (H), comprised of either DBCO-$W_3$ or DBCO-$2BXy_3$. The peptide antigens (A) comprised of LPs were linked to an extension (B1) that was linked to a linker precursor X1, azido-lysine (K') that was either left unlinked or was linked to a hydrophobic molecule (H), comprised of either DBCO-$W_3$ or DBCO-$2BXy_3$. FIG. 4 discloses SEQ ID NOS 190-199, 623 and 200, respectively, in order of appearance.

FIG. 7: Molecular weight and hydrodynamic behavior of peptide antigens (A) and peptide antigen conjugates delivering peptide antigens (A) comprised of either synthetic long peptides (SLP or "LP") or minimal ("Min") CD8 T cell epitopes derived from the B16 tumor cell line. The peptide antigens (A) comprised of LPs were linked to the linker precursor X1, azido-lysine (K'), that was either left unlinked to linked to a hydrophobic molecule (H), comprised of either DBCO-$2BXy_5$ or DBCO-$2B_5$. The peptide antigens (A) comprised of LPs were linked to an extension (B1) that was linked to a linker precursor X1, azido-lysine (K'), that was either left unlinked to linked to a hydrophobic molecule (H), comprised of either DBCO-$2BXy_5$ or DBCO-$2B_5$. FIG. 7 discloses SEQ ID NOS 201-224, respectively, in order of appearance.

FIG. 8: Impact of peptide antigen (A) length and potency of the TLR-7/8a linked to the hydrophobic molecule (H) on the immunogenicity of peptide antigen conjugates. Mice (N=5 per group) were immunized with different immunogenic compositions comprising peptide antigen conjugates delivering either the synthetic long peptide (LP), minimal CD8 T cell epitope (Min) or both the SLP and the Min of B16 tumor derived peptide antigens (A) linked to either the hydrophobic molecule (H) DBCO-$2BXy_5$ or DBCO-$2B_5$. Mice were immunized at days 0 and 14 and antigen-specific CD4 and CD8 T cell responses (% IFNg+ of total) were assessed from whole blood at day 24. The bar graphs show the sum of the averaged responses for each peptide antigen (M47, M44, M30, M25, M33, M27 and M08).

FIG. 13: Peptide antigen conjugates evaluated in FIG. 12. A peptide antigen (A) comprised of the minimal epitope, Cpne1 (Ser-Ser-Pro-Tyr-Ser-Leu-His-Tyr-Leu SEQ ID NO: 1) was linked to either or both B1 and/or B2 extensions comprising a cathepsin and or immuno-proteasomal cleavage site, additionally wherein the peptide antigen (A) was linked either directly or through the B2 extension to a linker precursor X1, azido-lysine (K'), that was linked to a DBCO molecule that was linked to the hydrophobic molecule (H), $2BXy_3$. FIG. 13 discloses SEQ ID NOS 225-245, respectively, in order of appearance.

FIG. 14: Impact of the charged molecule (C) and extensions (B1 and/or B2) on the in vivo immunogenicity of peptide antigen conjugates delivering a peptide antigen (A) comprised of a minimal CD8 T cell epitope. Mice (N=5 per group) were immunized with peptide antigen conjugates comprising different charged molecules (C) and extension(s) ($B_1$ and/or $B_2$) at days 0 and 14 and antigen-specific CD8 T cell responses (% IFNg+ of total CD8 T cells) were assessed from whole blood at days 10 (top panel) and day 24 (bottom panel). FIG. 14 discloses SEQ ID NOS 73-74, 71, 73-74 and 71, respectively, in order of appearance.

FIG. 15: Impact of the N- and C-terminal extensions (B1 and B2) on the in vitro potency for CD8 T cell activation. A minimal CD8 T cell epitope (Adpgk) peptide antigen (A) was linked to different extensions (B1 and B2) and assessed for the capacity to stimulate IFNg production from Adpgk-specific CD8 T cells. FIG. 15, B1 and B2 columns, discloses "SLVR" as SEQ ID NO: 7, "SPVR" as SEQ ID NO: 6, "ELVR" as SEQ ID NO: 5, "ELVL" as SEQ ID NO: 10, "KPLR" as SEQ ID NO: 8, "RLVS" as SEQ ID NO: 80, "SLVL" as SEQ ID NO: 4, "GGGG" as SEQ ID NO: 81, "GGSLVZ" as SEQ ID NO: 112, "GGSLVR" as SEQ ID NO: 13, "Antigen" column, discloses "ASMTNMELM" as SEQ ID NO: 77, and "Sequence" column, discloses SEQ ID NOS 246-253, 250, 254-255, 254, 256-262, 261, 256, 257, 263, 260, 264-277, 82 and 1, respectively, in order of appearance.

FIG. 18: Impact of peptide antigen conjugate net charge and hydrophobic molecule composition on hydrodynamic behavior. The hydrodynamic behavior of a range of different peptide antigen conjugates of Formula V at 0.1 mg/mL or 0.5 mg/mL in PBS at a pH of 7.4 was assessed by dynamic light scattering. The net charge of the peptide antigen conjugates and the number or mass average particle diameter is reported. Turbidity was determined by measuring the absorbance of the solution at 490 nm. Turbidity >0.04 indicates aggregation. FIG. 18 discloses SEQ ID NOS 278-463, 448, 464-466, 460, 467-527, 464 and 528-548, respectively, in order of appearance.

FIG. 22 discloses SEQ ID NOS 549, 249 and 550-553, respectively, in order of appearance.

FIG. 23: Impact of charged molecule (C or "C Block") composition on immunogenicity for generating CD8 T cell responses to a neoantigen minimal epitope, Adpgk, delivered as a peptide antigen conjugate of Formula V. (A) Peptide antigen conjugates with either a poly(K)-poly(D)- or PEG-based C block delivering a minimal epitope, Adpgk, were administered to mice (N=3 per group per dose) at different doses at days 0, 14 and 28, and neoantigen (Adpgk)-specific CD8 T cell responses were assessed from whole blood at day 36 (B). FIG. 23 discloses SEQ ID NOS 554-556, respectively, in order of appearance.

FIG. 24 discloses SEQ ID NO: 554.

FIG. 25: Impact of the composition of the hydrophobic molecule (H) and hydrodynamic behavior of the peptide antigen conjugate on CD4 and CD8 T cell responses. Mice (N=5 per group) were immunized with immunogenic compositions comprising a minimal CD8 T cell epitope and a CD4 T cell epitope (PADRE epitope) either as microparticles (MP) (>500 nm in diameter) or nanoparticle (NP) micelles (<200 nm in diameter) carrying varying amounts and potency of TLR-7/8 agonists. Mice were immunized at days 0 and 14 and antigen (Adpgk)-specific (A) CD8 T cell responses (% IFNg+ of total CD8 T cells) and (B) PADRE-specific CD4 T cell responses were assessed from whole blood at day 24. FIG. 25 discloses SEQ ID NOS 387, 377, 356, 557-559, 393, 383, 362 and 560-562, respectively, in order of appearance.

FIG. 27: (SEQ ID NOS: 83-85, 563-565, 441, 449, 451, 83-85, 563-565, 441, 449, 451, 563-565, 441, 449 and 451, respectively, in order of appearance) Particulate delivery of peptide neoantigens enhances CD8 T cell responses directed against the peptide antigen (A) based neoantigens. (A) Turbidity of different neoantigens as native LPs, LPs linked to a hydrophobic molecule ($2B_3W_2$) that assemble into microparticles ("MP-7/8a") or LPs synthesized as peptide antigen conjugate of Formula V that self-assembles into nanoparticles ("SNP-7/8a"). Turbidity >0.05 OD indicates aggregation. (B-E) Mice were immunized with native LPs admixed with polyICLC, or LPs delivered as MP-7/8a or SNP-7/8a at days 0 and 14 and CD8 T cell responses were assessed from whole blood on day 28. Data on log scale are reported as geometric mean with 95% CI; Comparison of multiple groups for statistical significance was determined using one-way or two-way ANOVA; ns=not significant; *, p=0.05; **, p=0.01.

FIG. 29 discloses SEQ ID NOS 566-572, 447, 441, 449, 442, 451, 446, 453, 566-572, 447, 441, 449, 442, 451, 446 and 453, respectively, in order of appearance.

FIG. 30: (SEQ ID NOS: 86, 83, 84, 87, 85, 88, 89, 447, 441, 449, 442, 451, 446 and 453, respectively, in order of appearance) Immunogenicity of peptide-based neoantigens delivered as LP-based peptide antigen conjugates of Formula V, wherein the charged molecule (C) is poly(lysine) and the hydrophobic molecule (H) is $2B_3W_2$, which self-assemble into nanoparticles co-delivering TLR-7/8a (referred to as "SNP-7/8a") as compared with native LPs admixed with polyICLC. Mice were immunized on days 0 and 14 and CD8 T cell responses were assessed from whole blood on day 28.

FIG. 31 discloses SEQ ID NOS 573, 526 and 574, respectively, in order of appearance.

FIG. 33 discloses SEQ ID NO: 441.

FIG. 34 discloses SEQ ID NOS 452, 574 and 518, respectively, in order of appearance.

FIG. 35 discloses SEQ ID NOS 575-578, respectively, in order of appearance.

FIG. 37 discloses SEQ ID NOS 580-585, respectively, in order of appearance.

FIG. 38 discloses SEQ ID NOS 586-602, respectively, in order of appearance.

FIG. 39 discloses SEQ ID NOS 603-605 and 605, respectively, in order of appearance.

FIG. 40 discloses SEQ ID NOS 606-610, respectively, in order of appearance.

FIG. 41 discloses SEQ ID NOS 603-605, 103 and 611, respectively, in order of appearance.

FIG. 42 discloses SEQ ID NO: 104.

FIG. 43: Shows the particle size and stability of peptide antigen conjugates of Formula V based on peptide antigens (A) linked to pre-formed Particles (P). FIG. 43 discloses SEQ ID NOS 612-615, respectively, in order of appearance.

FIG. 44: Shows the particle size and biological activity of peptide antigen conjugates delivering auto-antigens used for inducing tolerance. FIG. 44 discloses SEQ ID NOS 616-618, respectively, in order of appearance.

FIG. 45 discloses SEQ ID NOS 619, 620, 619, 621, 180 and 622, respectively, in order of appearance.

DETAILED DESCRIPTION

Figure 1:
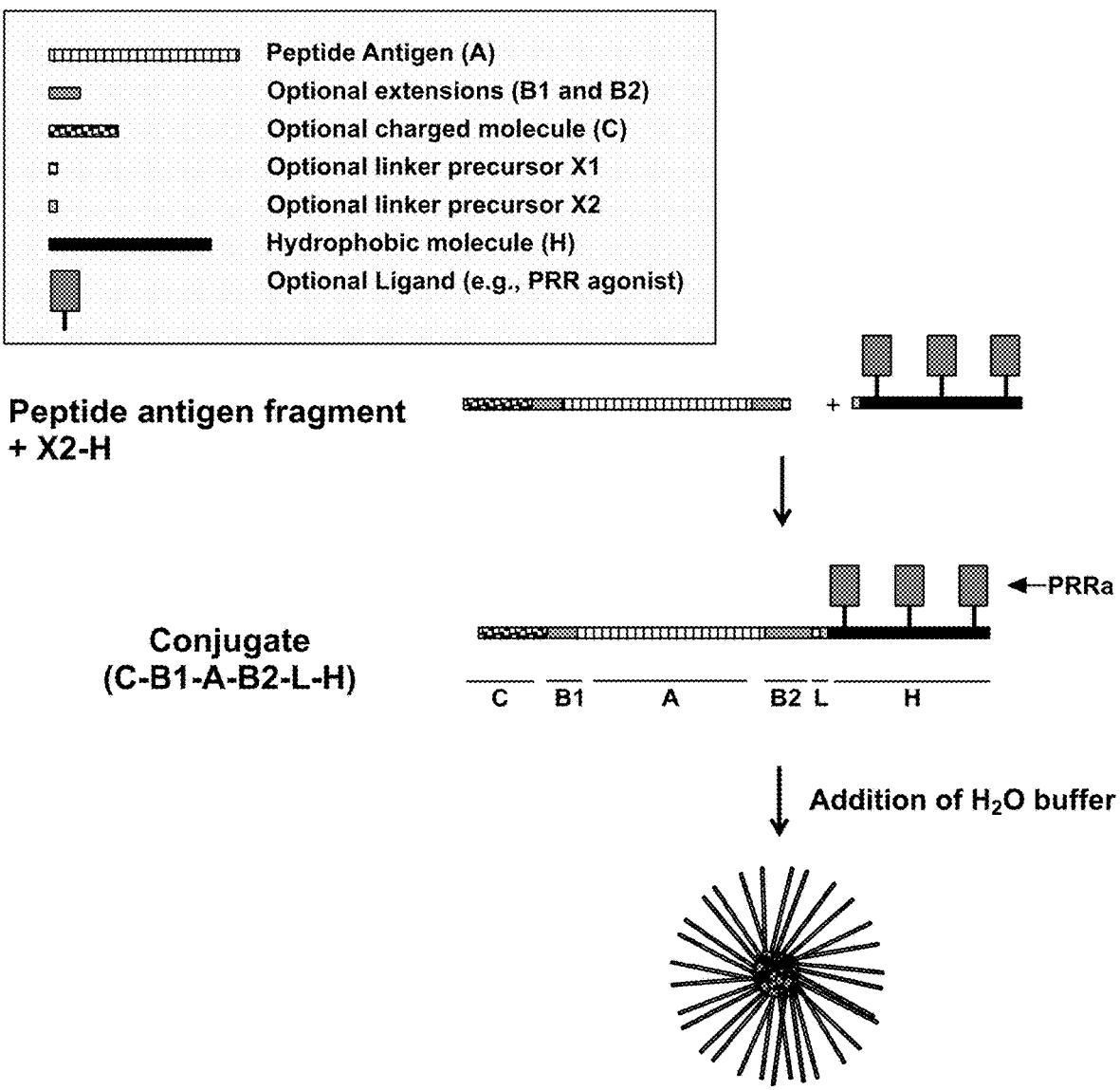
FIG. 1: Cartoon schematic of certain embodiments of peptide antigen conjugates

Details of terms and methods are given below to provide greater clarity concerning compounds, compositions, methods and the use(s) thereof for inducing an immune response in a subject for the purpose of guiding those of ordinary skill in the art in the practice of the present disclosure. The terminology in this disclosure is understood to be useful for the purpose of providing a better description of particular embodiments and should not be considered limiting.

About: In the context of the present disclosure, "about" means plus or minus 5% from a set amount. For example, "about 10" refers to 9.5 to 10.5. A ratio of "about 5:1" refers to a ratio from 4.75:1 to 5.25:1.

Adjuvant: Any material added to vaccines to enhance or modify the immunogenicity of an antigen. Adjuvants can be delivery systems, such as particles based on inorganic salts (e.g., aluminum hydroxide or phosphate salts referred to as alum), water-in-oil or oil-in-water emulsions or polymer particles (e.g., PLGA) in which antigen is simply admixed with or adsorbed, incorporated within or linked indirectly or directly through covalent interactions. Alternatively, adjuvants can be chemically defined molecules that bind to defined receptors and induce downstream signaling pathways, including pattern recognition receptor (PRR) agonists, such as synthetic or naturally occurring agonists of Toll-like receptors (TLRs), stimulator of interferon genes (STING), nucleotide-binding oligomerization domain-like receptors (NLRs), retinoic acid-inducible gene-I-like receptors (RLRs) or C-type lectin receptors (CLRs), as wells as biological molecules (a "biological adjuvant"), such as IL-2, RANTES, GM-CSF, TNF-α, IFN-γ, G-CSF, LFA-3, CD72, B7-1, B7-2, OX-40L, 4-1BBL. Small molecule analogs of nucleotide bases, such as hydroxyadenine and imidazoquinolines, that bind to Toll-like receptors-7 (TLR-7) and TLR-7/8a, respectively, as well as agonists of TLR-2/6, TLR-4, STING and NOD are used as exemplary PRR agonists in the present disclosure. The person of ordinary skill in the art is familiar with adjuvants (see: Perrie et al., Int J Pharm 364:272-280, 2008 and Brito et al., Journal of controlled release, 190C:563-579, 2014). In general, any PRR agonist or biological adjuvant listed herein can be joined to the peptide antigen conjugate of the present disclosure through any suitable means.

Administration: To provide or give to a subject an agent, for example, an immunogenic composition comprising a peptide antigen conjugate as described herein, by any effective route.

Exemplary routes of administration include, but are not limited to, oral, injection (such as subcutaneous, intramuscular, intradermal, intraperitoneal, and intravenous), transdermal (for example, topical), intranasal, vaginal, and inhalation routes.

"Administration of" and "administering a" compound should be understood to mean providing a compound, a prodrug of a compound, or a pharmaceutical composition as described herein. The compound or composition can be administered by another person to the subject or it can be self-administered by the subject.

Antigen-presenting cell (APC): Any cell that presents antigen bound to MHC class I or class II molecules to T cells, including but not limited to monocytes, macrophages, dendritic cells, B cells, T cells and Langerhans cells.

Antigen: Any molecule that contains an epitope that binds to a T cell or B cell receptor and can stimulate an immune response, in particular, a B cell response and/or a T cell response in a subject. The epitopes may be comprised of peptides, glycopeptides, lipids or any suitable molecules that contain an epitope that can interact with components of specific B cell or T cell proteins. Such interactions may generate a response by the immune cell. "Epitope" refers to the region of a peptide antigen to which B and/or T cell proteins, i.e., B-cell receptors and T-cell receptors, interact.

Antigens use in embodiments of the present disclosure may be selected from pathogens, cancerous cells, autoantigens or allergens. In some embodiments, the antigen can be a peptide-based antigen that can include a region of a polypeptide or protein from a pathogen (such as a virus, bacteria, or fungi) or a tissue of interest (such as a cancerous cell). In other embodiments, the antigen can be a whole protein or glycoprotein derived from a pathogen, or a peptide or glycopeptide fragment of the protein or glycoprotein. In other embodiments, the antigen can be a protein, or peptide fragments of a protein, that is expressed primarily by tumor tissue (but not healthy tissue) and is a tumor-associated antigen. In other embodiments, the antigen is protein or peptide that is associated with auto-immunity. In still other embodiments, the antigen is a protein or glycoprotein that is associated with allergies.

Many such antigens may be used according to embodiments of the invention and are discussed in greater detail herein.

Aromatic: Aromatic compounds are unsaturated cyclic rings with an odd number of pairs of pi orbital electrons that are delocalized between the carbon or nitrogen atoms forming the ring. Aromatic amino acids include those with a side chain comprising an aromatic group, such as such as phenylalanine, tyrosine, or tryptophan. Benzene, a 6-carbon ring containing three double bounds is a prototypical aromatic compound. Phenylalanine (Phe) and Tryptophan (Trp) are prototypical aromatic amino acids. Aryl may refer to an aromatic substituent and aryl-amine may refer to an aromatic group comprising an amine. An exemplary aromatic amine is aniline. Aromatic heterocycles refer to aromatic rings comprising cyclic ring structures comprising carbon and another atom, such as nitrogen, oxygen or sulfur. Nucleotide bases, such as adenine and cytosine, are exemplary aromatic heterocycles.

Biocompatible: Materials are considered biocompatible if they exert minimal destructive or host response effects while in contact with body fluids, cells, or tissues.

A biocompatible group may contain chemical moieties, including from the following classes: aliphatic, alicyclic, heteroaliphatic, heteroalicyclic, aryl, or heteroaryl. However, depending on the molecular composition, such moieties are not always biocompatible.

The term "biocompatibility" is alternatively taken to mean either minimal interactions with recognition proteins and/or other components of biological systems (e.g., naturally occurring antibodies, cell proteins including glycoproteins, or cells); or substances and functional groups specifically intended to cause interactions with components of biological systems (e.g., drugs and prodrugs), such that the result of the interactions are not substantially negative or destructive.

CD4: Cluster of differentiation 4, a surface glycoprotein that interacts with MHC Class II molecules present on the surface of other cells. A subset of T cells express CD4 and these cells are commonly referred to as helper T cells.

CD8: Cluster of differentiation 8, a surface glycoprotein that interacts with MHC Class I molecules present on the surface of other cells. A subset of T cells express CD8 and these cells are commonly referred to as cytotoxic T cells or killer T cells.

Charge: A physical property of matter that affects its interactions with other atoms and molecules, including solutes and solvents. Charged matter experiences electrostatic force from other types of charged matter as well as molecules that do not hold a full integer value of charge, such as polar molecules. Two charged molecules of like charge repel each other, whereas two charged molecules of different charge attract each other. Charge is often described in positive or negative integer units.

Charged molecule (C): A charged molecule (C) refers to any molecule that has one or more functional groups that are positively or negatively charged. The functional groups comprising the charged molecule may be partial or full integer values of charge. A charged molecule may be a molecule with a single charged functional group or multiple charged functional groups. Functional groups may be permanently charged or the functional groups comprising the charged molecule may have charge depending on the pH. The charged molecule may be comprised of positively charged functional groups, negatively charged functional groups or both positive and negatively charged functional groups. The net charge of the charged molecule may be positive, negative or neutral. The charge of a molecule can be readily estimated based on a molecule's Lewis structure and accepted methods known to those skilled in the art. Charge may result from inductive effects, e.g., atoms bonded together with differences in electron affinity may result in a polar covalent bond resulting in a partially negatively charged atom and a partially positively charged atom. For example, nitrogen bonded to hydrogen results in partial negative charge on nitrogen and a partial positive charge on the hydrogen atom. Alternatively, an atom may be considered to have a full integer value of charge when the number of electrons assigned to that atom is less than or equal to the atomic number of the atom. The charge of a functional group is determined by summing the charge of each atom comprising the functional group. The net charge of the charged molecule (C) is determined by summing the charge of each atom comprising the molecule. Those skilled in the art are familiar with the process of estimating charge of a molecule, or individual functional groups, by summing the formal charge of each atom in a molecule or functional group, respectively.

Charged molecules (C) may comprise negatively charged functional groups such as those that occur as the conjugate base of an acid at physiologic pH (e.g., functional groups with a pKa less than about 6.5), e.g., at a pH of about 7.4. These include but are not limited to molecules bearing carboxylates, sulfates, phosphates, phosphoramidates, and phosphonates. Charged molecules may comprise positively charged functional groups such as those that occur as the conjugate acid of a base at physiologic pH (e.g., functional groups wherein the pKa of the conjugate acid of a base is greater than about 8.5). These include but are not limited to molecules bearing primary, secondary and tertiary amines, as well as ammonium, guanidinium. Charged molecules may comprise functional groups with charge that is pH independent, including quaternary ammonium, phosphonium and sulfonium functional groups. In some embodiments, the charged molecule is a poly(amino acid) comprised of negatively or positively charged amino acids, or both negatively and positively charged amino acids. In some embodiments, the negatively charged amino acid is glutamic acid or aspartic acid. In other embodiments, the positively charged amino acid is lysine or arginine. Those skilled in the art recognize that many such embodiments are possible.

Click chemistry reaction: May refer to a bio-orthogonal reaction that joins two compounds together under mild conditions in a high yield reaction that generates minimal, biocompatible and/or inoffensive byproducts. An exemplary click chemistry reaction used in the present disclosure is the reaction of an azide group provided on a linker precursor X1 with an alkyne provided on a linker precursor X2 that forms a triazole Linker (L) through strain-promoted [3+2] azide-alkyne cyclo-addition.

Effective amount: The amount needed to induce a desired response. For example, the amount of an agent, either alone or with one or more additional agents, needed to induce an immune response, for example, to a peptide antigen conjugate.

Extension(s): The term extension is used herein to describe molecules linked to the N- or C-terminus of the peptide antigen (A) that are comprised of amino acids, non-natural amino acids; hydrophilic ethylene oxides monomers (i.e., PEG); hydrophobic alkane chains; or combinations thereof and function to modulate the rate of degradation of the peptide antigen (A). Extensions linked to the N-terminus of the peptide antigen are referred to as B1 and extensions linked to the C-terminus of the peptide antigen are referred to as B2. The extensions (B1 and B2) principally function to control the rate of degradation of the peptide antigen but may perform any one or more additional functions. In some embodiments, extensions (B1 and/or B2) may be linked to another molecule, such as a charged molecule (C) or hydrophobic molecule (H) and function as a linker as well as control the rate of release of the peptide antigen (A) from the other molecule. In additional embodiments, extensions (B1 and/or B2) function to provide distance, i.e. space, between any two heterologous molecules. In other embodiments, extensions (B1 and/or B2) function to impart hydrophobic or hydrophilic properties on the peptide antigen conjugate. In still other embodiments, the compositions of the extensions (B1 and/or B2) used as a linker may be selected to impart rigidity or flexibility between the peptide antigen (A) and a heterologous molecule. In preferred embodiments, extensions (B1 and/or B2) are peptide sequences that are selected for recognition and hydrolysis by enzymes, such as proteases. Note that the B1 and B2 extensions may also be referred to as B1 and B2 linkers or $B_1$ and $B_2$, respectively. Specific compositions of extensions that would be suitable for the practice of the present disclosure are described throughout.

Graft polymer: May be described as a polymer that results from the linkage of a polymer of one composition to the side chains of a second polymer of a different composition. A first polymer linked through co-monomers to a second polymer is a graft co-polymer. A first polymer linked through an end group to a second polymer may be described as a block polymer (e.g., A-B type di-block) or an end-grafted polymer.

Hydropathy index/GRAVY value: Is a number representing the hydrophobic or hydrophilic characteristics of an amino acid. There are a variety of scales that can be used to describe the relative hydrophobic and hydrophilic characteristics of amino acids comprising peptides. In the present disclosure, the Hydropathy scale of Kyte and Doolittle (Kyte J, Doolittle R F, J. Mol. Biol 157: 105-32, 1983) is used to calculate the grand average of hydropathy (GRAVY) value, sometimes referred to as the GRAVY score, of the sequence of amino acids comprising peptide antigen conjugates, including the peptide antigen (A), peptide-based N- and C-terminal optional extensions (B1 and B2) and the optional charged molecule (C). The GRAVY value of a peptide is the sum of the Hydropathy values of all amino acids comprising the peptide divided by the length (i.e. number of amino acids) of the peptide. The GRAVY value is a relative value. The larger the GRAVY value, the more hydrophobic a peptide sequence is considered, whereas the lower the GRAVY value, the more hydrophilic a peptide sequence is considered.

Hydrophilic: Refers to the tendency of a material to disperse freely in aqueous media. A material is considered hydrophilic if it has a preference for interacting with other hydrophilic material and avoids interacting with hydrophobic material. In some cases, hydrophilicity may be used as a relative term, e.g., the same molecule could be described as hydrophilic or not depending on what it is being compared to. Hydrophilic molecules are often polar and/or charged and have good water solubility, e.g., are soluble up to 0.1 mg/mL or more.

Hydrophobic: Refers to the tendency of a material to avoid contact with water. A material is considered hydrophobic if it has a preference for interacting with other hydrophobic material and avoids interacting with hydrophilic material. Hydrophobicity is a relative term; the same molecule could be described as hydrophobic or not depending on what it is being compared to. Hydrophobic molecules are often non-polar and non-charged and have poor water solubility, e.g., are insoluble down to 0.1 mg/mL or less.

Hydrophobic ligand: Is a molecule that binds to biological receptors and has hydrophobic characteristics. In some embodiments, hydrophobic ligands are arrayed along the backbone of a polymer thereby imparting hydrophobic properties to the polymer to which it is linked. In some embodiments, the hydrophobic ligand is a pattern recognition receptor agonist that has limited water solubility and may therefore be described as hydrophobic. In additional embodiments, the hydrophobic ligand is a TLR-7 or TLR-7/8 agonist, such as an imidazoquinoline.

Hydrophobic molecule (H): In the present disclosure, the term "hydrophobic molecule" (H) is used as a general term to describe a molecule with limited water solubility, or amphiphilic characteristics, that can be linked to peptide antigens resulting in a peptide antigen conjugate that forms particles in aqueous conditions. The hydrophobic molecule (H) in this context promotes particle assembly due to its poor solubility, or tendency to assemble into particles, in aqueous conditions over certain temperatures and pH ranges.

Hydrophobic molecules (H) as described herein are inclusive of amphiphilic molecules that may form supramolecular structures, such as micelles or bilayer-forming lamellar or multi-lamellar structures (e.g., liposomes or polymersomes), as well as compounds that are completely insoluble and form aggregates alone. The hydrophobic characteristics of the molecule may be temperature- and/or pH-responsive. In some embodiments, the hydrophobic molecule (H) is a polymer that is water soluble at low temperatures but is insoluble, or micelle-forming, at temperatures above, for example, 20° C., such as 20, 21, 22, 23, 24, 25, 26, 27, 28, 29, 30, 31, 32, 33, 34, 35, 36, 37, 38, 39 or 40° C. In other embodiments, the hydrophobic molecule (H) is a polymer that is water soluble at low pH, for example, at a pH below 6.5 but insoluble, for example, at a pH above 6.5. Examples of hydrophobic molecules (H) include but are not limited to fatty acids, cholesterol and its derivatives, long chain aliphatics, lipids and various polymers, such as polystyrene, poly(lactic-co-glycolic acid) (PLGA), as well as poly(amino acids) comprised of predominantly hydrophobic amino acids. In some embodiments, the hydrophobic molecule (H) is a hydrophilic polymer with multiple hydrophobic ligands attached. A variety of hydrophobic molecules useful for the practice of the present disclosure are disclosed herein.

Immune response: A change in the activity of a cell of the immune system, such as a B cell, T cell, or monocyte, as a result of a stimulus, either directly or indirectly, such as through a cellular or cytokine intermediary. In one embodiment, the response is specific for a particular antigen (an "antigen-specific response"). In one embodiment, an immune response is a T cell response, such as a CD4 T cell response or a CD8 T cell response. In one embodiment, an immune response results in the production of additional T cell progeny. In one embodiment, an immune response results in the movement of T cells. In another embodiment, the response is a B cell response, and results in the production of specific antibodies or the production of additional B cell progeny. In other embodiments, the response is an antigen-presenting cell response. "Enhancing an immune response" refers to co-administration of an adjuvant and an immunogenic agent, such as a peptide antigen, as part of a peptide antigen conjugate, wherein the adjuvant increases the desired immune response to the immunogenic agent compared to administration of the immunogenic agent to the subject in the absence of the adjuvant. In some embodiments, an antigen is used to stimulate an immune response leading to the activation of cytotoxic T cells that kills virally infected cells or cancerous cells. In some embodiments, an antigen is used to induce tolerance or immune suppression. A tolerogenic response may result from the unresponsiveness of a T cell or B cell to an antigen. A suppressive immune response may result from the activation of regulatory cells, such as regulatory T cells that downregulate the immune response, i.e. dampen then immune, response. Antigens administered to a patient in the absence of an adjuvant are generally tolerogenic or suppressive and antigens administered with an adjuvant are generally stimulatory and lead to the recruitment, expansion and activation of immune cells.

Immunogenic composition: A formulation of materials comprising an antigen and optionally an adjuvant that induces a measurable immune response against the antigen.

Ligand: Is a general term to describe any molecule that binds to a biological receptor. A pattern recognition receptor agonist is a specific type of Ligand that binds to a pattern recognition receptor and may also be referred to as an adjuvant or Ligand with adjuvant properties. For instance, a PRR agonist is a Ligand that binds to a PRR, such as a TLR. A Ligand that binds to a PRR (or PRRa) may also be referred to as an adjuvant, molecular adjuvant, adjuvant molecule or Ligand with adjuvant properties. A Ligand that has limited solubility in water may be to as a hydrophobic Ligand, while a ligand that is waster-soluble may be referred to as a hydrophilic Ligand. A hydrophobic ligand or hydrophilic ligand that has adjuvant properties may be referred to as a hydrophobic adjuvant or hydrophilic adjuvant, respectively.

Linked or coupled: The term "linked" or "coupled" means joined together, either directly or indirectly. A first moiety may be covalently or noncovalently linked to a second moiety. In some embodiments, a first molecule is linked by a covalent bond to another molecule. In some embodiments, a first molecule is linked by electrostatic attraction to another molecule. In some embodiments, a first molecule is linked by dipole-dipole forces (for example, hydrogen bonding) to another molecule. In some embodiments, a first molecule is linked by van der Waals forces (also known as London forces) to another molecule. A first molecule may be linked by any and all combinations of such couplings to another molecule.

The molecules may be linked indirectly, such as by using a linker. The molecules may be linked indirectly by interposition of a component that binds non-covalently to both molecules independently.

As used herein, "linked" and variations thereof, refer to maintaining molecules in chemical or physical association, including after immunization, at least until they contact a cell, particularly an immune cell.

In some embodiments, linked components are associated so that the components are not freely dispersible from one another, at least until contacting a cell, such as an immune cell. For example, two components may be covalently linked to one another so that the two components are incapable of separately dispersing or diffusing. In preferred embodiments, peptide antigen conjugates are comprised of peptide antigens (A) that are covalently linked to a hydrophobic molecule (H) or Particle (P) either directly or indirectly via an extension (B1 or B2). Peptide antigen conjugates comprising a hydrophobic molecule (H) assemble into particles in aqueous conditions, wherein two or more peptide antigen conjugates associate to form a stable wherein the individual peptide antigen conjugates and components comprising the peptide antigen conjugates are incapable of dispersing or diffusing prior to encountering a cell, such as an immune cell.

Linking is specifically distinguished from a simple mixture of antigen and adjuvant such as may be found, for example, in a conventional vaccine, for example a vaccine that contains a water-soluble peptide antigen mixed with an adjuvant. In a simple mixture, the components can be free to independently disperse within the vaccinated tissue and beyond.

Linkers, linker precursors and the Linker (L): A linker is a molecule or group of atoms that links or couples or joins together two or more moieties. The peptide antigen conjugates disclosed herein are complex molecules that comprise multiple different functional components (peptide antigen (A), hydrophobic molecule (H) or Particle (P), optional extensions (B1 and/or B2), optional charged molecule (C), optional Linker (L), or optional adjuvant(s), etc.) that may be linked, or joined together, through any suitable means. For example, a peptide antigen (A) that is linked to a hydrophobic molecule (H) may use a linker between the peptide antigen (A) and the hydrophobic molecule (H). The peptide antigen (A) may be linked to the hydrophobic molecule (H) or Particle (P) either directly or indirectly through the Linker (L), extensions (B1 or B2) or the charged molecule (C) through any suitable means, including any suitable linker. In some embodiments, the linker is covalently attached to both the moieties being coupled. In some embodiments, linkers are bifunctional, meaning the linker includes a functional group at two sites, wherein the functional groups are used to couple the linker to the two moieties. The two functional groups may be the same (which would be considered a homobifunctional linker) or different (which would be considered a heterobifunctional linker). For example, in some embodiments, a linker precursor X2 comprising a hetero-bifunctional linker further comprising an alkyne and an acid is used to link a hydrophobic molecule (H) bearing an amine and a peptide antigen (A) linked to a linker precursor X1 that bears an azide; the acid and alkyne of the linker precursor X2 are reacted to form amide and triazole bonds with the amine and azide respectively, thus linking the two heterologous molecules. In some embodiments, the linker precursor X2 comprising a heterobifunctional linker is a dibenzocyclooctyne (DBCO) molecule linked to an acid. In other embodiments, the linker precursor is an acid linked to a maleimide that joins an amine and thiol or a bis(carboxylic acid) that joins two amines. In still other embodiments, a tri- or multi-functional linker may be used, wherein the linkages are the same or different. In other embodiments, a cleavable N- or C-terminal peptide extension (B1 or B2) is used to link a peptide antigen (A) to a hydrophobic molecule (H). In some embodiments, the cleavable peptide extension (B1 or B2) is heterobifunctional, e.g., an N-terminal amine of a B2 extension is linked to the C-terminus of the peptide antigen (A) and the C-terminal carboxyl group of the B2 extension is linked directly to a hydrophobic molecule (H). An extension (B1 or B2) may function as a linker but not all linkers are extensions.

Linkers (L) are specific subsets of linkers that result from the reaction of the linker precursor X1 with the linker precursor X2 and function specifically to join the peptide antigen (A) to a hydrophobic molecule (H) or Particle (P) either directly or indirectly through an extension (B1 or B2) or charged molecule (C). Linkers perform the specific function of site-selectively coupling, i.e. joining or linking together the peptide antigen (A) with a hydrophobic molecule (H) or a Particle (P). A linker precursor X1 may be linked to a peptide antigen directly or indirectly through an extension (B1 or B2) typically during solid-phase peptide synthesis. Note that the linker precursor X1 linked directly to the N- or C-terminus of the peptide antigen (A) are not considered extensions as they do not specifically function to modulate the rate of degradation of the peptide antigen. While the linker precursor X1 may have some impact on the rate of the degradation of the peptide antigen (A), the linker precursor X1 is not selected to modulate the rate of degradation of the peptide antigen (A) or its release from other molecules and instead functions specifically to join the peptide antigen (A) to the hydrophobic molecule (H) or particle (P).

In some embodiments, a linker precursor X1 can be linked to a peptide antigen (A) during solid phase peptide synthesis; the linkage can be direct, or indirect via an extension (B1 or B2), including a degradable peptide linker. Typically, the linker precursor X1 linked directly or indirectly to the peptide antigen (A) is selected to promote a bio-orthogonal reaction with a linker precursor X2 provided on a hydrophobic molecule (H) or Particle (P). Bio-orthogonal reactions permit site-selective linkage of the peptide antigen (A) to the hydrophobic molecule (H) or Particle (P) without resulting in the modification of any amino acids comprising the peptide antigen (A). Preferred linker precursors X1 that permit bio-orthogonal reactions include those bearing azides or alkynes. Additional linker precursors X1 that permit site-selective reactivity, depending on the composition of the antigen, include thiols, hydrazines, ketones and aldehydes. In several embodiments, the linker precursor has an azide functional group. In some embodiments, the linker precursor X1 is a non-natural amino acid bearing an azide, for example, azido-lysine $Lys(N_3)$. In such embodiments, a peptide antigen (A) linked to the linker precursor X1 bearing an azide functionality may react with an alkyne bearing linker precursor X2 provided on a hydrophobic molecule (H) resulting in the formation of a triazole Linker that joins the peptide antigen (A) and the hydrophobic molecule (H). Various linker precursors (X1 and X2) and Linkers are described throughout Herein, the Linker and the linker precursor X1 may both be referred to as a Tag (T), though, the context of the Tag (T)

is used to discern whether the Tag (T) is a Linker or linker precursor (X1). A Tag (T) that is linked to a peptide antigen (A) either directly or indirectly through either the optional extension (B1 or B2) or the optional charged molecule (C) but is not linked to a hydrophobic molecule (H) or Particle (P), may also be referred to as a linker precursor X1. A Tag (T) that links the peptide antigen (A) to a hydrophobic molecule (H) or Particle (P) may also be referred to as a Linker (L). The linker precursor X2 reacts with the linker precursor X1 to form a Linker. The linker precursor X1 may sometimes be referred to as a Tag and the linker precursor X2 may be referred to as a tag reactive moiety or tag reactive molecule comprising a functional group that is specific or reactive towards the Tag.

Net charge: The sum of electrostatic charges carried by a molecule or, if specified, a section of a molecule.

Particle: A nano- or micro-sized supramolecular structure comprised of an assembly of molecules. Peptide antigen conjugates of the present disclosure comprise either peptide antigens (A) linked to pre-formed Particles (P) or hydrophobic molecules (H) that assemble into micelles or other supramolecular structures. Particles comprising peptide antigen conjugates can be taken up into cells (e.g., immune cells, such as antigen-presenting cells). In some embodiments, the peptide antigen conjugate forms a particle in aqueous solution. In some embodiments, particle formation by the peptide antigen conjugate is dependent on pH or temperature. In some embodiments, the nanoparticles comprised of peptide antigen conjugates have an average diameter between 5 nanometers (nm) to 500 nm. In some embodiments, the nanoparticles comprised of peptide antigen conjugates may be larger than 100 nm. In some embodiments, the nanoparticles comprised of peptide antigen conjugates are included in larger particle structures that are too large for uptake by immune cells (e.g., particles larger than about 5000 nm) and slowly release the smaller nanoparticles comprising the peptide antigen conjugate In some embodiments, the peptide antigen conjugates comprising a hydrophobic molecule (H) form nanoparticles. The nanoparticles form by association of peptide antigen conjugates through hydrophobic interactions and may therefore be considered a supramolecular assembly. In some embodiments, the nanoparticle is a micelle. In preferred embodiments, the nanoparticle micelles are between about 5 to 50 nm in diameter. In some embodiments, the peptide antigen conjugate forms micelles and the micelle formation is temperature-, pH- or both temperature- and pH-dependent. In some embodiments, the disclosed nanoparticles comprise peptide antigen conjugates that are comprised of peptide antigens (A) linked to a hydrophobic molecule (H) comprised of polymers linked to a Ligand with adjuvant properties, e.g. a PRR agonist; linking the peptide antigen together with the PRR agonist in the nanoparticles prevents the PRR agonist from dispersing freely following administration to a subject thereby preventing systemic toxicity.

The particle may be formed by an assembly of individual molecules comprising the peptide antigen conjugates, or in the case of a peptide antigen conjugate comprised of a peptide antigen (A) linked to a pre-formed Particle (P), the particle may be cross-linked through covalent or non-covalent interactions.

Pre-formed Particle (P)/Particle (P) of a formula: The pre-formed Particle (P) or simply 'Particle' (P) describes a Particle that is already formed prior to linkage to a peptide antigen (A). Thus, Particle (P) is used to describe the Particle of a formula and is distinct from the particles formed by assembly of two or more peptide antigen conjugates comprising a hydrophobic molecule (H). For clarity, the particles formed by the assembly of peptide antigens conjugates are distinct from pre-formed Particles (P) or Particles (P) of a formula. In some embodiments, a peptide antigen (A) can be linked directly or indirectly to a Particle (P) to form a peptide antigen conjugate, and the peptide antigen conjugate can be a particle in aqueous conditions.

To delineate between particles formed by peptide antigen conjugates and pre-formed Particles (P), the letter p is always capitalized in 'Particle' followed by a parenthetical capital 'P', i.e., "Particle (P)," when referring to a pre-formed Particle or Particle (P) of a formula. In some embodiments, the Particle (P) may be a PLGA Particle (P) that is formed in aqueous conditions and then linked to a peptide antigen (A) to form a peptide antigen conjugate that remains as particles in aqueous conditions. In some embodiments, the Particle (P) may be comprised of lipids, such as a liposomal Particle (P), that is formed in aqueous conditions and then linked to peptide antigens (A) to form a peptide antigen conjugate that remain as particles in aqueous conditions.

Pattern recognition receptors (PRRs): Receptors expressed by various cell populations, particularly innate immune cells that bind to a diverse group of synthetic and naturally occurring molecules referred to as pathogen-associated molecular patterns (PAMPS) as well as damage associated molecular patterns (DAMPs). PAMPs are conserved molecular motifs present on certain microbial organisms and viruses. DAMPs are cellular components that are released or expressed during cell death or damage.

PAMP or DAMP activation of pattern recognition receptors induces an intracellular signaling cascade resulting in the alteration of the host cell's physiology. Such physiological changes can include changes in the transcriptional profile of the cell to induce expression of a range of pro-inflammatory and pro-survival genes. The coordinated expression of these genes may enhance adaptive immunity.

There are several classes of PRRs. Non-limiting examples of PRRs include Toll-like receptors (TLRs), RIG-I-like receptors (RLRs), NOD-like receptors (NLRs), Stimulator of Interferon Genes receptor (STING), and C-type lectin receptors (CLRs). Agonists of such PRRs can be used to enhance an immune response to a target antigen.

Agonists of PRRs are adjuvants and may be referred to as Ligands or Ligands with adjuvant properties. In some embodiments of the present disclosure, PRR agonists are used as adjuvants to enhance the immune response to a peptide antigen.

Toll-like receptors (TLRs) 1-13 are transmembrane PRRs that recognize a diverse range of PAMPs. There are two broad categories of TLRs: those that are localized to the cell surface and those that are localized to the endosomal lumen. TLRs that are present on the cell surface are typically important in recognition of bacteria. TLRs that are localized to the lumen of endosomes, such as TLRs 3, 7, 8, and 9, serve to recognize nucleic acids and are thus typically important in recognition of viruses and therefore in the promotion of antiviral immune responses. Polyinosinic-polycytidylic acid is a ligand for TLR-3. TLR-7 and TLR-8 recognize single stranded RNA as well as nucleotide base analogs and imidazoquinolines. TLR-9 recognizes unmethylated deoxycytidylate-phosphate-deoxyguanylate (CpG) DNA, found primarily in bacteria.

The NOD-like receptors (NLRs) and the RIG-I-like receptors (RLRs) are localized to the cytoplasm. Non-limiting examples of RLRs include RIG-I, MDA5, and LGP2. There are 22 human NLRs that can be subdivided into the five structurally related NLR families A, B, C, P, and X. All NLRs have three domains: an N-terminal domain involved in signaling, a nucleotide-binding NOD domain, and a C-terminal leucine rich region (LRR) important for ligand recognition. Non-limiting examples of NLRs include NALP3 and NOD2.

For more information on pattern recognition receptors, see Wales et al., Biochem Soc Trans., 35:1501-1503, 2007.

Peptide or polypeptide: Two or more natural or non-natural amino acid residues that are joined together through an amide bond. The amino acid residues may contain post-translational modification(s) (e.g., glycosylation and/or phosphorylation). Such modifications may mimic post-translational modifications that occur naturally in vivo or may be non-natural. Any one or more of the components of the peptide antigen conjugate may be comprised of peptides.

There is no conceptual upper limit on the length of a peptide. The length of the peptide is typically selected depending on the application. In several embodiments, the hydrophobic molecule (H) is comprised of a peptide that can be between 3 to 1,000 amino acids in length, typically no more than 300 amino acids in length. In some embodiments, the N- and/or C-terminal extension (B1 and/or B2) is a peptide between about 1 to 8 amino acids in length. In some embodiments, the charged molecule (C) is a peptide comprised of positively, negatively or both positively and negatively charged amino acids and is typically no more than 16 amino acids in length.

In preferred embodiments, the peptide antigen (A) is a peptide between 5 to about 50 amino acids, typically about 7 to 35 amino acids, such as 7, 8, 9, 10, 11, 12, 13, 14 15, 16, 17, 18, 19, 20, 21, 22, 23, 24, 25, 26, 27, 28, 29, 30, 31, 32, 33, 34, 35 amino acids. In other embodiments, the peptide antigen (A) is about 50 amino acids or more in length. Thus, in some embodiments, the peptide antigen (A) may be considered a protein.

Note that the peptide antigen (A) may be a minimal epitope (sometimes referred to as min or ME) or long peptide (sometimes referred to as an LP or SLP) that comprises a minimal epitope. Therefore it is understood that when a minimal epitope or long peptide is said to be delivered as a peptide antigen conjugate, then the minimal epitope or the long peptide is the peptide antigen (A), unless stated otherwise.

In some embodiments, the optional charged molecule (C), antigen (A), optional extensions (B1 and B2), and linker precursor X1 are amino acids and may be prepared by solid phase peptide synthesis as a contiguous peptide sequence that is sometimes referred to as a "peptide antigen fragment." Note that calculation of the net charge or GRAVY of the peptide antigen fragment does not include the linker precursor X1.

Peptide sequences referring to the peptide antigen are designated as "PA", peptide sequences referring to the N-terminal extension (B1) are designated as "PN", and peptide sequences referring to the C-terminal extension (B2) are designated as "PC". Sequences of amino acids comprising peptide antigens (A) are represented by the formula, PA1 . . . PAn, where PA represents any amino acid residue comprising a peptide antigen (A) and n is an integer value. For example, an 8-amino acid peptide antigen (A) may be represented as PA1-PA2-PA3-PA4-PA5-PA6-PA7-PA8. Sequences of amino acids comprising N-terminal extensions (B1) are represented by the formula, PN . . . PNn, where PN represents any amino acid residue comprising an N-terminal extension and n is an integer value. Sequences of amino acids comprising C-terminal extensions (B2) are represented by the formula, PC1 . . . PCn, where PC represents any amino acid residue comprising a C-terminal extension and n is an integer value.

Peptide Modifications: Peptides may be altered or otherwise synthesized with one or more of several modifications as set forth below. In addition, analogs (non-peptide organic molecules), derivatives (chemically functionalized peptide molecules obtained starting from a peptide) and variants (homologs) of these peptides can be utilized in the methods described herein. The peptides described herein are comprised of a sequence of amino acids, analogs, derivatives, and variants, which may be either L- and/or D-versions. Such peptides may contain peptides, analogs, derivatives, and variants that are naturally occurring and otherwise.

Peptides can be modified through a variety of chemical techniques to produce derivatives having essentially the same activity as the unmodified peptides, and optionally having other desirable properties. For example, carboxylic acid groups of the peptide, whether at the carboxyl terminus or at a side chain, can be provided in the form of a salt of a pharmaceutically-acceptable cation or esterified to form a $CC_1$—$CC_{16}$ ester, wherein CC refers to a carbon chain (and thus, CC1 refers to a single carbon and CC16 refers to 16 carbons), or converted to an amide. Amino groups of the peptide, whether at the amino terminus or at a side chain, can be in the form of a pharmaceutically-acceptable acid addition salt, such as the HCl, HBr, acetic, trifluoroacetic, formic, benzoic, toluene sulfonic, maleic, tartaric and other organic salts, or can be modified or converted to an amide.

An amino acid can be modified such that it contains through a covalent linkage a PRR agonist, such as TLR agonist, e.g., an imidazoquinoline-based TLR-7 or TLR-7/8 agonist.

Peptides may be modified to contain substituent groups that contain a positive or negative charge or both. The positive and/or negative charge may be affected by the pH at which the peptide is present.

Hydroxyl groups of the peptide side chains may be converted to $CC_1$—$CC_{16}$ alkoxy or to a $CC_1$—$CC_{16}$ ester using well-recognized techniques, or the hydroxyl groups may be converted (e.g., sulfated or phosphorylated) to introduce negative charge. Phenyl and phenolic rings of the peptide side chains may be substituted with one or more halogen atoms, such as fluorine, chlorine, bromine or iodine, or with $CC_1$—$CC_{16}$ alkyl, $CC_1$—$CC_{16}$ alkoxy, carboxylic acids and esters thereof, or amides of such carboxylic acids. Methylene groups of the peptide side chains can be extended to homologous $CC_2$—$CC_4$ alkylenes. Thiols can be used to form disulfide bonds or thioethers, for example through reaction with a maleimide. Thiols may be protected with any one of a number of well-recognized protecting groups, such as acetamide groups. Those skilled in the art will also recognize methods for introducing cyclic structures into the peptides of this invention to select and provide conformational constraints to the structure that result in enhanced stability. Reference may be made to Greene et al., "Greene's Protective Groups in Organic Synthesis" Fourth Edition, John Wiley & Sons, Inc. 2006 for details of additional modifications that can be made to functional groups.

Peptidomimetic and organomimetic embodiments of the peptide antigen (A) are envisioned, whereby the three-dimensional arrangement of the chemical constituents of such peptido- and organomimetics mimic the three-dimensional arrangement of the peptide backbone and component amino acid side chains, resulting in such peptido- and organomimetics of an immunogenic peptide having measurable ability to induce tolerance or immune suppression, or enhanced ability to generate a stimulatory immune response, such as cytotoxic T cell or antibody response.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, PA, 15th Edition (1975), describes compositions and formulations suitable for pharmaceutical delivery of one or more therapeutic compositions, such as one or more therapeutic cancer vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional nontoxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polar: A description of the properties of matter. Polar is a relative term, and may describe a molecule or a portion of a molecule that has partial charge that arises from differences in electronegativity between atoms bonded together in a molecule, such as the bond between nitrogen and hydrogen. Polar molecules have a preference for interacting with other polar molecules and typically do not associate with non-polar molecules. In specific, non-limiting cases, a polar group may contain a hydroxyl group, or an amino group, or a carboxyl group, or a charged group. In specific, non-limiting cases, a polar group may have a preference for interacting with a polar solvent such as water. In specific, non-limiting cases, introduction of additional polar groups may increase the solubility of a portion of a molecule.

Polymer: A molecule containing repeating structural units (monomers). As described in greater detail throughout the disclosure, polymers may be used for any number of components of the peptide antigen conjugate and may be natural or synthetic. In preferred embodiments, a hydrophobic or amphiphilic polymer is used as the hydrophobic molecule (H) and drives particle assembly of the peptide antigen conjugates. In some embodiments, the peptide antigen (A) is a polymer comprising amino acids. In some embodiments, the extensions (B1 and B2) comprise polymers, such as, for example, PEG, poly(amino acids) or combinations thereof. The polymers included in the disclosed embodiments can form polymer nanoparticles that can be administered to a subject without causing adverse side effects. The polymers included in the disclosed embodiments can form polymer nanoparticles that can be administered to a subject to cause an immune response or to treat and/or ameliorate a disease. The polymers included in the disclosed embodiments may include a side chain with a functional group that can be utilized, for example, to facilitate linkage to an adjuvant or a molecule used to induce immune suppression or tolerance, such as macrolides, e.g., rapamycin. In several embodiments, the polymer can contain two or more polymer blocks linked through a linker to create a block co-polymer, such as an amphiphilic di-block co-polymer. In several embodiments, a polymer block may be predominantly hydrophobic in character. In several embodiments, the polymer consists of peptides, their analogs, derivatives, and variants. Various compositions of polymers useful for the practice of the invention are discussed in greater detail elsewhere.

Polymerization: A chemical reaction, usually carried out with a catalyst, heat or light, in which monomers combine to form a chainlike, or cross-linked, macromolecule (a polymer). The chains further can be combined by additional chemical synthesis using the appropriate substituent groups and chemical reactions. The monomers may contain reactive substances. Polymerization commonly occurs by addition or condensation. Addition polymerization occurs when an initiator, usually a free radical, reacts with a double bond in the monomer. The free radical adds to one side of the double bond, producing a free electron on the other side. This free electron then reacts with another monomer, and the chain becomes self-propagating, thus adding one monomer unit at a time to the end of a growing chain. Condensation polymerization involves the reaction of two monomers resulting in the splitting out of a water molecule. In other forms of polymerization, a monomer is added one at a time to a growing chain through the staged introduction of activated monomers, such as during solid phase peptide synthesis.

Purified: Having a composition that is relatively free of impurities or substances that adulterate or contaminate a substance. The term purified is a relative term and does not require absolute purity. Thus, for example, a purified peptide preparation is one in which the peptide or protein is more enriched than the peptide or protein is in its natural environment, for example, within a cell. In one embodiment, a preparation is purified such that the peptide antigen conjugate represents at least 50% of the total content of the preparation. Substantial purification denotes purification from other proteins or cellular components. A substantially purified protein is at least 60%, 70%, 80%, 90%, 95%, 98%, or 99% pure. Thus, in one specific, non-limiting example, a substantially purified protein is 90% free of other proteins or cellular components or contaminating peptides.

Soluble: Capable of becoming molecularly or ionically dispersed in a solvent to form a homogeneous solution. When referring to a peptide, a soluble peptide is understood to be a single molecule in solution that does not assemble into multimers or other supramolecular structures through hydrophobic or other non-covalent interactions. A soluble molecule is understood to be freely dispersed as single molecules in solution. In several embodiments, a peptide antigen can be a soluble peptide antigen that dissolves up to at least 0.1 mg/ml in phosphate buffered saline, pH 7.4 at room temperature. In other embodiments, a peptide antigen conjugate may be soluble in dimethylsulfoxide and/or other organic solvent(s) at room temperature, but may not be soluble in aqueous solvent(s), such as phosphate buffered saline, at pH 7.4 at room temperature. Hydrophobic molecules described herein are insoluble down to about 0.1 mg/mL. Solubility can be determined by visual inspection, by turbidity measurements or by dynamic light scattering.

Subject: Refers to both human and non-human animals, including birds and non-human mammals, such as rodents (for example, mice and rats), non-human primates (for example, rhesus macaques), companion animals (for example domesticated dogs and cats), livestock (for example pigs, sheep, cows, llamas, and camels), as well as non-domesticated animals (for example big cats).

Supramolecular: Refers to two or more molecules that associate through non-covalent interactions. In some embodiments, the molecules associate due to hydrophobic interactions. In some embodiments, the molecules associate due to electrostatic interactions. The association confers a new property to the supramolecular complex that was not shared by either of the constituent molecules, such as increased size, which affects the materials interactions with the immune system and different immune responses. For example, peptide antigen conjugates may aggregate to form supramolecular complexes.

T Cell: A type of white blood cell that is part of the immune system and may participate in an immune response. T cells include, but are not limited to, CD4 T cells and CD8 T cells. A CD4 T cell displays the CD4 glycoprotein on its surface and these cells are often referred to as helper T cells. These cells often coordinate immune responses, including antibody responses and cytotoxic T cell responses, however, CD4 T cells can also suppress immune responses or CD4 T cells may act as cytotoxic T cells. A CD8 T cell displays the CD8 glycoprotein on its surface and these cells are often referred to as cytotoxic or killer T cells, however, CD8 T cells can also suppress immune responses.

Telechelic: Is used to describe a polymer that has one or two reactive ends that may be the same or different. The word is derived from telos and chele, the Greek words for end and claw, respectively. A semi-telechelic polymer describes a polymer with only a single end group, such as a reactive functional group that may undergo additional reactions, such as polymerization. A hetero-telechelic polymer describes a polymer with two end groups, such as reactive functional groups, that have different reactive properties.

Herein, hydrophobic molecules (H) may be comprised of polymers with reactive groups at one or both ends. In some embodiments, an adjuvant is placed at one end of the polymer and the other end of the polymer may be reacted with a linker that is linked to a peptide antigen directly or indirectly through an extension (B1 or B2) or a Linker (L). In this example, the polymer is semi-telechelic with respect to the adjuvant, meaning the adjuvant is attached to only one end of the polymer chain comprising the hydrophobic molecule (H).

Treating, preventing, or ameliorating a disease: "Treating" refers to an intervention that reduces a sign or symptom or marker of a disease or pathological condition after it has begun to develop. For example, treating a disease may result in a reduction in tumor burden, meaning a decrease in the number or size of tumors and/or metastases, or treating a disease may result in immune tolerance that reduces systems associated with autoimmunity. "Preventing" a disease refers to inhibiting the full development of a disease. A disease may be prevented from developing at all. A disease may be prevented from developing in severity or extent or kind. "Ameliorating" refers to the reduction in the number or severity of signs or symptoms or marker of a disease, such as cancer.

Reducing a sign or symptom or marker of a disease or pathological condition related to a disease, refers to any observable beneficial effect of the treatment and/or any observable effect on a proximal, surrogate endpoint, for example, tumor volume, whether symptomatic or not. Reducing a sign or symptom associated with a tumor or viral infection can be evidenced, for example, by a delayed onset of clinical symptoms of the disease in a susceptible subject (such as a subject having a tumor which has not yet metastasized, or a subject that may be exposed to a viral infection), a reduction in severity of some or all clinical symptoms of the disease, a slower progression of the disease (for example by prolonging the life of a subject having a tumor or viral infection), a reduction in the number of relapses of the disease, an improvement in the overall health or well-being of the subject, or by other parameters well known in the art (e.g., that are specific to a particular tumor or viral infection). A "prophylactic" treatment is a treatment administered to a subject who does not exhibit signs of a disease or exhibits only early signs for the purpose of decreasing the risk or severity of developing pathology.

In one example, a desired response is to induce an immune response that leads to a reduction in the size, volume, rate of growth, or number (such as metastases) of a tumor in a subject. For example, the agent or agents can induce an immune response that decreases the size, volume, or number of tumors by a desired amount, for example by at least 5%, at least 10%, at least 15%, at least 20%, at least 25%, at least 30%, at least 50%, at least 75%, at least 90%, or at least 95% as compared to a response in the absence of the agent.

Tumor or cancer or neoplastic: An abnormal growth of cells, which can be benign or malignant, often but not always causing clinical symptoms. "Neoplastic" cell growth refers to cell growth that is not responsive to physiologic cues, such as growth and inhibitory factors.

A "tumor" is a collection of neoplastic cells. In most cases, tumor refers to a collection of neoplastic cells that forms a solid mass. Such tumors may be referred to as solid tumors. In some cases, neoplastic cells may not form a solid mass, such as the case with some leukemias. In such cases, the collection of neoplastic cells may be referred to as a liquid cancer.

Cancer refers to a malignant growth of neoplastic cells, being either solid or liquid. Features of a cancer that define it as malignant include metastasis, interference with the normal functioning of neighboring cells, release of cytokines or other secretory products at abnormal levels and suppression or aggravation of inflammatory or immunological response(s), invasion of surrounding or distant tissues or organs, such as lymph nodes, etc.

A tumor that does not present substantial adverse clinical symptoms and/or is slow growing is referred to as "benign."

"Malignant" means causing, or likely to cause in the future, significant clinical symptoms. A tumor that invades the surrounding tissue and/or metastasizes and/or produces substantial clinical symptoms through production and secretion of chemical mediators having an effect on nearby or distant body systems is referred to as "malignant."

"Metastatic disease" refers to cancer cells that have left the original tumor site and migrated to other parts of the body, for example via the bloodstream, via the lymphatic system, or via body cavities, such as the peritoneal cavity or thoracic cavity.

The amount of a tumor in an individual is the "tumor burden". The tumor burden can be measured as the number, volume, or mass of the tumor, and is often assessed by physical examination, radiological imaging, or pathological examination.

An "established" or "existing" tumor is a tumor that exists at the time a therapy is initiated. Often, an established tumor can be discerned by diagnostic tests. In some embodiments, an established tumor can be palpated. In some embodiments, an established tumor is at least 500 mm$^3$, such as at least 600 mm$^3$, at least 700 mm$^3$, or at least 800 mm$^3$ in size. In other embodiments, the tumor is at least 1 cm long. With regard to a solid tumor, an established tumor generally has a newly established and robust blood supply, and may have induced the regulatory T cells (Tregs) and myeloid derived suppressor cells (MDSC).

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The term "comprises" means "includes." Therefore, comprising "A" or "B" refers to including A, including B, or including both A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described herein. In case of conflict, the present specification, including explanations of terms, will control. In addition, the materials, methods, and examples are illustrative only and not intended to be limiting.

Immunogenic Compositions

Described herein are novel immunogenic compositions comprising particles that comprise a peptide antigen conjugate that further comprises a peptide antigen (A) linked to a Particle (P) or hydrophobic molecule (H). Peptide antigen conjugate refers to the compound that results from linking, e.g. covalently joining or otherwise, the peptide antigen (A) to the Particle (P) or hydrophobic molecule (H). The hydrophobic molecule (H) or Particle (P) induces the peptide antigen conjugate to assemble into particles that leads to an unexpected improvement in immune responses directed against the peptide antigen (A). The peptide antigen conjugate may additionally comprise an optional N-terminal extension (B1) and/or C-terminal extension (B2) linked to the N- and C-termini of the peptide antigen (A), respectively that provide unexpected improvements in manufacturing and biological activity; an optional charged molecule (C) that provides unexpected improvements in the stability of particles formed by peptide antigen conjugates, thereby leading to improved manufacturing and improved biological activity; and an optional Linker (L) that results from the reaction of linker precursor X1 linked to the peptide antigen (A) with the linker precursor X2 provided on the hydrophobic molecule (H) or Particle (P), thereby joining the peptide antigen (A) and hydrophobic molecule (H) and Particle (P) in an efficient process that leads to unexpected improvements in manufacturing efficiency of peptide antigen conjugates. The components comprising the peptide antigen conjugate may be linked through any suitable means and are described in greater detail throughout.

In some embodiments, the peptide antigen (A) is linked directly to a hydrophobic molecule (H) or Particle (P) to form a peptide antigen conjugate of the formula A-H or A-P. In other embodiments, the peptide antigen (A) is linked to a hydrophobic molecule (H) or Particle (P) through a Linker (L) to form a peptide antigen conjugate of the formula A-L-H or A-L-P. In still other embodiments, the peptide antigen (A) is linked to an extension (B1 or B2) that is linked either directly or through a Linker (L) to a hydrophobic molecule (H) or Particle (P) to form a peptide antigen conjugate of any one of the formulas, A-B2-H, A-B2-L-H, H-B1-A, H-L-B1-A, A-B2-P, A-B2-L-P, P-B1-A or P-L-B1-P. In some embodiments, the peptide antigen (A) is linked directly or through an extension (B1 and B2) to a linker precursor X1 to form a peptide antigen fragment of the formula, A-X1, A-B2-X1, X1-A or X1-B1-A, that reacts with a linker precursor X2 on a hydrophobic molecule (H) or Particle (P), i.e. X2-H or X2-P, to form a Linker (L) that joins the peptide antigen (A) to the hydrophobic molecule (H) or Particle (P), resulting in a peptide antigen conjugate of any one of the formulas, i.e. A-L-H, A-L-P, A-B2-L-H, A-B2-L-P, H-L-A, P-L-A, H-B1-A, or P-B1-A. In the present disclosure, such embodiments are shown to form particles in aqueous conditions that are shown to be useful for inducing an immune response in a subject.

In some embodiments, the peptide antigen (A) is linked to both extensions (B1 and B2). Such embodiments include peptide antigen conjugates of the formula B1-A-B2-H, B1-A-B2-L-H, B1-A-B2-P, B1-A-B2-L-P, H-B1-A-B2, H-L-B1-A-B2, P-B1-A-B2, or P-L-B1-A-B2. In the present disclosure, such embodiments are shown to form particles in aqueous conditions that are demonstrated to be useful for inducing an immune response in a subject.

In some embodiments, molecules that contain functional groups that impart electrostatic charge, i.e. charged molecules (C), are linked directly or indirectly through optional extensions (B1 and/or B2), the optional Linker (L) or the hydrophobic molecule (H) or Particle (P) to the peptide antigen (A). The charge imparted on the peptide antigen conjugate by the charged molecule stabilizes the supramolecular structures formed in aqueous conditions. Non-limiting examples of peptide antigen conjugates comprising charged molecules (C) include C-A-H, C-B1-A-H, C-A-B2-H, C-B1-A-B2-H, A-H(C), A-B2-H(C), B1-A-H(C), B1-A-B2-H(C), C1-A-H(C2), C1-A-B2-H(C2), C1-B1-A-H(C2), C1-B1-A-B2-H(C2), H-A-C, H-B1-A-C, H-A-B2-C, H-B1-A-B2-C, H(C)-A, H(C)—B1-A, H(C)-A-B2, H(C)—B1-A-B2, H(C1)-A-C2, H(C1)-B1-A-C2, H(C1)-A-B2-C2, H(C1)-B1-A-B2-C2, C-A-L-H, C-B1-A-L-H, C-A-B2-L-H, C-B1-A-B2-L-H, A-L-H(C), A-B2-L-H(C), B1-A-L-H(C), B1-A-B2-L-H(C), C1-A-L-H(C2), C1-A-B2-L-H(C2), C1-B1-A-L-H(C2), C1-B1-A-B2-L-H(C2), H-L-A-C, H-L-B1-A-C, H-L-A-B2-C, H-L-B1-A-B2-C, H(C)-L-A, H(C)-L-B1-A, H(C)-L-A-B2, H(C)-L-B1-A-B2, H(C1)-L-A-C2, H(C1)-L-B1-A-C2, H(C1)-L-A-B2-C2, H(C1)-L-B1-A-B2-C2, C-A-P, C-B1-A-P, C-A-B2-P, C-B1-A-B2-P, A-P(C), A-B2-P(C), B1-A-P(C), B1-A-B2-P(C), C1-A-P(C2), C1-A-B2-P(C2), C1-B1-A-P(C2), C1-B1-A-B2-P(C2), P-A-C, P-B1-A-C, P-A-B2-C, P-B1-A-B2-C, P(C)-A, P(C)—B1-A, P(C)-A-B2, P(C)—B1-A-B2, P(C1)-A-C2, P(C1)-B1-A-C2, P(C1)-A-B2-C2, P(C1)-B1-A-B2-C2, C-A-L-P, C-B1-A-L-P, C-A-B2-L-P, C-B1-A-B2-L-P, A-L-P(C), A-B2-L-P(C), B1-A-L-P(C), B1-A-B2-L-P(C), C1-A-L-P(C2), C1-A-B2-L-P(C2), C1-B1-A-L-P(C2), C1-B1-A-B2-L-P(C2), P-L-A-C, P-L-B1-A-C, P-L-A-B2-C, P-L-B1-A-B2-C, P(C)-L-A, P(C)-L-B1-A, P(C)-L-A-B2, P(C)-L-B1-A-B2, P(C1)-L-A-C2, P(C1)-L-B1-A-C2, P(C1)-L-A-B2-C2 or P(C1)-L-B1-A-B2-C2.

The charged molecule (C) stabilizes the particles formed by peptide antigen conjugates. The charged molecule (C) may be linked directly to the peptide antigen conjugate. Alternatively, the charged molecule (C) may be provided on a separate molecule that associates with the particles formed by peptide antigen conjugates. In some embodiments, the charged molecule (C) is linked to a hydrophobic molecule (H) to form a charged molecule conjugate of the formula C—H, or C-A'-H (wherein A' is a conserved antigen), that is mixed with a peptide antigen conjugate of the formula [C]—[B1]-A-[B2]-[L]-H, where [ ] denotes that the group is optional, in aqueous conditions and the resulting particles comprise C—H, or C-A'-H and the peptide antigen conjugate.

The hydrophobic molecule (H) may comprise any suitable molecule that induces the peptide antigen conjugate to assemble into particles in aqueous conditions. In some embodiments, the hydrophobic molecule (H) comprising a peptide antigen conjugate is a polymer with limited water solubility. In some embodiments, the hydrophobic molecule (H) is a temperature- or pH-responsive polymer that has limited water solubility at particular temperatures or pH values. In other embodiments, the hydrophobic molecule (H) is a lipid, fatty acid or cholesterol. Many hydrophobic molecules (H) are useful for the present disclosure and are described in greater detail throughout.

The particles formed by the peptide antigen conjugates disclosed herein are useful for inducing an immune response in a subject. In some embodiments, particles comprising peptide antigen conjugates that comprise a tumor-associated antigen are provided to a subject for inducing a T cell response, such as a cytotoxic CD4 or CD8 T cell response for the treatment or prevention of cancer. In some embodiments, particles comprising peptide antigen conjugates that comprise an infectious disease antigen are provided to a subject for inducing a T cell response, such as a cytotoxic CD4 or CD8 T cell response or antibody response for the treatment or prevention of an infectious disease. In some embodiments, particles comprising peptide antigen conjugates that comprise an auto-antigen are provided to a subject for inducing a tolerogenic or suppressive T cell response for the treatment of an auto-immune disease.

The peptide antigen conjugate comprises a peptide antigen (A), optional N- and/or C-terminal extensions (B1 and/or B2), optional Linker (L), Particle (P) or hydrophobic molecule (H) and optional charged molecule(s) (C). Each of these components are described below and in greater detail throughout.

Peptide Antigen (A)

The peptide antigen (A) may be any antigen that is useful for inducing an immune response in a subject. The peptide antigen (A) may be used to induce either a pro-inflammatory or tolerogenic immune response depending on the nature of the immune response required for the application. In some embodiments, the peptide antigen (A) is a tumor-associated antigen, such as a self-antigen, neoantigen or tumor-associated viral antigen (e.g., HPV E6/E7). In other embodiments, the peptide antigen (A) is an infectious disease antigen, such as a peptide derived from a protein isolated from a virus, bacteria, fungi or protozoan microbial pathogen. In still other embodiments, the peptide antigen (A) is a peptide derived from an allergen or an autoantigen, which is known or suspected to cause allergies or autoimmunity.

The peptide antigen (A) is comprised of a sequence of amino acids or a peptide mimetic that can induce an immune response, such as a T cell or B cell response in a subject. In some embodiments, the peptide antigen (A) comprises an amino acid or amino acids with a post-translational modification, non-natural amino acids or peptide-mimetics. The peptide antigen may be any sequence of natural, non-natural or post-translationally modified amino acids, peptide-mimetics, or any combination thereof, that have an antigen or predicted antigen, i.e. an antigen with a T cell or B cell epitope.

Immunogenic compositions may comprise one or more different peptide antigen conjugates each having a different peptide antigen (A) composition. In some embodiments, the immunogenic compositions comprise particles with up to 50 different peptide antigen conjugates each having a unique peptide antigen (A) composition. In some embodiments, the immunogenic compositions comprise mosaic particles that comprise 20 different peptide antigen conjugates. In other embodiments, the immunogenic compositions comprise mosaic particles that comprise 5 different peptide antigen conjugates. In some embodiments, the immunogenic compositions comprise 20 different particle compositions each assembled from a unique peptide antigen conjugate (i.e. each particle contains a single peptide antigen conjugate composition). In other embodiments, the immunogenic compositions comprise 5 different particle compositions each assembled from a unique peptide antigen conjugate (i.e. each particle contains a single peptide antigen conjugate composition). In still other embodiments, the immunogenic compositions comprise a single particle composition comprised of a single peptide antigen conjugate composition.

The length of the peptide antigen (A) depends on the specific application and is typically between about 5 to about 50 amino acids. In preferred embodiments, the peptide antigen (A) is between about 7 to 35 amino acids, e.g., 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids. In other embodiments, the peptide antigen is a fragment of a polypeptide. In still other cases, the peptide antigen is a full-length polypeptide, such as a protein antigen that may be recombinantly expressed. Peptide antigens (A) based on tumor-associated antigens, infectious disease antigens, allergens or auto-antigens may be delivered as the full-length sequence, though preferably no more than 50 amino acids in length. In preferred embodiments, the peptide antigen (A) is 7 to 35 amino acids, typically about 25. Thus, for a tumor-associated antigen, infectious disease antigen, allergen or auto-antigen greater than 25 amino acids in length, e.g., a 100 amino acid antigen, the antigen may be divided into 7 to 35 amino acid, e.g., 25 amino acid, peptide antigens (A) wherein each peptide antigen (A) contains a unique composition of amino acids; or, the peptide antigens (A) can be overlapping peptide pools wherein an antigen is divided into a set number of 7 to 35 amino acid, e.g., 25 amino acid, peptide antigens (A) that have overlapping sequences. For example, an overlapping peptide pool comprising a 100 amino acid antigen may be divided into eight 25 amino acid peptide antigens (A) that are each offset by 12 amino acids (i.e., each subsequent 25 amino acid peptide comprising a 100 amino acid peptide sequence starts at the $13^{th}$ amino acid position from the prior peptide). Those skilled in the art understand that many permutations exist for generating a peptide pool from an antigen.

In some embodiments, the peptide antigen (A) is a minimal CD8 or CD4 T cell epitope that comprises the portions of a tumor-associated antigen, infectious disease antigen, allergen or auto-antigen that are predicted in silico (or measured empirically) to bind MHC-I or MHC-II molecules. For tumor-associated antigens, the peptide antigen (A) that is a minimal CD8 or CD4 T cell epitope that is predicted in silico (or measured empirically) to bind MHC-I or MHC-II molecules should also be a sequence of amino acids that is unique to the tumor cell. Algorithms for predicting MHC-I or MHC-II binding are widely available (see Lundegaard et al., Nucleic Acids Res., 36:W509-W512, 2008 and http://www.cbs.dtu.dk/services/NetMHC/). In some embodiments of a personalized therapy for a particular subject (e.g., patient), the peptide antigen (A) comprising a peptide antigen conjugate may comprise a minimal CD8 T cell epitope from a tumor-associated antigen, infectious disease antigen, allergen or auto-antigen that is typically a 7-13 amino acid peptide that is predicted to have <1,000 nM binding affinity for a particular MHC-I allele that is expressed by that subject. In some embodiments of a personalized therapy for a particular subject (e.g., patient), the peptide antigen (A) may comprise a minimal CD4 T cell epitope from a tumor-associated antigen, infectious disease antigen, allergen or auto-antigen that is a 10-16 amino acid peptide that is predicted to have <1,000 nM binding affinity for a particular MHC-II allele that is expressed by that subject. In a preferred embodiment, when a minimal CD8 or CD4 T cell epitope cannot be identified for a tumor-associated antigen, infectious disease antigen, allergen or auto-antigen, or when the tumor-associated antigen, infectious disease antigen, allergen or auto-antigen contains multiple CD8 and CD4 T cell epitopes, the peptide antigen (A) may be between 16-35 amino acids may be up to 50 amino acids, e.g., up to 35 amino acids, up to 25 amino acids, or up to 20 amino acids, or up to 16 amino acids such that it may contain all possible CD8 or CD4 T cell epitopes.

In some embodiments of the present disclosure, the peptide antigen (A) is derived from tumor-associated antigens. Tumor-associated antigens can either be self-antigens that are present on healthy cells but are preferentially expressed by tumor cells, or neoantigens, which are aberrant proteins that are specific to tumor cells and are unique to individual patients. Suitable self-antigens include antigens that are preferentially expressed by tumor cells, such as CLPP, Cyclin-A1, MAGE-A1, MAGE-C1, MAGE-C2, SSX2, XAgE1b/GAGED2a, Melan-A/MART-1, TRP-1, Tyrosinase, CD45, glypican-3, IGF2B3, Kallikrein 4, KIF20A, Lengsin, Meloe, MUC5AC, surviving, prostatic acid phosphatase, NY-ESO-1 and MAGE-A3. Neoantigens arise from the inherent genetic instability of cancers, which can lead to mutations in DNA, RNA splice variants and changes in post-translational modification, all potentially leading to de novo protein products that are referred to collectively as neoantigens or sometimes predicted neoantigens. DNA mutations include changes to the DNA including nonsynonymous missense mutations, nonsense mutations, insertions, deletions, chromosomal inversions and chromosomal translocations, all potentially resulting in novel gene products and therefore neoantigens. RNA splice site changes can result in novel protein products and missense mutations can introduce amino acids permissive to post-translational modifications (e.g. phosphorylation) that may be antigenic. The instability of tumor cells can furthermore result in epigenetic changes and the activation of certain transcription factors that may result in selective expression of certain antigens by tumor cells that are not expressed by healthy, non-cancerous cells.

Peptide antigen conjugates used in personalized cancer vaccines should include peptide antigens (A) that comprise the portions of tumor-associated antigens that are unique to tumor cells. Peptides antigens (A) comprising neoantigens arising from a missense mutation should encompass the amino acid change encoded by 1 or more nucleotide polymorphisms. Peptides antigens (A) comprising neoantigens that arise from frameshift mutations, splice site variants, insertions, inversions and deletions should encompass the novel peptide sequences and junctions of novel peptide sequences. Peptides antigens (A) comprising neoantigens with novel post-translational modifications should encompass the amino acids bearing the post-translational modification(s), such as a phosphate or glycan. In preferred embodiments, the peptide antigen (A) comprises the 0-25 amino acids on either side flanking the amino acid change or novel junction that arises due to a mutation. In one embodiment, the peptide antigen (A) is a neoantigen sequence that comprises the 12 amino acids on either side flanking the amino acid change that arises from a single nucleotide polymorphism, for example, a 25 amino acid peptide, wherein the $13^{th}$ amino acid is the amino acid residue resulting from the single nucleotide polymorphism. In some embodiments, the peptide antigen (A) is a neoantigen sequence that comprises the 12 amino acids on either side flanking an amino acid with a novel post-translational modification, for example, a 25 amino acid peptide, wherein the $13^{th}$ amino acid is the amino acid residue resulting from the novel post-translational modification site. In other embodiments, the peptide antigen (A) is a neoantigen sequence that comprises 0-12 amino acids on either side flanking a novel junction created by an insertion, deletion or inversion. In some cases, the peptide antigen (A) comprising neoantigens resulting from novel sequences can encompass the entire novel sequence, including 0-25 amino acids on either side of novel junctions that may also arise.

Tumor-associated antigens suitable as peptide antigens (A) for immunogenic compositions of the present disclosure can be identified through various techniques that are familiar to one skilled in the art. Tumor-associated antigens can be identified by assessing protein expression of tumor cells as compared with healthy cells, i.e., non-cancerous cells from a subject. Suitable methods for assessing protein expression include but are not limited to immunohistochemistry, immunofluorescence, western blot, chromatography (i.e., size-exclusion chromatography), ELISA, flow cytometry and mass spectrometry. Proteins preferentially expressed by tumor cells but not healthy cells or by a limited number of healthy cells (e.g., CD20) are suitable tumor-associated antigens. DNA and RNA sequencing of patient tumor biopsies followed by bio-informatics to identify mutations in protein-coding DNA that are expressed as RNA and produce peptides predicted to bind to MHC-I or MHC-II alleles on patient antigen presenting cells (APCs), may also be used to identify tumor-associated antigens that are suitable as peptide antigens (A) for immunogenic compositions of the present disclosure.

In preferred embodiments, tumor-associated antigens suitable as peptide antigens (A) for immunogenic compositions are identified using mass spectrometry. Suitable peptide antigens (A) are peptides identified by mass spectrometry following elution from the MHC molecules from patient tumor biopsies but not from healthy tissues from the same subject (i.e., the peptide antigens are only present on tumor cells but not healthy cells from the same subject). Mass spectrometry may be used alone or in combination with other techniques to identify tumor-associated antigens. Those skilled in the art recognize that there are many methods for identifying tumor-associated antigens, such as neoantigens (see Yadav et al., Nature, 515:572-576, 2014) that are suitable as peptide antigens (A) for the practice of the disclosed invention.

In preferred embodiments, the tumor-associated antigens used as peptide antigens (A) are clonal or nearly clonal within the population of neoplastic cells, which may be considered heterogeneous in other respects.

Tumor-associated antigens selected for use as peptide antigens (A) in personalized cancer vaccination schemes may be selected based on mass spectrometry confirmation of peptide-MHC binding and/or in silico predicted MHC binding affinity and RNA expression levels within tumors. These data provide information on whether or not a tumor-associated antigen is expressed and presented by tumor cells and would therefore be a suitable target for T cells. Such criteria may be used to select the peptide antigens (A) used in a personalized cancer vaccine.

Personalized cancer vaccines based on immunogenic compositions may comprise one or more different peptide compositions each having a unique peptide antigen (A) composition. In some embodiments, personalized cancer vaccines may contain 10-50 different peptide antigen conjugate compositions that each has a unique peptide antigen (A). In preferred embodiments, immunogenic compositions comprise 20 different peptide antigen conjugates each comprising peptide antigens (A) of between 7-35 amino acids in length, such as 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acids, typically no more than 50. In a non-limiting example, immunogenic compositions comprised of particles formed from 20 different peptide antigen conjugates comprised of peptide antigens (A) 8 amino acids in length are used as a personalized cancer vaccine. In another non-limiting example, immunogenic compositions comprised of particles formed from 20 different peptide antigen conjugates comprised of peptide antigens (A) of 25 amino acids in length are used as a personalized cancer vaccine.

For patients with highly mutated tumors that have more than 50 tumor-associated neoantigens, a down-selection process may be used to select peptide antigens (A) for use in personalized cancer vaccines comprised of peptide antigen conjugates. In some embodiments, a down-selection process is used to select peptide antigens (A) comprising epitopes predicted to have the highest MHC binding affinity and RNA expression levels within tumor cells. Additional criteria may be applied for the selection of tumor-associated self-antigens or neoantigens. For example, predicted immunogenicity or predicted capacity of the peptide antigen (A) to lead to T cells that react with other self-antigens, which may lead to auto-immunity, are additional criteria considered. For instance, peptide antigens (A) that comprise tumor-associated antigens and have high predicted immunogenicity but also low potential to lead to auto-immunity are criteria used to select potential peptide antigens (A) for use in personalized cancer vaccines. In some embodiments, neoantigens that that would be expected to result in T cell or antibody responses that react with self-antigens found on healthy cells are not selected for use as peptide antigens (A). For patients with less than, for example, 20-50 predicted neoantigens, a down selection process may not be critical and so all 20-50 predicted neoantigens might be used as peptides antigens (A) in a personalized cancer vaccine.

Cancer vaccines may include peptide antigens (A) that comprise tumor-associated antigens that are patient-specific and/or tumor-associated antigens that are shared between patients. For example, the tumor-associated antigen can be a conserved self-antigen, such as NY-ESO-1 (testicular cancer) or gp100 (melanoma), or the antigen may be a cryptic epitope, such as Na17 (melanoma) that is not typically expressed by healthy cells but is conserved between patients. Immunogenic compositions of the present disclosure may include peptide antigens (A) that arise from so-called hot-spot mutations that are frequent mutations in certain genes or gene regions that occur more frequently than would be predicted by chance. Non-limiting examples of hot spot mutations include the V600E mutation in BRAF protein, which is common to melanoma, papillary thyroid and colorectal carcinomas, or KRAS G12 mutations, which are among the most common mutations, such as KRAS G12C. A number of suitable self-antigens as well as neoantigens that arise from hotspot mutations are known and are incorporated herein by reference: see Chang et al., Nature Biotechnology, 34:155-163, 2016; Vigneron, N., et al, Cancer Immunology, 13:15-20, 2013.

In some embodiments, the peptide antigen (A) can be from a hematological tumor. Non-limiting examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

In some embodiments, the peptide antigen (A) can be from a solid tumor. Non-limiting examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

In some embodiments, the peptide antigen (A) is a tumor-associated antigen from a breast cancer, such as a ductal carcinoma or a lobular carcinoma. In some embodiments, the peptide antigen (A) is a tumor-associated antigen from a prostate cancer. In some embodiments, peptide antigen (A) is a the tumor-associated antigen from a skin cancer, such as a basal cell carcinoma, a squamous cell carcinoma, a Kaposi's sarcoma, or a melanoma. In some embodiments, the peptide antigen (A) is a tumor-associated antigen from a lung cancer, such as an adenocarcinoma, a bronchiolaveolar carcinoma, a large cell carcinoma, or a small cell carcinoma. In some embodiments, the peptide antigen (A) is a tumor-associated antigen from a brain cancer, such as a glioblastoma or a meningioma. In some embodiments, the peptide antigen (A) is a tumor-associated antigen from a colon cancer. In some embodiments, the peptide antigen (A) is a tumor-associated antigen from a liver cancer, such as a hepatocellular carcinoma. In some embodiments, the peptide antigen (A) is a tumor-associated antigen from a pancreatic cancer. In some embodiments, peptide antigen (A) is a tumor-associated antigen from a kidney cancer, such as a renal cell carcinoma. In some embodiments, the peptide antigen (A) is a tumor-associated antigen from a testicular cancer.

In some embodiments, the peptide antigen (A) is a tumor-associated antigen derived from premalignant conditions, such as variants of carcinoma in situ, or vulvar intraepithelial neoplasia, cervical intraepithelial neoplasia, or vaginal intraepithelial neoplasia.

In some embodiments, the peptide antigen (A) is an antigen from an infectious agent, such as a virus, a bacterium, or a fungus. In additional embodiments, the peptide antigen (A) is a peptide or glycopeptide derived from an infectious agent; for example, the HIV Envelope fusion peptide or a V3 or V1/V2 glycopeptide from HIV.

In some embodiments, the peptide antigen (A) represents an auto-antigen. The auto-antigen may be identified and selected on the basis of screening a subject's own T cells for auto-reactivity against self-antigens presented in the context a patient's own MHC-I molecules. Alternatively, the peptide antigens may be selected using in silico methods to predict potential auto-antigens that (i) have a predicted high affinity for binding a subjects' own MHC-I molecules and (ii) are expressed and/or known to be associated with pathology accounting for a subject's auto-immune syndrome. In other embodiments, the peptide antigen represents a CD4 epitope derived from an allergen and is selected on the basis of the peptide antigen having a high binding affinity for a patient's own MHC-II molecules.

Those skilled in the art recognize that any peptide, protein or post-translationally modified protein (e.g., glycoprotein) that leads to an immune response and is useful in the prevention or treatment of a disease can be selected for use as a peptide antigen (A) for use in the immunogenic compositions of the present invention.

Extensions (B1 and B2):

The optional N- and C-terminal extensions (B1 and B2) denote molecules linked to the N- and C-terminus of the peptide antigen (A), respectively. The N- and C-terminal extensions B1 and B2 may be comprised of any one or more of the following: amino acids, including non-natural amino acids; hydrophilic ethylene oxide monomers (e.g., PEG); hydrophobic alkane chains; or the like; or combinations thereof. The N- and C-terminal extensions B1 and B2 are linked to the peptide antigen (A) through any suitable means, e.g., through stable amide bonds.

In some embodiments, the extensions (B1 and B2) function to control the rate of degradation of the peptide antigen (A) but may also perform any one or more additional functions. In some embodiments, the N- or C-terminal extension (B1 or B2) may be free (wherein one end of the N- or C-terminal extension is linked to the peptide antigen (A) and the other end is not linked to another molecule) and serve to slow degradation of the peptide antigen; for example, a B1 peptide-based extension may be linked to the N-terminus of the peptide antigen through an amide bond to slow degradation. In other embodiments, the N- and/or C-terminal extensions (B1 and/or B2) may be linked to a heterologous molecule and may function as a linker as well modulate peptide antigen (A) degradation. The N- and/or C-terminal extensions providing a linker function may link the peptide antigen either directly or indirectly through a Linker (L), to a Particle (P) or hydrophobic molecule (H), and/or a charged molecule (C).

In some embodiments, the extensions (B1 and/or B2) function to provide distance, i.e. space, between any two heterologous molecules. In other embodiments, the extensions (B1 and/or B2) function to impart hydrophobic or hydrophilic properties to the peptide antigen conjugate. In still other embodiments, the composition of the extensions (B1 and/or B2) may be selected to impart rigidity or flexibility. In other embodiments, the N- and/or C-terminal extensions (B1 and/or B2) may help stabilize the particles formed by the peptide antigen conjugate.

In some embodiments, the extensions (B1 and/or B2) are comprised of charged functional groups, e.g., charged amino acid residues (e.g., Arginine, Lysine), that impart electrostatic charge at physiologic pH. The number of charged residues present in the extension can be used to modulate the net charge of the peptide antigen conjugate. An algorithm is disclosed herein that describes a systematic process for selecting peptide-based extensions (B1 and/or B2) that are recognized by proteases and impart a particular electrostatic charge that functions to stabilize the particles formed by the peptide antigen conjugates.

Additionally, in some embodiments, C-terminal extensions (B2) added to peptide antigens (A) are selected to facilitate manufacturing of a peptides comprising [C]—[B1]-A-B2-[X1], wherein [ ] denotes the group is optional, by incorporating amino acid sequences into B2 that disrupt β-sheet formation and prevent sequence truncation during solid-phase peptide synthesis. In a non-limiting example, a C-terminal di-peptide linker (B2), Gly-Ser, is incorporated during solid-phase peptide synthesis as a pseudoproline dipeptide (e.g. Gly-Ser(Psi(Me,Me)pro)). In additional embodiments, a proline is included in the cathepsin cleavable C-terminal extension (B2) sequence, e.g., Ser-Pro-Leu-Arg (SEQ ID NO: 21); whereby the proline is included to both facilitate manufacturing and promote processing of the extension by endosomal proteases.

In some embodiments, the peptide antigen (A) is linked at the C-terminus to a B2 extension that is linked either directly or indirectly through a Linker (L) to a hydrophobic molecule (H) or Particle (P). In some embodiments, a B1 extension is linked to the N-terminus of the peptide antigen and a B2 extension is linked at the C-terminus of the peptide antigen (A), wherein either B1 or B2 are linked either directly or via a Linker (L) to a Particle (P) or hydrophobic molecule (H). In other embodiments, a peptide antigen (A) is linked at the N-terminus to a B2 extension that is linked either directly or via a Linker (L) to a Particle or Hydrophobic molecule (H). In some embodiments, a charged molecule (C) is linked to an extension, B1 or B2, that is linked to the N- or C-terminus of the peptide antigen (A), respectively, wherein the extension that is not linked to the charged molecule (C) is linked either directly or via a Linker (L) to the hydrophobic molecule (H) or Particle (P). In additional embodiments, charged molecules (C) are linked to both B1 and B2 extensions that are linked to both the N- and C-termini of the peptide antigen (A), respectively. In additional embodiments, charged molecules (C) are linked to the B1 extension linked to the N-terminus of the peptide antigen (A) but not to the B2 extension attached to the C-terminus of the peptide antigen (A), which may be linked either directly or through a Linker (L) to a hydrophobic molecule (H) or Particle (P). A linker precursor X1 or Linker (L) may be linked to either of the extensions (B1 or B2) through any suitable means, such as an amide bond. In preferred embodiments, the extensions (Bland B2) are peptide sequences that are selected for recognition and hydrolysis by enzymes, such as proteases. The extensions (B1 and B2) are preferably cleavable peptides, including amino acids recognized by either or both endosomal proteases or the immuno-proteasome.

As described in greater detail here, the composition of the extensions (B1 or B2) comprised of degradable peptides is dependent on whether the extension is linked to the N-terminus (B1) or C-terminus (B2) of the peptide antigen (A).

In some embodiments, the N-terminal extension (B1) is a peptide sequence between about 1 to 8 amino acids in length, such as 1, 2, 3, 4, 5, 6, 7, or 8 amino acids, typically no more than 10 amino acids in length that is linked to the peptide antigen (A) through, e.g., an amide bond formed between a carboxyl group of the extension (B1) and the alpha amine of the N-terminal residue of the peptide antigen (A). The amide bond between B1 and the peptide antigen (A) may be cleaved by enzymes. It is understood that it is customary to number the amino acid positions in order of proximal to distal from the cleavage site, with amino acid positions C-terminal to the cleavage site indicated by the prime symbol (e.g., Pn'). For example, for a tetrapeptide extension (PN4-PN3-PN2-PN1) linked to the N-terminus of a peptide antigen (A) that is an octapeptide (PA1'-PA2'-PA3'-PA4'-PA5'-PA6'-PA7'-PA8'), e.g., PN4-PN3-PN2-PN1-PA1'-PA2'-PA3'-PA4'-PA5'-PA6'-PA7'-PA8', the amide bond between PN1-PA1' is recognized and hydrolyzed by an enzyme.

In some embodiments, the N-terminal extension (B1) is an enzyme degradable tetrapeptide that is recognized by endosomal proteases, wherein the PN1 position of a tetrapeptide extension (e.g., PN4-PN3-PN2-PN1) is preferably selected from arginine, lysine, citrulline, glutamine, threonine, leucine, norleucine, or methionine, for example, PN4-PN3-PN2-Arg; PN2 is selected from glycine, valine, leucine or isoleucine; PN3 is selected from glycine, serine, alanine, proline or leucine; and, PN4 is selected from glycine, serine, arginine, lysine, aspartic acid or glutamic acid. In some embodiments, the N-terminal extension (B1) is an enzyme degradable tripeptide that is recognized by endosomal proteases, wherein the PN1 position of a tripeptide extension (e.g., PN3-PN2-PN1) is preferably selected from arginine, lysine, citrulline, glutamine, threonine, leucine, norleucine, or methionine; PN2 is selected from glycine, valine, leucine or isoleucine; and PN3 is selected from glycine, serine, alanine, proline or leucine. In some embodiments, the N-terminal extension (B1) is an enzyme degradable di-peptide that is recognized by endosomal proteases, wherein the PN1 position of a dipeptide extension (e.g., PN2-PN1) is preferably selected from arginine, lysine, citrulline, glutamine, threonine, leucine, norleucine, or methionine; and PN2 is selected from glycine, valine, leucine or isoleucine. In still additional embodiments, the N-terminal extension (B1) is an amino acid that is recognized by endosomal proteases, wherein the PN1 position is preferably selected from arginine, lysine, citrulline, glutamine, threonine, leucine, norleucine, or methionine.

In other embodiments, the N-terminal extension (B1) is an enzyme degradable peptide that is recognized by the immuno-proteasome, wherein the P1 position of a tetrapeptide extension (PN4-PN3-PN2-PN1) is preferably selected from isoleucine, leucine, norleucine or valine, for example, PN4-PN3-PN2-Leu.

In additional embodiments, the N-terminal extension (B1) is an enzyme degradable peptide that is recognized by both endosomal proteases and the immuno-proteasome, wherein the PN5 and PN1 positions of an octapeptide extension (PN8-PN7-PN6-PN5-PN4-PN3-PN2-PN1) are selected from arginine, lysine, citrulline, glutamine, threonine, leucine, norleucine, or methionine for the PN5 position recognized by cathepsins, and isoleucine, leucine, norleucine or valine for the PN1 position recognized by the immuno-proteasome; for example, PN8-PN7-PN6-Arg-PN4-PN3-PN2-Leu. A non-limiting example of an N-terminal extension (B1) recognized by cathepsins and the immuno-proteasome is Lys-Pro-Leu-Arg-Tyr-Leu-Leu-Leu (SEQ ID NO: 3).

Non-limiting examples of tetrapeptide N-terminal extensions (B1) that are recognized by the immuno-proteasome include: Ser-Leu-Val-Cit, Ser-Leu-Val-Leu (SEQ ID NO: 4), Ser-Pro-Val-Cit, Glu-Leu-Val-Arg (SEQ ID NO: 5), Ser-Pro-Val-Arg (SEQ ID NO: 6), Ser-Leu-Val-Arg (SEQ ID NO: 7), Lys-Pro-Leu-Arg (SEQ ID NO: 8), Lys-Pro-Val-Arg (SEQ ID NO: 9), Glu-Leu-Val-Cit, Glu-Leu-Val-Leu (SEQ ID NO: 10), Glu-Pro-Val-Cit and Lys-Pro-Val-Cit. Non-limiting examples of tripeptide N-terminal extensions (B1) include: Leu-Val-Cit, Leu-Val-Leu, Pro-Val-Cit, Leu-Val-Arg, Pro-Val-Arg, Pro-Leu-Arg, Gly-Val-Ser. Non-limiting examples of di-peptide N-terminal extensions (B1) include: Val-Cit, Val-Leu, Val-Arg, Leu-Arg. Non-limiting examples of single amino acid N-terminal extensions (B1) include Cit, Arg, Leu or Lys. In the above examples, Arg can be replaced with Lys; Lys can be replaced with Arg; Glu can be replaced with Asp; and Asp can be replaced with Glu. Note that Cit=citrulline.

In some embodiments, the extension (B2) is a degradable peptide linked to the C-terminal residue of the peptide antigen (A) and is comprised of amino acid sequences that are recognized and hydrolyzed by certain proteases. In some embodiments, the C-terminal extension (B2) is a peptide sequence between about 1 to 8 amino acids in length, such as 1, 2, 3, 4, 5, 6, 7, or 8 amino acids, typically no more than 10 amino acids. In preferred embodiments, the C-terminal extension (B2) is linked to the peptide antigen (A) via an amide bond formed between the C-terminal carboxyl group of the peptide antigen (A) and the alpha amine of the N-terminal residue of the extension (B2). The amide bond between B2 and the peptide antigen (A) may be cleaved by enzymes. Note that it is customary to number the amino acid positions in order of proximal to distal from the cleavage site, with amino acid positions C-terminal to the cleavage site indicated by the prime symbol (e.g., Pn'). For example, for a tetrapeptide extension (PC1'-PC2'-PC3'-PC4') linked to the C-terminus of an octapeptide antigen (PA8-PA7-PA6-PA5-PA4-PA3-PA2-PA1), e.g., PA8-PA7-PA6-PA5-PA4-PA3-PA2-PA1-PC1'-PC2'-PC3'-PC4', the amide bond between PA1-PC1' is recognized and hydrolyzed by an enzyme.

In preferred embodiments, C-terminal extensions (B2) are amino acid sequences that are selected to promote immuno-proteasome recognition and cleavage and optionally endosomal protease recognition. As peptide antigens (A) typically contain a C-terminal residue, for example, leucine, that promotes hydrolysis by the immuno-proteasome, e.g., at the amide bond proximal to the C-terminal residue of the peptide antigen (A), extensions linked to the C-terminus of the peptide antigen (A) should be selected to promote immuno-proteasome recognition and cleavage at the amide bond proximal to the C-terminus of the peptide antigen (A). The immuno-proteasome favors small, non-charged amino acids at the PC1' position adjacent to the C-terminal amino acid, PA1, of the peptide antigen (A), e.g., the amide bond between PA1-PC1'. However, endosomal proteases favor bulky hydrophobic amino acids (e.g., leucine, norleucine, methionine or glutamine) and basic amino acids (i.e., arginine and lysine). Therefore, C-terminal extensions may be selected to promote recognition by either or both classes of proteases.

In some embodiments, a peptide antigen (A) with the sequence PA8-PA7-PA6-PA5-PA4-PA3-PA2-PA1 is linked to a C-terminal peptide extension (B2) with the sequence PC1' ... PCn', wherein n is an integer value from 1 to 8, for example, PA8-PA7-PA6-PA4-PA3-PA2-PA1-PC1' ... PCn'. The composition of the C-terminal extension (B2) depends on the length of the extension sequence used. In some embodiments, the C-terminal extension, B2, is a single amino acid PC1' selected from Gly, Ala, Ser, Arg, Lys, Cit, Gln, Thr, Leu, Nle or Met. In additional embodiments, the C-terminal extension, B2, is a dipeptide, PC1'-PC2', wherein PC1' is selected from Gly, Ala or Ser; and PC2' is selected from Gly, Ala, Ser, Pro, Arg, Lys, Cit, Gln, Thr, Leu, Nle, or Met. In additional embodiments, the C-terminal extension, B2, is a tripeptide, PC1'-PC2'-PC3', wherein P1' is selected from Gly, Ala, or Ser; PC2' is selected from Gly, Ala, Ser, or Pro; and PC3' is selected from Gly, Ser, Arg, Lys, Cit, Gln, Thr, Leu, Nle or Met.

In additional embodiments, the C-terminal extension, B2, is a tetrapeptide extension, PC1'-PC2'-PC3'-PC4', wherein PC1' is selected from glycine, alanine or serine; PC2' is selected from glycine, alanine, serine, proline or leucine; PC3' is selected from glycine, alanine, serine, valine, leucine or isoleucine; and PC4' is selected from arginine, lysine, citrulline, glutamine, threonine, leucine, norleucine or methionine. In additional embodiments, the C-terminal extension, B2, is a pentapeptide, PC1'-PC2'-PC3'-PC4'-PC5', wherein PC1' is selected from glycine, alanine or serine; PC2' is selected glycine, alanine, serine, proline, arginine, lysine, glutamic acid or aspartic acid; PC3' is selected from glycine, alanine, serine, proline or leucine; PC4' is selected from glycine, alanine, valine, leucine or isoleucine; and PC5' is selected from arginine, lysine, citrulline, glutamine, threonine, leucine, norleucine or methionine. In additional embodiments, the C-terminal extension, B2, is a hexapeptide, PC1'-PC2'—PC3'-PC4'-PC5'-PC6', wherein PC1' is selected from glycine, alanine or serine; PC2' is selected from glycine, alanine, serine or proline; PC3' is selected from glycine, serine, proline, arginine, lysine, glutamic acid or aspartic acid; PC4' is selected from proline or leucine; PC5' is selected from glycine, alanine, valine, leucine or isoleucine; and PC6' is selected from arginine, lysine, citrulline, glutamine, threonine, leucine, norleucine or methionine.

Non-limiting examples of hexapeptide C-terminal extensions (B2) include Gly-Gly-Lys-Leu-Val-Arg (SEQ ID NO: 11), Gly-Gly-Lys-Pro-Leu-Arg (SEQ ID NO: 12), Gly-Gly-Ser-Leu-Val-Arg (SEQ ID NO: 13), Gly-Gly-Ser-Leu-Val-Cit (SEQ ID NO: 112); Gly-Gly-Ser-Pro-Val-Cit (SEQ ID NO: 113), Gly-Gly-Ser-Leu-Val-Leu (SEQ ID NO: 14), Gly-Gly-Glu-Leu-Val-Arg (SEQ ID NO: 15), Gly-Gly-Glu-Leu-Val-Leu (SEQ ID NO: 16). Non-limiting examples of pentapeptide C-terminal extensions (B2) include Gly-Ser-Leu-Val-Arg (SEQ ID NO: 17), Gly-Ser-Leu-Val-Cit (SEQ ID NO: 114), Gly-Lys-Pro-Val-Cit (SEQ ID NO: 115), Gly-Lys-Pro-Val-Arg (SEQ ID NO: 18), Gly-Ser-Leu-Val-Leu (SEQ ID NO: 19), Gly-Glu-Leu-Val-Leu (SEQ ID NO: 20). Non-limiting examples of tetrapeptide C-terminal extensions (B2) include Ser-Leu-Val-Cit, Ser-Leu-Val-Leu (SEQ ID NO: 4), Ser-Pro-Val-Cit, Glu-Leu-Val-Arg (SEQ ID NO: 5), Ser-Pro-Val-Arg (SEQ ID NO: 6), Ser-Leu-Val-Arg (SEQ ID NO: 7), Lys-Pro-Leu-Arg (SEQ ID NO: 8), Glu-Leu-Val-Cit, Glu-Leu-Val-Leu (SEQ ID NO: 10), Glu-Pro-Val-Cit, Glu-Gly-Val-Cit. Non-limiting examples of tripeptide C-terminal extensions (B2) include Gly-Ser-Gly, Gly-Ser-Arg, Gly-Ser-Leu, Gly-Ser-Cit, Gly-Pro-Gly, Gly-Pro-Arg, Gly-Pro-Leu, Gly-Pro-Cit. Non-limiting examples of di-peptide C-terminal extensions (B2) include Gly-Ser; Gly-Pro, Val-Cit, Gly-Arg Gly-Cit. Non-limiting examples of single amino acid C-terminal extensions (B2) include Gly, Ser, Ala, Arg, Lys, Cit, Val, Leu, Met, Thr, Gln or Nle. In the above examples, Arg can be replaced with Lys; Lys can be replaced with Arg; Glu can be replaced with Asp; and Asp can be replaced with Glu.

The C-terminal linker (B2) linked to the C-terminus of the peptide antigen (A) may be selected for recognition (i.e. hydrolysis) by both the immuno-proteasome and endosomal proteases. In a non-limiting example, a peptide antigen (A) with the sequence PA8-PA7-PA6-PA5-PA4-PA3-PA2-PA1 is linked at the C-terminus to a C-terminal tetrapeptide extension (B2) with the sequence PC1'-PC2'—PC3'-PC4', wherein PC1' is selected from glycine, alanine or serine and PC4' is selected from arginine, lysine, citrulline, glutamine, threonine, leucine, norleucine, or methionine, for example, Ser-P3-P2-Arg. In some embodiments, an antigen with the sequence PA8-PA7-PA6-PA5-PA4-PA3-PA2-PA1 is linked at the C-terminus to a C-terminal hexapeptide extension (B2) with the sequence PC1'-PC2'-PC3'-PC4'—PC5'-PC6', wherein PC1' and PC2' are selected from glycine, alanine, proline or serine and PC6' is selected from arginine, lysine, citrulline, glutamine, threonine, leucine, norleucine, or methionine, for example, Gly-Gly-PC3'-PC4'-PC5'-Arg. A non-limiting example of a C-terminal extension (B2) that promotes processing by both the immuno-proteasome and cathepsins that is linked to the C-terminus of the peptide antigen (A) is Gly-Gly-Lys-Pro-Leu-Arg (SEQ ID NO: 12). An additional non-limiting example of a C-terminal extension (B2) that is linked at the C-terminus of a peptide antigen (A) that favors processing by the immuno-proteasome and cathepsins is Gly-Gly-Ser-Leu-Val-Cit (SEQ ID NO: 112) or Gly-Gly-Ser-Pro-Val-Cit (SEQ ID NO: 113).

Linkers (L) and Linkers Precursors (X1 and X2)

A subset of linkers that perform the specific function of site-selectively coupling, i.e. joining or linking together the peptide antigen (A) with a hydrophobic molecule (H) or a Particle (P) are referred to as "Linkers (L)." The Linker (L) forms as a result of the reaction between a linker precursor X1 and a linker precursor X2. For instance, a linker precursor X1 that is linked directly, or indirectly via an extension (B1 or B2) or charged molecule (C) to the peptide antigen (A) may react with a linker precursor X2 attached to the hydrophobic molecule (H) or Particle (P) to form a Linker (L) that links the peptide antigen (A) to the hydrophobic molecule (H) or Particle (P). The linker precursor X1 allows for site-selective linkage of the peptide antigen (A) to a Particle (P) or hydrophobic molecule (H). In some embodiments, a peptide antigen (A) linked either directly or through an extension (B1 or B2) to a linker precursor X1 may be produced and isolated and then added separately to a Particle (P) or hydrophobic molecule (H) that contains a linker precursor X2 that selectively reacts to form a Linker (L) joining the peptide antigen (A) and the Particle (P) or hydrophobic molecule (H).

A Linker (L) or linker precursor X1 may be linked to a peptide antigen (A) at either the N- or C-terminus of the peptide antigen either directly or indirectly through an N-terminal extension (B1) or C-terminal extension (B2), respectively. In preferred embodiments, the Linker (L) or linker precursor X1 is linked to the peptide antigen (A) or an extension (B1 or B2) through an amide bond. Note that a Linker (L) or linker precursor X1 linked directly to the N- or C-terminus of the peptide antigen is not considered an extension.

Suitable linker precursors X1 are those that react selectively with a linker precursors X2 on the Particle (P) or hydrophobic molecule (H) without linkages occurring at any other site of the peptide antigen (A) or optional extensions (B1 and/or B2) or optional charged molecule (C). This selectivity is important for ensuring a linkage can be formed between the peptide antigen (A) and a Particle (P) or hydrophobic molecule (H) without modification to the peptide antigen (A). The Linker (L) may link a peptide antigen (A) directly or indirectly through an extension (B1 or B2) to a Particle (P) or hydrophobic molecule (H) through covalent and/or high affinity interactions. In preferred embodiments, the linker precursor X1 forms a covalent bond with a linker precursor X2 on the Particle or hydrophobic molecule (H).

In preferred embodiments, the Linker (L) is formed as a result of a bio-orthogonal "click chemistry" reaction between the linker precursors X1 and X2. In some embodiments, the click chemistry reaction is a catalyst free click chemistry reaction, such as a strain-promoted azide-alkyne cycloaddition reaction that does not require the use of copper or any catalyst. Non-limiting examples of linker precursors X1 that permit bio-orthogonal reactions include molecules comprising functional groups selected from azides, alkynes, tetrazines and transcyclooctenes. In some embodiments, a linker precursor X1 comprising an azide reacts with a linker precursor X2 to form a triazole Linker. In other embodiments, a linker precursor X1 comprising a tetrazine reacts with a linker precursor X2 comprising a transcyclooctene (TCO) to form a Linker comprising the inverse demand Diels-Alder ligation product. In preferred embodiments, the linker precursor X1 is a non-natural amino acid bearing an azide functional group that reacts with a linker precursor X2 comprising an alkyne present that undergoes 1,3-dipolar cycloaddition to form a stable triazole ring. In preferred embodiments, the X2 linker precursor linked to the Particle (P) or hydrophobic molecule (H) comprises an alkyne that undergoes strain-promoted cycloaddition, such as dibenzocyclooctyne (DBCO). In additional embodiments, the X1 linker precursor is an alkyne that reacts with a linker precursor X2 comprising an azide that is present on the Particle (P) or hydrophobic molecule (H).

In other embodiments, linker precursors X1 that permit site-selective reactivity depending on the composition of the peptide antigen (A) may comprise functional groups that include thiols, hydrazines, ketones and aldehydes. In some embodiments, a linker precursor X1 comprising a thiol reacts with a linker precursor X2 comprising a pyridyl-disulfide or maleimide to form a disulfide or thioether Linker, respectively. In other embodiments, a linker precursor X1 comprising a hydrazine reacts with a linker precursor X2 comprising a ketone or aldehyde to form a hydrazone Linker. In some embodiments, the linker precursor X1 is a natural or non-natural amino acid residue with a thiol functional group, such as a cysteine, that reacts with a linker precursor X2 comprising a thiol reactive functional group such as maleimide or pyridyl disulfide.

In some embodiments, the linker precursor X1 is a peptide sequence that is ligated to another peptide sequence comprising the linker precursor X2 provided on the Particle (P) or hydrophobic molecule (H). In other embodiments, the linker precursor X1 binds to a complementary molecule comprising the linker precursor X2 on the Particle (P) or hydrophobic molecule (H) through high affinity, non-covalent, interactions, for example, through coiled-coil interactions or electrostatic interactions. In other embodiments, the linker precursor X1 binds to a protein, for example, biotin, which forms high affinity interactions with a protein, for example, streptavidin.

Those skilled in the art recognize that suitable pairs of functional groups, or complementary molecules, selected for linker precursors X1 and X2 may be transposable between X1 and X2. For example, a Linker comprised of a triazole may be formed from linker precursors X1 and X2 comprising an azide and alkyne, respectively, or from linker precursors X1 and X2 comprising an alkyne and azide, respectively. Thus, any suitable functional group pair resulting in a Linker may be placed on either X1 or X2.

Particular linker precursors (X1 and X2) and Linkers (L) presented in this disclosure provide unexpected improvements in manufacturability and improvements in biological activity. Many such linker precursors (X1 and X2) and Linkers (L) may be suitable for the practice of the invention and are described in greater detail throughout.

The linker precursor (X1) may be attached to either the N- or C-terminus of the peptide antigen (A) either directly or indirectly through an extension (B1 or B2) or charged molecule (C).

In some embodiments, the linker precursor X1 is an amino acid linked to the C-terminus of the peptide antigen (A) either directly or indirectly through a B2 extension or charged molecule (C) and has the formula:
wherein the functional group (FG) is selected to react specifically with a FG on the linker precursor X2

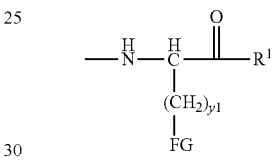

and is typically selected from amine, azide, hydrazine or thiol; $R^1$ is typically selected from OH or $NH_2$ and y1 is any integer, such as 1, 2, 3, 4, 5, 6, 7 or 8; and the alpha amine of the amino acid is typically linked to the C-terminal amino acid of the extension B2 or the C-terminal amino acid of the peptide antigen (A) if there is no B2 extension.

In other embodiments, the linker precursor X1 is linked to the N-terminus of the peptide antigen (A) either directly or indirectly through an extension (B1 or B2) or charged molecule (C) and has the formula:

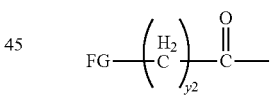

wherein the functional group (FG) is selected to react with the linker precursor X2 and is typically selected from amine, azide, hydrazine or thiol; y2 is any integer, typically 1, 2, 3, 4, 5, 6, 7 or 8; and the carbonyl is typically linked to the alpha amine of the N-terminal amino acid of the extension B1 or the peptide antigen (A) when B1 is not present.

The linker precursor X2 provided on the hydrophobic molecule (H) or Particle (P) comprises a functional group that is selected to allow for a selective reaction with the linker precursor X1 to form the Linker (L). In some embodiments, functional groups comprising X2 include carbonyls, such as activated esters/carboxylic acids or ketones that react with amines or hydrazines provided on the linker precursor X1 to form Linkers (L) comprising an amide or hydrazone. In other embodiments, functional groups comprising X2 include azides that react with alkynes provided on the linker precursor X1 to form triazoles. In still other embodiments, the functional group comprising X2 is selected from maleimides or disulfides that react with thiols provided on the linker precursor X1 to form Linkers (L) comprising thioethers or disulphides. The linker precursor X2 may be attached to the hydrophobic molecule (H) or Particle (P) through any suitable means. In some embodiments, the hydrophobic molecule (H) comprises a peptide and X2 is linked to the N-terminus of the peptide-based hydrophobic molecule (H).

The Linker (L) may comprise a triazole formed between linker precursors X1 and X2 comprising an azide and an alkyne, respectively. In some embodiments, the Linker comprising a triazole results from the reaction of an azido containing linker precursor X1 and an alkyne (e.g., cyclooctyne) containing linker precursor X2. In some embodiments, the azido containing linker precursor X1 is a non-natural amino acid bearing an azide functional group that is linked to the N-terminus of peptide antigen (A) or extension (B1) or the C-terminus of the peptide antigen (A) or extension (B2). The azide functional group provides a reactive handle that is linked either directly to the peptide antigen (A) or indirectly via the N-terminal extension (B1) or the C-terminal extension (B2) and selectively reacts with an alkyne (e.g., cyclooctyne) containing linker precursor X2 that is linked to a hydrophobic molecule (H) or Particle (P), thereby forming a triazole Linker (L) that joins the peptide antigen (A) to the hydrophobic molecule (H) or Particle (P).

In some embodiments, the linker precursor X1 is an azido amino acid linked to the C-terminus of the peptide antigen (A) either directly or indirectly through a B2 extension or charged molecule (C) and has the formula:

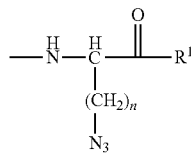

wherein the alpha amine of the amino acid is linked to the C-terminal amino acid of B2, or the peptide antigen (A) if there is no B2 extension; $R^1$ is selected from OH or $NH_2$ and n is any integer, such as 1, 2, 3, 4, 5, 6, 7, 8. Non-limiting examples of azido containing linker precursors X1 are 5-azido-2-amino pentanoic acid, 4-azido-2-amino butanoic acid and 3-azido-2-amino propanoic acid.

In other embodiments when the azido containing linker precursor X1 is linked to the N-terminal extension (B1), or directly to the N-terminus of the peptide antigen (A) when B1 is not present, the linker precursor X1 has the formula: wherein the carbonyl is typically linked to the alpha amine of the N-terminal amino acid of the extension

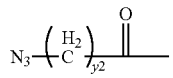

B1 or the peptide antigen (A) when B1 is not present; and y2 is any integer, typically 1, 2, 3, 4, 5, 6, 7 or 8. Non-limiting examples of azido-containing linker precursors include 6-azido-hexanoic acid, 5-azido-pentanoic acid, 4-azido-butanoic acid and 3-azido-propanoic acid.

In some embodiments, wherein the linker precursor X1 comprises an azide, the linker precursor X2 comprises an alkyne moiety. Non-limiting examples of alkynes include aliphatic alkynes, cyclooctynes, such as dibenzylcyclooctyne (DBCO or DIBO), difluorooctyne (DIFO), and biarylazacyclooctynone (BARAC). In some specific embodiments, the alkyne containing linker precursor X2 comprises a DBCO molecule.

In some embodiments, the C-terminal extension (B2) is linked to the peptide antigen (A) through an amide bond at the C-terminus of the peptide antigen (A) which, in turn, is linked via the Linker (L) to the hydrophobic block (H). An example of such a C-terminal linked peptide antigen conjugate is $(A)_{7-35}$-B2-L-H, where $(A)_{7-35}$ represents a peptide antigen comprising from 7 to 35 amino acids. In a non-limiting example, a peptide antigen (A) with the octapeptide sequence PA8-PA7-PA6-PA5-PA4-PA3-PA2-PA1 is linked at the C-terminus to a tetrapeptide extension (B2), for example, Ser-Leu-Val-Arg (SEQ ID NO: 7) that is linked to the azido containing linker precursor (X1) azido-lysine (6-azido 2-amino hexanoic acid, Lys(N3)) which in turn reacts with the dibenzocyclooctyne (DBCO) moiety of the cyclooctyne containing linker precursor (X2) that is linked to the hydrophobic molecule (H) to produce PA8-PA7-PA6-PA5-PA4-PA3-PA2-PA1-Ser-Leu-Val-Arg-Lys(N3-DBCO-H) ("Ser-Leu-Val-Arg-Lys(N3-DBCO-H)" disclosed as SEQ ID NO: 116).

In some alternative embodiments, the peptide antigen (A) is linked to the N-terminal extension (B1) at the N-terminus of the peptide antigen (A) which, in turn, is linked via the Linker (L) to the hydrophobic block (H). In a non-limiting example, a peptide antigen with the sequence PA1'-PA2'-PA3'-PA4'-PA5'-PA6'-PA7'-PA8' is linked at the N-terminus to a tetrapeptide extension (PN4-PN3-PN2-PN1), for example, Ser-Leu-Val-Arg (SEQ ID NO: 7) that is linked to azido-pentanoic acid (Azp) which in turn reacts with the dibenzocyclooctyne (DBCO) moiety of the cyclooctyne containing linker precursor (X2) that is linked to the hydrophobic molecule (H): H-DBCO-Azp-Ser-Leu-Val-Arg-PA1'-PA2'-PA3'-PA4'-PA5'-PA6'-PA7'-PA8' ("Azp-Ser-Leu-Val-Arg" disclosed as SEQ ID NO: 117).

Other Linkers and Linkages

Linkers generally refer to any molecules that join together any two or more heterologous molecules of the peptide antigen conjugate and may additionally perform any one or more of the following functions: I) increase or decrease water solubility; II) increase distance between any two components, i.e. heterologous molecules, of the peptide antigen conjugate; III) impart rigidity or flexibility; or IV) control/modulate the rate of degradation/hydrolysis of the link between any two or more heterologous molecules. Specific types of linkers used herein are named. Linkers (L) are a specific type of linker molecule used to site-specifically link the peptide antigen (A) to a Particle (P) or a hydrophobic molecule (H) either directly or indirectly through an extension (B1 or B2). Note that the N- and C-terminal extensions, B1 and B2, placed at the N- and C-terminus of a peptide antigen (A), respectfully, may be linked to a heterologous molecule, such as a charged molecule (C), Linker (L), Particle (P) or hydrophobic molecule (H), or any heterologous molecule, and therefore function as a linker. For clarity, while any molecule placed at the N- or C-terminus of the peptide antigen (A) is an N- or C-terminal extension (B1 or B2), the extension may also serve as a linker when it is linked to another molecule, e.g., charged molecule (C). Thus, as defined herein, a linker at the N- or C-terminus of an antigen is always an extension (B1 or B2) but an extension is not always a linker.

The linkers used to join any two components of the peptide antigen conjugate, for example, a peptide antigen (A) linked to a hydrophobic molecule (H) indirectly through an extension (B1 or B2) may be through any suitable means. The linker may use covalent or non-covalent means to join any two or more components, i.e. heterologous molecules, for example a peptide antigen (A) and hydrophobic molecule (H).

In preferred embodiments, a linker may join, i.e. link, any two components of the peptide antigen conjugate through a covalent bond. Covalent bonds are the preferred linkages used to join any two components, i.e. heterologous molecules, of the peptide antigen conjugate and ensure that no component is able to immediately disperse from the other components, e.g. the peptide antigen and hydrophobic molecule (H), following administration to a subject. Moreover, covalent linkages typically provide greater stability over non-covalent linkages and help to ensure that each component of the peptide antigen conjugate is co-delivered to antigen presenting cells at or near the proportions of each component that was administered.

In a non-limiting example of a covalent linkage, a click chemistry reaction may result in a triazole that links, i.e. joins together, any two components of the peptide antigen conjugate. In several embodiments, the click chemistry reaction is a strain-promoted [3+2] azide-alkyne cycloaddition reaction. An alkyne group and an azide group may be provided on respective molecules comprising the peptide antigen conjugate to be linked by "click chemistry". In some embodiments, a ligand, such as a TLR agonist, bearing an azide functional group is coupled to a hydrophobic molecule (H) having an appropriate reactive group, such as an alkyne, for example, a dibenzylcyclooctyne (DBCO). In additional embodiments, an X1 linker precursor bearing a thiol functional group is linked either directly or through an N- or C-terminal extension (B1 or B2) to the peptide antigen (A). The thiol can be linked to a hydrophobic molecule (H) having an appropriate reactive group such as an alkyne, alkene, maleimide, resulting in a thioether bond, or the thiol may be reacted with a pyridyl disulfide, e.g., resulting in a disulfide linkage. In some embodiments, an amine is provided on one molecule and may be linked to another molecule by reacting the amine with any suitable electrophilic group such as carboxylic acids, acid chlorides or activated esters (for example, NHS ester), which results in an amide bond formation, or the amine may be reacted with alkenes (via Michael addition), aldehydes, and ketones (via Schiff base). In preferred embodiments, the linker precursor X1, optional N- and C-terminal extensions (B1 and B2), optional charged molecule (C) and peptide antigen (A) are linked together through amide bonds as a single peptide sequence produced by solid-phase peptide synthesis. There are a number of suitable reactions available that result in a covalent bond, i.e. link, that will be familiar to the skilled person.

The type of linker used to join any two or more heterologous molecules, i.e. distinct components of the peptide antigen conjugate, can be selected to perform specific functions and meet specific requirements of the application. Typically, the linker is capable of forming covalent bonds between two or more heterologous molecules of the peptide antigen conjugate, wherein the components are a peptide antigen (A), Particle (P) or hydrophobic molecule (H), optional N- and C-terminal extensions (B1 and B2), optional Linker (L); optional charged molecule (C); optional second polymer (that is linked to the hydrophobic molecule (H); and optional Ligand, such as a PRR agonist.

There are many suitable linkers that are well known to those of skill in the art and include, but are not limited to, straight or branched-chain carbon linkers, heterocyclic carbon linkers, rigid aromatic linkers, flexible ethylene oxide linkers, peptide linkers, or a combination thereof. In some embodiments, the carbon linker can include a C1-C18 alkane linker, such as a lower alkyl C4; the alkane linkers can serve to increase the space between two or more heterologous molecules, while longer chain alkane linkers can be used to impart hydrophobic characteristics. Alternatively, hydrophilic linkers, such as ethylene oxide linkers, may be used in place of alkane linkers to increase the space between any two or more heterologous molecules and increase water solubility. In other embodiments, the linker can be an aromatic compound, or poly(aromatic) compound that imparts rigidity. The linker molecule may comprise a hydrophilic or hydrophobic linker. In several embodiments, the linker includes a degradable peptide sequence that is cleavable by an intracellular enzyme (such as a cathepsin or the immuno-proteasome).

In some embodiments, the linker may be comprised of poly(ethylene oxide) (PEG). The length of the linker depends on the purpose of the linker. For example, the length of the linker, such as a PEG linker, can be increased to separate components of an immunogenic composition, for example, to reduce steric hindrance, or in the case of a hydrophilic PEG linker can be used to improve water solubility. The linker, such as PEG, may be a short linker that may be at least 2 monomers in length. The linker, such as PEG, may be between about 4 and about 24 monomers in length, such as 4, 5, 6, 7, 8, 9, 10, 11, 12, 13, 14, 15, 16, 17, 18, 19, 20, 21, 22, 23, 24 monomers in length or more. In some embodiments, a Ligand is linked to a hydrophobic molecule (H) though a PEG linker.

In some embodiments, where the linker comprises a carbon chain, the linker may comprise a chain of between about 1 or 2 and about 18 carbons, such as 1, 2, 3, 4, 5, 6, 7, 8, 9, 10, 11, 12, 13, 14, 15, 16, 17, 18 carbons in length or more. In some embodiments, where the linker comprises a carbon chain, the linker may comprise a chain of between about 12 and about 20 carbons. In some embodiments, where the linker comprises a carbon chain, the linker may comprise a chain of between no more than 18 carbons. In some embodiments, a Ligand, such as a PRR agonist, is linked to the hydrophobic molecule (H) through a lower alkyl.

In some embodiments, the linker is cleavable under intracellular conditions, such that cleavage of the linker results in the release of any component linked to the linker, for example, a peptide antigen.

For example, the linker can be cleavable by enzymes localized in intracellular vesicles (for example, within a lysosome or endosome or caveolea) or by enzymes, in the cytosol, such as the proteasome, or immuno-proteasome. The linker can be, for example, a peptide linker that is cleaved by protease enzymes, including, but not limited to proteases that are localized in intracellular vesicles, such as cathepsins in the lysosomal or endosomal compartment. The peptide linker is typically between 1-10 amino acids, such as 1, 2, 3, 4, 5, 6, 7, 8, 9, 10, or more (such as up to 20) amino acids long, such as 11, 12, 13, 14, 15, 16, 17, 18, 19, 20 or more amino acids long. Certain dipeptides are known to be hydrolyzed by proteases that include cathepsins, such as cathepsins B and D and plasmin, (see, for example, Dubowchik and Walker, 1999, Pharm. Therapeutics 83:67-123). For example, a peptide linker that is cleavable by the thiol-dependent protease cathepsin-B, can be used (for example, a Phe-Leu or a Gly-Phe-Leu-Gly (SEQ ID NO: 23) linker). Other examples of such linkers are described, for example, in U.S. Pat. No. 6,214,345, incorporated herein by reference.

In a specific embodiment, the peptide linker cleavable by an intracellular protease is a Val-Cit linker or a Phe-Lys linker (see, for example, U.S. Pat. No. 6,214,345, which describes the synthesis of doxorubicin with the Val-Cit linker).

Particular sequences for the cleavable peptide in the linker can be used to promote processing by immune cells following intracellular uptake. For example, several embodiments of the immunogenic compositions disclosed herein form particles in aqueous conditions, which are internalized by immune cells, such as antigen-presenting cells (e.g., dendritic cells). The cleavable peptide linker can be selected to promote processing (i.e. hydrolysis) of the peptide linker following intracellular uptake by the immune cells. The sequence of the cleavable peptide linker can be selected to promote processing by intracellular proteases, such as cathepsins in intracellular vesicles or the proteasome or immuno-proteasome in the cytosolic space.

In several embodiments, linkers comprised of peptide sequences of the formula Pn . . . P4-P3-P2-P1 are used to promote recognition by cathepsins, wherein P1 is selected from arginine, lysine, citrulline, glutamine, threonine, leucine, norleucine, or methionine; P2 is selected from glycine, leucine, valine or isoleucine; P3 is selected rom glycine, serine, alanine, proline or leucine; and P4 is selected from glycine, serine, arginine, lysine aspartic acid or glutamic acid. In a non-limiting example, a tetrapeptide linker of the formula P4-P3-P2-P1 linked through an amide bond to a heterologous molecule and has the sequence Lys-Pro-Leu-Arg (SEQ ID NO: 8). For clarity, the amino acid residues (Pn) are numbered from proximal to distal from the site of cleavage, which is C-terminal to the P1 residue, for example, the amide bond between P1-P1' is hydrolyzed. Suitable peptide sequences that promote cleavage by endosomal and lysosomal proteases, such as cathepsin, are well described in the literature (see: Choe, et al., J. Biol. Chem., 281:12824-12832, 2006).

In several embodiments, linkers comprised of peptide sequences are selected to promote recognition by the proteasome or immuno-proteasome. Peptide sequences of the formula Pn . . . P4-P3-P2-P1 are selected to promote recognition by proteasome or immuno-proteasome, wherein P1 is selected from basic residues and hydrophobic, branched residues, such as arginine, lysine, leucine, isoleucine and valine; P2, P3 and P4 are optionally selected from leucine, isoleucine, valine, lysine and tyrosine. In a non-limiting example, a cleavable linker of the formula P4-P3-P2-P1 that is recognized by the proteasome is linked through an amide bond at P1 to a heterologous molecule and has the sequence Tyr-Leu-Leu-Leu (SEQ ID NO: 24). Sequences that promote degradation by the proteasome or immuno-proteasome may be used alone or in combination with cathepsin cleavable linkers. In some embodiments, amino acids that promote immuno-proteasome processing are linked to linkers that promote processing by endosomal proteases. A number of suitable sequences to promote cleavage by the immuno-proteasome are well described in the literature (see: Kloetzel, et al., Nat. Rev. Mol. Cell Biol., 2:179-187), 2001, Huber, et al., Cell, 148:727-738, 2012, and Harris et al., Chem. Biol., 8:1131-1141, 2001).

In preferred embodiments, the N- and C-terminal extensions (B1 and B2) that are linked to the N- and C-termini of the peptide antigen (A), respectively, are linked to additional molecules, e.g., a charged molecule (C) and hydrophobic molecule (H), respectively, and are comprised of cleavable peptides. In several embodiments, cleavable peptide extensions are placed at either or both the N- and/or C-termini of the peptide antigen (A). Cleavable peptide extensions placed at the N-terminus of the peptide antigen (A) are N-terminal extensions ($B_1$) but may additionally function as linkers when the extension is linked to another molecule, e.g., a charged molecule (C), in addition to the peptide antigen. Extensions placed at the C-terminus of the peptide antigen (A) are C-terminal extensions ($B_2$), but may additionally function as linkers when the extension is linked to another molecule, e.g., a hydrophobic molecule (H). The preferred sequences of cleavable peptides comprising the linkers at either the N- or C-terminus ($B_1$ and $B_2$) are distinct and are described in greater detail throughout.

In other embodiments, any two or more components of the peptide antigen conjugates may be joined together through a pH-sensitive linker that is sensitive to hydrolysis under acidic conditions. A number of pH-sensitive linkages are familiar to those skilled in the art and include for example, a hydrazone, semicarbazone, thiosemicarbazone, cis-aconitic amide, orthoester, acetal, ketal, or the like (see, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661). In preferred embodiments, the linkage is stable at physiologic pH, e.g., at a pH of about 7.4, but undergoes hydrolysis at lysosomal pH, ~ pH 5-6.5. In some embodiments, a Ligand, such as a TLR-7/8 agonist, is linked to a hydrophobic molecule (H) through a FG that forms a pH-sensitive bond, such as the reaction between a ketone and a hydrazine to form a pH labile hydrazone bond. In other embodiments, a peptide antigen (A) is linked either directly or indirectly through an extension (B1 or B2) to a linker precursor X1 that bears a ketone group and is linked to a linker precursor X2 comprising a hydrazine on a hydrophobic molecule (H). A pH-sensitive linkage, such as a hydrazone, provides the advantage that the bond is stable at physiologic pH, at about pH 7.4, but is hydrolyzed at lower pH values, such as the pH of intracellular vesicles.

In other embodiments, the linker comprises a linkage that is cleavable under reducing conditions, such as a reducible disulfide bond. Many different linkers used to introduce disulfide linkages are known in the art (see, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880, 935.). In some embodiments, a peptide antigen (A) is linked either directly or indirectly through an extension (B1 or B2) to a linker precursor X1 that bears a thiol functional group that forms a disulfide bond with a X2 linker precursor comprising a pyridyl disulfide linked to a hydrophobic molecule (H).

In yet additional embodiments the linkage between any two components of the peptide antigen conjugate can be formed by an enzymatic reaction, such as expressed protein ligation or by sortase (see: Fierer, et al., Proc. Natl. Acad. Sci., 111:W1176-1181, 2014 and Theile et al., Nat. Protoc., 8:1800-1807, 2013.) chemo-enzymatic reactions (Smith, et al., Bioconjug. Chem., 25:788-795, 2014) or non-covalent high affinity interactions, such as, for example, biotin-avidin and coiled-coil interactions (Pechar, et al., Biotechnol. Adv., 31:90-96, 2013) or any suitable means that are known to those skilled in the art (see: Chalker, et al., Acc. Chem. Res., 44:730-741, 2011, Dumas, et al., Agnew Chem. Int. Ed. Engl., 52:3916-3921, 2013).

Particle (P) or Hydrophobic Molecule (H)

Immunogenic compositions of the present disclosure comprise peptide antigen conjugates that further comprise a pre-formed Particle (P) or a hydrophobic molecule (H). Peptide antigen conjugates comprising a Particle (P) occur as particles in aqueous conditions. In some embodiments, peptide antigen conjugates comprising hydrophobic molecules (H) may occur as single soluble molecules in organic solvents (e.g., DMSO) but assemble into particles in aqueous conditions. In other embodiments, peptide antigen conjugates comprising hydrophobic molecules (H) may occur as single soluble molecules in organic solvents (e.g., DMSO) and in aqueous conditions over certain temperature and pH ranges but assemble into particles in aqueous conditions over certain temperatures and pH ranges, e.g. at physiologic temperature and pH.

The purpose of the Particle (P) or hydrophobic molecule (H) is to render the peptide antigen conjugate into a particulate format as a means to modulate pharmacokinetics and promote uptake by antigen-presenting cells. The particles formed by peptide antigen conjugates should be a size between about 10 nm to 10,000 nm in diameter. In preferred embodiments, the particles are nanoparticles that are a size that can be taken up into the endosomal system of cells (such as immune cells). The nanoparticles can be in an average size range of about 10 nm to about 500 nm in diameter. Thus, in some embodiments, the nanoparticles can average about 10 nm, about 20 nm, about 30 nm, about 40 nm, about 50 nm, about 100 nm, 200 nm, 300 nm, 400 nm or 500 nm in diameter. In other embodiments, the nanoparticles can average from about 10-50 nm, or about 10-100 nm, or about 10-200 nm or about 10-500 nm in diameter. In preferred embodiments, the particle size ranges from about 20-200 nm in diameter. The particles in the composition can vary in size, but will generally fall within the size ranges set forth herein. For example, greater than 50%, greater than 55%, greater than 60%, greater than 65%, greater than 70%, greater than 75%, greater than 80%, greater than 85%, greater than 90%, greater than 91%, greater than 92%, greater than 93%, greater than 94%, greater than 95%, greater than 96%, greater than 97%, greater than 98% or greater than 99% of the particles in the composition will fall within the size ranges set forth herein. In some embodiments, the peptide antigen (A) may be linked to an extension (B1 or B2) that is linked either directly or via a Linker (L) to Particles (P) or hydrophobic molecules (H) that assemble into particles that are too large for uptake by immune cells (e.g., particles larger than about 5,000 nm) and that form a depot at the injection site.

In some embodiments, the peptide antigen (A) is linked to a pre-formed Particle (P). The Particle (P) may be comprised of hydrophobic materials, such as polymers or lipids, cross-linked hydrophilic polymers, such as hydrogels, or cross-linked hydrophobic polymers, such as cross-linked polystyrene, that retain structure in aqueous conditions. Non-limiting examples of Particles (P) include, polymer particles, such as poly(lactic-co-glycolic acid) (PLGA), polymersomes or polaxomers; lipid-based micelles, liposomes, or multi-lamellar vesicles; oil in water emulsions, such as mineral oil-in-water and water-in-mineral oil emulsions; and inorganic salt particles, such as aluminum phosphate or aluminum hydroxide salt particles (i.e. Alum). In some embodiments, the Particle (P) is a liposomal nanoparticle. In other embodiments, the Particle (P) is an iron particle. In still other embodiments, the Particle (P) is a polymer particle.

The efficiency of peptide antigen (A) linkage to pre-formed Particles (P) depends on the nature of the peptide antigen and the type of linkage used. For example, peptide antigens (A) may be adsorbed or incorporated inside the Particles (P) and the efficiency of this process may be empirically determined for each peptide antigen (A), as the nature of the peptide antigen (A) can influence adsorption and incorporation. Peptide antigens (A) may be linked to the Particle (P) through high affinity interactions (e.g., electrostatic) or a covalent bond, wherein a Particle (P) has a set number of reactive sites that will dictate the number of peptide antigens (A) that can be linked to the Particle (P). For immunogenic compositions comprising multiple different peptide antigens (A), for example 20 different peptide antigens (A), multiple copies of each type of peptide antigen (A) may be delivered on separate Particles (P) or multiple copies of all 20 types of peptide antigens (A) may be delivered on the same particle (P).

A limitation of pre-formed Particles (P) is that the ratio of antigen to Particle (P) cannot be easily controlled. Alternatively, in preferred embodiments the peptide antigen (A) is linked either directly or via a Linker (L) to a hydrophobic molecule (H) that promotes particle assembly in aqueous conditions. The peptide antigen conjugate comprised of a peptide antigen (A) optionally linked through an extension (B1 or B2) that is linked either directly or via a Linker (L) to a hydrophobic molecule (H) is a molecularly defined entity and the ratio of peptide antigens (A) to the hydrophobic molecule (H) can be precisely controlled. In preferred embodiments, the ratio is 1:1 peptide antigen (A) to hydrophobic molecule (H). In additional non-limiting examples, the ratio may be from 1:3 to 3:1 peptide antigens (A) to hydrophobic molecules (H).

In contrast to preformed-particles, the peptide antigen conjugate may be formed by linking the peptide antigen (A) directly or indirectly through an extension (B1 or B2) and/or a Linker (L) to a hydrophobic block (H) producing a chemically defined single molecule. The hydrophobic molecule (H) is a molecule with substantially limited water solubility, or is amphiphilic in properties, and capable of assembling into supramolecular structures, e.g., micellar, nano- or micro-particles in aqueous conditions. In preferred embodiments, the hydrophobic molecule (H) is insoluble, or forms micelles, in aqueous conditions down to about 0.1 mg/mL or about 0.01 mg/mL.

The hydrophobic molecule (H) may be chosen from any molecules comprising higher alkanes, cyclic aromatics, fatty acids, compounds deriving from terpenes/isoprenes or polymers that have limited water solubility and/or amphiphilic characteristics that results in the molecules assembling into particles in aqueous conditions. Exemplary higher alkanes include but are not limited to octane, nonane, decane, undecane, dodecane, tridecane, tetradecane, pentadecane, hexadecane, heptadecane and octadecane. Exemplary cyclic aromatics include but are not limited to benzene and fused benzene ring structures or heterocyclic aromatic molecules. Exemplary saturated and unsaturated fatty acids include but are not limited to myristic acid, palmitic acid, stearic acid or oleic acid. In some embodiments, the hydrophobic molecule (H) is a fatty acid, for example myristic acid. In other embodiments, the hydrophobic molecule (H) comprises a diacyl lipid, such as 1,2-dioleoyl-sn-glycero-3-phosphoethanolamine or 1,2-distearoyl-sn-glycero-3-phosphoethanolamine or a lipopeptide, e.g., Pam2Cys. In some embodiments, the fatty acid or lipid based hydrophobic molecule (H) may further comprise a PEG. Exemplary compounds deriving from terpenes/isoprene include sterol derivatives, such as cholesterol, and squalene. In some embodiments, the hydrophobic molecule (H) comprises cholesterol.

In preferred embodiments, the hydrophobic molecule (H) is a polymer with limited water solubility or is amphiphilic and capable of assembling into particles, e.g., micelles in aqueous conditions. Exemplary polymers include but are not limited to PLGA, hydrophobic poly(amino acids), poly(benzyl glutamate), polystyrene, polaxomers based on ethylene oxide propylene oxide monomers and temperature-responsive polymers, such as poly(N,N'-diethyl acrylamide), poly(N-n-propylacrlyamide), Poly(N-isopropylacrylamide), poly[di(ethelyene glycol)methacrylate methyl ether] and certain PEGylated poly(amino acids), such as Poly(γ-(2-methoxyethoxy)esteryl-L-glutamate). In some embodiments, the hydrophobic molecule (H) is a poly(amino acid) comprised of hydrophobic amino acids. In preferred embodiments, the hydrophobic molecule (H) comprising a poly(amino acid) is comprised of amino acids that comprise aromatic rings. In other embodiments, the hydrophobic molecule (H) is a poly(amino acid) that is linked to Ligands, such as PRR agonists. In other embodiments, the hydrophobic molecule (H) is an A-B type di-block co-polymer. In some embodiments, the di-block co-polymer is temperature-responsive and is capable of assembling into particles in response to a temperature shift. In some embodiments, the hydrophobic molecule (H) comprising an A-B type di-block co-polymer further comprises Ligands, such as PRR agonist, linked to one block of the di-block co-polymer. Polymers useful as hydrophobic molecules (H) for peptide antigen conjugates are described in greater detail below.

Polymers

The hydrophobic molecule (H) or Particle (P) may comprise a linear or branched polymer. The polymer can be a homo-polymer, a co-polymer or a terpolymer. The polymer can be comprised of one or many different types of monomer units. The polymer can be a statistical copolymer or alternating copolymer. The polymer can be a block copolymer, such as the A-B type, or the polymer can be comprised of a grafted copolymer, whereby two polymers are linked through polymer analogous reaction.

The hydrophobic molecule (H) or Particle (P) may comprise polymers comprising naturally occurring and/or non-natural monomers and combinations thereof. Natural biopolymers may include peptides comprised of amino acids (sometimes referred to as poly(amino acids)); a specific example is poly(tryptophan). The natural biopolymer may be chemically modified. For example, biopolymers comprised of glutamic acid or lysine residues may be modified at the gamma carboxyl or epsilon amino groups, respectively, for the attachment of a Ligand. Biopolymers can be polysaccharides, which may include but are not limited to glycogen, cellulose and dextran. Additional examples include polysaccharides that occur in nature, including alginate and chitosan. Polymers may also be comprised of naturally occurring small molecules, such as lactic acid or glycolic acid, or may be a copolymer of the two (i.e., PLGA).

In some embodiments, the hydrophobic molecule (H) or Particle (P) is comprised of an anionic (e.g., poly(acidic)) polymer or cationic (e.g., poly(basic)) polymer or combinations of anionic and cationic polymers. Cationic polymers can bind to negatively charged peptides by electrostatic interaction or may be useful for complexing negatively charged nucleic acids, such as DNA and RNA. In some embodiments, the polymer is a water insoluble zwitterion at pH 7.4 but carries a net positive charge at pH less than about 6 and is water soluble. In some embodiments, the hydrophobic molecule (H) comprising a first polymer carries a positive or negative charge that is complementary to the negative or positive charge, respectively, on a second polymer and the first and second polymers form an electrostatic complex through charge neutralization that renders the complex insoluble. In some embodiments, the cationic polymer can be a naturally occurring or synthetic poly(amine), such as poly(lysine) or poly(ethylenimine) (PEI). In additional embodiments, the cationic polymer can be a poly(amido amine) (PAA) or poly(beta amino ester) (PBAE) produced from the Michael addition reaction of amines with either bis(acrylamides) or bis(acrylesters). Non-limiting examples of cationic polymers that can be used in the disclosed embodiments include poly(ethylenimine), poly(allylanion hydrochloride; PAH), putrescine, cadaverine, poly(lysine) (PL), poly(arginine), poly(trimethylenimine), poly(tetramethylenimine), poly(propylenimine), aminoglycoside-polyamine, dideoxy-diamino-b-cyclodextrin, spermine, spermidine, cadaverine, poly(2-dimethylamino)ethyl methacrylate, poly(histidine), cationized gelatin, dendrimers, chitosan, and any combination thereof. The cationic polymer may contain a quaternary ammonium group, such as that present on methylated chitosan. Alternatively, the polymer may be an anionic polymer. In some non-limiting examples the polyanionic polymer is poly(glutamic acid). In alternative embodiments the polyanionic polymer is poly(aspartic acid). The polymer can be a polyphoshphoester-based polymer. The polymer may comprise natural anionic polyscaccharides, including, e.g., algininc acid, comprised of 1-4)-linked β-D-mannuronate and guluronic acid. The polymer may comprise nucleotides. Other polyanionic polymers may be equally suited.

In some embodiments, the hydrophobic molecule (H) is a water soluble cationic polymer over certain pH ranges but is uncharged and water insoluble at pH ranges around physiologic pH 7.4. In some embodiments, the hydrophobic molecule (H) is a polymer that comprises aromatic amines wherein the pKa of the conjugate acid of the aromatic amine is less than 7.5. At pH below the pKa of the aromatic amines, the aromatic amine is protonated and therefore endows the polymer with positive charge. A non-limiting example of a hydrophobic molecule (H) comprised of a polymer comprising aromatic amines is poly(phenylalanine amine). In some embodiments, the hydrophobic molecule (H) is a polymer that comprises nitrogen heterocycles wherein the pKa of a nitrogen atom comprising the heterocycle is less than 7.5. At pH below the pKa of a nitrogen atom comprising the heterocycle, the nitrogen is protonated and endows the polymer with positive charge. A non-limiting example of a hydrophobic molecule (H) comprised of a polymer comprising a heterocycle with protonatable (i.e. basic) nitrogen atoms is poly(histidine). Herein, we report the unexpected finding that hydrophobic molecules comprised of polymers that comprise a protonatable nitrogen (e.g., aromatic amine) provide unexpected improvements in manufacturing, particle stability and biological activity.

In some embodiments, the hydrophobic molecule (H) can be a poly(diethylene glycol methyl ether methacrylate)-(DEGMA) based polymer. In additional embodiments, the hydrophobic molecule (H) is a polymer that may include monomers of (meth)acrylates, (meth)acrylamides, styryl and vinyl moieties. Specific examples of (meth)acrylates, (meth)acrylamides, as well as styryl- and vinyl-based monomers include N-2-hydroxypropyl(methacrylamide) (HPMA), hydroxyethyl(methacrylate) (HEMA), Styrene and vinylpyrrolidone (PVP), respectively. The polymer can be a thermoresponsive polymer comprised of monomers of N-isopropylacrylamide (NIPAAm); N-isopropylmethacrylamide (NIPMAm); N,N'-diethylacrylamide (DEAAm); N-(L)-(1-hydroxymethyl)propyl methacrylamide (HMPMAm); N,N'-dimethylethylmethacrylate (DMEMA), 2-(2-methoxyethoxy)ethyl methacrylate (DEGMA). In some embodiments, the hydrophobic polymer is a polymer comprising HPMA, or HPMA DEGMA monomers. In some embodiments, the polymer comprising HPMA and DEGMA monomers is an A-B type di-block polymer. An unexpected finding reported herein is that peptide antigens (A) linked to A-B type di-block co-polymers comprising an HPMA hydrophilic block assemble into nanoparticle micelles of uniform size independent of the peptide antigen (A) composition.

The hydrophobic molecule (H) may also comprise polymers based on cyclic monomers that include cyclic urethanes, cyclic ethers, cyclic amides, cyclic esters, cyclic anhydrides, cyclic sulfides and cyclic amines.

Hydrophobic molecules (H) based on polymers comprising cyclic monomers may be produced by ring opening polymerization and include polyesters, polyethers, polyamines, polycarbonates, polyamides, polyurethanes and polyphosphates; specific examples may include but are not limited to polycaprolactone and poly(ethylenimine) (PEI). Suitable polymers may also be produced through condensation reactions and include polyamides, polyacetals and polyesters.

In some embodiments, the hydrophobic molecule (H) is a polymer that can include from 3 to 10,000 monomer units. In preferred embodiments, the polymer includes from about 3 to 300 monomer units, such as from 3 to 10, e.g., 3, 4, 5, 6, 7, 8, 9 10 monomer units; or from about 10 to 100 monomer units, e.g., 10, 20, 30, 40, 50, 60, 70, 80, 90, 100; or from about 100 to 200 monomer units; or from about 200 to 300 monomer units, typically no more than 1,000 monomer units. In some embodiments, the polymer may comprise up to 1,000 to 10,000 monomer units. Typically, at least five monomers are needed to form a sufficient size of the hydrophobic molecule (H) to promote particle formation of the peptide antigen conjugate, though, unexpectedly, hydrophobic molecules (H) comprised of polymers with as few as 3 monomers that include aromatic rings were sufficient to drive particle assembly of peptide antigen conjugates. Increasing the length of the polymer from 3 to 5 and 5 to 10 monomers increases the strength of the forces promoting particle formation, leading to more stable and larger sized particles formed by the peptide antigen conjugates. In preferred embodiments, the hydrophobic molecule (H) comprising the peptide antigen conjugate is a polymer comprised of between 5-100 monomers, which results in the formation of approximately 10-300 nm diameter particles in aqueous conditions. In additional embodiments, the polymer comprising the hydrophobic molecule (H) is comprised of about 300 monomers and results in peptide antigen conjugates that assemble into particles between about 20 to 500 nm, or about 100-500 nm.

In some embodiments, the average molecular weight of the polymer comprising the hydrophobic molecule (H) may be between about 1,000 to 1,000,000 g/mol. In preferred embodiments, the average molecular weight of the polymer is between about 1,000 and 60,000 g/mol. In some embodiments, the polymer molecular weight is between about 1,000 and 5,000, or between about 5,000 and 10,000, or between about 10,000 and 20,000, or between about 20,000 and 30,000, or between about 25,000, and 60,000. In some embodiments, the hydrophobic molecule (H) is an A-B type di-block polymer with an average molecular weight of between about 10,000 g/mol to about 60,000 g/mol, such as about 10,000 g/mol, 20,000 g/mol, 30,000 g/mol, 40,000 g/mol, 50,000 g/mol or 60,000 g/mo. In some embodiments, the polymer is an A-B type di-block polymer wherein the ratio of the molecular weights of the A block and B blocks are about 1:5 to about 5:1. In non-limiting examples, the A-B type di-block polymer with an average molecular weight of about 60,000 g/mol is comprised of an A block with an average molecular weight of about 10,000 g/mol and a B block with an average molecular weight of about 50,000 g/mol; an A block with an average molecular weight of about 20,000 g/mol and a B block with an average molecular weight of about 40,000 g/mol; an A block with an average molecular weight of about 30,000 g/mol and a B block with an average molecular weight of about 30,000 g/mol; an A block with an average molecular weight of about 40,000 g/mol and a B block with an average molecular weight of about 20,000 g/mol; an A block with an average molecular weight of about 50,000 g/mol and a B block with an average molecular weight of about 10,000 g/mol.

The polydispersity, Mw/Mn, of the polymer may range from about 1.0 to about 5.0. Polymers may be formed by a variety of polymerization techniques. Peptide and nucleotide-based polymers may be prepared by solid-phase synthesis and will have polydispersity of 1.0 as the polymers are molecularly defined. Polymers formed by chain growth polymerization will have polydispersities >1.0. Polymers may be synthesized by living polymerization techniques or solution free radial polymerization. In preferred embodiments, peptide based biopolymers are synthesized by solid-phase peptide synthesis. Peptide (or "poly(amino acid)") based polymers comprising amino acids with aromatic rings, such as tryptophan, though hydrophobic in aqueous conditions, provided unexpected improvements in manufacturing by solid-phase synthesis as compared with peptides (or "poly(amino acids)") without aromatic rings. Thus, in preferred embodiments, hydrophobic molecules (H) based on peptides produced by solid phase synthesis include amino acids comprising aromatic rings. In additional embodiments, acrylamide- and acrylate-based polymers are synthesized by reversible addition-fragmentation chain-transfer (RAFT) polymerization. In additional embodiments, poly(amino acids) and poly(phosphoesters) are synthesized by ring opening polymerization.

In some embodiments, the hydrophobic molecule (H) may comprise a polymer that further comprises a Ligand or Ligands, such as PRR agonists. In some embodiments, the polymer-based hydrophobic molecules (H) may include monomers that comprise at least one functional group that can be coupled to a Ligand, or to a linker that can be coupled to a Ligand. In other embodiments, the polymer-based hydrophobic molecule (H) may comprise Ligands that are linked to the ends and/or side chains of the polymer.

In preferred embodiments of immunogenic compositions for the treatment or prevention of cancer and infectious diseases, the hydrophobic molecule (H) is a polymer that is linked to Ligands. In some embodiments, the Ligand that is linked to the polymer-based hydrophobic molecule (H) comprises an aromatic ring structure. In some embodiments, the Ligand linked to the polymer is hydrophobic and promotes increased stability of the particles formed by the peptide antigen conjugate in aqueous conditions. In other embodiments, the Ligand that is linked to the polymer-based hydrophobic molecule (H) comprises a heterocyclic aromatic ring. In some embodiments, the ligand that is linked to the polymer-based hydrophobic molecule (H) comprises an aromatic ring further comprising an aryl amine. In some embodiments, the ligand attached to the hydrophobic molecule (H) is a hydrophobic ligand comprising a heterocyclic aromatic ring, optionally wherein the hydrophobic Ligand further comprises an aromatic amine (i.e. Ar—$NH_2$). In embodiments, wherein the hydrophobic molecule (H) comprises a Ligand that comprises an aromatic group, optionally comprising a heterocycle and/or aryl amine, we report the unexpected finding that such hydrophobic molecule (H) are highly soluble in pharmaceutically acceptable organic solvents, such as DMSO and ethanol, but insoluble in aqueous buffers.

In some embodiments, the Ligand linked to the polymer-based hydrophobic molecule (H) is a pattern recognition receptor agonist (PRRa), such as an agonist of STING, NOD receptors or TLRs that has adjuvant properties. The Ligand with adjuvant properties linked to the polymer may be, or be derived from, any suitable adjuvant compound, such as a PRR agonist. Suitable Ligands with adjuvant properties includes compounds that include small organic molecules, i.e., molecules having a molecular weight of less than about 3,000 Daltons, although in some embodiments the adjuvant may have a molecular weight of less than about 700 Daltons and in some cases the adjuvant may have a molecular weight from about 200 Daltons to about 700 Daltons.

The hydrophobic molecule (H) in preferred embodiments of immunogenic compositions used for the treatment or prevention of cancer or infectious diseases is a polymer linked to Ligands with adjuvant properties. The Ligands with adjuvant properties, such as PRR agonists, can be linked to the side chains or end groups of the polymer through any suitable linker. In some embodiments, monomers comprising a polymer-based hydrophobic molecule (H) comprise a side chain comprising at least one functional group that can be coupled to a Ligand with adjuvant properties, or to a linker that can be coupled to a Ligand with adjuvant properties. In some embodiments, wherein the polymer-based hydrophobic molecule (H) comprises a Ligand with adjuvant properties, all of the monomers of the polymer are linked to the Ligand with adjuvant properties. In other embodiments, wherein the hydrophobic molecule (H) comprises a Ligand with adjuvant properties, not all of the monomers in the polymer are linked to the adjuvant.

In some embodiments wherein the hydrophobic molecule (H) comprises a polymer linked to a Ligand with adjuvant properties through monomer units distributed along the backbone of the polymer, increasing the density of the Ligand on the polymer leads to an unexpected improvement in immune responses to the peptide antigen (H).

In certain embodiments, the mole ratio of Ligands with adjuvants properties, such as PRR agonists, to monomers of the polymer may be selected from about 1:100 to 1:1 mol/mol (or about 1 mol % to about 100 mol %), such as from 1:2.5 to 1:1 mol/mol.

The density of the Ligand with adjuvant properties, such as PRR agonists, linked to the polymer can be varied as needed for particular applications. The Ligand with adjuvant properties, such as PRR agonists, may be linked to the polymer from 1 to 100 mol %, such as from 1 to 10 mol % or from 50-100 mol %. Mol % refers to the percentage of monomers comprising the polymer that are linked to Ligand with adjuvant properties, such as PRR agonists. For example, 10 mol % Ligand (e.g., PRR agonists) is equal to 10 monomer units linked to the Ligand from a total 100 monomer units. The remaining 90 may be macromolecule-forming monomeric units, which are not linked to the Ligand.

The density of Ligands, such as Ligands with adjuvant properties, linked to a polymer-based hydrophobic molecule (H) should be selected to ensure that the peptide antigen conjugate (i) is soluble in pharmaceutically acceptable organic solvents, such as DMSO; (ii) can form stable nanoparticles in aqueous conditions at physiologic temperature and pH; and/or (iii) is capable of inducing an immune response, particularly a T cell response, in a subject.

The optimal density of Ligands, such as PRR agonists, linked to the polymer depends on the polymer composition, polymer length, as well as the composition of the Ligand. When the Ligand is a hydrophobic/amphiphilic molecule with low water solubility, such as an imidazoquinoline-based Toll-like receptor-7 and -8 agonist (TLR-7/8a) and the polymer alone is water soluble (i.e. the polymer not linked to the Ligand is water soluble), the Ligand is typically linked to the polymer at a density of about 20-100 mol % when the polymer is comprised of between about 5-30 monomer units; 10-50 mol % when the polymer is comprised of between 30-100 monomer units; or at a density of between 5-20 mol % when the polymer is comprised of between 100-300 monomer units. In general, the mol % of the Ligand with adjuvant properties is higher for shorter polymers and lower for longer polymers.

The optimal density of the Ligand with adjuvant properties, e.g. PRRa, attached to hydrophilic or temperature-responsive polymers that are greater than 10,000 g/mol and based on co-monomers selected from N-2-hydroxypropyl (methacrylamide) (HPMA), hydroxyethyl(methacrylate) (HEMA), Styrene, vinylpyrrolidone (PVP), N-isopropy-lacrylamide (NIPAAm); N-isopropylmethacrylamide (NIP-MAm); N,N'-diethylacrylamide (DEAAm); N-(L)-(1-hy-droxymethyl)propyl methacrylamide (HMPMAm); N,N'-dimethylethylmethacrylate (DMEMA), 2-(2-methoxyethoxy)ethyl methacrylate (DEGMA) or substituted poly(phosphoesters) is from 1 to 25%, e.g., the density of the adjuvant attached to the polymer can be about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24% or about 25%.

In some embodiments, the hydrophobic molecule (H) is an amphiphilic A-B type di-block co-polymer wherein one block is hydrophobic and the other block is hydrophilic. In some embodiments, where the hydrophobic molecule (H) is an amphiphilic A-B type di-block co-polymer and the Ligand is hydrophobic, such as an imidazoquinoline TLR-7/8 agonist, the Ligand is preferably linked to the hydrophobic block at a density of between about 1 to 50 mol %, typically about 1 to 20 mol %. In some embodiments, where the hydrophobic molecule (H) is an amphiphilic A-B type di-block co-polymer and the Ligand is hydrophilic, the Ligand is preferably linked to the hydrophilic block at a density of between about 1 to 20 mol %, or at the hydrophilic end of the hydrophilic block and therefore the A-B type di-block co-polymer is semi-telechelic with respect to the Ligand. In a non-limiting example, the hydrophobic molecule (H) comprises a temperature-responsive A-B type di-block co-polymer comprising an HPMA block and a DEGMA block and an imidazoquinoline TLR-7/8 agonist is linked to the DEGMA block at a density of between about 1 to 5 mol %. In an additional non-limiting example, the hydrophobic molecule (H) comprises an A-B type di-block polymer comprising an HPMA co-polymer hydrophobic block and an HPMA homopolymer hydrophilic block and an imidazoquinoline TLR-7/8 agonist is linked to the HPMA co-polymer hydrophobic block at a density of between about 20 mol %. In some embodiments, the hydrophobic molecule is a tri-block co-polymer, e.g., A-B-A or other multi-block co-polymers compositions.

An unexpected finding reported herein is that peptide antigens (A) linked to A-B type di-block co-polymers comprising an HPMA hydrophilic block linked to Ligands with adjuvant properties assemble into nanoparticles micelles of uniform size independent of the peptide antigen (A) composition and this improved reliability of nanoparticle micelle formation was associated with increased magnitude of T cell immunity. In a non-limiting example, a peptide antigen (A) is linked to a di-block co-polymer comprised of an HPMA co-polymer hydrophobic block (i.e., p[(HPMA)-co-(MA-b-Ala-2B)]) and an HPMA homopolymer hydrophilic block (i.e., p(HPMA)) through a triazole linker (Lys(N3)-DBCO) to form a peptide antigen conjugate p{[(HPMA)-co-(MA-b-Ala-2B)]-b-p(HPMA)}-DBCO-(Lys(N3))-A, wherein 2B is a TLR-7/8a also referred to as Compound 1. In additional embodiments, a peptide antigen (A) is linked to a di-block co-polymer comprised of a DEGMA co-polymer hydrophobic block (i.e., p[(DEGMA)-co-(MA-b-Ala-2B)]) and an HPMA homopolymer hydrophilic block (i.e., p(HPMA)) through a triazole linker (Lys(N3)-DBCO) to form a peptide antigen conjugate p{[(DEGMA)-co-(MA-b-Ala-2B)]-b-p(HPMA)}-DBCO-(Lys(N3))-A, wherein 2B is a TLR-7/8a also referred to as Compound 1. In other embodiments, a peptide antigen (A) is linked to a di-block co-polymer comprised of a DEGMA homopolymer linked to a ligand with adjuvant properties (i.e., 2BXy-p[(DEGMA)) and an HPMA homopolymer hydrophilic block (i.e., p(HPMA)) through a triazole linker (Lys(N3)-DBCO) to form a peptide antigen conjugate 2BXy-p{[(DEGMA)-co-(MA-b-Ala-2B)]-b-p(HPMA)}-DBCO-(Lys(N3))-A, wherein the peptide antigen (A) and 2BXy (TLR-7/8a also referred to as Compound 2) are linked at a single site on opposite ends of the polymer, which makes the polymer hetero-telechelic.

In several embodiments, the hydrophobic molecule (H) is a poly(amino acid)-based polymer that is comprised of co-monomers of glutamic acid or aspartic acid and aromatic and/or hydrophobic amino acids, such as phenylalanine, amino phenylalanineamine (or "phenylalanineamine"), tryptophan, tyrosine, benzyl glutamate, histidine, leucine, isoleucine, norleucine and valine, and one or more Ligands with adjuvant properties, e.g., PRRa, are attached to the polymer through the gamma carboxylic acid of the glutamic acid or the beta carboxylic acid of aspartic acid. In preferred embodiments, the hydrophobic molecule (H) is a poly (amino acid)-based polymer comprised of co-monomers of glutamic acid and tryptophan, wherein one or more Ligands with adjuvant properties, e.g., PRRa, are linked to the glutamic acid residues through the gamma carboxylic acid. In additional embodiments, the hydrophobic molecule (H) is a poly(amino acid)-based polymer compromised of co-monomers of lysine and aromatic and/or hydrophobic amino acids, such as phenylalanine, amino phenylalanine, histidine, tryptophan, tyrosine, benzyl glutamate, leucine, isoleucine, norleucine and valine, wherein one or more Ligands with adjuvant properties, e.g., PRRa, are attached to the polymer through the epsilon amine of lysine. In preferred embodiments, the hydrophobic molecule (H) is a poly (amino acid)-based polymer comprised of co-monomers of lysine and tryptophan, wherein one or more Ligands with adjuvant properties, e.g., PRRa, are linked to lysine through the epsilon amine. In preferred embodiments, wherein the hydrophobic molecule (H) is a poly(amino acid) co-polymer linked to one or more Ligands with adjuvant properties, e.g., PRRa, the polymer is between 5-30 amino acids in length and the adjuvant is attached at a density from 20 to 100 mol %, such as 30%, 50%, 60%, 80% and 100 mol %. In additional embodiments, the Ligand is attached only to a single end of the poly(amino acid) polymer, i.e., a semi-telechelic polymer. Herein, we report the unexpected finding that hydrophobic molecules (H) comprised of poly(amino acid)-based co-polymers that further comprise aromatic groups, such as aromatic amino acids (e.g., phenylalanine, amino phenylalanine, histidine, tryptophan, tyrosine, benzyl glutamate) or aromatic Ligands (e.g., imidazoquinolines) linked to the polymer, result in unexpected improvements in manufacturability, through improved organic solvent solubility, and improved particle stability and biological activity of peptide antigen conjugates, as compared with poly(amino acids) predominantly comprised of aliphatic amino acids or aliphatic Ligands. Thus, in preferred embodiments, hydrophobic molecules (H) comprised of poly(amino acids), or other classes of polymers, include one or more aromatic amino acids and/or Ligands that comprise an aromatic group.

In additional embodiments, the hydrophobic molecule (H) is a poly(amino acid)-based polymer comprised entirely of glutamic acid, aspartic acid or non-natural amino acid residues bearing a carboxylic acid wherein the Ligand with adjuvant properties is linked to all of the glutamic acid, aspartic acid or non-natural amino acid residues, i.e., the Ligand with adjuvant properties is attached at a density of 100 mol %. In additional embodiments, the hydrophobic molecule (H) is a poly(amino acid)-based polymer comprised entirely of Lysine or non-natural amino acids bearing a free amine and the Ligand with adjuvant properties is linked to all of the lysine or non-natural amino acid residues, i.e., the adjuvant is attached at a density of 100 mol %. In additional embodiments, PEGylated co-monomers, such as γ-(2-methoxyethoxy)esteryl-L-glutamate) are included to endow the co-polymer with temperature-responsive properties. In other embodiments, temperature-responsive polymers may be grafted to the pendant side chains of the poly(amino acid) to form a graft co-polymer. In additional embodiments, a temperature-responsive polymer may be linked to the end of the poly(amino acid) polymers to form a temperature-responsive di-block polymer. In still additional embodiments, a second polymer that is hydrophobic may be linked to the poly(amino acid) polymer that is linked to Ligands with adjuvant properties either through pendant side groups to form a graft co-polymer, or to the end of the poly(amino acid) to form a di-block co-polymer.

In some embodiments, the hydrophobic molecule (H) is a poly(amino acid)-based polymer linked to a Ligand, such as a hydrophobic Ligand with adjuvant properties, and has the formula:

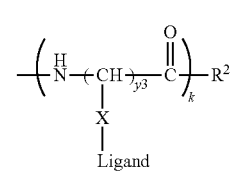

Formula I

In Formula I, $R^2$ is typically selected from one of hydrogen, hydroxyl or amine. In some embodiments, $R^2$ is linked to a Ligand or another polymer through any suitable linker molecule. The number of methylene units, $y3$, is typically 1 to 6, such as 1, 2, 3, 4, 5, or 6. The N-terminal amine of the poly(amino acid) of Formula I is typically linked to the linker precursor X2 or may be linked to the peptide antigen (A) either directly or via an extension (B1 or B2). The number of monomer repeats is indicated by k, and is typically between 3 and 300. Any suitable linker, X, is used to link the Ligand, such as a hydrophobic Ligand with adjuvant properties, to the poly(amino acid) backbone. In some embodiments, the linker X can be linked to a second polymer that is linked to Ligands. In some embodiments, the monomers k may be linked to two or more different ligands.

In some embodiments, the poly(amino acid)-based polymers of Formula I is:

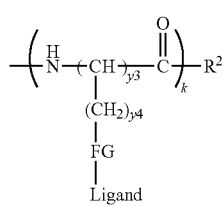

wherein y4 is any integer, such as 0 to 6, e.g., 0, 1, 2, 3, 4, 5, or 6. The Ligand may be linked to the functional groups (FG) through any suitable means and the FG is any suitable functional group, including amine, carboxylic acid, thiol, hydroxyl, azide, alkyne, hydrazine, aldehyde or ketone for attachment, i.e. linkage, of a Ligand, either directly or via a linker.

When y3 is equal to 1, the poly(amino acid)-based polymers of Formula I is:

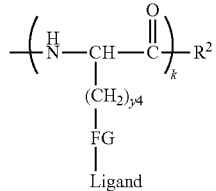

The N-terminus of the poly(amino acid) of Formula I may be linked through the Linker (L) to the peptide antigen (A) through any suitable means. In some embodiments, the N-terminus of the poly(amino acid) of Formula I is linked directly to the C-terminus of the peptide antigen (A) or to the C-terminus of the B2 extension through an amide bond. In other embodiments, the N-terminus of the poly(amino acid) of Formula I is linked to a linker precursor (X2) that reacts with a linker precursor (X1) that is linked directly or through an extension (B1 or B2) to the peptide antigen (A). In some embodiments, a cyclooctyne (e.g., DBCO) containing linker precursor (X2) is attached to the N-terminus of the poly (amino acid) of Formula I and reacts with an azido containing linker precursor (X1) to form a triazole bond.

In some embodiments, poly(amino acid)-based hydrophobic molecule (H) may comprise hydrophobic amino acids (e.g., aromatic amino acids), or hydrophobic amino acids (e.g., aromatic amino acids) and amino acids linked to Ligands, as well as additional amino acids, such as charged or hydrophilic amino acids, that are useful for compensating or modulating the physical and chemical characteristics of the hydrophobic molecule (H) to produce a material that is preferably soluble during manufacturing in organic solvents but is capable of forming particles in aqueous conditions. Thus, in some embodiments, the hydrophobic molecule (H) is a poly(amino acid)-based polymer that has the formula:

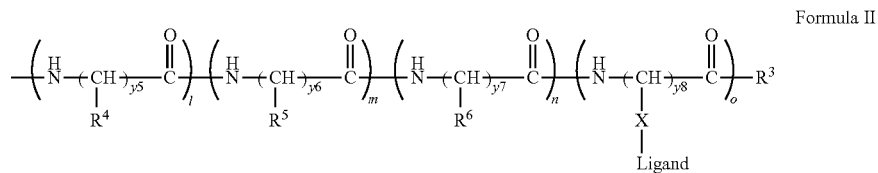

Formula II

The poly(amino acid)-based polymer of Formula II typically comprises the monomer, l, and optional monomers, m, n and o. $R^3$ is typically selected from one of hydrogen, hydroxyl or amine. In some embodiments, $R^3$ is a Ligand, such as a Ligand with adjuvant properties, or another polymer that is linked to the hydrophobic molecule (H) through any suitable linker molecule. The number of methylene units denoted by y5, y6, y7, and y8, is typically 1 to 6, such as 1, 2, 3, 4, 5, or 6. The N-terminal amine of the poly(amino acid) of Formula I is typically linked to the linker precursor X2 or may be linked to the peptide antigen (A) either directly or via an extension (B1 or B2). In typical embodiments, the poly(amino acid)-based polymer of Formula II comprises monomers, l, that are selected from any natural or non-natural amino acid wherein $R^4$ is selected from lower alkyl or aromatic groups and endow the polymer backbone with hydrophobic properties. In some embodiments, the $R^4$ included in Formula II can be selected from

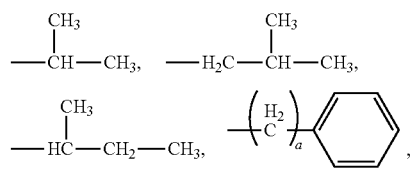

where $a = 1$ to 6

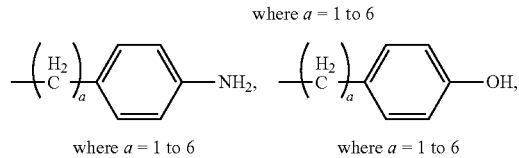

where $a = 1$ to 6    where $a = 1$ to 6

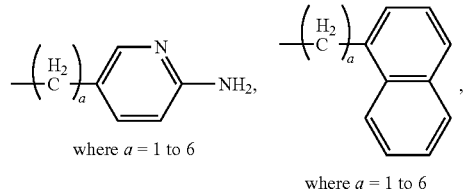

where $a = 1$ to 6

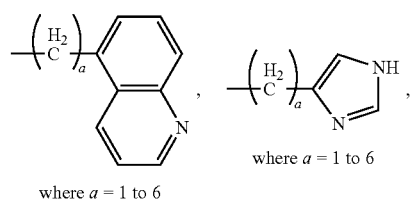

where $a = 1$ to 6    where $a = 1$ to 6

[Chemical structure: -(CH2)a- attached to indole NH, where a = 1 to 6]

[Chemical structure: -(CH2)a-X-phenyl, where a = 1 to 6]

[Chemical structure: -(CH2)a-X-phenyl-NH2, where a = 1 to 6]

[Chemical structure: -(CH2)a-X-phenyl-OH, where a = 1 to 6]

[Chemical structure: -(CH2)a-X-pyridyl-NH2, where a = 1 to 6]

[Chemical structure: -(CH2)a-X-naphthyl, where a = 1 to 6]

[Chemical structure: -(CH2)a-X-quinolinyl, where a = 1 to 6]

[Chemical structure: -(CH2)a-X-imidazole-NH, where a = 1 to 6]

[Chemical structure: -(CH2)a-X-indole-NH, where a = 1 to 6]

[Chemical structures: -CH2-phenyl, -CH2-phenyl-NH2,]

[Chemical structures: -CH2-phenyl-OH, -CH2-imidazole-NH,]

[Chemical structure: -CH2-indole-NH,]

[Chemical structure: -(CH2)2-C(=O)-O-CH2-phenyl,]

[Chemical structure: -CH2-C(=O)-NH-CH2-phenyl, or]

[Chemical structure: -(CH2)2-C(=O)-O-(CH2-CH2-O)2-CH3]

wherein X of $R^4$ is any suitable linker.

In some embodiments, the poly(amino acid)-based polymer of Formula II comprises optional co-monomers, m, that are selected from any natural or non-natural amino acid, such as a PEG amino acid spacer (e.g., m of Formula II is —NH—(CH$_2$—CH$_2$—O)$_{y9}$—(CH$_2$)$_{y10}$—(CO)—, wherein y9 is an integer typically between 1 and 24 and y10 is an integer typically between 1 and 3) or an amino acid with a small substituent, wherein, e.g., $R^5$ is selected from Hydrogen, lower alkyl or a lower alkyl comprising a hydroxyl and is provided to increase the spacing or flexibility of the polymer backbone. In some embodiments, the $R^5$ included in Formula II can be selected from —H, —CH$_3$, —(CH$_2$)$_b$—OH, where b = 1 to 6.

In some embodiments, the poly(amino acid)-based polymer of Formula II comprises optional co-monomers, n, that are selected from any natural or non-natural amino acid, wherein $R^6$ is selected from any group comprising a functional group that carriers charge either permanently or at a specific pH. In some embodiments, the $R^6$ included in Formula II can be selected from —(CH$_2$)$_d$—NH$_2$, where d = 1 to 6

—(CH$_2$)$_d$—COOH, where d = 1 to 6

—(CH$_2$)$_d$—NH—C(=NH)—NH$_2$, where d = 1 to 6

—(CH$_2$)$_d$—S$^+$(R)(R), where d = 1 to 6, where R = lower alkyl

—(CH$_2$)$_d$—N$^+$(R)(R)(R), where d = 1 to 6, where R = lower alkyl

—(CH$_2$)$_d$—O—S(=O)$_2$—OH, where d = 1 to 6

—(CH$_2$)$_d$—O—P(=O)(OH)—OH, where d = 1 to 6

In some embodiments, the poly(amino acid)-based polymer of Formula II comprises optional co-monomers, o, that are selected from any natural or non-natural amino acid, wherein a Ligand is linked through any suitable linker, X, to the monomer, o. The Ligand may be a Ligand with adjuvant properties. The Ligand linked to poly(amino acids) of Formula II may be hydrophobic, hydrophilic, amphiphilic, charged or neutral in properties. The poly(amino acid)-based polymer of Formula II comprising monomer o may further comprise monomer units, 1, m and n, that compensate for the properties of the Ligand attached to monomer o.

In poly(amino acid)-based polymers of Formula II, the number of monomer repeats is indicated by l, m, n and o, wherein the sum of l, m, n and o is typically any integer between 3 and 300. Each of the different types of monomers, l, m, n or o, may be the same or different. The monomers denoted by "l" endow the poly(amino acid)-based polymer of Formula II with hydrophobic properties, i.e., render the polymer a water insoluble hydrophobic molecule (H). The hydrophobic monomers, l, may be the same or different and typically comprise an aromatic ring. In preferred embodiments, the hydrophobic monomers, l, comprise a heterocyclic and/or amine-substituted aromatic ring. The optional co-monomers denoted by "m" may be used to increase the flexibility or spacing of different monomers comprising the polymer backbone. The optional co-monomers denoted by "n" comprise charged functional groups. The optional co-monomer denoted by "o" is used for the attachment of a Ligand, such as a PRR agonist. In some embodiments, the Ligand linked to the monomer, o, through any suitable linker is a PRR agonist. In some embodiments, the monomer, o, is linked to a Ligand that carries a positive or negative charge and is adjacent to a monomer, n, of the opposite charge. In some embodiments, a charged co-monomer, n, is placed adjacent to a co-monomer, o, comprising a functional group of the opposite charge of the functional group comprising the co-monomer n and the opposing charges result in zero net charge, thus the monomer n functions to neutralize charge carried by the Ligand attached to monomer o.

The percentage of monomers, l, m, n and o comprising the poly(amino acid)-based polymer of Formula II depends on the specific application. In some embodiments, the poly (amino acid)-based polymer of Formula II is comprised entirely of the monomer l. In other embodiments, the poly(amino acid)-based polymer of Formula II is comprised of co-monomers, l and o, such as between 5 to 95 mol % monomer l and about 95 to 5 mol % monomer o. In some embodiments, the poly(amino acid)-based polymer of Formula II comprises co-monomers, l and m, wherein m provides space, i.e. distance, between the hydrophobic monomers, l, and may reduce polymer rigidity. In other embodiments, the poly(amino acid)-based polymer of Formula II comprises monomers, l, m and o, wherein monomers m provide space between the bulky substituents comprising monomers l and o. In other embodiments, the poly(amino acid)-based polymer of Formula II comprises monomers, l and o, and optionally monomers m and n, wherein monomer n is used to modulate the charge of the polymer backbone. In certain embodiments, the poly(amino acid)-based polymer of Formula II is comprised entirely of monomers m and o. In other embodiments the poly(amino acid)-based polymer of Formula II is comprised entirely of monomers m, n and o, or just n and o. In still other embodiments, the poly(amino acid)-based polymer of Formula II comprises monomers l, m, n and o.

Wherein the poly(amino acid)-based polymer of Formula II comprises an adjuvant, the percentage of monomers comprising the polymer represented by the monomer o, which is linked to an adjuvant via any suitable linker is typically 10 to 60%, for example, between 2 to 12 amino acids of a polymer that is 20 amino acids in length are monomer o. In some embodiments of the poly(amino acid) polymers of Formula II, l is the majority monomer unit. In additional embodiments, the poly(amino acid)-based polymer of Formula II is comprised entirely of the l monomer, i.e. all monomers are the l monomer, optionally wherein the adjuvant is attached to the end of the poly(amino acid) either directly or indirectly via a second polymer or through any suitable linker molecule.

Wherein the polymer of Formula II is a copolymer comprising o monomers, the Ligand may be linked to pendant functional groups (FG) distributed along the backbone of the polymer such as shown here:

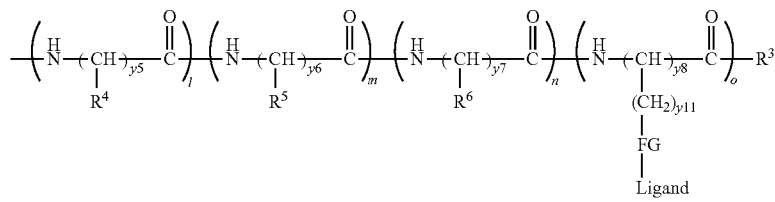

wherein y11 denotes the number of methylene units and is any integer, such as 0 to 6, e.g., 0, 1, 2, 3, 4, 5, or 6. The functional group (FG) is any suitable functional group, including amine, carboxylic acid, thiol, hydroxyl, azide, alkyne, hydrazine, aldehyde or ketone that allow for attachment, i.e. linkage, of a Ligand, either directly or via a linker.

In some embodiments, y5, y6, y7 and y8 are equal to 1 and the polymer of Formula II is:

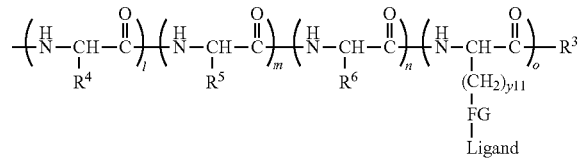

Ligands with adjuvant properties may be linked to any of the hydrophobic molecules (H) of the present disclosure. In certain embodiments, Ligands with adjuvant properties are linked to polymers of Formula II. Ligands with adjuvant properties may be linked to poly(amino acid)-based polymers of Formula II through pendant functional groups (FG) on the o monomers; at the ends of the polymer; or indirectly through another molecule or polymer that is grafted to the pendant functional groups (FG) or at the ends of the polymer. In preferred embodiments, the functional group (FG) of monomers o link the Ligands with adjuvant properties, or other Ligand molecules, to the poly(amino acid) backbone through a covalent bond. In some embodiments, the FG comprising monomer o of Formula II can be linked to a second polymer. The FG included in Formula II can be selected from carboxylic acid, aldehyde, ketone, amine, hydrazine, thiol, azide or alkyne, or any suitable functional group that can be used to link a Ligand or another polymer to the polymer backbone.

In preferred embodiments, the N-terminus of the poly (amino acid) of Formula II is linked through the Linker (L) to the peptide antigen (A), either directly or through an extension (B1 or B2) through the reaction of the linker precursors X1 and X2. In some embodiments, the N-terminus of the poly(amino acid) of Formula II is linked directly (i.e. no Linker (L) is present) to the C-terminus of the peptide antigen (A) or to the C-terminus of the B2 extension through an amide bond. In other embodiments, the N-terminus of the poly(amino acid) of Formula II is linked to cyclooctyne (DBCO) containing linker precursor (X2) that reacts with azido containing linker precursor (X1) that is linked either directly or through an extension (B1 or B2) to the peptide antigen (A).

The poly(amino acid) of Formula I or Formula II is a hydrophobic molecule (H) that may be linked either through the N-terminal amine, C-terminal carboxylic acid or through optional side chains, e.g., through the functional groups of co-monomers, directly or indirectly through a Linker (L) or an extension (B1 or B2) to a peptide antigen (A). In some embodiments, the poly(amino acid) of Formula I or Formula II is a hydrophobic molecule (H) that is linked at to a peptide antigen (A) resulting in a peptide antigen conjugate of the formula [C]—[B1]-A-[B2]-[L]-H, or [B1]-A-[B2]-[L]-H(C) wherein [ ] denotes that the group is optional.

In preferred embodiments, the poly(amino acid) of Formula I or Formula II is a hydrophobic molecule (H) that is linked at the N-terminus to a Linker (L) that is linked to a C-terminal extension (B2) that is linked to the C-terminus of a peptide antigen (A) that is linked at the N-terminus to an N-terminal extension (B1) that is linked to a charged molecule (C).

For example: C-B1-A-B2-T-H

In additional embodiments, the charged molecule (C) may be linked directly to the hydrophobic molecule (H) comprised of a poly(amino acid) of Formula I or Formula II, or via a Linker (L) that is linked to the peptide antigen (A) via an extension. Here, for A-B$_2$-L(C)—H, it is intended that the parenthesis notation indicates that L is linked to both C and H.

For example: A-B2-L(C)—H or A-B2-L-H(C)

In further embodiments, the poly(amino acid) of Formula I or Formula II is a hydrophobic molecule (H) that is linked at the N-terminus to a Linker (L) that is linked to both an optional charged (C) molecule and a C-terminal extension (B2) that is linked to the C-terminus of a peptide antigen (A).

For example: A-B2-(C-L)-H

In preferred embodiments, the hydrophobic block comprises a poly(amino acid) wherein a Ligand with adjuvant properties is attached to side groups distributed along the backbone of the poly(amino acid). The Ligand with adjuvant properties may either be hydrophobic or hydrophilic, charged or uncharged in properties. In preferred embodiments, the Ligand with adjuvant properties is a PRR agonist.

In several embodiments, the Ligand with adjuvant properties can be a pattern recognition receptor (PRR) agonist. Non-limiting examples of pattern recognition receptor (PRR) agonists include TLR-1/2/6 agonists (e.g., lipopeptides and glycolipids, such as Pam2cys or Pam3cys lipopeptides); TLR-3 agonists (e.g., dsRNA, such as PolyI.C, and nucleotide base analogs); TLR-4 agonists (e.g., lipopolysaccharide (LPS) derivatives, for example, monophosphoryl lipid A (MPL) and small molecule is a derivative or analog of pyrimidoindole); TLR5 agonists (e.g., Flagellin); TLR-7 & -8 agonists (e.g., ssRNA and nucleotide base analogs, including derivatives of imidazoquinolines, hydroxy-adenine, benzonapthyridine and loxoribine); and TLR-9 agonists (e.g., unmethylated CpG); Stimulator of Interferon Genes (STING) agonists (e.g., cyclic dinucleotides, such as cyclic diadenylate monophosphate); C-type lectin receptor (CLR) agonists (such as various mono, di, tri and polymeric sugars that can be linear or branched, e.g., mannose, Lewis-X tri-saccharides, etc.); RIG-I-like receptor (RLR) agonists; and NOD-like receptor (NLR) agonists (such as peptidogylcans and structural motifs from bacteria, e.g., meso-diaminopimelic acid and muramyl dipeptide); and combinations thereof. In several embodiments, the pattern recognition receptor agonist can be a TLR agonist, such as an imidazoquinoline-based TLR-7/8 agonist. For example, the Ligand with adjuvant properties can be Imiquimod (R837) or Resiquimod (R848), which are approved by the FDA for human use.

In several embodiments, the Ligand with adjuvant properties can be a TLR-7 agonist, a TLR-8 agonist and/or a TLR-7/8 agonist. Numerous such agonists are known, including many different imidazoquinoline compounds.

Imidazoquinolines are of use in the methods disclosed herein. Imidazoquinolines are synthetic immunomodulatory drugs that act by binding Toll-like receptors 7 and 8 (TLR-7/TLR-8) on antigen presenting cells (e.g., dendritic cells), structurally mimicking these receptors' natural ligand, viral single-stranded RNA. Imidazoquinolines are heterocyclic compounds comprising a fused quinoline-imidazole skeleton. Derivatives, salts (including hydrates, solvates, and N-oxides), and prodrugs thereof also are contemplated by the present disclosure. Particular imidazoquinoline compounds are known in the art, see for example, U.S. Pat. Nos. 6,518,265; and 4,689,338. In some non-limiting embodiments, the imidazoquinoline compound is not imiquimod and/or is not resiquimod.

In some embodiments, the Ligand with adjuvant properties can be a small molecule having a 2-aminopyridine fused to a five membered nitrogen-containing heterocyclic ring, including but not limited to imidazoquinoline amines and substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, aryloxy or arylalkyleneoxy substituted imidazoquinoline amines, and imidazoquinoline diamines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines.

In some embodiments, the ligand with adjuvant properties is an imidazoquinoline with the formula:

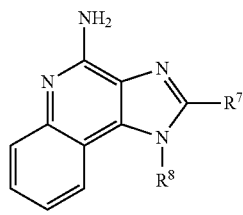

Formula III

In Formula III, $R^7$ is selected from one of hydrogen, optionally-substituted lower alkyl, or optionally-substituted lower ether; and $R^8$ is selected from one of optionally substituted arylamine, or optionally substituted lower alkylamine. $R^8$ may be optionally substituted to a linker that links to a polymer. An unexpected finding was that in some compounds wherein $R^8$ was selected from a lower alkylamine, while the compound was less potent than $R^8$ selected from an arylamine, the quality of response was improved. Thus, moderate potency Adjuvants of Formula III led to better quality responses. Note: Adjuvants (s) of Formula III are a type of Ligand and may be referred to as Adjuvants of Formula III or Ligands with adjuvant properties.

In some embodiments, the $R^7$ included in Formula III can be selected from hydrogen,

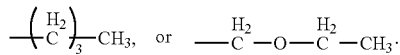

In some embodiments, $R^8$ can be selected from

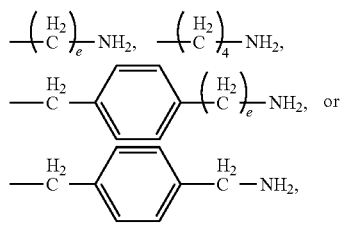

wherein e denotes the number of methylene unites is an integer from 1 to 4.

In some embodiments, $R^8$ can be

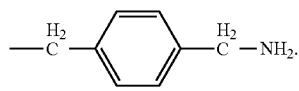

In some embodiments, $R^8$ can be

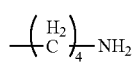

In some embodiments, $R^7$ can be

and $R^8$ can be

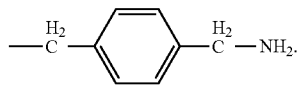

Non-limiting examples of hydrophobic molecules (H) comprised of poly(amino acids) of Formula I linked to adjuvants of Formula III include:

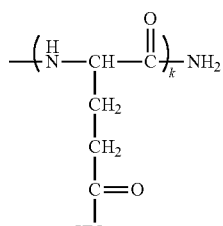

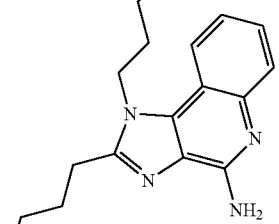

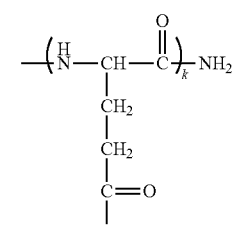

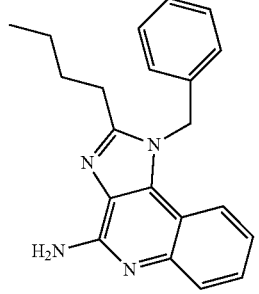

wherein k is between 3-300. For example, when k=5, the peptide is comprised of 5 amino acids linked to Adjuvants of Formula III. In some embodiments, hydrophobic molecules (H) comprised of poly(amino acids) of Formula I linked to adjuvants of Formula III may be linked either directly or indirectly via a Linker (L) and/or extension (either B1 or B2) to a peptide antigen (A) that is optionally linked to a charged molecule (C) through any suitable means to form a peptide antigen conjugate. In some embodiments, the N-terminus of the poly(amino acid) of Formula I linked to adjuvants of Formula III is linked directly to the C-terminus of the peptide antigen (A) or to the C-terminus of the B2 extension through an amide bond. In other embodiments, the N-terminus of the poly(amino acid) of Formula I linked to adjuvants of Formula III is linked to a clickable linker precursor X2, e.g., alkyne or DBCO, or a thiol-reactive linker precursor X2, e.g., maleimide, that reacts with a linker precursor X2 that is linked directly or through an extension (B1 or B2) to the peptide antigen (A). In preferred embodiments, a DBCO linker precursor X1 is attached to the N-terminus of the poly(amino acid) of Formula I linked to adjuvants of Formula III and is used to react with an azide bearing linker precursor X2 that is linked either directly or through an extension (B1 or B2) to a peptide antigen (A).

A non-limiting example of a hydrophobic molecule (H) comprised of poly(amino acids) of Formula II linked to adjuvants of Formula III includes:

acid) of Formula II linked to Adjuvants of Formula III is linked either directly or indirectly through a Linker (L) and/or extension (B1 or B2) to a peptide antigen (A) through any suitable means. In some embodiments, the N-terminus of the poly(amino acid) of Formula II linked to Adjuvants of Formula III is linked directly to the C-terminus of the peptide antigen (A) or to the C-terminus of the B2 extension through an amide bond. In other embodiments, the N-terminus of the poly(amino acid) of Formula II linked to adjuvants of Formula III is linked to a clickable linker precursor X2, e.g., DBCO, or a thiol-reactive linker precursor X2, e.g., maleimide, that reacts with a linker precursor X1 that is linked either directly or through an extension (B1 or B2) to the peptide antigen (A). In preferred embodiments, a DBCO linker precursor X2 is attached to the N-terminus of the poly(amino acid) of Formula II linked to Adjuvants of Formula III and is used to react with a linker precursor X1 bearing an azide functional group.

An unexpected finding disclosed herein is that the length, i.e. the number of monomer units, of poly(amino acids) of either Formula I or Formula II linked to adjuvants of Formula III comprising the hydrophobic molecule (H) of peptide antigen conjugates is a major determinant that impacts the magnitude of T cell responses generated against

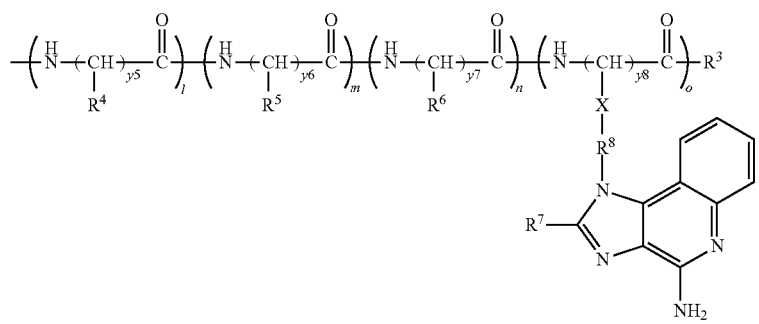

For example:

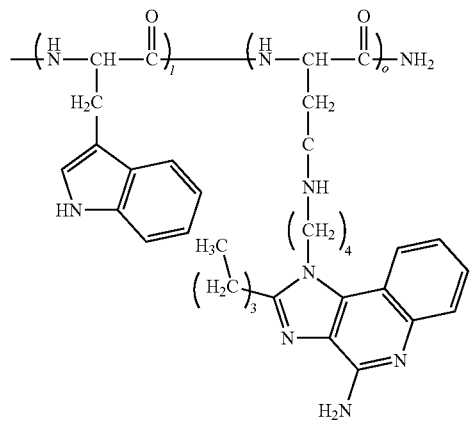

wherein co-monomer 1 is typically an integer between 3-300, and optional co-monomer o is typically an integer between 3-300 amino acid residues, wherein the sum of 1 and o is typically between about 3-300. Alternatively, o is 0 and the polymer is entirely comprised of 1, i.e., the polymer is a poly(tryptophan) polymer that is not linked to adjuvants. In some embodiments, the N-terminus of the poly(amino the peptide antigen (A). Accordingly, peptide antigen conjugates comprised of hydrophobic molecules (H) comprised of poly(amino acids) of Formula I or Formula II with 5 or more monomers units were found to promote higher quality and magnitude of T cell responses as compared with poly (amino acids) of the same formula that are less than 5 amino acids in length. An additional finding was that the number of Adjuvants of Formula III linked to poly(amino acids) of Formula I or Formula II also had an impact on the magnitude of the immune response generated, with peptide antigen conjugates comprising hydrophobic molecules (H) of Formula I or II comprising 3 or more Adjuvants of Formula III leading to higher magnitude T cell responses as compared with peptide antigen conjugates comprising hydrophobic molecules (H) of Formula I or II comprising less than 3 Adjuvants of Formula III. Non-limiting explanations for these findings are that the increased length of the hydrophobic molecule (H) of Formula I or Formula II linked to adjuvants of Formula III ensures the formation of micelles or other supramolecular structures when linked to even hydrophilic peptide antigens and that such particle formation leads to improved immune responses, possibly through improved pharmacokinetics and cellular uptake that is attributed to particles, but not soluble materials. An additional non-limiting explanation is that increasing lengths of the hydrophobic molecule (H) comprised of poly(amino acids) of Formula I or Formula II linked to adjuvants of Formula III leads to improved stability, e.g. kinetic stability, of the particles formed by the peptide antigen conjugates in aqueous buffer; improved stability of the particles ensures that the particle remains intact, thereby delaying clearance (either renal or hepatic) of the peptide antigen conjugates comprising the particles and promoting uptake by antigen presenting cells.

An additional unexpected finding disclosed herein is that the potency of the Adjuvant of Formula III linked to poly (amino acids) of Formula I or Formula II comprising the hydrophobic molecules (H) of peptide antigen conjugates was found to be inversely related to the magnitude and breadth of T cell responses generated against peptide antigens after multiple immunization. Accordingly, disclosed herein we show that poly(amino acids) of Formula I linked to adjuvants of Formula III, wherein $$R^7 = -\left(\overset{H_2}{C}\right)_3-CH_3 \quad \text{and} \quad R^8 = -\left(\overset{H_2}{C}\right)_4-NH_2,$$

referred to as Compound 1, lead to higher magnitude and breadth of T cell responses as compared with poly(amino acids) of Formula I linked to adjuvants of Formula III wherein $$R^7 = -\left(\overset{H_2}{C}\right)_3-CH_3 \quad \text{and}$$

-continued

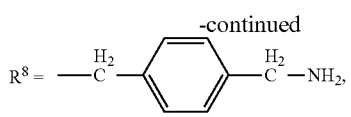

referred to as Compound 2.

A non-limiting explanation is that the lower potency of adjuvants of Formula III, wherein

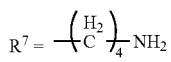

leads to less inflammation than adjuvants of Formula III wherein

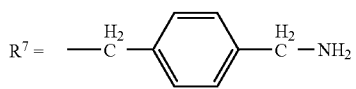

and that the moderate inflammation induced by the lower potency agonists leads to less exhaustion of T cell responses, providing higher magnitude and breadth of T cell responses overall.

Based on these findings a preferred embodiment for hydrophobic molecules (H) comprised of a poly(amino acid) of Formula I linked to adjuvants of Formula III is:

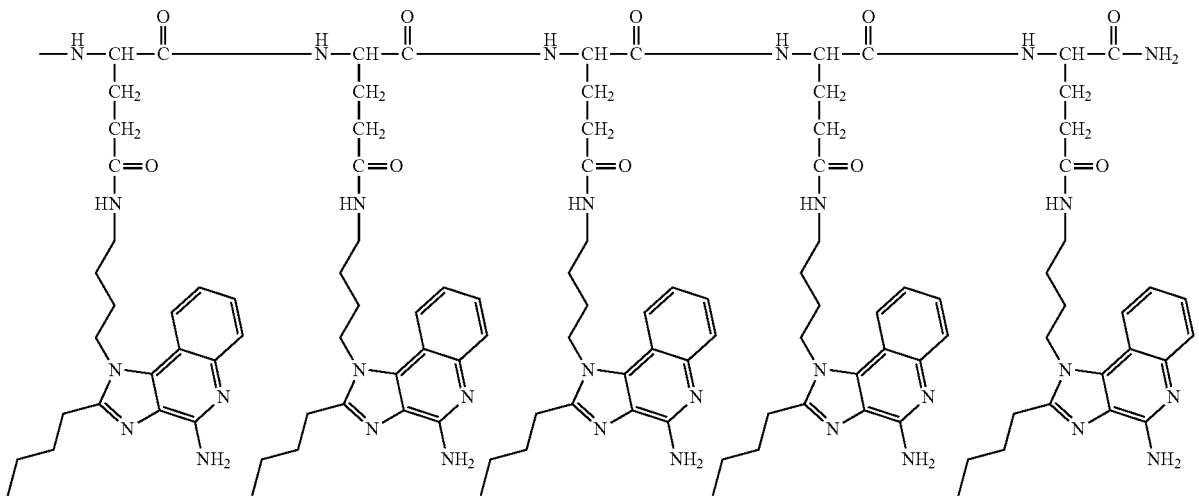 [SMILES: CCCCc1nc2c(N)nc3ccccc3c2n1CCCCNC(=O)CCC(NC(=O)C(CCC(=O)NCCCCn1c(CCCC)nc2c(N)nc3ccccc3c21)NC(=O)C(CCC(=O)NCCCCn1c(CCCC)nc2c(N)nc3ccccc3c21)NC(=O)C(CCC(=O)NCCCCn1c(CCCC)nc2c(N)nc3ccccc3c21)NC(=O)C(CCC(=O)NCCCCn1c(CCCC)nc2c(N)nc3ccccc3c21)NC)C(N)=O]

Disclosed herein we report the unexpected finding that hydrophobic molecules (H) based on poly(amino acids) of Formula II linked to adjuvants of Formula III lead to a significant increase in the magnitude and quality of T cell responses when the poly(amino acid) polymer is comprised of between 5-10 amino acids, wherein between 60-100% of the co-polymer is comprised of co-monomer o linked to adjuvants of Formula III wherein

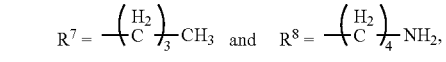

Compound 1. In preferred embodiments, co-monomer 0 comprises between 20-60% of monomer units of poly(amino acids) of Formula II, for example, 60%.

For example:

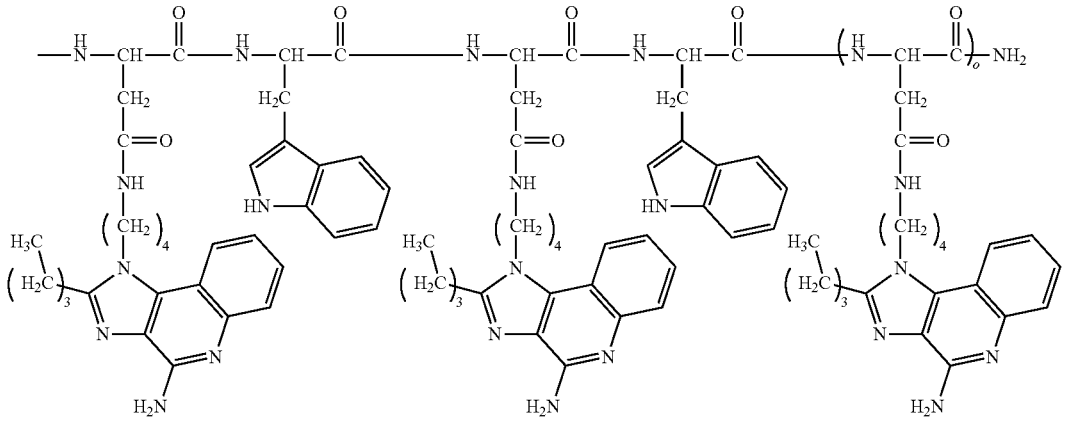

The unexpected data disclosed herein reveal that the length of the polymer comprising the hydrophobic molecule (H) and the number and potency of Ligands with adjuvant properties (i.e. TLR-7/8 agonists of Formula III) attached are major determinants of the magnitude and quality of immune responses generated against peptide antigens (A) delivered as peptide antigen conjugates. These data suggest that the hydrophobic molecules (H) comprised of poly (amino acids) that are comprised of hydrophobic amino acids and/or amino acids linked to Ligands should be sufficiently long to permit particle formation when linked to any peptide antigen (A), including highly hydrophilic peptide antigens (A) that will counter the tendency of the poly(amino acid)-based hydrophobic molecule (H) to drive particle assembly. Poly(amino acids) of insufficient length, for example, less than 3 amino acids in length, may not provide sufficient hydrophobic surface area to promote particle formation in aqueous conditions when linked to certain peptide antigens, particularly hydrophilic peptide antigens with high charge density. Therefore, as disclosed herein, poly(amino acids) of Formula I or Formula II should be greater than 3 amino acids in length, preferably between 5-30 amino acids in length, such as 5, 6, 7, 8, 9, 10, 20 or 30 amino acids in length. Longer poly(amino acids), such as poly(amino acids) greater than 30 amino acids, such as about 30, 40 or 50 amino acids in length may be generated, e.g., by solid-phase peptide synthesis. As an alternative to solid-phase peptide synthesis, solution polymerization reactions may be used to generate long chain poly(amino acids) comprised of hydrophobic monomers.

Herein we disclose an additional unexpected finding that Compound 1, which has an in vitro determined potency for TLR-7 activity (i.e. EC50) of 108 nmolar leads to improved T cell responses following repeat immunizations as compared with a more potent agonist, Compound 2, which has an in vitro determined potency for TLR-7 activity (i.e. EC50) of 18.7 nmolar. These data suggest that the potency of adjuvants included in the immunogenic composition can be modulated to optimize immune responses and that innate immune activation by the adjuvant can be moderated to provide the appropriate level of stimulation required to optimize T cell immunity. The level of innate immune stimulation may be moderated by delivering multiple, e.g., 3 or more, moderate potency agonists (i.e., agonists with EC50>100 nmolar) on the peptide antigen conjugates or by delivering less than 3 high potency agonists (i.e., agonists with EC50<100 nmolar).

The potency of various TLR-7, TLR-8 and combined TLR-7 & -8 agonists can be readily ascertained from the literature. Imidazoquinoline- and adenine-based TLR-7 and TLR-7/8 agonists have been described (see: Shukla, et al. J. Med. Chem., 53:4450-4465, 2010 and Gerster, et al., J. Med. Chem., 2005, U.S. Pat. No. 6,069,149 and Hirota, et al., J. Med. Chem., 45:5419-5422, 2002 that are incorporated by reference herein) and reveal that aromatic linkers, such as benzyl and xylyl linkers, selected for $R^2$ of adjuvants of Formula III result in compounds with increased potency for TLR-7 as compared compound where $R^2$ of adjuvants of Formula III is selected from a lower alkyl.

Based on the unexpected findings described herein, preferred embodiments of hydrophobic molecules (H) comprised of poly(amino acids) of Formula I or Formula II linked to adjuvants of Formula III are typically between 5-30 amino acids in length, wherein the density of the co-monomers linked to Adjuvants of Formula III is between 20-100 mol %. Optionally, when the Adjuvant of Formula III includes $R^8$ selected from a lower alkyl, e.g., Compound 1, the density of amino acids linked to Compound 1 should be between 40-100%, such as 60%. Optionally, when the Adjuvant of Formula III includes $R^8$ selected from an aromatic, e.g., Compound 2, the density of amino acids linked to Compound 2 should be less than 20%, or between 1-2 molecules of Compound 2 delivered on each polymer.

In preferred embodiments, the density of adjuvants of Formula III linked to polymers with molecular weights less than about 10,000 g/mol and based on co-monomers selected from N-2-hydroxypropyl(methacrylamide) (HPMA), hydroxyethyl(methacrylate) (HEMA), Styrene, vinylpyrrolidone (PVP), N-isopropylacrylamide (NI-PAAm); N-isopropylmethacrylamide (NIPMAm); N,N'-diethylacrylamide (DEAAm); N-(L)-(1-hydroxymethyl)propyl methacrylamide (HMPMAm); N,N'-dimethylethylmethacrylate (DMEMA), 2-(2-methoxyethoxy)ethyl methacrylate (DEGMA) or substituted poly(phosphoesters) is from about 5 to 100 mol %, e.g., the density of the adjuvant attached to the polymer can be about 5-6%, about 6-7%, about 8-9%, about 9-10%, about 10-11%, about 11-12%, about 12-13%, about 13-14%, about 15-16%, about 17-18%, about 18-20%, about 25%, about 30%, about 40%, about 50%, about 60%, about 70%, about 80%, about 90% or about 100%.

In preferred embodiments, the density of adjuvants of Formula III linked to polymers with molecular weights higher than 10,000 g/mol and based on co-monomers selected from N-2-hydroxypropyl(methacrylamide) (HPMA), hydroxyethyl(methacrylate) (HEMA), Styrene, vinylpyrrolidone (PVP), N-isopropylacrylamide (NIPAAm); N-isopropylmethacrylamide (NIPMAm); N,N'-diethylacrylamide (DEAAm); N-(L)-(1-hydroxymethyl)propyl methacrylamide (HMPMAm); N,N'-dimethylethylmethacrylate (DMEMA), 2-(2-methoxyethoxy)ethyl methacrylate (DEGMA) or substituted poly(phosphoesters) is from about 1 to 25 mol %, e.g., the density of the adjuvant attached to the polymer can be about 1-2%, about 2-3%, about 3-4% about 5-6%, about 6-7%, about 7-8%, about 8-9%, about 9-10%, about 10-11%, about 11-12%, about 13-14%, about 14-15%, about 16-17%, about 17-18%, about 19-20%, about 20%, about 21%, about 22%, about 23%, about 24%, or about 25%.

In additional embodiments, a second polymer, which is comprised of hydrophobic and/or temperature-responsive monomers, is linked to either the end or side groups of poly(amino acids) of Formula I or Formula II linked to adjuvants of Formula III.

A non-limiting example of a hydrophobic molecule (H) comprised of a temperature-responsive DEGMA-based polymer grafted to a poly(amino acid) of Formula I linked to adjuvants of Formula III is provided here for clarity:

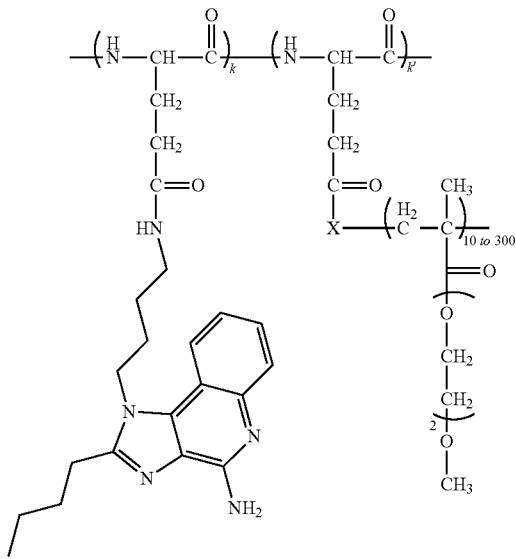

wherein co-monomer k is typically an integer between 3-300 and co-monomer k' is typically an integer between 3-300 amino acid residues, wherein the sum of k and k' is typically between about 3-300. In preferred embodiments, k is between about 3-10 and k is between about 1-10. The linker, X, can be any suitable linker molecule and m is typically about 10-300 monomer units. The N-terminus of the poly (amino acid) is linked either directly or indirectly through a Linker (L) and/or extension (B1 or B2) to the peptide antigen (A) through any suitable means to form a peptide antigen conjugate that may additional comprise a charged molecule (C).

A non-limiting example of a hydrophobic molecule (H) comprised of a temperature-responsive DEGMA-based polymer linked to the end of a poly(amino acid) of Formula I linked to adjuvants of Formula III is provided here for clarity:

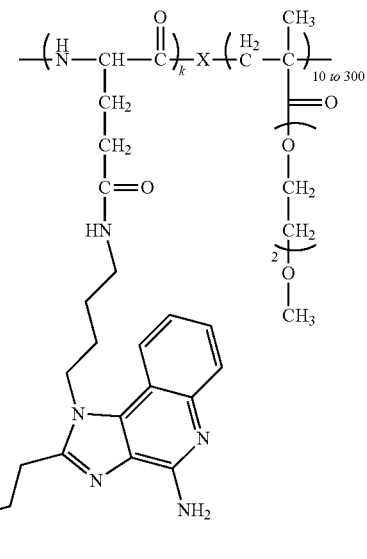

wherein co-monomer k is typically an integer between 3-100 monomer units. The linker, X, can be any suitable linker molecule. In preferred embodiments, k' is between about 3-10 monomer units. The N-terminus of the poly(amino acid) is linked either directly or indirectly through a Linker (L) and/or extension (B1 or B2) to the peptide antigen (A) through any suitable means to form a peptide antigen conjugate that may additional comprise a charged molecule (C).

A non-limiting example of a hydrophobic molecule (H) comprised of a poly-phosphoester-based polymer linked to the end of a poly(amino acid) of Formula I linked to adjuvants of Formula III is provided here for clarity:

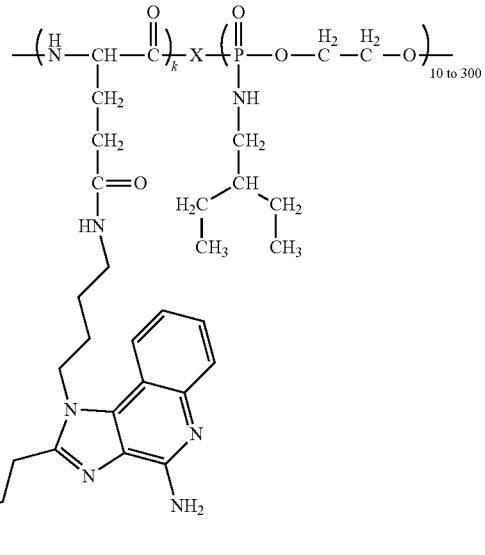

wherein co-monomer k is typically an integer between 3-100 monomer units. The linker, X, can be any suitable linker molecule. In preferred embodiments, k is between about 5-10 monomer units and m is between about 10-300 monomer units. The N-terminus of the poly(amino acid) is linked either directly or indirectly through a Linker (L) and/or extension (B1 or B2) to the peptide antigen (A) through any suitable means to form a peptide antigen conjugate that may additional comprise a charged molecule (C).

A non-limiting example of a hydrophobic molecule (H) comprised of a poly(benzyl glutamate)-based polymer linked to the end of a poly(amino acid) of Formula I linked to adjuvants of Formula III is provided here for clarity:

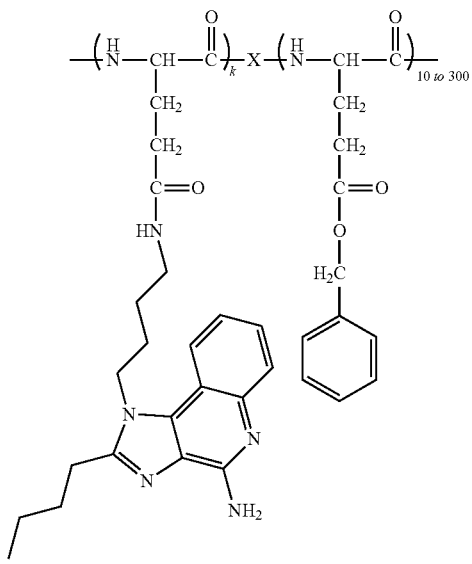

wherein co-monomer k is typically an integer between 3-100 monomer units and m is typically an integer between 50-300 amino acid residues. The linker can be any suitable linker molecule. In preferred embodiments, x is between about 5-10 monomer units and m is between about 10-300 monomer units. The N-terminus of the poly(amino acid) is linked either directly or indirectly through a Linker (L) and/or extension (B1 or B2) to the peptide antigen (A) through any suitable means to form a peptide antigen conjugate that may additional comprise a charged molecule (C).

In a non-limiting example, a peptide antigen (A) is linked to a Particle (P) or hydrophobic molecule (H) and may additionally comprise optional extensions (B1 and/or B2) and an optional Linker (L) to yield a peptide antigen conjugate of Formula IV, wherein [ ] denote that the group is optional:

[B1]-A-[B2]-[L]-P,[B1]-A-[B2]-[L]-H,P-[L]-[B1]-A-[B2] or H-[L]-[B1]-A-[B2]     Formula IV The peptide antigen (A) of Formula IV is comprised of an integer number of amino acids, n, wherein n is typically between 7-35, such as 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acids, and the hydrophobic molecule (H) is typically a poly(amino acid) of Formula I or II linked to an Adjuvant of Formula III.

A non-limiting example of a peptide antigen conjugate of Formula IV comprised of a peptide antigen (A) that is optionally linked at the N-terminus to a cathepsin cleavable tetrapeptide extensions (B1=Lys-Pro-Leu-Arg SEQ ID NO: 8) and at the C-terminus to a combined immuno-proteasome and cathepsin cleavable hexapeptide extension (B$_2$=Gly-Gly-Ser-Leu-Val-Arg SEQ ID NO: 13) that is linked to a triazole Linker (L) that is linked to a hydrophobic molecule (H) comprised of a poly(amino acid) of Formula I that is linked to an Adjuvant of Formula III is shown here as an example (SEQ ID NOS 8 and 13 shown below):

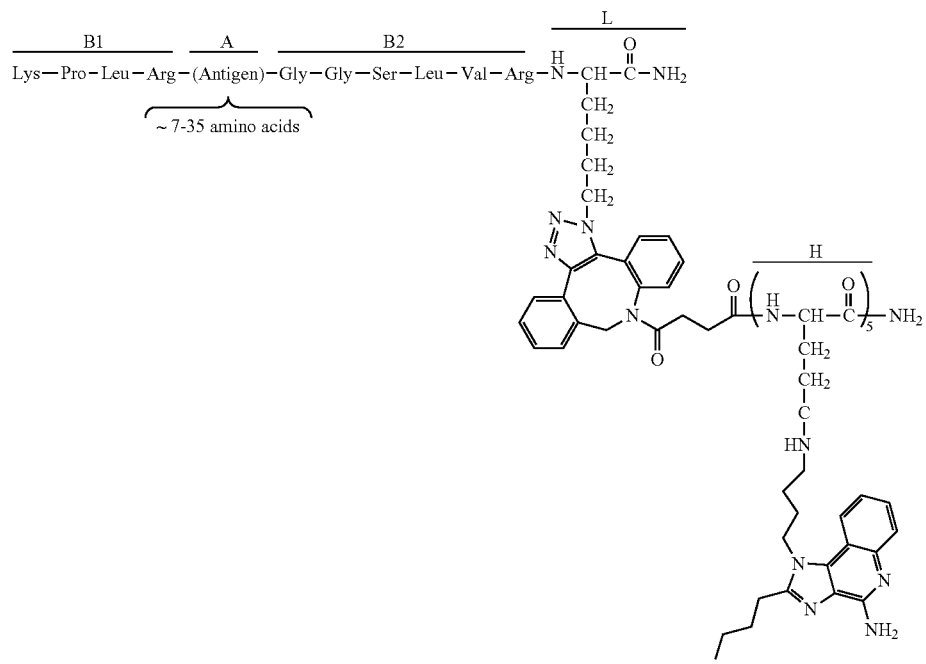

Optional Charged Molecule (C)

The peptide antigen conjugates disclosed herein are comprised of peptide antigens (A) linked to a Particle (P) or a hydrophobic molecule (H) and may additionally comprise optional extensions (B1 and/or B2), an optional Linker (L) and an optional charged molecule (C), where C=denotes a charged molecule bearing functional groups that impart electrostatic charge. The immunogenic compositions disclosed herein comprising peptide antigens linked to a Particle (P) or to a hydrophobic molecule (H) that assemble into particles in aqueous conditions may flocculate without sufficient surface charge to stabilize the particles. Thus, charged molecules (C) may be optionally linked to peptide antigen conjugates as a means to stabilize the particles and prevent flocculation; or, alternatively, charged molecules (C) may be incorporated into particles comprising peptide antigen conjugates as a means to stabilized particles. Thus the purpose of the charged molecule (C) is to control the net charge of particles formed by peptide antigen conjugates as means to promote stability of those particles.

A charged molecule (C) refers to any molecule that has one or more functional groups that are positively or negatively charged in aqueous buffers at a pH of about 7.4. The functional groups comprising the charged molecule (C) may be partial or full integer values of charge. A charged molecule (C) may be a molecule with a single charged functional group or multiple charged functional groups. The net charge of the charged molecule (C) may be positive, negative or neutral. The charge of functional groups comprising the charged molecule (C) may be dependent or independent of the pH of the solution in which the charged molecule (C) is dispersed, such is the case, for example, for tertiary amines and quaternary ammonium compounds that are pH dependent and pH independent, respectively. The charge of a molecule can be readily estimated based on the molecule's Lewis structure and accepted methods known to those skilled in the art. Charge may result from inductive effects, e.g., atoms bonded together with differences in electron affinity may result in a polar covalent bond resulting in a partially negatively charged atom and a partially positively charged atom. For example, nitrogen bonded to hydrogen results in partial negative charge on nitrogen and a partial positive charge on the hydrogen atom. Alternatively, an atom in a molecule may be considered to have a full integer value of charge when the number of electrons assigned to that atom is less than or equal to the atomic number of the atom. The charge of the molecule is determined by summing the charge of each atom comprising the molecule. Those skilled in the art are familiar with the process of estimating charge of a molecule by summing the formal charge of each atom in a molecule.

The charged molecule (C) may either carry a net negative, net positive or neutral charge and depends on the net charge of the peptide antigen conjugate needed for the specific application of the invention disclosed herein. For example, most cell surfaces are known to carry a net negative charge. Thus, net positively charged particles may interact with all cell surfaces without a high degree of specificity. In contrast, net negatively charged particles will be electrostatically repulsed from most cell surfaces but have been shown to promote selective uptake by certain antigen-presenting cell populations. For example, positively charged particles delivered intravenously into the circulation have been found to accumulate in the liver and lungs as well as within antigen-presenting cells in the spleen, whereas negatively charged particles have been found to preferentially accumulate in antigen-presenting cells in the spleen following intravenous administration. Thus, the net charge of the charged molecule (C) can be adjusted to meet the specific demands of the application.

In some embodiments, the charged molecule (C) has a net negative charge and is comprised of functional groups that carry a negative charge at physiologic pH, at a pH of about 7.4. Suitable charged molecules (C) that carry a net negative charge include molecules bearing functional groups (e.g., functional groups with a pKa less than about 6.5) that occur as the conjugate base of an acid at physiologic pH, at a pH of about 7.4. These include but are not limited to molecules bearing carboxylates, sulfates, phosphates, phosphoramidates, and phosphonates. The charged molecule (C) bearing a caboxylate can be but is not limited to glutamic acid, aspartic acid, pyruvic acid, lactic acid, glycolic acid, glucuronic acid, citrate, isocitrate, alpha-keto-glutarate, succinate, fumarate, malate, and oxaloacetate and derivatives thereof. In preferred embodiments, the negatively charged molecule (C) is comprised of a molecule with between 1-20 negatively charged functional groups, such as 1, 2, 3, 4, 5, 6, 7, 8, 9, 10, 11, 12, 13, 14, 15, 16, 17, 18, 19 or 20 negatively charged functional groups, though, typically no more than 16 negatively charged functional groups. In some embodiments, the charged molecule (C) is a poly(glutamic acid) peptide of between 2-6 amino acids in length. A poly(glutamic acid) sequence comprised of 1, 2, 3, 4, 5 or 6 amino acids would be expected to carry a negative charge of −1, −2, −3, −4, −5 and −6 at pH 7.4, respectively. In additional embodiments, the charged molecule (C) is phosphoserine or sulfoserine.

In certain embodiments, the charged molecule (C) has a net negative charge and is comprised of 1 or more negatively charged amino acids. In preferred embodiments, the charged molecule (C) with a net negative charge is comprised of between 1 to 20 negatively charged amino acids, e.g., 1, 2, 3, 4, 5, 6, 7, 8, 9, 10, 11, 12, 13, 14, 15, 16, 17, 18, 19 or 20. In a non-limiting example, a charged molecule (C) is comprised of 16 aspartic acid monomers, e.g., Asp-Asp-Asp-Asp-Asp-Asp-Asp-Asp-Asp-Asp-Asp-Asp-Asp-Asp-Asp-Asp (SEQ ID NO: 25), is used to prepare a charged molecule (C) with a net negative charge of −16; a charged molecule (C) comprised of 15 aspartic acid monomers, e.g., Asp-Asp-Asp-Asp-Asp-Asp-Asp-Asp-Asp-Asp-Asp-Asp-Asp-Asp-Asp (SEQ ID NO: 26), is used to prepare a charged molecule (C) with a net negative charge of −15; a charged molecule (C) comprised of 14 aspartic acid monomers, e.g., Asp-Asp-Asp-Asp-Asp-Asp-Asp-Asp-Asp-Asp-Asp-Asp-Asp-Asp (SEQ ID NO: 27), is used to prepare a charged molecule (C) with a net negative charge of −14; a charged molecule (C) comprised of 13 aspartic acid monomers, e.g., Asp-Asp-Asp-Asp-Asp-Asp-Asp-Asp-Asp-Asp-Asp-Asp-Asp (SEQ ID NO: 28), is used to prepare a charged molecule (C) with a net negative charge of −13; a charged molecule (C) comprised of 12 aspartic acid monomers, e.g., Asp-Asp-Asp-Asp-Asp-Asp-Asp-Asp-Asp-Asp-Asp-Asp (SEQ ID NO: 29), is used to prepare a charged molecule (C) with a net negative charge of −12; a charged molecule (C) comprised of 11 aspartic acid monomers, e.g., Asp-Asp-Asp-Asp-Asp-Asp-Asp-Asp-Asp-Asp-Asp (SEQ ID NO: 30), is used to prepare a charged molecule (C) with a net negative charge of −11; a charged molecule (C) comprised of 10 aspartic acid monomers, e.g., Asp-Asp-Asp-Asp-Asp-Asp-Asp-Asp-Asp-Asp (SEQ ID NO: 31), is used to prepare a charged molecule (C) with a net negative charge of −10; a charged molecule (C) comprised of 9 aspartic acid monomers, e.g., Asp-Asp-Asp-Asp-Asp-Asp-Asp-Asp-Asp (SEQ ID NO: 32), is used to prepare a charged molecule (C) with a net negative charge of −9; a charged molecule (C) comprised of 8 aspartic acid monomers, e.g., Asp-Asp-Asp-Asp-Asp-Asp-Asp-Asp (SEQ ID NO: 33), is used to prepare a charged molecule (C) with a net negative charge of −8; a charged molecule (C) comprised of 7 aspartic acid monomers, e.g., Asp-Asp-Asp-Asp-Asp-Asp-Asp (SEQ ID NO: 34), is used to prepare a charged molecule (C) with a net negative charge of −7; a charged molecule (C) comprised of 6 aspartic acid monomers, e.g., Asp-Asp-Asp-Asp-Asp-Asp (SEQ ID NO: 35), is used to prepare a charged molecule (C) with a net negative charge of −6; a charged molecule (C) comprised of 5 aspartic acid monomers, e.g., Asp-Asp-Asp-Asp-Asp (SEQ ID NO: 36), is used to prepare a charged molecule (C) with a net negative charge of −5; a charged molecule (C) comprised of 4 aspartic acid monomers, e.g., Asp-Asp-Asp-Asp (SEQ ID NO: 37), is used to prepare a charged molecule (C) with a net negative charge of −4; a charged molecule (C) comprised of 3 aspartic acid monomers, e.g., Asp-Asp-Asp, is used to prepare a charged molecule (C) with a net negative charge of −3; a charged molecule (C) comprised of 2 aspartic acid monomers, e.g., Asp-Asp, is used to prepare a charged molecule (C) with a net negative charge of −2; a charged molecule (C) comprised of 1 aspartic acid monomer, e.g., Asp, is used to prepare a charged molecule (C) with a net negative charge of −1. In the above examples, aspartic acid (Asp) may be replaced with any suitable negatively charged amino acid, including but not limited to glutamic acid, sulfo-serine, or phosphor-serine, wherein the negatively charged amino acids may be the same or different.

In some embodiments the charged molecule (C) has a net positive charge and is comprised of positively charged functional groups. Suitable positively charged molecules (C) include those with functional groups that carry positive charge at physiologic pH, at a pH of about 7.4, such as the conjugate acid of weak bases, wherein the pKa of the conjugate acid of the base is greater than about 8.5. Suitable positively charged molecules (C) include but are not limited to molecules bearing primary, secondary and tertiary amines, as well as quaternary ammonium, guanidinium, phosphonium and sulfonium functional groups. Suitable molecules bearing ammonium functional groups include, for example, imidazolium, and tetra-alkyl ammonium compounds. In some embodiments, the charged molecule (C) is comprised of quaternary ammonium compounds that carry a permanent positive charge that is independent of pH.

Non-limiting examples of positively charged functional groups that have charge independent of pH include:

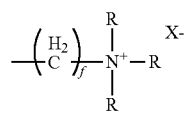

where f = 1 to 6 where R = lower alkyl

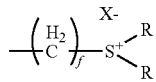

where f = 1 to 6 where R = lower alkyl wherein X⁻ is any suitable counter anion.

In additional embodiments, the charged molecule (C) is comprised of functional groups that occur as the conjugate acid of a base at physiologic pH, such as, for example, primary, secondary and tertiary amines. In preferred embodiments, the positively charged molecule (C) is comprised of between 1-20 positively charged functional groups, such as 1, 2, 3, 4, 5, 6, 7, 8, 9, 10, 11, 12, 13, 14, 15, 16, 17, 18, 19 or 20 positively charged functional groups, though, typically no more than 16 charged functional groups. In some embodiments, the charged molecule (C) is a poly(lysine) peptide of between 1-6 amino acids in length. A poly(lysine) sequence comprised of 1, 2, 3, 4, 5 or 6 amino acids would be expected to carry a positive charge of +1, +2, +3, +4, +5 or +6 respectively, at pH 7.4. In additional embodiments, the charged molecule (C) is a poly(arginine) peptide of between 2-6 amino acids in length.

In certain embodiments, the charged molecule (C) has a net positive charge and is comprised of 1 or more positively charged amino acids. In preferred embodiments, the charged molecule (C) with a net positive charge is comprised of between 1 to 20 positively charged amino acids, e.g., 1, 2, 3, 4, 5, 6, 7, 8, 9, 10, 11, 12, 13, 14, 15, 16, 17, 18, 19 or 20. In a non-limiting example, a charged molecule (C) comprised of 16 lysine monomers, e.g., Lys-Lys-Lys-Lys-Lys-Lys-Lys-Lys-Lys-Lys-Lys-Lys-Lys-Lys-Lys-Lys (SEQ ID NO: 38), is used to prepare a charged molecule (C) with a net positive charge of +16; a charged molecule (C) comprised of 15 lysine monomers, e.g., Lys-Lys-Lys-Lys-Lys-Lys-Lys-Lys-Lys-Lys-Lys-Lys-Lys-Lys-Lys (SEQ ID NO: 39), is used to prepare a charged molecule (C) with a net positive charge of +15; a charged molecule (C) comprised of 14 lysine monomers, e.g., Lys-Lys-Lys-Lys-Lys-Lys-Lys-Lys-Lys-Lys-Lys-Lys-Lys-Lys (SEQ ID NO: 40), is used to prepare a charged molecule (C) with a net positive charge of +14; a charged molecule (C) comprised of 13 lysine monomers, e.g., Lys-Lys-Lys-Lys-Lys-Lys-Lys-Lys-Lys-Lys-Lys-Lys-Lys (SEQ ID NO: 41), is used to prepare a charged molecule (C) with a net positive charge of +13; a charged molecule (C) comprised of 12 lysine monomers, e.g., Lys-Lys-Lys-Lys-Lys-Lys-Lys-Lys-Lys-Lys-Lys-Lys (SEQ ID NO: 42), is used to prepare a charged molecule (C) with a net positive charge of +12; a charged molecule (C) comprised of 11 lysine monomers, e.g., Lys-Lys-Lys-Lys-Lys-Lys-Lys-Lys-Lys-Lys-Lys (SEQ ID NO: 43), is used to prepare a charged molecule (C) with a net positive charge of +11; a charged molecule (C) comprised of 10 lysine monomers, e.g., Lys-Lys-Lys-Lys-Lys-Lys-Lys-Lys-Lys-Lys (SEQ ID NO: 44), is used to prepare a charged molecule (C) with a net positive charge of +10; a charged molecule (C) comprised of 9 lysine monomers, e.g., Lys-Lys-Lys-Lys-Lys-Lys-Lys-Lys-Lys (SEQ ID NO: 45), is used to prepare a charged molecule (C) with a net positive charge of +9; a charged molecule (C) comprised of 8 lysine monomers, e.g., Lys-Lys-Lys-Lys-Lys-Lys-Lys-Lys (SEQ ID NO: 46), is used to prepare a charged molecule (C) with a net positive charge of +8; a charged molecule (C) comprised of 7 lysine monomers, e.g., Lys-Lys-Lys-Lys-Lys-Lys-Lys (SEQ ID NO: 47), is used to prepare a charged molecule (C) with a net positive charge of +7; a charged molecule (C) comprised of 6 lysine monomers, e.g., Lys-Lys-Lys-Lys-Lys-Lys (SEQ ID NO: 48), is used to prepare a charged molecule (C) with a net positive charge of +6; a charged molecule (C) comprised of 5 lysine monomers, e.g., Lys-Lys-Lys-Lys-Lys (SEQ ID NO: 49), is used to prepare a charged molecule (C) with a net positive charge of +5; a charged molecule (C) comprised of 4 lysine monomers, e.g., Lys-Lys-Lys-Lys (SEQ ID NO: 50), is used to prepare a charged molecule (C) with a net positive charge of +4; a charged molecule (C) comprised of 3 lysine monomers, e.g., Lys-Lys-Lys, is used to prepare a charged molecule (C) with a net positive charge of +3; a charged molecule (C) comprised of 2 lysine monomers, e.g., Lys-Lys, is used to prepare a charged molecule (C) with a net positive charge of +2; a charged molecule (C) comprised of 1 lysine, e.g., Lys, is used to prepare a charged molecule (C) with a net positive charge of +1. In the above examples, Lysine (Lys) may be replaced with any suitable positively charged amino acid, including but not limited to trimethyl-lysine or arginine, wherein the positively charged amino acids may be the same or different.

Charged molecules (C) may additionally comprise small non-charged, hydrophilic amino acids, or hydrophilic linkers, e.g., ethylene oxide that function to i) improve water solubility and ii) increase the distance between charged functional groups to prevent incomplete ionization. For instance, ionization of one functional group on a polymer may impact the pKa of neighboring functional groups through local effects. For example, protonation of an amine in close proximity to a second amine may lower the pKa of the conjugate acid of the second amine. To reduce the impact of local effects on the ionization potential of neighboring functional groups, a linker molecule may be used to increase the distance between charged functional groups comprising the charged molecule. The linker molecule may comprise between 1-5 small, non-charged hydrophilic amino acids, e.g., 1, 2, 3, 4, and 5 amino acids. Alternatively, the linker may comprise an ethylene oxide (i.e, PEG) linker between 1-4 monomers units, e.g., 1, 2, 3, or 4 ethylene oxide monomers in length. In preferred embodiments, 1 to 2 small, non-charged hydrophilic amino acids are placed between neighboring charged amino acids comprising the charged molecule (C), wherein the amino acids are linked through amide bonds. In certain embodiments, a serine is placed between each charged amino acid comprising a charged molecule (C) with a net positive charge. In preferred embodiments, the charged molecule (C) is comprised of repeating dipeptides of lysine and serine, i.e. $(Lys-Ser)_n$, where n is typically any integer between 1-20, e.g., 1, 2, 3, 4, 5, 6, 7, 8, 9, 10, 11, 12, 13, 14, 15, 16, 17, 18, 19 or 20 (SEQ ID NO: 118). As other examples, a serine is placed between each charged amino acid of a tripeptide charged molecule (C) with a net +2 charge, e.g., Lys-Ser-Lys; a serine is placed between each charged amino acid of a 5 amino acid charged molecule (C) with a net +3 charge, e.g., Lys-Ser-Lys-Ser-Lys (SEQ ID NO: 51); a serine is placed between each charged amino acid of a 7 amino acid charged molecule (C) with a net +4 charge, e.g., Lys-Ser-Lys-Ser-Lys-Ser-Lys (SEQ ID NO: 52). In the above examples, Lysine (Lys) may be replaced with any suitable positively charged amino acid, including but not limited to trimethyl-lysine or arginine, wherein the positively charged amino acids may be the same or different.

In certain embodiments, a serine is placed between each charged amino acid comprising a charged molecule (C) with a net negative charge. In preferred embodiments, the charged molecule is comprised of repeating dipeptides of aspartic acid and serine, i.e. $(Asp-Ser)_n$, where n is typically any integer between 1-20, e.g., 1, 2, 3, 4, 5, 6, 7, 8, 9, 10, 11, 12, 13, 14, 15, 16, 17, 18, 19 or 20 (SEQ ID NO: 119). For example, a serine is placed between each charged amino acid of a tripeptide charged molecule (C) with a net −2 charge, e.g., Asp-Ser-Asp; a serine is placed between each charged amino acid of a 5 amino acid charged molecule (C) with a net −3 charge, e.g., Asp-Ser-Asp-Ser-Asp (SEQ ID NO: 53); a serine is placed between each charged amino acid of a 7 amino acid charged molecule (C) with a net −4 charge, e.g., Asp-Ser-Asp-Ser-Asp-Ser-Asp (SEQ ID NO: 54). In the above examples, aspartic acid (Asp) may be replaced with any suitable negatively charged amino acid, including but not limited to glutamic acid, sulfo-serine, or phospho-serine, wherein the negatively charged amino acids may be the same or different.

In additional embodiments, the charged molecule (C) is comprised of both negatively and positively charged amino acids. Di-peptides comprised of amino acids of opposite charge, e.g., Lys-Asp, are referred to as zwitterion dipeptides because they are predicted to have a net neutral, 0, charge at pH 7.4. One or more zwitterion dipeptides can be included in the charged molecule (C) as a means to i) improve water solubility and ii) provide a prevailing charge (e.g., net negative or net positive) over certain pH ranges. For instance, a zwitterion di-peptide can be used to increase the hydrophilic character of a peptide sequence without increasing or decreasing the charge of a peptide sequence at pH 7.4. However, the zwitterion can be used to impart a net charge at a particular pH. For instance, excluding the contribution of the N-terminal amine and the C-terminal carboxylic acid in this example, the zwitterion di-peptide, Lys-Asp, has a net charge of 0 at pH 7.4, but a net charge of +1 at pH<4 and a net charge of −1 at pH>10. One or more zwitterion di-peptides can be added to the sequence of charged molecules (C); for example, one di-peptide, Lys-Asp; two di-peptides Lys-Asp-Lys-Asp (SEQ ID NO: 55); three di-peptides, Lys-Asp-Lys-Asp-Lys-Asp (SEQ ID NO: 56) and so forth. In the above examples, Lysine (Lys) may be replaced with any suitable positively charged amino acid, including but not limited to trimethyl-lysine or arginine, and aspartic acid (Asp) may be replaced with any suitable negatively charged amino acid, including but not limited to glutamic acid, sulfo-serine, or phospho-serine, wherein the positively or negatively charged amino acids may be the same or different.

The composition of the charged molecule (C) is selected to provide the net charge needed of a peptide antigen conjugate for the specific application. In several embodiments disclosed herein, the charged molecule (C) is a positively charged poly(amino acid) comprised of lysines or arginines, or lysines or arginines and non-charged amino acids. In some embodiments the charged moiety comprised sulfonium or quaternary ammonium functional groups that carry pH independent positive charge. In several embodiments disclosed herein, the charged molecule (C) is a negatively charged poly(amino acid) comprised of glutamic acid or aspartic acid, or glutamic acid or aspartic acid and non-charged amino acids. In some embodiments the charged moiety comprises phosphate or sulfate groups, such as sulfoserine or phosphoserine. In additional embodiments, the charged molecule is comprised of lysines or arginines and glutamic acid or aspartic acid, or lysines or arginines and glutamic acid or aspartic acid as well as non-charged amino acids. Both positive and negatively charged functional groups may be included on the same charged molecule (C). The charged molecule (C) may be positive, negative or neutral but the net charge of the peptide antigen conjugate should be non-zero, for example, greater than +3 or less than −3 net charges are preferred and depend on the specific application.

An additional consideration regarding charged molecules (C), is the counterion selected. Non-limiting examples of charged molecules (C) bearing functional groups with positive charge include but are not limited to halides, including chloride, bromide and iodide anions, and conjugate bases of acids, including, phosphate, sulfates, sulfites and carboxylate anions including formate, succinate, acetate and trifluoroacetate. Suitable counterions for charged molecules (C) bearing functional groups with negative charge include but are not limited to hydrogen and alkali and alkaline earth metals, including, for example, sodium, potassium, magnesium and calcium, or conjugate acids of weak bases, such as ammonium compounds.

The charged molecule (C) may be linked directly to the peptide antigen (A) either directly, or indirectly through an extension (B1 or B2), a Linker (L), a Liker and extension (B1 or B2), or a Particle (P) or hydrophobic molecule (H) that is linked directly or indirectly through a Linker (L) and/or extension (B1 or B2) to the peptide antigen.

A non-limiting example of a peptide antigen conjugate of Formula V comprising a charged molecule (C=Lys-Lys) linked to a cathepsin cleavable tetrapeptide extension ($B_1$=Lys-Pro-Leu-Arg SEQ ID NO: 8) (collectively SEQ ID NO: 187) at the N-terminus of a peptide antigen (A) that is linked at the C-terminus to a cathepsin cleavable hexapeptide extension ($B_2$=Gly-Gly-Ser-Leu-Val-Arg SEQ ID NO: 13) that is linked to a triazole Linker (L) that is linked to a hydrophobic molecule (H) comprised of a poly(amino acid) of Formula I that is linked to an Adjuvant of Formula III is provided here (SEQ ID NOS 187 and 13 disclosed below):

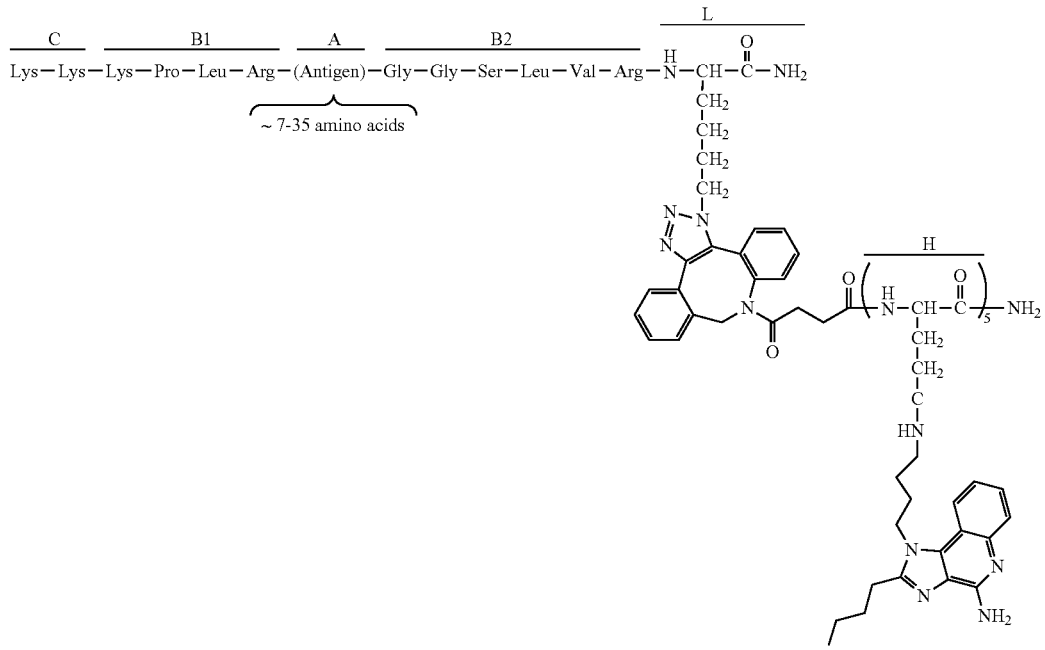

In some embodiments, the charged molecule (C) is linked to an optional N- or C-terminal extension (B1 or B2) that is linked to either the N- or C-terminus, respectively, of a peptide antigen (A) that is linked either at the C- or N-terminus, respectively, to an optional extension (B2) that is linked either directly or via a Linker (L) to either a Particle (P) or hydrophobic molecule (H) to yield a peptide antigen conjugate of Formula V, wherein [ ] denotes that the group is optional:

C—[B1]-A-[B2]-[L]-P,C—[B1]-A-[B2]-[L]-H,P-[L]-[B1]-A-[B2]—C, or H-[L]-[B1]-A-[B2]—C    Formula V In several embodiments, the charged molecule (C) is placed at the N-terminus of a peptide antigen conjugate of Formula V, wherein the charged molecule (C) is linked to an N-terminal extension (B1) comprised of a cathepsin cleavable tetrapeptide extension (B1=PN4-PN3-PN2-PN1) that is linked to the N-terminus of a peptide antigen (A) that is linked at the C-terminus to a C-terminal extension (B2) comprised of a combined immuno-proteasome and cathepsin cleavable hexapeptide extension (B2=PC1'-PC2'-PC3'-PC4'-PC5'-PC6') that is linked to a Linker (L) that is linked to a hydrophobic molecule (H) or Particle (P). The peptide antigen (A) of a peptide antigen conjugate of Formula V is comprised of an integer number of amino acids, n, wherein n is typically between 7-35 amino acids and the hydrophobic molecule (H) is typically a poly(amino acid) of Formula I or II linked to an Adjuvant of Formula III.

In additional embodiments, a charged molecule (C; or C1 and C2 when there are two charged molecules present) may be linked directly to the hydrophobic molecule (H) or to the Linker (L) that is linked to the C-terminal extension (B2) that is linked to the C-terminus of a peptide antigen (A) that is optionally linked at the N-terminus to an N-terminal extension (B1) that is optionally linked to an additional optional charged moiety (C1); or the charged molecule (C; or C1 and C2 when there are two charged molecules present) may be linked directly to the hydrophobic molecule (H) or to the Linker (L) that is linked to the N-terminal extension (B1) that is linked to the N-terminus of a peptide antigen (A) that is optionally linked at the C-terminus to a C-terminal extension (B2) that is optionally linked to an additional optional charged moiety (C2) to yield a peptide antigen conjugate of Formula VI, wherein [ ] denote that the group is optional:

[B1]-A-[B2]-L(C)—H,[B1]-A-[B2]-L-H(C),[C1]—[B1]-A-[B2]-L(C2)-H,[C1]—[B1]-A-[B2]-L-H (C2),H-L(C)—[B1]-A-[B2],H(C)—[B1]-A-[B2], H-L(C1)-[B1]-A-[B2]-C2or H(C1)-[B1]-A-[B2]—C2    Formula VI In several embodiments, the charged molecule (C) is placed at the C-terminus of a peptide antigen conjugate of Formula VI, wherein the charged molecule (C) is linked to a Linker (L) that is optionally linked to a C-terminal extension (B2) comprised of an immuno-proteasome, cathepsin or combined immuno-proteasome and cathepsin cleavable extension typically between 1 to 6 amino acids in length (B2=PC1', PC1'-PC2', PC1'-PC2'-PC3', PC1'-PC2'-PC3'-PC4', PC1'-PC2'-PC3'-PC4'-PC5', or PC1'-PC2'-PC3'-PC4'-PC5'-PC6') that is linked to the C-terminus of a peptide antigen (A) that is optionally linked at the N-terminus to a cathepsin cleavable extension typically between 1 to 4 amino acids in length (B1=PN1, PN2-PN1, PN3-PN2-PN1 or PN4-PN3-PN2-PN1), wherein the Linker (L) is additionally linked to a hydrophobic molecule (H), shown here:

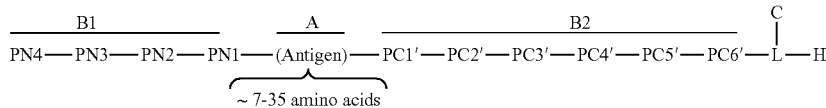

The peptide antigen (A) of the peptide antigen conjugate of Formula VI is comprised of an integer number of amino acids, n, wherein n is typically between 7-35 amino acids, or up to 50 amino acids, and the hydrophobic molecule is typically a poly(amino acid) of Formula I or II linked to an Adjuvant of Formula III.

A non-limiting example of a peptide antigen conjugate of Formula VI comprised of a charged molecule (e.g, C=Lys-Lys) linked via an amide bond to the C-terminus of a Linker (L) that is linked to a combined immuno-proteasome and cathepsin cleavable hexapeptide C-terminal extension (e.g., B2=Gly-Gly-Ser-Leu-Val-Arg SEQ ID NO: 13) that is linked to the C-terminus of a peptide antigen (A) that is linked at the N-terminus to a cathepsin cleavable tetrapeptide N-terminal extension (e.g., B1=Lys-Pro-Leu-Arg SEQ ID NO: 8), wherein the Linker (L) is additionally linked to a hydrophobic molecule (H) that is comprised of a poly (amino acid) of Formula I that is linked to an Adjuvant of Formula III is provided (SEQ ID NOS 8 and 13 disclosed below):

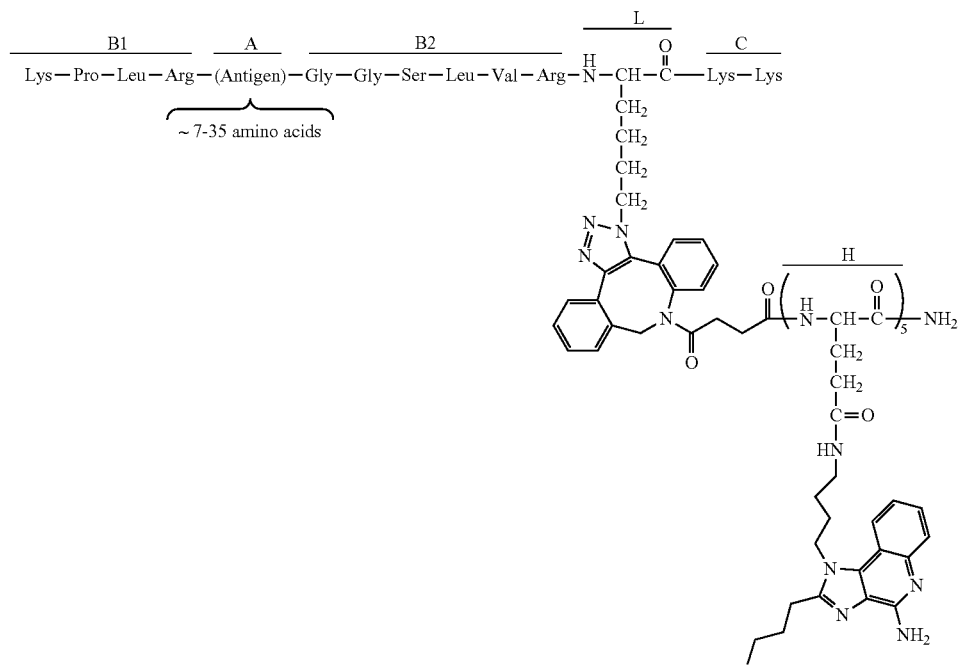

An additional non-limiting example of a peptide antigen conjugate of Formula VI, B1-A-B2-L-H(C), is a charged moiety (C=Lys-Lys-Lys-Lys-Lys SEQ ID NO: 49) linked via a linker to a hydrophobic molecule (H) that is comprised of a poly(amino acid) of Formula I that is linked to an Adjuvant of Formula III that is linked to a Linker (L) that is linked to a combined immuno-proteasome and cathepsin cleavable hexapeptide C-terminal extension (B2=Gly-Gly-Ser-Leu-Val-Arg SEQ ID NO: 13) that is linked to the C-terminus of a peptide antigen (A) and the N-terminus of the peptide antigen (A) is linked to a cathepsin cleavable tetrapeptide N-terminal extension (B1=Lys-Pro-Leu-Arg SEQ ID NO: 8) (SEQ ID NOS 8, 13 and 49 disclosed below):

(N3-DBCO-H)-Glu-Lys (SEQ ID NO: 120), wherein the Glu-Lys sequence is linked to the C-terminus of the Linker (L) (Lys(N3-DBCO), resulting in a peptide antigen conjugate with a predicted net charge of +4 at pH 7.4. Here, the hydrophobic molecule (H) is assumed to have a negligible contribution to the charge of the peptide antigen conjugate. Note, that the composition of the charged moiety (C) and extension sequences (B1 and B2) can be selected to provide a particular number of charged residues that provide the desired net charge and hydropathy of the peptide sequence comprising the peptide antigen conjugate as described in greater detail below. In preferred embodiments, the number of charged functional groups comprising the charged moiety (C) is modulated such that the net charge of the peptide

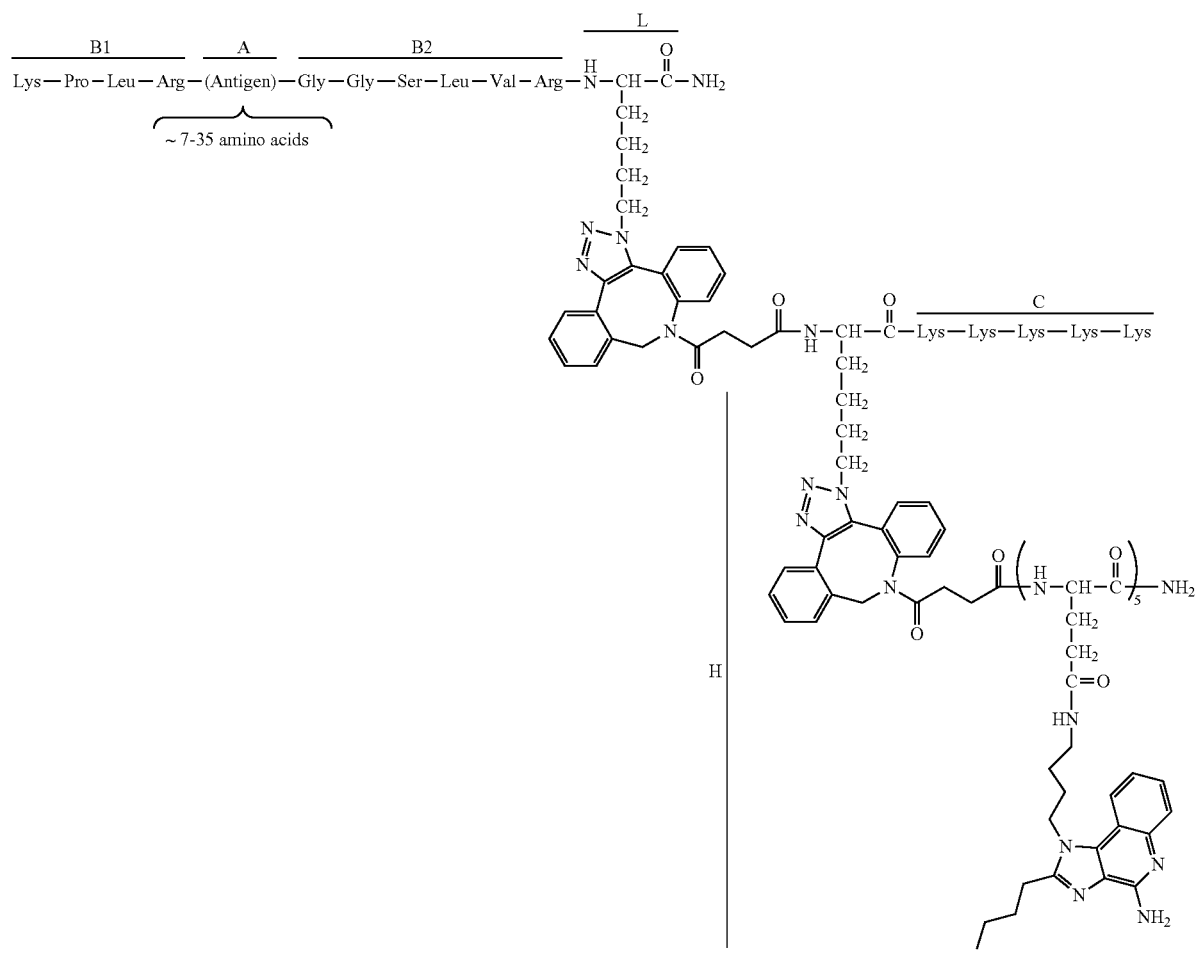

In a non-limiting example of a peptide antigen conjugate of Formula VI, B1-(A)$_{7-35}$-B2-L(-C)—H, a peptide antigen (A) with the sequence Ala-Lys-Phe-Val-Ala-Ala-Trp-Thr-Leu-Lys-Ala-Ala-Ala (SEQ ID NO: 22) is linked to an N-terminal extension (B1) with the sequence Ser-Leu-Val-Arg (SEQ ID NO: 7) and a C-terminal extension (B2) with the sequence Ser-Leu-Val-Arg (SEQ ID NO: 7) that is linked to a linker precursor X1, e.g., Lys(N3), that is linked to both a charged moiety (C) comprised of a dipeptide with the sequence Glu-Lys and a linker precursor X2, comprising a DBCO molecule that is linked to the hydrophobic molecule (H), for example: Ser-Leu-Val-Arg-Ala-Lys-Phe-Val-Ala-Ala-Trp-Thr-Leu-Lys-Ala-Ala-Ala-Ser-Leu-Val-Arg-Lys antigen conjugate comprising the charged moiety (C), peptide antigen (A), optional extensions (B1 and/or B2), Linker (L) and hydrophobic molecule (H) is between about −3 to −10 or between +3 to +10.

Peptide antigen conjugates of Formula VI, wherein the charged moiety (C) is linked to the hydrophobic molecule (H), may be advantageous for the rapid production of personalized therapies, such as personalized cancer vaccines. The hydrophobic molecule (H) that is linked to a charged molecule (C) and a linker precursor X2 (e.g, X2 comprising a cyclooctyne) can be prepared in bulk and then readily combined with any peptide antigen (A) bearing a linker precursor X1 (e.g., X1 comprising an azide) to form a peptide antigen conjugate of the Formula VI, [C1]—[B1]-A-[B2]-L-H(C2), or H(C)-L-[B1]-A-[B2]—[C2], wherein [ ] denotes the group is optional.

The function of the charged moiety (C) is to stabilize nanoparticles formed by peptide antigen conjugates in aqueous conditions. While the hydrophobic molecule (H) induces particle formation of peptide antigen conjugates, the optional charged molecule (C) provides a countervailing force that prevents flocculation and, in some embodiments, drives the peptides antigen conjugates to assemble into nanoparticle micelles with a surface charge provided by the charged moiety (C).

In some embodiments, the peptide antigen conjugate does not comprise a charged molecules, such as [B1]-A-[B2]-[L]-H, where [ ] denotes that the group is optional. Non-limiting examples include, A-H, A-L-H, A-B2-H, A-B2-L-H, B1-A-B2-L-H. Peptide antigen conjugates that do not comprise a charged molecule (C) may undergo aggregation in aqueous conditions. To improve stability of particles formed by peptide antigen conjugates that do not comprise a charged moiety (C), a charged or amphiphilic molecule can be added. In some embodiments, a first peptide antigen conjugate that does not comprise a charged moiety (C) (i.e., [B1]-A-[B2]-[L]-H) is mixed with a second peptide antigen conjugate comprising a charged moiety (e.g., C—[B1]-A-[B2]-[L]-H) in a DMSO solution and then resuspended in aqueous conditions to form stable nanoparticles. In other embodiments, a peptide antigen conjugate that does not comprise a charged molecule (C) (i.e. [B1]-A-[B2]-[L]-H) is mixed with a hydrophobic molecule (H) linked to a charged molecule (C), such as C—H, in a DMSO solution and then resuspended in aqueous conditions to form stable nanoparticles.

In some embodiments, a peptide antigen conjugate that does not comprise a charged molecule (C), such as [B1]-A-[B2]-[L]-H, where [ ] denotes that the group is optional, is combined with an amphiphilic carrier, C—[B1]-[A']—[B2]-[L]-H, wherein [ ] denotes the group is optional and optional A' is a conserved antigen (i.e. not patient-specific). In some embodiments, a peptide antigen conjugate comprising a charged molecule (C) is combined with an amphiphilic carrier. The amphiphilic carrier serves to stabilize nanoparticles, such as nanoparticle micelles formed by peptide antigen conjugates.

Selection of the charged molecule and extensions (B1 and B2)

The composition of the optional extensions, B1 and B2, linked at the N- and C-terminus of the peptide antigen (A), respectively, together with the optional charged molecule(s) (C), should be selected to: I) achieve the appropriate net charge and balance of hydrophilic and hydrophobic characteristics that are required to stabilize the particles formed by the peptide antigen conjugates in aqueous buffers at physiologic temperature and pH of about 7.4; and II) ensure that peptide antigens (A) delivered in the context of the peptide antigen conjugate can be processed to release minimal CD4 and/or CD8 T cell epitopes provided on the peptide antigen (A), such that the epitopes can be presented within the context of MHC Class I and Class II molecules. The following description discloses specific compositions of B1 and B2 extensions together with charged molecules (C) that lead to unexpected improvements in control over the size and stability of particles formed by peptide antigen conjugates and/or improvements in the processing and presentation of the CD4 and/or CD8 T cell epitopes provided as peptide antigens (A) on those particles that lead to significantly enhanced T cell responses.

An unexpected finding disclosed herein is that peptide antigens (A) containing minimal CD8 T cell epitopes delivered as peptide antigen conjugates, e.g., peptide antigen conjugates of the Formula IV, V and VI, are most efficiently processed in vitro and lead to higher CD8 T cell responses in vivo when a C-terminal enzyme degradable extension (B2) is used at the C-terminus between the peptide antigen (A) and a hydrophobic molecule (H) and/or when an N-terminal enzyme degradable extension (B1) is used between the N-terminus of the peptide antigen (A) and a charged molecule (C). In some embodiments, including a B1 extension comprising a cathepsin cleavable site between the charged molecule (C) and the peptide antigen (A) (e.g., C-B1-A-[B2]-[L]-H, where [ ] denotes that the group is optional), led to more efficient processing of the minimal T cell epitope from the peptide antigen conjugate that was associated with higher magnitude T cell response in vivo. Thus, preferred embodiments of Formula V and VI should use cathepsin cleavable sequences as N-terminal (B1) and C-terminal (B2) extensions, to allow for efficient processing and presentation of the peptide antigens (A) provided as particles comprising peptide antigen conjugates.

An additional unexpected finding relates to the identification of the net charge required to stabilize particles formed by some embodiments of peptide antigen conjugates. Highly hydrophobic peptide antigens (A) delivered as peptide antigen conjugates have the propensity to aggregate in aqueous conditions. To counter this tendency, charged molecules (C) and certain extensions (B1 or B2) may be selected for attachment to the peptide antigen conjugates, for example, see Formulas V and VI, or a conjugate comprising a charged molecule (e.g., C-[A']-[L]-H, where A' is a conserved antigen and [ ]denotes that the group is optional) may be added to particles comprising peptide antigen conjugates. An unexpected finding disclosed herein is that the amount of charge (i.e. net charge) required to stabilize the particles formed by some embodiments of peptide antigen conjugates, e.g., peptide antigen conjugates of Formulas V and VI comprising a poly(amino acid) based hydrophobic molecule (H), depends on the hydropathy (i.e., hydrophobic properties) of the peptide antigen fragment, which comprises the peptide antigen (A), optional charged molecules (C) and optional extensions (B1 and B2). We report the unexpected finding that the net charge useful for stabilizing particles formed by certain embodiments of peptide antigen conjugates can be determined based on the hydropathy of the peptide antigen (A) or the peptide antigen fragment. Thus, in preferred embodiments, the net charge of a peptide antigen conjugate is selected based on the calculated hydropathy of the peptide antigen (A) and is modulated by the charged molecule (C) and optionally the extensions (B1 and/or B2). In other embodiments, the net charge of a peptide antigen conjugate is selected based on the calculated hydropathy of the peptide antigen fragment and is modulated by the charged molecule (C). For clarity, the linker precursors (X1 and X2), Linker (L) and hydrophobic molecule (H) or Particle (P) are not considered in the determination of the hydropathy value for peptide antigens (A) or peptide antigen fragments used to select net charge of peptide antigen conjugates. Thus, the hydropathy of a peptide antigen conjugate is equivalent to the hydropathy of the peptide antigen fragment.

The hydropathy of the peptide antigen (A) or peptide antigen fragment, inclusive of the peptide antigen (A), optional charged molecule (C) and optional extensions (B1 and/or B2) may be calculated using any one of a variety of methods available for determining the hydrophobic/hydrophilic characteristics of a peptide. As a non-limiting example, a method for determining the hydropathy of peptide antigens (A) or the peptide antigen fragment is to calculate the grand average of hydropathy (GRAVY) value using the method by Kyte and Doolittle as described below. The following Hydropathy values, with estimates provided for non-natural amino acids (i.e., citrulline, sulfoserine, phosphoserine and trimethyllysine), were based on the method of Kyte and Doolittle and are used for calculating GRAVY values herein:

| Amino acid | Code | Hydropathy values | Charge |
| --- | --- | --- | --- |
| Isoleucine (Ile) | I | 4.5 | 0 |
| Valine (Val) | V | 4.2 | 0 |
| Leucine (Leu) | L | 3.8 | 0 |
| Phenylalanine (Phe) | F | 2.8 | 0 |
| Cysteine (Cys) | C | 2.5 | 0 |
| Methionine (Met) | M | 1.9 | 0 |
| Alanine (Ala) | A | 1.8 | 0 |
| Glycine (Gly) | G | −0.4 | 0 |
| Threonine (Thr) | T | −0.7 | 0 |
| Tryptophan (Trp) | W | −0.9 | 0 |
| Serine (Ser) | S | −0.8 | 0 |
| Tyrosine (Tyr) | Y | −1.3 | 0 |
| Proline (Pro) | P | −1.6 | 0 |
| Histidine (His) | H | −3.2 | 0.1 |
| Glutamic acid (Glu) | E | −3.5 | −1 |
| Glutamine (Gln) | Q | −3.5 | 0 |
| Aspartic acid (Asp) | D | −3.5 | −1 |
| Asparagine (Asn) | N | −3.5 | 0 |
| Lysine (Lys) | K | −3.9 | 1 |
| Citruline (Cit) | Z | −4 | 0 |
| Arginine (Arg) | R | −4.5 | 1 |
| Trimethyl Lysine | K(Me)3 | −4.5 | 1 |
| Phosphoserine | S-Phospho | −4.5 | −1 |
| Sulfoserine | S-Sulfo | −4.5 | −1 |

The process for determining the GRAVY value of a peptide is to sum the Hydropathy values of each individual amino acid comprising the peptide and then divide by the total length of the peptide. For example, a 9-amino acid peptide antigen (A) with the sequence Val-Val-Ile-Ala-Ile-Phe-Ile-Ile-Leu (SEQ ID NO: 57) has a GRAVY value of 3.86 (e.g., (4.2+4.2+4.5+1.8+4.5+2.8+4.5+4.5+3.8)/9 amino acids). As a non-limiting example, the same peptide antigen (A), i.e., Val-Val-Ile-Ala-Ile-Phe-Ile-Ile-Leu (SEQ ID NO: 57) prepared as a peptide antigen fragment by solid-phase peptide synthesis, wherein a charged molecule (C=Lys-Ser-Lys-Gly-Gly SEQ ID NO: 58) is linked to an N-terminal extension (B1=Lys-Pro-Leu-Arg SEQ ID NO: 8) at the N-terminus of the peptide antigen and to a C-terminal extension (B2=Gly-Gly-Lys-Leu-Val-Arg SEQ ID NO: 11) at the C-terminus that is linked to a linker precursor X1 (wherein X1 is Lys(N$_3$)—NH$_2$) is: Ac-Lys-Ser-Lys-Gly-Gly-Lys-Pro-Leu-Arg-Val-Val-Ile-Ala-Ile-Phe-Ile-Ile-Leu-Gly-Gly-Lys-Leu-Val-Arg-Lys(N$_3$)—NH$_2$ (SEQ ID NO: 121) and has a GRAVY value of 0.75 and a net charge of +6.

Determination of the GRAVY value of the peptide antigen fragment or peptide (A) provides a description of the hydrophobic/hydrophilic characteristics of a peptide sequence. In general, GRAVY values less than zero typically indicate that a peptide is comprised of primarily hydrophilic amino acids, whereas GRAVY values greater than zero indicate that a peptide is comprised of primarily hydrophobic amino acid residues. An unexpected finding reported herein is that as the GRAVY value of a peptide antigen (A) or peptide antigen fragment increases, the magnitude of net charge (either positive or negative) required to stabilize particles formed by peptide antigen conjugates comprising the peptide antigen (A) (or peptide antigen fragment) also increases. Thus, peptide antigens (A), or peptide antigen fragments, with higher GRAVY values typically require a higher net charge to ensure stability of particles formed by peptide antigen conjugates.

The GRAVY value of a peptide antigen (A) or the peptide antigen fragment, which is calculated based on the amino acid composition of the peptide antigen (A) an optional charged molecule (C) and/or optional extensions (B1 and/or B2) (and excludes contribution of any amino acids that may comprise the linker precursors (X1 and X2), Linker (L) and hydrophobic molecule (H) or Particle (P)), may be calculated to determine the net charge required to ensure stable particle formation by some embodiments of peptide antigen conjugates. Note: the GRAVY of the peptide antigen conjugate is considered to be equivalent to the GRAVY of the peptide antigen fragment; thus the GRAVY value of a peptide antigen fragment may also refer to the GRAVY value of the peptide antigen conjugate.

In some embodiments, the GRAVY value of the peptide antigen (A) is used to determine the net charge required to stabilize particles formed by the peptide antigen conjugates. As a non-limiting example, the peptide antigen conjugate should have a net charge of ≥(greater than or equal to)+6 or (less than or equal to)−6 when the GRAVY value for the peptide antigen (A) is greater than 0.75; the net charge should be (greater than or equal to)+5 or (less than or equal to)−5 when the GRAVY value is between 0.25-0.75; the net charge should be (greater than or equal to)+4 or (less than or equal to)−4 when the GRAVY value is less than 0.25. In preferred embodiments, the net charge is greater than or equal to +4 or less than or equal to −4, depending on whether a net positive or net negative charge is required, respectively. In some embodiments, peptide antigens (A) with a GRAVY value less than 0.25 are synthesized as peptide antigen conjugates with a net positive charge of about +4 to +15, for example, +4, +5, +6, +7, +8, +9, +10, +11, +12, +13, +14 or +15, though, typically between about +4 to +12; or with a net negative charge of about −4 to −15, for example, −4, −5, −6, −7, −8, −9, −10, −11, −12, −13, −14 or −15, though, typically between about −4 to −12. In some embodiments, peptide antigens (A) with a GRAVY value between 0.25-0.75 are synthesized as peptide antigen conjugates with a net positive charge of about +5 to +15, for example, +5, +6, +7, +8, +9, +10, +11, +12, +13, +14, +15, though, typically between about +5 to +12; or with a net negative charge of about −5 to −15, for example, −5, −6, −7, −8, −9, −10, −11, −12, −13, −14 or −15, though, typically between about −5 to −15. In some embodiments, peptide antigens (A) with a GRAVY value greater than 0.75 are synthesized as peptide antigen conjugates with a net positive charge of about +6 to +15, for example, +6, +7, +8, +9, +10, +11, +12, +13, +14, +15, though, typically between about +6 to +12; or with a net negative charge of about −6 to −15, for example, −6, −7, −8, −9, −10, −11, −12, −13, −14 or −15, though, typically between about −6 to −12.

In one embodiment of the process for selecting the charged molecule (C) and optional extensions (B1 and/or B2) to produce a peptide antigen conjugate of desire net charge, the process may comprise the steps of (i) determining the GRAVY and the charge of the peptide antigen (A); and (ii) selecting a charged molecule (C) and optional extensions (B1 and/or B2) to achieve a sufficient number of charged functional groups to reach the desired net charge. In a non-limiting example, the net charge needed for a peptide antigen conjugate may vary depending on the peptide antigen (A) hydropathy according to the following criteria: greater than or equal to +6 charge is needed for 25 to 35 amino acid peptide antigens (A) with a GRAVY value greater than 0.75; greater than or equal to +5 charge is needed for 25 to 35 amino acid peptide antigens (A) with GRAVY values between 0.25 to 0.75; and greater than or equal to +4 charge is needed for 25 to 35 amino acid peptide antigens (A) with GRAVY less than 0.25. Thus, in this non-limiting example, a 25 amino acid peptide antigen (A) with a GRAVY value of 2.0 and charge of +2 should be combined with a charged molecule (C) and optional extensions (B1 and/or B2) comprising a net charge of at least +4 to achieve a net charge of the peptide antigen conjugate of +6. In an additional non-limiting example, the net charge needed for a peptide antigen conjugate may vary depending on the peptide antigen (A) hydropathy according to the following criteria: less than or equal to −6 charge is needed for 25 to 35 amino acid peptide antigens (A) with a GRAVY value greater than 0.75; less than or equal to −5 charge is needed for 25 to 35 amino acid peptide antigens (A) with GRAVY values between 0.25 to 0.75; and less than or equal to −4 charge is needed for 25 to 35 amino acid peptide antigens (A) with GRAVY less than 0.25. Thus, in this non-limiting example, a peptide antigen (A) with a GRAVY value of 2.0 and charge of +2 should be combined with a charged molecule (C) and optional extensions (B1 and/or B2) comprising a net charge of −8 to achieve a net charge of the peptide antigen conjugate of −6.

In some embodiments, determination of the GRAVY value for the peptide antigen fragment, including the optional charged molecule (C), optional extensions (B1 and/or B2) and peptide antigen (A) is used to determine the net charge required to stabilize particles formed by the peptide antigen conjugates. As a non-limiting example, the peptide antigen conjugate should have a net charge of ≥(greater than or equal to)+6 or (less than or equal to)−6 when the GRAVY value of the peptide antigen fragment is greater than 0.75; the net charge should be (greater than or equal to)+5 or (less than or equal to)−5 when the GRAVY value is between 0.25-0.75; the net charge should be (greater than or equal to)+4 or (less than or equal to)−4 when the GRAVY value is less than 0.25. In preferred embodiments, the net charge is greater than or equal to +4 or less than or equal to −4, depending on whether a net positive or net negative charge is required, respectively. In some embodiments, peptide antigen fragments with a GRAVY value less than 0.25 have a net positive charge of about +4 to +15, for example, +4, +5, +6, +7, +8, +9, +10, +11, +12, +13, +14 or +15, though, typically between about +4 to +12; or a net negative charge of about −4 to −15, for example, −4, −5, −6, −7, −8, −9, −10, −11, −12, −13, −14 or −15, though, typically between about −4 to −12. In some embodiments, peptide antigen fragments with a GRAVY value between 0.25-0.75 have a net positive charge of about +5 to +15, for example, +5, +6, +7, +8, +9, +10, +11, +12, +13, +14, +15, though, typically between about +5 to +12; or a net negative charge of about −5 to −15, for example, −5, −6, −7, −8, −9, −10, −11, −12, −13, −14 or −15, though, typically between about −5 to −12. In some embodiments, peptide antigen fragments with a GRAVY value greater than 0.75 have a net positive charge of about +6 to +15, for example, +6, +7, +8, +9, +10, +11, +12, +13, +14, +15, though, typically between about +6 to +12; or a net negative charge of about −6 to −15, for example, −6, −7, −8, −9, −10, −11, −12, −13, −14 or −15, though, typically between about −6 to −12.

An additional unexpected finding is that the magnitude of net charge required to stabilize particles formed by certain embodiments of peptide antigen conjugates, e.g., peptide antigen conjugates of Formula V and Formula VI, generally increases with the length of the peptide antigen (A). In some embodiments, 7 to 14 amino acid peptide antigens (A) are synthesized as peptide antigen conjugates with net charge greater than or equal to +6 or less than or equal to −6; 15 to 24 amino acid peptide antigens (A) are synthesized as peptide antigen conjugates with net charge greater than or equal to +7 or less than or equal to −7; and 25 to 35 amino acid peptide antigens (A) are synthesized as peptide antigen conjugates with net charge greater than or equal to +8 or less than or equal to −8.

In some embodiments, immunogenic compositions comprise particles comprised of peptide antigen conjugates of the formula [B1]-A-[B2]-[L]-H and charged molecule (C) conjugates of the formula C-[A']-[L]-H, wherein [ ] denotes that the group is optional and A' is an optional conserved antigen (i.e. not patient specific), additionally wherein the molar ratio of [B1]-A-[B2]-[L]-H to C-[A']-[L]-H is selected from a range of from 1:20 to 20:1, such as 1:20, 1:10, 1:5, 1:2, 1:1, 2:1, 5:1, 10:1 and 20:1, and the net charge of C-[A']-[L]-H is negative and selected from −2 to −20, such as −2, −3, −4, −5, −6, −7, −8, −9, −10, −11, −12, −13, −14, −15, −16, −17, −18, −19 or −20, typically about −4 to about −12 or positive and selected from +2 to +20, such as +2, +3, +4, +5, +6, +7, +8, +9, +10, +11, +12, +13, +15, +16, +17, +18, +19 or +20, typically about +4 to +12. In a non-limiting example, an immunogenic composition comprises particles comprising 1 molar equivalent of a peptide antigen conjugate, Ala-Ser-Met-Thr-Asn-Met-Glu-Leu-Met-Ser-Ser-Lys(N3-DBCO-H)—$NH_2$ (SEQ ID NO: 122), which carries a net charge of 0 (note that the peptide fragment has a C-terminal amide), and 1 molar equivalent of a charged molecule (C) conjugate comprised of $(Lys)_5$-Lys (N3-DBCO-NH)—$NH_2$ (SEQ ID NO: 123), which carries a net charge of +6; the ratio of peptide antigen conjugate to charged molecule conjugate is 1:1 and the net charge of each set of those two molecules is +6. Thus, the net charge of the particles can be adjusted by modulating the ratio of the peptide antigen conjugate to the charged molecule (C) conjugate or by modulating the net charge of the charged molecule conjugate. In preferred embodiments, the ratio of the peptide antigen conjugate to charged molecule is from about 1:4 to 4:1 and the net charge of the charged molecule is selected such that the average net charge of molecules comprising the particles is about +4 to about +12 or about −4 to about −12. For example, a particle comprising a 1:1 mole ratio of peptide antigen conjugates to charged molecule conjugates (C), wherein the peptide antigen conjugate has a net charge of 0, the average net charge of molecules is +4 when the net charge of the charged molecule (C) conjugate is +8.

For certain applications, positively charged peptide antigen conjugates may be useful. In some embodiments, a peptide antigen conjugate may comprise a peptide antigen (A), a charged molecule (C) comprising positively charged functional groups, a hydrophobic molecule (H) or Particles (P), optional extensions (B1 and/or B2) and an optional Linker (L). The composition of charged molecules (C) and optional extensions (B1 and/or B2) are selected to maximize particle stability and biological activity of the peptide antigen conjugates. In some embodiments, a peptide antigen conjugate of Formula V comprised of a charged molecule (C) with a net positive charge is linked to an N-terminal peptide extension (B1) that is linked to a peptide antigen (A) that is linked to a C-terminal peptide extension (B2) that is linked either directly or through a Linker (L) to a hydrophobic molecule (H) and the resulting peptide antigen conjugate has a net positive charge. In this example, the hydrophobic molecule (H) linked through the C-terminus of the peptide antigen (A) functions to induce particle formation and the charged molecule (C) linked through the N-terminus of the peptide antigen (A) functions to stabilize the particles through high positive charge density at the surface of those particles. Thus, optional B2 extensions placed proximal to the hydrophobic molecule (H) of net positively charged peptide antigen conjugates of Formula V, wherein the charged molecule (C) is linked through the N-terminus of the peptide antigen (A), are preferably comprised of non-charged and hydrophobic amino acids that help to promote particle formation and are typically selected from single amino acids, such as glycine, seine, citrulline, leucine, norleucine or methionine; dipeptides, such as Gly-Cit, Gly-Ser or Gly-Leu; tripeptides, such as Gly-Ser-Cit, Gly-Pro-Cit, or Gly-Pro-Gly; tetrapeptides, such as Ser-Pro-Val-Cit or Gly-Pro-Gly-Cit; pentapeptides, such as Gly-Ser-Val-Leu-Cit (SEQ ID NO: 124), Gly-Pro-Val-Leu-Cit (SEQ ID NO: 125); or hexapeptides, such as Gly-Gly-Ser-Leu-Val-Cit (SEQ ID NO: 112), or Gly-Gly-Ser-Pro-Val-Cit (SEQ ID NO: 113). In some embodiments, a C-terminal extension (B2) that includes a single charged amino acid is used and is typically selected from single amino acids, such as arginine or lysine; dipeptides, such as Gly-Arg or Gly-Lys; tripeptides, such as Gly-Ser-Arg or Gly-Ser-Lys; tetrapeptides such as Gly-Pro-Gly-Arg (SEQ ID NO: 59), Gly-Ser-Val-Arg (SEQ ID NO: 60) or Ser-Leu-Val-Arg (SEQ ID NO: 7) (where Arg can be replaced with Lys); pentapeptides, such as Gly-Ser-Leu-Val-Arg (SEQ ID NO: 17) (where Arg can be replaced with Lys); and hexapeptides such as Gly-Gly-Ser-Leu-Val-Arg (SEQ ID NO: 13) or Gly-Gly-Ser-Pro-Val-Arg (SEQ ID NO: 61) (where Arg can be replaced with Lys). B1 extensions placed proximal to the charged molecule (C) of positively charged peptide antigen conjugates of Formula V, wherein the charged molecule (C) is linked through the N-terminus of the peptide antigen (A), preferably contain a charged amino acid, such as an Arg or Lys, and are typically selected from single amino acids selected from Arg or Lys; dipeptides selected from Val-Arg or Leu-Arg (where Arg can be replaced with Lys); tripeptides selected from Pro-Val-Arg or Gly-Val-Arg (where Arg can be replaced with Lys); or tetrapeptides selected from Lys-Leu-Val-Arg (SEQ ID NO: 62), Lys-Pro-Val-Arg (SEQ ID NO: 9), Lys-Pro-Leu-Arg (SEQ ID NO: 8), Ser-Leu-Val-Arg (SEQ ID NO: 7) and Ser-Pro-Val-Arg (SEQ ID NO: 6) (where Arg can be replaced with Lys). The different extensions, B1 and B2 can be combined with any charged molecule (C), peptide antigen (A), hydrophobic molecule (H) or Particle (P) and Linker (L) to achieve the Grand average of hydropathy (GRAVY) value and net charge of the peptide antigen conjugate needed for the intended application.

In some embodiments, a peptide antigen conjugate of Formula V with net positive charge comprises a charged molecule (C), typically comprising between 4 to 12 positively charged functional groups, e.g., $(Lys)_{4-12}$ (SEQ ID NO: 126), that is linked to a di-peptide N-terminal extension (B1), e.g. Val-Arg, that is linked to a peptide antigen (A), which typically comprises between 7 to 35 amino acids, that is linked to a C-terminal extension (B2), e.g., Ser-Pro-Val-Cit, that is linked to a Linker (Lys(N3)-DBCO) that is linked to a hydrophobic molecule (H) comprised of poly(amino acids) of Formula I or Formula II linked to adjuvants of Formula III.

For certain applications, negatively charged peptide antigen conjugates are required. In some embodiments, a peptide antigen conjugate may comprise a peptide antigen (A), a charged molecule (C) comprising negatively charged functional groups, a hydrophobic molecule (H) or Particles (P), optional extensions (B1 and/or B2) and an optional Linker (L). The composition of charged molecules (C) and optional extensions (B1 and/or B2) are selected to maximize particle stability and biological activity of the peptide antigen conjugates. In some embodiments, a peptide antigen conjugate of Formula V comprised of a charged molecule (C) with net negative charge is linked to an N-terminal peptide extension (B1) that is linked to a peptide antigen (A) that is linked to a C-terminal peptide extension (B2) that is linked either directly or through a Linker (L) to a hydrophobic molecule (H) and the resulting peptide antigen conjugate has a net negative charge. Thus, the B2 extension placed proximal to the hydrophobic molecule (H) of net negatively charged peptide antigen conjugates of Formula V, wherein the charged molecule (C) is linked through the B1 extension at the N-terminus of the peptide antigen (A), are preferably comprised of non-charged and hydrophobic amino acids that help to promote particle formation and are typically selected from single amino acids, such as glycine, serine, citrulline, leucine, norleucine or methionine; dipeptides, such as Gly-Ser, Gly-Cit or Gly-Leu; tripeptides, such as Gly-Ser-Cit, Gly-Pro-Cit, or Gly-Pro-Gly; tetrapeptides, such as Ser-Pro-Val-Cit, Ser-Pro-Val-Cit or Gly-Pro-Gly-Cit; pentapeptides, such as Gly-Ser-Val-Leu-Cit (SEQ ID NO: 124), Gly-Pro-Val-Leu-Cit (SEQ ID NO: 125); or hexapeptides, such as Gly-Gly-Ser-Leu-Val-Cit (SEQ ID NO: 112), or Gly-Gly-Ser-Pro-Val-Cit (SEQ ID NO: 113) or Gly-Gly-Ser-Pro-Leu-Cit (SEQ ID NO: 127). In some embodiments, a C-terminal extension (B2) that includes a single charged amino acid is used and is typically selected from single amino acids, such as arginine or lysine; dipeptides, Gly-Arg (where Arg can be replaced with Lys); tripeptides, such as Gly-Ser-Arg (where Arg can be replaced with Lys); tetrapeptides such as Gly-Pro-Gly-Arg (SEQ ID NO: 59), Gly-Ser-Val-Arg (SEQ ID NO: 60), Ser-Leu-Val-Arg (SEQ ID NO: 7), Asp-Leu-Val-Cit or Asp-Leu-Val-Leu (SEQ ID NO: 63) (where Asp can be replaced with Glu and Arg can be replaced with Lys); pentapeptides, such as Gly-Ser-Leu-Val-Arg (SEQ ID NO: 17) or Gly-Asp-Leu-Val-Leu (SEQ ID NO: 64) or Gly-Asp-Leu-Val-Arg (SEQ ID NO: 65); and hexapeptides such as Gly-Gly-Ser-Leu-Val-Arg (SEQ ID NO: 13) or Gly-Gly-Ser-Pro-Val-Arg (SEQ ID NO: 61) where Asp can be replaced with Glu and Arg can be replaced with Lys); or Gly-Ser-Glu-Leu-Val-Arg (SEQ ID NO: 66) or Gly-Gly-Asp-Pro-Val-Arg (SEQ ID NO: 67) (where Asp can be replaced with Glu and Arg can be replaced with Lys). B1 extensions placed proximal to the charged molecule (C) of net negatively charged peptide antigen conjugates of Formula V, wherein the charged molecule (C) is linked through the N-terminus of the peptide antigen via the B1 extension preferably contain a charged amino acid, such as an Asp or Glu, and are typically selected from single amino acids such as Cit, Leu, Arg or Lys; dipeptides selected from Val-Cit, Leu-Cit, Val-Arg or Leu-Arg (where Arg can be replaced with Lys); tripeptides selected from Pro-Val-Arg, Pro-Val-Cit, Gly-Val-Arg or Gly-Val-Cit (where Arg can be replaced with Lys); or tetrapeptides selected from Ser-Leu-Val-Arg (SEQ ID NO: 7), Ser-Pro-Val-Arg (SEQ ID NO: 6), Ser-Pro-Leu-Cit, Ser-Leu-Val-Cit, Ser-Pro-Val-Cit, Asp-Leu-Val-Arg (SEQ ID NO: 68), Asp-Pro-Val-Arg (SEQ ID NO: 69), Asp-Leu-Val-Cit, Asp-Leu-Val-Leu (SEQ ID NO: 63), Ser-Gly-Val-Cit or Asp-Pro-Val-Cit (where Arg can be replaced with Lys and Asp can be replaced with Glu). The different extensions, B1 and B2 can be combined with any charged molecule (C), peptide antigen (A) and hydrophobic molecule (H) or Particle (P) to achieve the Grand average of hydropathy (GRAVY) value and net charge of the peptide antigen conjugate needed.

In some embodiments, a peptide antigen conjugate of Formula V with net negative charge comprises a charged molecule (C), typically comprising between 6 to 14 negatively charged functional groups, e.g., $(Glu)_{6-14}$ (SEQ ID NO: 128), that is linked to a di-peptide N-terminal extension (B1), e.g. Val-Cit, that is linked to a peptide antigen (A), which typically comprises between 7 to 35 amino acids, that is linked to a C-terminal extension (B2), e.g., Ser-Pro-Val-Cit, that is linked to a Linker (Lys(N3)-DBCO) that is linked to a hydrophobic molecule (H) comprised of poly(amino acids) of Formula I or Formula II linked to adjuvants of Formula III.

In several embodiments, addition of a charged molecule (C) and/or extensions (B1 and B2) reduced the GRAVY value of the peptide antigen fragment comprising the peptide antigen (A) and increased the net charge of the sequence, which was associated with unexpected improvements in manufacturing of the peptide antigen fragment. In several embodiments, addition of a charged molecule (C) comprising one or more lysines (Lys) or arginine (Arg) amino acid residues led to the successful synthesis and HPLC purification of a peptide antigen fragment comprising a peptide antigen (A) that was otherwise not manufacturable as the native peptide antigen (i.e., the native peptide antigen with no other modifications). In several embodiments, a peptide antigen (A) linked to a C-terminal extension (B2) comprised of one or more proline, pseudo proline (Pro), arginine (Arg) or lysine (Lys) amino acids led to the successful synthesis of a peptide antigen fragment comprising a peptide antigen (A) that was otherwise not manufacturable as the native peptide antigen (i.e., the native peptide antigen with no other modifications). In several embodiments, addition of one or more aromatic amines, such as phenylalanine amine, to a peptide antigen fragment or peptide antigen conjugate produced entirely by solid-phase peptide synthesis led to the successful synthesis of the peptide antigen fragment or peptide antigen conjugate comprising a peptide antigen (A) that was otherwise not manufacturable as the native peptide antigen (i.e., the native peptide antigen with no other modifications).

Selection of Peptide Antigens (A) for Use in Personalized Cancer Vaccines

In some embodiments, the peptide antigen (A) comprising the peptide antigen conjugate is specific to an individual patient. The peptide antigen conjugate comprising peptide antigens (A) that are specific to individual patients may be used for personalized therapies, such as for use as a personalized cancer vaccine or a personalized vaccine for inducing tolerance or suppression for treating autoimmunity or allergies.

The selection of peptide antigens (A) for inclusion in a personalized cancer vaccine is a multi-step process, wherein some steps may be dispensable.

The first step involves the identification of tumor-associated antigens that are specific to the tumor, or, relative to normal tissue, are over-expressed by the tumor. Accordingly, tumor tissue and normal tissue are obtained. Tumor tissue and normal tissue may be fixed in formalin and paraffin embedded, or may be freshly isolated tissue. Normal tissue may be blood containing leukocytes. The tumor tissue and normal tissue is processed to isolate DNA. The DNA is further processed and sequenced to identify differences between the tumor DNA and normal tissue DNA. These DNA differences may be single- or di- or higher order nucleotide changes that result in a non-synonymous mutation, insertions and deletions that result in frameshift mutations, splice site mutations that result in alternate splice variants, or stop codons that can be read through resulting in single amino acid deletions. Further mutations may be possible through chromosomal translocations or inversions or duplications. There are numerous ways that changes at the DNA level can give rise to aberrant peptide sequences and/or peptides with aberrant post-translational modifications that are tumor-specific and may be referred to as neoantigens or predicted neoantigens.

The second-step involves the determination of whether or not the tumor-associated antigens identified in step 1 are in fact expressed by the tumor. Tumor RNA is isolated, processed, and sequenced to determine if mutations identified by step 1 are expressed as RNA by the tumor cells. Peptide antigens (A) comprising mutations identified from DNA sequencing of tumor and normal tissue may be selected for inclusion in a personalized cancer vaccine on the basis of RNA expression level. Additionally, tumor associated self-antigens that produce higher levels of RNA in tumor as compared with non-cancerous tissues may be selected as peptide antigens (A) for inclusion. Mutations wherein no RNA transcript is identified are generally not selected as a peptide antigen (A) for inclusion in a vaccine. Peptide antigens (A) comprising mutations or tumor-associated self-antigens may be prioritized on the basis of RNA expression level of the mutant peptide (i.e. neoantigen) or tumor-associated self-antigens, for example, more highly expressed mutations or tumor-associated self-antigens may be prioritized. Multiple criteria may be used simultaneously in the selection of peptide antigens (A) for inclusion in a personalized cancer vaccine. For example, RNA expression level and predicted MHC binding affinity of epitopes contained by a mutant peptide (i.e. neoantigen) or tumor-associated self-antigen may be used together to select the optimal set of peptide antigens (A) for inclusion in a personalized cancer vaccine. In such a scenario, a peptide antigen (A) containing a T cell epitope with moderate binding affinity that is very highly expressed may be prioritized over a different peptide antigen (A) containing a T cell epitope that has a higher binding affinity but is expressed by the tumor at a very low level.

Another consideration is how clonal, or conserved, a mutation or tumor-associated self-antigen is across different tumor cells that comprise a tumor. The clonality of a mutation is assessed by comparing the frequency of the mutation to the frequency of the wildtype variant in the tumor isolated DNA. Tumor-associated neoantigens or self-antigens may be selected for use as peptide antigens (A) for inclusion in personalized cancer vaccines comprised of peptide antigen conjugates on the basis of clonality or near clonality of the mutation they comprise. For example, peptide antigens (A) may be prioritized for inclusion if they are predicted to be present in >50% of tumor cells, >75% of tumor cells, >85% of tumor cells, >95% of tumor cells, or >99% of tumor cells.

In some embodiments, peptide antigens (A) for inclusion in a personalized cancer vaccine comprised of peptide antigen conjugates may be further prioritized on the basis of the predicted binding of the epitopes contained within the antigen for a given MHC class I and/or class II molecule as determined by an in silico binding algorithm. In a non-limiting example, the MHC type of each subject is first identified through sequencing. Then, each mutant peptide (i.e. neoantigen) or tumor-associated self-antigen identified by any suitable means (e.g., DNA sequencing, RNA expression or mass spectrometry) is tested for predicted binding to each MHC molecule present in the subject, which, in the case of human patients, for example, may be up to 6 unique Class I MHC alleles. There are several publicly available algorithms that can be used to predict MHC binding, including the netMHC artificial neural network, the stabilized matrix method, and the Immune Epitope Database (IEDB) Analysis Resource Consensus algorithm. Non-public algorithms may also be used. Peptide antigens (A) that contain an epitope with a high predicted binding affinity are more likely to induce an immune response than peptide antigens (A) containing epitopes with a low predicted binding affinity. An unexpected finding disclosed herein is that greater than 50% of peptide antigens (A), including predicted neoantigens, that have an epitope with predicted binding affinity of less than the 0.5 percentile by the IEDB consensus algorithm are able to generate T cells responses (i.e. CD8 T cell responses) when administered using immunogenic compositions comprising peptide antigen conjugates described herein. Based on this unexpected finding, peptide antigens (A), including peptide antigens (A) comprising predicted neoantigens, that contains an epitope with a binding affinity less than 0.5 percentile with the IEDB consensus algorithm may be selected for use in the personalized cancer vaccines comprising peptide antigen conjugates.

Additionally, mass spectrometry confirmation of antigen binding to MHC, or algorithms trained on mass spectrometry binding of antigens to MHC, may be used to select peptide antigens (A) for inclusion in a personalized cancer vaccine. In this scenario, tumor tissue is processed to identify peptides that are bound to MHC molecules. Peptides that are identified on the surface of tumor cells but not normal cells, which may be mutant peptides (i.e. neoantigen), proteasomal splice-variants or tumor-associated self-antigens, may be prioritized for inclusion in a personalized cancer vaccine. An unexpected finding disclosed herein is that a high proportion (i.e. 7 out of 7) of predicted neoantigens, which were selected for use in a personalized cancer vaccine on the basis of mass spectrometry confirmed binding to MHC-I on tumor cells, led to high magnitude CD8 T cell responses when delivered as a peptide antigen (A) in immunogenic compositions comprising a peptide antigen conjugate, suggesting that mass spectrometry, or predictive algorithms based on mass spectrometry, may be reliable filters for selecting neoantigens for use as peptide antigens (A) in personalized cancer vaccines comprised of peptide antigen conjugates.

Peptide antigens (A) may also be selected for inclusion on the basis of a T cell recognition assay. For example, one may use an assay wherein synthetic peptides (or expression systems that produce the peptide in situ) comprising predicted neoantigens or tumor-associated self-antigens are added to an in vitro culture of T cells derived from the blood, tumor tissue, or other tissue from a subject. T cell recognition of a given peptide could be assessed, for example, by an ELISpot assay, or by flow cytometry. Antigens recognized in an in vitro T cell assay may be prioritized for inclusion as a peptide antigen (A) in a personalized vaccine comprised of peptide antigen conjugates.

Finally, peptide antigens (A) may be selected based on any number of predictive algorithms. Peptide antigens (A) that are predicted to be immunogenic or efficacious based on predictive algorithms trained on large data sets may be used. Additionally, predictive algorithms may be used to select peptide neoantigens that are predicted to lead to T cell responses that are specific for the mutant epitope but not the wild-type epitope, i.e., T cells that are not cross-reactive for self-antigens.

Any combination of the above methods may be used for the identification and selection of peptide antigens (A) comprising neoantigens or tumor-associated self-antigens or the like for use in a personalized cancer vaccine comprised of peptide antigen conjugates.

Peptide Antigen (A) Length and the Effects on the Induction of CD8 and CD4 T Cell Responses for Personalized Cancer Vaccines A single nucleotide polymorphism that results in a non-synonymous amino acid substitution can appear in any position in a peptide epitope that binds to Class I MHC, which are typically 8-13 amino acids in length. Therefore, to cover all possible epitopes which may bind a given Class I MHC, a peptide antigen (A) comprising a neoantigen for use in a personalized cancer vaccine may include 12 amino acids on either side of the non-synonymous mutation, making a peptide of 25 amino acids in length, with the mutant amino acid as the middle (13th) residue. Alternatively, a peptide antigen (A) may include only the minimal epitope (8-13 amino acids in length) that is predicted to bind to Class I MHC. Alternatively, personalized cancer vaccine could contain both a peptide antigen (A) comprising the 25 amino acid neoantigen and a peptide antigen (A) comprising only the predicted minimal epitope of a neoantigen.

The peptide binding pocket of MHC Class II typically binds peptides of 12-16 amino acids and in some as many as 20 or more amino acids. Therefore, a personalized cancer vaccine that is comprised of peptide antigens (A) that contain only the predicted Class I binding minimal epitopes (which are typically 8-13 amino acids in length) is unlikely to induce CD4 T cell responses. However, a cancer vaccine that contains 25 amino acid (or "25-mer") peptide antigens (A) may but not always induce CD4 T cell responses targeting a given mutation.

A 25 amino acid (or "25 mer") peptide antigen (A) in a cancer vaccine may induce lower level CD8 T cell responses compared to a peptide antigen (A) comprising the exact ~7 to 12 amino acid minimal epitope, possibly due to differences in the efficiency of processing and presentation of different lengths of peptide antigens. Thus, 25 amino acid peptide antigens (A) included in a cancer vaccine may result in lower magnitude CD8 T cell responses compared to those induced by peptide antigens (A) comprising minimal epitopes. Accordingly, in some embodiments, a 25 amino acid peptide antigen (A) included in a cancer vaccine comprised of peptide antigen conjugates results in no detectable CD8 T cell responses, whereas the 7 to 12 amino acid peptide antigen (A) comprising the exact minimal epitope results in detectable CD8 T cell responses. In additional embodiments, a 25 amino acid peptide antigen (A) included in a cancer vaccine comprised of peptide antigen conjugates results in detectable CD4 T cell responses, a 7 to 12 amino acid peptide antigen (A) comprising the exact minimal epitope results in no detectable CD4 T cell responses. Based on these unexpected findings, in some embodiments, two lengths of peptide antigens (A) comprising the same epitope, both the minimal CD8 T cell epitope (referred to as the "Min" or minimal epitope (ME)) and the 25 amino acid peptide (referred to as a synthetic long peptide (SLP) or long peptide), may be included as peptide antigens (A) in personalized cancer vaccines comprised of peptide antigen conjugates. In some embodiments, peptide antigens (A) that consist of the minimal CD4 and CD8 T cell epitopes are included in a personalized cancer vaccine comprised of peptide antigen conjugates. In additional embodiments, peptide antigens (A) consisting of minimal CD8 T cell and peptide antigens (A) comprising a universal CD4 T cell epitope and optionally peptide antigens (A) consisting of minimal CD4 T cell epitopes are included in personalized cancer vaccines comprised of peptide antigen conjugates. In preferred embodiments, peptide antigens (A) included in a personalized vaccine comprised of peptide antigen conjugates is 7 to 35 amino acids, typically 15 to 35 amino acids, e.g., 25 amino acids.

Combination Immunotherapy

The peptide antigen conjugates disclosed herein may be used in immunogenic compositions to treat tumors or infectious diseases. The peptide antigen conjugates may be used alone or in combination with other therapies. For the treatment of cancers, immunogenic compositions comprised of peptide antigen conjugates may be used prior to, during or after any form of treatment, such as surgery, radiation therapy or chemotherapy. In preferred embodiments, the immunogenic compositions comprising the peptide antigen conjugates are used in combination with immuno-modulators, such as cytokines (e.g., IL-2), anti-tumor antibodies, checkpoint inhibitors (such as anti-PD1) antibodies, or other small molecules or biologics that reverse immune-suppression, directly kill tumor cells or potentiate the immune response against the tumor. In preferred embodiments, a cancer vaccine based on peptide antigen conjugates is provided to a tumor-bearing subject in combination with a checkpoint inhibitor (e.g., anti-PD1, anti-PDL1 anti-CTLA4). In preferred embodiments, the cancer vaccine, e.g., personalized cancer vaccine is provided to a subject prior to administration of the checkpoint inhibitor. The peptide antigen conjugates disclosed herein may also be used in heterologous prime-boost immunizations, such as a prime or boost with a peptide antigen conjugate and a prime or boost with a heterologous vaccine, such as a viral vector.

Composition Formulation

The immunogenic compositions comprised of peptide antigen conjugates disclosed herein can be formulated as pharmaceutical compositions prepared for administration to a subject and which include a therapeutically effective amount of one or more of the immunogens as described herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Immunogenic compositions for administration to a subject can be pharmaceutical compositions and can include at least one further pharmaceutically acceptable additive such as carriers, thickeners, diluents, buffers, preservatives, surface active agents and the like in addition to the molecule of choice. Immunogenic compositions can also include one or more additional active ingredients such as antimicrobial agents, anesthetics, and the like. The pharmaceutically acceptable carriers useful for these formulations are conventional. *Remington's Pharmaceutical Sciences*, by E. W. Martin, Mack Publishing Co., Easton, PA, 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

To formulate the immunogenic compositions, the disclosed nanoparticle components or a solution containing the disclosed nanoparticle components can be combined with various pharmaceutically acceptable additives, as well as a base or vehicle for dispersion of the nanoparticles. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, NJ), Freund's adjuvant, MPL™ (3-O-deacylated monophosphoryl lipid A; Corixa, Hamilton, IN) and IL-12 (Genetics Institute, Cambridge, MA), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The immunogenic compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

The instant disclosure also includes kits, packages and multi-container units containing the herein described immunogenic compositions, active ingredients, and/or means for administering the same for use in the prevention and treatment of diseases and other conditions in mammalian subjects. In one embodiment, these kits include a container or formulation that contains one or more of the immunogenic compositions described herein. In one example, the immunogenic composition is formulated in a pharmaceutical preparation for delivery to a subject. The immunogenic composition is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

Methods of Inducing an Immune Response

The immunogenic compositions including a peptide antigen (A) as described herein may be used to elicit an immune response to the peptide antigen (A) in a subject. Subjects that can benefit from the disclosed methods include human and veterinary subjects.

In some embodiments, a subject is selected for treatment that has, or is at risk for developing, an infection with an infectious agent that comprises the peptide antigen, for example because of exposure or the possibility of exposure to the infectious agent. Following administration of a therapeutically effective amount of a disclosed immunogenic composition, the subject can be monitored for the infection, symptoms associated with the infection, or both.

In some embodiments, a subject is selected for treatment that has, or is at risk for developing, a cancer, such as a malignant tumor. Following administration of a therapeutically effective amount of a disclosed immunogen, the subject can be monitored for the presence of the cancer, a reduction in tumor burden, any appropriate symptom of the cancer, or a combination thereof.

Typical subjects intended for treatment with the therapeutics and methods of the present disclosure include humans, as well as non-human primates and other animals. To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize the disease or condition. These and other routine methods allow the clinician to select patients in need of therapy using the methods and pharmaceutical compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The administration of a therapeutically effective amount of an immunogenic composition including a peptide antigen as disclosed herein can be for prophylactic or therapeutic purposes. When provided prophylactically, the immunogenic composition is provided in advance of any symptom, for example in advance of infection or development of a tumor. The prophylactic administration of the immunogenic composition serves to prevent or ameliorate subsequent development of the disease or condition. Hence in some embodiments the methods involves selecting a subject at risk for contracting an infection or developing a tumor, and administering a therapeutically effective amount of a disclosed therapeutically effective amount of a disclosed immunogenic composition. The immunogenic composition can thus be provided prior to the anticipated exposure to the infectious agent, or development of the tumor, so as to attenuate the anticipated severity, duration or extent of an infection or tumor, and/or any associated disease symptoms.

When provided therapeutically, the disclosed immunogenic composition can be provided at or after the onset of a symptom of disease or condition, for example after development of a symptom of infection, or diagnosis of infection, or development of a symptom of a tumor, or diagnosis of a tumor. Treatment of the infection or tumor can include delaying and/or reducing signs or symptoms of the infection or tumor in the subject. In some examples, treatment using the methods disclosed herein prolongs the time of survival of the subject.

The immunogenic composition can be used in coordinate immunization protocols or combinatorial formulations.

In some embodiments, a therapeutically effective amount of a disclosed immunogenic composition can be administered to a subject to treat or inhibit an infectious agent in a subject. An infectious agent is an agent that can infect a subject, including, but not limited to, viruses, bacteria, and fungi. The subject can be selected for treatment that has, is suspected of having or is at risk of developing an infection with the infectious agent. In some embodiments, the infectious agent is a virus, a bacteria, or a fungus as described above, and the peptide antigen includes an antigen from the particular virus, bacteria, or fungus.

In some embodiments, a therapeutically effective amount of a disclosed immunogenic composition can be administered to a subject to treat or inhibit a tumor and/or a cancer in a subject. The subject can be selected for treatment that has, is suspected of having or is at risk of developing the tumor and/or cancer. In some embodiments, treating the tumor and/or cancer in the subject decreases growth and/or proliferation of the tumor. The tumor can be any tumor of interest and can be benign or malignant.

Treatment of the tumor is generally initiated after the diagnosis of the tumor, or after the initiation of a precursor condition (such as dysplasia or development of a benign tumor). Treatment can be initiated at the early stages of cancer, for instance, can be initiated before a subject manifests symptoms of a condition, such as during a stage I diagnosis or at the time dysplasia is diagnosed. However, treatment can be initiated during any stage of the disease, such as but not limited to stage I, stage II, stage III and stage IV cancers. In some examples, treatment is administered to these subjects with a benign tumor that can convert into a malignant or even metastatic tumor.

Treatment initiated after the development of a condition, such as malignant cancer, may result in decreasing the severity of the symptoms of one of the conditions, or completely removing the symptoms, or reducing metastasis, tumor volume or number of tumors. In some example, the tumor becomes undetectable following treatment. In one aspect of the disclosure, the formation of tumors, such as metastasis, is delayed, prevented or decreased. In another aspect, the size of the primary tumor is decreased. In a further aspect, a symptom of the tumor is decreased. In yet another aspect, tumor volume is decreased.

Subjects can be screened prior to initiating the disclosed therapies, for example to determine whether the subject has a tumor. The presence of a tumor can be determined by methods known in the art, and typically include cytological and morphological evaluation. The tumor can be an established tumor. The cells can be in vivo or ex vivo, including cells obtained from a biopsy. The presence of a tumor indicates that the tumor can be treated using the methods provided herein.

The therapeutically effective amount will depend upon the severity of the disease and the general state of the patient's health. A therapeutically effective amount is that which provides either subjective relief of a symptom(s) or an objectively identifiable improvement as noted by the clinician or other qualified observer. In one embodiment, a therapeutically effective amount is the amount necessary to inhibit tumor growth, or the amount that is effective at reducing a sign or a symptom of the tumor. In another embodiment, a therapeutically effective amount is the amount necessary to inhibit infection by an infectious agent, or the amount that is effective at reducing a sign or a symptom of the infection. The therapeutically effective amount of the agents administered can vary depending upon the desired effects and the subject to be treated. In some examples, therapeutic amounts are amounts which eliminate or reduce the patient's tumor burden, or which prevent or reduce the proliferation of metastatic cells, or which reduce the load of infectious agent in the subject.

The actual dosage of the immunogenic composition will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

EXAMPLES

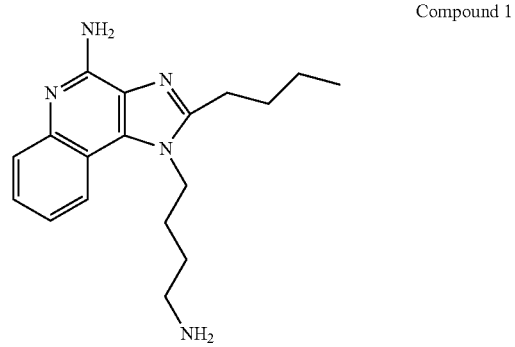 [SMILES: CCCCc1nc2c(N)nc3ccccc3c2n1CCCCN]

Compound 1

Figure 3:
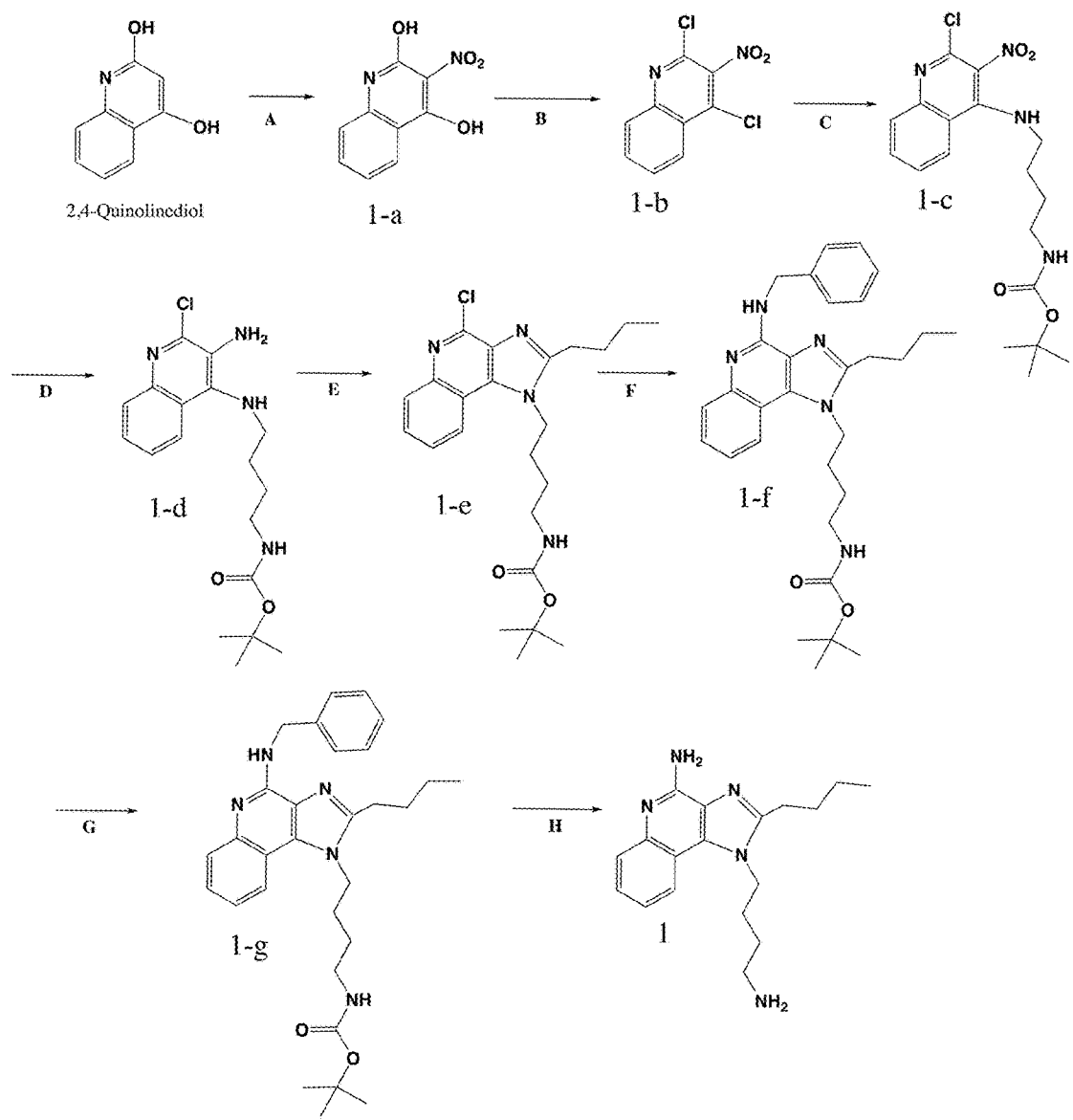
FIG. 3: Schematic for the synthesis of Compound 1.

Compound 1, 1-(4-aminobutyl)-2-butyl-1H-imidazo[4,5-c]quinolin-4-amine, referred to as 2B, was synthesized according to the scheme shown in FIG. 3.

1-c. Starting from 2,4-quinolinediol, the intermediate, 1-b, was prepared as previously described (Lynn G M, et al., *Nat Biotechnol* 33(11):1201-1210, 2015). To 21 g of 1-b (87.8 mmol, 1 eq) in 210 mL of triethylamine (TEA) (10% w/w) was added 16.34 g (87.8 mmol, 1 eq) of N-boc-1,4-butanediamin while stirring vigorously. The reaction mixture was heated to 70° C. and monitored by HPLC, which confirmed that the reaction was complete after 2 hours. The triethylamine was removed under vacuum and the resulting oil was dissolved in 200 mL of dichloromethane and then washed with 3×100 mL DI $H_2O$. The organic layer was dried with $Na_2SO_4$ and then removed under vacuum and the resulting oil was triturated with 1:1 (v:v) hexane and diethyl ether to yield 30.7 g of yellow crystals of intermediate 1-c. MS (APCI) calculated for $C_{18}H_{23}ClN_4O_4$, m/z 394.1 found, 394.9.

1-d. 30.7 g (76.4 mmol) of intermediate 1-c was dissolved in 300 mL of ethyl acetate in a Parr Reactor vessel that was bubbled with argon, followed by the addition of 3 g of 10% platinum on carbon. The reaction vessel was kept under argon and then evacuated and pressurized with $H_2$ (g) several times before pressurizing to 55 PSI $H_2$ (g) while shaking vigorously. The $H_2$ (g) was continually added until the pressure stabilized at 55 PSI, at which point the reaction was determined to be complete. The reaction mixture from the Parr Reactor was then filtered through celite end evaporated to dryness to obtain a yellow oil that was triturated with 1:1 hexanes/ether to yield white crystals that were collected by filtration to obtain 27.4 g of spectroscopically pure white crystals of 1-d. MS (APCI) calculated for $C_{18}H_{25}ClN_4O_2$, m/z 364.2, found 365.2.

1-e. To 10 g (27.4 mmol, 1 eq) of 1-d in 50 mL of THF was added 7.7 mL of triethylamine (54.8 mmol, 2 eq) followed by the drop wise addition of 3.6 g of valeroyl chloride (30.1 mmol, 1.1 eq) in 30 mL of THF while stirring vigorously while the reaction mixture was on ice. After 90 minutes, the ice bath was removed and the THF was removed under vacuum, resulting in a yellow oil that was dissolved in 100 mL of dichloromethane (DCM) that was washed with 3×50 mL of pH 5.5 100 mM acetate buffer. The DCM was removed under vacuum in an oil that was triturated with ethyl acetate to obtain 10.4 g of a white solid that was dissolved in methanol with 1 g of CaO (s), which was heated at 100° C. for 5 hours while stirring vigorously. The reaction mixture was filtered and dried to yield 10.2 g of an off-white solid, intermediate, 1-e. MS (ESI) calculated for $C_{23}H_{31}ClN_4O_2$, m/z 430.21, found 431.2.

1-f. To 10.2 g (23.7 mmol, 1 eq) of 1-e was added 30.4 g (284 mmol, 12 eq) of benzylamine liquid, which was heated to 110° C. while stirring vigorously. The reaction was complete after 10 hours and the reaction mixture was added to 200 mL ethyl acetate and washed 4×100 mL with 1 M HCl. The organic layer was dried with $Na_2SO_4$ and then removed under vacuum and the resulting oil was recrystallized from ethyl acetate to obtain 10.8 g of spectroscopically pure white crystals of intermediate, 1-f. MS (ESI) calculated for $C_{30}H_{39}N_5O_2$, m/z 501.31, found 502.3

Compound 1. 10.8 g (21.5 mmol) of 1-f was dissolved in 54 mL of concentrated (>98%) $H_2SO_4$ and the reaction mixture was stirred vigorously for 3 hours. After 3 hours, viscous red reaction mixture was slowly added to 500 mL of DI $H_2O$ while stirring vigorously. The reaction mixture was stirred for 30 minutes and then filtered through Celite, followed by the addition of 10 M NaOH until the pH of the solution was ~ pH 10. The aqueous layer was then extracted with 6×200 mL of DCM and the resulting organic layer was dried with $Na_2SO_4$ and reduced under vacuum to yield a spectroscopically pure white solid. $^1$H NMR (400 MHZ, DMSO-d6) δ 8.03 (d, J=8.1 HZ, 1H), 7.59 (d, J=8.1 Hz, 1H), 7.41 (t, J=7.41 Hz, 1H), 7.25 (t, J=7.4 Hz, 1H), 6.47 (s, 2H), 4.49 (t, J=7.4 Hz, 2H), 2.91 (t, J=7.78 Hz, 2H), 2.57 (t, J=6.64 Hz, 1H), 1.80 (m, 4H), 1.46 (sep, J=7.75 Hz, 4H), 0.96 (t, J=7.4 Hz, 3H). MS (ESI) calculated for $C_{18}H_{25}N_5$, m/z 311.21, found 312.3.

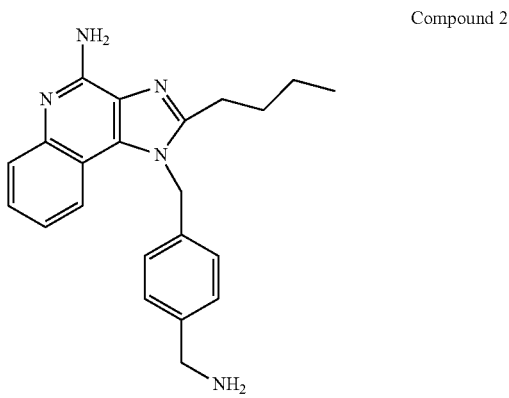 [SMILES: CCCCc1nc2c(N)nc3ccccc3c2n1Cc1ccc(CN)cc1]

Compound 2

Compound 2, 1-(4-(aminomethyl)benzyl)-2-butyl-1H-imidazo[4,5-c]quinolin-4-amine, referred to as 2BXy, was previously described (see: Lynn G M, et al., In vivo characterization of the physicochemical properties of polymer-linked TLR agonists that enhance vaccine immunogenicity. *Nat Biotechnol* 33(11):1201-1210, 2015, and Shukla N M, et al. Syntheses of fluorescent imidazoquinoline conjugates as probes of Toll-like receptor 7. *Bioorg Med Chem Lett* 20(22):6384-6386, 2010). 1H NMR (400 MHz, DMSO-d6) δ 7.77 (dd, J=8.4, 1.4 Hz, 1H), 7.55 (dd, J=8.4, 1.2 Hz, 1H), 7.35-7.28 (m, 1H), 7.25 (d, J=7.9 Hz, 2H), 7.06-6.98 (m, 1H), 6.94 (d, J=7.9 Hz, 2H), 6.50 (s, 2H), 5.81 (s, 2H), 3.64 (s, 2H), 2.92-2.84 (m, 2H), 2.15 (s, 2H), 1.71 (q, J=7.5 Hz, 2H), 1.36 (q, J=7.4 Hz, 2H), 0.85 (t, J=7.4 Hz, 3H). MS (APCI) calculated for $C_{22}H_{25}N_5$ m/z 359.2, found 360.3

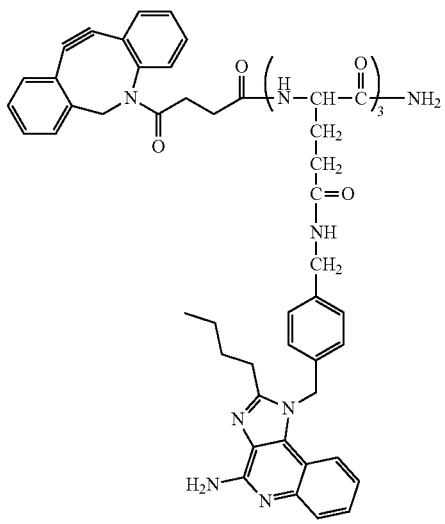

Compound 3

Compound 3, referred to as DBCO-2BXy₃, 2BXy₃ or DBCO-(Glu(2BXy)₃), was synthesized starting from an Fmoc-(Glu)₃-NH₂ precursor prepared by solid-phase peptide synthesis. 50 mg of Fmoc-(Glu)₃-NH₂ (0.08 mmol, 1 eq), 143 mg of Compound 2 (0.40 mmol, 5 eq), 84 mg of 2-chloro-4,6-dimethoxy-1,3,5-triazine (CDMT) (0.48 mmol, 6 eq) and 48.5 mg of 4-methylmorpholine (NMM) (0.48 mmol, 6 eq) were added to 3.25 mL of DMSO while stirring vigorously at room temperature under ambient air. The reaction progress was monitored by HPLC (AUC 254 nm). 1 additional equivalent of Compound 2 and 2 additional equivalents of both CDMT and NMM were added after 30 minutes. After 2 hours, the reaction was complete and the reaction mixture was added to 50 mL of a 1M HCl solution to precipitate the Fmoc protected intermediate, which was collected by centrifuging the solution at 3000 g at 4° C. for 10 minutes. The HCl solution was discarded and the Fmoc protected intermediate was collected as a solid white pellet. The white solid was re-suspended in 50 mL of a 1M HCl solution and spun at 3000 g at 4° C. for 5 minutes; the 1 M HCl solution was discarded and the product was collected as a solid pellet. This process was repeated and then the solid was collected and dried under vacuum to yield 156.1 mg of the Fmoc protected intermediate in quantitative yield. The Fmoc protected product was then added to 1.5 mL of a 20% piperidine in DMF solution for 30 minutes at room temperature to yield the deprotected product that was then precipitated from 50 mL of ether and centrifuged at 3000 g at 4° C. for 30 minutes. The product was collected as a solid pellet and then washed twice more with ether, followed by drying under vacuum to yield 126.4 mg of the intermediate. 60 mg of the resulting intermediate, NH₂-(Glu-2BXy)₃-NH₂, (0.042 mmol, 1 eq) was then reacted with 18.6 mg (0.046 mmol, 1.1 eq) of DBCO-NHS ester (Scottsdale, Arizona, USA) and 8.5 uL of triethylamine (0.084 mmol, 2 eq) in 1 mL of DMSO for 6 hours at room temperature. The resulting product, Compound 3, was purified on a preparatory HPLC system using a gradient of 30-70% acetonitrile/H₂O (0.05% TFA) over 12 minutes on an Agilent Prep-C18 column, 50×100 mm, 5 µm. The product eluted at 7.0 minutes and the resulting fractions were collected, frozen and then lyophilized to obtain 40.12 mg (55.7% yield) of a spectroscopically pure (>95% AUC at 254 nm) white powder. MS (ESI) calculated for $C_{100}H_{106}N_{20}O_8$ m/z 1714.85, found 858.9 (M/2)⁺

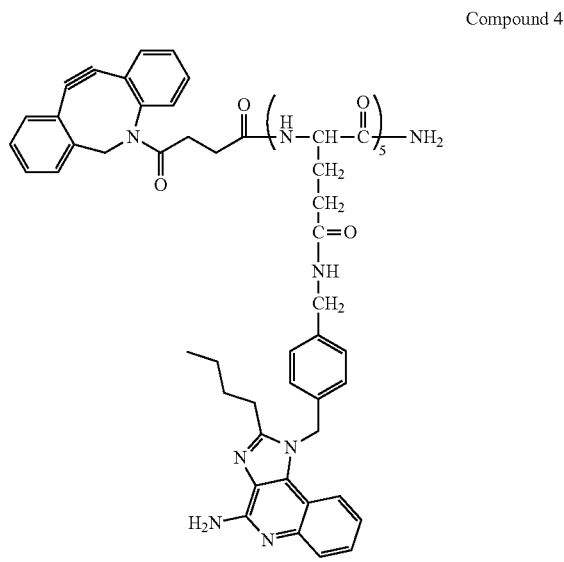

Compound 4

(SEQ ID NO: 129)

Compound 4, referred to as DBCO-2BXy₅, 2BXy₅ or DBCO-(Glu(2BXy)₅) (Compound 4 disclosed as SEQ ID NO: 129), was synthesized using the same procedure as described for Compound 3, except Fmoc-(Glu)₅-NH₂ (SEQ ID NO: 130) was used as the starting material for conjugation of Compound 2. Compound 4 was purified on a preparatory HPLC system using a gradient of 38-48% acetonitrile/H₂O (0.05% TFA) over 12 minutes on an Agilent Prep-C18 column, 50×100 mm, 5 µm. The product eluted at 8.0 minutes and the resulting fractions were collected, frozen and then lyophilized to obtain 45.9 mg (63.4% yield) of a spectroscopically pure (>95% AUC at 254 nm) white powder. MS (ESI) calculated for $C_{154}H_{166}N_{32}O_{12}$ m/z 2655.34, found 886.6 (M/3)⁺.

Compound 5

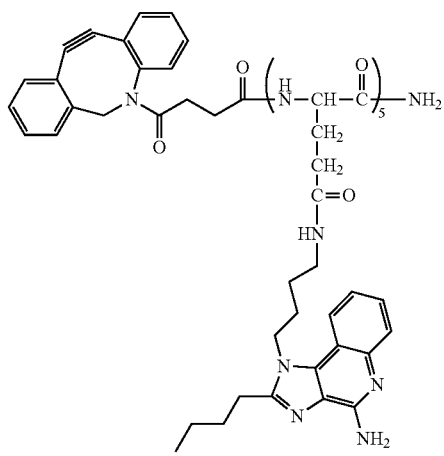

(SEQ ID NO: 131)

Compound 5, referred to as DBCO-2B$_5$, 2B$_5$ or DBCO-(Glu(2B)$_5$) (Compound 5 disclosed as SEQ ID NO: 131), was synthesized using the same procedure as described for Compound 3, except Fmoc-(Glu)$_5$-NH$_2$ (SEQ ID NO: 130) was used as the starting material for conjugation of Compound 1. Compound 5 was purified on a preparatory HPLC system using a gradient of 33-45% acetonitrile/H$_2$O (0.05% TFA) over 12 minutes on an Agilent Prep-C18 column, 50×100 mm, 5 μm. The product eluted at ~10.0 minutes and the resulting fractions were collected, frozen and then lyophilized to obtain 25.2 mg (62.6% yield) of a spectroscopically pure (>95% AUC at 254 nm) white powder. MS (ESI) calculated for $C_{134}H_{166}N_{32}O_{12}$ m/z 2415.34, found 1209.3 (M/2)$^+$.

Compound 6

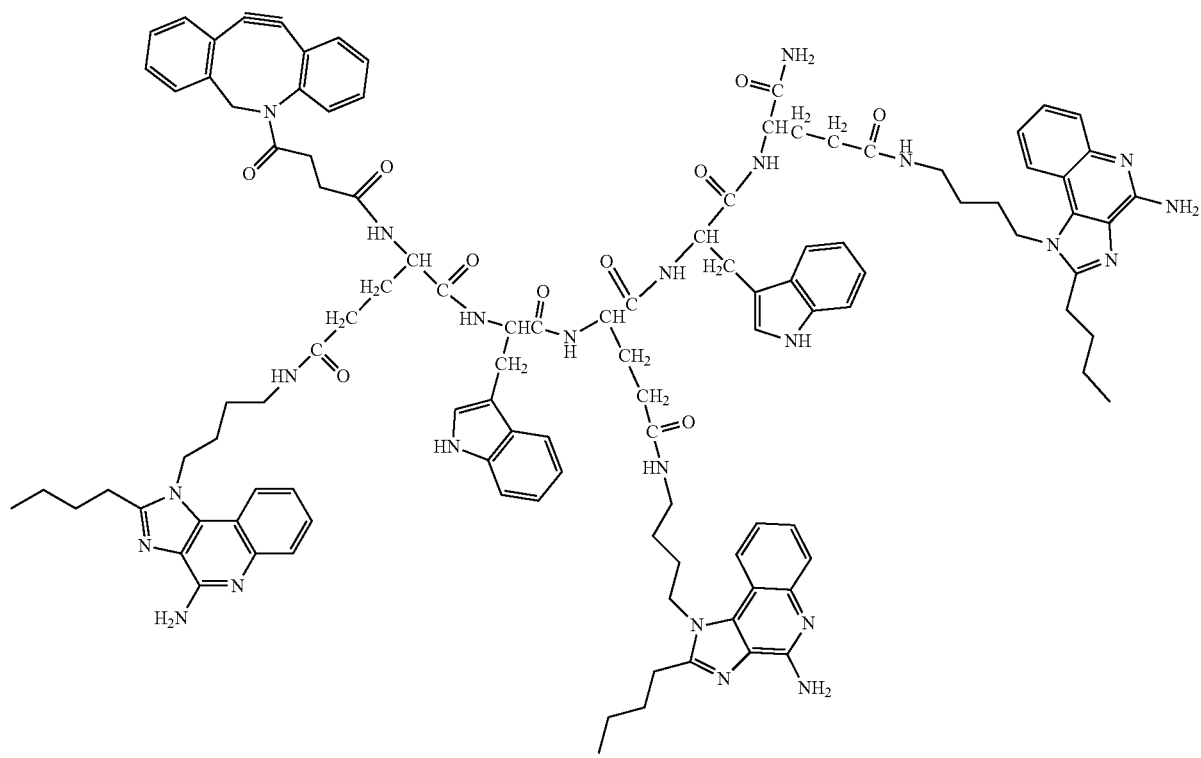

(SEQ ID NO: 132)

Compound 6, referred to as DBCO-2B$_3$W$_2$, 2B$_3$W$_2$ or DBCO-(Glu(2B))$_3$(Trp)$_2$) (Compound 6 disclosed as SEQ ID NO: 132), was synthesized using the same procedure as described for Compound 3, except Fmoc-Glu-Trp-Glu-Trp-Glu-NH$_2$ (SEQ ID NO: 133) was used as the starting material for conjugation of Compound 1. Compound 6 was purified on a preparatory HPLC system using a gradient of 33-47% acetonitrile/H$_2$O (0.05% TFA) over 12 minutes on an Agilent Prep-C18 column, 50×100 mm, 5 μm. The product eluted at ~8 minutes and the resulting fractions were collected, frozen and then lyophilized to obtain 197 mg (50.6% yield) of a spectroscopically pure (>95% AUC at 254 nm) white powder. MS (ESI) calculated for C$_{110}$H$_{126}$N$_{24}$O$_{10}$ m/z 1943.01, found 973.0 (M/2)$^+$.

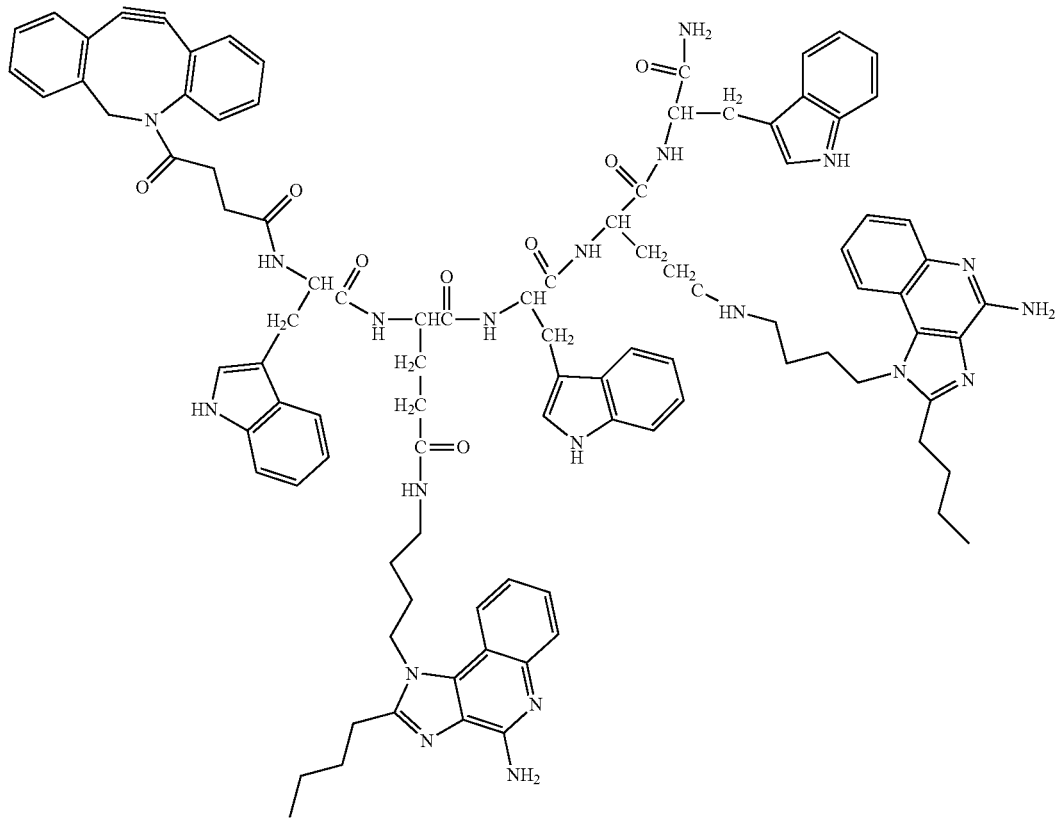

Compound 7

(SEQ ID NO: 134)

Compound 7, referred to as DBCO-2B$_2$W$_3$, 2B$_2$W$_3$ or DBCO-(Glu(2B))$_2$(Trp)$_3$) (Compound 7 disclosed as SEQ ID NO: 134), was synthesized using the same procedure as described for Compound 3, except Fmoc-Trp-Glu-Trp-Glu-Trp-NH$_2$ (SEQ ID NO: 135) was used as the starting material for conjugation of Compound 1. Compound 7 was purified on a preparatory HPLC system using a gradient of 35-65% acetonitrile/H$_2$O (0.05% TFA) over 12 minutes on an Agilent Prep-C18 column, 50×100 mm, 5 μm. The product eluted at ~9 minutes and the resulting fractions were collected, frozen and then lyophilized to obtain 11.6 mg (62.5% yield) of a spectroscopically pure (>95% AUC at 254 nm) white powder. MS (ESI) calculated for C$_{98}$H$_{106}$N$_{20}$O$_9$ m/z 1706.85, found 854.9 (M/2)$^+$.

Compound 8

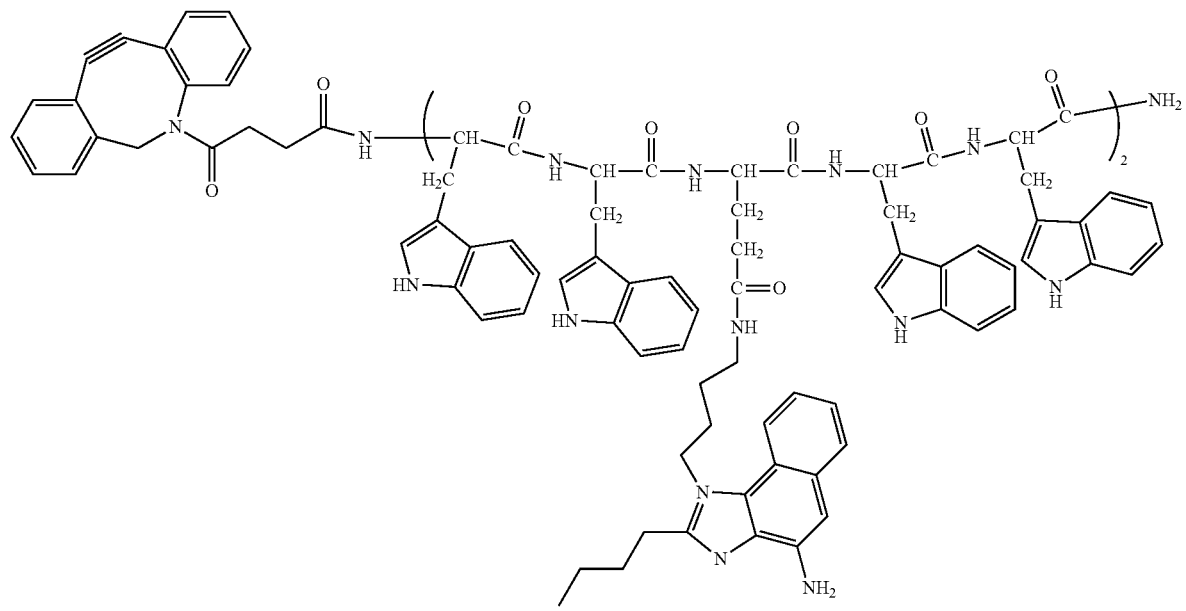

(SEQ ID NO: 136)

Compound 8, referred to as DBCO-2B₂W₈, 2B₂W₈ or DBCO-(Glu(2B))₂(Trp)₈ (Compound 8 disclosed as SEQ ID NO: 136), was synthesized using the same procedure as described for Compound 3, except Fmoc-Trp-Trp-Glu-Trp-Trp-Trp-Trp-Glu-Trp-Trp-NH₂ (SEQ ID NO: 137) was used as the starting material for conjugation of Compound 1. Compound 8 was purified on a preparatory HPLC system using a gradient of 35-85% acetonitrile/H₂O (0.05% TFA) over 12 minutes on an Agilent Prep-C18 column, 50×100 mm, 5 μm. The product eluted at ~8.0 minutes and the resulting fractions were collected, frozen and then lyophilized to obtain 3.3 mg (16.3% yield) of a spectroscopically pure (>95% AUC at 254 nm) white powder. MS (ESI) calculated for $C_{153}H_{156}N_{30}O_{14}$ m/z 2637.24, found 1320.2 (M/2)⁺.

Compound 9

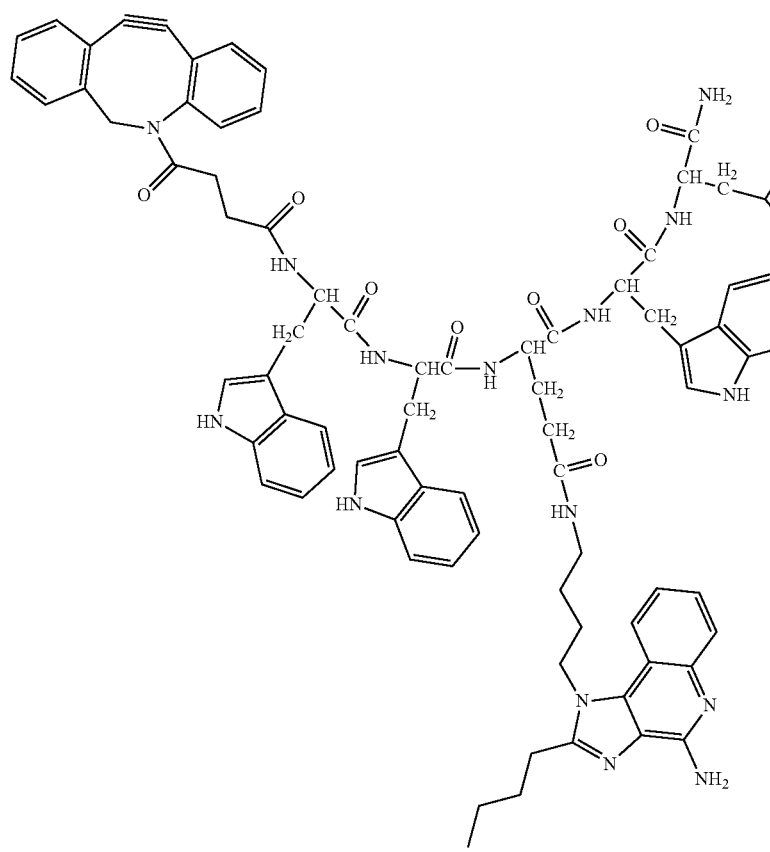

(SEQ ID NO: 138)

Compound 9 referred to as DBCO-2B₁W₄, 2B₁W₄ or DBCO-(Glu(2B)₁(Trp)₄) (Compound 9 disclosed as SEQ ID NO: 138), was synthesized using the same procedure as described for Compound 3, except Fmoc-Trp-Trp-Glu-Trp-Trp-NH₂ (SEQ ID NO: 139) was used as the starting material for conjugation of Compound 1. Compound 9 was purified on a preparatory HPLC system using a gradient of 50-55% acetonitrile/H₂O (0.05% TFA) over 12 minutes on an Agilent Prep-C18 column, 50×100 mm, 5 µm. The product eluted at 8.9 minutes and the resulting fractions were collected, frozen and then lyophilized to obtain 9.7 mg (55.4% yield) of a spectroscopically pure (>95% AUC at 254 nm) white powder. MS (ESI) calculated for $C_{86}H_{86}N_{16}O_8$ m/z 1470.68, found 736.6 (M/2)⁺.

Compound 10

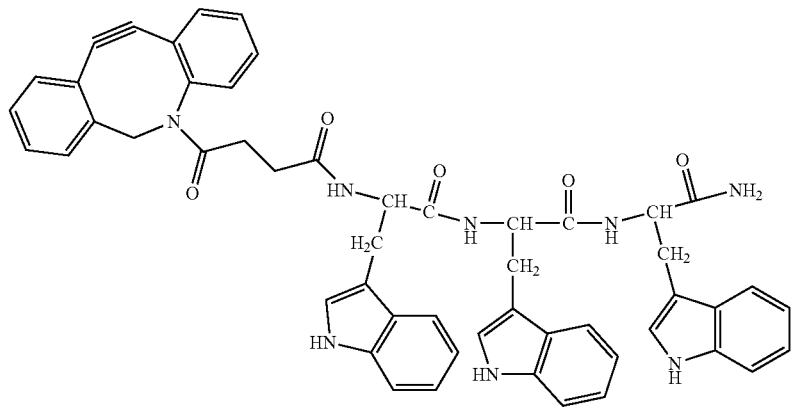

Compound 10, referred to as DBCO-W₃, W₃ or DBCO-(Trp)₃, was synthesized by reacting 50.2 mg (0.08 mmol, 1 eq) of a tri-peptide precursor NH₂-(Trp)₃-NH₂ that was prepared by solid phase peptide synthesis with 35 mg of DBCO-NHS (0.096 mmol, 1.1 eq) and 44 mg of triethylamine (0.44 mmol, 5 eq) in 1.5 mL of DMSO. Compound 10 was purified on a preparatory HPLC system using a gradient of 30-95% acetonitrile/H$_2$O (0.05% TFA) over 12 minutes on an Agilent Prep-C18 column, 50×100 mm, 5 μm. The product eluted at ~9 minutes and the resulting fractions were collected, frozen and then lyophilized to obtain 31.2 mg (41.5% yield) of a spectroscopically pure (>95% AUC at 254 nm)

Compound 11

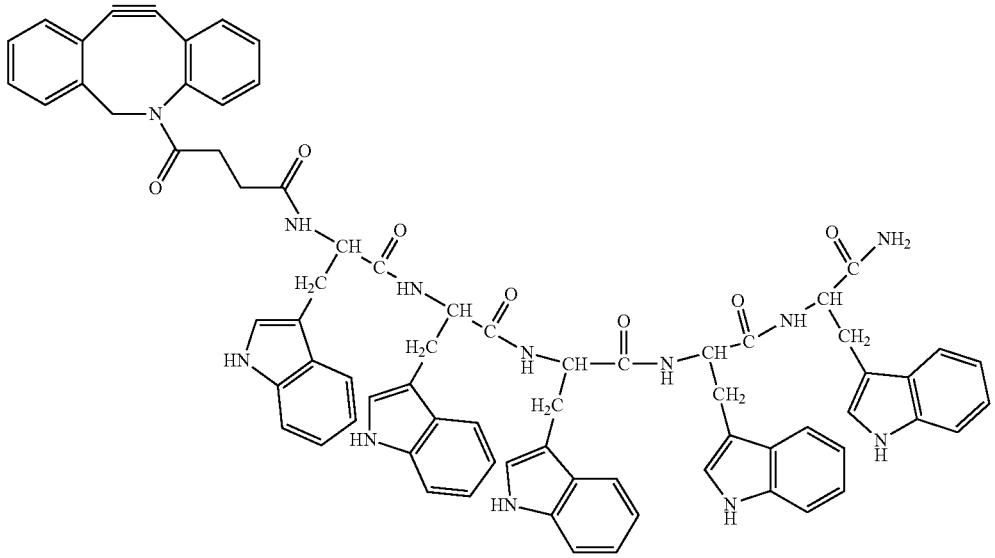

(SEQ ID NO: 140)

Compound 11, referred to as DBCO-W$_5$, W$_5$ or DBCO-(Trp)$_5$ (Compound 11 disclosed as SEQ ID NO: 140), was synthesized using the same procedure as for Compound 10 except NH$_2$-(Trp)$_5$-NH$_2$ (SEQ ID NO: 70) was used as the peptide precursor for conjugation to DBCO-NHS. Compound 11 was purified on a preparatory HPLC system using a gradient of 30-95% acetonitrile/H$_2$O (0.05% TFA) over 12 minutes on an Agilent Prep-C18 column, 50×100 mm, 5 μm. The product eluted at ~10 minutes and the resulting fractions were collected, frozen and then lyophilized to obtain 28.7 mg (44.1% yield) of a spectroscopically pure (>95% AUC at 254 nm) white powder. MS (ESI) calculated for C$_{74}$H$_{66}$N$_2$O$_7$ m/z 1234.52, found 1235.6 (M+H)$^+$ Compound 12

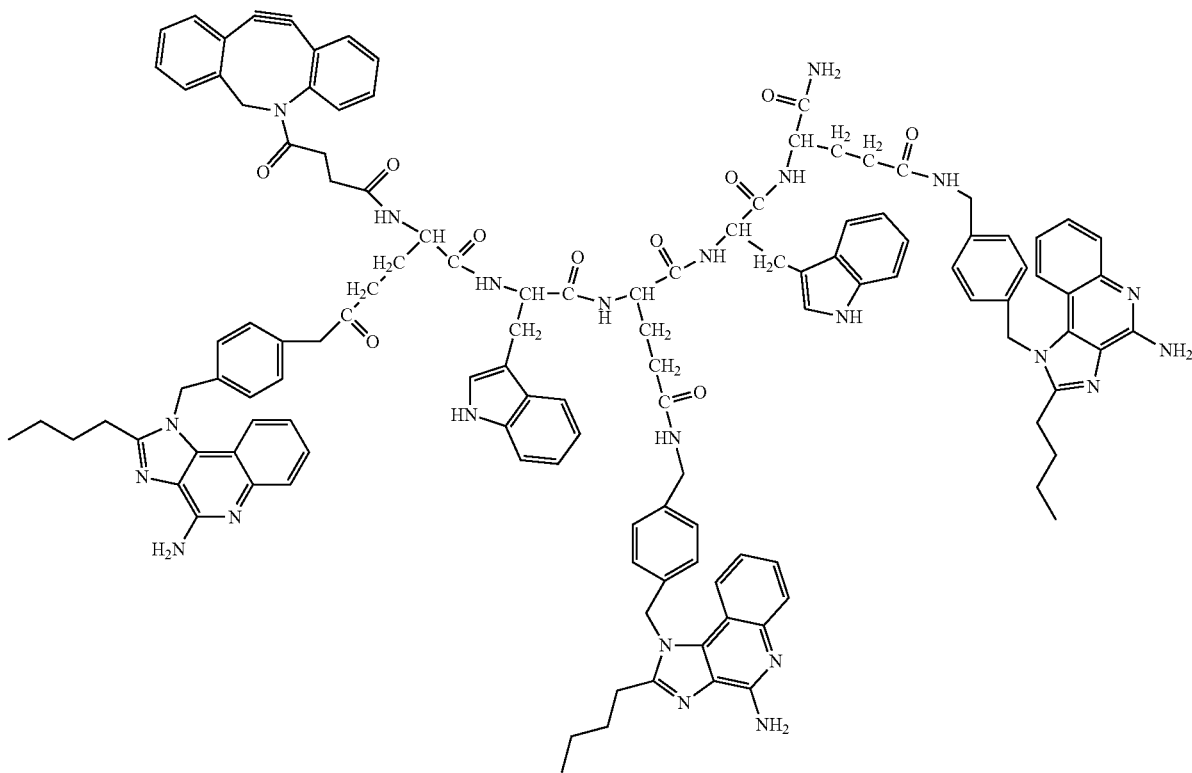

(SEQ ID NO: 141)

Compound 12, referred to as DBCO-2BXy$_3$W$_2$, 2BXy$_3$W$_2$ or DBCO-(Glu(2BXy)$_3$(Trp)$_2$) (Compound 12 disclosed as SEQ ID NO: 141), was prepared using Fmoc-Glu-Trp-Glu-Trp-Glu-NH$_2$ (SEQ ID NO: 133) and Compound 2 as the starting materials. 500 mg of Fmoc-Glu-Trp-Glu-Trp-Glu-NH$_2$ (SEQ ID NO: 133) (0.5 mmol, 1 eq), 595.6 mg of Thiazoline-2-Thiol (TT) (5 mmol, 10 eq), and 575.7 mg of 1-Ethyl-3-(3-dimethylaminopropyl)carbodiimide (EDC) (3 mmol, 6 eq) were suspended in 26 mL of DCM. 18.3 mg of 4-(Dimethylamino)pyridine (DMAP) (0.2 mmol, 0.3 eq) was added and the reaction mixture was stirred at room temperature. The reaction progress was monitored by analytical HPLC. After 4 hours, an additional four equivalents of TT and two equivalents of EDC were added. After stirring overnight, two equivalents of TT and a half equivalent of EDC were added. After 6 hours, the reaction was complete. The DCM was removed under vacuum and the solid was taken up in 6 mL of dry DMSO. 539.3 mg of Compound 2 (1.5 mmol, 3 eq) was added and the reaction mixture was stirred for 2 hours at room temperature. The conjugated intermediate was then precipitated from 300 mL of 1 M HCl and centrifuged at 3000 g at 4° C. for 10 minutes. The pellet was collected and washed once more with 1 M HCl and once with DI water. The final collected pellet was frozen and dried under vacuum. 809.06 mg of Fmoc-2BXy$_3$W$_2$—NH$_2$ (0.4 mmol, 1 eq)) was dissolved in 4 mL of 20% piperidine in DMF. The reaction mixture was stirred at room temperature for 1 hour. The deprotected intermediate was then precipitated from 100 mL of ether and centrifuged at 3000 g at 4° C. for 10 minutes. The product was collected as a solid pellet and then washed twice more with ether, followed by drying under vacuum to yield the intermediate. 729 mg NH$_2$-2BXy$_3$W$_2$—NH$_2$ (0.4 mmol, 1 eq) was dissolved in 6 mL of dry DMSO. 488.8 mg of DBCO-NHS (1.2 mmol, 3 eq) was added and the reaction mixture was stirred at room temperature for 1 hour. The resulting product was purified on a preparatory HPLC system using a gradient of 36-46% acetonitrile/H2O (0.05% TFA) over 12 minutes on an Agilent Prep C-18 column, 50×100 mm, 5 μm. The resulting fractions were combined, frozen and lyophilized to give 239 mg (38.1% yield) of a spectroscopically pure of white powder. MS (ESI) Calculated for $C_{122}H_{126}N_{24}O_{10}$ m/z 2087.65 found 697 (m/3)$^+$.

Compound 13

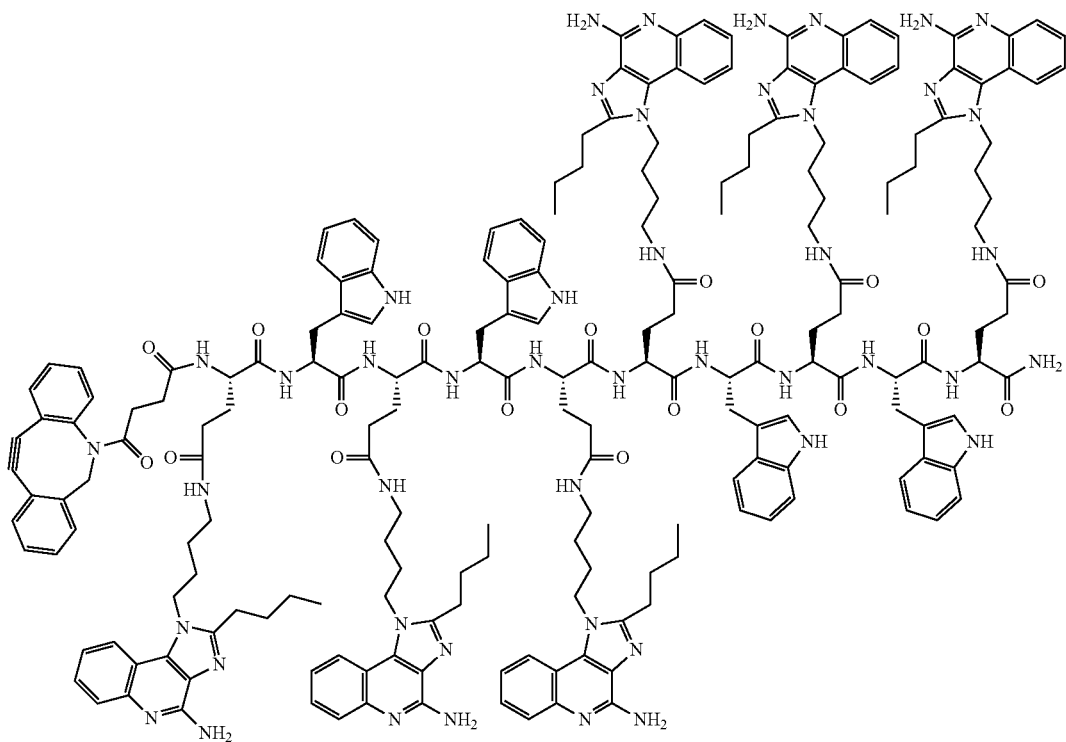

(SEQ ID NO: 142)

Compound 13, referred to as DBCO-2B$_6$W$_4$, 2B$_6$W$_4$ or DBCO-(Glu(2B)$_6$(Trp)$_4$) (Compound 13 disclosed as SEQ ID NO: 142), was synthesized using the same procedure as described for Compound 3, except Fmoc-(Glu-Trp-Glu-Trp-Glu)$_2$-NH$_2$ (SEQ ID NO: 143) was used as the starting material for conjugation of Compound 1. Compound 13 was purified on a preparatory HPLC system using a gradient of 24-45% acetonitrile/1H$_2$O (0.05% TFA) over 10 minutes on an Agilent Prep-C18 column, 30×100 mm, 5 μm. The fractions were collected, frozen and then lyophilized to obtain a spectroscopically pure (>95% AUC at 254 nm) white powder. MS (ESI) calculated for C$_{201}$H$_{236}$N$_{46}$O$_{18}$ m/z 3582.4, found 717.7 (M/5)$^+$.

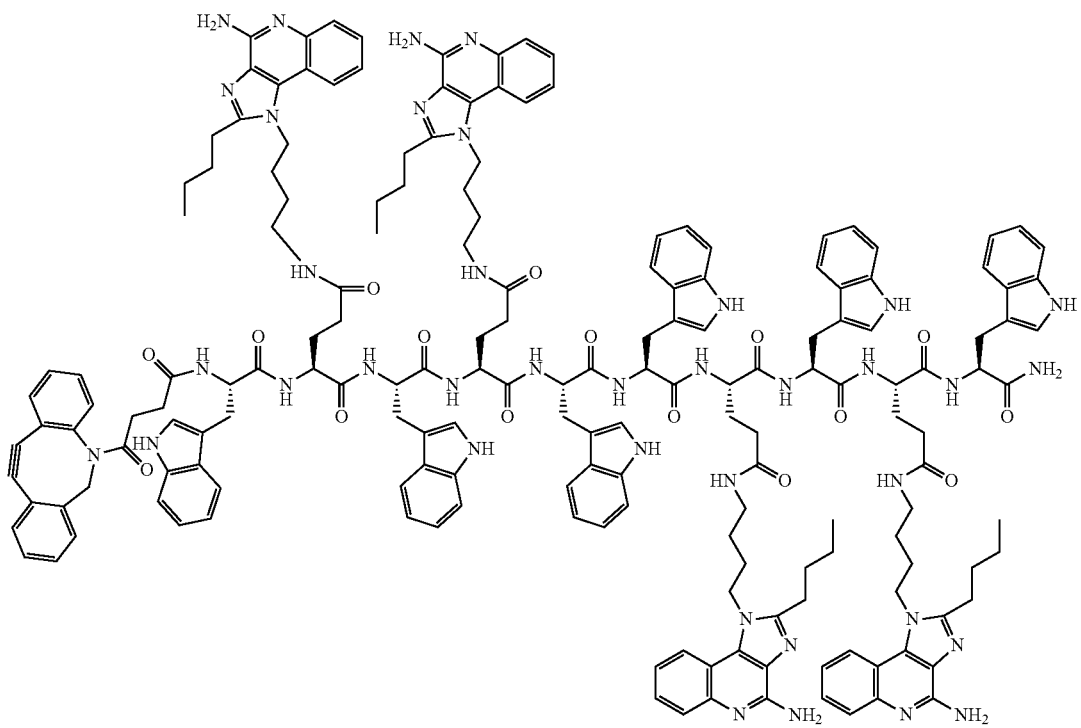

Compound 14

(SEQ ID NO: 144)

Compound 14, referred to as DBCO-2B₄W₆, 2B₄W₆ or DBCO-(Glu(2B))₄(Trp)₆) (Compound 14 disclosed as SEQ ID NO: 144), was synthesized using the same procedure as described for Compound 3, except Fmoc-(Trp-Glu-Trp-Glu-Trp)₂-NH₂ (SEQ ID NO: 145) was used as the starting material for conjugation of Compound 1. Compound 14 was purified on a preparatory HPLC system using a gradient of 24-45% acetonitrile/H₂O (0.05% TFA) over 10 minutes on an Agilent Prep-C18 column, 30×100 mm, 5 μm. The fractions were collected, frozen and then lyophilized to obtain a spectroscopically pure (>95% AUC at 254 nm) white powder. MS (ESI) calculated for $C_{177}H_{196}N_{38}O_{16}$ m/z 3111.7, found 777.5 (M/4)⁺.

Compound 15

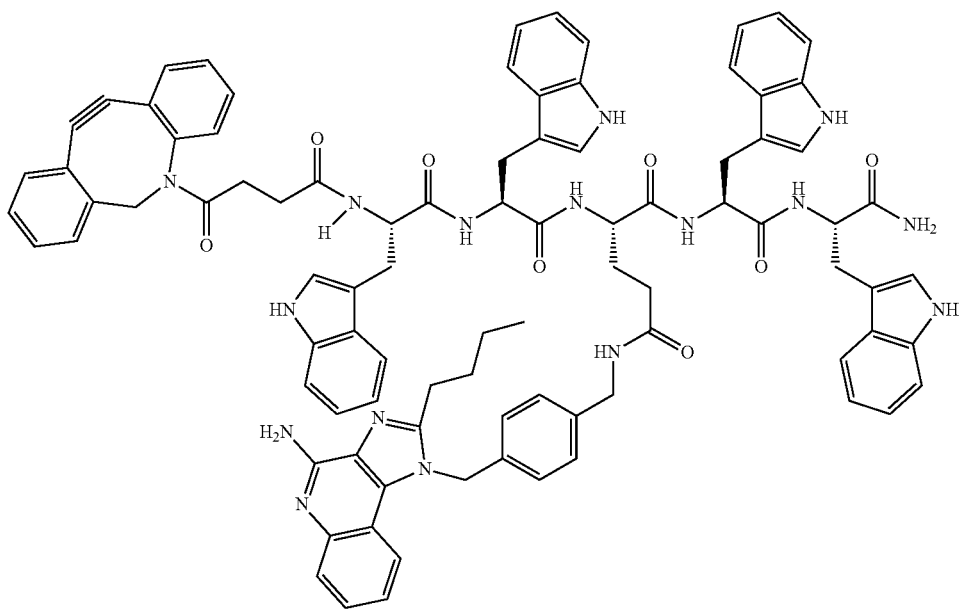

(SEQ ID NO: 146)

Compound 15, referred to as DBCO-2BXy$_1$W$_4$, 2BXy$_1$W$_4$ or DBCO-(Glu(2BXy)$_1$(Trp)$_4$) (Compound 15 disclosed as SEQ ID NO: 146), was prepared using the same procedure as described for Compound 3, except Fmoc-Trp-Trp-Glu-Trp-Trp-NH$_2$ (SEQ ID NO: 139) was used as the starting material. Compound 15 was purified on a preparatory HPLC system using a gradient of 40-70% acetonitrile/ H$_2$O (0.05% TFA) over 16 minutes on an Agilent Prep-C18 column, 30×100 mm, 5 µm. The resulting fractions were collected, frozen and then lyophilized to obtain 3.4 mg (73.3% yield) of a spectroscopically pure (>95% AUC at 254 nm) white powder. MS (ESI) calculated for C$_{90}$H$_{85}$N$_{15}$O$_9$ m/z 1519.67, found 760.5 (M/2)$^+$.

Compound 16

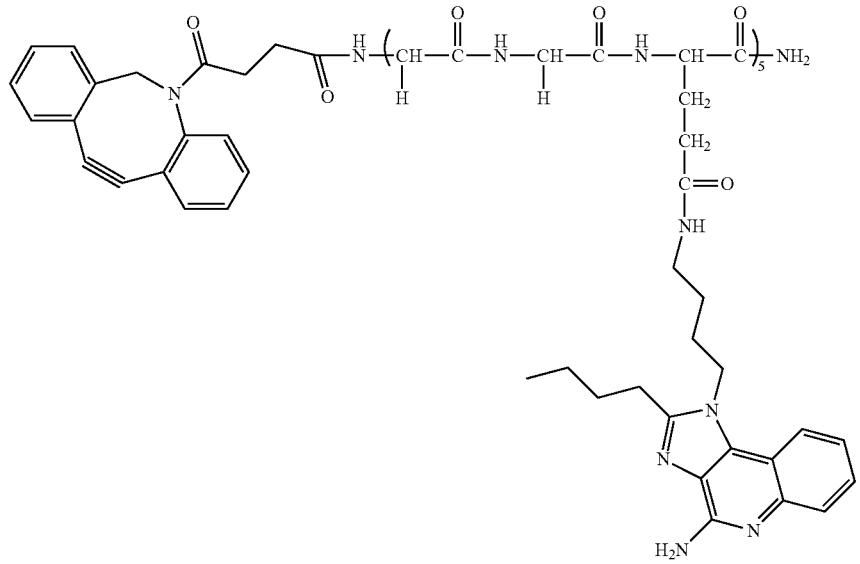

(SEQ ID NO: 147)

Compound 16, referred to as DBCO-(GG2B)$_5$, 2B$_5$G$_{10}$ or DBCO-(Glu(2B)$_5$(Gly)$_{10}$) (Compound 16 disclosed as SEQ ID NO: 147), was synthesized using the same procedure described for Compound 3, except Fmoc-(Gly-Gly-Glu)$_5$-NH$_2$ (SEQ ID NO: 148) and Compound 1 were used as the starting materials. Compound 16 was purified on a preparatory HPLC system using a gradient of 22-42% acetonitrile/$H_2O$ (0.05% TFA) over 12 minutes on an Agilent Prep-C18 column, 30×100 mm, 5 μm. The product eluted at 7 minutes and the resulting fractions were collected, frozen and then lyophilized to obtain 22.8 mg (36.2% yield) of a spectroscopically pure (>95% AUC at 254 nm) white powder. MS (ESI) calculated $C_{154}H_{196}N_{42}O_{22}$ for m/z 2985.51, found 598.5 $(M/5)^+$.

Compound 17
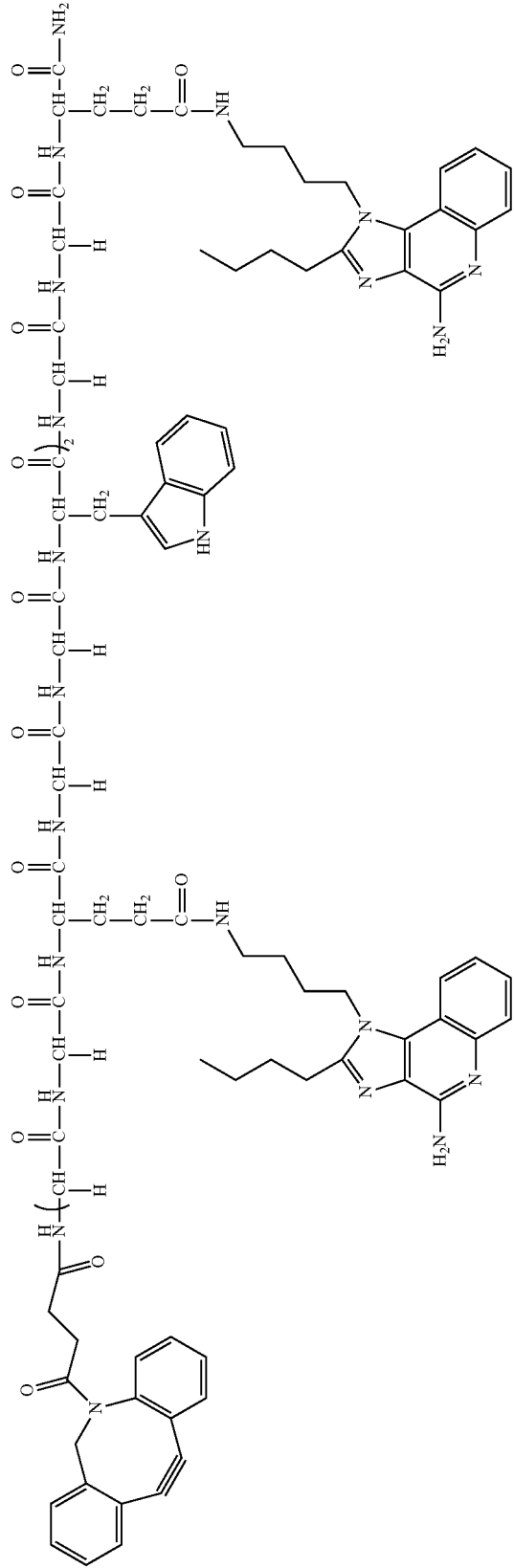
(DEQ ID NO: 149)

Compound 17, referred to as DBCO-(GG2BGGW)₂GG2B, 2B₃W₂G₁₀ or DBCO-(Glu(2B)₃(Trp)₂(Gly)₁₀) (Compound 17 disclosed as SEQ ID NO: 149), was synthesized from Fmoc-(Gly-Gly-Glu-Gly-Gly-Trp)₂-Gly₂-Glu-NH₂ (SEQ ID NO: 150) precursor prepared by solid-phase peptide synthesis and Compound 1. 235.4 mg of Fmoc-(Gly-Gly-Glu-Gly-Gly-Trp)₂-Gly₂-Glu-NH₂ (SEQ ID NO: 150) (0.15 mmol, 1 eq) was dissolved in 2 mL of 20% Piperidine in DMF. After 30 minutes the reaction was complete and the product was precipitated from 100 mL of ether and centrifuged at 3000 g at 4° C. for 10 minutes. The product was collected as a solid pellet and then washed twice more with ether, followed by drying under vacuum to yield ~200 mg of the deprotected intermediate. 200 mg (0.15 mmol, 1 eq) of NH₂-(Gly-Gly-Glu-Gly-Gly-Trp)₂-Gly₂-Glu-NH₂ (SEQ ID NO: 151) was dissolved in 2 mL of dry DMSO and 89.73 mg of DBCO-NHS (0.22 mmol, 1.5 eq) was added followed by TEA (0.22 mmol, 1.5 eq). The reaction mixture was stirred at room temperature for 1 hour. The resulting DBCO intermediate was purified on a preparatory HPLC system using a gradient of 30-50% acetonitrile/H2O (0.05% TFA) over 12 minutes on an Agilent Prep C-18 column, 50×100 mm, 5 μm. The resulting fractions were combined, frozen and lyophilized to give the intermediate. 25 mg of DBCO-(Gly-Gly-Glu-Gly-Gly-Trp)₂-Gly₂-Glu-NH₂ (SEQ ID NO: 152) (0.015 mmol, 1 eq) and 17.11 mg of Compound 1 (0.055 mmol, 3.6 eq) were dissolved in 1.2 mL of dry DMSO. TEA (0.183 mmol, 12 eq) was added and the reaction mixture was stirred at room temperature for 5 minutes. 19.17 mg of HATU (0.05 mmol, 3.3 eq) was added and the reaction mixture was stirred at room temperature. The progress of the reaction was monitored by LC-MS. 1.2 additional equivalents of Compound 1 and 1.1 equivalents HATU were added after 1 hour. After 2 hours, the reaction was complete. The resulting product was purified on a preparatory HPLC system using a gradient of 30-60% acetonitrile/H2O (0.05% TFA) over 12 minutes on an Agilent Prep C-18 column, 30×100 mm, 5 μm. The resulting fractions were combined, frozen and lyophilized to give a spectroscopically pure white powder. MS (ESI) Calculated for $C_{130}H_{156}N_{34}O_{20}$ m/z 2515.96 found 839 (m/3)⁺.

Compound 18, referred to as Bis(TT), was synthesized using Suberic acid and 2-thiazoline-2-thiol (TT) as starting materials. Briefly, 500 mg of Suberic acid (2.87 mmol, 1 eq), 752.7 mg of TT (6.31 mmol, 2.2 eq) and 1.431 g of EDC (7.46 mmol, 2.6 eq) were dissolved in 17.5 mL of dry DMSO. 70.15 mg of DMAP (0.57 mmol, 0.2 eq) was added and the reaction mixture was stirred at room temperature for 1 hour. The reaction mixture was diluted with DCM and washed twice with 1 M HCl and once with DI water. The organic fractions were dried with sodium sulfate and evaporated under reduced pressure to provide a yellow solid in quantitative yield.

Compound 19

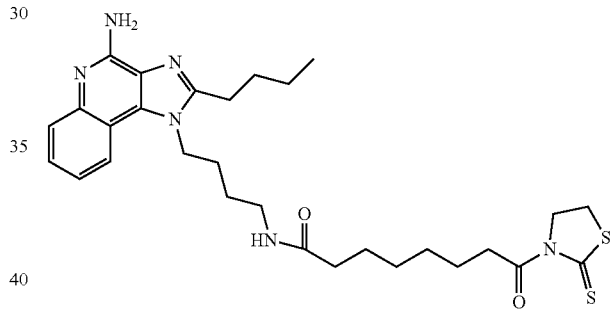

Compound 18

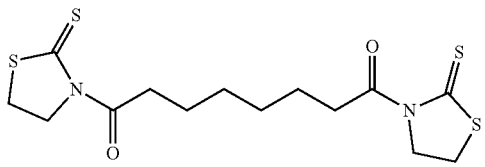

Compound 19, referred to as 2B-TT, was synthesized using Compound 18 and Compound 1 as starting materials. Briefly, 50 mg (0.16 mmol, 1 eq) of Compound 1 was dissolved in 0.6 mL of methanol and added dropwise to a vigorously stirring solution of 301.1 mg of Compound 18 (0.8 mmol, 5 eq) in 1.93 mL of DCM. After 30 minutes, the reaction mixture was injected directly onto a column and purified by flash chromatography using a 2-step gradient: 5% methanol in DCM over 5 column volumes (CVs), followed by a 5-50% methanol in DCM gradient over 20 CVs. The fractions were combined and the solvent was removed under vacuum. MS (ESI) calculated for $C_{29}H_{40}N_6O_2S_2$ m/z 568.27 found 569.3 (m+H)⁺.

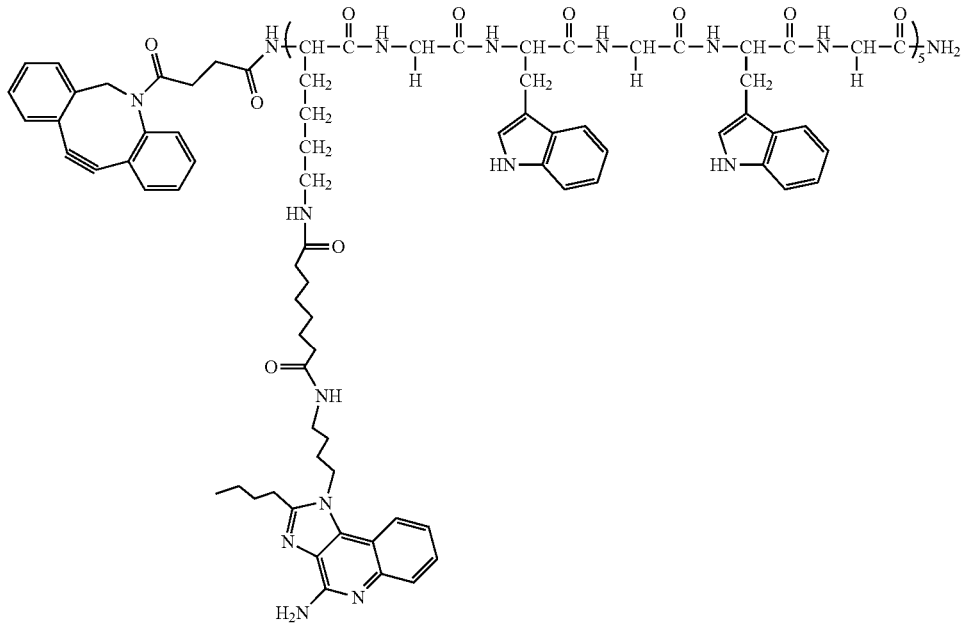

Compound 20

(SEQ ID NO: 153)

Compound 20 referred to as DBCO-(2BGWGWG)$_5$, 2B$_5$W$_{10}$G$_{15}$ or DBCO-(Glu(2B)$_5$(Trp)$_{10}$(Gly)$_{15}$) (Compound 20 disclosed as SEQ ID NO: 153), was synthesized from an Fmoc-(Lys-Gly-Trp-Gly-Trp-Gly)$_5$-NH$_2$ (SEQ ID NO: 154) peptide precursor that was prepared by solid-phase peptide synthesis and Compound 19. 49.8 mg (0.01 mmol, 1 eq) of Fmoc-(Lys-Gly-Trp-Gly-Trp-Gly)$_5$-NH$_2$ (SEQ ID NO: 154) was dissolved in 0.5 mL of dry DMSO. To this solution was added 0.492 mL of Compound 19 (0.03 mmol, 2.5 eq) as a 40 mg/mL stock solution in dry DMSO. TEA (0.01 mmol, 1 eq) was added and the reaction mixture was stirred at room temperature for 4 hours. Analytical HPLC using a gradient of 45-65% acetonitrile/H2O (0.05% TFA) over 10 minutes showed complete conversion to the penta-substituted intermediate. The reaction was quenched by addition of amino-2-propanol (0.03 mmol, 2.5 eq) and then 0.5 mL of 20% piperidine in DMF was added and the reaction mixture was stirred at room temperature for 30 minutes. The reaction mixture was added to 50 mL of ether and centrifuged at 3000 g at 4° C. for 10 minutes. The product was collected as a solid pellet and then washed twice more with ether, followed by drying under vacuum to yield the deprotected intermediate. 73.4 mg of the deprotected intermediate (0.0131 mmol, 1 eq) was dissolved in 0.5 mL of dry DMSO, followed by the addition of 0.066 mL (0.0196 mmol, 1.5 eq) of DBCO-NHS (40 mg/mL) and TEA (0.0131 mmol, 1 eq). The reaction was stirred for 1 hour at room temperature and then quenched by the addition of amino-2-propanol (0.0196 mmol, 1.5 eq). The product was then precipitated from 50 mL of 1 M HCl and centrifuged at 3000 g at 4° C. for 10 minutes. The product was collected as a solid pellet and then washed once more with 1 M HCl and once more with DI water. The final collected pellet was dried under vacuum to yield 15.1 mg (26% yield) of the final product. MS (ESI) calculated for C$_{319}$H$_{396}$N$_{72}$O$_{42}$ m/z 5909.1 found 1183 (m/5)$^+$.

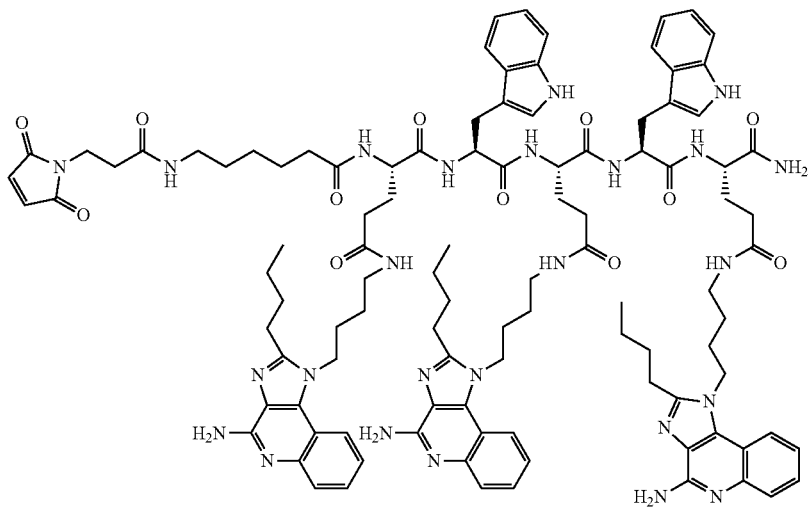

Compound 21

(SEQ ID NO: 155)

Compound 21, referred to as Mal-2B$_3$W$_2$ or Mal-(Glu (2B)$_3$(Trp)$_2$) (Compound 21 disclosed as SEQ ID NO: 155), was synthesized starting from an Fmoc-(Glu)$_3$(Trp)$_2$-NH$_2$ (SEQ ID NO: 156) and Compound 1. 100 mg of Fmoc-(Glu)$_3$(Trp)$_2$-NH$_2$ (SEQ ID NO: 156) (0.1 mmol 1 eq) and 112.1 mg of Compound 1 (0.36 mmol, 3.6 eq) were dissolved in 8 mL of dry DMF. TEA (1.2 mmol, 12 eq) was added and the solution was cooled with an ice bath while stirring for 5 minutes. HATU (0.33 mmol, 3.3 eq) was added and the reaction mixture was stirred at 4 C for 1 hour. The reaction mixture was then added to 50 mL of 1 M HCl and centrifuged at 3000 g at 4° C. for 10 minutes. The product was collected as a solid pellet and then washed once more with 1 M HCl and once more with DI water to give the conjugated intermediate. 188 mg of Fmoc-2B$_3$W$_2$—NH$_2$ (0.1 mmol, 1 eq) was then dissolved in 2 mL of 20% piperidine in DMF solution and stirred for 30 minutes at room temperature. The deprotected intermediate was precipitated from 100 mL of ether and centrifuged at 3000 g at 4° C. for 30 minutes. The product was collected as a solid pellet and then washed twice more with ether, followed by drying under vacuum to yield the deprotected intermediate. 30 mg of NH$_2$-2B$_3$W$_2$—NH$_2$ (0.018 mmol, 1 eq) was dissolved in 0.3 mL of dry DMSO, followed by the addition of 22 mg of Succinimidyl 6-((beta-maleimideopropionamido)hexanoate (SMPH) (0.058 mmol, 3.2 eq). The reaction mixture was stirred for 1 hour at room temperature and the resulting product was purified on a preparatory HPLC system using a gradient of 30-50% acetonitrile/H2O (0.05% TFA) over 12 minutes on an Agilent Prep C-18 column, 50×100 mm, 5 μm. The product eluted at 4.75 minutes and the resulting fractions were combined, frozen and lyophilized to give 23 mg (66.7% yield) of a spectroscopically pure white powder. MS (ESI) calculated for C$_{104}$H$_{129}$N$_{25}$O$_{12}$ 1921.33, found 961 (m/2)$^+$.

Compound 22

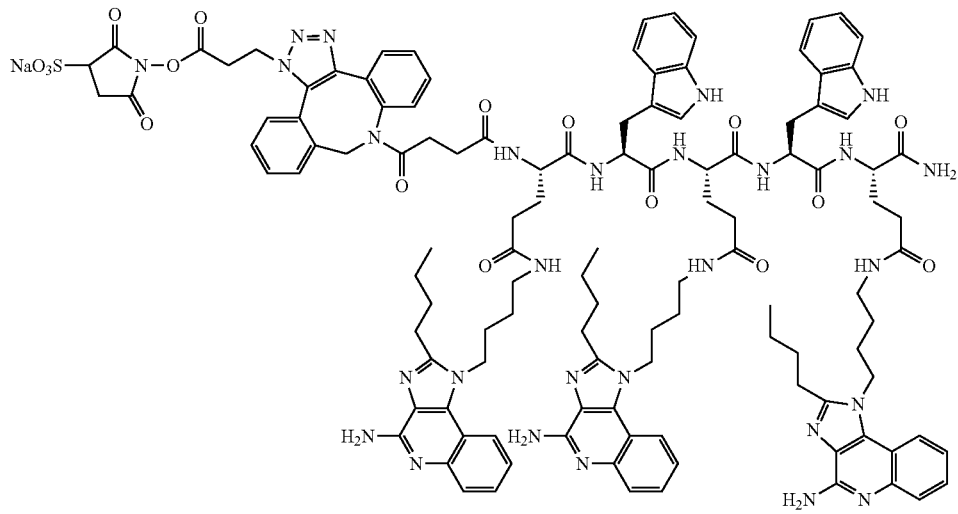

(SEQ ID NO: 157)

Compound 22, referred to as NHS-2B₃W₂(Compound 22 disclosed as SEQ ID NO: 157), was synthesized by reacting 125 ug (0.0004 mmol, 1 eq) of 3-Azidopropionic Acid Sulfo-NHS Ester (Az-NHS, Click Chemistry Tools) with 0.8 mg of (0.0004 mmol, 1.0 eq) Compound 6 in dry DMSO. HPLC showed full conversion to the to the NHS activated compound, which was used immediately for conjugation peptides bearing a reactive amine. MS (ESI) calculated for $C_{117}H_{133}N_{28}O_{17}S$ m/z 2234 found 1119 (m/2)⁺.

Compound 23

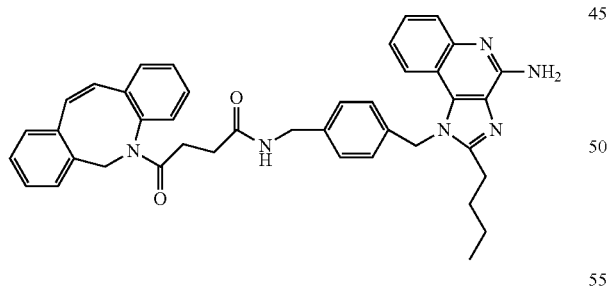

Compound 23, referred to as DBCO-2BXy, was synthesized by reacting 5.0 mg (0.01 mmol, 1 eq) of DBCO-NHS with 4.91 mg (0.011 mmol, 1.1 eq) of Compound 2 in dry DMSO. The DMSO solution was dissolved in ethyl acetate and then washed with 1M HCl. The organic layer was removed under vacuum to obtain ~3 mg of a spectroscopically pure white solid. MS (ESI) calculated $C_{41}H_{40}N_6O_2$ for 646.31, found 647.3 (m/2)⁺.

Compound 24

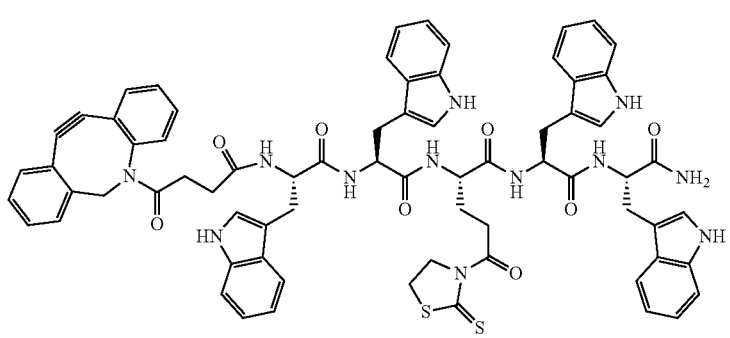

(SEQ ID NO: 158)

Compound 24, referred to as DBCO-WWTTWW or W₄TT (Compound 24 disclosed as SEQ ID NO: 158), was prepared using NH₂-Trp-Trp-Glu-Trp-Trp-NH₂ (SEQ ID NO: 159) prepared by solid phase peptide synthesis. 32.8 mg of NH₂-Trp-Trp-Glu-Trp-Trp-NH₂ (SEQ ID NO: 159) (0.04 mmol, 1 eq) was dissolved in 0.5 mL of dry DMSO and 15.5 mg (0.04 mmol, 1 eq) of DBCO-NHS was added followed by addition of TEA (0.04 mmol, 1 eq). The reaction mixture was stirred at room temperature for 1 hour. The resulting To the reaction mixture was added 0.06 mg of DMAP (0.001 mmol, 0.1 eq) while stirring vigorously at room temperature. After 2 hour, an additional 3.3 equivalents of TT, 4.0 equivalents of EDC and 0.1 equivalents of DMAP were added and reaction was complete after 3 hours total. The DBCO-WWTTWW was used as an intermediate in subsequent steps.

Compound 25

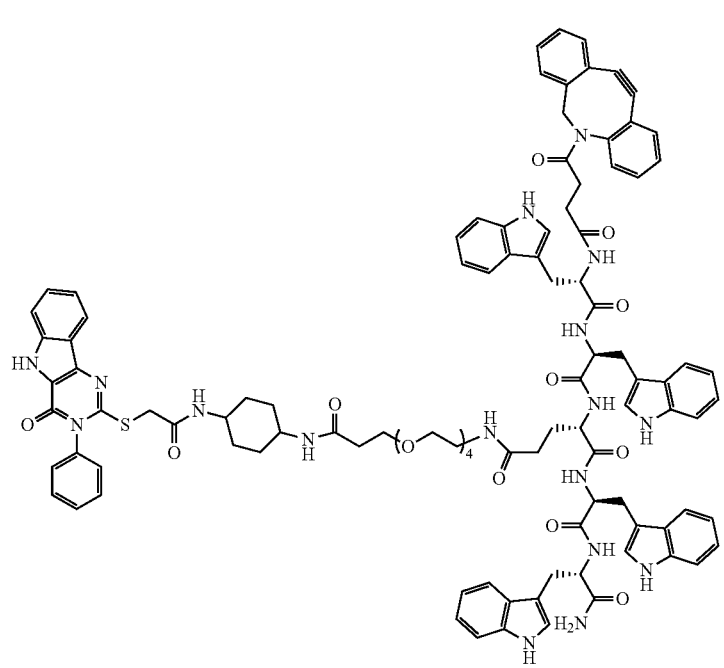

(SEQ ID NO: 161)

DBCO intermediate was purified on a preparatory HPLC system using a gradient of 40-70% acetonitrile/H2O (0.05% TFA) over 16 minutes on an Agilent Prep C-18 column, 30×100 mm, 5 μm. The resulting fractions were combined, frozen and lyophilized. To TT activate the DBCO-peptide, 6.1 mg of DBCO-Trp-Trp-Glu-Trp-Trp-NH₂ (SEQ ID NO: 160) (0.005 mmol, 1 eq), 0.68 mg of TT (0.006 mmol, 1.1 eq) and 1.26 mg of EDC (0.007 mmol, 1.3 eq) were dissolved in 0.2 mL of a 1:1 solution of DMSO and DCM.

Compound 25, referred to as DBCO-WWPIWW, WW(PI)WW or PIW₄ (Compound 25 disclosed as SEQ ID NO: 161). Primido-indole-Peg₄-NH₂ (PI-NH2, TLR-4 agonist) was prepared as previously described (Lynn G M, et al., In vivo characterization of the physicochemical properties of polymer-linked TLR agonists that enhance vaccine immunogenicity. *Nat Biotechnol* 33(11):1201-1210, 2015). To 3.6 mg of PINH2 (0.005 mmol, 2 eq) was added 3.31 mg of Compound 33 (0.0026 mmol, 1 eq) and TEA (0.003 mmol, 1.1 eq) in DMSO and the was stirred overnight at room temperature. The resulting product was purified on a preparatory HPLC system using a gradient of 45-75% acetonitrile/H2O (0.05% TFA) over 16 minutes on an Agilent Prep C-18 column, 30×100 mm, 5 µm. The resulting fractions were combined, frozen and lyophilized. MS (ESI) calculated for $C_{103}H_{107}N_{17}O_{15}S$ m/z 1854.77, found 928.6 (m/2)$^+$.

stirred for 1 hour at room temperature. The reaction mixture was added to 15 mL of DI water and centrifuged. The pellet was collected and further washed three times with DI water and lyophilized. The intermediate (DBCO-WWPeg2NH$_2$WW) was taken up in 0.1 mL of dry DMSO and 2.58 mg of Compound 26 (0.0026 mmol, 1 eq) was added as a 100 mg/mL stock solution in DCM. The reaction Compound 26

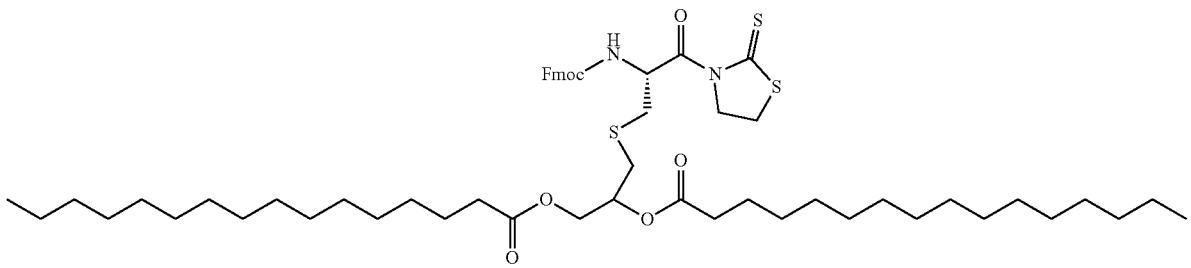

Compound 26, referred to as Pam2Cys-TT or P2C-TT, which is a TLR-2/6 agonist, was synthesized using the same procedure as Compound 24, except Fmoc-Pam2Cys-Acid was used as the starting material and the reaction was monitored with TLC (1% methanol in DCM). The procedure produced a yellow solid in quantitative yield that was used as intermediate in subsequent reaction steps.

mixture was stirred for 1 hour at room temperature and then DCM was removed under vacuum followed by the addition of 0.2 mL of 20% piperidine in DMF. The reaction mixture was stirred for 30 minutes at room temperature then diluted with DCM and washed three times with DI water. The organic layer was dried with sodium sulfate and evaporated. The resulting oil was dissolved in DMSO and purified on a Compound 27

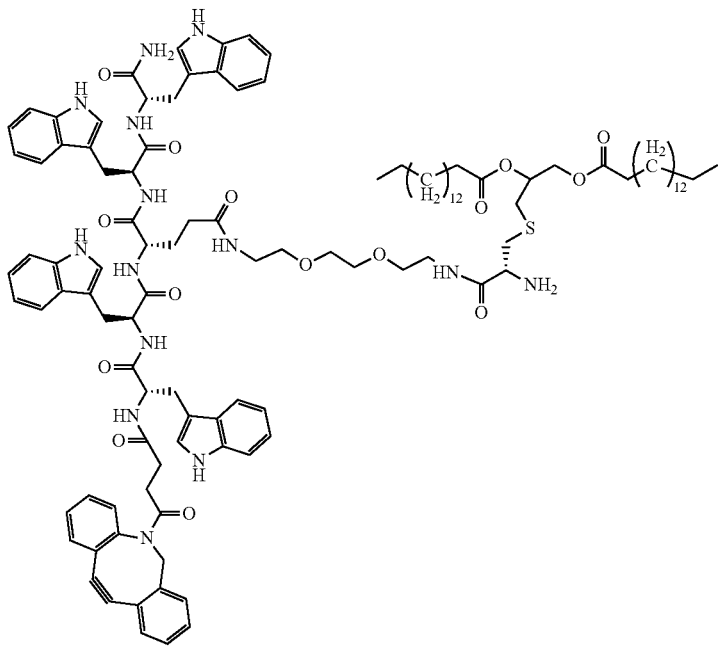

(SEQ ID NO: 162)

Compound 27, referred to as DBCO-WWPam2CysWW, WW(P2C)WW or P2C(W)$_4$ (Compound 27 disclosed as SEQ ID NO: 162), was prepared using Compound 24, PEG$_2$-diamine, and Compound 26 as starting materials. First, 1.15 mg of Peg$_2$-diamine (0.008 mmol, 3 eq) was added to the reaction mixture containing 3.31 mg of Compound 24 (0.0026 mmol, 1 eq) and the reaction mixture was preparatory HPLC system using a gradient of 70-100% Isopropanol/H2O (0.05% TFA) over 16 minutes on an Agilent Prep C-18 column, 9.4×100 mm, 5 µm. The resulting fractions were combined and evaporated to provide the product, DBCO-WWPam2CysWW. Product molecular weight verified based on the MS (ESI+) for peptide antigen conjugates of Compound 27.

Compound 28

(SEQ ID NO: 163)

Compound 28, referred to as NH$_2$-GK (DBCO)GW$_5$ (Compound 28 disclosed as SEQ ID NO: 163), was synthesized using Fmoc-Gly-Lys-Gly-(Trp)$_5$-NH$_2$ (SEQ ID NO: 164) prepared by solid phase peptide synthesis and DBCO-NHS as the starting materials. 50 mg of Fmoc-Gly-Lys-Gly-(Trp)$_5$-NH$_2$ (SEQ ID NO: 164) (0.04 mmol, 1 eq) was dissolved in 0.25 mL of dry DMSO. TEA (0.04 mmol, 1 eq) was added and the solution was stirred at room temperature for 5 minutes. 14.24 mg of DBCO-NHS (0.04 mmol, 1 eq) was added and the reaction mixture was stirred for 1 hour at room temperature. The reaction was quenched with amino-2-propanol (0.04 mmol, 1 eq) and 0.5 mL of 20O piperidine in DMF was added. The reaction mixture was stirred at room temperature for 30 minutes. The product was then precipitated from 50 mL of ether and centrifuged at 3000 g at 4° C. for 10 minutes. The product was collected as a solid pellet and then washed twice more with ether, followed by drying under vacuum. The product was purified on a preparatory HPLC system using a gradient of 25-45% acetonitrile/H2O (0.05% TFA) over 10 minutes on an Agilent Prep C-18 column, 30×100 mm, 5 μm. The product eluted at 9.4 minutes and the resulting fractions were combined, frozen and lyophilized to obtain a spectroscopically pure off-white solid. MS (ESI) calculated for $C_{84}H_{84}N_{16}O_{10}$ m/z 1477.64 found 739.6 (m/2)$^+$.

Compound 29

Compound 29, referred to as CL264-Azide, hydroxyadenine-Azide or TLR-7-azide, which is a TLR-7 agonist, was synthesized using CL264 (Invigogen, San Diego, CA, USA) and Azido-propyl-amine as starting materials. 5 mg of CL264 (0.012 mmol, 1 eq) and 6.1 mg of Azido-propyl-amine (0.061 mmol, 5 eq) were dissolved in dry DMF. TEA (0.073 mmol, 6 eq) was added and the solution was cooled to OC with an ice bath. 27.6 mg of HATU (0.073 mmol, 6 eq) was added and the reaction was stirred at OC for 1 hour. Compound 29 was purified on a preparatory HPLC system using a gradient of 20-40% acetonitrile/H2O (0.05% TFA) over 10 minutes on an Agilent Prep C-18 column, 30×100 mm, 5 μm. The product eluted at 5 minutes and the resulting fractions were combined, frozen and lyophilized. MS (ESI) calculated for $C_{22}H_{29}N_{11}O_3$ m/z 495.25 found 496.3 (m+H)$^+$.

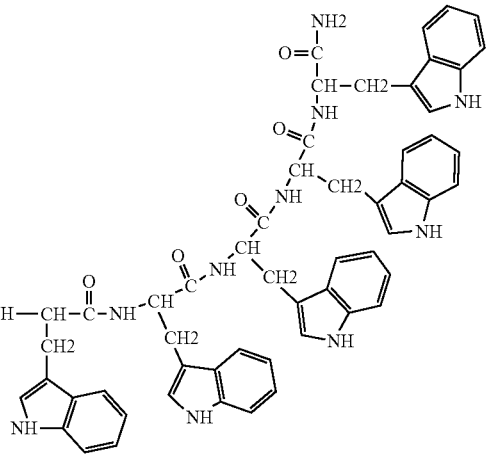

Compound 30

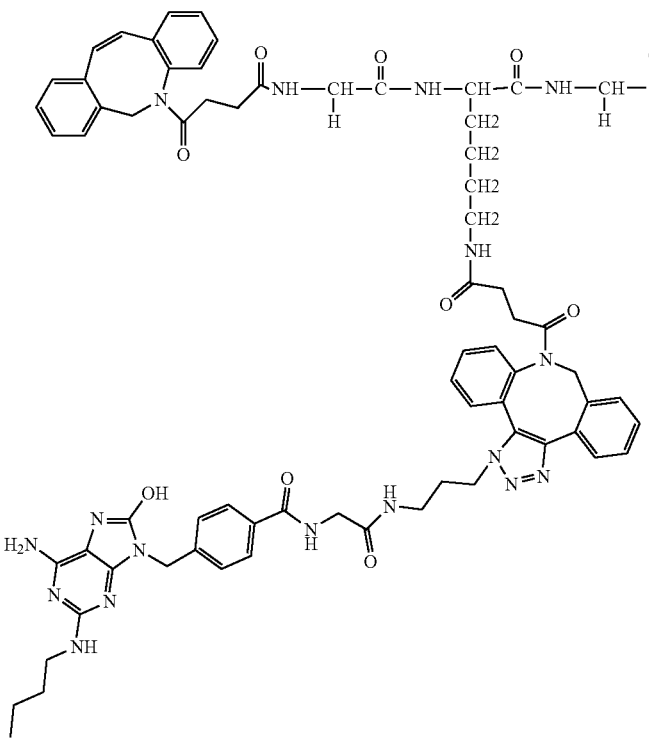

(SEQ ID NO: 165)

Compound 30, referred to as DBCO-GK(CL264)G-W$_5$, Cl264-(W)$_5$ or DBCO-Gly-Lys(DBCO-CL264)-Gly-(Trp)$_5$-NH$_2$ (Compound 30 disclosed as SEQ ID NO: 165) was synthesized using Compounds 28 and 29 as the starting materials. 5 mg of Compound 28 (0.0034 mmol, 1 eq) was dissolved in 0.25 mL of dry DMSO and 1.68 mg of Compound 29 (0.0034 mmol, 1 eq) was added and the reaction mixture was stirred for 2 hours, followed by the addition of 1.5 mg of DBCO-NHS (0.0037 mmol, 1.1 eq) and 0.5 eq of TEA. The reaction mixture was stirred overnight at room temperature and then the product the product was purified on a preparatory HPLC system using a gradient of 25-55% acetonitrile/H2O (0.05% TFA) over 10 minutes on an Agilent Prep C-18 column, 30×100 mm, 5 µm. The product eluted at 9.4 minutes and the resulting fractions were combined, frozen and lyophilized to obtain a spectroscopically pure white solid. MS (ESI) calculated for $C_{125}H_{128}N_{28}O_{15}$ m/z 2261.01 found 1132.2 (m/2)$^+$.

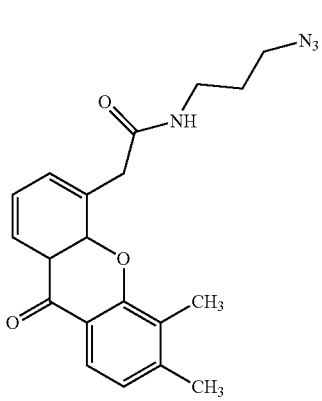

Compound 31

Compound 31, referred to as DMXAA-Azide, which is a STING agonist, was synthesized using the same procedure as Compound 29, except DMXAA (Invivogen) was used as the starting material. Compound 31 was purified on a preparatory HPLC system using a gradient of 35-65% acetonitrile/H2O (0.05% TFA) over 10 minutes on an Agilent Prep C-18 column, 30×100 mm, 5 μm. The product eluted at 6 minutes and the resulting fractions were combined, frozen and lyophilized to obtain a spectroscopically pure white solid. MS (ESI) calculated for $C_{20}H_{22}N_4O_3$ m/z 366.42 found 365.2

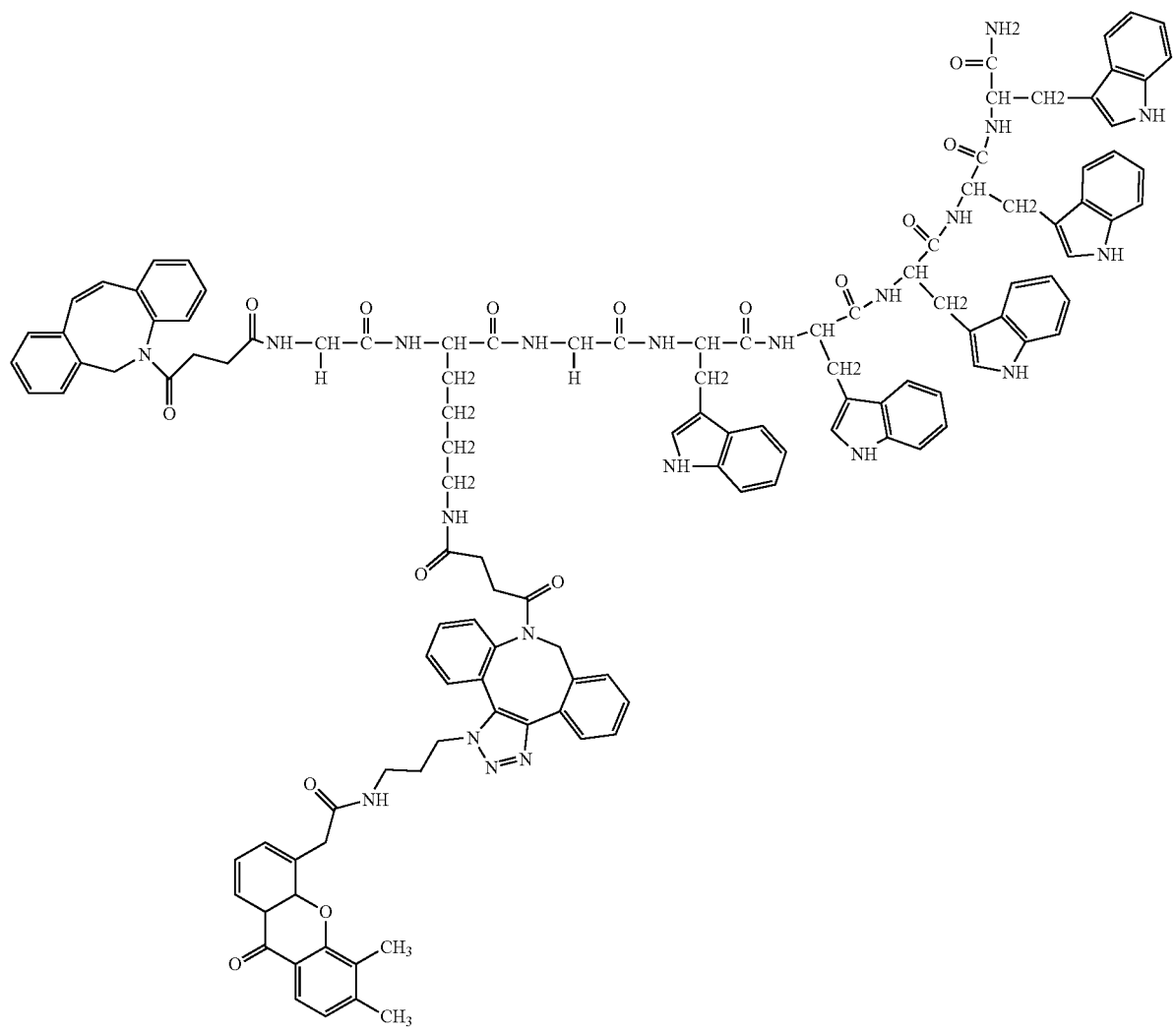

Compound 32

(SEQ ID NO: 166)

Compound 32, referred to as DBCO-GK (DMXAA)-G-$W_5$, DMXAA-$(W)_5$, DMXAA-W5 or DBCO-Gly-Lys (DBCO-DMXAA)-Gly-$(Trp)_5$-$NH_2$ (Compound 32 disclosed as SEQ ID NO: 166) was synthesized using the same procedure as Compound 30, except Compound 31 was used as the agonist cargo. Compound 32 was purified on a preparatory HPLC system using a gradient of 45-85% acetonitrile/H2O (0.05% TFA) over 10 minutes on an Agilent Prep C-18 column, 30×100 mm, 5 um. MS (ESI) calculated for $C_{123}H_{121}N_{21}O_{15}$ m/z 2131.94 found 1067.6 (m/2)*.

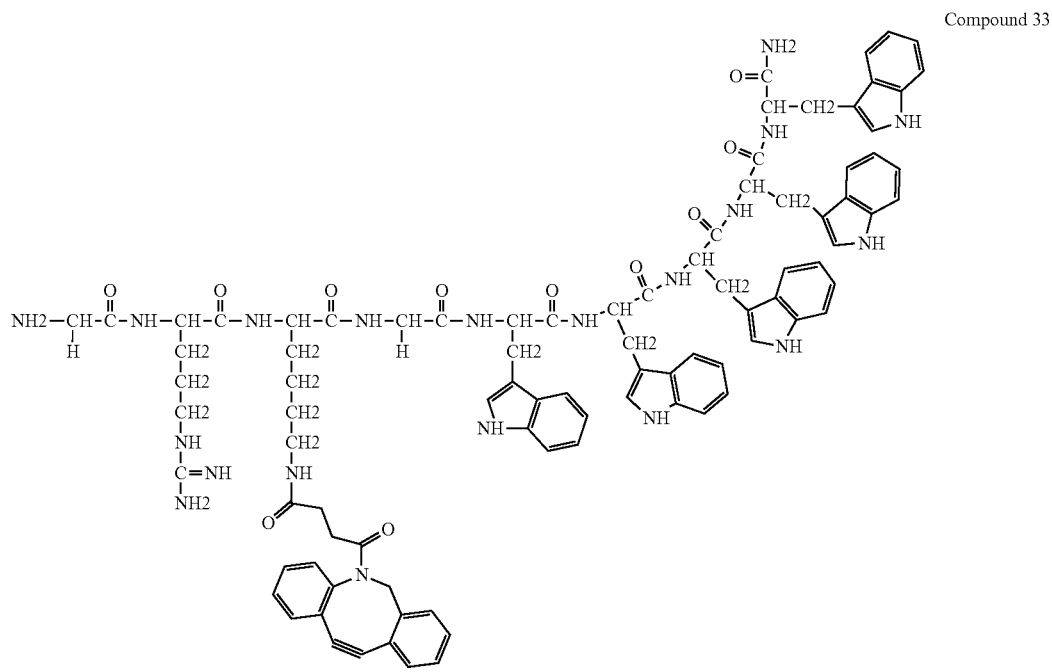 [SMILES: N=C(N)NCCCC(NC(=O)CN)C(=O)NC(CCCCNC(=O)CCC(=O)N1Cc2ccccc2C#Cc2ccccc21)C(=O)NCC(=O)NC(Cc1c[nH]c2ccccc12)C(=O)NC(Cc1c[nH]c2ccccc12)C(=O)NC(Cc1c[nH]c2ccccc12)C(=O)NC(Cc1c[nH]c2ccccc12)C(=O)NC(Cc1c[nH]c2ccccc12)C(N)=O]

Compound 33

Compound 33, referred to as NH$_2$-GRK(DBCO)GW$_5$, NH$_2$-Gly-Arg-Lys(DBCO)-Gly-(Trp)$_5$-NH$_2$ (Compound 33 disclosed as SEQ ID NO: 167) was synthesized using the same procedure as Compound 28, except Fmoc-GRKGW$_5$-NH$_2$ (SEQ ID NO: 168), which was produced by solid phase peptide synthesis, was used as the starting material. Compound 33 was purified on a preparatory HPLC system using a gradient of 25-55% acetonitrile/H2O (0.05% TFA) over 10 minutes on an Agilent Prep C-18 column, 30×100 mm, 5 µm. The product eluted at 7.5 minutes and the resulting fractions were combined, frozen and lyophilized. MS (ESI) calculated for C$_{90}$H$_{96}$N$_{20}$O$_{11}$ m/z 1633.74 found 817.5 (m/2)$^+$.

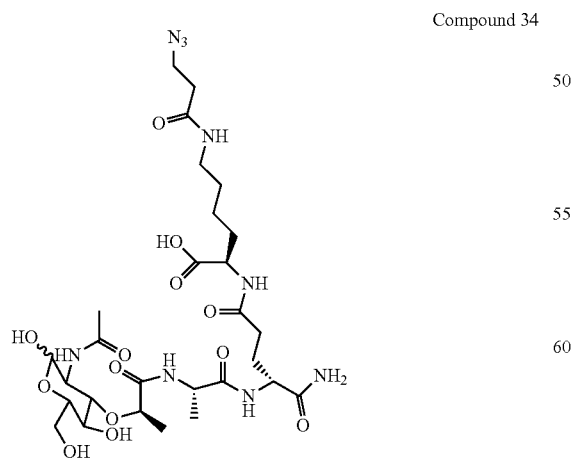

Compound 34

Compound 34, referred to as Muramyl Azide, which is a NOD 2 agonist, was synthesized using Muramyl tri-lysine (M-TriLys, Invivogen) and Azido propionic acid sulfo NHS as starting materials. 5 mg of Muramyl tri-lysine (0.008 mmol, 1 eq) was dissolved in 0.5 mL of dry DMSO with TEA (0.02 mmol, 2.5 eq) and 2.2 mg of Azido propionic acid sulfo NHS (0.008 mmol, 1 eq) were added. The reaction mixture was stirred at room temperature for 2 hours. The reaction mixture was quenched with amino-2-propanol (0.008 mmol, 1 eq) and the intermediate was used immediately for reaction.

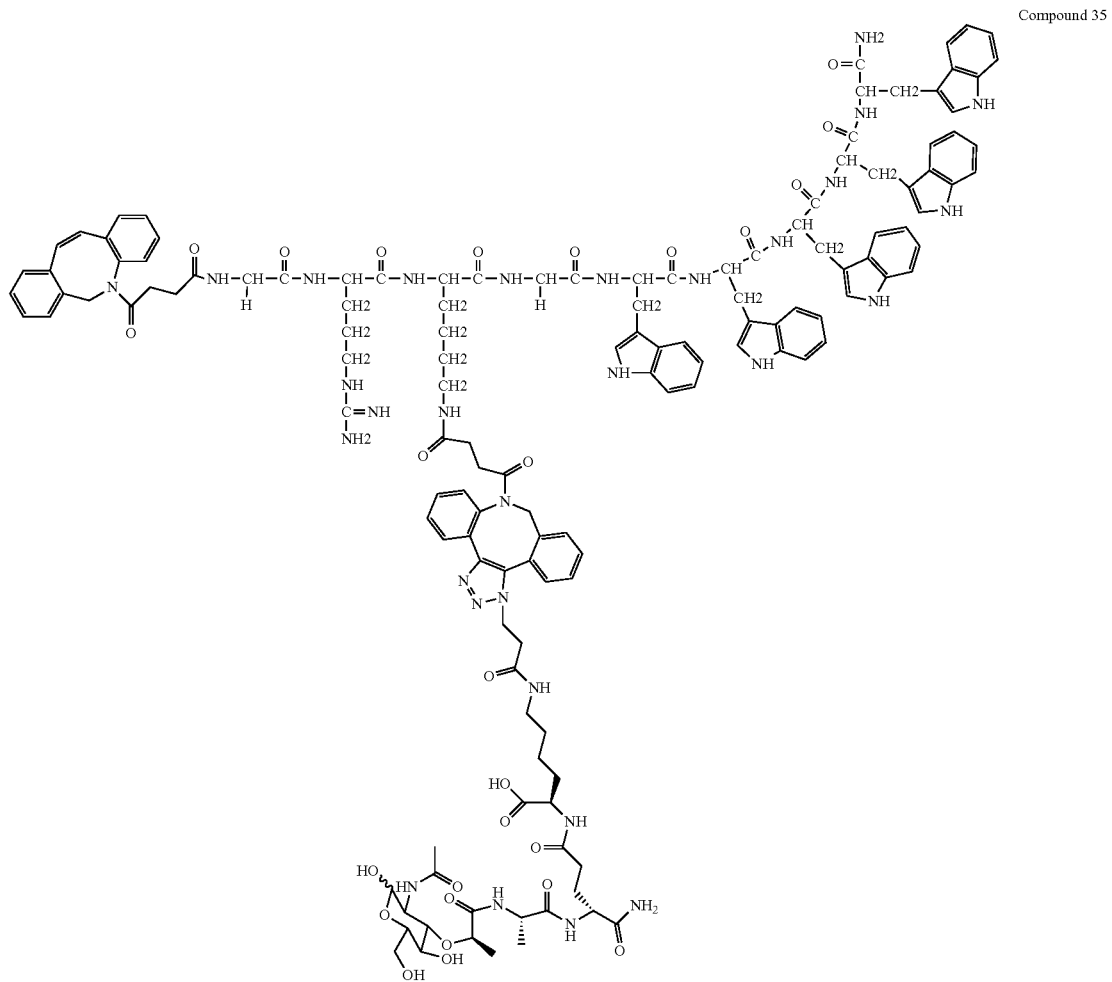

(SEQ ID NO: 169)

Compound 35, referred to as DBCO-GRK(Muramyl)GW$_5$, Muramyl-W$_5$ or DBCO(Muramyl)W$_5$ (Compound 35 disclosed as SEQ ID NO: 169) was synthesized using the same procedure Compound 30, except Compounds 33 and 34 were used as starting material. Compound 35 was purified on a preparatory HPLC system using a gradient of 35-65% acetonitrile/H2O (0.05% TFA) over 10 minutes on an Agilent Prep C-18 column, 30×100 mm, 5 μm. The product eluted at 4.6 minutes and the resulting fractions were combined, frozen and lyophilized. MS (ESI) calculated for $C_{137}H_{158}N_{30}O_{26}$ m/z 2639.2 found 1319.5 (m/2)$^+$.

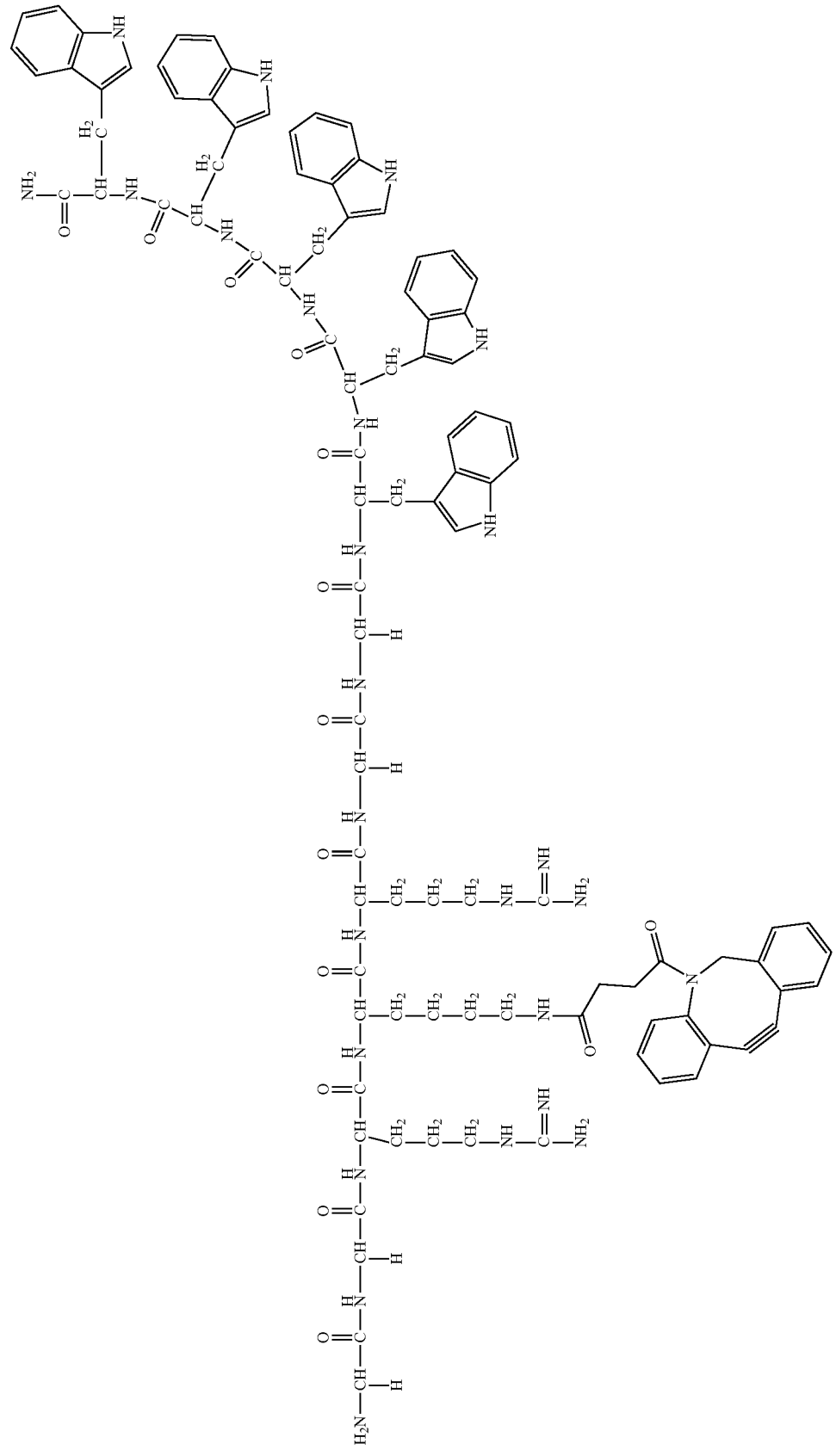
Compound 36 (SEQ ID NO: 170)

Compound 36, referred to as NH$_2$-GGRK(DBCO)RGGW$_5$ (Compound 36 disclosed as SEQ ID NO: 170), was synthesized using the same procedure as Compound 28, except Fmoc-GGRKRGGW$_5$-NH$_2$ (SEQ ID NO: 171), which was prepared by solid phase peptide synthesis, was used as the starting material. Compound 36 was purified on a preparatory HPLC system using a gradient of 25-45% acetonitrile/H$_2$O (0.05% TFA) over 10 minutes on an Agilent Prep-C18 column, 30×100 mm, 5 m. The product eluted at 7.8 minutes and the resulting fractions were collected, frozen and then lyophilized to obtain a spectroscopically pure (>95% AUC at 254 nm) white powder. MS (ESI) calculated for C$_{100}$H$_{114}$N$_{26}$O$_{14}$ m/z 1902.9, found 951.4 (m/2)$^+$.

Compound 37
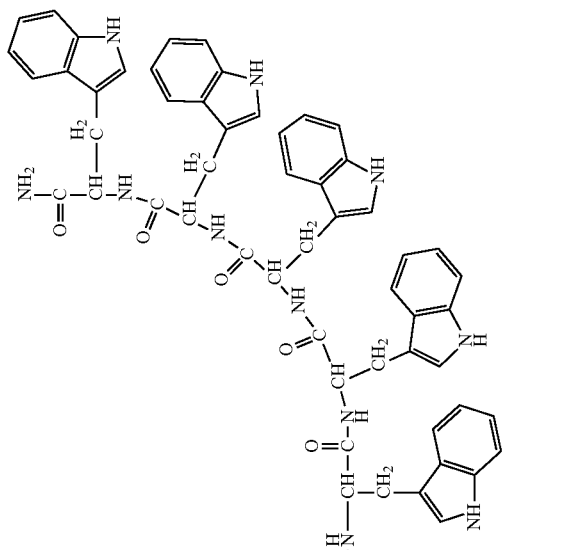
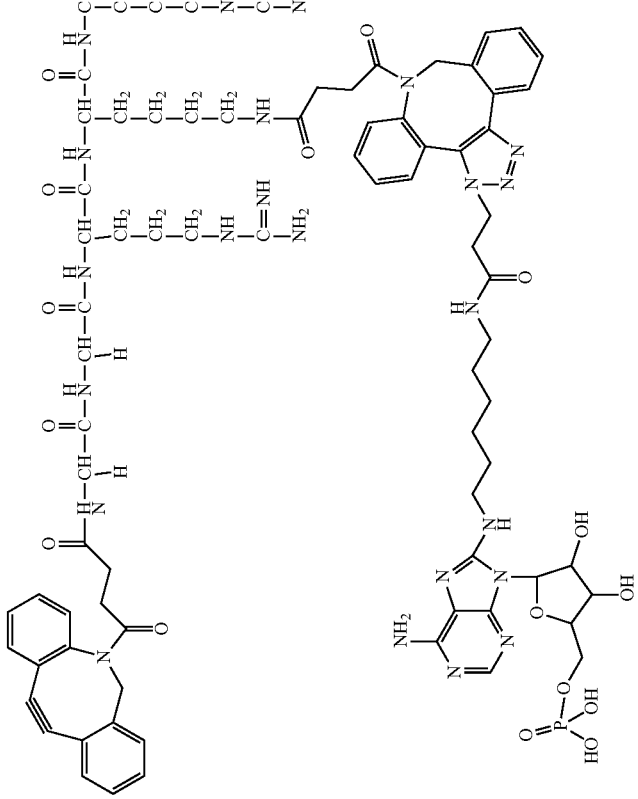
(SEQ ID NO: 172)

Compound 37, referred to as DBCO-GGRK(AMP) RGGW$_5$ or DBCO(AMP)W$_5$ (Compound 37 disclosed as SEQ ID NO: 172) was synthesized using the same procedure as Compound 30, except Compounds 36 and adenosine monophosphate 8-(6-Aminohexyl)aminoadenosine 5' monophosphate (Sigma-Aldrich) substituted with azido-proprionic acid were used as starting materials. Compound 37 was purified on a preparatory HPLC system using a gradient of 30-60% acetonitrile/H2O (0.05% TFA) over 10 minutes on an Agilent Prep C-18 column, 30×100 mm, 5 µm. The product eluted at 5.2 minutes and the resulting fractions were combined, frozen and lyophilized to obtain a spectroscopically pure white solid. MS (ESI) calculated for $C_{138}H_{158}N_{37}O_{24}P$ 2748.2 found 917.5 (m/3)$^+$.

Compound 38

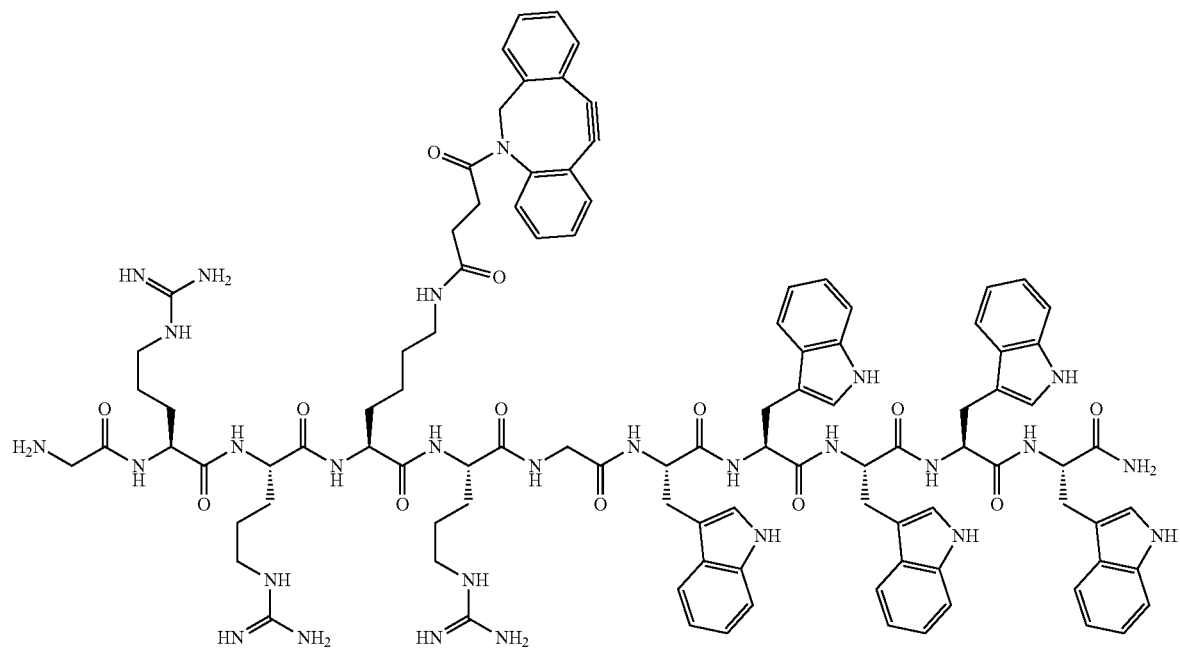

(SEQ ID NO: 173))

Compound 38, referred to as NH$_2$-GRRK (DBCO)-RGW$_5$ (Compound 38 disclosed as SEQ ID NO: 173), was synthesized using the same procedure as Compound 28, except Fmoc-GRRKRGW$_5$-NH$_2$ (SEQ ID NO: 174) was used as the starting material. Compound 38 was purified on a preparatory HPLC system using a gradient of 25-55% acetonitrile/H$_2$O (0.05% TFA) over 10 minutes on an Agilent Prep-C18 column, 30×100 mm, 5 µm. The product eluted at 5.1 minutes and the resulting fractions were collected, frozen and then lyophilized to obtain a spectroscopically pure (>95% AUC at 254 nm) white powder. MS (ESI) calculated for $C_{102}H_{120}N_{28}O_{13}$ m/z 1944.96, found 973.4 (m/2)$^+$.

Compound 39

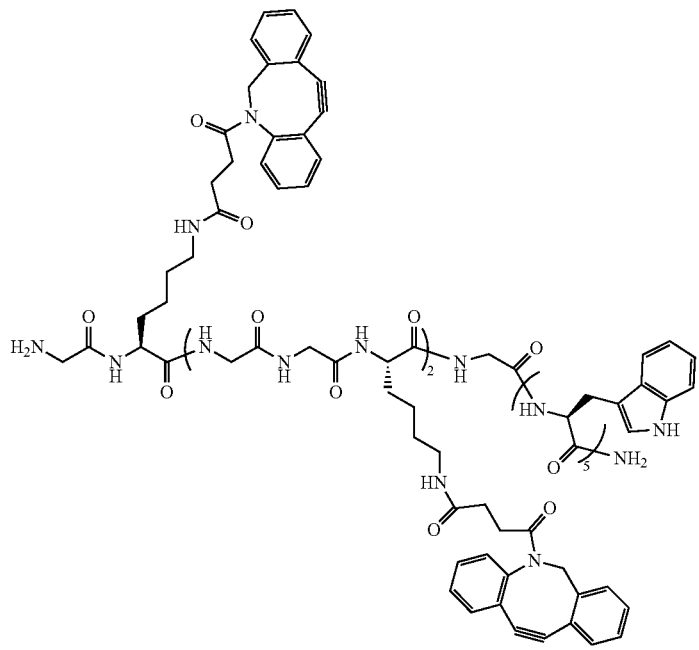

(SEQ ID NO: 175)

Compound 39, referred to as NH$_2$-GK(DBCO)[GGK(DBCO)]$_2$GW$_5$ (Compound 39 disclosed as SEQ ID NO: 175), was synthesized using the same procedure as Compound 28, except Fmoc-GK(GGK)$_2$GW$_5$-NH$_2$ (SEQ ID NO: 176) was used as the starting material and three additional equivalents of TEA and DBCO-NHS were used. Compound 39 was purified on a preparatory HPLC system using a gradient of 45-85% acetonitrile/H$_2$O (0.05% TFA) over 10 minutes on an Agilent Prep-C18 column, 30×100 mm, 5 μm. The resulting fractions were collected, frozen and then lyophilized to obtain the title compound as a spectroscopically pure (>95% AUC at 254 nm) white powder. MS (ESI) calculated for C$_{142}$H$_{146}$N$_{26}$O$_{20}$ m/z 2535.12 found 1269 (m/2)$^+$.

Compound 40
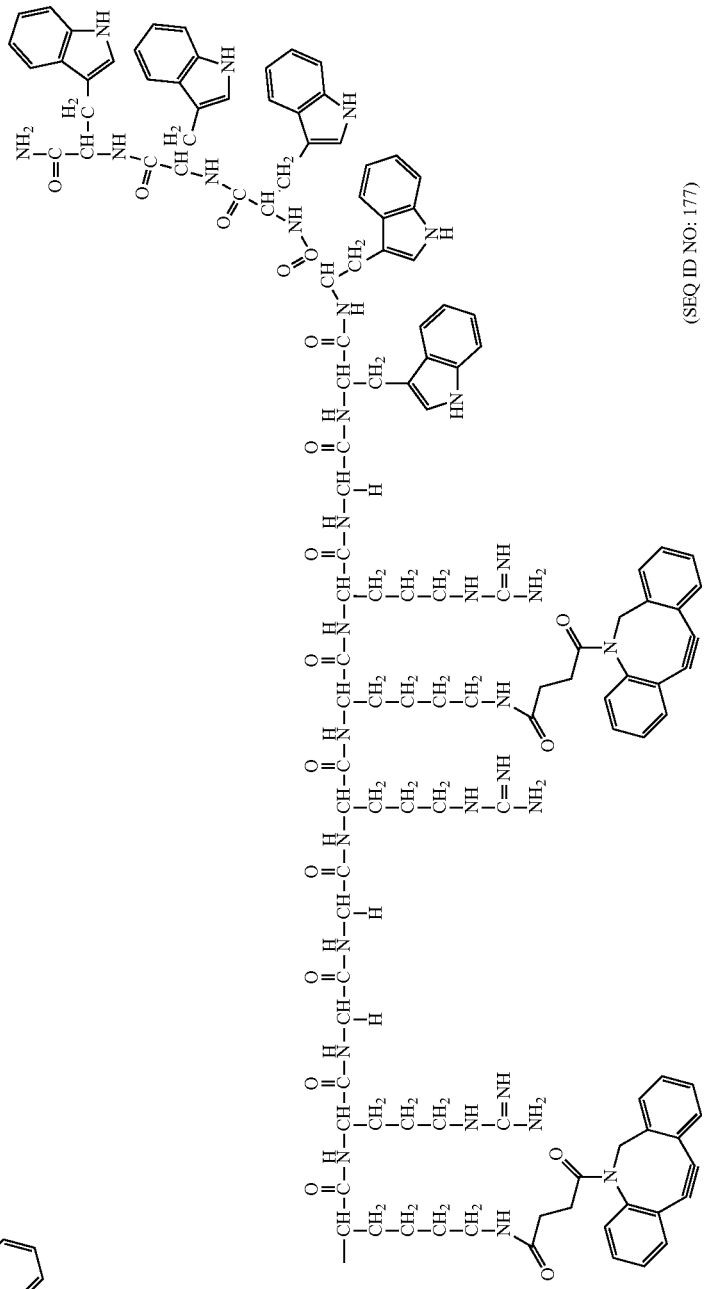
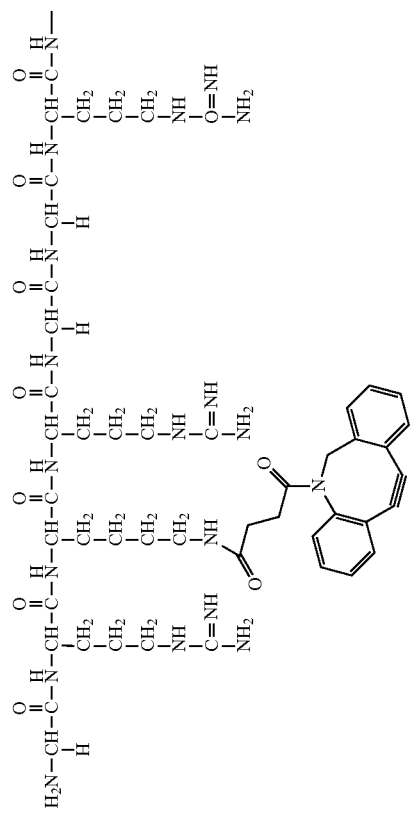
(SEQ ID NO: 177)

Compound 40, referred to as $NH_2$-[GRK(DBCO)RG]$_3$—$W_5$ (Compound 40 disclosed as SEQ ID NO: 177), was synthesized using the same procedure as Compound 39, except $NH_2$-[GRK(DBCO)RG]$_3$—$W_5$ (SEQ ID NO: 177) was used as the starting material. Compound 40 was purified on a preparatory HPLC system using a gradient of 35-65% acetonitrile/$H_2O$ (0.05% TFA) over 10 minutes on an Agilent Prep-C18 column, 30×100 mm, 5 μm. The resulting fractions were collected, frozen and then lyophilized to obtain a spectroscopically pure (>95% AUC at 254 nm) white powder. MS (ESI) calculated for $C_{178}H_{218}N_{50}O_{26}$ m/z 3471.31, found 695.6 $(m/5)^+$.=

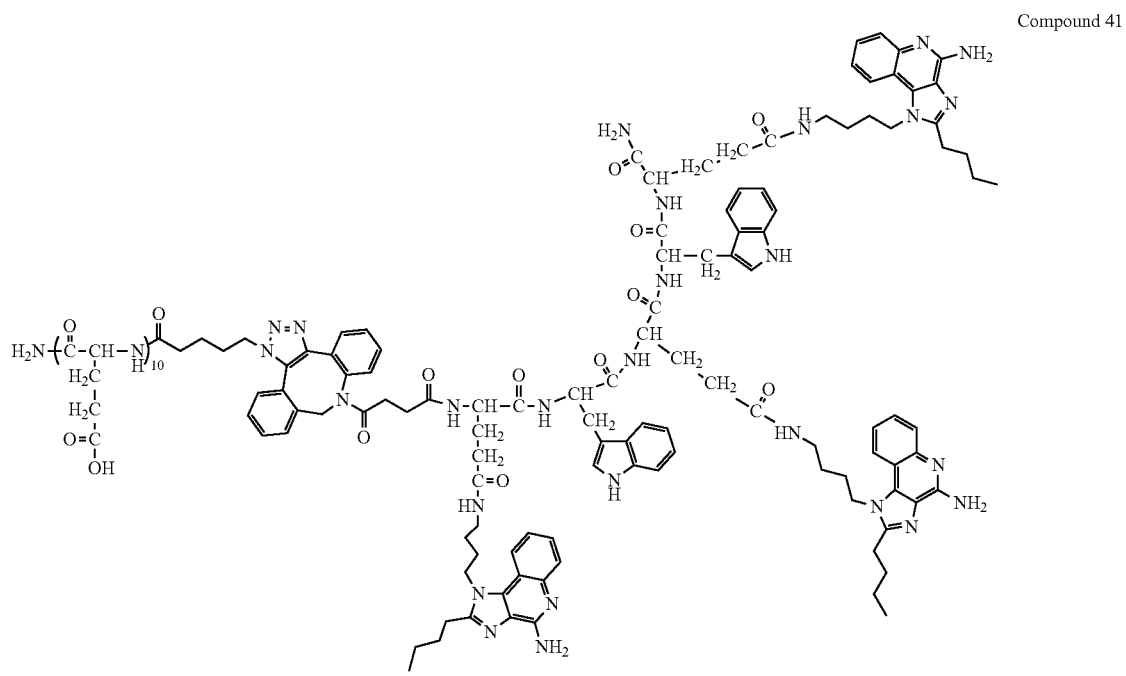

Compound 41

Compound 41, referred to as $E_{10}$-$2B_3W_2$, was synthesized using Azido-(Glu)$_{10}$-$NH_2$ (SEQ ID NO: 178) and Compound 6 as the starting materials. 5 mg of Azido-(Glu)$_{10}$-$NH_2$ (SEQ ID NO: 178) (0.0035 mmol, 1 eq) was dissolved in dry DMSO and 6.77 mg of Compound 6 (0.0035 mmol, 1 eq) as a 40 mg/mL solution in dry DMSO was added. The reaction mixture was stirred overnight at room temperature. Compound 41 was purified on a preparatory HPLC system using a gradient of 25-45% acetonitrile/$H_2O$ (0.05% TFA) over 10 minutes on an Agilent Prep-C18 column, 30×100 mm, 5 μm. The resulting fractions were collected, frozen and then lyophilized to obtain 11.8 mg of a spectroscopically pure (>95% AUC at 254 nm) white powder in quantitative yield. MS (ESI) calculated for m/z 3377.31, found 1127 $(M/3)^+$.

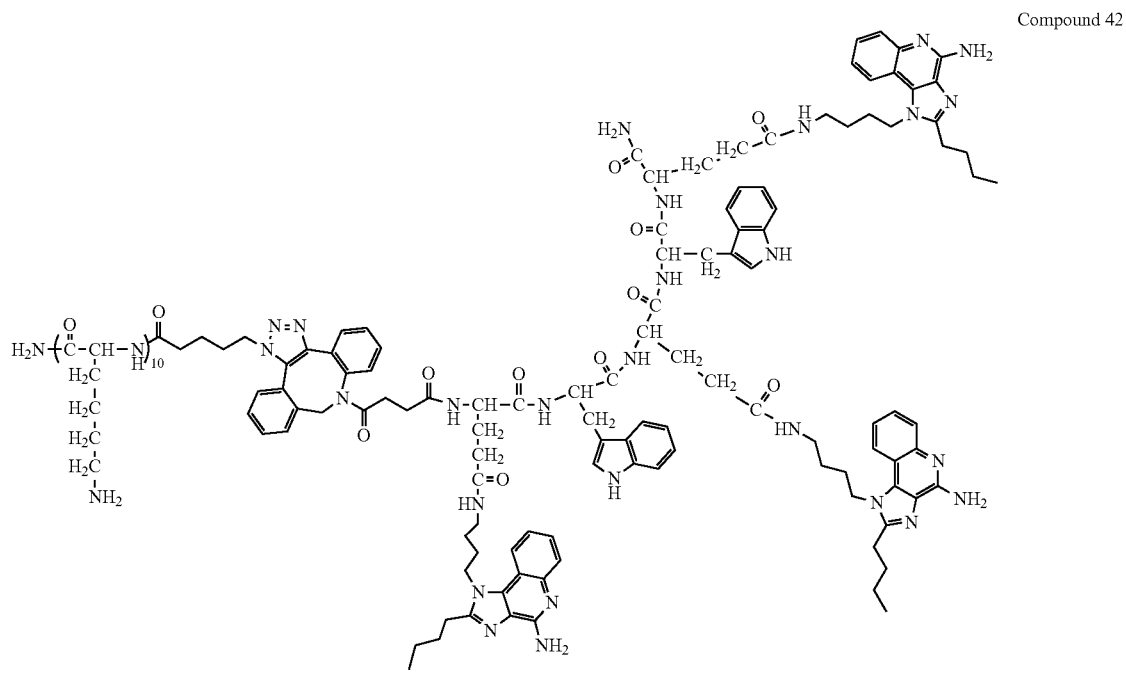

Compound 42

Compound 42, referred to as K₁₀-2B₃W₂ was synthesized using the same procedure as Compound 41, except Azido-(Lys)₁₀-NH₂ (SEQ ID NO: 179) was used as the starting material. Compound 42 was purified on a preparatory HPLC system using a gradient of 20-40% acetonitrile/H₂O (0.05% TFA) over 10 minutes on an Agilent Prep-C18 column, 30×100 mm, 5 μm. The resulting fractions were collected, frozen and then lyophilized to obtain a spectroscopically pure (>95% AUC at 254 nm) white powder in quantitative yield. MS (ESI) calculated for m/z 3367.58, found 482 (M/7)⁺.

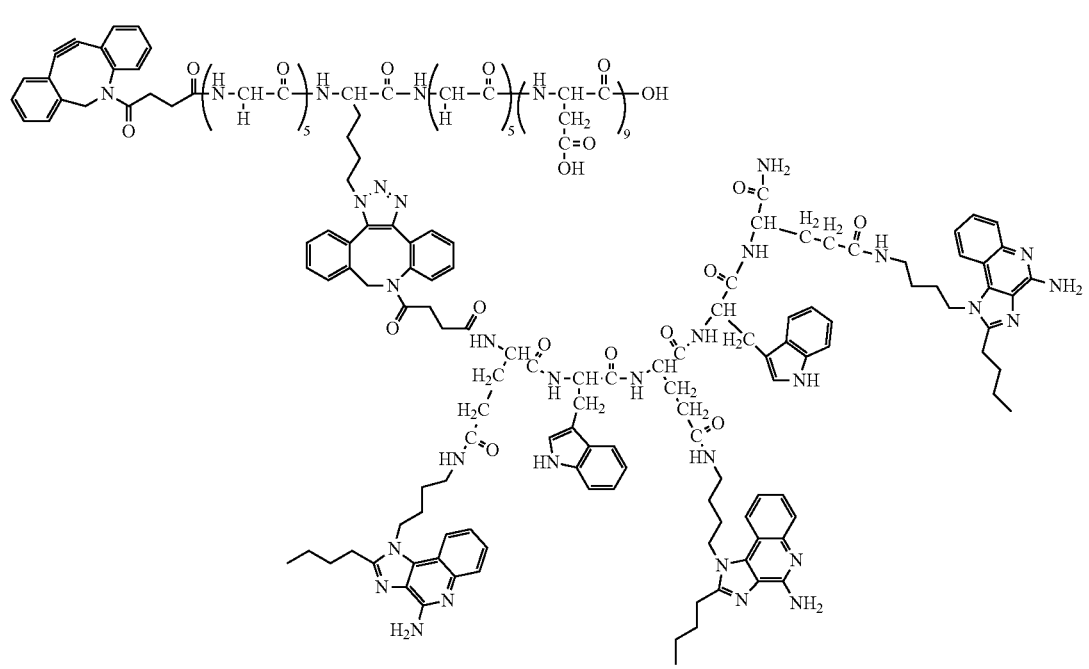

Compound 43

Compound 43, referred to as DBCO-G$_5$-2B$_3$W$_2$-G$_5$-D$_9$ or DBCO-2B$_3$W$_2$(D)$_9$ was synthesized using NH$_2$-(Gly)$_5$-Lys(N$_3$)-(Gly)$_5$-(Asp)$_9$-NH$_2$ (SEQ ID NO: 181), Compound 6 and DBCO-NHS as starting materials. 5 mg of NH$_2$-(Gly)$_5$-Lys(N$_3$)-(Gly)$_5$-(Asp)$_9$-NH$_2$ (SEQ ID NO: 181) (0.0028 mmol, 1 eq) was dissolved in 0.1 mL of dry DMSO and 6.56 mg of Compound 6 (0.0034 mmol, 1.2 eq) was added. The reaction mixture was stirred overnight at room temperature. 3.55 mg of DBCO-NHS (0.0084 mmol, 3 eq) was added followed by TEA (0.0028 mmol, 1 eq). The reaction mixture was stirred for 2 hours at room temperature. Compound 43 was purified on a preparatory HPLC system using a gradient of 30-40% acetonitrile/H$_2$O (0.05% TFA) over 12 minutes on an Agilent Prep-C18 column, 30×100 mm, 5 μm. The resulting fractions were collected, frozen and then lyophilized to obtain 3.8 mg (33.7% yield) of the title compound as a spectroscopically pure (>95% AUC at 254 nm) white powder. MS (ESI) calculated for m/z 4008.31, found 1003.3 (m/4)$^+$.

Compound 44, referred to as DBCO-G$_5$-2B$_3$W$_2$-G$_5$-D$_8$ or DBCO-2B$_3$W$_2$(D)$_8$ was synthesized using the same procedure as Compound 43, except NH$_2$-(Gly)$_5$-Lys(N$_3$)-(Gly)$_5$-(Asp)$_8$-NH$_2$ (SEQ ID NO: 182) was used as the starting material. Compound 44 was purified on a preparatory HPLC system using a gradient of 30-40% acetonitrile/H$_2$O (0.05% TFA) over 12 minutes on an Agilent Prep-C18 column, 30×100 mm, 5 μm. The resulting fractions were collected, frozen and then lyophilized to obtain the title compound as a spectroscopically pure (>95% AUC at 254 nm) white powder. MS (ESI) calculated for m/z 3894.52, found 974.6 (m/4)$^+$.

Compound 45, referred to as DBCO-G$_5$-2B$_3$W$_2$-G$_5$-D$_7$ or DBCO-2B$_3$W$_2$(D)$_7$ was synthesized using the same procedure as Compound 43, except NH$_2$-(Gly)$_5$-Lys(N$_3$)-(Gly)$_5$-(Asp)$_7$-NH$_2$ (SEQ ID NO: 183) was used as the starting material. Compound 45 was purified on a preparatory HPLC system using a gradient of 29-39% acetonitrile/H$_2$O (0.05% TFA) over 12 minutes on an Agilent Prep-C18 column, 30×100 mm, 5 μm. The resulting fractions were collected, frozen and then lyophilized to obtain the title compound as a spectroscopically pure (>95% AUC at 254 nm) white powder. MS (ESI) calculated for m/z 3779.43, found 945.8 (m/4)$^+$.

Compound 46, referred to as DBCO-G$_5$-2B$_3$W$_2$-G$_5$-D$_6$ or DBCO-2B$_3$W$_2$(D)$_6$ was synthesized using the same procedure as Compound 43, except NH$_2$-(Gly)$_5$-Lys(N$_3$)-(Gly)$_5$-(Asp)$_6$-NH$_2$ (SEQ ID NO: 184) was used as the starting material. Compound 46 was purified on a preparatory HPLC system using a gradient of 29-39% acetonitrile/H$_2$O (0.05% TFA) over 12 minutes on an Agilent Prep-C18 column, 30×100 mm, 5 μm. The resulting fractions were collected, frozen and then lyophilized to obtain the title compound as a spectroscopically pure (>95% AUC at 254 nm) white powder. MS (ESI) calculated for m/z 3664.35, found 917.1 (m/4)$^+$.

Compound 47, referred to as DBCO-G$_5$-2B$_3$W$_2$-G$_5$-D$_5$ or DBCO-2B$_3$W$_2$(D)$_5$ was synthesized using the same procedure as Compound 43, except NH$_2$-(Gly)$_5$-Lys(N$_3$)-(Gly)$_5$-(Asp)$_5$-NH$_2$ (SEQ ID NO: 185) was used as the starting material. Compound 47 was purified on a preparatory HPLC system using a gradient of 29-41% acetonitrile/H$_2$O (0.05% TFA) over 12 minutes on an Agilent Prep-C18 column, 30×100 mm, 5 μm. The resulting fractions were collected, frozen and then lyophilized to obtain the title compound as a spectroscopically pure (>95% AUC at 254 nm) white powder. MS (ESI) calculated for m/z 3549.26, found 1184.1 (m/3)$^+$.

Compound 48

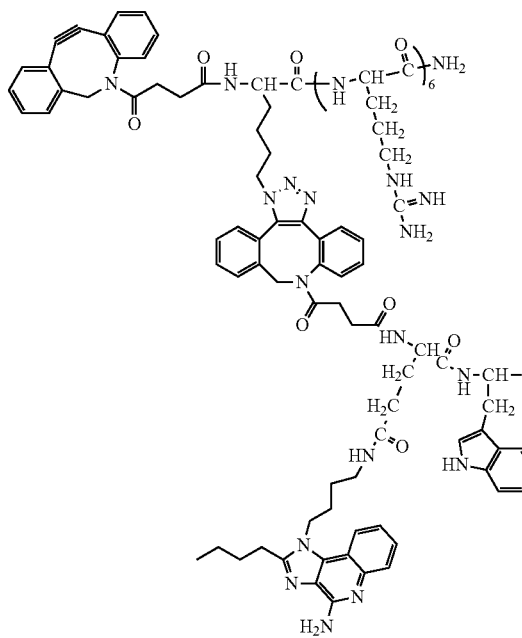
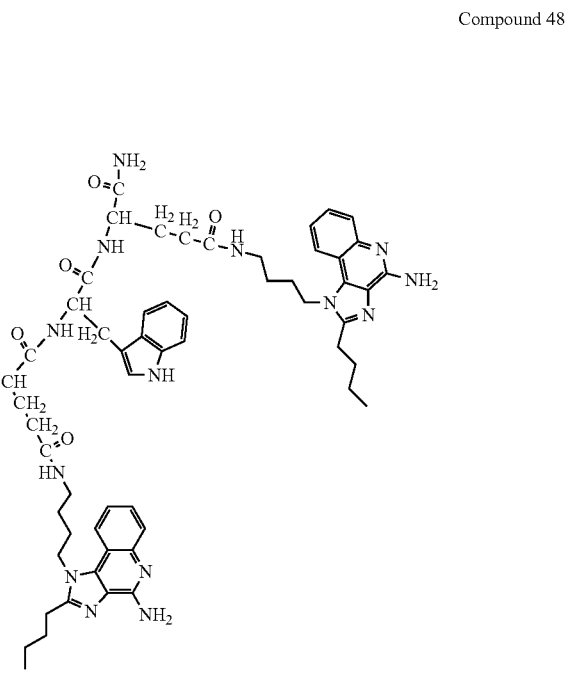

Compound 48, referred to as DBCO-2B$_3$W$_2$—R$_6$ or DBCO-2B$_3$W$_2$(R)6 was synthesized using the same procedure as Compound 43, except NH$_2$-Lys(N$_3$)-(Arg)$_6$-NH$_2$ (SEQ ID NO. 186) was used as the starting material. Compound 48 was purified on a preparatory HPLC system using a gradient of 26-36% acetonitrile/H$_2$O (0.05% TFA) over 12 minutes on an Agilent Prep-C18 column, 30×100 mm, 5 m. The resulting fractions were collected, frozen and then lyophilized to obtain 17.8 mg (51.8% yield) of the title compound as a spectroscopically pure (>95% AUC at 254 nm) white powder. MS (ESI) calculated for m/z 3338.19, found 478.1 (m/7)+.

Compound 49

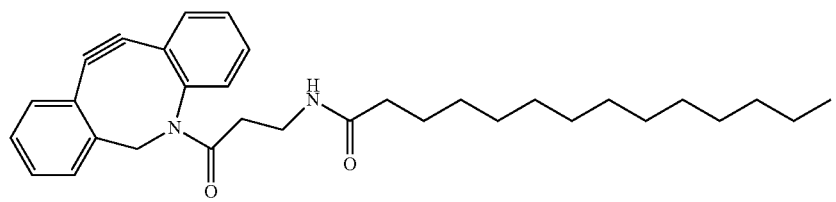

Compound 49, referred to as Myr-DBCO or C14-DBCO was prepared from Myristoyl Chloride and DBCO-Amine. 50 mg of DBCO-Amine (0.18 mmol, 1 eq) was dissolved in 0.5 mL of DCM. TEA (0.22 mmol, 1.2 eq) was added and the solution was stirred for 5 minutes at room temperature. Myristoyl Chloride (0.16 mmol, 0.9 eq) was added and the reaction mixture was stirred for 1 hour at room temperature. TLC (2.5% methanol in DCM) showed a new spot with rf of 0.5 for Myr-DBCO. The reaction mixture was injected on a flash chromatography column and purified using a gradient of 0-3% methanol in DCM over 12 CVs. The fractions were collected and dried to provide 86 mg of Myr-DBCO in quantitative yield. MS (ESI) calculated for $C_{32}H_{42}N_2O_2$ m/z 486.32 found 487.3 (m+H)+.

Compound 50

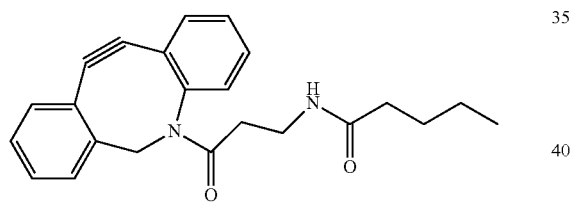

Compound 50, referred to as Val-DBCO or C5-DBCO was prepared using the same procedure described for Compound 49, except Valeroyl Chloride was used as the starting material. Val-DBCO was purified on a preparatory HPLC system using a gradient of 40-60% acetonitrile/H₂O (0.05% TFA) over 12 minutes on an Agilent Prep-C18 column, 30×100 mm, 5 μm. The resulting fractions were collected, frozen and then lyophilized to obtain 80 mg of Val-DBCO in quantitative yield. MS (ESI) calculated for $C_{23}H_{24}N_2O_2$ m/z 360.18 found 361.2 (m+H)+.

Compound 51

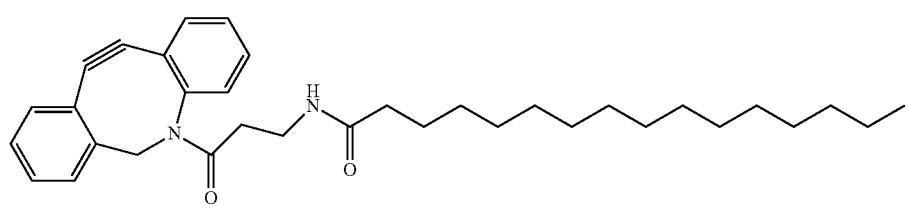

Compound 51, referred to as Plm-DBCO or C16-DBCO was prepared using the same procedure described for Compound 49, except Palmitoyl Chloride was used as the starting material. Compound 51 was purified by flash chromatography using a gradient of 0-3% methanol in DCM over 12 CVs. The fractions were collected and dried to provide 80 mg of Plm-DBCO in quantitative yield. MS (ESI) calculated for $C_{34}H_{46}N_2O_2$ m/z 514.36 found 515.3 $(m+H)^+$.

Compound 52

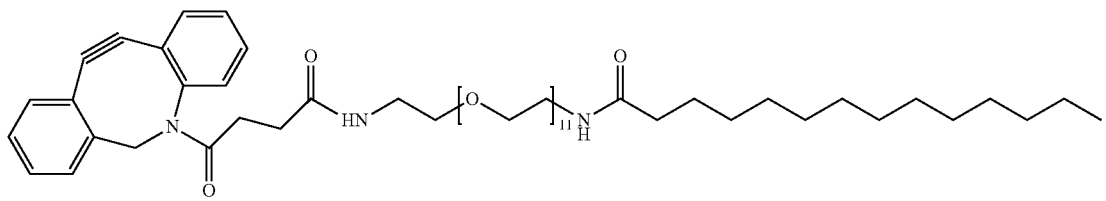

Compound 52, referred to as Myr-Peg$_{11}$-DBCO or C14-PEG11-DBCO was synthesized using Myristoyl Chloride, Boc-Peg$_{11}$-Amine and DBCO-NHS as starting materials. 116.06 mg Boc-Peg$_{11}$-Amine (0.18 mmol, 1 eq) was dissolved in 0.5 mL of DCM. TEA (0.22 mmol, 1.2 eq) was added and the reaction mixture was stirred for 5 minutes at room temperature. Myristoyl Chloride was added and the reaction was stirred at room temperature for 1 hour. The reaction mixture was diluted with DCM and washed twice with 1 M HCl and once with DI water. The organic layer was dried with sodium sulfate and evaporated. The intermediate was dissolved in 0.35 mL of DCM and 0.15 mL of TFA was added. The reaction mixture was stirred for 30 minutes at room temperature then dried by blowing with air and further dried under high vacuum. 122.5 mg of the oil (0.162 mmol, 1 eq) was dissolved in 0.5 mL of DCM. TEA (0.49 mmol, 3 eq) was added and the solution was stirred for 5 minutes at room temperature. 65.19 mg of DBCO-NHS (0.162 mmol, 1 eq) was added and the reaction mixture was stirred for 1 hour at room temperature. The reaction mixture was injected on a flash chromatography column and purified using a gradient of 0-15% methanol in DCM over 15 CVs. The fractions were collected and dried to provide Myr-Peg$_{11}$-DBCO. Product molecular weight verified based on the MS (ESI+) for peptide antigen conjugates of Compound 52.

Compound 53

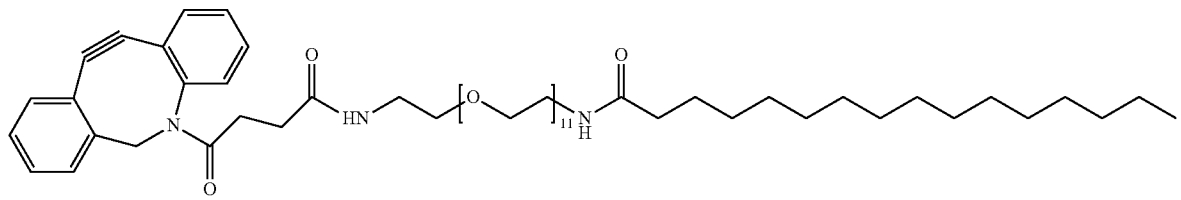

Compound 53, referred to as Plm-Peg$_{11}$-DBCO or C16-PEG11-DBCO was synthesized using the same procedure as Compound 52, except Palmitoyl Chloride was used as the starting material. Plm-Peg$_{11}$-DBCO was purified by flash chromatography using a gradient of 0-15% methanol in DCM over 15 CVs. The fractions were collected and dried to provide Plm-Peg$_{11}$-DBCO. Product molecular weight verified based on the MS (ESI+) for peptide antigen conjugates of Compound 53.

Compound 54

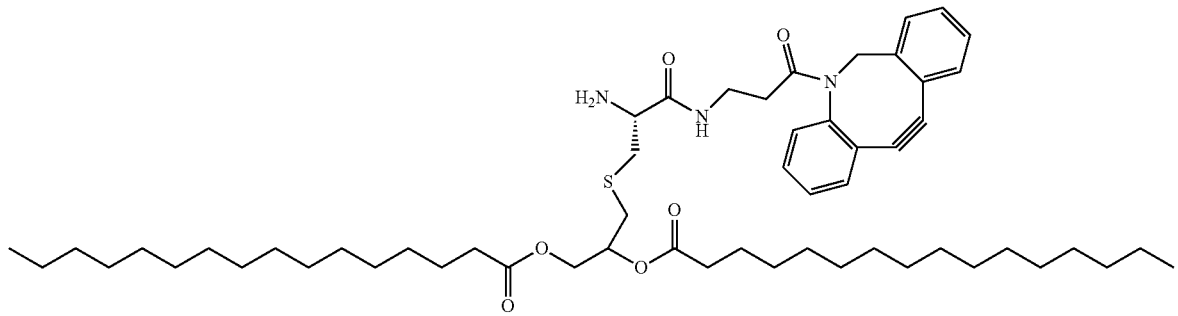

Compound 54, referred to as NH₂—Pam2Cys-DBCO, was synthesized using Compound 26 and DBCO-Amine as starting materials. 30 mg of Compound 26 (0.03 mmol, 1 eq) was prepared as a 100 mg/mL stock solution in DCM. To this stock solution was added 8.34 mg of DBCO-Amine (0.03 mmol, 1 eq) also as a 100 mg/mL stock solution in DCM. The reaction mixture was stirred for 1 hour at room temperature then injected on a flash chromatography column and purified. The gradient used was a stepwise gradient from 0-5% methanol in DCM (5 CV hold, 1 CV to increase methanol concentration by 1%). The fractions were collected and dried to provide the DBCO intermediate. 26 mg of Fmoc-Pam2Cys-DBCO (0.023 mmol, 1 eq) was dissolved in 1 mL of 20% Piperidine in DMF and stirred for 30 minutes at room temperature. The reaction mixture was diluted with DCM and washed three times with DI water. The organic layer was dried with sodium sulfate and evaporated. The solid was taken up in 0.5 mL of DCM and injected on a flash chromatography column and purified. The gradient used was a stepwise gradient from 0-5% methanol in DCM. The fractions were collected and dried to provide NH₂-Pam2Cys-DBCO. Product molecular weight verified based on the MS (ESI+) for peptide antigen conjugates of Compound 54.

Compound 55, referred to as NH₂—Pam2Cys-Peg$_{11}$-DBCO, was synthesized using Compound 26, Boc-Peg$_{11}$-Amine, and DBCO NHS as starting materials. 60 mg of Compound 26 (0.06 mmol, 1 eq) was dissolved in 0.6 mL of DCM. 38.9 mg of Boc-Peg$_{11}$-Amine (0.06 mmol, 1 eq) was added and the reaction mixture was stirred at room temperature for 30 minutes. The DCM was removed under vacuum and the oil was taken up in DMSO and added to DI water. The water was centrifuged at 3000 g for 5 minutes and the pellet was collected and dried under vacuum. The PEGylated intermediate was dissolved in 0.35 mL of DCM and 0.15 mL of TFA was added. The reaction mixture was stirred at room temperature for 30 minutes then blown dry with air and further dried under high vacuum. 71.76 mg of the Boc deprotected oil (0.05 mmol, 1 eq) was dissolved in 1 mL of DMSO and TEA (0.1 mmol, 2 eq) was added followed by 20.3 mg of DBCO-NHS (0.05 mmol, 1 eq). The reaction mixture was stirred for 1 hour at room temperature. 0.5 mL of 20% piperidine in DMF was added and the reaction mixture was stirred for 30 minutes at room temperature. The reaction mixture was diluted with DCM and washed three times with pH 9.5 Sodium Bicarbonate. The organic layer was dried with sodium sulfate and evaporated. The solid was taken up in 0.5 mL of DCM and injected on a flash chromatography column and purified. The gradient used was 0-10% methanol in DCM over 30 CVs. This provided the product in 6.7% overall yield. Product molecular weight verified based on the MS (ESI+) for peptide antigen conjugates of Compound 55.

Compound 55

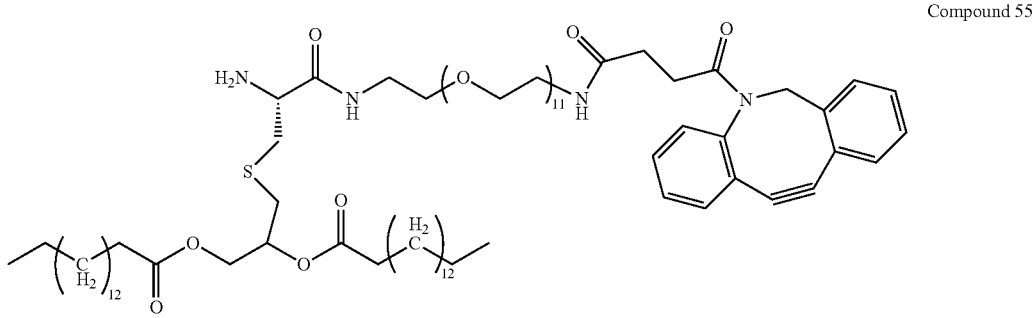

Compound 56

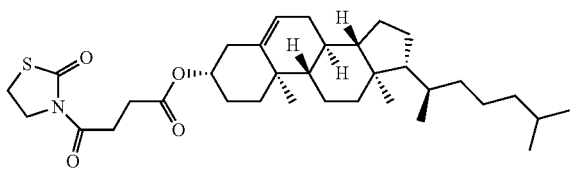

Compound 56, referred to as Chol-TT, was prepared using Cholesteryl hemisuccinate and TT as starting materials. 100 mg of Choleteryl hemisuccinate (0.21 mmol, 1 eq), 26.94 mg of TT (0.23 mmol, 1.1 eq), and 51.20 mg of EDC (0.27 mmol, 1.3 eq) were dissolved in 1 mL of DCM. 2.51 mg of DMAP (0.02 mmol, 0.1 eq) was added and the reaction mixture was stirred at room temperature. After 1 hour, the bright yellow reaction mixture was diluted with DCM and washed twice with 1 M HCl and once with DI water. The organic layer was dried with sodium sulfate and evaporated to give 120 mg of a yellow solid in quantitative yield. Product molecular weight verified based on the MS (ESI+) for peptide antigen conjugates of Compound 56.

Compound 57

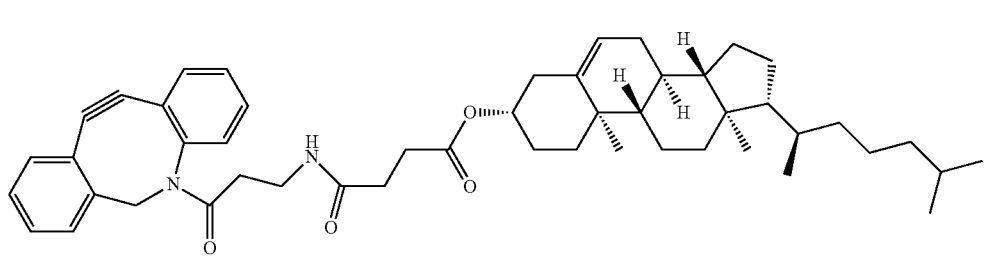

Compound 57, referred to as Chol-DBCO, was prepared from Compound 56 and DBCO-Amine. 106.28 mg of Compound 56 (0.18 mmol, 1 eq) and 50 mg of DBCO-Amine (0.18 mmol, 1 eq) were dissolved in 0.5 mL of DCM and stirred at room temperature. Over the course of an hour the bright yellow color of the solution faded and TLC in DCM indicated complete absence of Compound 56. The reaction mixture was injected on a flash chromatography column and purified using a gradient of 0-3% methanol in DCM over 12 CVs. The fractions were collected and dried to provide 139 mg of Chol-DBCO in quantitative yield. Product molecular weight verified based on the MS (ESI+) for peptide antigen conjugates of Compound 57.

Compound 58

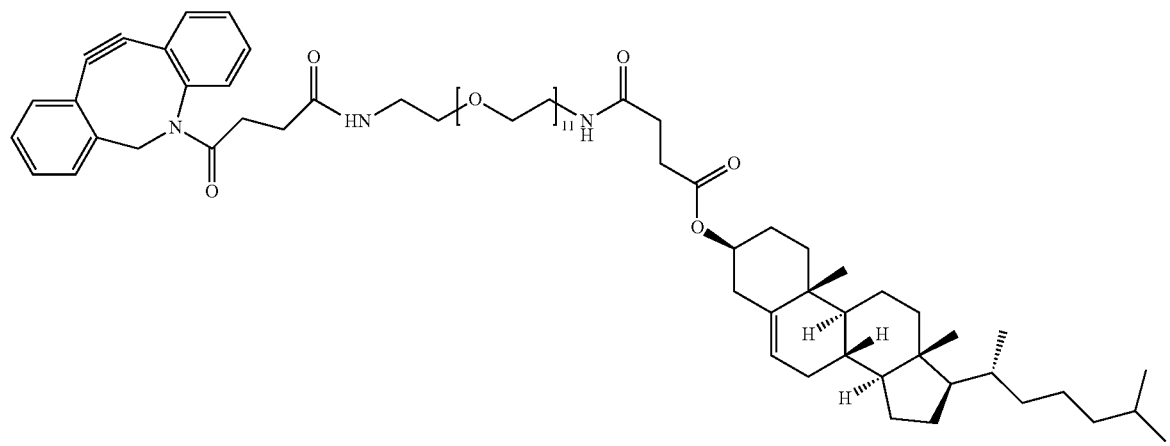

Compound 58, referred to as Chol-Peg$_{11}$-DBCO, was prepared from Compound 56, Boc-Peg$_{11}$-amine and DBCO-NHS. 50 mg of Compound 56 (0.085 mmol, 1 eq) was dissolved in 0.5 mL of DCM. 60.38 mg of Boc-Peg$_{11}$-amine (0.09 mmol, 1.1 eq) was added and the reaction mixture was stirred at room temperature. Over the course of an hour the bright yellow color of the solution faded and TLC in DCM showed complete absence of Compound 56. To the reaction mixture was added 150 μL of TFA to make a 30% solution in DCM. The reaction mixture was stirred for 30 minutes at room temperature then dried by blowing with air and further dried under high vacuum. 86.25 mg of the oil (0.085 mmol, 1 eq) was dissolved in 0.5 mL of DCM. TEA (0.26 mmol, 3 eq) was added and the solution was stirred for 5 minutes at room temperature. 34.26 mg of DBCO-NHS (0.085 mmol, 1 eq) was added and the reaction mixture was stirred for 1 hour at room temperature. The reaction mixture was injected on a flash chromatography column and purified using a gradient of 0-15% methanol in DCM over 15 CVs. The fractions were collected and dried to provide Chol-Peg$_{11}$-DBCO.

Compound 59

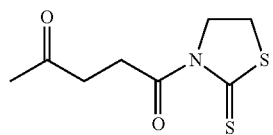

Compound 59, referred to as LA-TT, was synthesized using Levulinic acid and TT as the starting materials. 500 mg of Levulinic acid (4.3 mmol, 1 eq), 564.7 mg of TT (4.7 mmol, 1.1 eq), and 1.032 g of EDC (5.4 mmol, 1.3 eq) were dissolved in 10 mL of dry DMSO. 52.6 mg of DMAP (0.4 mmol, 0.1 eq) was added and the reaction mixture was stirred at room temperature for 2 hours. Compound 59 was worked up by diluting in Ethyl Acetate and washing twice with 1 M HCl and once with DI water. The organic layer was dried with sodium sulfate and removed under vacuum. The solid was recrystallized from Ethyl Acetate. MS (ESI) calculated for $C_8H_{11}NO_2S_2$, m/z, 217.02, found 218 (M+H)$^+$.

Compound 60

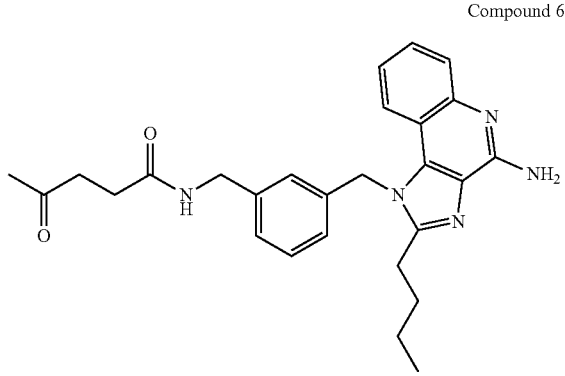

Compound 60, referred to as LA-2BXy, was synthesized using Compound 59 and Compound 2 as starting materials. 50 mg of Compound 59 (0.23 mmol, 1 eq) and 82.62 mg of Compound 2 (0.23 mmol, 1 eq) were dissolved in 1 mL of DMSO. The reaction mixture was stirred at room temperature for 1 hour. TLC (35% ethyl acetate in hexane) showed disappearance of both starting materials. Compound 60 was purified on a preparatory HPLC system using a gradient of 15-30% acetonitrile/H$_2$O (0.05% TFA) over 10 minutes on an Agilent Prep-C18 column, 30×100 mm, 5 μm. MS (ESI) calculated for $C_{27}H_{31}N_5O_2$, m/z, 457.25, found 458.3 (M+H)$^+$.

Compound 61

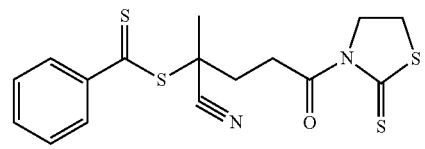

Compound 61, referred to as CTA-TT, was synthesized using the same procedure as Compound 59, except 4-Cyano-4-(thiobenzoylthio)pentanoic acid (CTA) was used as the starting material and DCM was used as the solvent. Compound 61 was worked up by diluting in DCM and washing twice with 1 M HCl and once with DI water. The organic layer was dried with sodium sulfate and removed under vacuum. The solid was recrystallized from Ethyl Acetate. MS (ESI) calculated for $C_{16}H_{16}N_2OS_4$, m/z, 380.01, found 381.1 (M+H)$^+$.

Compound 62

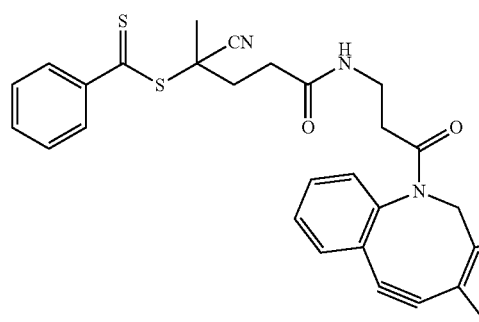

Compound 62, referred to as CTA-DBCO, was synthesized from "CTA-NHS" (4-Cyano-4-(phenylcarbonothioyl-thio)pentanoic acid N-succinimidyl ester, Sigma-Aldrich) and DBCO-Amine (Click Chemistry Tools). 210 mg of CTA-NHS (0.56 mmol, 1 eq) and 167.8 mg of DBCO-Amine (0.61 mmol, 1.1 eq) were dissolved in 2 mL of dry DMSO and stirred at room temperature for 2 hours. The reaction mixture was diluted with DCM and washed twice with 1M HCl and once with DI water. The organic layer was dried with sodium sulfate and evaporated. Compound 62 was purified on a preparatory HPLC system using a gradient of 50-70% acetonitrile/H$_2$O (0.05% TFA) over 10 minutes on an Agilent Prep-C18 column, 30×100 mm, 5 μm. MS (ESI) calculated for $C_{31}H_{27}N_3O_2S_2$ m/z 537.7, found 538.2 (M+H)$^+$.

Compound 63

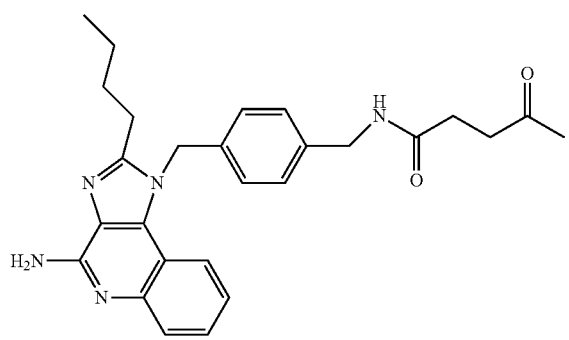

Compound 63, referred to as CTA-2BXY, was synthesized using the same procedure as Compound 60, except Compound 61 and Compound 2 were used as starting materials. Compound 63 was purified on a preparatory HPLC system using a gradient of 40-50% acetonitrile/H$_2$O (0.05% TFA) over 12 minutes on an Agilent Prep-C18 column, 50×100 mm, 5 μm. MS (ESI) calculated for C$_{35}$H$_{36}$N$_6$OS$_2$ m/z 620.83, found 621.2 (M+H)$^+$.

Compound 64

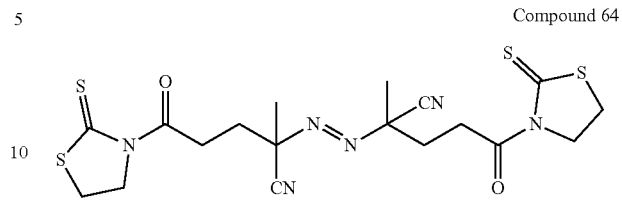

Compound 66, referred to as ACVA-TT, was synthesized using the same procedure as Compound 59, except 4,4'-Azobis(4-cyanovaleric acid) was used as the starting material and the equivalents of TT, EDC, and DMAP were doubled to reflect a doubling of active sites. Compound 66 was worked up by diluting in Ethyl Acetate and washing twice with 1 M HCl and once with DI water. The organic layer was dried with sodium sulfate and removed under vacuum. The solid was recrystallized from DCM:Ether. MS (ESI) calculated for C$_{18}$H$_{22}$N$_6$O$_2$S$_4$, m/z, 482.65, found 483.1 (M+H)$^+$.

Compound 65

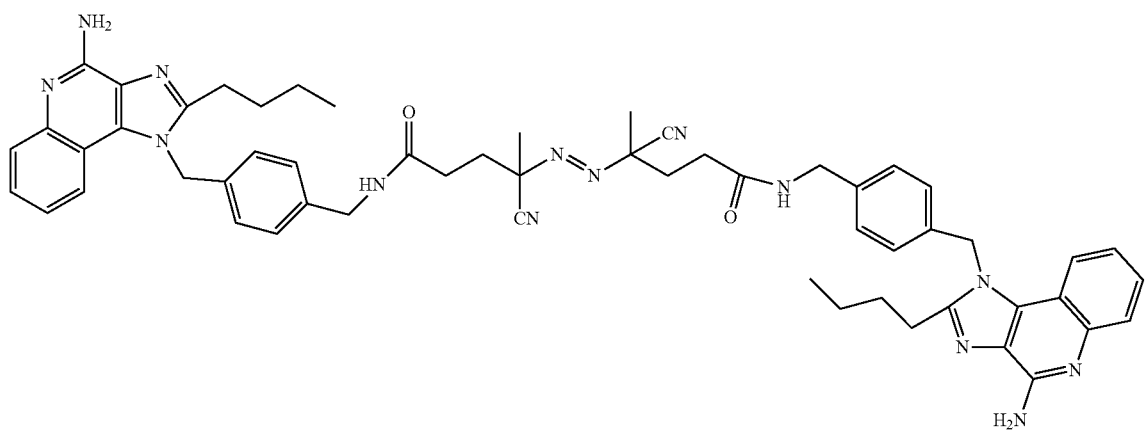

Compound 65, referred to as ACVA-2BXy, was synthesized using the same procedure as Compound 60, except Compound 64 was used as the starting material and the equivalents of Compound 2 were doubled to reflect a doubling of active sites. Compound 65 was purified on a preparatory HPLC system using a gradient of 28-48% acetonitrile/H$_2$O (0.05% TFA) over 10 minutes on an Agilent Prep-C18 column, 50×100 mm, 5 μm. MS (ESI) calculated for C$_{56}$H$_{62}$N$_{14}$O$_2$ m/z 963.21, found 482.4 (M/2)$^+$.

Compound 66

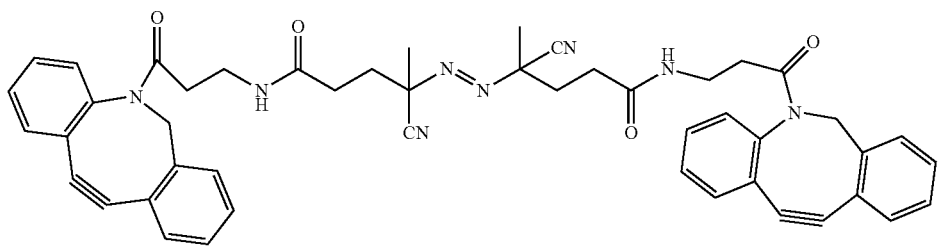

Compound 66, referred to as ACVA-DBCO, was synthesized using the same procedure as Compound 60, except Compound 64 and DBCO-Amine (Click Chemistry Tools) were used as the starting materials. Compound 66 was purified by flash chromatography using a gradient of 0-3% methanol in DCM over 15 CVs. MS (ESI) calculated for $C_{48}H_{44}N_8O_4$ m/z 796.93, found 797.3 (M+H)$^+$.

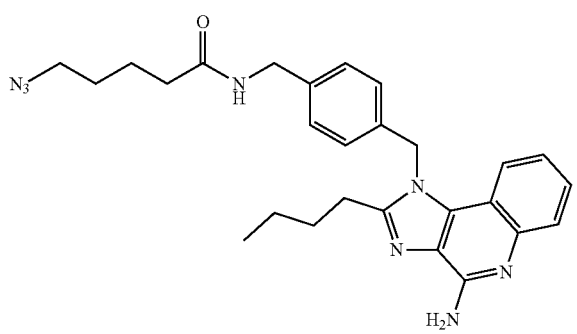

Compound 67

Compound 67, referred to as Azp-2BXY, was synthesized from 5-Azido-Pentanoic Acid (Azp) and Compound 2. 16.2 mg of Azp (0.114 mmol, 1.1 eq), 12.3 mg of TT (0.103 mmol, 1 eq) and 27.2 mg of EDC (0.142 mmol, 1.3 eq) were dissolved in 0.5 mL of dry DMSO. 1.4 mg of DMAP was added and the reaction mixture was stirred for 2 hours at room temperature. 37.09 mg of Compound 2 (0.103 mmol, 1 eq) was added and the reaction mixture was stirred for 1 hour at room temperature. Compound 67 was purified on a preparatory HPLC system using a gradient of 22-42% acetonitrile/H$_2$O (0.05% TFA) over 10 minutes on an Agilent Prep-C18 column, 30×100 mm, 5 µm. MS (ESI) calculated for $C_{27}H_{32}N_8O$ m/z 484.27, found 485.3 (M+H)$^+$.

Compound 68 also referred to as (HPMA-2B)-b-(HPMA)-DBCO or p{[(HPMA)-co-(MA-b-Ala-2B)]-b-p(HPMA)}-DBCO The micelle-forming di-block co-polymer (A-B type) was produced by RAFT polymerization in two synthetic steps using the precursors HPMA and MA-b-Ala-TT prepared as previously described (see: Lynn G M, et al. *Nat Biotechnol* 33(11):1201-1210, 2015), as well as 2-Cyano-2-propyl benzodithioate ("CTA-ABIN," Sigma Aldrich) Azobisisobutyronitrile ("AIBN, Sigma Aldrich), Compound 1 and Compound 66. The hydrophobic block A was prepared by co-polymerizing HPMA with MA-b-Ala-TT using the CTA-AIBN as a chain transfer agent and AIBN as an initiator at 70° C. for 16 h in a tert-butyl alcohol/DMSO mixture. The hydrophobic block B was subsequently subjected to a chain-extension polymerization through the RAFT mechanism by adding HPMA in the presence of AIBN at 70° C. for an additional 16 hours. The A-B di-block co-polymer, p{[(HPMA)-co-(MA-b-T)]-b-p(HPMA)}-DTB was isolated by precipitation to yield a green solid. The DTB group on one end of the co-polymer was replaced by reacting with Compound 66 at 80° C. for 2 hours in DMSO, followed by the addition of Compound L The product was precipitated and then purified by LH-20 to yield Compound 68, which was then used for reaction with peptide antigens to yield different types of peptide antigen conjugates, e.g, p{[(HPMA)-co-(MA-b-Ala-2B)]-b-p(HPMA)}-DBCO-(Peptide antigen) that are fully described below.

Compound 68

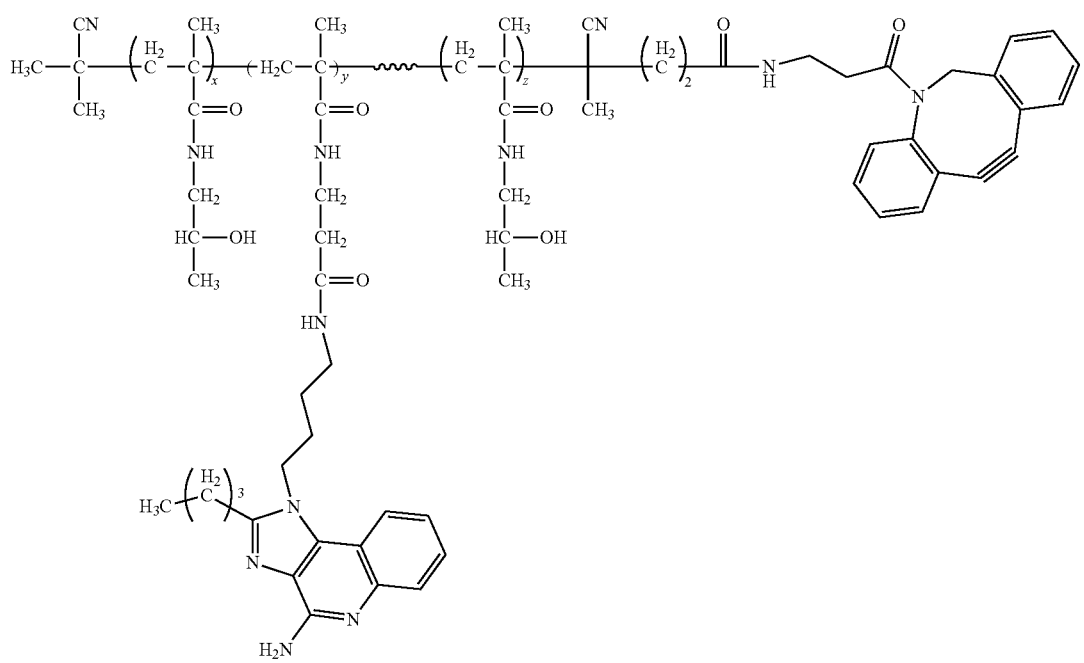

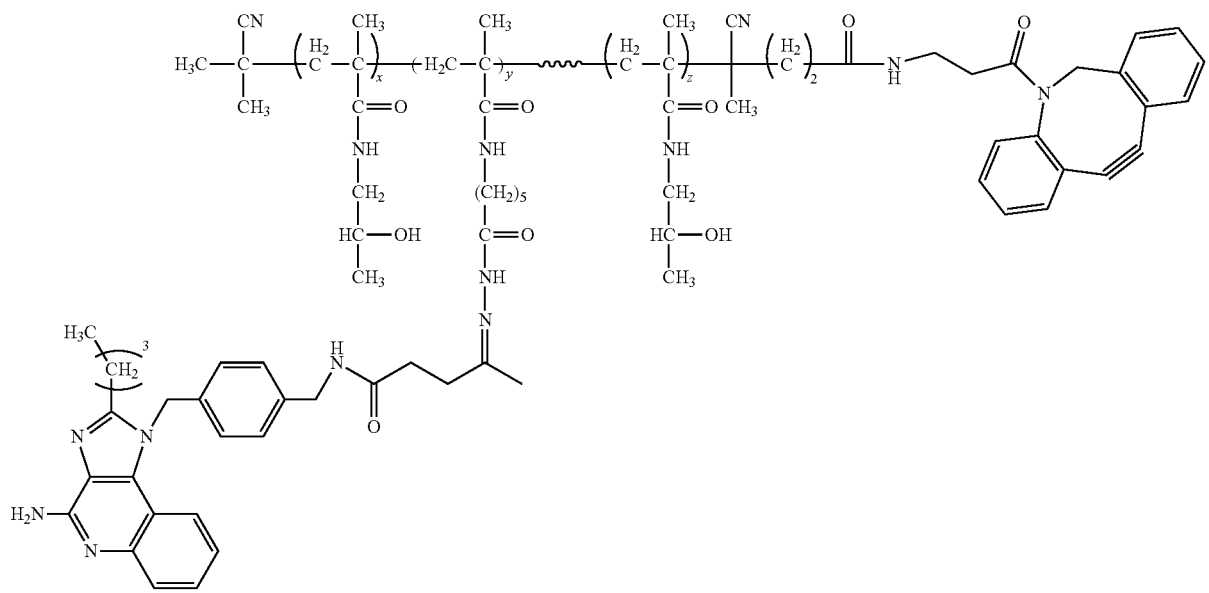

Compound 69

Compound 69 also referred to as (HPMA-NHNH-2BXy)-b-(HPMA)-DBCO or p{[(HPMA)-co-(MA-Acap-NHN=CH-2BXy)]-b-p(HPMA)}-DBCO. The micelle-forming di-block co-polymer (A-B type) was produced by RAFT polymerization in two synthetic steps using the precursors HPMA and MA-Acap-NHNH-Boc prepared as previously described (see: Lynn G M, et al. *Nat Biotechnol* 33(11):1201-1210, 2015), as well as 2-Cyano-2-propyl benzodithioate ("CTA-ABIN," Sigma Aldrich) Azobisisobutyronitrile ("AIBN, Sigma Aldrich), Compound 60 and Compound 66. The hydrophobic block A was prepared by co-polymerizing HPMA with MA-Acap-NHNH-Boc using the CTA-AIBN as a chain transfer agent and AIBN as an initiator at 70° C. for 16 h in a tert-butyl alcohol/DMSO mixture. The hydrophobic block B was subsequently subjected to a chain-extension polymerization through the RAFT mechanism by adding HPMA in the presence of AIBN at 70° C. for an additional 16 hours. The A-B di-block co-polymer, p p{[(HPMA)-co-(MA-Acap-NHN=CH-2BXy)]b-p(HPMA)}-DTB was isolated by precipitation and then Boc-deprotected in 30% trifluoracetic acid TFA/DCM The TFA/DCM was removed under vacuum and then DTB group on one end of the co-polymer was replaced by reacting with Compound 66 at 80° C. for 2 hours in DMSO, followed by the addition of Compound 60. The product was precipitated and then purified by LH-20 to yield Compound 69, which was then used for reactions with peptide antigens to yield different types of peptide antigen conjugates, e.g. p{[(HPMA)-co-(MA-b-Ala-2B)]-b-p(HPMA)}-DBCO-(Peptide antigen) that are fully described below.

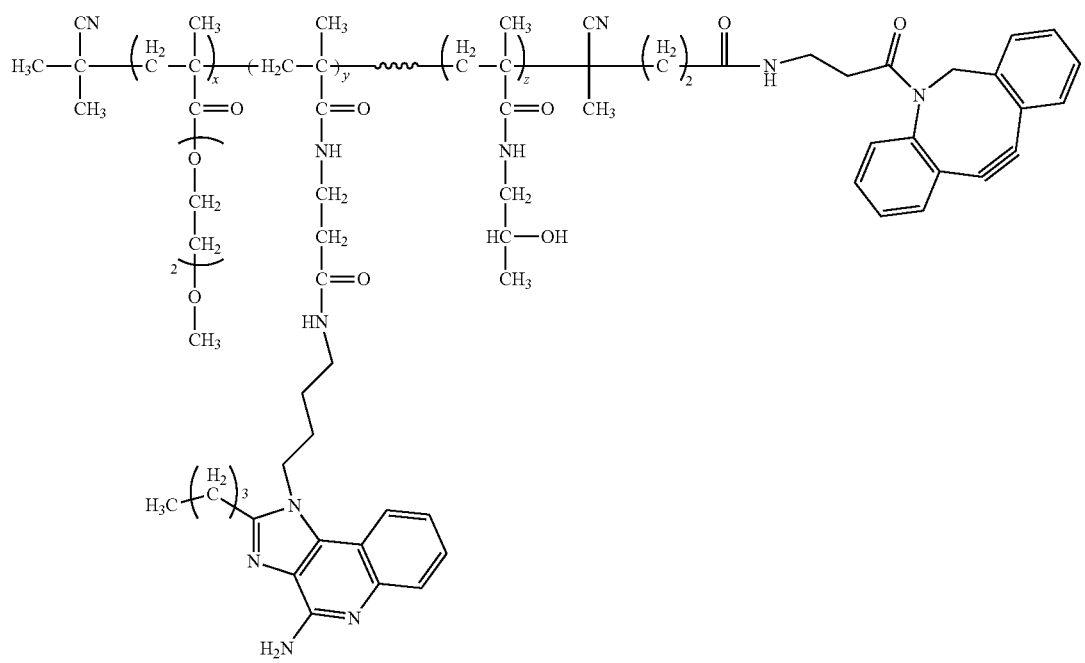

Compound 70

Compound 70 also referred to as (DEGMA-2B)-b-(HPMA)-DBCO or p{[(DEGMA)-co-(MA-b-Ala-2B)]-b-p(HPMA)}-DBCO. The temperature-responsive micelle-forming di-block co-polymer (A-B type) was produced by RAFT polymerization in two synthetic steps using the precursors DEGMA, HPMA and MA-b-Ala-TT prepared as previously described (see: Lynn G M, et al. *Nat Biotechnol* 33(11):1201-1210, 2015), as well as 2-Cyano-2-propyl benzodithioate ("CTA-ABIN," Sigma Aldrich) Azobisisobutyronitrile ("AIBN, Sigma Aldrich), Compound 1 and Compound 66. The temperature-responsive hydrophobic block A was prepared by co-polymerizing DEGMA with MA-b-Ala-TT using the CTA-AIBN as a chain transfer agent and AIBN as an initiator at 70° C. for 16 h in a tert-butyl alcohol/DMSO mixture. The hydrophobic block B was subsequently subjected to a chain-extension polymerization through the RAFT mechanism by adding HPMA in the presence of AIBN at 70° C. for an additional 16 hours. The A-B di-block co-polymer, p{[(DEGMA)-co-(MA-b-Ala-2B)]-b-p(HPMA)}-DTB was isolated by precipitation to yield a green solid. The DTB group on one end of the co-polymer was replaced by reacting with Compound 66 at 80° C. for 2 hours in DMSO, followed by the addition of Compound 1. The product was precipitated and then purified by LH-20 to yield Compound 70, which was then used for reaction with peptide antigens to yield different types of peptide antigen conjugates, e.g., p{[(DEGMA)-co-(MA-b-Ala-2B)]-b-p(HPMA)}-DBCO-(Peptide antigen) that are fully described below.

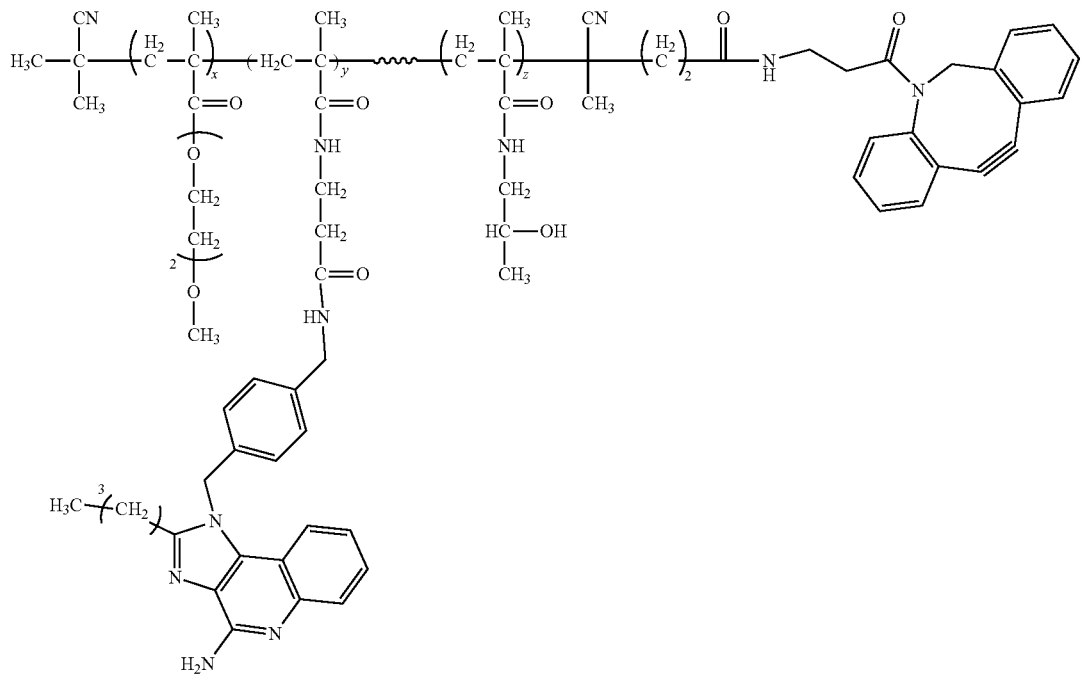

Compound 71

Compound 71 also referred to as (DEGMA-2BXy)-b-(HPMA)-DBCO or p{[(DEGMA)-co-(MA-b-Ala-2BXy)]-b-p(HPMA)}-DBCO was prepared using the same procedure as Compound 70, except compound 2 was used as the Ligand. The product was precipitated and then purified by LH-20 to yield Compound 68, which was then used for reaction with peptide antigens to yield different types of peptide antigen conjugates, e.g., p{[(DEGMA)-co-(MA-b-Ala-2BXy)]-b-p(HPMA)}-DBCO-(Peptide antigen) that are fully described below.

using Compound 63 as a chain transfer agent and Compound 65 as an initiator at 70° C. for 16 h in a tert-butyl alcohol/DMSO mixture. The hydrophobic block B was subsequently subjected to a chain-extension polymerization through the RAFT mechanism by adding HPMA in the presence of AIBN at 70° C. for an additional 16 hours. The A-B di-block co-polymer, 2BXy-[p(DEGMA)-b-p(HPMA)]-DTB was isolated by precipitation and the DTB group on one end of the co-polymer was replaced by reacting with Compound 66

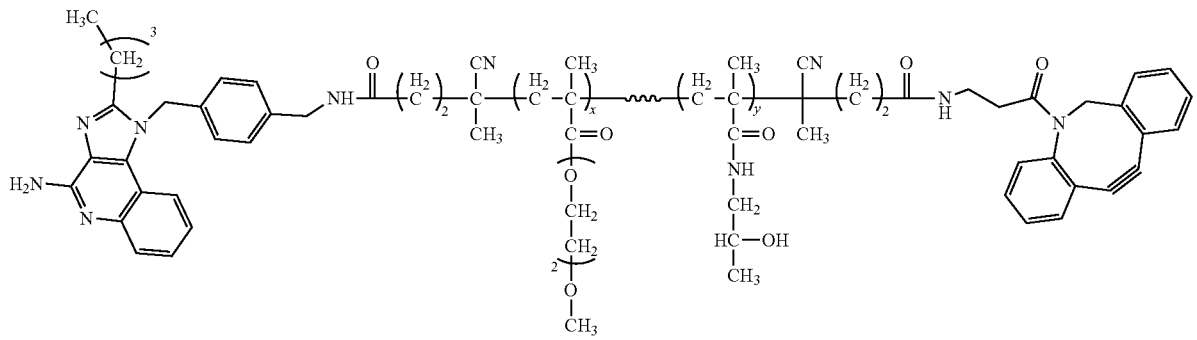

Compound 72

Compound 72 also referred to as 2BXy-DEGMA-b-HPMA-DBCO. The micelle-forming di-block co-polymer (A-B type) was produced by RAFT polymerization in two synthetic steps using the precursors DEGMA, HPMA, Compound 63, Compound 65 and Compound 66. The hydrophobic block A was prepared by co-polymerizing DEGMA at 80° C. for 2 hours in DMSO The product was precipitated and then purified by LH-20 to yield Compound 72 which was then used for reaction with peptide antigens to yield different types of peptide antigen conjugates, e.g., 2BXy-p[(DEGMA)-b-p(HPMA)]-DB(O-(Peptide antigen) that are fully described below.

Example 2: Reaction of a Peptide Antigen Fragment and a Hydrophobic Molecule (H) to Produce a Peptide Antigen Conjugate A peptide antigen fragment comprised of a peptide antigen (A), optional charged molecule (C), optional extensions (B1 and/or B2) and linker precursor X1, e.g., [C]—[B1]-A-[B2]—X1, where [ ] denotes that the group is optional in this example, may be reacted with X2 linked to a hydrophobic molecule (H), e.g., X2-H, to provide a peptide antigen conjugate, e.g., [C]—[B1]-A-[B2]-L-H. Wherein a peptide antigen fragment comprises a linker precursor X1 comprising an azide, e.g., azido-lysine (Lys(N3)) sometimes referred to as K', the peptide antigen fragment may be reacted with a linker precursor X2 comprising an alkyne, such as a DBCO, that is linked to a hydrophobic molecule (H) to form a triazole Linker (L). As non-limiting examples, Compounds 3 to 5 are examples of hydrophobic molecules (H) of Formula I bearing a DBCO linker precursor X2 that are additionally linked to Adjuvants of Formula III (i.e. TLR-7/8a); Compounds 6 to 11 are examples of hydrophobic molecules (H) of Formula I bearing a DBCO linker precursor X2 that are additionally linked to Adjuvants of Formula III (i.e. TLR-7/8a); and, Compounds 10 to 11 are examples of hydrophobic molecules (H) of Formula II bearing a DBCO linker precursor X2 but do not contain a Ligand with adjuvant properties.

Figure 2:
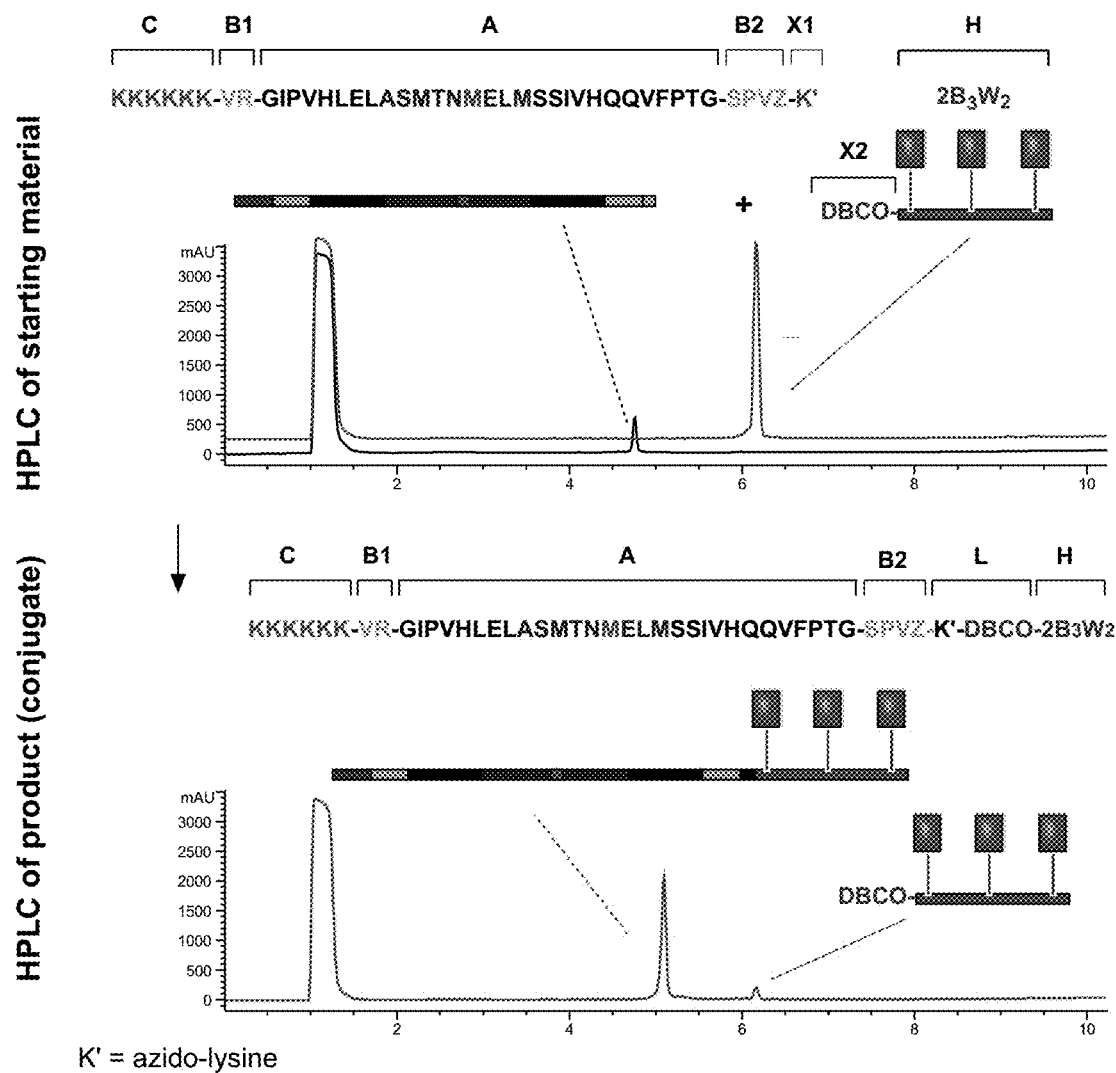
FIG. 2: General scheme for the synthesis of peptide antigen conjugates by reacting a peptide antigen fragment comprising a linker precursor X1 bearing an azide with a linker precursor X2 bearing a DBCO to form a triazole Linker (L) that links the peptide antigen (A) to the hydrophobic molecule (H).

A non-limiting example shown in FIG. 2, is the reaction of a hydrophobic molecule (H) linked to a linker precursor X2 comprising a DBCO that is reacted at a 1.1 to 1 molar ratio with a peptide antigen fragment comprising an azide bearing linker precursor X1. As indicated in the HPLC chromatogram, the DBCO on the hydrophobic molecule (H) reacts with a linker precursor X1 comprising an azide, resulting in a triazole Linker (L) that is linked to a B2 extension that links to a peptide antigen (A) that is linked to a B1 extension that is linked to a charged molecule (C), thereby joining the peptide antigen (A) and hydrophobic molecule (H) to provide a peptide antigen conjugate. Hundreds of examples of different peptide antigen conjugates formed by the reaction of an azide bearing peptide antigen fragment with a DBCO bearing hydrophobic molecule (H) are described throughout. As the reaction of the azide and DBCO is reliable and consistent across all of the peptide antigen conjugates produced, a full description of the reaction used to form the conjugates as well as their characterization is not provided. Note: that the molecular weight of the peptide antigen conjugates arising from the cycloaddition is the sum of the mass of the starting materials.

Wherein a peptide antigen fragment comprises a linker precursor X1 comprising a thiol, e.g., cysteine (Cys) sometimes referred to as C, the peptide antigen fragment may be reacted with a hydrophobic molecule (H) bearing a linker precursor X2 comprising a maleimide, e.g., Compound 21, that results in a thio-ether based Linker (L). Wherein a peptide antigen fragment comprises a linker precursor X1 comprising an amine, e.g., Lysine (Lys) sometimes referred to as K, the peptide antigen fragment may be reacted with a hydrophobic molecule (H) bearing a linker precursor X2 comprising an activated ester, such as a NHS, e.g., Compound 22, that results in the formation of an amide bond.

Example 3: Synthesis and Biological Characterization of Peptide Antigen Conjugates of Formula IV Prior studies have reported the delivery of T cell epitopes as ~20-40 amino acid synthetic "long" peptides (SLPs or LP) combined with various vaccine adjuvants as a means to induce CD8 T cell responses. However, the impact of peptide length and hydrodynamic behavior, as well as co-delivery of the peptide with immuno-stimulants, such as TLRa, on immunogenicity have not been adequately studied. To provide greater insights as to how different parameters of peptide-based antigens impact T cell immunity, we systematically evaluated how different properties of the peptide antigen conjugates of Formula IV described herein impact CD4 and CD8 T cell responses in vivo.

Impact of Peptide Antigen Hydrodynamic Behaviour, Peptide Antigen (A) Length and Co-Delivery of a TLR-7/8a on CD8 T Cell Responses It was not clear a priori how the length of the peptide antigen (A) delivered as peptide antigen conjugates of the present disclosure would impact immunogenicity, specifically, the magnitude and quality of the CD8 and/or CD4 T cell response generated.

To systematically investigate how peptide antigen (A) length impacts immunogenicity of peptide antigen conjugates of Formula IV, two model neoantigen CD8 T cell epitopes, Irgq and Cpne1, derived from the murine tumor model, MC38, were produced as peptide antigen conjugates, wherein the peptide antigens (A) was either the 26 amino acid synthetic long peptides (SLPs or "LP") or the 10 amino acid minimal epitope (ME or "Min") (FIG. 4). The SLP-based peptide antigens (A) were linked at the C-terminus to a linker precursor X1, azido-lysine (K'), that was linked to a linker precursor X2, DBCO, that was linked to the N-terminus of a hydrophobic molecule (H); whereas the minimal epitope peptide antigens (A) were linked to a C-terminal extension (B2) that was linked to a linker precursor X2, DBCO, that was linked to the N-terminus of a hydrophobic molecule (H) to generate peptide antigen conjugates of Formula IV summarized in FIG. 4.

The general scheme for the synthesis of the peptide antigen conjugates was to react 1.0 equivalent of the peptide antigen fragment bearing a reactive azide with 1.2 equivalents of the DBCO bearing hydrophobic molecule (H) in DMSO at room temperature. The reaction was complete after 24 hours and did not require further purification.

We first assessed the hydrodynamic behavior of the peptide antigens (A) and peptide antigen conjugates (FIG. 4). Notably, peptide antigens (A) comprising the minimal epitopes (Mins) and LPs of both Irgq and Cpne1 were found to be water soluble up to 0.1 mg/mL, however, attachment of the peptide antigens (A) to either of the two hydrophobic molecules (H), $W_3$ or $2BXy_3$, led to the resulting peptide antigen conjugates undergoing particle formation, with the exception of the peptide antigen conjugate delivering the peptide antigen (A) comprising the LP of Cpne1 attached to $W_3$. These results indicate that peptide antigen conjugates of Formula IV induce particle formation of water-soluble peptides and that increasing the length of the hydrophobic molecule (H) or using more hydrophobic monomers (e.g., Glu(2BXy) versus Tryptophan) improves the reliability of particle formation.

Accordingly, it was found unexpectedly that a majority of peptide antigen conjugates tested formed particles when the hydrophobic molecule (H) of Formula I was comprised of 5 or more monomer units linked to adjuvants of Formula III, while hydrophobic molecules (H) of Formula I or II with less than 5 monomer units, such as 1 or 3 monomer units, less reliably induced particle formation. Based on these data, preferred embodiments of the hydrophobic molecules (H) used in peptide antigen conjugates are comprised of 5 or more monomer units to ensure particle formation of highly hydrophilic and/or charged peptide antigens (A). Though, in some embodiments, the hydrophobic molecule (H) may be 3 or more monomer units, such as 3, 4, 5, 6, 7, 8, 9, 10, 20, 30 or more monomer units, typically up to about 300 monomer units in length.

Figure 5:
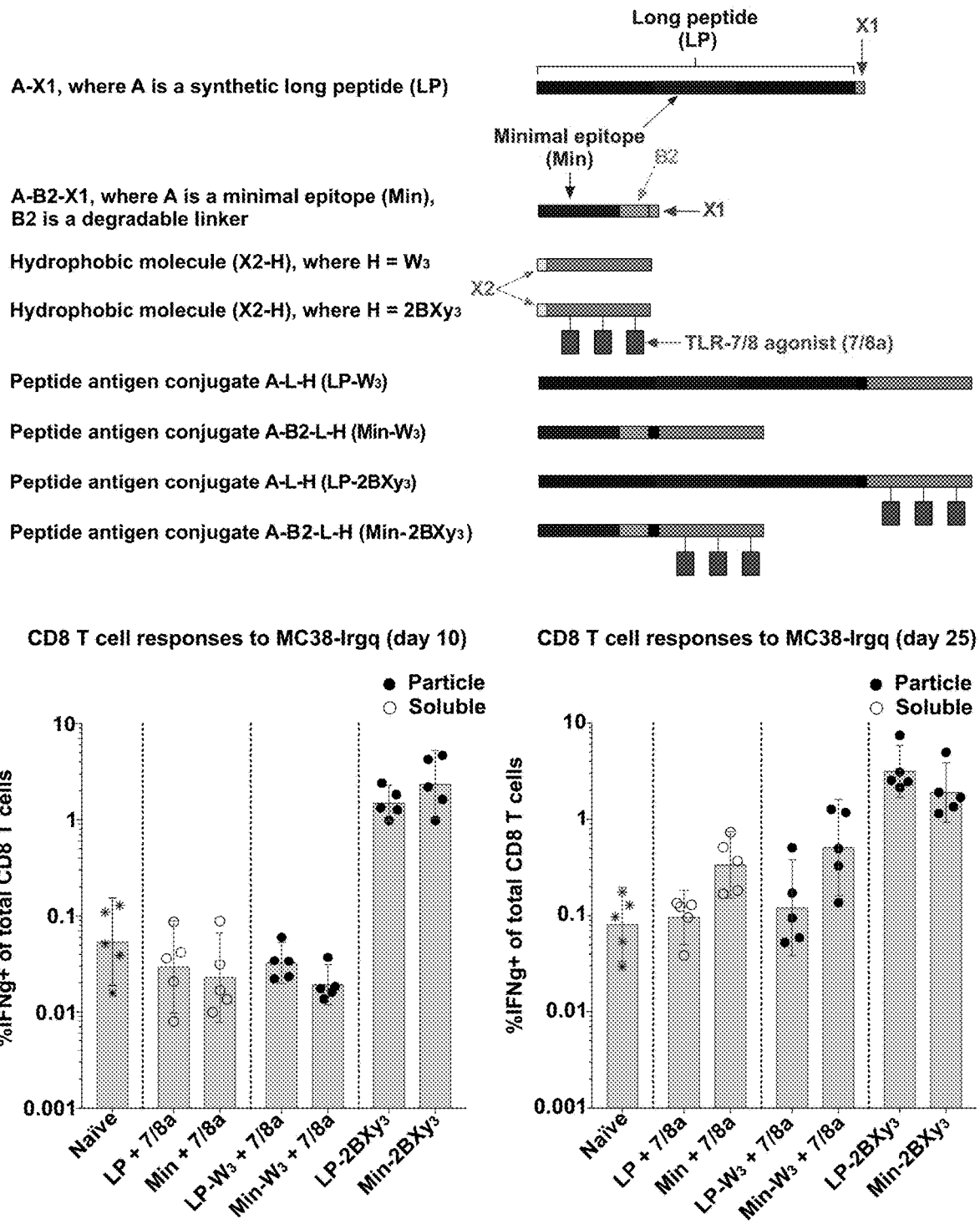
FIG. 5: Impact of peptide antigen (A) length, hydrodynamic behavior and co-delivery of a TLR-7/8 agonist (TLR-7/8a) on the immunogenicity of a peptide-based neoantigen (Irgq). Mice (N=5 per group) were immunized with different immunogenic compositions comprising peptide antigens (A) based on either the synthetic long peptide (LP, sometimes referred to as "SLP") or the minimal CD8 T cell epitope (Min, sometimes referred to as ME) of the antigen Irgq derived from the MC38 tumor cell line either as the peptide antigen (A) alone admixed with the TLR-7/8a adjuvant; as the peptide antigen (A) linked to a hydrophobic molecule (H), $W_3$, and admixed with the TLR-7/8a adjuvant; or as the peptide antigen (A) linked to a hydrophobic molecule (H) co-delivering a TLR-7/8a adjuvant, $2BXy_3$. Mice were immunized at days 0 and 14 and antigen-specific CD8 T cell responses (% IFNg+ of total CD8 T cells) were assessed from whole blood at days 0 and 25. Open circles indicate that the peptide antigen (A) was soluble (i.e. non-particulate), whereas closed circles indicate that the mice received a particulate immunogenic composition of the peptide antigen (A).
Figure 6:
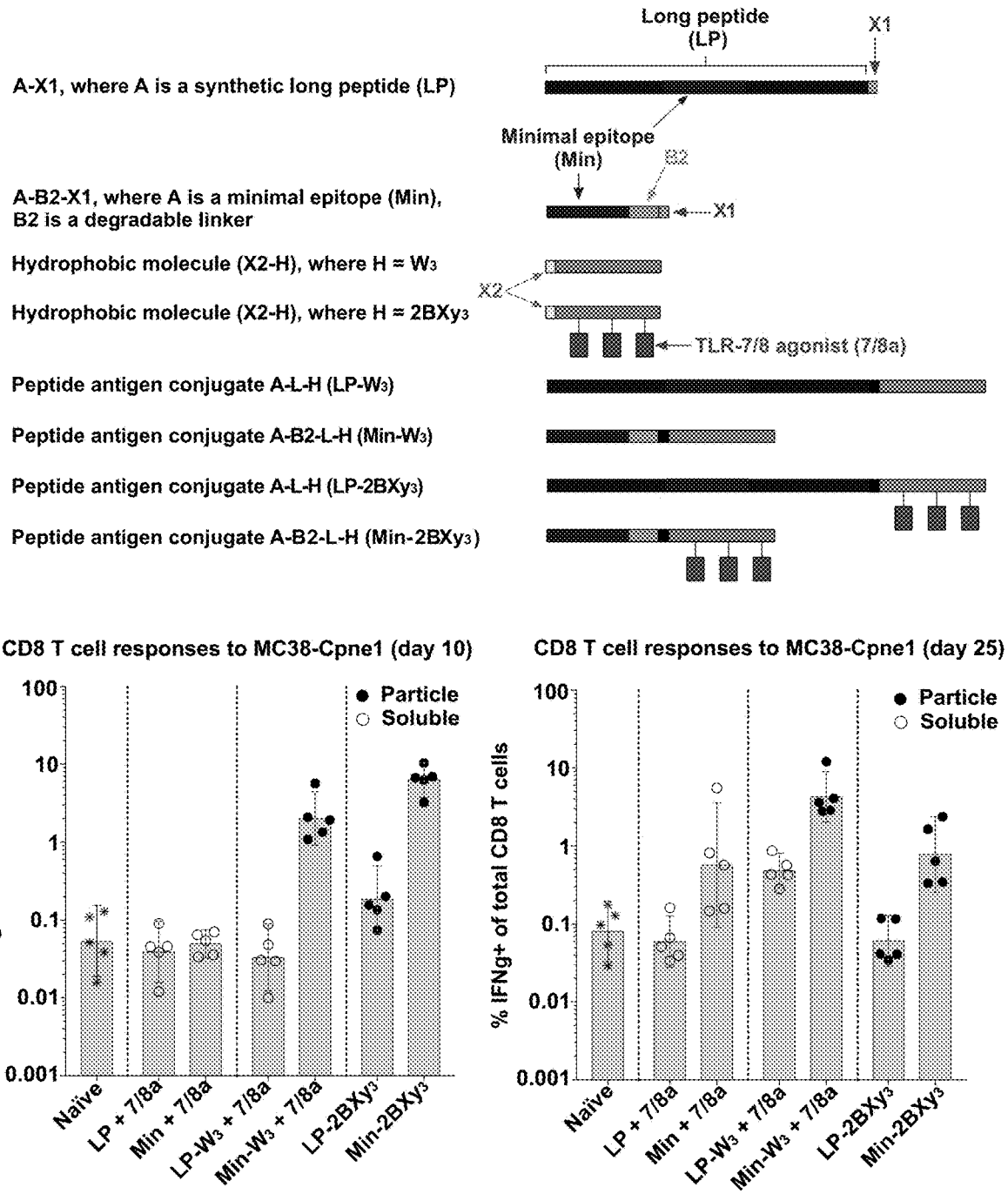
FIG. 6: Impact of peptide antigen (A) length, hydrodynamic behavior and co-delivery of a TLR-7/8a adjuvant on the immunogenicity of a peptide-based neoantigen (Cpne1). Mice (N=5 per group) were immunized with different immunogenic compositions comprising peptide antigens (A) based on either the synthetic long peptide (LP) or minimal CD8 T cell epitope (Min) of the antigen Cpne1 derived from the MC38 tumor cell line either as the peptide antigen (A) alone admixed with the TLR-7/8a adjuvant; as the peptide antigen (A) linked to a hydrophobic molecule (H), $W_3$, and admixed with the TLR-7/8a adjuvant; or as the peptide antigen (A) linked to a hydrophobic molecule (H) co-delivering a TLR-7/8a adjuvant, $2BXy_3$. Mice were immunized at days 0 and 14 and antigen-specific CD8 T cell responses (% IFNg+ of total CD8 T cells) were assessed from whole blood at days 0 and 25. Open circles indicate that the peptide antigen (A) was soluble (i.e. non-particulate), whereas closed circles indicate that the mice received a particulate immunogenic composition of the peptide antigen (A).

We next assessed how hydrodynamic behavior of the peptide antigen conjugate, as well as the peptide antigen (A) length and co-delivery of a TLR-7/8a adjuvant comprising the peptide antigen conjugate impacts immunogenicity in vivo. Peptide antigen conjugates delivering peptides antigens (A) comprised of either 26 amino acid long peptides (LP) or 10 amino acid minimal epitopes (Mins) were either mixed with the small molecule TLR-7/8a, Compound 2, referred to as 2BXy; linked to the hydrophobic molecule (H), $W_3$, and mixed with 2BXy; or, the peptide antigens (A) were linked to the hydrophobic molecule (H), $2BXy_3$, which forms particles and ensures co-delivery of the peptide antigen (A) with the TLR-7/8a adjuvant (See FIGS. 4-6). The mice immunized with the peptide antigen conjugates delivering peptide antigens (A) comprised of minimal epitopes linked to the hydrophobic molecule (H), $2BXy_3$, provided the highest magnitude CD8 T cell responses (>1% IFNg+ CD8 T cells of total) after a single immunization, indicating that co-delivery of the minimal epitope with the TLR-7/8a in a particle format is an efficient approach for eliciting CD8 T cell responses. Notably, the soluble minimal epitope and soluble LP mixed with TLR-7/8a induced the lowest CD8 T cell responses that were not statistically significant as compared with the naïve groups, indicating that the soluble form of the peptide antigen (A) is the least immunogenic (FIGS. 5 and 6). Finally, while the peptide antigen conjugates delivering peptide antigens (A) comprised of either minimal epitopes of Irgq or LP of Irgq linked to the hydrophobic molecule (H), $2BXy_3$, provided comparable magnitude of CD8 T cell responses, the peptide antigen conjugates delivering peptide antigens (A) comprised of the minimal epitope Cpne1 induced nearly 10-fold higher CD8 T cell responses as compared with peptide antigen conjugates delivering Cpne1 as the LP.

To further investigate the role of peptide antigen (A) length on immunogenicity for promoting CD4 and CD8 T cell immunity for peptide antigen conjugates of Formula IV, 7 predicted minimal CD8 T cell epitopes (i.e. predicted neoantigens) derived from the murine tumor model, B16, were delivered either as 27 amino acid synthetic long peptides (LPs) or 10 amino acid minimal epitopes (referred to as ME or Min) as peptide antigens (A) comprising the peptide antigen conjugates of Formula IV (See FIG. 7). The LP-based peptide antigens (A) were linked directly at the C-terminus to a linker precursor X1, azido-lysine (K'), that was linked to a linker precursor X2, DBCO, that was linked to the N-terminus of a hydrophobic molecule (H); whereas the minimal epitope peptide antigens (A) were linked to a C-terminal extension (B2) that was linked to a linker precursor X2, DBCO, that was linked to the N-terminus of a hydrophobic molecule (H) to generate peptide antigen conjugates of Formula IV summarized in FIG. 7. The peptide antigens (A) were linked either to $2BXy_5$ or $2B_5$ hydrophobic molecules (H) to form peptide antigen conjugates. Comparing $2BXy_5$ with $2B_5$, which are structurally similar but differ in terms of potency for TLR-7, allowed for the evaluation of how inflammation impacts immunogenicity. Mice were immunized with immunogenic compositions comprised of peptide antigen conjugates delivering peptide antigens (A) as either the minimal epitopes (Mins), the LPs or both the minimal epitopes and the LPs. The magnitude of CD4 and CD8 T cell responses were evaluated 2 weeks following 2 immunizations (FIG. 8).

A striking and unexpected finding was that the mice that received the peptide antigen conjugates delivering peptide antigens (A) comprising minimal epitopes ("Min") induced the highest magnitude CD8 T cell responses, whereas the peptide antigen conjugates delivering peptide antigens (A) comprising the LPs induced the lower level CD8 T cell responses. This trend was apparent for both of the hydrophobic molecules (H), $2BXy_5$ and $2B_5$. Accordingly, for the peptide antigen conjugates delivering the peptide antigen (A) comprising the LP linked to the hydrophobic molecule (H), $2BXy_5$, the CD8 T cell responses were ~0.35% and CD4 T cell responses were ~0.25% (FIG. 8). In contrast, for the group of mice that received the peptide antigen conjugates delivering the peptide antigen (A) comprising the minimal epitope linked to the hydrophobic molecule, $2BXy_5$ the CD8 T cell responses were ~1.9% and CD4 T cell responses at were ~0.1%, providing about a 6-fold increase in CD8 T cell responses over the peptide antigen conjugates delivering the LP but undetectable CD4 T cell responses. In the group of mice that received the peptide antigen conjugates delivering peptide antigens (A) comprising both the minimal epitope and LP ("LP+min"), the CD8 T cell responses were ~0.6% and the CD4 T cell responses were ~0.5%, providing a balance of both CD4 and CD8 T cells (FIG. 8).

A similar trend was observed for the peptide antigen conjugates using the $2B_5$ hydrophobic molecule (H), which includes the less potent TLR-7/8 agonist, 2B, as compared with the hydrophobic molecule (H), $2BXy_5$, which includes 2BXy. Accordingly, in the group that received peptide antigen conjugates that included the $2B_5$ hydrophobic molecule (H) and peptide antigens (A) comprising LP, there were CD8 T cell responses detected at ~1.0% and CD4 T cell responses at ~0.75%, whereas in the group that received peptide antigen conjugates delivering peptide antigens (A) comprising Min alone, there were CD8 T cell responses at ~4.5% and CD4 T cell responses at ~0.1%, a nearly 4-fold increase in CD8 T cell responses but undetectable CD4 T cell responses. In the group that received a vaccine that comprised peptide antigen conjugates delivering peptide antigens (A) comprising the minimal epitope and LP linked to the hydrophobic molecule (H) $2B_5$, the CD8 T cell responses were ~2.2% and the CD4 T cell responses were ~0.95% (FIG. 8).

Figure 9:
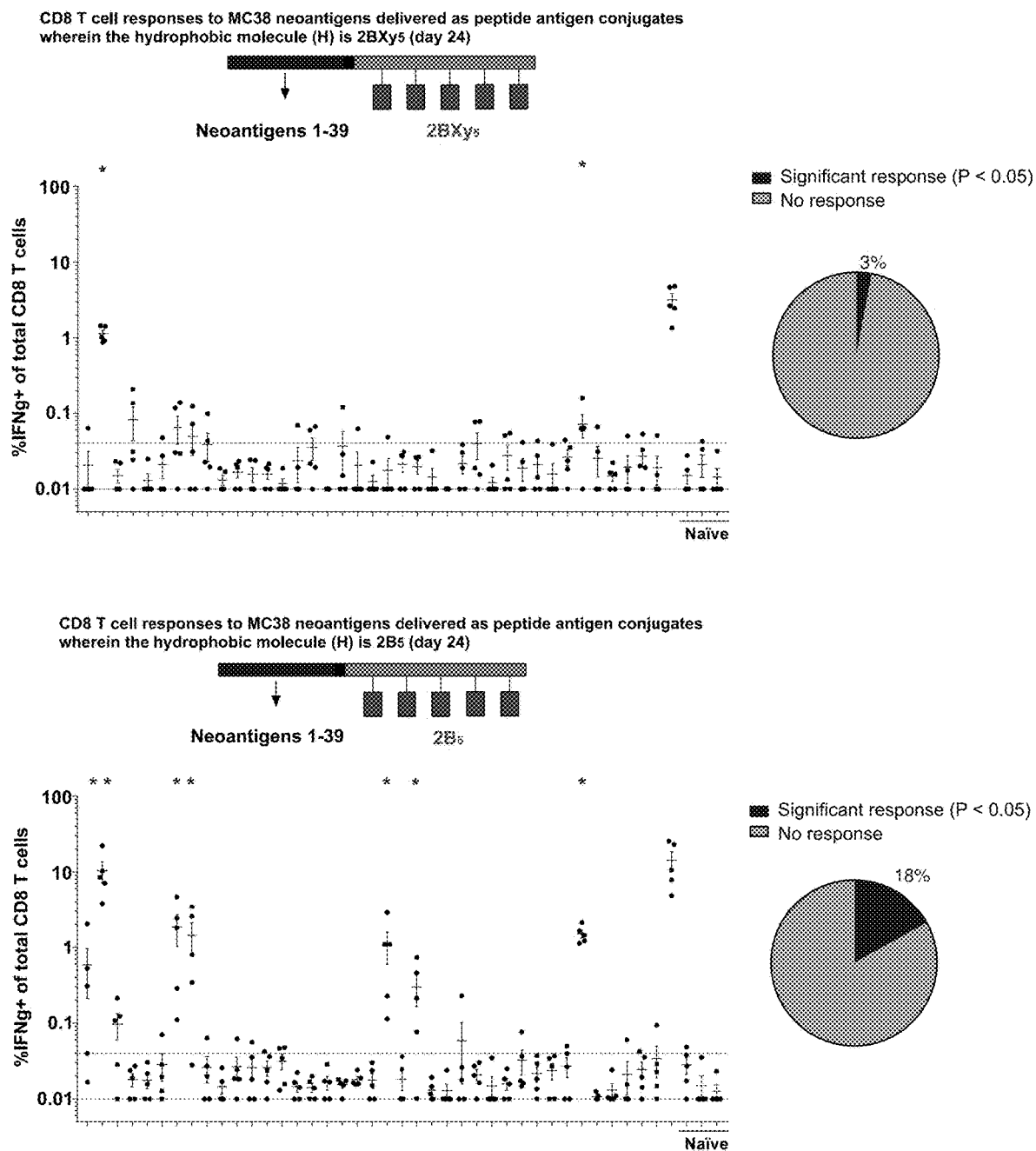
FIG. 9: Impact of the potency of the TLR-7/8a linked to the hydrophobic molecule (H) on the immunogenicity and breadth of T cell responses generated against a library of peptide neoantigens. Mice (N=5 per group) were immunized with immunogenic compositions comprising 4 unique peptide antigen conjugates delivering a distinct MC38 tumor derived minimal CD8 T cell epitopes (40 total epitopes) that were linked to either $2BXy_5$ or $2B_5$ hydrophobic molecules (H). Mice were immunized at days 0 and 14 and antigen-specific CD8 T cell responses (% IFNg+ of total CD8 T cells) were assessed from whole blood at day 24. The CD8 T cell responses against each of the 40 epitopes is shown. The proportion of peptide antigens (A) comprising minimal CD8 T cell epitopes that led to CD8 T cell responses is shown in the pie chart.

In summary, the use of the ME (or "Min") as the peptide antigen (A) of the peptide antigen conjugates of Formula IV led to an unexpected and marked increase in the CD8 T cell response as compared with the peptide antigen (A) comprising the LP. However, this also led to a reduction in the CD4 T cell responses. Importantly, inclusion of peptide antigen conjugates delivering the LP and Min as peptide antigens (A) in immunogenic compositions administered to the mice led to a restoration of the CD4 T cell response and an unexpectedly higher CD8 T cell response as compared with peptide antigen conjugates delivering peptide antigens (A) comprised of the LP alone. Another key finding was that the amount of inflammation had a marked impact on immunogenicity. The hydrophobic molecule (H), $2B_5$, contains the TLR-7/8a, Compound 1, which is nearly 10-fold less potent than Compound 2, 2BXy, delivered on the hydrophobic molecule (H), $2BXy_5$. Therefore, the nearly 3- to 4-fold increase in CD4 and CD8 T cell responses for peptide antigen conjugates comprising the hydrophobic molecule (H), $2B_5$, as compared with those using $2BXy_5$, suggest that moderation of the amount of inflammation through modulation of adjuvant potency may be preferred for achieving the optimal level of immunogenicity for peptide antigen conjugates of the present disclosure. Indeed, in a screen of the immunogenicity of 40 different peptide-based neoantigens derived from the MC38 murine tumor cell line, personalized cancer vaccines based on peptide antigen conjugates delivering peptides antigens (A) comprised of minimal epitopes linked to the hydrophobic molecule (H), $2B_5$, led to a 6-fold improvement in the breadth of CD8 T cell responses achieved as compared with peptide antigen conjugates comprised of minimal epitopes linked to the hydrophobic molecule (H), $2BX_{y5}$ (FIG. 9).

Figure 10:
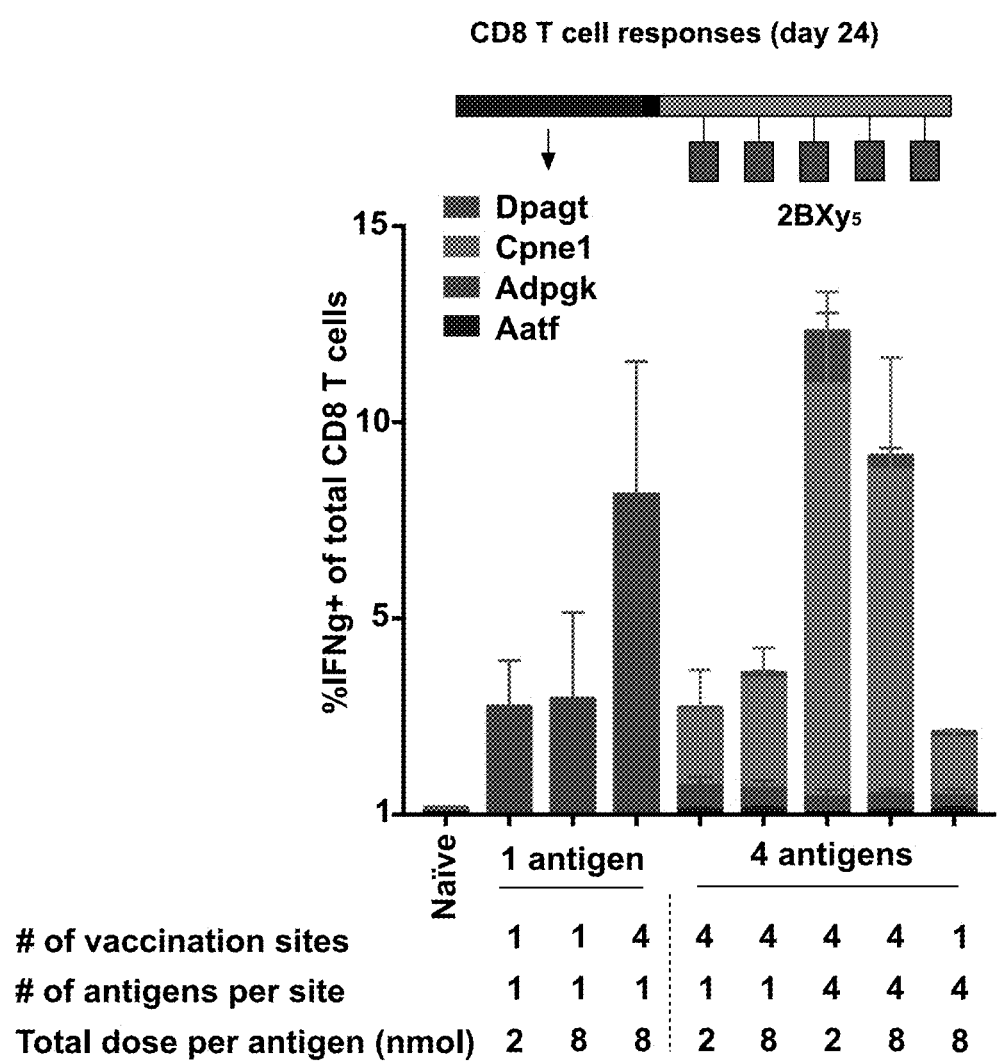
FIG. 10: Impact of the number and dose of peptide antigens (A), as well as the number of vaccination sites, on the immunogenicity of peptide based neoantigens. Mice (N=5 per group) were either immunized with peptide antigen conjugates comprising a single minimal CD8 T cell epitope (Adpgk), or peptide antigen conjugates comprising 4 different minimal CD8 T cell epitopes (Dpagt, Cpne1, Adpgk and Aatf). The dose of the peptide antigen (A) and number of vaccination sites was varied for the different groups. Mice were immunized at days 0 and 14 and antigen-specific CD8 T cell responses (% IFNg+ of total CD8 T cells) were assessed from whole blood at day 24.

An additional unexpected finding related to studies seeking to identify the optimal means of dosing multiple different T cell epitopes as peptide antigen conjugates. Prior studies have suggested that dosing multiple T cells epitopes at the same site that bind the same MHC molecule may compete for binding to MHC molecules on APCs and that this may result in competition for presentation to T cells, thereby lowering the magnitude of T cell responses to epitopes delivered together, as compared with epitopes delivered alone as a single epitope per immunization site. While we observed that administering immunogenic compositions including peptide antigen conjugates comprising a single epitope to mice resulted in a higher magnitude T cell response against that epitope, as compared with co-administering the same epitope with 3 different peptide antigen conjugates comprising different epitopes that all bind the same MHC molecule at either 1 or 4 sites (FIG. 10), an unexpected finding that was delivery of those same 4 epitopes at 4 separate sites (i.e. 1 unique epitope per site) in the same animal led to lower responses than delivering all 4 epitopes together at 4 sites (FIG. 10). This was unexpected and paradoxical to the current paradigm, which would suggest that it is better to dose multiple epitopes at distinct sites to avoid competition between epitopes, rather than delivering multiple epitopes together at multiple sites. These data suggest a new paradigm for delivering multiple different epitopes based on maximizing the number of sites where each epitope is administered. Therefore, in preferred methods of inducing an immune response, immunogenic compositions comprising multiple different peptide antigens (A) are dosed at multiple sites to maximize the immune response.

Example 3: Peptide Antigen Conjugates of Formula V

The prior data demonstrate how parameters of peptide antigen conjugates of Formula IV impact immunogenicity. These data show that peptide antigen conjugates that ensure co-delivery of peptide antigens (A) with TLR-7/8a in particles is a preferred embodiment for inducing CD8 T cell immunity. A limitation of peptide antigen conjugates of Formula IV is that the particles formed by this approach may have variable size and stability owing to variability in the composition of the peptide antigens (A) linked to the hydrophobic molecules (H). One possible means of stabilizing the particles formed by peptide antigen conjugates is by introducing surface charge that prevents particle aggregation and stabilizes the particles formed by the peptide antigen conjugates in aqueous media.

Figure 11:
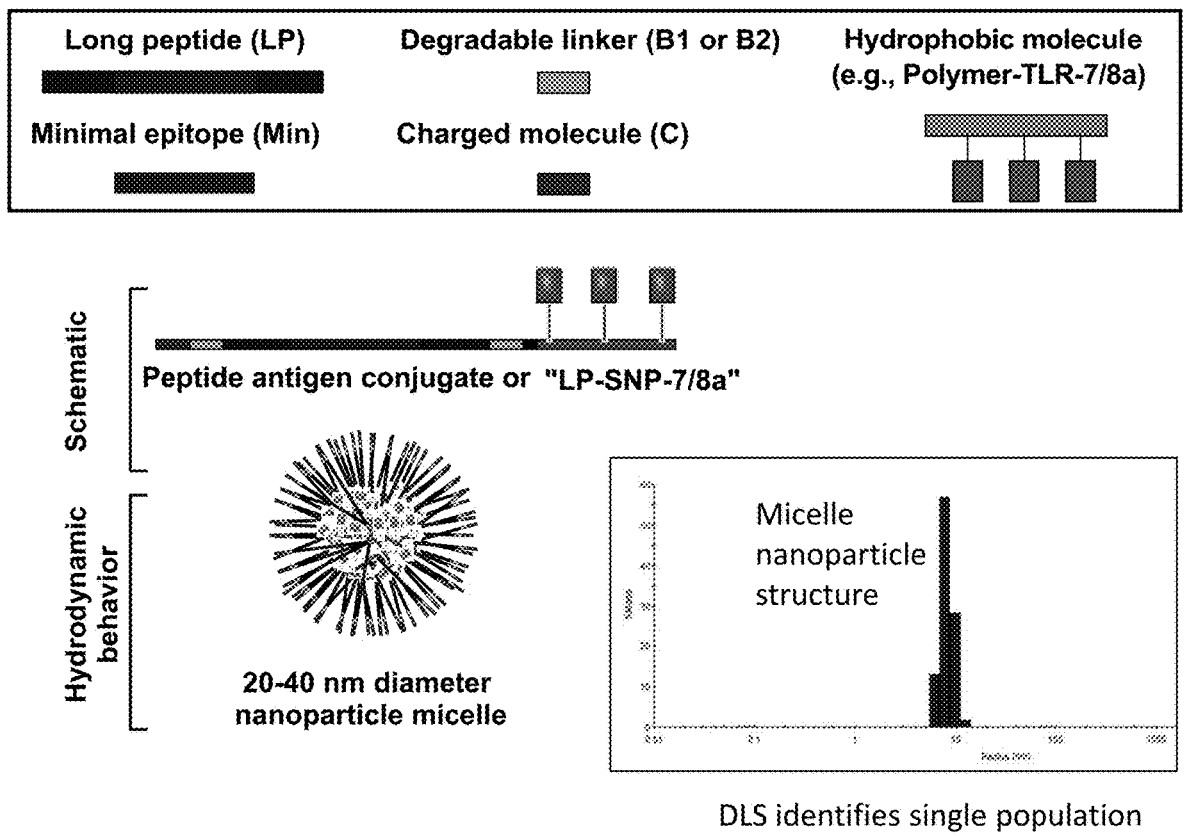
FIG. 11: Schematic of a peptide antigen conjugate of Formula V.

Peptide antigen conjugates of Formula V allow for stable particles of a defined size to be formed by appending a charged molecule (C) to a peptide antigen (A) that is linked to a hydrophobic molecule (H) (FIG. 11). However, directly conjugating a charged molecule (C) and/or a hydrophobic molecule (H) immediately adjacent to a peptide antigen (A) may cause interference with the processing and presenting machinery of the APC that allows for presentation of minimal epitopes within the context of MHC-I and MHC-II. Thus, to ensure efficient processing of peptide antigens (A) based on minimal epitopes (Mins) or LPs delivered using peptide antigen conjugates of Formula V, we evaluated the use of enzyme degradable extensions (B1 and B2) linking the peptide antigen (A) to the charged molecule (C) and hydrophobic molecule (H) at the N- and C-termini, respectively (FIG. 11).

Figure 12:
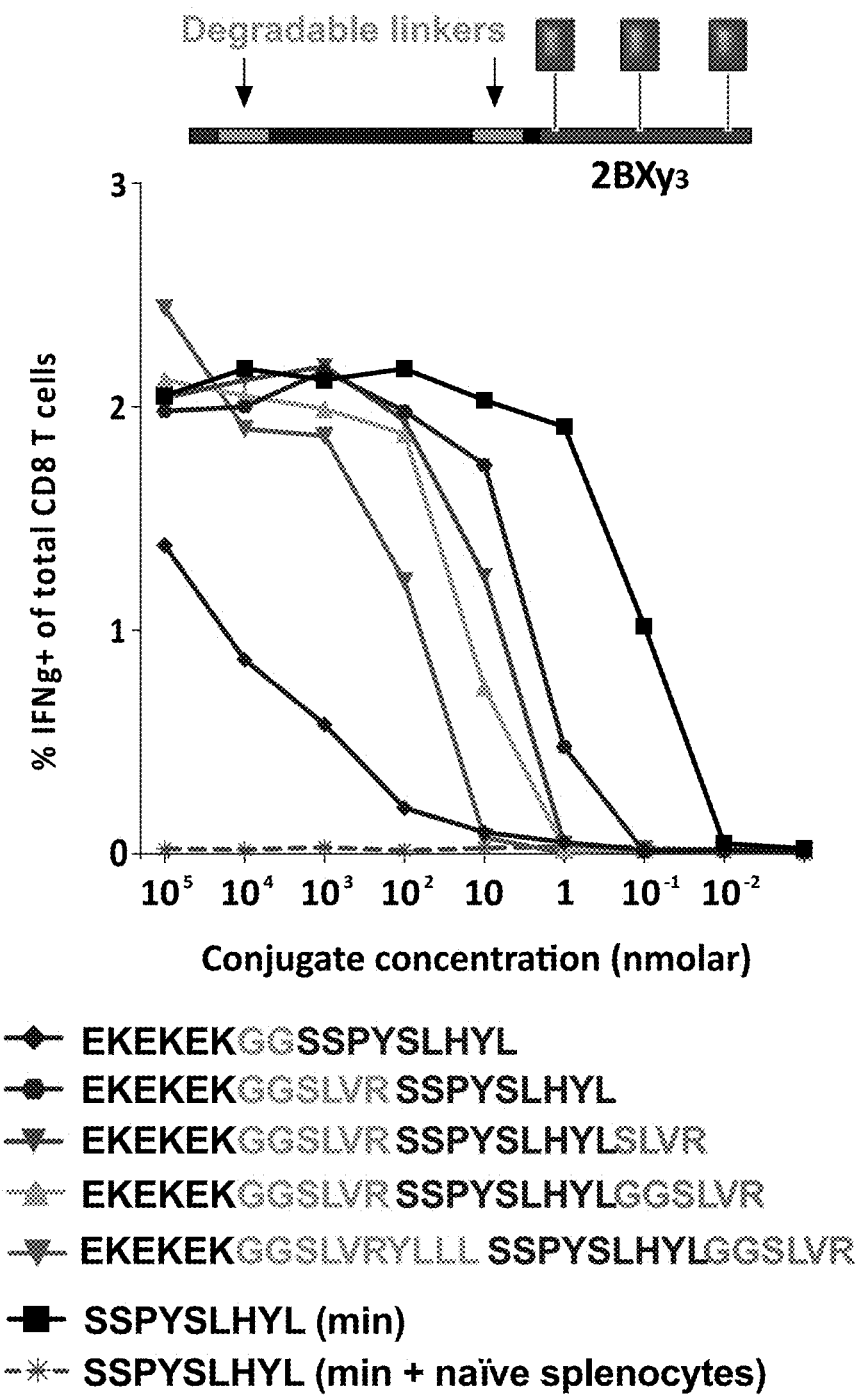
FIG. 12: (SEQ ID NOS: 98-102, followed by SEQ ID NO: 1 (SSPYSLHYL), respectively, in order of appearance) Impact of the N- and C-terminal extensions (B1 and B2) on the in vitro potency for CD8 T cell activation. A splenocyte culture with APCs and neoantigen (Cpne1)-specific CD8 T cells was stimulated in vitro with minimal CD8 T cell epitope (Cpne1) peptide antigens (A) linked to different extensions (B1 and B2) and assessed for their capacity to stimulate IFNg production of the Cpne1-specific CD8 T cells.

To evaluate the impact of the extensions (B1 and B2) on the processing of minimal CD8 T cell epitopes from peptide antigen conjugates of Formula V, we synthesized a series of peptides wherein a charged molecule (C) was linked to an optional extension (B1) at the N-terminus of a minimal epitope, Cpne1, that was linked to an optional extension (B2) at the C-terminus to a linker precursor X1 (Lys(N3)) and evaluated how the charged molecule (C) and extensions (B1 and/or B2) impacted the in vitro potency of the peptide antigens (A) for activating Cpne1-specific CD8 T cells. As shown in FIG. 12, peptide sequences were prepared using cathepsin cleavable extensions, or combined cathepsin cleavable and immuno-proteasomal extensions, at either or both the N- and C-termini (B1 and/or B) of the minimal epitopes. These peptide antigen (A) sequences linked to extensions (B1 and/or B2) were added to splenocyte cultures at different concentrations to assess the efficiency of the different constructs for promoting uptake and presentation of the minimal epitope, Cpne1, by APCs.

As expected, the minimal epitope (U, FIG. 12), which requires no processing and can be directly loaded in the context of MHC-I and presented to APCs was the most efficient and provided the highest potency (lowest EC50) in vitro. However, addition of a charged molecule (C) (Glu-Lys-Glu-Lys-Glu-Lys SEQ ID NO: 71) directly to the N-terminus of the minimal epitope (*) without the use of a degradable extension (B1) led to a nearly 10,000-fold decrease in potency as compared with the minimal epitope used alone. Notably, the activity of the minimal epitope was restored simply by placing an enzyme degradable tetrapeptide extension (B1) (i.e. Ser-Leu-Val-Arg SEQ ID NO: 7) between the charged molecule (C) and the minimal epitope (Hexagons, FIG. 12). Placing an additional cathepsin cleavable extension (B2) at the C-terminus (i.e., Ser-Leu-Val-Arg SEQ ID NO: 7), or combining an immuno-proteasome degradable sequence with the cathepsin cleavable extension at the N-terminus (B1) (Ser-Leu-Val-Arg-Tyr-Leu-Leu-Leu SEQ ID NO: 72) or C-terminus ($B_2$) (Gly-Gly-Ser-Leu-Val-Arg SEQ ID NO: 13) had minimal additional impact on potency as compared with using a single tetrapeptide extension (B1) between the charged molecule (C) and the minimal epitope peptide antigen (A).

The next studies sought to evaluate the impact of the enzyme degradable extensions (B1 and B2) on the efficiency of antigen cross-presentation in vivo using peptide antigen conjugates of Formula V, wherein the hydrophobic molecule (H) was $2BXy_3$.

The general scheme for the synthesis of the peptide antigen conjugates of Formula V was to react 1.0 equivalent of the peptide antigen bearing a reactive azide with 1.2 equivalents of the DBCO bearing hydrophobic molecule (H) in DMSO at room temperature. The reaction was complete after 24 hours and did not require further purification.

As shown in FIG. 13, peptide antigen conjugates were synthesized with different charged molecules (C) (e.g., Lys-Ser-Lys-Ser-Lys-Ser SEQ ID NO: 73, Glu-Ser-Glu-Ser-Glu- Ser SEQ ID NO: 74 and Glu-Lys-Glu-Lys-Glu-Lys SEQ ID NO: 71) using different combinations of enzyme degradable extensions at the N- and C-termini (B1 and B2) of the minimal epitope, Cpne1. Mice were vaccinated with the different immunogenic compositions reported in FIG. 13 at 0 and 14 days and T cell responses were assessed from whole blood at days 10 (FIG. 14A) and 28 (FIG. 14B). Consistent with the in vitro data from FIG. 12, placing any of the three charged molecules (C) at the N-terminus of the minimal epitope, without use of a B1 extension, resulted in complete abrogation of CD8 T cell responses (~0.1% IFN-γ+ of total CD8+ T cells) after assessing responses in whole blood of animals primed with a single immunization (FIG. 14). However, placing a cathepsin cleavable extension (B1) between the charged molecule (C) and the N-terminus of the peptide antigen (A) comprised of the minimal epitope resulted in a nearly 10-fold increase in CD8 T cell responses of the peptide antigen conjugates using the positively charged molecule (C) (Lys-Ser-Lys-Ser-Lys-Ser SEQ ID NO: 73) and a modest improvement in CD8 T cell responses for the peptide antigen conjugates with the ES and EK charged molecules (C) (FIG. 14). Among the groups vaccinated with peptide antigen conjugates comprising a positively charged molecule (C) (Lys-Ser-Lys-Ser-Lys-Ser SEQ ID NO: 73), addition of both an N-terminal and a C-terminal cathepsin cleavable extension (B1 and B2) resulted in CD8 T cell responses of about 3.5% after a single immunization, while addition of immunoproteasomal sequences at B1 and/or B2, in addition to the cathepsin cleavable sequences, led to only a modest further increase in the magnitude of the CD8 T cell responses (FIG. 14). Trends were consistent in the data after 2 immunizations for the peptide antigen conjugates using all 3 sets of charged molecules (C): including N- and C-terminal cathepsin cleavable extensions (B1 and B2) between the charged molecule (C) and hydrophobic molecules (H), respectively, generally led to the highest magnitude responses, with little to no improvement in responses by addition of an immuno-proteasomal linker.

These data exemplify the unexpected finding that a cathepsin cleavable peptide extension (B1), e.g., such as Ser-Leu-Val-Arg (SEQ ID NO: 7), placed at the N-terminus of peptide antigens of peptide antigen conjugates of Formula V is a preferred embodiment to promote antigen presentation in vitro and cross-priming of CD8 T cells in vivo. Modest additional improvements in CD8 T cell responses were seen when cathepsin cleavable peptide extensions were placed at both the N- and C-termini and when the cathepsin cleavable extension (B2) at the C-terminus was combined with a sequence that additionally favors immuno-proteasome processing (e.g., the dipeptide, Gly-Gly, of Gly-Gly-Ser-Leu-Val-Arg SEQ ID NO: 13). In summary, preferred embodiments of peptide antigen conjugates include a cathepsin cleavable extension (B1) between the N-terminus of the peptide antigen (A) and any additional components, e.g., charged molecules (C); and optionally a cathepsin or combined cathepsin and immuno-proteasome degradable extension (B2) at the C-terminus.

Figure 16:
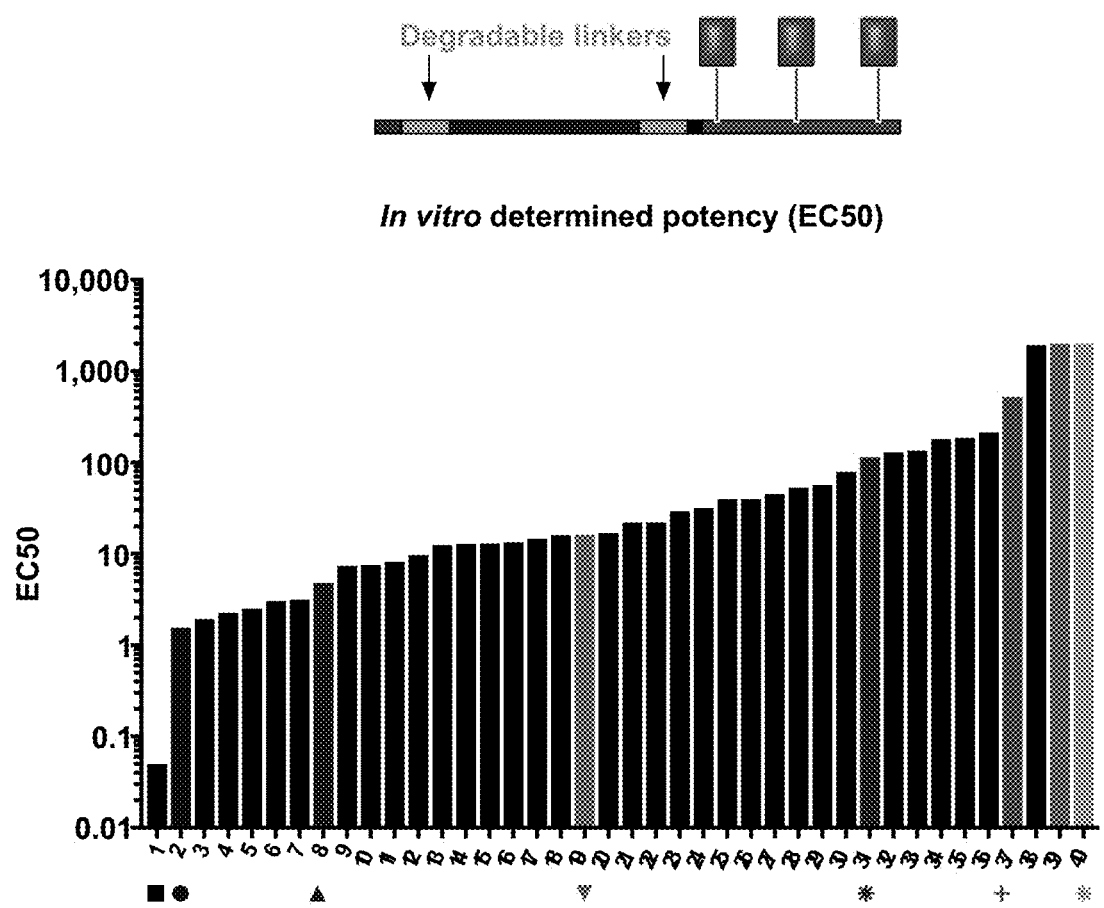
FIG. 16: The effective concentration at half maximal activity (EC50) is shown for the different peptide antigen conjugates evaluated in FIG. 15. A lower EC50 indicates higher potency.
Figure 17:
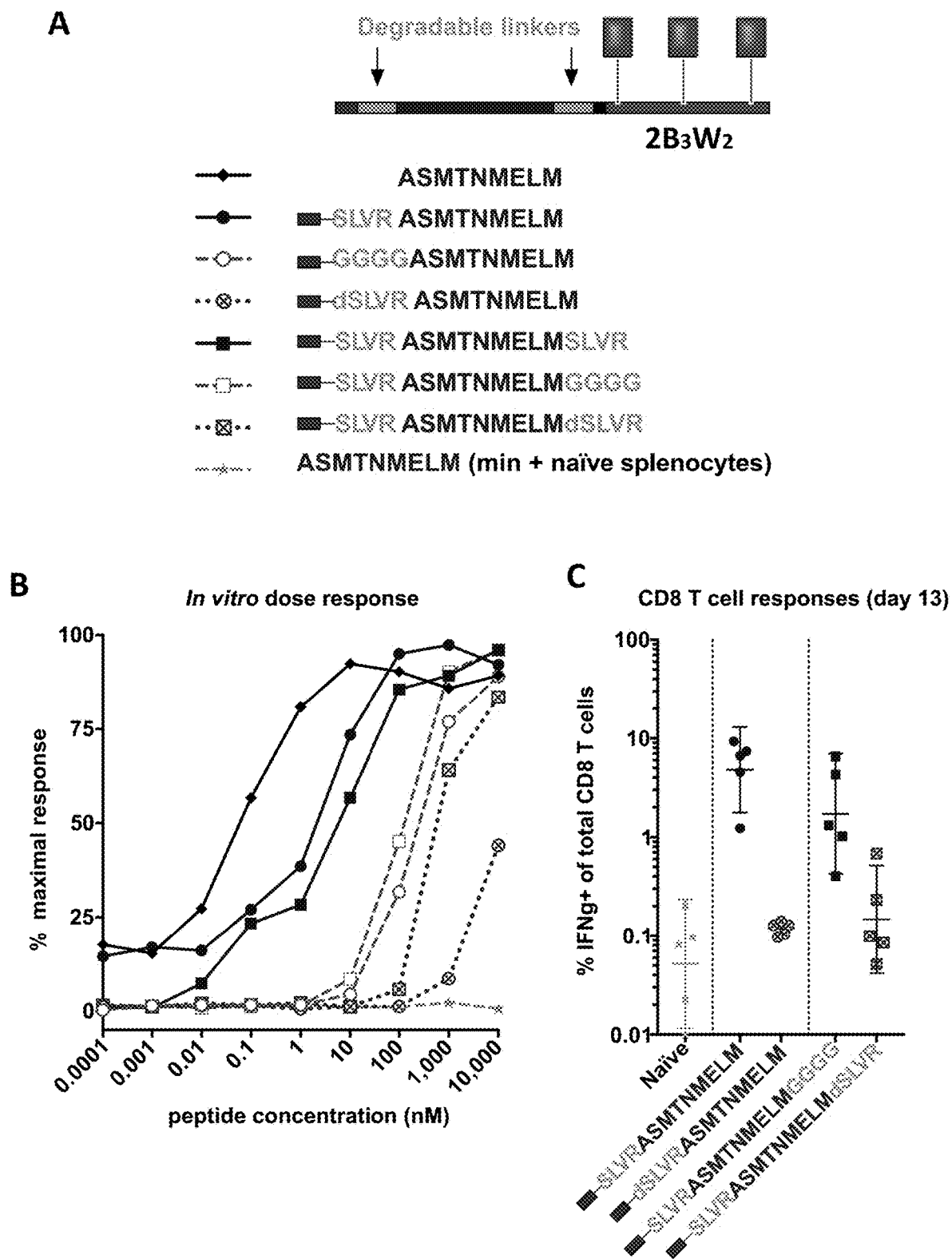
FIG. 17: (SEQ ID NOS: 77, 105-110, 105, 107, 109 and 110, respectively, in order of appearance) Impact of the N- and C-terminal extensions (B1 and B2) on the in vitro potency for CD8 T cell activation and in vivo potency for eliciting de novo CD8 T cell responses. (A) A minimal CD8 T cell epitope (Adpgk) peptide antigen (A) was linked to different extensions (B1 and B2) and assessed for the capacity to stimulate IFNg production from Adpgk-specific CD8 T cells (B). The capacity of peptide antigen conjugates, with different N- and C-terminal extensions (B1 and B2) linked to the hydrophobic molecule (H) $2B_3W_2$ was assessed on day 13 after a single immunization.

To extend these findings, we synthesized peptide antigen conjugates with different combinations and compositions of cathepsin degradable extensions at the N- and C-termini (B1 and B2) of the minimal epitope, Adpgk (FIG. 15). The different compositions of peptides shown in FIG. 15 were added to splenocyte cultures at different concentrations to assess the efficiency of the different constructs for promoting uptake and presentation of the minimal epitope, Adpgk, by APCs. The in vitro determined potency (EC50) for the peptide antigen, Adpgk, with different combinations and compositions of cathepsin degradable extensions at the N- and C-termini (B1 and B2) is shown in FIG. 16. To confirm the in vitro findings, a subset of the sequences, based on the formula C-B1-A-B2-X1, shown in FIG. 15 were linked to the hydrophobic molecule (H), $2B_3W_2$, and then administered to mice. CD8 T cell responses was assessed at day 13 (FIG. 17) and are consistent with the results from the in vitro screens, confirming that cathepsin degradable extensions linking the peptide antigen (A) to the charged molecule (C) and hydrophobic molecule (H) at the N- and C-termini, respectively, can lead to improved antigen presentation in vitro as well as improved efficiency of antigen cross-presentation in vivo.

Impact of Net Charge and Extension Sequence (B1 and B2) on Particle Size

While it is understood that the surface charge of particles influences their stability in solution, the impact of charge density and net charge of peptide antigen conjugates on the size and stability of supramolecular assemblies of those peptide antigen conjugates in aqueous solutions has not been well studied.

To provide a greater understanding of how charge density and the net charge of amphiphilic macromolecules impacts the hydrodynamic behavior of self-assembling particles, we synthesized a series of peptide antigen conjugates of Formula V (FIG. 18) with varying composition of peptide antigens (A), charged molecules (C), extensions (B1 and B2) and hydrophobic molecules (H) and evaluated how these parameters impact the size and stability of particles formed by peptide antigen conjugates suspended in aqueous solutions at a pH of about 7.4 (FIG. 18).

Figure 19:
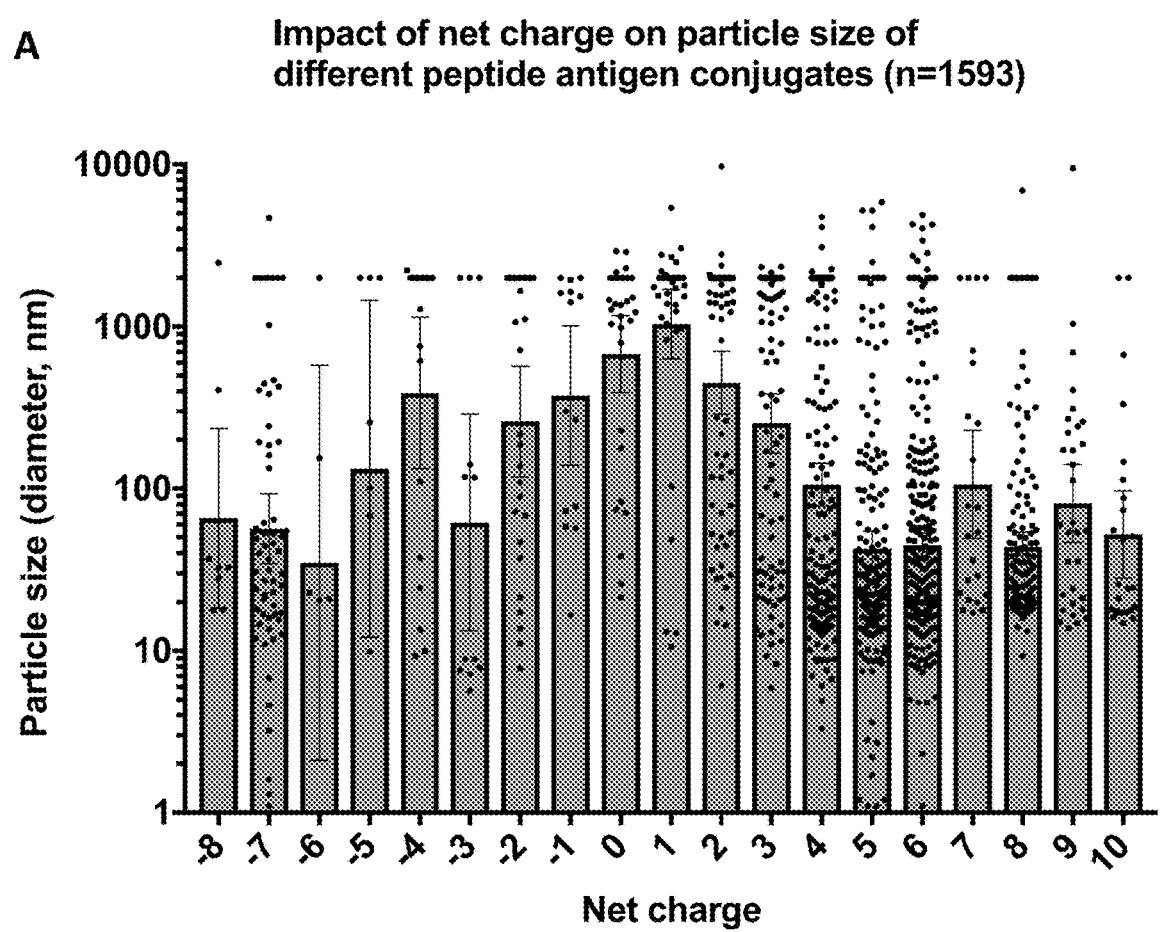
FIG. 19: Impact of peptide antigen conjugate net charge on hydrodynamic behavior. (A) The impact of net charge on the hydrodynamic behavior of a range of different peptide antigen conjugates of Formula V suspended at 0.1 mg/mL or 0.5 mg/mL in PBS at a pH of 7.4 was assessed by dynamic light scattering. (B) Figure panel B shows a curated list of the data shown in Figure panel (A). (C) GRAVY frequency distribution and (D) charge frequency distribution of the antigens delivered as peptide antigen conjugates. (E) Particle size of matched LP neoantigens (n=39) prepared as peptide antigen conjugates of Formula V that self-assemble into nanoparticles co-delivering a TLR-7/8a ("SNP-7/8a") with either +6 or ≥+8 net charge. (F) Impact of peptide antigen conjugate net charge and grand average of hydropathy (GRAVY) on hydrodynamic behavior. The hydrodynamic behavior of a range of different peptide antigen conjugates suspended at 0.1 mg/mL in PBS at a pH of 7.4 was assessed by dynamic light scattering. The number average particle diameter as a function of net charge and GRAVY value is reported.
Figure 19:
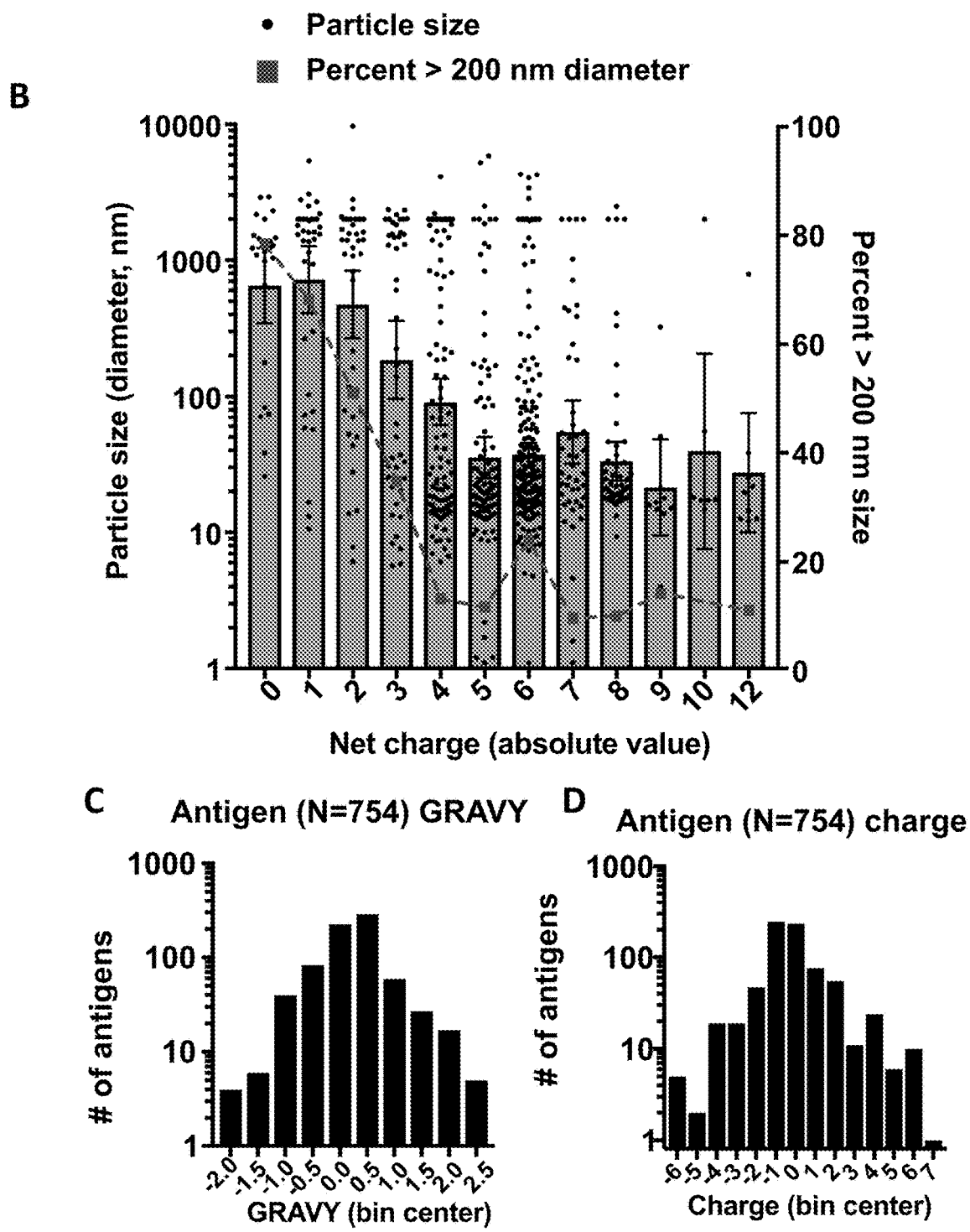
Figure 19:
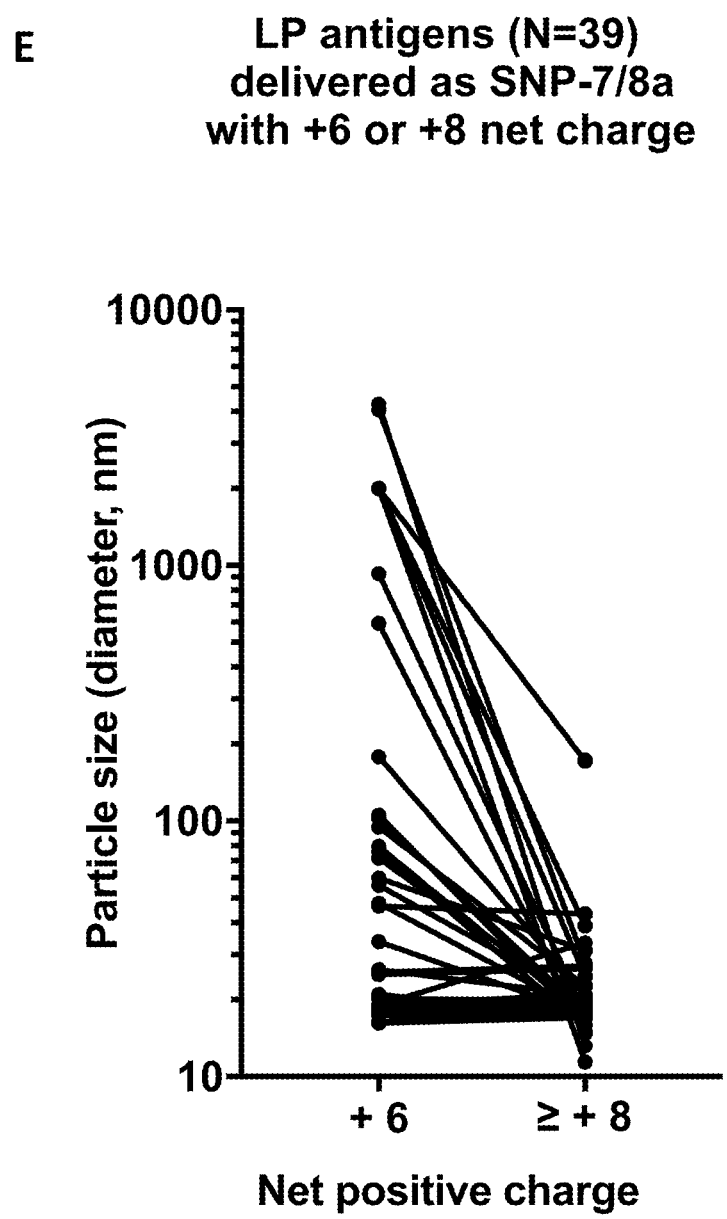
Figure 19:
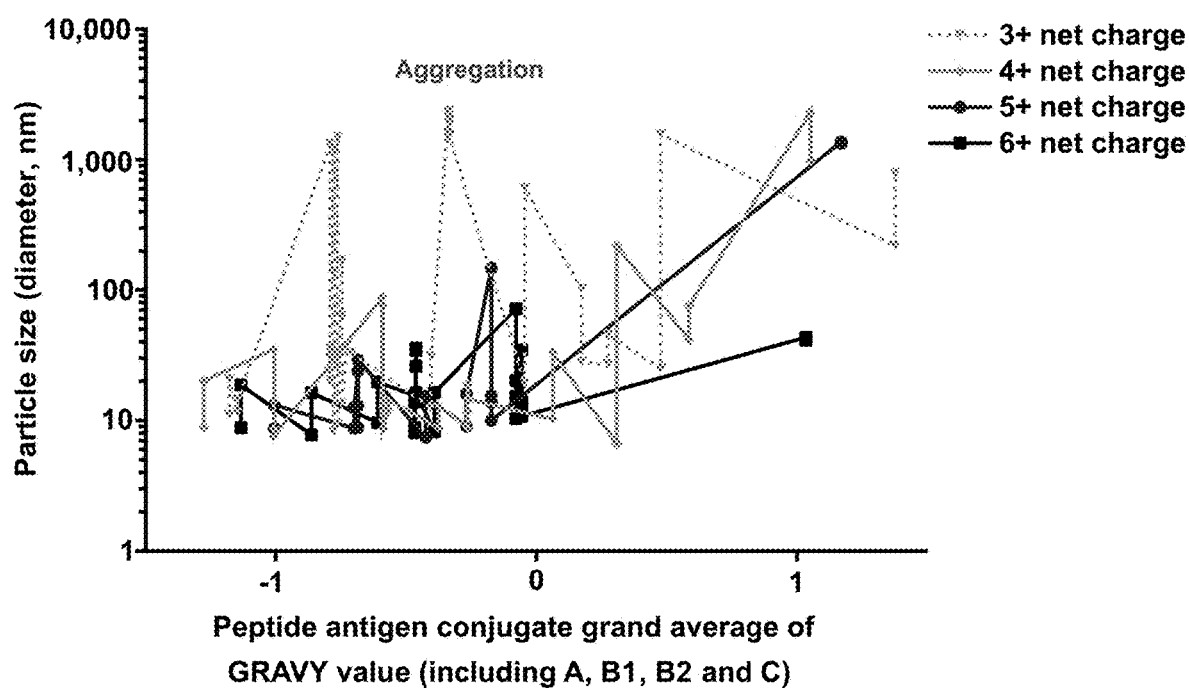

Our initial studies investigated how increasing the net charge impacts particle size and stability of peptide antigen conjugates of Formula V (FIGS. 18 and 19). Our results show an inverse relationship between the magnitude of charge and the size of the particles formed with peptide antigen conjugates of Formula V delivering a broad range of different peptide antigens (A) (N=754), with about 90% of peptide antigens (A) delivered as peptide antigen conjugates of Formula V with a net charge (absolute value)>6 assembling into ~20-40 nm nanoparticle micelles. Notably, the magnitude of net charge required to ensure nanoparticle micellization was highly dependent on the length and hydropathy of the peptide antigen (A), with most peptide antigen conjugates delivering LP-based peptide antigens (A) forming micelles as peptide antigen conjugates with a net charge of +8 or higher, or −8 or lower, but with the most highly hydrophobic antigens requiring a net charge of up to +10 or higher, or −10 or lower, to ensure stable nanoparticle micelle formation.

A major challenge for peptide-based PCVs is that they must ensure formulation consistency using any possible peptide antigen that can result from the human genome. To evaluate the generalizability of SP-7/8a as a PCV, we first computed the charge and hydropathy frequency distribution of all possible 25 amino acid peptides (11.3M 25-mers) resulting from canonical transcripts, including all possible missense mutations (72.6M 24-mers). Unexpectedly, our results suggest that greater than 98% of 25 amino acid peptide-based neoantigens will have a charge between −6 to +6 (at pH 7.4) and a grand average of hydropathy (GRAVY) between +2 and −2. These results indicate that the charge and hydropathy distribution of the mouse neoantigens used herein are representative of the characteristics of the in silico predicted human neoantigens (FIGS. 19 C&D). Notably, even modest increases of about 2 to 4 integer units of net charge results in markedly improved stability of the particles formed by peptide antigen conjugates of Formula V. Accordingly, while about 25% or more of LP neoantigens delivered as peptide antigen conjugates of Formula V with a net charge of +6 aggregated, the same LP neoantigens delivered as peptide antigen conjugates of Formula V with a net charge greater than or equal to +8 assembled into stable nanoparticle micelles (FIG. 19 E). These results show that Mins and LP peptide antigens delivered as peptide antigen conjugates of Formula V with net charge greater than or equal to +6 and +8 (or less than or equal to −6 and −8), respectively, reliably assemble into nanoparticle micelles. Importantly these unexpected findings suggest that peptide antigen conjugates must be able to accommodate 25 amino acid peptide antigens (A) with a range of charge from about −6 to about +6 to ensure that a sufficient net charge is applied to 98% of possible 25 amino acid neoantigens; therefore at least 13 unique charged molecule (C) and optional extension (B1 and/or B2) combinations are needed to ensure that a sufficient amount of charge is added (e.g., bearing 2, 3, 4, 5, 6, 7, 8, 9, 10, 11, 12, 13 and 14 charged functional groups) to the peptide antigen (A) to achieve the needed net charge of the peptide antigen conjugate.

To more thoroughly examine the trend between the net charge of peptide antigen conjugates and the size and stability of particles formed by the peptide antigen conjugates in aqueous buffers, we investigated the interplay between the grand average of hydropathy (GRAVY) value of the peptide sequence comprising the peptide antigen conjugates (e.g., the peptide antigen fragment, inclusive of the peptide-based charged molecule (C), peptide extensions (B1 and B2) and peptide antigen (A)) and the size and stability of particles formed (FIG. 19F). There was a strong interdependence between the GRAVY value, net charge and particle size. Accordingly, many of the peptide antigen conjugates with a net charge of +4 and a grand average of hydropathy (GRAVY) value less than 0 formed stable particles (FIG. 19F). In contrast, about 25% of peptide antigen conjugates with a net charge of +4 and a GRAVY value greater than 0 formed aggregates, while few peptide antigen conjugates with a net charge of +6 and a GRAVY value greater than 0 formed aggregates. These data indicate that, in preferred embodiments, the magnitude of net charge should be selected to offset the GRAVY value of the peptide antigen (A) delivered. In preferred embodiments, the composition of the charged molecule (C) and extensions (B1 and B2) are selected to provide peptide antigen conjugates with greater than or equal to +4 net charge, or less than or equal to −4 charge to promote the formation of stable particles formed by peptide antigen conjugates, with greater than +6 or less than −6 net charge used to ensure stable nanoparticle formation of even the most hydrophobic peptide antigens (A) (FIG. 19 F). Indeed, highly hydrophobic LP-based antigens may require even greater absolute value of net charge. As such, peptide antigen conjugates should have net charge: greater than or equal to +8, or less than or equal to −8, for LP peptide antigens (A) with a GRAVY value less than 0.25; greater than or equal to +9, or less than or equal to −9, for LP peptide antigens (A) with a GRAVY value between about 0.25 and 0.75; and, greater than or equal to +10, or less than or equal to −10, for LP peptide antigens (A) with a GRAVY value greater than 0.75, wherein LP is used to refer a peptide antigen (A) that is longer than a minimal epitope, e.g. a peptide antigen greater than 15 amino acids, typically 20 or more, such as 25 amino acids.

It should be noted that our analysis included peptide antigens with extremes of compositions, in terms of charge and hydropathy. Accordingly, 3 unique peptide antigens representing the most—i.e., the $90^{th}$ percentile or higher of—hydrophobic (Val-Val-Ile-Ala-Ile-Phe-Ile-Ile-Leu (SEQ ID NO: 57)), positively charged (Lys-Asn-His-Arg-Asn-Arg-Qln-Val-Ile SEQ ID NO: 75), and negatively charged (Ser-Pro-Glu-Arg-Asn-Asp-Trp-Glu-Pro-Leu SEQ ID NO: 76)-sequences among a total of 1,377 predicted neoantigens taken from 4 murine tumor cell lines, as well as a validated CD8 T cell epitope (Ala-Ser-Met-Thr-Asn-Met-Glu-Leu-Met-Ser-Ser (SEQ ID NO: 2)), were selected for evaluation. A peptide antigen (A) comprising a validated CD4 T cell epitope (PADRE=Ala-Lys-Phe-Val-Ala-Ala-Trp-Thr-Leu-Lys-Ala-Ala-Ala SEQ ID NO: 22) was also included in the analysis as a known universal CD4 T cell epitope (FIG. 18).

Impact of Hydrophobic Molecule (H) Length and Composition on Particle Size

Figure 20:
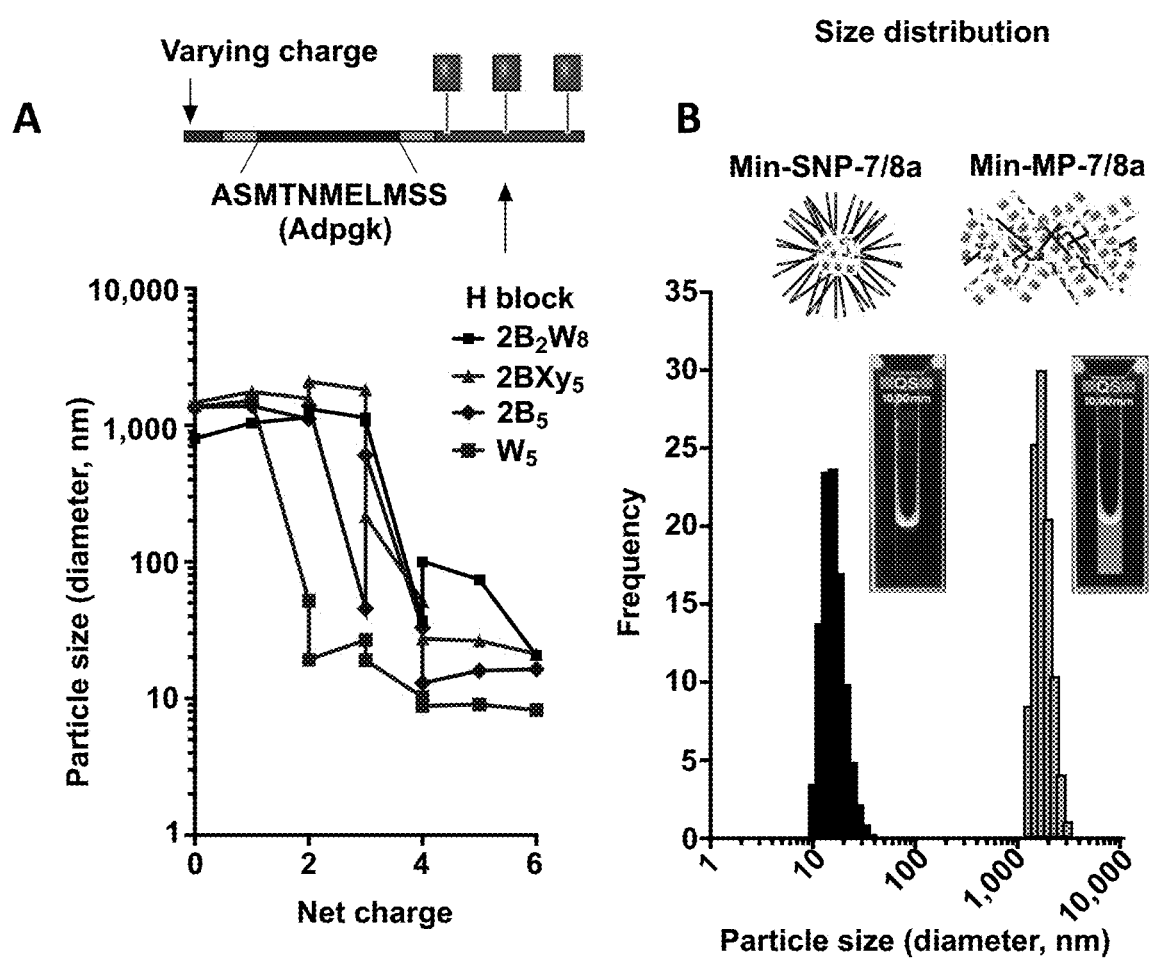
FIG. 20: Impact of peptide antigen conjugate net charge and hydrophobic molecule (H) length and composition on the hydrodynamic behavior of peptide antigen conjugates of Formula V. The hydrodynamic behavior of different peptide antigen conjugates suspended at 0.1 mg/mL in PBS at a pH of 7.4 with varying net charge and hydrophobic molecule composition delivering a model neoantigen-based minimal epitope (Min), Ala-Ser-Met-Thr-Asn-Met-Glu-Leu-Met-Ser-Ser (SEQ ID NO: 2) ("Adpgk") was assessed by dynamic light scattering. (A) The number average particle diameter is reported as a function of the net charge of the peptide antigen conjugate for 4 different hydrophobic molecules ($2B_2W_8$, $2BXy_5$, $2B_5$, $W_5$). (B) Size distribution data is shown for a peptide antigen conjugate with +6 net charge that self-assembles into nanoparticles ("Min-SNP-7/8a") and a peptide antigen conjugated delivered the same peptide antigen (A) but with a net charge of 0 that assembles into microparticles/aggregates ("Min-MP-7/8a").

While the net charge on the peptide antigen conjugates was found to be critical for promoting stability of the particles formed, we next explored additional factors that impact particle size. Prior studies have shown that the length of macromolecules comprising micelles, liposomes and polymersomes can be modulated to vary the sizes of particles formed. Thus, using a model CD8 T cell epitope as the peptide antigen (A) delivered as a peptide antigen conjugate of Formula V, we evaluated how the length and composition of the hydrophobic molecule (H) impacts the particle size (FIG. 20). Consistent with the prior data, we found that size and stability of the particles formed by the peptide antigen conjugates was highly dependent on the net charge of the peptide antigen conjugate across a range of different hydrophobic molecules (H) used (FIG. 20). Using a net charge of +4 or higher, the smallest hydrophobic molecule (H), $W_5$, comprised of 5 tryptophan units, led to the smallest particles with an average diameter of ~10 nm, while the largest hydrophobic molecule (H) used in this example, $2B_2W_8$, led to particles between 30-100 nm in diameter (FIG. 20). Notably, the intermediate sized hydrophobic molecules (H), $2B_5$ and $2BXy_5$ led to intermediate sized particles of ~10-30 nm sized particles in diameter, when the net charge was greater than or equal to +4.

Altogether, these results provide the unexpected findings of how precisely defined chemical parameters of the charged molecule (C) and hydrophobic molecule (H) can be used to tune the size and stability of particles formed by peptide antigen conjugates.

Impact of Net Charge on Particle Size and Stability of Peptide Antigen Conjugates Delivering Highly Hydrophobic Peptide Antigens (A)

Figure 21:
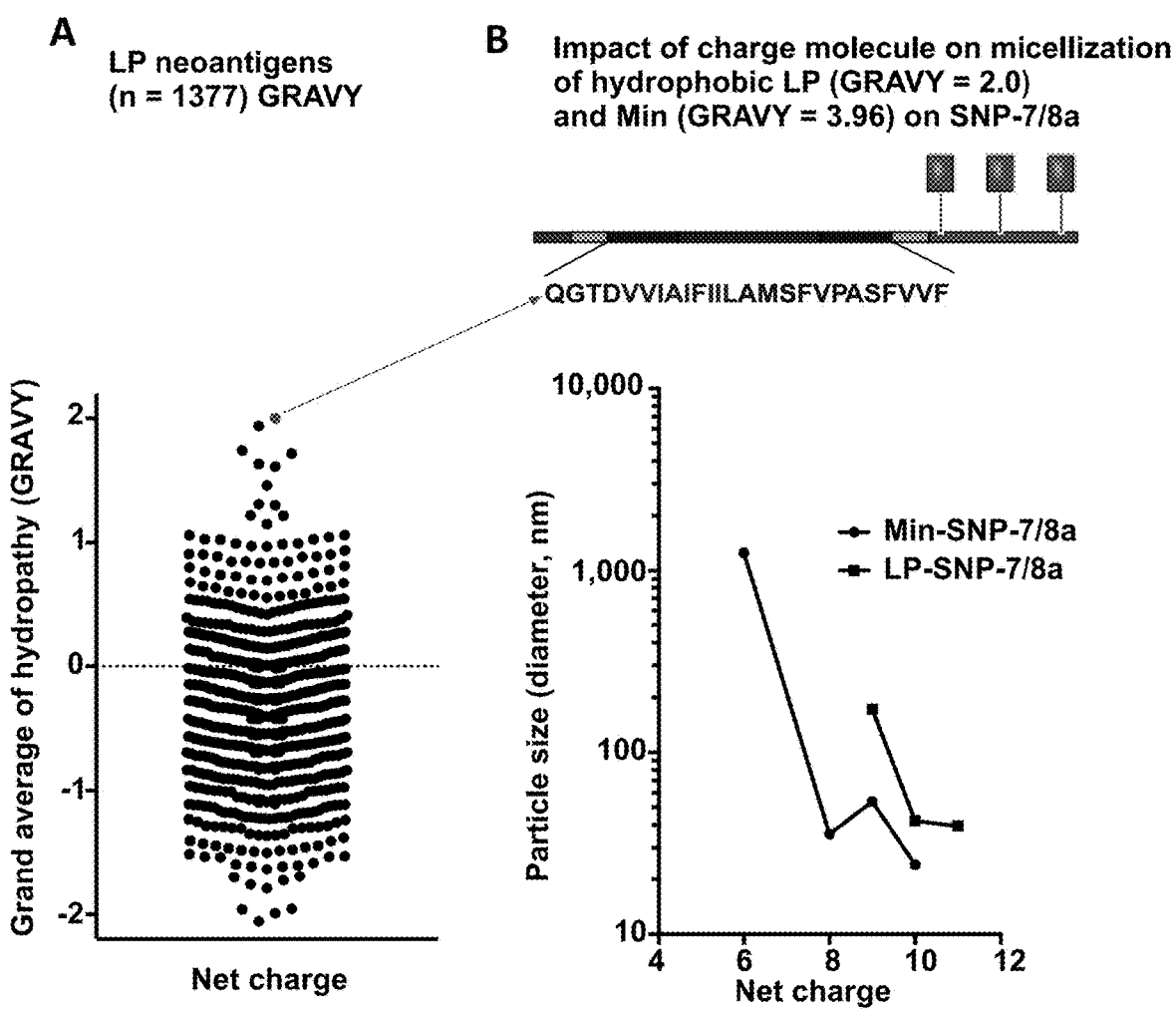
FIG. 21: (SEQ ID NO: 96) Impact of net charge on hydrodynamic behavior of a peptide antigen conjugate of Formula V delivering a hydrophobic peptide antigen. (A) Grand average of hydropathy (GRAVY) distribution plot of 1,377 LP neoantigens from 4 murine tumor models (B16.F10, MC38, 3123 and Panc02). (B) The most hydrophobic LP neoantigen identified in figure panel (A) (red closed circle) was prepared as an LP and Min delivered as a peptide antigen conjugate of Formula V that self-assembles into nanoparticles co-delivering a TLR-7/8a ("SNP-7/8a") and assessed for the impact of net charge (absolute value) on particle size. Particle size was assessed by dynamic light scattering with the peptide antigen conjugate suspended at 0.5 mg/mL in PBS at a pH of 7.4. The mass average particle diameter is reported as a function of the net charge of the peptide antigen conjugate.

To demonstrate the tolerability of peptide antigen conjugates of Formula V for delivering peptide antigens (A) that are highly hydrophobic, we selected the most hydrophobic LP neoantigen amongst a library of 1,377 peptide neoantigens from 4 murine tumor lines and synthesized the peptide antigen as either the LP or Min delivered as a peptide antigen conjugate of Formula V that self-assembles into nanoparticles co-delivering a TLR-7/8a (SNP-7/8a) (FIG. 21). While equal to or greater than 8 net charge was required to stabilize the hydrophobic Min (GRAVY=3.96) delivered as SNP-7/8a, a net charge of equal to or greater than 10 was required to stabilize the hydrophobic LP (GRAVY=2.0) delivered as SNP-7/8a (FIG. 21). An additional unexpected finding was that the native LP and min were not manufacturable by solid-phase peptide synthesis; however, adding the charged molecule (C) and extensions (B1 and B2) to the peptide antigen (A) on resin during solid-phase peptide synthesis improved manufacturing by preventing sequence truncation and allowing for HPLC purification due to improved solubility in aqueous and organic solvents.

Figure 22:
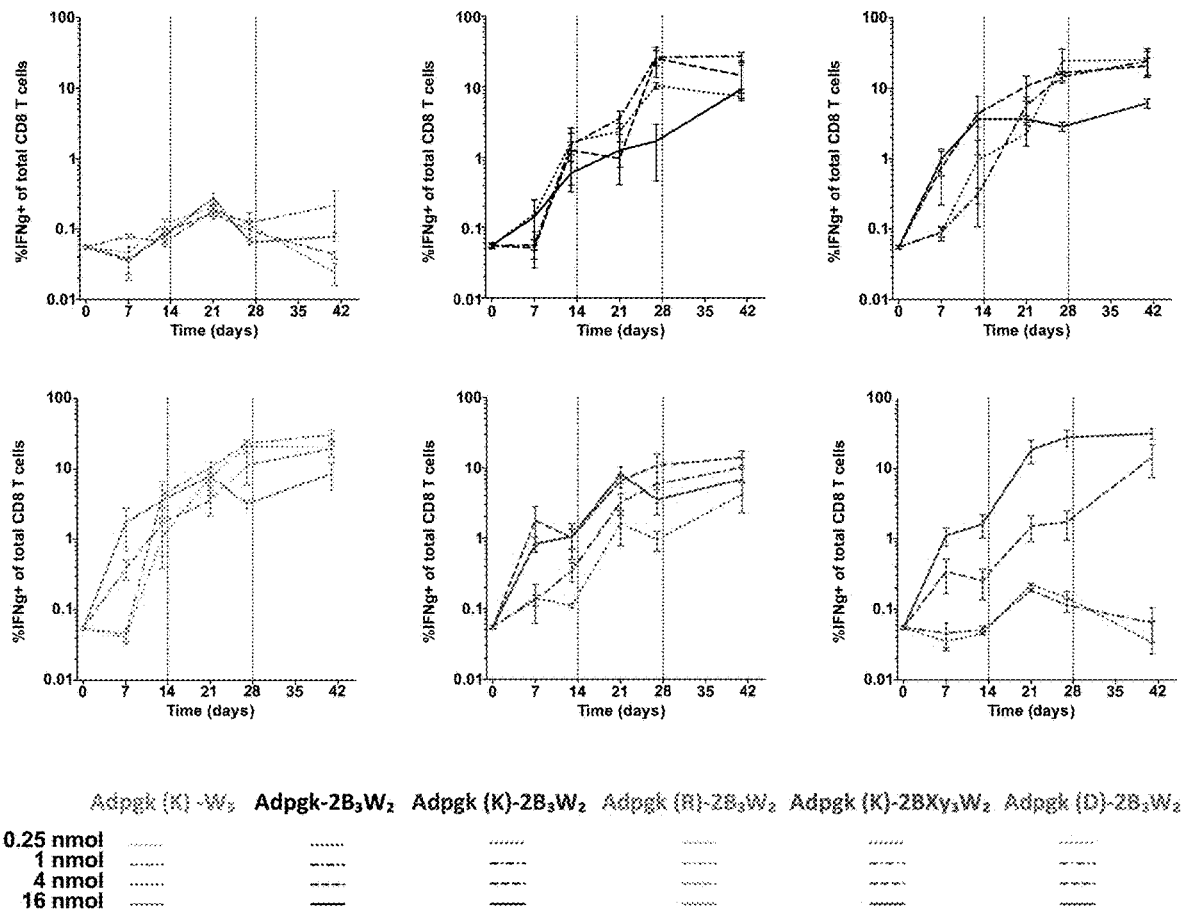
FIG. 22: Impact of charged molecule (C or "C Block") and hydrophobic molecule (H or "H Block") composition on immunogenicity for generating CD8 T cell responses to a neoantigen minimal epitope, Adpgk, delivered as a peptide antigen conjugate of Formula V. (A-E) Peptide antigen conjugates with varying charged molecule composition (either poly(K), poly(R), poly(D), or none) and hydrophobic molecule composition (either $W_5$, $2BXy_3W_2$ or $2B_3W_2$) delivering a minimal epitope, Adpgk, were administered to mice (N=3 per group per dose) at different doses at days 0, 14 and 28, and neoantigen (Adpgk)-specific CD8 T cell responses were assessed from whole blood at serial time points thereafter.
Figure 24:
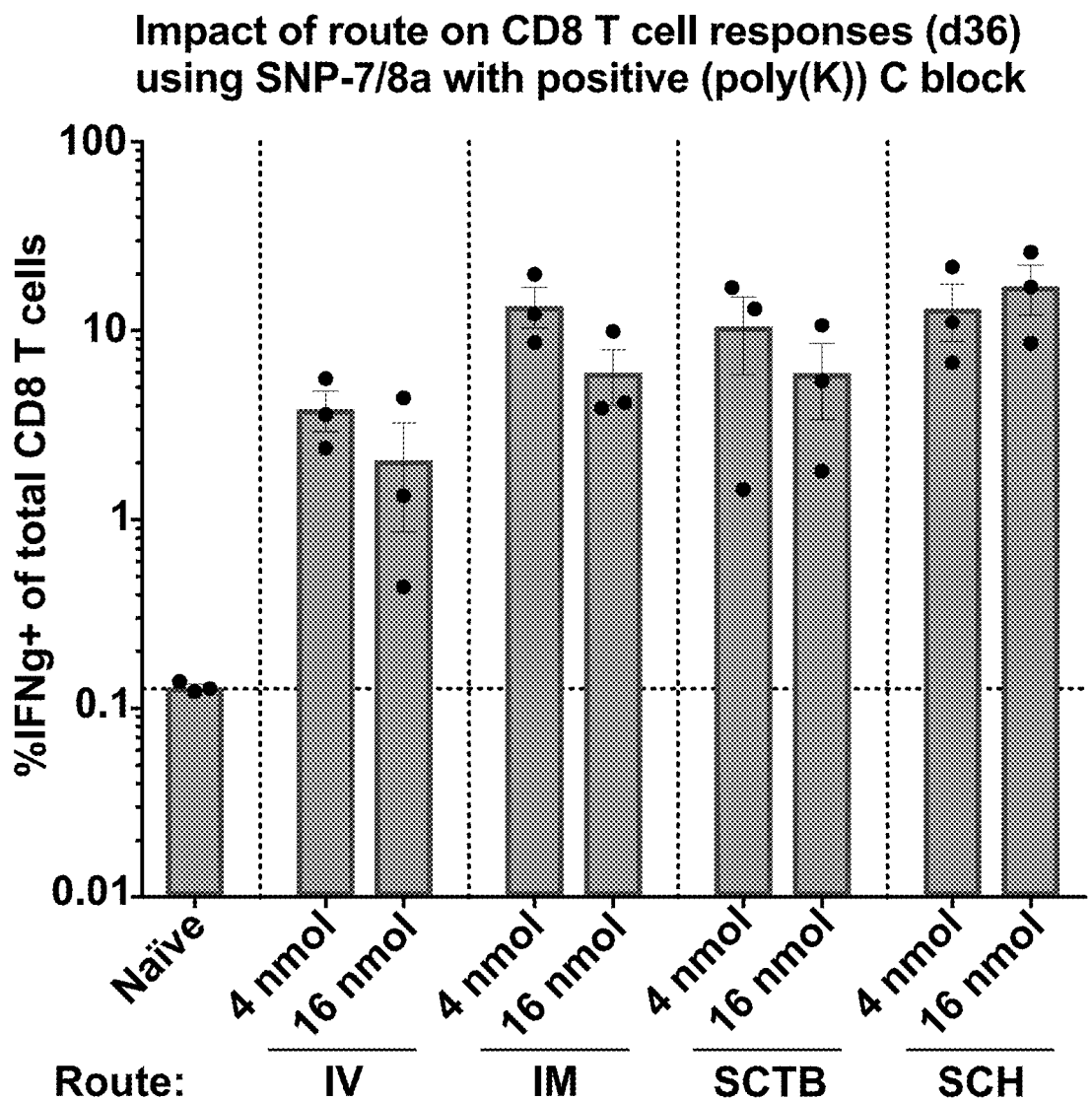
FIG. 24: Impact of the route of administration on CD8 T cell responses generated by peptide antigen conjugates ("SNP-7/8a"). A peptide antigen conjugate with a poly(K) charged molecule (C) and a $2B_3W_2$ hydrophobic molecule (H) delivering a neoantigen minimal epitope (Adpgk=Ala-Ser-Met-Thr-Asn-Met-Glu-Leu-Met (SEQ ID NO: 77)) was administered to mice at days 0, 14 and 28 and neoantigen (Adpgk)-specific CD8 T cell responses were assessed from whole blood at day 36.

Impact of Peptide Antigen Conjugate Charged Molecule (C) and Hydrophobic Molecule (H) Composition on Immunogenicity Our above results indicate that net charge is critical for stabilizing nanoparticle micelles formed by peptide antigen conjugates. We next investigated the impact of the charged molecule (C) and hydrophobic molecule (H) compositions on immunogenicity of peptide antigen conjugates delivering a minimal epitope, Adpgk (FIGS. 22 to 24). While the peptide antigen conjugate of Formula V without an adjuvant induced no CD8 T cell responses (FIG. 22), all of the other compositions of peptide antigen conjugates linked to a TLR-7/8a induced robust CD8 T cell responses (FIG. 22). Notably, while the peptide antigen conjugate of Formula IV, without the charged molecule (C), and the peptide antigen conjugates of Formula V with either lysine (i.e. poly(K)) or arginine (i.e. poly(R))-based charged molecules (C), induced robust CD8 T cell responses even when administered down to 0.25 nmol doses, the same neoantigen administered as a peptide antigen conjugate of Formula V with an aspartic acid (i.e. poly(D))-based charged molecule (C) induced no CD8 T cell responses when administered at 0.25 or 1 nmol, but induced high magnitude CD8 T cell responses when administered at 4 and 16 nmol, Notably, the negatively charged peptide antigen conjugate (FIG. 22) induced the highest magnitude CD8 T cell responses after multiple immunizations (~30% IFNg+ of total CD8 T cells), about 1.5-2× higher than the CD8 T cell responses induced by either the peptide antigen conjugate of Formula IV or the positively charged peptide antigen conjugates of Formula V. These results suggest that, while peptide antigen conjugates that self-assemble into microparticles (FIG. 22) or positively charged nanoparticles (FIG. 22) are more potent for inducing CD8 T cell responses as compared with negatively charged peptide antigen conjugates, negatively charged peptide antigen conjugates that self-assemble into nanoparticles co-delivering TLR-7/8a (SNP-7/8a) may induce CD8 T cell responses that are more boostable, providing higher magnitude responses after multiple immunizations.

To extend our findings, we evaluated how the charged molecule (C) composition of peptide antigen conjugates impacts CD8 T cell responses following the subcutaneous route of administration (FIG. 23). Notably, peptide antigen conjugates of Formula V with either negatively or positively charged poly(amino acid)-based charged molecules (C), either poly(K) or poly(D), respectively, induced higher magnitude CD8 T cell responses than peptide antigen conjugates of Formula V with a neutral, PEG-based B1 extension (FIG. 23).

Importantly, peptide-antigen conjugates of Formula V that self-assemble into nanoparticles co-delivering TLR-7/8a (SNP-7/8a) were found to be highly immunogenic for eliciting CD8 T cell responses following common routes of vaccination (intramuscular (IM), subcutaneous (SC)) as well as the intravenous route (FIG. 24).

Impact of Peptide Antigen Conjugate Particle Size and Adjuvant Potency and Composition on Immunogenicity It was previously unknown how particle size and the amount and potency of TLR agonists impact T cell responses after a single or after multiple ('booster') immunizations. The prior state of the art would suggest that increasing amounts or potency of immuno-stimulant would lead to higher or at least non-inferior CD8 T cell responses; however, the impact of immuno-stimulant, e.g., TLR agonist, amount and potency on priming and boosting of CD8 T cell responses in vivo has not been well studied. Therefore, our next studies sought to assess how particle size and the amount and potency of agonist delivered on peptide antigen conjugates of Formula V impact immunogenicity.

To determine how particle size and agonist composition affected immunogenicity, mice were vaccinated with immunogenic compositions comprising two peptide antigen conjugates, one delivering a peptide antigen (A) comprising a minimal CD8 T cell epitope and the other delivering a peptide antigen (A) comprising a minimal CD4 T cell epitope (FIG. 25). The peptide antigen conjugates of Formula V were distinguished on the basis of whether they form small (~20-100 nm diameter nanoparticles (NP)) or large (~1,000 nm diameter microparticles (MP)) particles delivering different amounts and potencies of TLR-7/8 agonists. Within each set of small or large particles, the peptide antigen conjugates comprised a hydrophobic molecule (H) that contained either 1, 2, 3, or 5 molecules of Compound 1, 2B, or 5 molecules of the higher potency agonist, Compound 2, 2BXy. Mice were vaccinated twice with a given immunogenic composition and T cell responses were measured in the blood 1 week after each vaccination.

A striking and unexpected finding was that for both the small (20-100 nm) and large particles (~1000 nm), increasing amounts of the agonist 2B linked to the hydrophobic molecule (H), led to increased CD4 and CD8 T cell responses, with peptide antigen conjugates linked to hydrophobic molecules (H) comprising only a single 2B molecule, leading to the lowest CD8 and CD4 T cell responses. Both CD4 and CD8 T cell responses increased by adding two 2B molecules, with a modest additional increase after adding 3 or 5 2B molecules to the hydrophobic molecules (H). Consistent with our prior and unexpected data (FIGS. 6 and 7) showing that peptide antigen conjugates comprising hydrophobic molecules (H) delivering 3 or more molecules of the more potent agonist TLR-7/8a, 2BXy, resulted in lower CD8 T cell responses after multiple immunizations as compared with peptide antigen conjugates comprising hydrophobic molecules (H) delivering 3 or more molecules of the less potent agonist, 2B, the results from FIG. 25, show that $2BXy_5$ results in lower CD8 and CD4 T cell responses as compared with use of the hydrophobic molecule (H) delivering the moderate potency agonist, $2B_5$. This unexpected finding—wherein a higher potency agonist results in lower immune responses—would not have been predicted on the basis of previous findings in the literature.

In summary, increasing the number of the agonist, Compound 1, 2B, to the peptide antigen conjugates resulted in generally higher CD8 T cell responses, but these responses decreased in magnitude when the innate stimulant changed to a higher potency agonist. Therefore, preferred embodiments use either high densities of moderate potency TLR-7/8a agonists or low densities of high potency TLR-7/8a for inducing optimal CD4 and CD8 T cell response using immunogenic compositions comprising peptide antigen conjugates.

Particle Size

Another striking and unexpected finding was that the immunogenic compositions comprising peptide antigen conjugates that formed small particles, ~10-200 nm diameter particles, led to higher magnitude CD4 and CD8 T cell responses as compared with peptide antigen conjugates that formed larger particles (>1,000 nm diameter). For example, in the group that received immunogenic compositions comprising peptide antigen conjugates linked to the hydrophobic molecule (H) $2B_5$ and that formed small particles, the CD8 T cell responses were about ~2.5% compared to ~0.5% for the group that received immunogenic compositions comprising peptide antigen conjugates linked to the hydrophobic molecule (H) 2B$_5$ that formed large particles (FIG. 25). Similarly, CD8 T cell responses in the group that received immunogenic compositions comprising peptide antigen conjugates linked to the hydrophobic molecule (H) 2B$_3$W$_2$ as a small particle were approximately 10-fold higher than the group that received immunogenic compositions comprising peptide antigen conjugates linked to the hydrophobic molecule (H) 2B$_3$W$_2$ as a large particle.

In summary, these data show that the size of the particles formed by the peptide antigen conjugates used in immunogenic compositions had a large and unexpected impact on the CD8 T cell response. Therefore, peptide antigen conjugates that form particles of 20-100 nm are the preferred embodiment for use in immunogenic compositions to elicit optimal T cell immunity.

Altogether, these studies elucidate the precise physical and chemical parameters that are optimal for maximizing CD4 and CD8 T cell responses using peptide antigen conjugates of the present disclosure.

An additional unexpected finding was that the hydrodynamic behavior and stability of the particles formed by the peptide antigen conjugates depended on both the net charge and Grand average of hydropathy (GRAVY) value, as determined using the methods of Kyte and Doolittle (see: Kyte J, Doolittle R F, A simple method for displaying the hydropathic character of a protein, J. Mol. Biol 157: 105-32, 1983), of the peptide sequence comprising the peptide antigen conjugate. Note: the GRAVY value and charge determination excluded the contributions of the Linker (L) and the hydrophobic molecule (H) or Particle (P).

Accordingly, peptide antigen conjugates delivering: highly hydrophobic peptide antigens (A) with GRAVY values >0.75 reliably formed stable particles in aqueous buffers at pH about pH 7.4 when the net charge of the peptide antigen conjugate was ≥(greater than or equal) to +6 or ≤(less than or equal) to −6; moderately hydrophobic peptide antigens (A), with GRAVY values between 0.25-0.75 reliably formed stable particles in aqueous buffers at pH about pH 7.4 when the net charge of the peptide antigen conjugate was ≥(greater than or equal to)+5 or ≤(less than or equal to)−5; and peptide antigens (A) with GRAVY values less than 0.25 reliably formed stable particles in aqueous buffers at pH about pH 7.4 when the net charge was ≥(greater than or equal to)+4 or ≤(less than or equal to)−4. Thus, based on our unexpected findings, the appropriate composition of charged molecules (C) and extension sequences (B1 and B2) can be selected to modulate charge as a means to promote stable particle formation of peptide antigen conjugates delivering any composition of peptide antigen (A).

Impact of the Hydrodynamic Behavior of the Peptide Neoantigen on Immunogenicity

Figure 26:
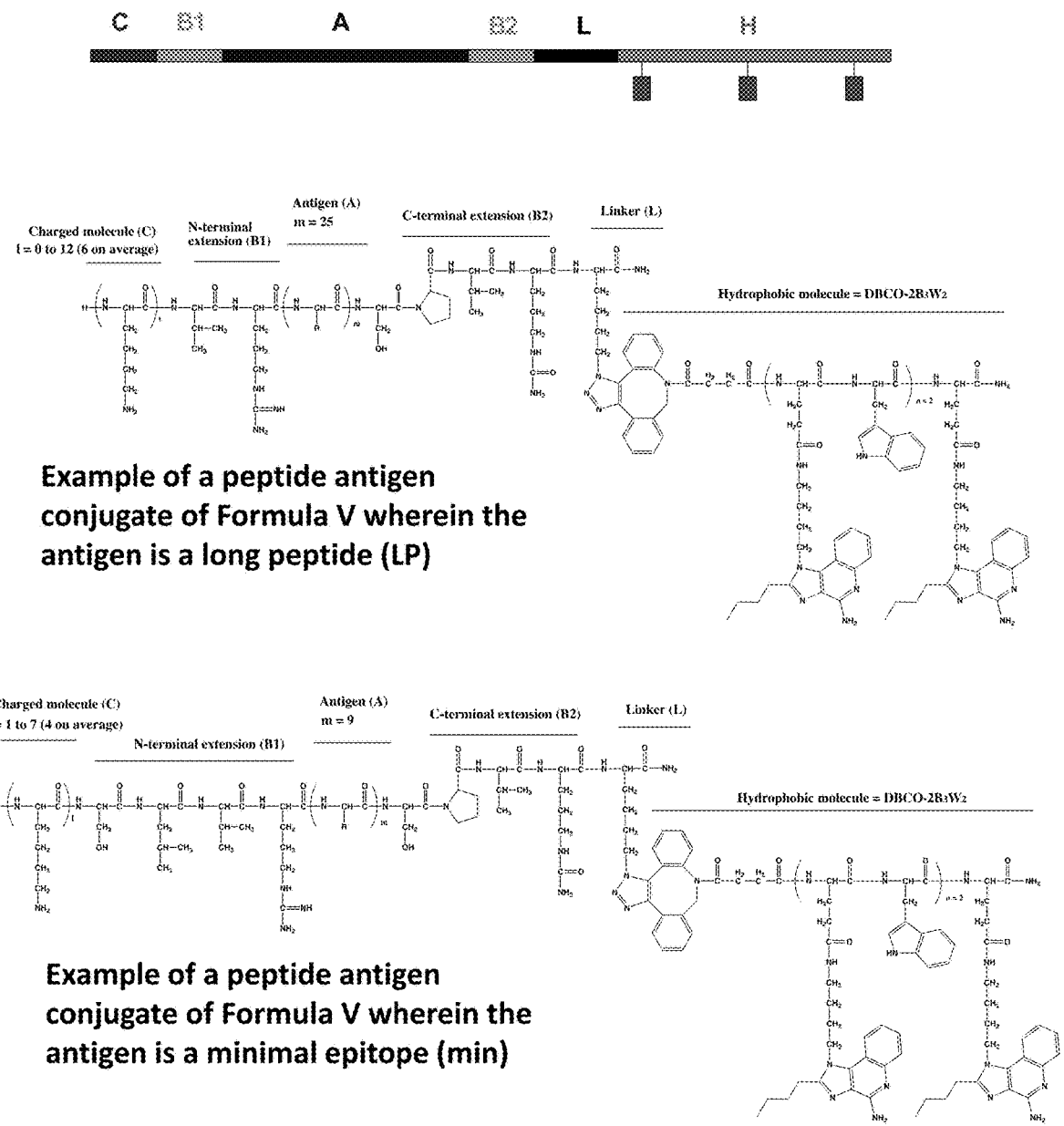
FIG. 26: Cartoon and chemical schematic of peptide antigen conjugates with a poly(K) charged molecule (C) and a $2B_3W_2$-based hydrophobic molecule (H) delivering either LP or Min epitope forms of peptide antigens.

We next evaluated whether more consistent formulations using peptide antigen conjugates of Formula V that self-assemble into nanoparticles co-delivering a TLR-7/8a (SNP-7/8a) (FIG. 26) would translate to improved immunogenicity of CTL responses as compared with linking LP neoantigens to a hydrophobic polymer-TLR-7/8a without charge stabilization that results in microparticle/aggregates (MP-7/8a), or the more conventional approach of admixing LP neoantigens with a particulate adjuvant (LP+polyICLC) (FIG. 27). We selected three LP neoantigens for evaluation, Adpgk, Cpne1 and Irgq. While Adpgk assembles into particles as the native LP, both the Cpne1 and Irgq LPs are water soluble (FIG. 27 A).

Consistent with our earlier findings, only the neoantigen LPs delivered as particles induced CD8 T cell responses in vivo (FIGS. 27 B&C). Accordingly, the soluble LPs Cpne1 and Irgq admixed with pICLC induced no CD8 T cell responses, while the same neoantigens delivered as either a MP-7/8a (microparticle/aggregates) or SNP-7/8a (nanoparticle) led to the generation of high magnitude CD8 T cell immunity (FIG. 27 B-E). While soluble LPs admixed with pICLC were inactive, as described earlier, the particle LP, Adpgk, induced a significant increase in CD8 T cell responses over background, indicating that the physical form of the peptide neoantigen but not the adjuvant, i.e. pICLC, likely accounted for the weak T cell responses by Cpne1 and Irgq LPs admixed with pICLC.

Among the formulations delivering neoantigens in a particle format, the nanoparticle micelle (SNP-7/8a), based on peptide antigen conjugates of Formula V, provided the highest magnitude responses, followed by the microparticle (MP-7/8a) formulations and finally the LP alone admixed with adjuvant (FIG. 27 B-E). Notably, the responses by the nanoparticle micelle (SNP-7/8a) after a single immunization were significantly (~5-10-fold) higher than responses by the microparticle formulations, while the responses after two or three immunizations were comparable, indicating that the smaller, nanoparticle micelles have a faster kinetic of T cell induction as compared with the microparticles.

Figure 28:
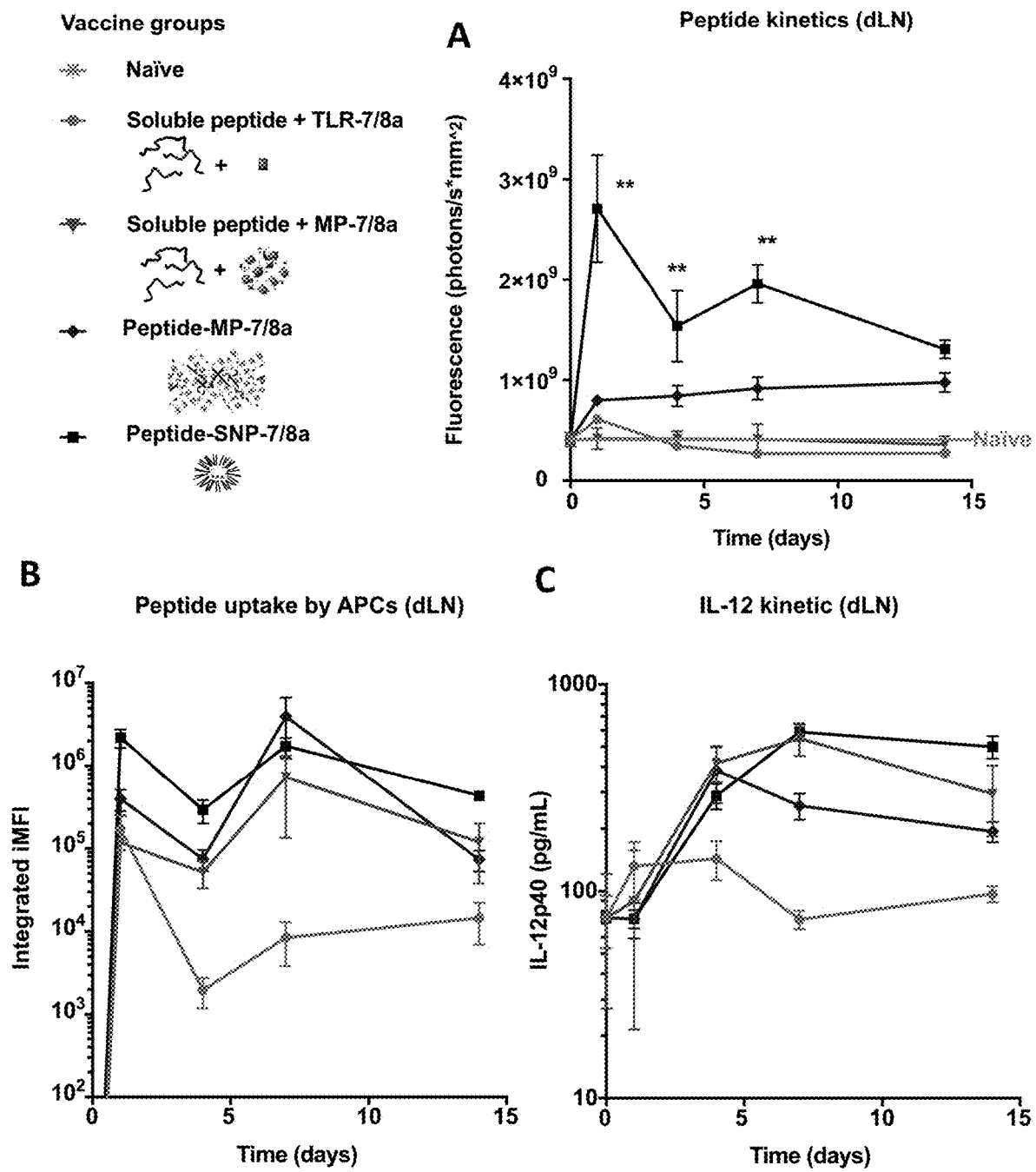
FIG. 28: Mechanism accounting for the improved immunogenicity of peptide antigen conjugates that self-assemble into nanoparticles co-delivering TLR-7/8a (SNP-7/8a). (A-C) The minimal epitope, Adpgk, was fluorescently labeled and then administered subcutaneously into the hind footpads of mice at day 0 as either a soluble peptide admixed with a small molecule TLR-7/8a (7/8a), a soluble peptide admixed with MP-7/8a, or covalently linked to MP-7/8a or SNP-7/8a. Lymph nodes (N=5 per time point per group) draining the site of immunization were collected at serial time points thereafter and assessed for peptide quantity (E), peptide uptake by lymph node APCs on a per cell basis (F) and IL-12p40 cytokine production (G). Data are reported at mean±SEM. Comparison of multiple groups for statistical significance was determined using one-way or two-way ANOVA; ns=not significant; *, p=0.05; **, p=0.01.

Mechanistic studies to account for the observed differences in immunogenicity revealed that the peptide antigen conjugates that form stable nanoparticle micelles resulted in the highest amount of neoantigen uptake into draining lymph nodes with an early peak in concentrations and uptake by lymph node APCs at day 1, while the microparticle showed slower uptake into lymph nodes, with concentrations peaking at day 7, which may account for the slower kinetic of CD8 T cell responses resulting from the microparticle (FIG. 28). In contrast, the soluble neoantigen admixed with either soluble or particle adjuvant showed limited uptake of neoantigen into draining lymph nodes. Despite all of the particle formulations of adjuvant inducing comparable magnitude and kinetics of innate immune activation in lymph nodes, only the particle forms of antigen resulted in CD8 T cell responses. Limited accumulation of the soluble neoantigen in lymph nodes likely accounts for its inability to induce CD8 T cell responses.

Impact of Peptide Length on Immunogenicity

Figure 29:
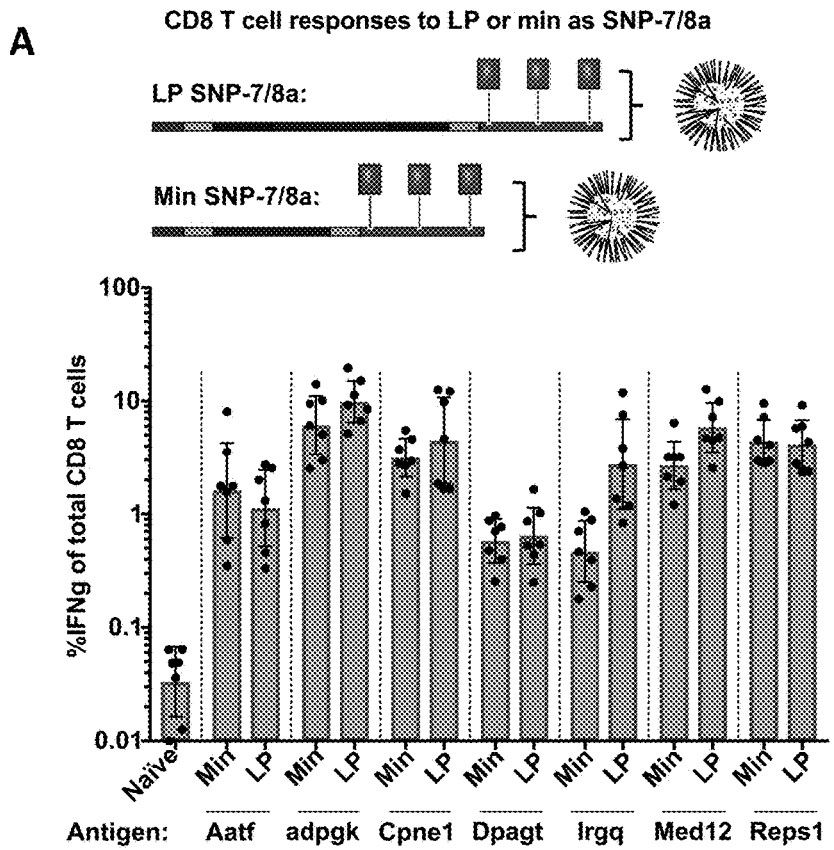
FIG. 29: Immunogenicity of peptide-based neoantigens delivered as either LPs or Mins as peptide antigen conjugates of Formula V that self-assemble into nanoparticles co-delivering a TLR-7/8a (SNP-7/8a). Different peptide-based neoantigens were prepared as either LPs or Mins delivered as peptide antigen conjugates wherein the charged molecule (C) is poly(lysine) and the hydrophobic molecule (H) is $2B_3W_2$, which self-assemble into nanoparticles co-delivering TLR-7/8a (referred to as "SNP-7/8a"). Mice (N=7/group) were immunized with either the LP or Min form of peptide-based neoantigens linked to SNP-7/8a at days 0 and 14. (A) CD8 T cell responses and (B) CD4 T cell responses were assessed from whole blood on day 28. Data on log scale are reported as geometric mean with 95% CI; Comparison of multiple groups for statistical significance was determined using one-way or two-way ANOVA; ns=not significant; *, p=0.05; **, p=0.01.

Peptide length is considered a major factor that impacts the peptide antigen (A) immunogenicity. We therefore investigated how the length of peptide neoantigens delivered as peptide antigen conjugates of Formula V that self-assemble into nanoparticles co-delivering TLR-7/8a ("SNP-7/8a") impact the magnitude of CD4 and CD8 T cell responses generated in vivo (FIG. 29). Seven peptide neoantigens derived from the MC38 tumor cell line were prepared as either minimal epitope (mins) or LP-based peptide antigens (A) delivered as peptide antigen conjugates of Formula V, referred to as SNP-7/8a here, and then administered to mice. Our results show that both the min and LP forms of neoantigens delivered as SNP-7/8a elicit comparable magnitude of CD8 T cell responses that are about 10-100-fold higher than background, including against 4 neoantigens previously reported to be non-immunogenic (FIG. 29 A). As expected, however, the LPs elicited significantly higher CD4 T cell responses as compared with the mins, likely because the mins are too short to encode the CD4 epitope (FIG. 29 B). Importantly, these results indicate that peptide length has minimal impact on CD8 T cell responses and suggests that short peptides (7-14 amino acids) containing the minimal CD4 or CD8 epitopes, which are more efficient to manufacture, when properly formulated in particles, may be preferred for use in vaccines over LPs (>20 amino acids). Indeed, improvements in MHC-II prediction algorithms should enable the use of minimal epitopes for eliciting both CD4 and CD8 T cell responses thereby circumventing the need to use LPs.

Benchmarking Immunogenicity of Peptide Neoantigens Delivered as Peptide Antigen Conjugates as Compared with Conventional Approaches We next benchmarked the activity of our peptide antigen conjugates of Formula V that self-assemble into nanoparticles co-delivering TLR-7/8a ("SNP-7/8a") with a conventional peptide-based vaccine approach of admixing native LPs with the particulate adjuvant polyI-CLC (FIG. 30). Consistent with the findings of Yadav et al (Yadav M, et al. Nature 515(7528):572-576 (2014), only 2 of the 7 mass-spectrometry validated predicted neoantigens (Reps1 and Adpgk, both of which are particulate) were immunogenic when combined with pICLC; however, all 7 of the LP neoantigens elicited high magnitude CD8 T cell responses as SNP-7/8a, i.e. as peptide antigens (A) delivered as peptide antigen conjugates of Formula V (FIG. 30). Notably, all 7 of the neoantigens shown in FIG. 30 were confirmed to bind tumor MHC-I by mass spectrometry, which provides the unexpected finding that mass spec is a reliable filter for predicting immunogenicity of peptide antigens (A), e.g., neoantigens.

Figure 31:
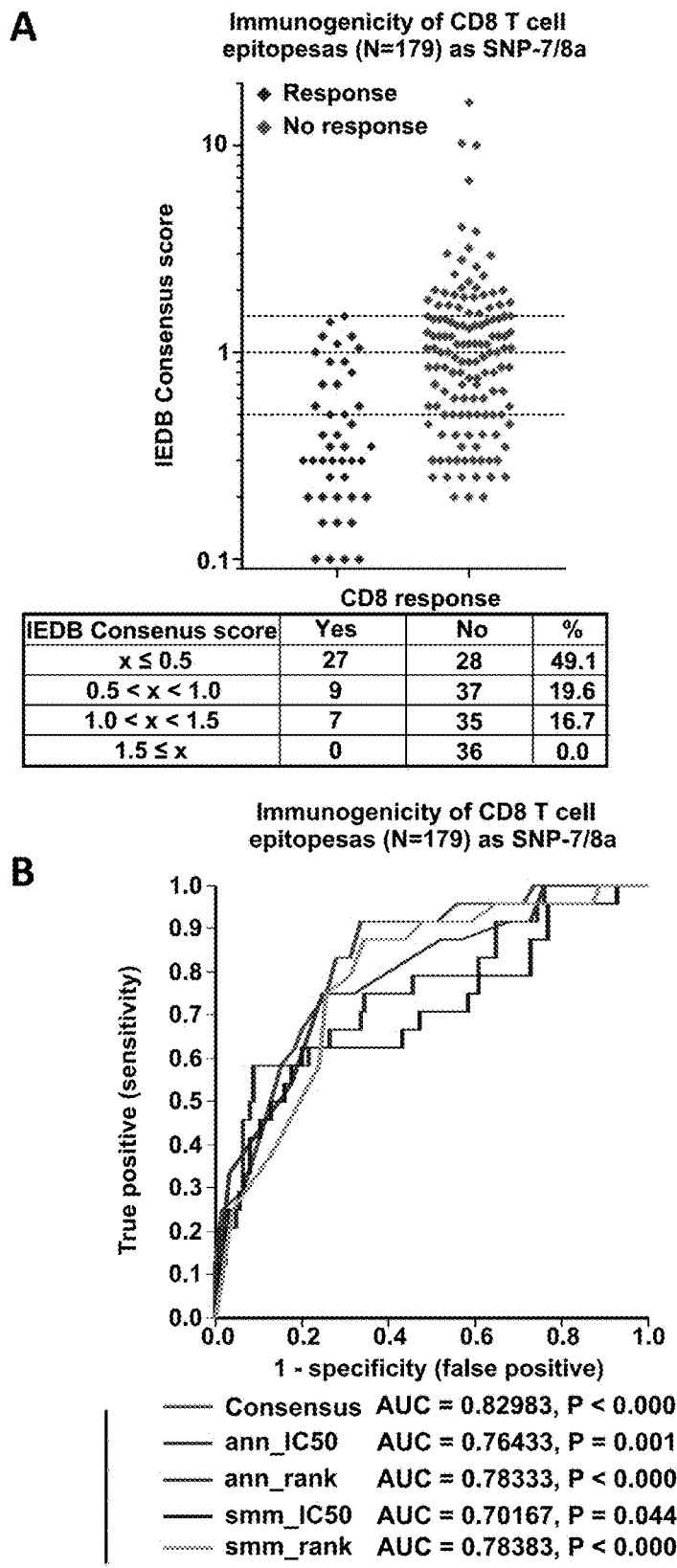
FIG. 31: Relationship between immunogenicity and predicted binding affinity. (A) Immunogenicity of minimal epitopes (N=179) for generating CD8 T cell responses when delivered as peptide antigens conjugates, wherein the hydrophobic molecule (H) is a polymer-TLR-7/8a, plotted against predicted binding affinity using the immune epitope database (IEDB) consensus algorithm. (B) Receiver operator characteristic (ROC) curves for the sensitivity and specificity of different MHC-I binding prediction algorithms based on a cutoff of 0.5 consensus score or 500 nM as a binder.

Relationship Between Minimal Epitope Predicted Binding Affinity and Immunogenicity Our results show that that peptide-based neoantigens delivered as peptide antigen conjugates of Formula V that self-assemble into nanoparticles co-delivering TLR-7/8a ("SNP-7/8a") are a highly efficient approach for eliciting CD4 and CD8 T cell responses. Through improved efficiency of the vaccine platform, it may be possible to refine prediction algorithms for immunogenicity. Indeed, we observed a strong correlation between predicted MHC-I binding and immunogenicity after screening 192 unique CD8 T cell epitopes in vivo with SNP-7/8a, with nearly 50% of the high affinity epitopes (IEDB Consensus Score <0.5 percentile) leading to CD8 T cell responses, which is a nearly 5-fold increase in the efficiency of priming CD8 T cell responses as compared with published responses (FIG. 31). These results show that in silico predicted binding affinity, particularly the IEDB consensus score is highly predictive of peptide antigen (A) immunogenicity.

Figure 32:
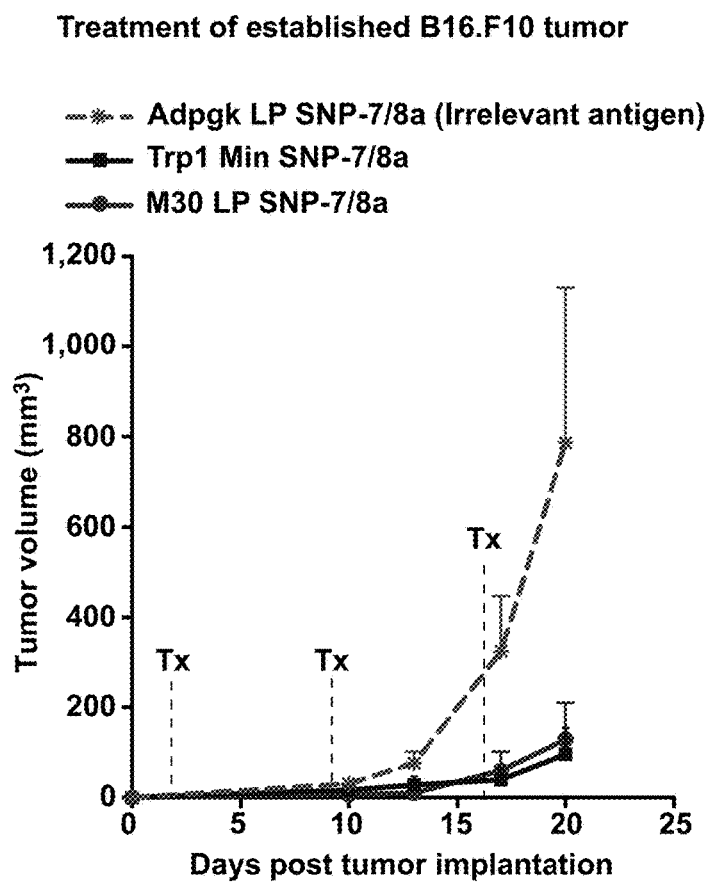
FIG. 32: Self-antigens and neoantigens delivered as peptide antigens (A) on peptide antigen conjugates of Formula V that self-assemble into nanoparticles co-delivering a TLR-7/8a (SNP-7/8a) elicit CD8 and CD4 T cell-mediated clearance of an established melanoma. Mice with established B16.F10 tumors were treated with PD1 and either SNP-7/8a delivering Adpgk LP (CD8 T cell epitope not present in B16.F10), a self-antigen, Trp1, minimal CD8 T cell epitope, or a neoantigen, M30 LP that has a CD4 T cell epitope, on days 2, 9 and 16.
Figure 33:
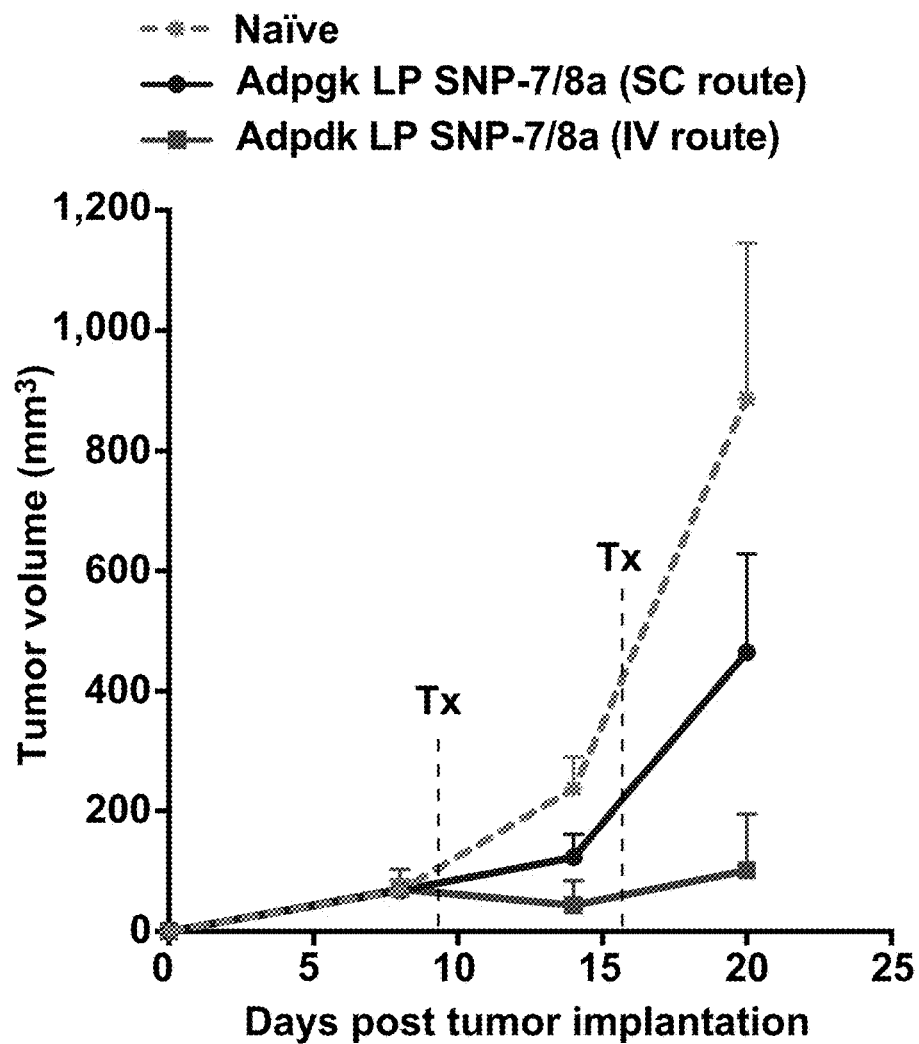
FIG. 33: Neoantigens delivered as peptide antigen conjugates of Formula V that self-assemble into nanoparticles co-delivering a TLR-7/8a (SNP-7/8a) administered by the subcutaneous and intravenous routes elicit robust CD8 T cell-mediated clearance of an established tumor. Mice with established MC38 tumors were vaccinated with Adpgk LP-SNP-7/8a by either the subcutaneous or intravenous routes on days 9 and 16 and tumor volume was assessed at serial time points thereafter.
Figure 34:
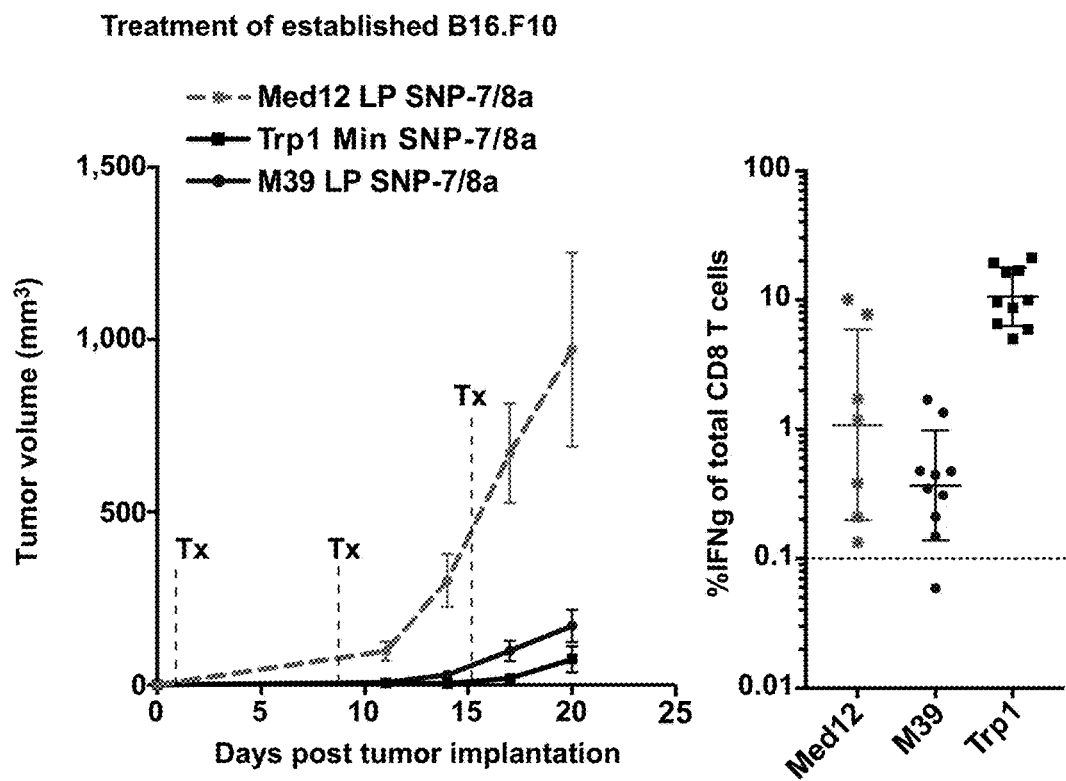
FIG. 34: Neoantigens delivered as peptide antigen conjugates of Formula V that self-assemble into nanoparticles co-delivering a TLR-7/8a (SNP-7/8a) elicit CD8 T cell-mediated clearance of an established melanoma. Mice with established B16.F10 tumors were treated with PDL1 and either SNP-7/8a delivering Med12 (MC38 neoantigen with a CD8 T cell epitope), Trp1 (B16 self-antigen with a CD8 T cell epitope) or M39 (B16 neoantigen with a CD8 T cell epitope) on days 1, 8 and 15. (A) Tumor growth was monitored and (B) CD8 T cell responses were assessed on day 17.
Figure 35:
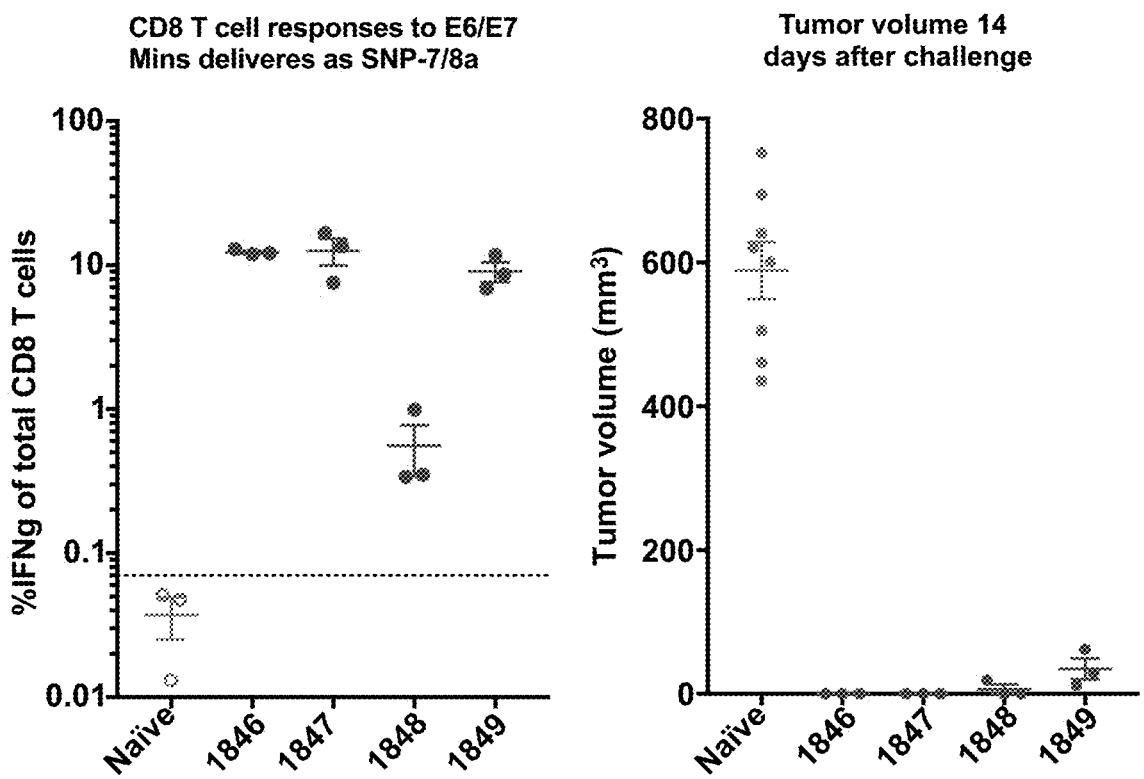
FIG. 35: Viral (HPV) antigens delivered as peptide antigen conjugates of Formula V that self-assemble into nanoparticles co-delivering a TLR-7/8a (SNP-7/8a) elicit CD8 T cell-mediated rejection of an HPV+ tumor. (A & B) Mice were immunized with different E6 and E7 peptide minimal epitopes (mins) derived from HPV delivered as peptide antigens conjugates of Formula V, wherein the charged molecule (C) is poly(lysine) and the hydrophobic molecule (H) is $2B_3W_2$, which self-assemble into nanoparticles co-delivering TLR-7/8a (referred to as "SNP-7/8a") at days 0 and 14. (A) CD8 T cell responses were assessed at day 28 and mice were challenged with an HPV+ cancer cell line (TC1) and (B) tumor volume was assessed at day 14 after challenge.

Peptide Antigen Conjugates Elicit Robust Tumor-Associated (Self-Antigen, Neoantigen and Viral Antigen)-Specific CD8 and CD4 T Cell Responses that Mediate Tumor Clearance In Vivo We investigated whether CD8 T cell responses against previously reported non-immunogenic epitopes could lead to improved clearance of established tumors (FIGS. 32-33). Our results show that several neoantigens from two tumor models, MC38 and B16.F10, that were previously reported to be non-immunogenic led to clearance of established tumors when delivered as peptide antigen conjugates of Formula V that self-assemble into nanoparticles co-delivering TLR-7/8a ("SNP-7/8a"). Notably, while Kreiter et al previously reported that neoantigen-specific CD4 T cell responses primarily mediated clearance of established B16.F10 tumors, we observed that improved efficiency of the vaccine can mobilize both neoantigen-specific CD4 and CD8 T cell responses to mediate clearance of B16.F10 (FIGS. 32 and 34). Importantly, these findings extended beyond the use of neoantigens, as both viral antigens (HPV E6 and E7, FIG. 35) and self-antigens (Trp1, FIG. 32) delivered as SNP-7/8a elicited high magnitude CD8 T cell responses that was associated with improved tumor clearance.

Figure 36:
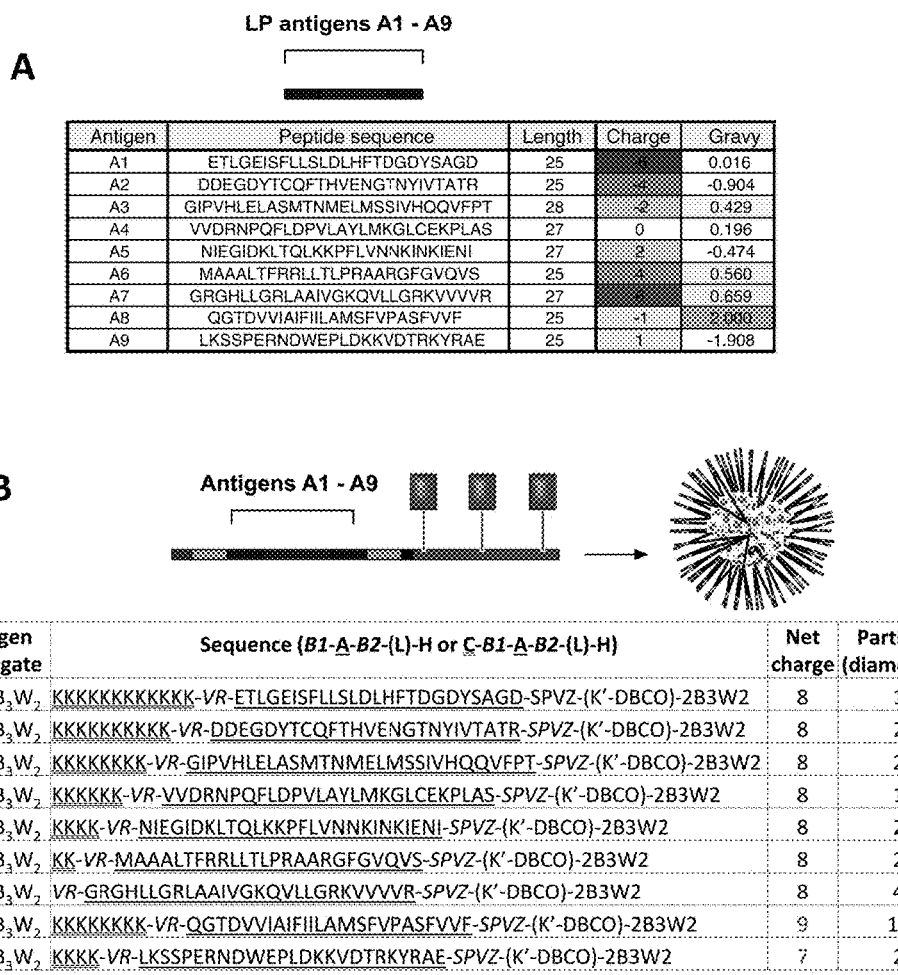
FIG. 36: (SEQ ID NOS: 90, 91, 83, 92-97, 462, 463, 448, 464, 465, 474, 460, 579 and 467, respectively, in order of appearance) Particle size and stability of multi-antigen particles. (A) Neoantigen LPs as peptide antigens (A) (A1 through A9) with a range of charge (−6 to +6) and hydropathy (GRAVY from −2 to +2) were (B) synthesized as peptide antigen conjugates of Formula V, wherein the charged molecule (C) is poly(K), B1 is VR, B2 is SPVZ (SEQ ID NO: 111), the X1 linker precursor is azido-lysine ("X" also referred to as K') and the hydrophobic molecule (H) is $2B_3W_2$, that self-assemble into nanoparticles co-delivering TLR-7/8a (SNP-7/8a). The peptide antigen conjugates were suspended at 0.5 mg/mL in PBS pH 7.4 and assessed for turbidity (OD 490 nm) and particle size (diameter, nm). (C) Multi-antigen particles comprising multiple different peptide antigen conjugates (A1-A9) were mixed together at different ratios in a DMSO solution (scenarios 1-7) and then suspended at 0.5 mg/mL in PBS pH 7.4 and assessed for turbidity (OD 490 nm) and particle size (diameter, nm). The percent of each peptide antigen conjugate comprising the multi-antigen particles for each scenario is provided in the table.
Figure 36:
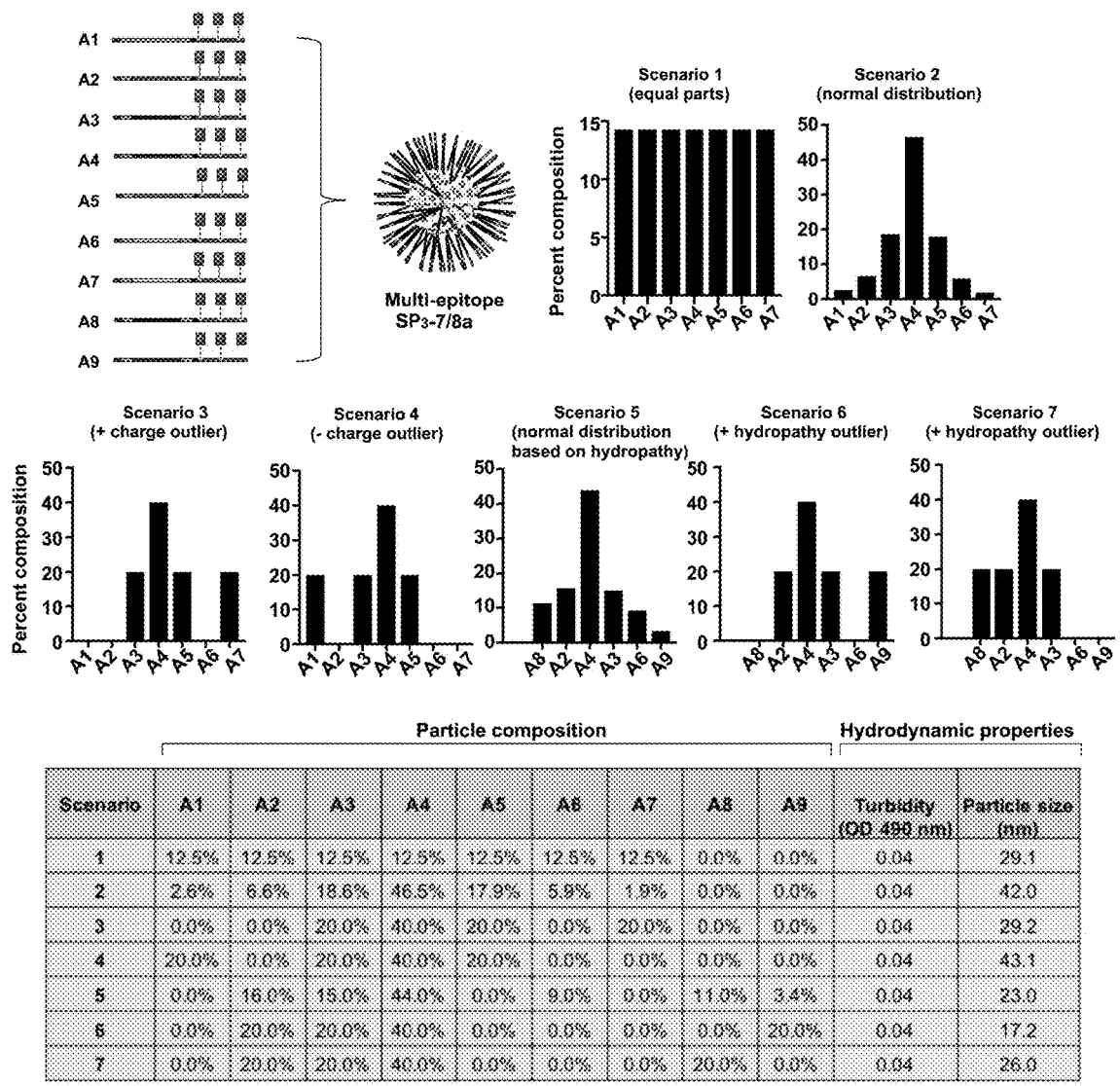

Particles Comprising Multiple Different Peptide Antigen Conjugates are Stable and Exhibit Uniform Particle Size PCV approaches will likely require administration of multiple different epitopes to patients to increase the breadth of T cell responses. Therefore, we evaluated the tolerance of peptide antigen conjugates of Formula V that self-assemble into nanoparticles co-delivering TLR-7/8a (SNP-7/8a) for use in multi-antigen particle vaccines comprising multiple different peptide antigen conjugates (FIG. 36). Particle comprising multiple different peptide antigen conjugates provided consistent particle size, between 20-40 nm, irrespective of the neoantigen LP composition (FIG. 36).

Figure 37:
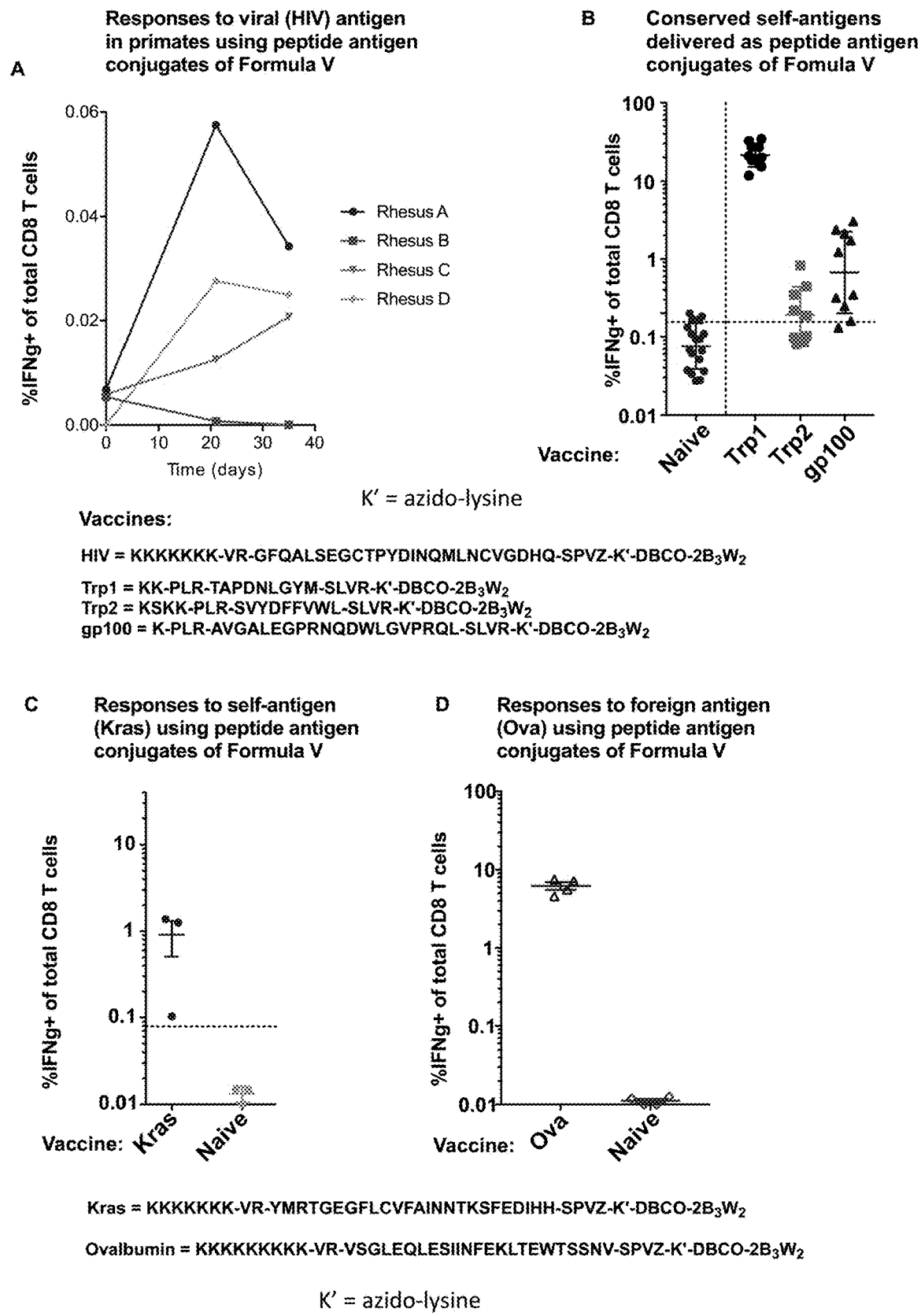
FIG. 37: Shows T cell responses induced by peptide antigen conjugates of Formula V delivering tumor-associated self-antigens, an infectious disease (HIV) antigen and a foreign antigen.

Peptide Antigen Conjugates of Formula V Delivering Tumor-Associated Self-Antigens or Infectious Disease Antigens To extend our findings above, we evaluated the generalizability of using peptide antigen conjugates as a universal vaccine platform for inducing T cell immunity. As shown in FIG. 37, peptide antigen conjugates of Formula V delivering peptide antigens (A) comprising an oncogene (Kras), a peptide derived from a virus (HIV) and a foreign antigen (i.e. Ovalbumin) all formed stable nanoparticles and induced high magnitude T cell responses in vivo.

Figure 38:
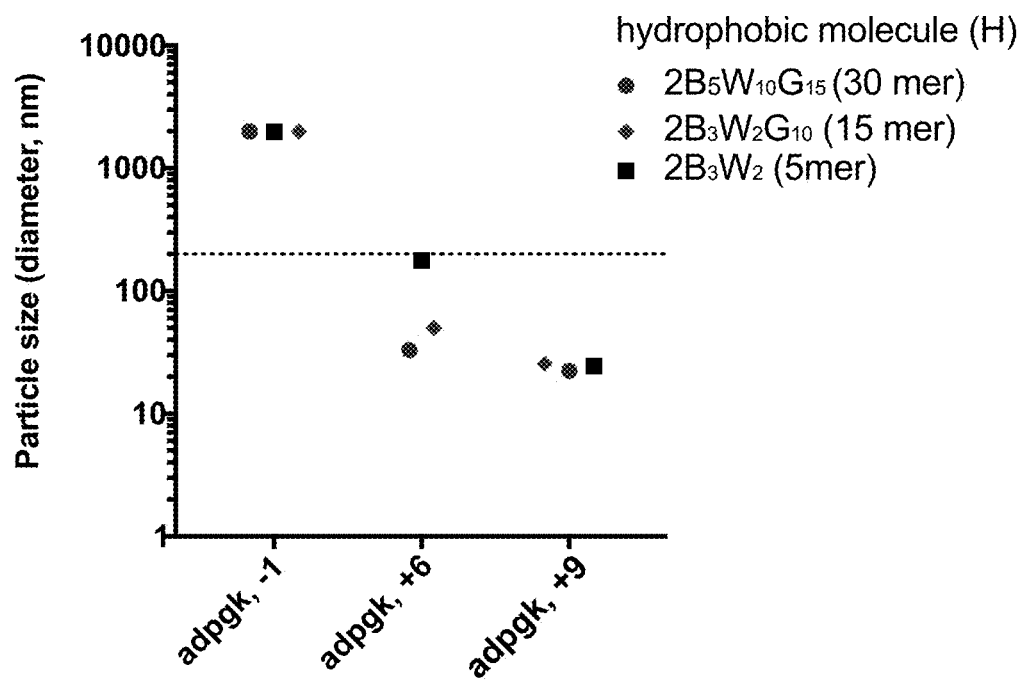
FIG. 38: Shows the particle size and biological activity of peptide antigen conjugates of Formula V comprised of different charged molecules (C) or different hydrophobic molecules (H) based on poly(amino acids) of Formula II linked to adjuvants of Formula III.

Particle Size and Biological Activity of Peptide Antigen Conjugates of Formula V Comprised of Different Charged Molecules (C) or Different Hydrophobic Molecules (H) Based on Poly(Amino Acids) of Formula II Linked to Adjuvants of Formula III As demonstrated above, peptide antigen conjugate vaccines are a modular platform that can allow for broad range of different compositions of each of the components, e.g., charged molecules (C), extensions (B1 and B2), peptide antigens (A), Linkers (L), and hydrophobic molecules (H). In some embodiments, it may be important for including a charged molecule (C) that comprises functional groups that are pH independent over most physiologically relevant pH ranges, e.g., from pH 4.5 to about pH 8.5. Therefore, we synthesized peptide antigen conjugates with either net negative or net positive charge using charged molecules (C) that comprised phosphoserine or trimethyl-lysine (pH independent quaternary ammonium) amino acids, respectively (FIG. 38). Our results show that the peptide antigen conjugates including phosphoserine or trimethyl-lysine based charged molecules (C) form stable nanoparticles and induce high magnitude T cell responses, whereas peptide antigen conjugates without a charged molecule (C) form aggregates.

To extend these findings, we produced peptide antigen conjugates with different lengths, 30 amino acids (Compound 20 referred to as $2B_5W_{10}G_{10}$) and 15 amino acids (Compound 16 referred to as $2B_5G_{10}$), of DBCO bearing hydrophobic molecules (H) based on poly(amino acids) of Formula II linked to adjuvant of Formula III. An unexpected finding was that increasing the content of amine and aromatic groups on the hydrophobic blocks led to improved organic solvent solubility and therefore improved manufacturing as compared with hydrophobic blocks with fewer aromatic groups or amines. Accordingly, despite being a longer change, $2B_5W_{10}G_{10}$ and its peptide precursors were more efficient to manufacture than $2B_5G_{10}$ and it's precursors.

The two different hydrophobic molecules (H), $2B_5W_{10}G_{10}$ and $2B_5G_{10}$ were linked to peptide antigen fragments, comprising long peptide-based neoantigens as the peptide antigen (A), through a triazole Linker (L) to form peptide antigen conjugates of Formula V. Consistent with our earlier findings, stable nanoparticle formation was dependent on the net charge of the peptide antigen conjugates comprising the different hydrophobic molecules (H) (FIG. 38). Unexpectedly, despite the high density of hydrophobic groups on the hydrophobic molecules (H), both peptide antigen conjugates formed stable nanoparticle micelles and induced high magnitude T cell responses in vivo (FIG. 38). In some embodiments, a longer hydrophobic molecule (H) is used to improve kinetic stability of the peptide antigen conjugates, such as may be required for vaccines delivered by the intravenous route.

Figure 39:
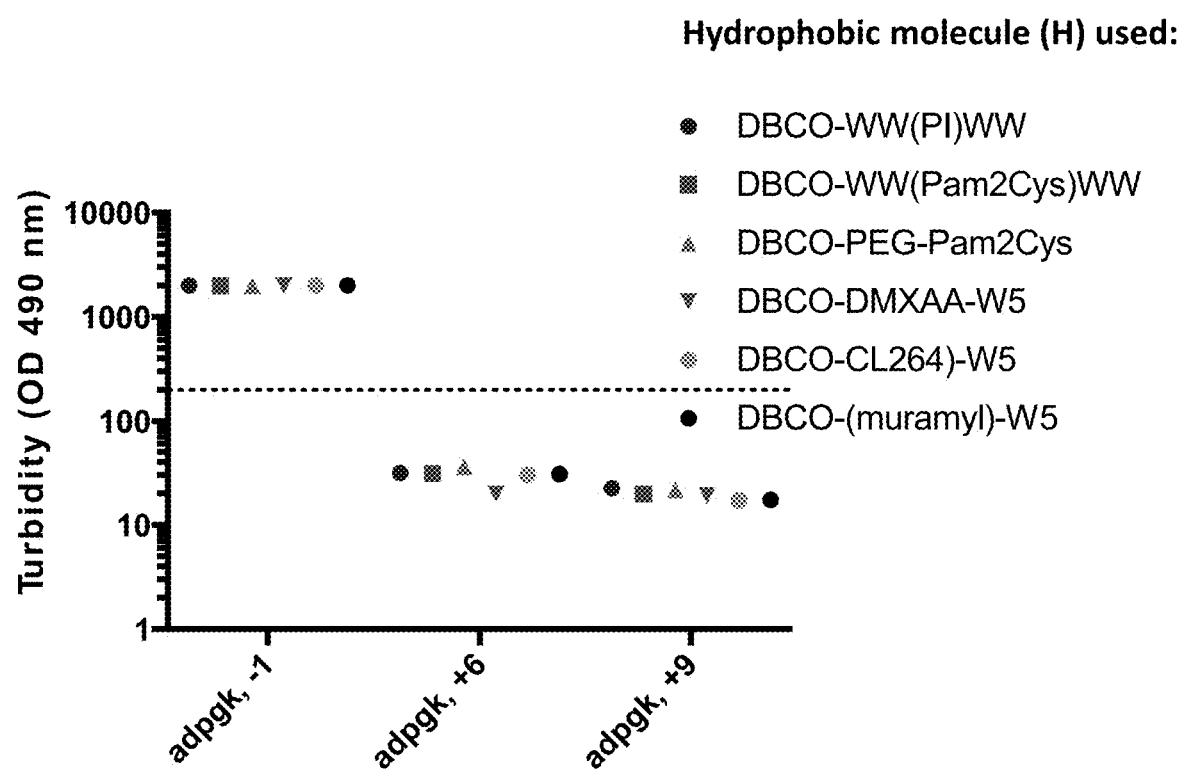
FIG. 39: Shows the particle size and biological activity of peptide antigen conjugates of Formula V comprised of different hydrophobic molecules (H) based on poly(amino acids) of Formula II linked to different PRR agonists.

Particle Size and Biological Activity of Peptide Antigen Conjugates of Formula V Comprised of Different Hydrophobic Molecules (H) Based on Poly(Amino Acids) of Formula II Linked to Different PRR Agonists While the above examples of immunogenic compositions primarily used peptide antigen conjugates comprised of hydrophobic molecules (H) linked to a TLR-7/8a (e.g., adjuvants of Formula III) or not linked to a Ligand, hydrophobic molecules (H) may be linked to any Ligand. In some embodiments, a Ligand with adjuvant properties is included on the hydrophobic molecule (H), while in other embodiments, a Ligand that does not have adjuvant properties is included on the hydrophobic molecule. To demonstrate the generalizability of peptide antigen conjugates delivering different Ligands with adjuvant properties, we synthesized peptide antigen conjugates of Formula V comprised of hydrophobic molecules (H) of Formula II linked to different Ligands, including a TLR-4 agonist (i.e. WW(PI)WW), a TLR-2/6 agonist (i.e. WW(PI)WW), a TLR-7 agonist (i.e. CL264-$W_5$), a NOD agonist (Muramyl-$W_5$) and an agonist of STING (i.e., DMXAA-$W_5$). Consistent with our earlier findings, stable nanoparticle formation was dependent on the net charge of the peptide antigen conjugates comprising the different hydrophobic molecules (FIG. 39), with all of the different immunogenic compositions based on hydrophobic molecules (H) comprising different Ligands with adjuvant properties inducing measurable T cell immunity. Notably, the TLR-7 agonist induced the highest magnitude responses and therefore, TLR-7 or TLR-7/8 agonists are used in preferred embodiments of peptide antigen conjugates for inducing T cell responses either for the prevention or treatment of infectious diseases or cancer.

Attachment of the Peptide Antigen (A) to a Hydrophobic Molecule (H) Using Different Linker Chemistries (Amide and Thio-Ether)

Figure 40:
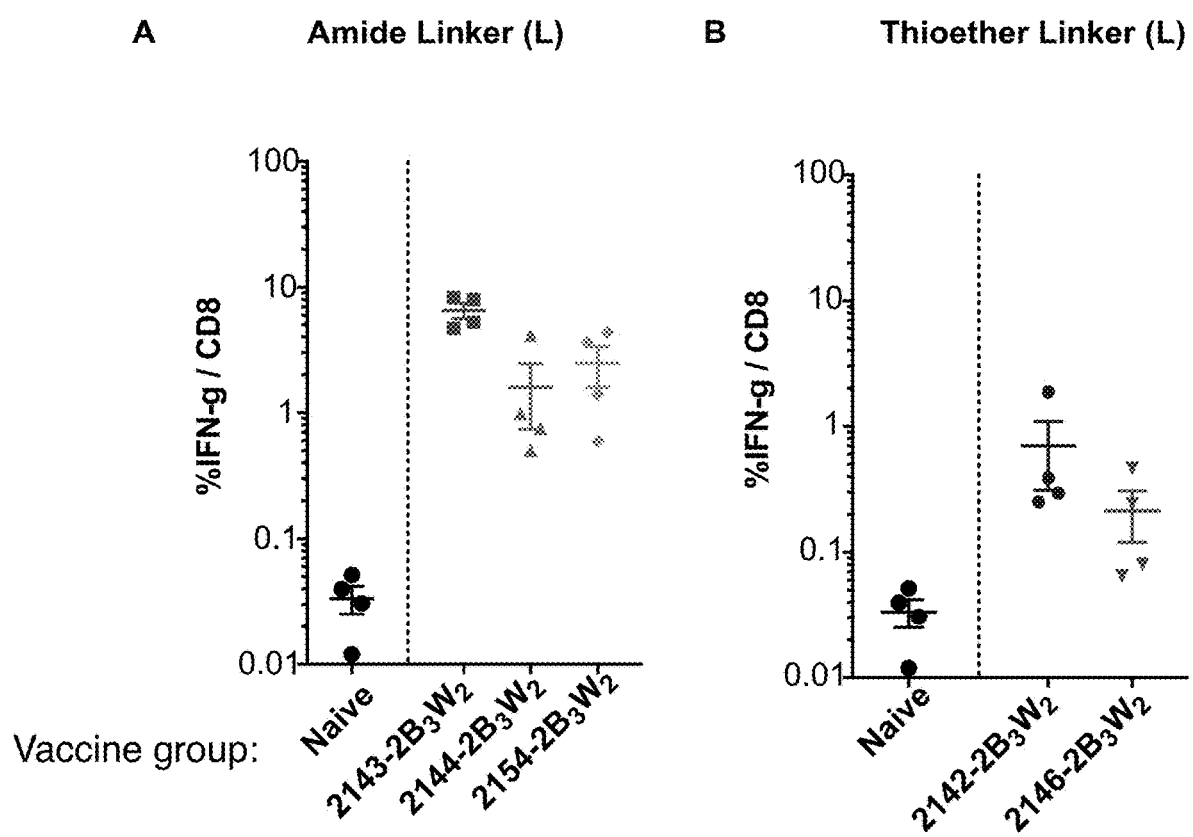
FIG. 40: Shows the particle size and biological activity of peptide antigen conjugates of Formula V where the peptide antigen (A) is linked to a hydrophobic molecule (H) using different linker chemistries (amide and thio-ether).

While preferred embodiments of peptide antigen conjugates use click chemistry to form a Linker (L) from linker precursor X1 and linker precursor X2, other types of linker chemistry are suitable. Thus, peptide antigen conjugates of Formula V were linked to hydrophobic molecules (H) using either amide or thio-ether based Linkers (L), wherein the Linker (L) was either linked through the N- or C-terminus of the peptide antigen (A). Our results show that peptide antigens (A) either linked through the N- or C-terminus of the peptide antigen (via a B1 or B2) extension to a Linker (L) comprising either an amide or thio-ether led to peptide antigen conjugates that formed stable nanoparticles and induced high magnitude T cell responses in vivo (FIG. 40), albeit peptide antigens (A) linked via an amide Linker (L) to the hydrophobic molecule (B) induced higher magnitude responses as compared with those linked using a thioether Linker (L). Thus, in preferred embodiments, stable amide or triazole Linkers (L) are used to linker peptide antigens (A) to hydrophobic molecules (H) either directly or via extensions (B1 or B2).

Figure 41:
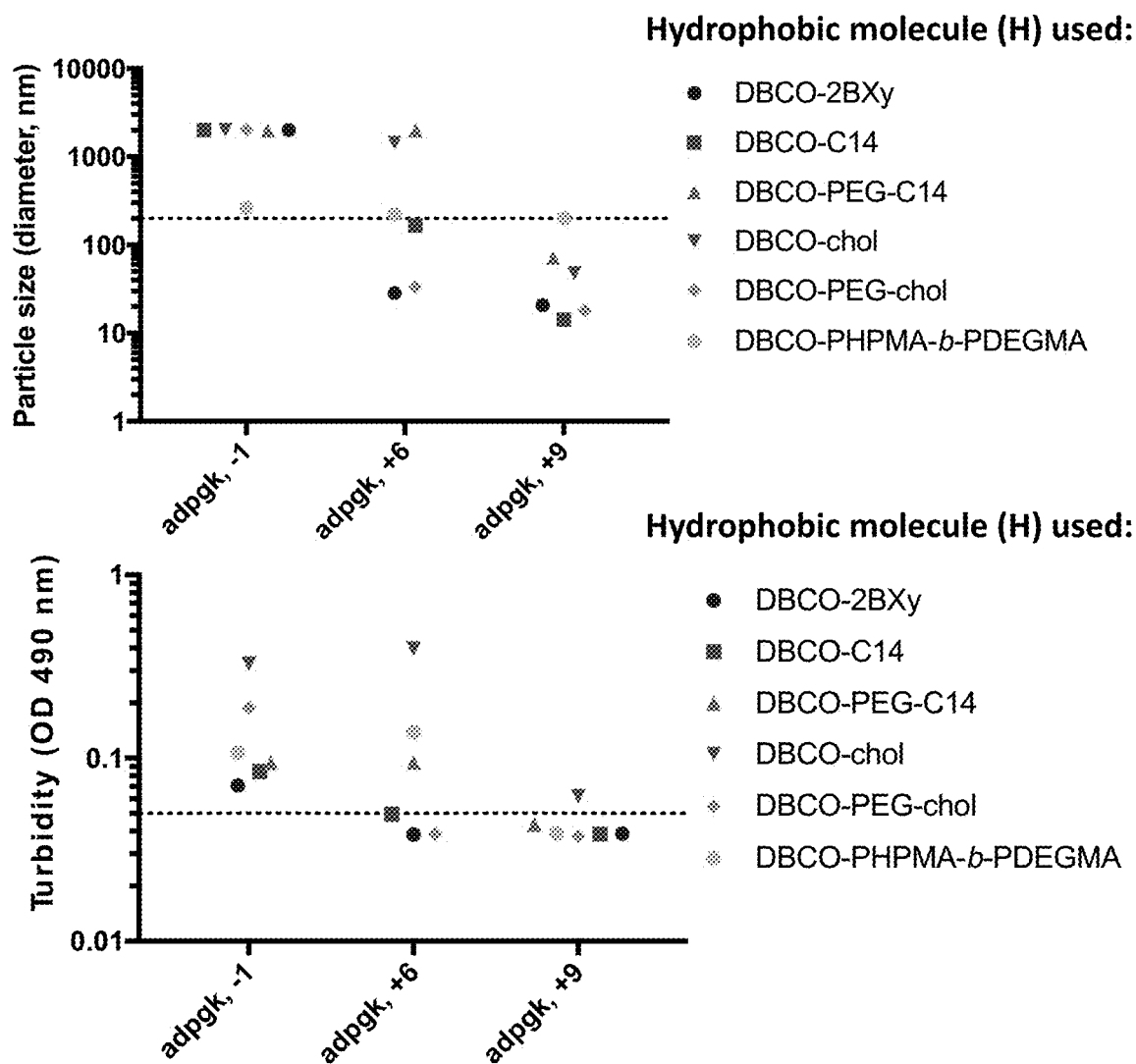
FIG. 41: Shows the particle size and biological activity of peptide antigen conjugates of Formula V comprised of different hydrophobic molecules (H) based on fatty acids, lipids and cholesterol.
Figure 41:
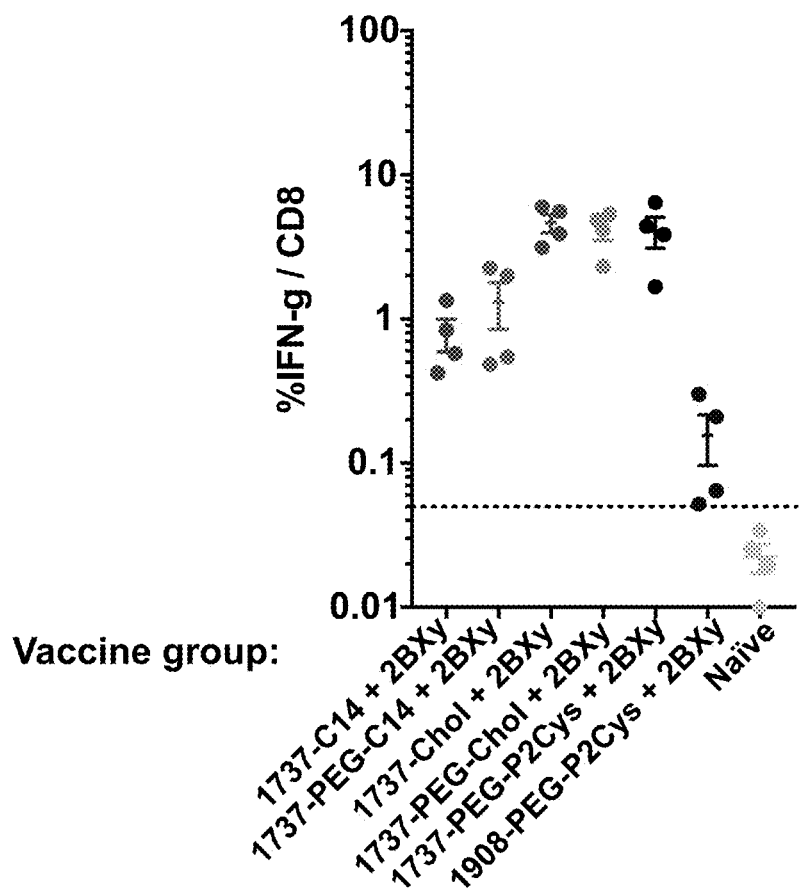

Particle Size and Biological Activity of Peptide Antigen Conjugates of Formula V Comprised of Different Hydrophobic Molecules (H) Based on Fatty Acids, Lipids and Cholesterol While preferred embodiments of peptide antigen conjugates use hydrophobic molecules (H) comprised of polymers, e.g., poly(amino acids) or A-B type di-block co-polymers, hydrophobic molecules (H) may be based on a variety of other hydrophobic molecules, such as fatty acids, lipids, and cholesterol. Thus, peptide antigen conjugates of Formula V were linked to hydrophobic molecules (H) based on myristic acid (Myr or C14, Compounds 49 and 52), palimitic acid (Palm or C16, Compounds 51 and 53), cholesterol (Chol, Compounds 57 and 58) and a diacyl lipid (Pam2Cys, Compounds 54 and 55) Consistent with our earlier findings, stable nanoparticle formation was dependent on the net charge of the peptide antigen conjugates comprising the different hydrophobic molecules (FIG. 41), with net charge greater than or equal to +6 leading to stable nanoparticle formation. Importantly, immunogenic compositions of peptide antigen conjugates based on the fatty acid, cholesterol and lipid based hydrophobic molecules (H) induced high magnitude T cell responses in vivo (FIG. 41). While fatty acid, cholesterol and lipid based particles demonstrated suitable performance in terms of particle formation and biological activity as peptide antigen conjugates, one limitation is that hydrophobic molecules (H) based on fatty acids, cholesterol and lipids are more difficult to manufacture due to limited solubility of these materials in many solvents (e.g., poor solubility in DMSO, DMF and many alcohols) thus requiring biologically harsher chlorinated solvents (e.g., dichloromethane and chloroform), which makes characterization and purification more challenging, especially for personalized vaccine strategies, and increases safety risks, as compared, e.g., with hydrophobic molecules (H) comprised of polymers comprising aromatic groups that are soluble in most organic solvents (e.g., DMSO, methanol, ethanol, acetonitrile, etc.).

Figure 42:
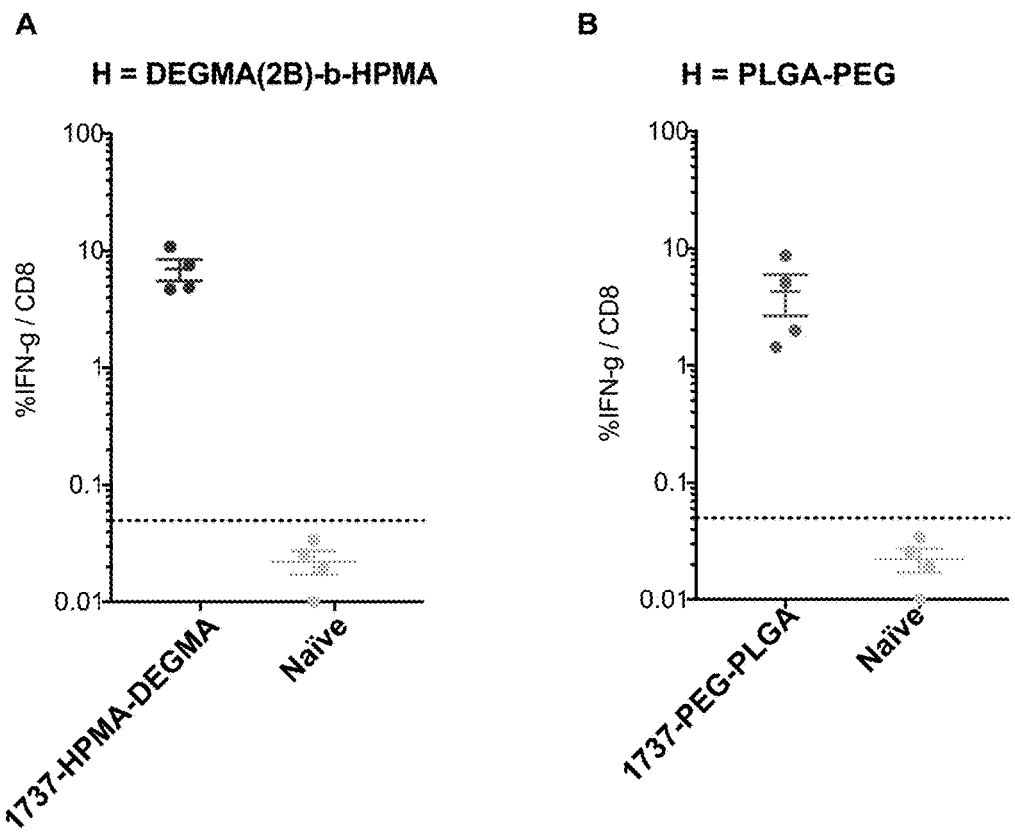
FIG. 42: Shows the particle size and biological activity of peptide antigen conjugates of Formula IV and V comprised of different hydrophobic molecules (H) based A-B type di-block co-polymers.

Particle Size and Biological Activity of Peptide Antigen Conjugates of Formula IV and V Comprised of Different Hydrophobic Molecules (H) Based A-B Type Di-Block Co-Polymers Peptide antigen conjugates of Formula IV and Formula V were prepared by attaching peptide antigens (A) to HPMA-based di-block co-polymers (See: Compounds 68 to 72). Unexpectedly, the micelle-forming di-block co-polymers formed highly stable nanoparticle micelles independent of the net charge of the peptide antigen fragment (FIG. 42). Thus, in some embodiments wherein the hydrophobic molecule (H) is a di-block co-polymer comprised of HPMA monomers, peptide antigen conjugates of Formula IV may be preferred. The di-block may form particle in aqueous conditions independent of temperature, or particle formation may be temperature dependent. Moreover, a Ligand may be included on either of the two blocks, either at the ends or the side groups of the di-block co-polymer. Our results show that the A-B type di-block polymer comprised of HPMA monomers ensures stable nanoparticle formation and results in high magnitude T cell responses when included as a hydrophobic molecule (H) of immunogenic compositions comprising peptide antigen conjugates (FIG. 42).

Particle Size and Stability of Peptide Antigen Conjugates of Formula V Based on Peptide Antigens (A) Linked to Particles In preferred embodiments, the peptide antigen conjugate comprises a hydrophobic molecule (H); however, in some embodiments, the peptide antigen conjugate comprises a pre-formed Particle (P). The dependency of the charge of the peptide antigen fragment on the stability of particles based on peptide antigen conjugates of Formula V comprising a Particle (P) was assessed by attaching peptide antigen fragments (C-B1-A-B2-) with different net charge to pre-formed Particles (P) based on liposomes, polystyrene, silic and iron oxide particles. Consistent with our earlier findings, stable nanoparticle formation was dependent on the net charge of the peptide antigen conjugates comprising the different hydrophobic molecules (FIG. 43).

Particle Size and Biological Activity of Peptide Antigen Conjugates Delivering Auto-Antigens Used for Inducing Tolerance Peptide antigen conjugates may also be used for inducing tolerance or suppressive regulatory T cells. In preferred embodiments for inducing tolerance or immune suppression, a Ligand with adjuvant properties is typically not included. Instead, the peptide antigen conjugate should comprise a particle comprising the peptide antigen (A), a hydrophobic molecule (H) or Particle (P) and optional Linker (L), charged molecule (C) and extensions (B1 and/or B2), wherein a Ligand with adjuvant properties is not included. To evaluate the generalizability of the peptide antigen conjugates described herein for use to induce tolerance or suppression, model auto-antigens for inducing arthritis (i.e. Collagen II) and a CNS syndrome that resembles MS (i.e. myelin oligodendrocyte glycoprotein, "MOG") were produced as peptide antigens (A) on peptide antigen conjugates of Formula V. Consistent with our earlier results, autoantigens delivered on peptide antigen conjugates of Formula V assembled into stable nanoparticles and induced low level regulatory T cell responses (FIG. 44).

Particle Size and Biological Activity of Particles Comprised of A-H+C-H or A-H(C) (Formula VI)

Figure 45:
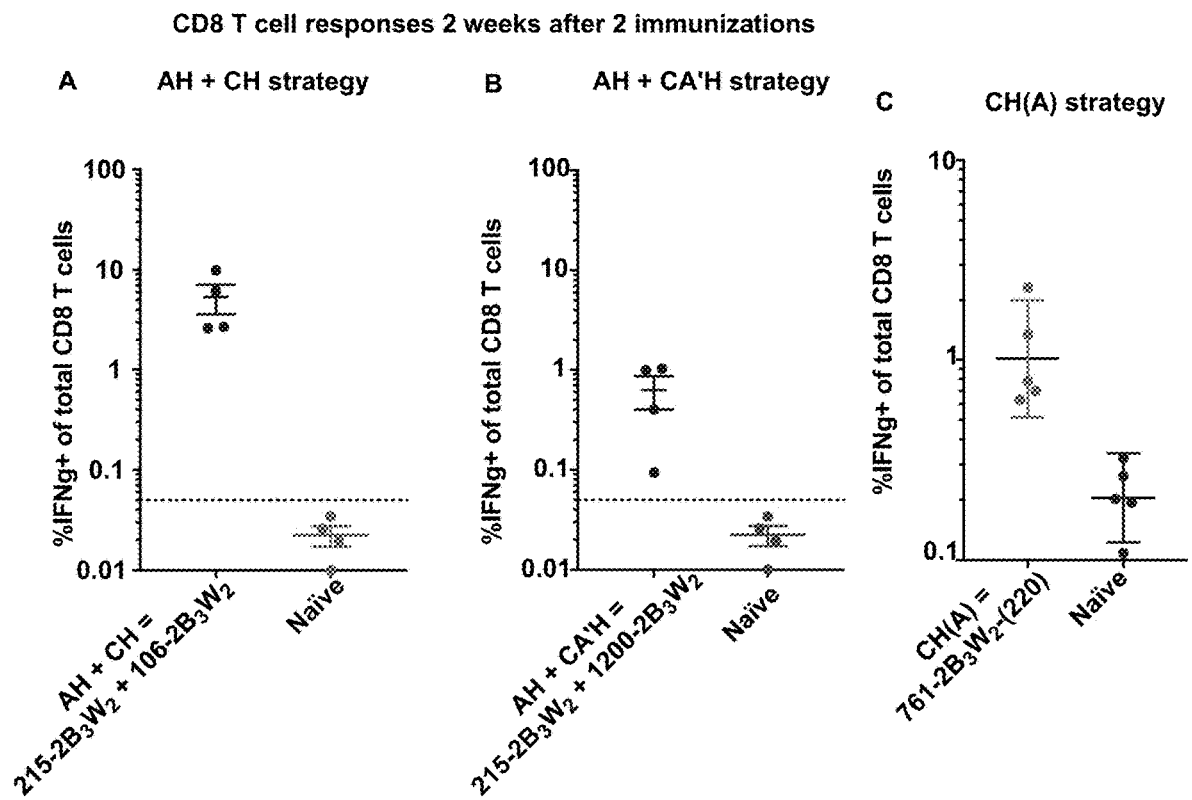
FIG. 45: shows the particle size and biological activity of particles comprised of A-H+C-H or A-H(C) (Formula VI).

In some embodiments, the immunogenic composition comprises a particle comprised of peptide antigen conjugates without charged molecules (e.g., A-[B2]-[L]-H) mixed with charged molecule conjugates (e.g., C-[A']-[L]-H]. For example, a peptide antigen conjugate comprised of a LP neoantigen (Adpgk) was linked through a triazole Linker (L) to the hydrophobic molecule $2B_3W_2$, to form a peptide antigen conjugate (A-L-H) that was mixed with a charged molecule conjugate (C—H), Compound 42 ($K_{10}$-$2B_3W_2$) to form stable nanoparticles that induced high magnitude T cell immunity (FIG. 45). In another embodiment, a peptide antigen conjugate comprised of a LP neoantigen (Adpgk) was linked through a triazole Linker (L) to the hydrophobic molecule $2B_3W_2$, to form a peptide antigen conjugate (A-L-H) that was mixed with a charged molecule conjugate additionally comprising a conserved antigen A' (i.e., C-A'-H) to form stable nanoparticles that induced high magnitude T cell immunity (FIG. 45).

Alternatively, the charged molecule (C) may be linked to the hydrophobic molecule (H) that is linked to a peptide antigen (A) to form a peptide antigen conjugate of Formula VI. In a non-limiting example, a peptide neoantigen (Adpgk) is delivered as a peptide antigen (A) on a peptide antigen conjugate of the formula A-[L]-H(C) and the resulting conjugate was found to form stable nanoparticles and high magnitude T cell immunity. Thus, in preferred embodiments of immunogenic compositions comprising particles, a charged molecule (C) may be provided either through a direct or indirect linkage to the peptide antigen (A) or on a separate molecule that associates with particles formed by peptide antigen conjugates.

Importantly, the present disclosure describes novel peptide-based vaccine approaches, referred to as peptide antigen conjugates, that lead to unexpected improvements in the magnitude and breadth of T cells generated against peptide antigens (A), including tumor-associated antigens (self-antigens, neoantigens and viral antigens), infectious diseases antigens and foreign antigens. Immunogenic compositions comprising peptide antigen conjugates that exclude adjuvants were also found to induce low level tolerogenic/suppressive responses against autoantigens, which may be useful for treating auto-immunity and/or allergies.

In the present disclosure, we demonstrate an unexpected finding that peptide antigens (A) comprising the minimal epitope (ME) can result in higher magnitude CD8 T cell responses than the same ME delivered as a synthetic long peptide (SLP) when both are normalized for pharmacokinetics by delivering both as nanoparticles comprised of peptide antigen conjugates. Additionally, we provide examples where a ME delivered within an SLP as a peptide antigen conjugate does not lead to CD8 T cell responses after a single immunization but the ME delivered as a peptide antigen conjugate does, presumably through more efficient processing that leads to increased cell-surface presentation of the ME within the context of MHC I molecules by APCs. Such ME based vaccines were found to expand the breadth of T cell responses, which were additionally shown to be functional in the context of reducing the growth of established tumors. Therefore, based on our unexpected findings, preferred embodiments of immunogenic compositions use peptide antigen conjugates delivering peptide antigens (A) based on minimal epitopes, or a combination of MEs with SLPs. Though, in some embodiments, the peptide antigen (A) is a SLP (or "LP").

Furthermore, to provide improved control over material loading and the size and stability of particles delivering peptide antigens (A) with a range of properties, we disclose herein a novel approach for delivering peptide antigens (A) as peptide antigen conjugates that assemble into micellar and nano-sized supramolecular associates in aqueous buffers. Importantly, we show how the composition of peptide antigen conjugates, including optional particle-stabilizing charged molecule (C), hydrophobic molecule (H) optional (Linker) and optional extension sequences (B1 and B2) can be optimized to ensure stable particles of defined sizes can be achieved for any possible peptide antigen (A). We show that reliable particle formation and improved stability can be achieved by tuning the length and hydrophobic characteristics of the hydrophobic molecule (H) as well as by modulating the charge of particles formed by peptide antigen conjugates.

As a means for improving the processing of T cell epitopes comprising the peptide antigen conjugate, we demonstrate the utility of using N- and C-terminal extensions (B1 and B2 or 'extensions') that are stable in aqueous conditions but are preferentially hydrolyzed by enzymes within the endosomes of antigen-presenting cells, thereby restricting the processing and presentation of the antigen to such cells, and promoting efficient release of the minimal CD8 and/or CD4 T cell epitope within APCs.

Finally, in the present disclosure, we systematically evaluated the optimal composition, number and potency of PRR agonist based immuno-stimulants required for promoting T cell immunity. We provide data that the progressive increase in the number and potency of TLR agonists that induce the production of IL-12 and type-I IFNs results initially in improved magnitude of the T cell responses, but in a novel and unexpected finding, that additional increases result in narrower antigenic breadth and lower magnitude of T cells responses. Therefore, we report the composition, number and potency of immuno-stimulants (i.e. PRR agonists) attached to the hydrophobic molecule (H) that are preferred for providing the optimal magnitude, quality and breadth of T cell immunity.

In summary, the unexpected findings disclosed herein relate to:
i. The optimal length of peptide antigens (A) used in cancer vaccines to ensure reliable priming of T cell immunity.
ii. Use of peptide antigen extension sequences, i.e., N- and/or C-terminal extensions (B1 and/or B2), that facilitate manufacturing of peptide-based vaccines, promote particle stability and facilitate processing to permit efficient presentation by APCs.
iii. The composition of charged molecules (C) and net charge of peptide antigen conjugates needed to induce and stabilize particles of an optimal size for promoting T cell immunity.
iv. How hydrophobic molecule length (H) and composition imparts on the size and stability of particles formed by peptide antigen conjugates, as well as their immunogenicity in vivo.
v. How the potency and qualitative characteristics of the Ligand (e.g., PRR agonist) included on the hydrophobic molecules (H) imparts on the breadth, magnitude and quality of T cell responses.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers; or the inclusion of a stated composition or compositions, but not the exclusion of any other composition or compositions.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

What is claimed is:

1. A peptide antigen conjugate comprising a hydrophobic molecule represented by Formula (1):

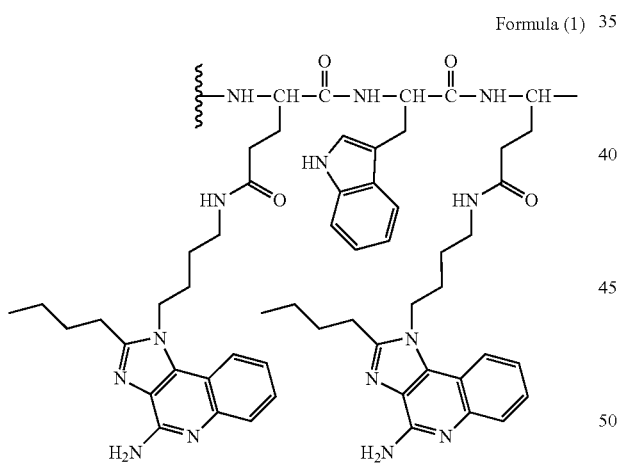

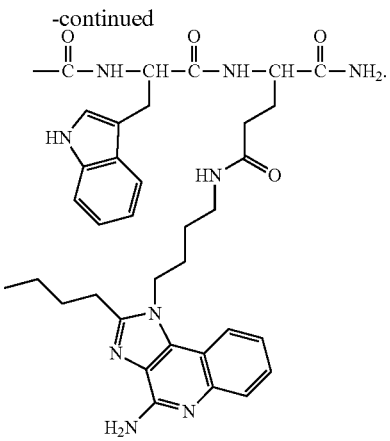

* * * * *

SEQUENCE LISTING

```
<160> NUMBER OF SEQ ID NOS: 623

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ser Pro Tyr Ser Leu His Tyr Leu
1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ser Met Thr Asn Met Glu Leu Met Ser Ser
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Pro Leu Arg Tyr Leu Leu Leu
1               5

<210> SEQ ID NO 4
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 4

Ser Leu Val Leu
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Leu Val Arg
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Pro Val Arg
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Leu Val Arg
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Pro Leu Arg
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Pro Val Arg
1
```

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Leu Val Leu
1

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Lys Leu Val Arg
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Lys Pro Leu Arg
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Ser Leu Val Arg
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Ser Leu Val Leu
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Glu Leu Val Arg
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Glu Leu Val Leu
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ser Leu Val Arg
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Lys Pro Val Arg
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ser Leu Val Leu
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Glu Leu Val Leu
1               5

<210> SEQ ID NO 21
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Pro Leu Arg
1

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Lys Phe Val Ala Ala Trp Thr Leu Lys Ala Ala Ala
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Phe Leu Gly
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Leu Leu Leu
1

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Asp Asp Asp Asp Asp Asp Asp Asp Asp Asp Asp Asp Asp Asp
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Asp Asp Asp Asp Asp Asp Asp Asp Asp Asp Asp Asp Asp Asp
```

```
1               5                   10                  15
```

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Asp Asp Asp Asp Asp Asp Asp Asp Asp Asp Asp Asp Asp Asp
1               5                   10
```

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Asp Asp Asp Asp Asp Asp Asp Asp Asp Asp Asp Asp Asp
1               5                   10
```

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Asp Asp Asp Asp Asp Asp Asp Asp Asp Asp Asp Asp
1               5                   10
```

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Asp Asp Asp Asp Asp Asp Asp Asp Asp Asp Asp
1               5                   10
```

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Asp Asp Asp Asp Asp Asp Asp Asp Asp Asp
1               5                   10
```

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic

```
                peptide

<400> SEQUENCE: 32

Asp Asp Asp Asp Asp Asp Asp Asp Asp
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Asp Asp Asp Asp Asp Asp Asp
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Asp Asp Asp Asp Asp Asp
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Asp Asp Asp Asp Asp
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Asp Asp Asp Asp
1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Asp Asp Asp
1

<210> SEQ ID NO 38
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Lys Lys Lys Lys Lys Lys Lys Lys Lys Lys Lys Lys Lys Lys Lys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Lys Lys Lys Lys Lys Lys Lys Lys Lys Lys Lys Lys Lys Lys
1               5                   10                  15

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Lys Lys Lys Lys Lys Lys Lys Lys Lys Lys Lys Lys Lys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Lys Lys Lys Lys Lys Lys Lys Lys Lys Lys Lys Lys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Lys Lys Lys Lys Lys Lys Lys Lys Lys Lys Lys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43
```

Lys Lys Lys Lys Lys Lys Lys Lys Lys Lys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Lys Lys Lys Lys Lys Lys Lys Lys Lys
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Lys Lys Lys Lys Lys Lys Lys Lys
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Lys Lys Lys Lys Lys Lys Lys
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Lys Lys Lys Lys Lys Lys
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Lys Lys Lys Lys Lys
1               5

<210> SEQ ID NO 49
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 49

Lys Lys Lys Lys Lys
1               5

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Lys Lys Lys
1

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Ser Lys Ser Lys
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Ser Lys Ser Lys Ser Lys
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Ser Asp Ser Asp
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ser Asp Ser Asp Ser Asp
1               5
```

```
<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Asp Lys Asp
1

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Asp Lys Asp Lys Asp
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Val Ile Ala Ile Phe Ile Ile Leu
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Ser Lys Gly Gly
1               5

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Pro Gly Arg
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

Gly Ser Val Arg
1

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Ser Pro Val Arg
1               5

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Leu Val Arg
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Leu Val Leu
1

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Asp Leu Val Leu
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Asp Leu Val Arg
1               5

<210> SEQ ID NO 66
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 66

Gly Ser Glu Leu Val Arg
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Gly Asp Pro Val Arg
1               5

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Leu Val Arg
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Pro Val Arg
1

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: AMIDATION

<400> SEQUENCE: 70

Trp Trp Trp Trp Trp
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71
```

```
Glu Lys Glu Lys Glu Lys
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Leu Val Arg Tyr Leu Leu Leu
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Ser Lys Ser Lys Ser
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Glu Ser Glu Ser Glu Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Asn His Arg Asn Arg Gln Val Ile
1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Pro Glu Arg Asn Asp Trp Glu Pro Leu
1               5                   10

<210> SEQ ID NO 77
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 77

Ala Ser Met Thr Asn Met Glu Leu Met
1               5

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: AMIDATION

<400> SEQUENCE: 78

Gly Gly Glu Gly Gly Trp Gly Gly Glu Gly Gly Trp Gly Gly Glu
1               5                   10                  15

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: AMIDATION

<400> SEQUENCE: 79

Trp Trp Glu Trp Trp
1               5

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Leu Val Ser
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Gly Gly
1

<210> SEQ ID NO 82
<211> LENGTH: 28
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 82

Gly Ile Pro Val His Leu Glu Leu Ala Ser Met Thr Asn Arg Glu Leu
1               5                   10                  15

Met Ser Ser Ile Val His Gln Gln Val Phe Pro Thr
            20                  25

<210> SEQ ID NO 83
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ile Pro Val His Leu Glu Leu Ala Ser Met Thr Asn Met Glu Leu
1               5                   10                  15

Met Ser Ser Ile Val His Gln Gln Val Phe Pro Thr
            20                  25

<210> SEQ ID NO 84
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Phe Thr Gly Ser Asn Gly Asp Pro Ser Ser Pro Tyr Ser Leu His
1               5                   10                  15

Tyr Leu Ser Pro Thr Gly Val Asn Glu Tyr
            20                  25

<210> SEQ ID NO 85
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Ala Arg Asp Glu Thr Ala Ala Leu Leu Asn Ser Ala Val Leu Gly
1               5                   10                  15

Ala Ala Pro Leu Phe Val Pro Pro Ala Asp
            20                  25

<210> SEQ ID NO 86
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Lys Leu Leu Ser Phe Met Ala Pro Ile Asp His Thr Thr Met Ser
1               5                   10                  15

Asp Asp Ala Arg Thr Glu Leu Phe Arg Ser
            20                  25

```
<210> SEQ ID NO 87
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Ala Gly Gln Ser Leu Val Ile Ser Ala Ser Ile Ile Val Phe Asn
1               5                   10                  15

Leu Leu Glu Leu Glu Gly Asp Tyr Arg
            20                  25

<210> SEQ ID NO 88
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Ile Asp Pro Ser Ser Ser Val Leu Phe Glu Tyr Met Glu Lys Pro
1               5                   10                  15

Asp Phe Ser Leu Phe Ser Pro
            20

<210> SEQ ID NO 89
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg
            20                  25

<210> SEQ ID NO 90
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Thr Leu Gly Glu Ile Ser Phe Leu Leu Ser Leu Asp Leu His Phe
1               5                   10                  15

Thr Asp Gly Asp Tyr Ser Ala Gly Asp
            20                  25

<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

Asp Asp Glu Gly Asp Tyr Thr Cys Gln Phe Thr His Val Glu Asn Gly
1               5                   10                  15

Thr Asn Tyr Ile Val Thr Ala Thr Arg
            20                  25

<210> SEQ ID NO 92
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Val Val Asp Arg Asn Pro Gln Phe Leu Asp Pro Val Leu Ala Tyr Leu
1               5                   10                  15

Met Lys Gly Leu Cys Glu Lys Pro Leu Ala Ser
            20                  25

<210> SEQ ID NO 93
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asn Ile Glu Gly Ile Asp Lys Leu Thr Gln Leu Lys Lys Pro Phe Leu
1               5                   10                  15

Val Asn Asn Lys Ile Asn Lys Ile Glu Asn Ile
            20                  25

<210> SEQ ID NO 94
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met Ala Ala Ala Leu Thr Phe Arg Arg Leu Leu Thr Leu Pro Arg Ala
1               5                   10                  15

Ala Arg Gly Phe Gly Val Gln Val Ser
            20                  25

<210> SEQ ID NO 95
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Arg Gly His Leu Leu Gly Arg Leu Ala Ala Ile Val Gly Lys Gln
1               5                   10                  15

Val Leu Leu Gly Arg Lys Val Val Val Arg
            20                  25

<210> SEQ ID NO 96
<211> LENGTH: 25
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 96

Gln Gly Thr Asp Val Val Ile Ala Ile Phe Ile Ile Leu Ala Met Ser
1               5                   10                  15

Phe Val Pro Ala Ser Phe Val Val Phe
            20                  25

<210> SEQ ID NO 97
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Lys Ser Ser Pro Glu Arg Asn Asp Trp Glu Pro Leu Asp Lys Lys
1               5                   10                  15

Val Asp Thr Arg Lys Tyr Arg Ala Glu
            20                  25

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Lys Glu Lys Glu Lys Gly Gly Ser Ser Pro Tyr Ser Leu His Tyr
1               5                   10                  15

Leu

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu Lys Glu Lys Glu Lys Gly Gly Ser Leu Val Arg Ser Ser Pro Tyr
1               5                   10                  15

Ser Leu His Tyr Leu
            20

<210> SEQ ID NO 100
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Lys Glu Lys Glu Lys Gly Gly Ser Leu Val Arg Ser Ser Pro Tyr
1               5                   10                  15

Ser Leu His Tyr Leu Ser Leu Val Arg
            20                  25
```

<210> SEQ ID NO 101
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Lys Glu Lys Glu Lys Gly Gly Ser Leu Val Arg Ser Ser Pro Tyr
1               5                   10                  15

Ser Leu His Tyr Leu Gly Gly Ser Leu Val Arg
            20                  25

<210> SEQ ID NO 102
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Lys Glu Lys Glu Lys Gly Gly Ser Leu Val Arg Tyr Leu Leu Leu
1               5                   10                  15

Ser Ser Pro Tyr Ser Leu His Tyr Leu Gly Gly Ser Leu Val Arg
            20                  25                  30

<210> SEQ ID NO 103
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Citrulline
<220> FEATURE:
<221> NAME/KEY: MOD_RES
<222> LOCATION: (44)..(44)
<223> OTHER INFORMATION: Azido-Lys attached to a fatty acid (C14),
      cholesterol or lipid

<400> SEQUENCE: 103

Lys Lys Lys Lys Lys Lys Lys Lys Lys Val Arg Gly Ile Pro Val His
1               5                   10                  15

Leu Glu Leu Ala Ser Met Thr Asn Met Glu Leu Met Ser Ser Ile Val
            20                  25                  30

His Gln Gln Val Phe Pro Thr Ser Pro Val Xaa Lys
        35                  40

<210> SEQ ID NO 104
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Citrulline
<220> FEATURE:
<221> NAME/KEY: MOD_RES
<222> LOCATION: (44)..(44)
<223> OTHER INFORMATION: Azido-Lys attached to an A-B type di-block co-polymer

<400> SEQUENCE: 104

Lys Lys Lys Lys Lys Lys Lys Lys Val Arg Gly Ile Pro Val His
1               5                   10                  15

Leu Glu Leu Ala Ser Met Thr Asn Met Glu Leu Met Ser Ser Ile Val
            20                  25                  30

His Gln Gln Val Phe Pro Thr Ser Pro Val Xaa Lys
        35                  40

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Leu Val Arg Ala Ser Met Thr Asn Met Glu Leu Met
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Gly Gly Gly Ala Ser Met Thr Asn Met Glu Leu Met
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid

<400> SEQUENCE: 107

Ser Leu Val Arg Ala Ser Met Thr Asn Met Glu Leu Met
1               5                   10

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Leu Val Arg Ala Ser Met Thr Asn Met Glu Leu Met Ser Leu Val
1               5                   10                  15

Arg

<210> SEQ ID NO 109
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 109

Ser Leu Val Arg Ala Ser Met Thr Asn Met Glu Leu Met Gly Gly Gly
1               5                   10                  15

Gly

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: D-amino acid

<400> SEQUENCE: 110

Ser Leu Val Arg Ala Ser Met Thr Asn Met Glu Leu Met Ser Leu Val
1               5                   10                  15

Arg

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline

<400> SEQUENCE: 111

Ser Pro Val Xaa
1

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Citrulline

<400> SEQUENCE: 112

Gly Gly Ser Leu Val Xaa
1               5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
```

```
<223> OTHER INFORMATION: Citrulline

<400> SEQUENCE: 113

Gly Gly Ser Pro Val Xaa
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline

<400> SEQUENCE: 114

Gly Ser Leu Val Xaa
1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline

<400> SEQUENCE: 115

Gly Lys Pro Val Xaa
1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Azido-Lys-DBCO

<400> SEQUENCE: 116

Ser Leu Val Arg Lys
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Azido-pentanoic acid

<400> SEQUENCE: 117

Xaa Ser Leu Val Arg
1               5
```

```
<210> SEQ ID NO 118
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-20 "Lys Ser"
      repeating units

<400> SEQUENCE: 118

Lys Ser Lys Ser Lys Ser Lys Ser Lys Ser Lys Ser Lys Ser Lys Ser
1               5                   10                  15

Lys Ser Lys Ser Lys Ser Lys Ser Lys Ser Lys Ser Lys Ser Lys Ser
            20                  25                  30

Lys Ser Lys Ser Lys Ser Lys Ser
        35                  40

<210> SEQ ID NO 119
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-20 "Asp Ser"
      repeating units

<400> SEQUENCE: 119

Asp Ser Asp Ser Asp Ser Asp Ser Asp Ser Asp Ser Asp Ser Asp Ser
1               5                   10                  15

Asp Ser Asp Ser Asp Ser Asp Ser Asp Ser Asp Ser Asp Ser Asp Ser
            20                  25                  30

Asp Ser Asp Ser Asp Ser Asp Ser
        35                  40

<210> SEQ ID NO 120
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys-DBCO

<400> SEQUENCE: 120

Ser Leu Val Arg Ala Lys Phe Val Ala Ala Trp Thr Leu Lys Ala Ala
1               5                   10                  15

Ala Ser Leu Val Arg Lys
            20

<210> SEQ ID NO 121
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (25)..(25)
<223> OTHER INFORMATION: Azido-Lys

<400> SEQUENCE: 121

Lys Ser Lys Gly Gly Lys Pro Leu Arg Val Val Ile Ala Ile Phe Ile
1               5                   10                  15

Ile Leu Gly Gly Lys Leu Val Arg Lys
            20                  25

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Azido-Lys-DBCO

<400> SEQUENCE: 122

Ala Ser Met Thr Asn Met Glu Leu Met Ser Ser Lys
1               5                   10

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Azido-Lys-DBCO

<400> SEQUENCE: 123

Lys Lys Lys Lys Lys Lys
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline

<400> SEQUENCE: 124

Gly Ser Val Leu Xaa
1               5

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Citrulline
```

```
<400> SEQUENCE: 125

Gly Pro Val Leu Xaa
1               5

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: This sequence may encompass 4-12 residues

<400> SEQUENCE: 126

Lys Lys Lys Lys Lys Lys Lys Lys Lys Lys Lys Lys
1               5                   10

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Citrulline

<400> SEQUENCE: 127

Gly Gly Ser Pro Leu Xaa
1               5

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(14)
<223> OTHER INFORMATION: This sequence may encompass 6-14 residues

<400> SEQUENCE: 128

Glu Glu Glu Glu Glu Glu Glu Glu Glu Glu Glu Glu Glu Glu
1               5                   10

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-(4-(aminomethyl)benzyl)-2-butyl-1H-
      imidazo[4,5-c]quinolin-4-amine Glu
<220> FEATURE:
<221> NAME/KEY: MOD_RES
<222> LOCATION: (2)..(2)
<223> OTHER INFORMATION: 1-(4-(aminomethyl)benzyl)-2-butyl-1H-
      imidazo[4,5-c]quinolin-4-amine Glu
<220> FEATURE:
```

```
<221> NAME/KEY: MOD_RES
<222> LOCATION: (3)..(3)
<223> OTHER INFORMATION: 1-(4-(aminomethyl)benzyl)-2-butyl-1H-
      imidazo[4,5-c]quinolin-4-amine Glu
<220> FEATURE:
<221> NAME/KEY: MOD_RES
<222> LOCATION: (4)..(4)
<223> OTHER INFORMATION: 1-(4-(aminomethyl)benzyl)-2-butyl-1H-
      imidazo[4,5-c]quinolin-4-amine Glu
<220> FEATURE:
<221> NAME/KEY: MOD_RES
<222> LOCATION: (5)..(5)
<223> OTHER INFORMATION: 1-(4-(aminomethyl)benzyl)-2-butyl-1H-
      imidazo[4,5-c]quinolin-4-amine Glu

<400> SEQUENCE: 129

Glu Glu Glu Glu Glu
1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Glu Glu Glu Glu Glu
1               5

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (2)..(2)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (3)..(3)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (4)..(4)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (5)..(5)
<223> OTHER INFORMATION: 1-(4-aminobutyl)-2-butyl-1H-imidazo[4,5-
      c]quinolin-4-amine Glu

<400> SEQUENCE: 131

Glu Glu Glu Glu Glu
1               5

<210> SEQ ID NO 132
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (3)..(3)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (5)..(5)
<223> OTHER INFORMATION: 1-(4-aminobutyl)-2-butyl-1H-imidazo[4,5-
      c]quinolin-4-amine Glu

<400> SEQUENCE: 132

Glu Trp Glu Trp Glu
1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Glu Trp Glu Trp Glu
1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (4)..(4)
<223> OTHER INFORMATION: 1-(4-aminobutyl)-2-butyl-1H-imidazo[4,5-
      c]quinolin-4-amine Glu

<400> SEQUENCE: 134

Trp Glu Trp Glu Trp
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Trp Glu Trp Glu Trp
1               5

<210> SEQ ID NO 136
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (8)..(8)
<223> OTHER INFORMATION: 1-(4-aminobutyl)-2-butyl-1H-imidazo[4,5-
      c]quinolin-4-amine Glu

<400> SEQUENCE: 136

Trp Trp Glu Trp Trp Trp Trp Glu Trp Trp
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Trp Trp Glu Trp Trp Trp Trp Glu Trp Trp
1               5                   10

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1-(4-aminobutyl)-2-butyl-1H-imidazo[4,5-
      c]quinolin-4-amine Glu

<400> SEQUENCE: 138

Trp Trp Glu Trp Trp
1               5

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Trp Trp Glu Trp Trp
1               5

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Trp Trp Trp Trp Trp
```

```
<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-(4-(aminomethyl)benzyl)-2-butyl-1H-
      imidazo[4,5-c]quinolin-4-amine Glu
<220> FEATURE:
<221> NAME/KEY: MOD_RES
<222> LOCATION: (3)..(3)
<223> OTHER INFORMATION: 1-(4-(aminomethyl)benzyl)-2-butyl-1H-
      imidazo[4,5-c]quinolin-4-amine Glu
<220> FEATURE:
<221> NAME/KEY: MOD_RES
<222> LOCATION: (5)..(5)
<223> OTHER INFORMATION: 1-(4-(aminomethyl)benzyl)-2-butyl-1H-
      imidazo[4,5-c]quinolin-4-amine Glu

<400> SEQUENCE: 141

Glu Trp Glu Trp Glu
1               5

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (3)..(3)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (5)..(5)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (6)..(6)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (8)..(8)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (10)..(10)
<223> OTHER INFORMATION: 1-(4-aminobutyl)-2-butyl-1H-imidazo[4,5-
      c]quinolin-4-amine Glu

<400> SEQUENCE: 142

Glu Trp Glu Trp Glu Glu Trp Glu Trp Glu
1               5                   10

<210> SEQ ID NO 143
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 143

Glu Trp Glu Trp Glu Glu Trp Glu Trp Glu
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (4)..(4)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (7)..(7)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (9)..(9)
<223> OTHER INFORMATION: 1-(4-aminobutyl)-2-butyl-1H-imidazo[4,5-
      c]quinolin-4-amine Glu

<400> SEQUENCE: 144

Trp Glu Trp Glu Trp Trp Glu Trp Glu Trp
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Trp Glu Trp Glu Trp Trp Glu Trp Glu Trp
1               5                   10

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1-(4-(aminomethyl)benzyl)-2-butyl-1H-
      imidazo[4,5-c]quinolin-4-amine Glu

<400> SEQUENCE: 146

Trp Trp Glu Trp Trp
1               5

<210> SEQ ID NO 147
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (6)..(6)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (9)..(9)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (12)..(12)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (15)..(15)
<223> OTHER INFORMATION: 1-(4-aminobutyl)-2-butyl-1H-imidazo[4,5-
      c]quinolin-4-amine Glu

<400> SEQUENCE: 147

Gly Gly Glu Gly Gly Glu Gly Gly Glu Gly Gly Glu Gly Gly Glu
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gly Glu Gly Gly Glu Gly Gly Glu Gly Gly Glu Gly Gly Glu
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (9)..(9)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (15)..(15)
<223> OTHER INFORMATION: 1-(4-aminobutyl)-2-butyl-1H-imidazo[4,5-
      c]quinolin-4-amine Glu

<400> SEQUENCE: 149

Gly Gly Glu Gly Gly Trp Gly Gly Glu Gly Gly Trp Gly Gly Glu
1               5                   10                  15
```

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Gly Glu Gly Gly Trp Gly Gly Glu Gly Gly Trp Gly Gly Glu
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Gly Glu Gly Gly Trp Gly Gly Glu Gly Gly Trp Gly Gly Glu
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Gly Glu Gly Gly Trp Gly Gly Glu Gly Gly Trp Gly Gly Glu
1               5                   10                  15

<210> SEQ ID NO 153
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 1-(4-aminobutyl)-2-butyl-1H-imidazo[4,5-
      c]quinolin-4-amine Lys
<220> FEATURE:
<221> NAME/KEY: MOD_RES
<222> LOCATION: (7)..(7)
<223> OTHER INFORMATION: 1-(4-aminobutyl)-2-butyl-1H-imidazo[4,5-
      c]quinolin-4-amine Lys
<220> FEATURE:
<221> NAME/KEY: MOD_RES
<222> LOCATION: (13)..(13)
<223> OTHER INFORMATION: 1-(4-aminobutyl)-2-butyl-1H-imidazo[4,5-
      c]quinolin-4-amine Lys
<220> FEATURE:
<221> NAME/KEY: MOD_RES
<222> LOCATION: (19)..(19)
<223> OTHER INFORMATION: 1-(4-aminobutyl)-2-butyl-1H-imidazo[4,5-
      c]quinolin-4-amine Lys
<220> FEATURE:
<221> NAME/KEY: MOD_RES
<222> LOCATION: (25)..(25)
<223> OTHER INFORMATION: 1-(4-aminobutyl)-2-butyl-1H-imidazo[4,5-
      c]quinolin-4-amine Lys

<400> SEQUENCE: 153

```
Lys Gly Trp Gly Trp Gly Lys Gly Trp Gly Trp Gly Lys Gly Trp Gly
1               5                   10                  15

Trp Gly Lys Gly Trp Gly Trp Gly Lys Gly Trp Gly Trp Gly
            20                  25                  30

<210> SEQ ID NO 154
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Lys Gly Trp Gly Trp Gly Lys Gly Trp Gly Trp Gly Lys Gly Trp Gly
1               5                   10                  15

Trp Gly Lys Gly Trp Gly Trp Gly Lys Gly Trp Gly Trp Gly
            20                  25                  30

<210> SEQ ID NO 155
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (3)..(3)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (5)..(5)
<223> OTHER INFORMATION: 1-(4-aminobutyl)-2-butyl-1H-imidazo[4,5-
      c]quinolin-4-amine Glu

<400> SEQUENCE: 155

Glu Trp Glu Trp Glu
1               5

<210> SEQ ID NO 156
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Trp Glu Trp Glu
1               5

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-(4-aminobutyl)-2-butyl-1H-imidazo[4,5-
      c]quinolin-4-amine Glu
```

```
<220> FEATURE:
<221> NAME/KEY: MOD_RES
<222> LOCATION: (3)..(3)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (5)..(5)
<223> OTHER INFORMATION: 1-(4-aminobutyl)-2-butyl-1H-imidazo[4,5-
      c]quinolin-4-amine Glu

<400> SEQUENCE: 157

Glu Trp Glu Trp Glu
1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: thiazoline-2 thiol Glu

<400> SEQUENCE: 158

Trp Trp Glu Trp Trp
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Trp Trp Glu Trp Trp
1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Trp Glu Trp Trp
1               5

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Primido-indole-Peg4NH2 Glu

<400> SEQUENCE: 161

Trp Trp Glu Trp Trp
1               5
```

```
<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pam2Cys-Peg2NH2 Glu

<400> SEQUENCE: 162

Trp Trp Glu Trp Trp
1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys-DBCO

<400> SEQUENCE: 163

Gly Lys Gly Trp Trp Trp Trp Trp
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Lys Gly Trp Trp Trp Trp Trp
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys-DBCO-CL264

<400> SEQUENCE: 165

Gly Lys Gly Trp Trp Trp Trp Trp
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: Lys-DBCO-DMXAA

<400> SEQUENCE: 166

Gly Lys Gly Trp Trp Trp Trp Trp
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys-DBCO

<400> SEQUENCE: 167

Gly Arg Lys Gly Trp Trp Trp Trp Trp
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Arg Lys Gly Trp Trp Trp Trp Trp
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys-DBCO-Muramyl

<400> SEQUENCE: 169

Gly Arg Lys Gly Trp Trp Trp Trp Trp
1               5

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys-DBCO

<400> SEQUENCE: 170

Gly Gly Arg Lys Arg Gly Gly Trp Trp Trp Trp Trp
1               5                   10

<210> SEQ ID NO 171
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Gly Arg Lys Arg Gly Gly Trp Trp Trp Trp Trp
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys-AMP

<400> SEQUENCE: 172

Gly Gly Arg Lys Arg Gly Gly Trp Trp Trp Trp Trp
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys-DBCO

<400> SEQUENCE: 173

Gly Arg Arg Lys Arg Gly Trp Trp Trp Trp Trp
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Arg Arg Lys Arg Gly Trp Trp Trp Trp Trp
1               5                   10

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys-DBCO
<220> FEATURE:
<221> NAME/KEY: MOD_RES
<222> LOCATION: (5)..(5)
<223> OTHER INFORMATION: Lys-DBCO
<220> FEATURE:
<221> NAME/KEY: MOD_RES
```

```
<222> LOCATION: (8)..(8)
<223> OTHER INFORMATION: Lys-DBCO

<400> SEQUENCE: 175

Gly Lys Gly Gly Lys Gly Gly Lys Gly Trp Trp Trp Trp Trp
1               5                   10

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Lys Gly Gly Lys Gly Gly Lys Gly Trp Trp Trp Trp Trp
1               5                   10

<210> SEQ ID NO 177
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys-DBCO
<220> FEATURE:
<221> NAME/KEY: MOD_RES
<222> LOCATION: (8)..(8)
<223> OTHER INFORMATION: Lys-DBCO
<220> FEATURE:
<221> NAME/KEY: MOD_RES
<222> LOCATION: (13)..(13)
<223> OTHER INFORMATION: Lys-DBCO

<400> SEQUENCE: 177

Gly Arg Lys Arg Gly Gly Arg Lys Arg Gly Gly Arg Lys Arg Gly Trp
1               5                   10                  15

Trp Trp Trp Trp
            20

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Glu Glu Glu Glu Glu Glu Glu Glu Glu Glu
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Lys Lys Lys Lys Lys Lys Lys Lys Lys Lys
1               5                   10
```

<210> SEQ ID NO 180
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Glu Glu Glu Glu
1

<210> SEQ ID NO 181
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Azido-Lys

<400> SEQUENCE: 181

Gly Gly Gly Gly Gly Lys Gly Gly Gly Gly Gly Asp Asp Asp Asp Asp
1               5                   10                  15

Asp Asp Asp Asp
            20

<210> SEQ ID NO 182
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Azido-Lys

<400> SEQUENCE: 182

Gly Gly Gly Gly Gly Lys Gly Gly Gly Gly Asp Asp Asp Asp Asp Asp
1               5                   10                  15

Asp Asp Asp

<210> SEQ ID NO 183
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Azido-Lys

<400> SEQUENCE: 183

Gly Gly Gly Gly Gly Lys Gly Gly Gly Gly Gly Asp Asp Asp Asp Asp
1               5                   10                  15

Asp Asp

<210> SEQ ID NO 184
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Azido-Lys

<400> SEQUENCE: 184

Gly Gly Gly Gly Gly Lys Gly Gly Gly Gly Asp Asp Asp Asp Asp
1               5                   10                  15

Asp

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Azido-Lys

<400> SEQUENCE: 185

Gly Gly Gly Gly Gly Lys Gly Gly Gly Gly Asp Asp Asp Asp Asp
1               5                   10                  15

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Azido-Lys

<400> SEQUENCE: 186

Lys Arg Arg Arg Arg Arg Arg
1               5

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Lys Lys Lys Pro Leu Arg
1               5

<210> SEQ ID NO 188
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
```

```
<221> NAME/KEY: MOD_RES
<222> LOCATION: (42)..(42)
<223> OTHER INFORMATION: Azido-Lys

<400> SEQUENCE: 188

Lys Lys Lys Lys Lys Lys Val Arg Gly Ile Pro Val His Leu Glu Leu
1               5                   10                  15

Ala Ser Met Thr Asn Met Glu Leu Met Ser Ser Ile Val His Gln Gln
            20                  25                  30

Val Phe Pro Thr Gly Ser Pro Val Xaa Lys
        35                  40

<210> SEQ ID NO 189
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys attached to a hydrophobic molecule on
      the sidechain

<400> SEQUENCE: 189

Lys Lys Lys Lys Lys Lys Val Arg Gly Ile Pro Val His Leu Glu Leu
1               5                   10                  15

Ala Ser Met Thr Asn Met Glu Leu Met Ser Ser Ile Val His Gln Gln
            20                  25                  30

Val Phe Pro Thr Gly Ser Pro Val Xaa Lys
        35                  40

<210> SEQ ID NO 190
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys

<400> SEQUENCE: 190

Lys Ala Arg Asp Glu Thr Ala Ala Leu Leu Asn Ser Ala Val Leu Gly
1               5                   10                  15

Ala Ala Pro Leu Phe Val Pro Pro Ala Asp Lys
            20                  25

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys

<400> SEQUENCE: 191
```

```
Ala Ala Leu Leu Asn Ser Ala Val Leu Gly Ser Leu Val Arg Lys
1               5                   10                  15

<210> SEQ ID NO 192
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 192

Lys Ala Arg Asp Glu Thr Ala Ala Leu Leu Asn Ser Ala Val Leu Gly
1               5                   10                  15

Ala Ala Pro Leu Phe Val Pro Pro Ala Asp Lys
            20                  25

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 193

Ala Ala Leu Leu Asn Ser Ala Val Leu Gly Ser Leu Val Arg Lys
1               5                   10                  15

<210> SEQ ID NO 194
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 194

Lys Ala Arg Asp Glu Thr Ala Ala Leu Leu Asn Ser Ala Val Leu Gly
1               5                   10                  15

Ala Ala Pro Leu Phe Val Pro Pro Ala Asp Lys
            20                  25

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
``` the sidechain

<400> SEQUENCE: 195

Ala Ala Leu Leu Asn Ser Ala Val Leu Gly Ser Leu Val Arg Lys
1               5                   10                  15

<210> SEQ ID NO 196
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys

<400> SEQUENCE: 196

Asp Phe Thr Gly Ser Asn Gly Asp Pro Ser Ser Pro Tyr Ser Leu His
1               5                   10                  15

Tyr Leu Ser Pro Thr Gly Val Asn Glu Tyr Lys
            20                  25

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys

<400> SEQUENCE: 197

Ser Ser Pro Tyr Ser Leu His Tyr Leu Ser Ser Leu Val Arg Lys
1               5                   10                  15

<210> SEQ ID NO 198
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 198

Asp Phe Thr Gly Ser Asn Gly Asp Pro Ser Ser Pro Tyr Ser Leu His
1               5                   10                  15

Tyr Leu Ser Pro Thr Gly Val Asn Glu Tyr Lys
            20                  25

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)

<223> OTHER INFORMATION: Azido-Lys attached to a hydrophobic molecule on
      the sidechain

<400> SEQUENCE: 199

Ser Ser Pro Tyr Ser Leu His Tyr Leu Ser Ser Leu Val Arg Lys
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 200

Ser Ser Pro Tyr Ser Leu His Tyr Leu Ser Ser Leu Val Arg Lys
1               5                   10                  15

<210> SEQ ID NO 201
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 201

Asp Ser Gly Ser Pro Phe Pro Ala Ala Val Ile Leu Arg Asp Ala Leu
1               5                   10                  15

His Met Ala Arg Gly Leu Lys Tyr Leu His Gln Lys
            20                  25

<210> SEQ ID NO 202
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 202

Ala Asn Phe Glu Ser Gly Lys His Lys Tyr Arg Gln Thr Ala Met Phe
1               5                   10                  15

Thr Ala Thr Met Pro Pro Ala Val Glu Arg Leu Lys
            20                  25

<210> SEQ ID NO 203
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 203

Arg Glu Gly Val Glu Leu Cys Pro Gly Asn Lys Tyr Glu Met Arg Arg
1               5                   10                  15

His Gly Thr Thr His Ser Leu Val Ile His Asp Lys
            20                  25

<210> SEQ ID NO 204
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 204

Gly Arg Gly His Leu Leu Gly Arg Leu Ala Ala Ile Val Gly Lys Gln
1               5                   10                  15

Val Leu Leu Gly Arg Lys Val Val Val Arg Lys
            20                  25

<210> SEQ ID NO 205
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 205

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu Lys
            20                  25

<210> SEQ ID NO 206
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 206

Glu Phe Lys His Ile Lys Ala Phe Asp Arg Thr Phe Ala Asn Asn Pro
1               5                   10                  15

Gly Pro Met Val Val Phe Ala Thr Pro Gly Met Lys
            20                  25
```

<210> SEQ ID NO 207
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 207

Ser Thr Ala Asn Tyr Asn Thr Ser His Leu Asn Asn Asp Val Trp Gln
1               5                   10                  15

Ile Phe Glu Asn Pro Val Asp Trp Lys Glu Lys Lys
            20                  25

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 208

Ala Ala Val Ile Leu Arg Asp Ala Leu His Ser Leu Val Arg Lys
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 209

Gln Thr Ala Met Phe Thr Ala Thr Met Pro Ser Leu Val Arg Lys
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 210

Leu Cys Pro Gly Asn Lys Tyr Glu Met Arg Ser Leu Val Arg Lys
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 211

Ala Ala Ile Val Gly Lys Gln Val Leu Leu Ser Leu Val Arg Lys
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Azido-Lys attached to a hydrophobic molecule on
      the sidechain

<400> SEQUENCE: 212

Phe Gln Glu Phe Val Asp Trp Glu Asn Val Ser Ser Leu Val Arg Lys
1               5                   10                  15

<210> SEQ ID NO 213
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 213

Asp Ser Gly Ser Pro Phe Pro Ala Ala Val Ile Leu Arg Asp Ala Leu
1               5                   10                  15

His Met Ala Arg Gly Leu Lys Tyr Leu His Gln Lys
            20                  25

<210> SEQ ID NO 214
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 214

Ala Asn Phe Glu Ser Gly Lys His Lys Tyr Arg Gln Thr Ala Met Phe
1               5                   10                  15

```
Thr Ala Thr Met Pro Pro Ala Val Glu Arg Leu Lys
            20                  25

<210> SEQ ID NO 215
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 215

Arg Glu Gly Val Glu Leu Cys Pro Gly Asn Lys Tyr Glu Met Arg Arg
1               5                   10                  15

His Gly Thr Thr His Ser Leu Val Ile His Asp Lys
            20                  25

<210> SEQ ID NO 216
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 216

Gly Arg Gly His Leu Leu Gly Arg Leu Ala Ala Ile Val Gly Lys Gln
1               5                   10                  15

Val Leu Leu Gly Arg Lys Val Val Val Arg Lys
            20                  25

<210> SEQ ID NO 217
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 217

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu Lys
            20                  25

<210> SEQ ID NO 218
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 218

Glu Phe Lys His Ile Lys Ala Phe Asp Arg Thr Phe Ala Asn Asn Pro
1               5                   10                  15

Gly Pro Met Val Val Phe Ala Thr Pro Gly Met Lys
            20                  25

<210> SEQ ID NO 219
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 219

Ser Thr Ala Asn Tyr Asn Thr Ser His Leu Asn Asn Asp Val Trp Gln
1               5                   10                  15

Ile Phe Glu Asn Pro Val Asp Trp Lys Glu Lys Lys
            20                  25

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 220

Ala Ala Val Ile Leu Arg Asp Ala Leu His Ser Leu Val Arg Lys
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 221

Gln Thr Ala Met Phe Thr Ala Thr Met Pro Ser Leu Val Arg Lys
1               5                   10                  15

<210> SEQ ID NO 222
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 222

Leu Cys Pro Gly Asn Lys Tyr Glu Met Arg Ser Leu Val Arg Lys
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 223

Ala Ala Ile Val Gly Lys Gln Val Leu Leu Ser Leu Val Arg Lys
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Azido-Lys attached to a hydrophobic molecule on
      the sidechain

<400> SEQUENCE: 224

Phe Gln Glu Phe Val Asp Trp Glu Asn Val Ser Ser Leu Val Arg Lys
1               5                   10                  15

<210> SEQ ID NO 225
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 225

Lys Ser Lys Ser Lys Ser Gly Gly Ser Ser Pro Tyr Ser Leu His Tyr
1               5                   10                  15

Leu Lys

<210> SEQ ID NO 226
<211> LENGTH: 22
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 226

Lys Ser Lys Ser Lys Ser Gly Gly Ser Leu Val Arg Ser Ser Pro Tyr
1               5                   10                  15

Ser Leu His Tyr Leu Lys
            20

<210> SEQ ID NO 227
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 227

Lys Ser Lys Ser Lys Ser Gly Gly Ser Leu Val Arg Ser Ser Pro Tyr
1               5                   10                  15

Ser Leu His Tyr Leu Ser Leu Val Arg Lys
            20                  25

<210> SEQ ID NO 228
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 228

Lys Ser Lys Ser Lys Ser Gly Gly Ser Leu Val Arg Ser Ser Pro Tyr
1               5                   10                  15

Ser Leu His Tyr Leu Gly Gly Ser Leu Val Arg Lys
            20                  25

<210> SEQ ID NO 229
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 229

Lys Ser Lys Ser Lys Ser Gly Gly Ser Leu Val Arg Tyr Leu Leu Leu
1               5                   10                  15

Ser Ser Pro Tyr Ser Leu His Tyr Leu Lys
```

```
              20                  25

<210> SEQ ID NO 230
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Azido-Lys attached to a hydrophobic molecule on
      the sidechain

<400> SEQUENCE: 230

Lys Ser Lys Ser Lys Ser Gly Gly Ser Leu Val Arg Tyr Leu Leu Leu
1               5                   10                  15

Ser Ser Pro Tyr Ser Leu His Tyr Leu Ser Leu Val Arg Lys
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 231

Lys Ser Lys Ser Lys Ser Gly Gly Ser Leu Val Arg Tyr Leu Leu Leu
1               5                   10                  15

Ser Ser Pro Tyr Ser Leu His Tyr Leu Gly Gly Ser Leu Val Arg Lys
            20                  25                  30

<210> SEQ ID NO 232
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 232

Glu Ser Glu Ser Glu Ser Gly Gly Ser Ser Pro Tyr Ser Leu His Tyr
1               5                   10                  15

Leu Lys

<210> SEQ ID NO 233
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
``` the sidechain

<400> SEQUENCE: 233

Glu Ser Glu Ser Glu Ser Gly Gly Ser Leu Val Arg Ser Ser Pro Tyr
1               5                   10                  15

Ser Leu His Tyr Leu Lys
            20

<210> SEQ ID NO 234
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 234

Glu Ser Glu Ser Glu Ser Gly Gly Ser Leu Val Arg Ser Ser Pro Tyr
1               5                   10                  15

Ser Leu His Tyr Leu Ser Leu Val Arg Lys
            20                  25

<210> SEQ ID NO 235
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 235

Glu Ser Glu Ser Glu Ser Gly Gly Ser Leu Val Arg Ser Ser Pro Tyr
1               5                   10                  15

Ser Leu His Tyr Leu Gly Gly Ser Leu Val Arg Lys
            20                  25

<210> SEQ ID NO 236
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 236

Glu Ser Glu Ser Glu Ser Gly Gly Ser Leu Val Arg Tyr Leu Leu Leu
1               5                   10                  15

Ser Ser Pro Tyr Ser Leu His Tyr Leu Lys
            20                  25

<210> SEQ ID NO 237
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Azido-Lys attached to a hydrophobic molecule on
      the sidechain

<400> SEQUENCE: 237

Glu Ser Glu Ser Glu Ser Gly Gly Ser Leu Val Arg Tyr Leu Leu Leu
1               5                   10                  15

Ser Ser Pro Tyr Ser Leu His Tyr Leu Ser Leu Val Arg Lys
            20                  25                  30

<210> SEQ ID NO 238
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 238

Glu Ser Glu Ser Glu Ser Gly Gly Ser Leu Val Arg Tyr Leu Leu Leu
1               5                   10                  15

Ser Ser Pro Tyr Ser Leu His Tyr Leu Gly Gly Ser Leu Val Arg Lys
            20                  25                  30

<210> SEQ ID NO 239
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 239

Glu Lys Glu Lys Glu Lys Gly Gly Ser Ser Pro Tyr Ser Leu His Tyr
1               5                   10                  15

Leu Lys

<210> SEQ ID NO 240
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 240

Glu Lys Glu Lys Glu Lys Gly Gly Ser Leu Val Arg Ser Ser Pro Tyr
```

```
1               5                   10                  15

Ser Leu His Tyr Leu Lys
            20

<210> SEQ ID NO 241
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 241

Glu Lys Glu Lys Glu Lys Gly Gly Ser Leu Val Arg Ser Ser Pro Tyr
1               5                   10                  15

Ser Leu His Tyr Leu Ser Leu Val Arg Lys
            20                  25

<210> SEQ ID NO 242
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Azido-Lys attached to a hydrophobic molecule on
      the sidechain

<400> SEQUENCE: 242

Glu Lys Glu Lys Glu Lys Gly Gly Ser Leu Val Arg Ser Ser Pro Tyr
1               5                   10                  15

Ser Leu His Tyr Leu Gly Gly Ser Leu Val Arg Lys
            20                  25

<210> SEQ ID NO 243
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 243

Glu Lys Glu Lys Glu Lys Gly Gly Ser Leu Val Arg Tyr Leu Leu Leu
1               5                   10                  15

Ser Ser Pro Tyr Ser Leu His Tyr Leu Lys
            20                  25

<210> SEQ ID NO 244
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (30)..(30)
<223> OTHER INFORMATION: Azido-Lys attached to a hydrophobic molecule on
      the sidechain

<400> SEQUENCE: 244

Glu Lys Glu Lys Glu Lys Gly Gly Ser Leu Val Arg Tyr Leu Leu Leu
1               5                   10                  15

Ser Ser Pro Tyr Ser Leu His Tyr Leu Ser Leu Val Arg Lys
            20                  25                  30

<210> SEQ ID NO 245
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 245

Glu Lys Glu Lys Glu Lys Gly Gly Ser Leu Val Arg Tyr Leu Leu Leu
1               5                   10                  15

Ser Ser Pro Tyr Ser Leu His Tyr Leu Gly Gly Ser Leu Val Arg Lys
            20                  25                  30

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Azido-Lys attached to a hydrophobic molecule on
      the sidechain

<400> SEQUENCE: 246

Ala Ser Met Thr Asn Met Glu Leu Met Lys
1               5                   10

<210> SEQ ID NO 247
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Citrulline
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 247

Ser Leu Val Arg Ala Ser Met Thr Asn Met Glu Leu Met Ser Pro Val
1               5                   10                  15

Xaa Lys
```

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 248

Ser Leu Val Arg Ala Ser Met Thr Asn Met Glu Leu Met Arg Lys
1               5                   10                  15

<210> SEQ ID NO 249
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 249

Ala Ser Met Thr Asn Met Glu Leu Met Ser Leu Val Arg Lys
1               5                   10

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 250

Ser Leu Val Arg Ala Ser Met Thr Asn Met Glu Leu Met Lys
1               5                   10

<210> SEQ ID NO 251
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Azido-Lys attached to a hydrophobic molecule on
      the sidechain

<400> SEQUENCE: 251

Ser Leu Val Arg Ala Ser Met Thr Asn Met Glu Leu Met Gly Pro Lys
1               5                   10                  15

<210> SEQ ID NO 252

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 252

Ser Leu Val Arg Ala Ser Met Thr Asn Met Glu Leu Met Ser Pro Val
1               5                   10                  15

Arg Lys

<210> SEQ ID NO 253
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 253

Ser Leu Val Arg Ala Ser Met Thr Asn Met Glu Leu Met Ser Leu Val
1               5                   10                  15

Arg Lys

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 254

Ser Pro Val Arg Ala Ser Met Thr Asn Met Glu Leu Met Lys
1               5                   10

<210> SEQ ID NO 255
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 255

Glu Leu Val Arg Ala Ser Met Thr Asn Met Glu Leu Met Lys
1               5                   10
```

```
<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 256

Glu Leu Val Leu Ala Ser Met Thr Asn Met Glu Leu Met Lys
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 257

Glu Leu Val Xaa Ala Ser Met Thr Asn Met Glu Leu Met Lys
1               5                   10

<210> SEQ ID NO 258
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 258

Ser Leu Val Arg Ala Ser Met Thr Asn Met Glu Leu Met Lys Pro Leu
1               5                   10                  15

Arg Lys

<210> SEQ ID NO 259
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Azido-Lys attached to a hydrophobic molecule on
      the sidechain

<400> SEQUENCE: 259

Ser Leu Val Arg Ala Ser Met Thr Asn Met Glu Leu Met Gly Ser Gly
```

```
1               5                   10                  15

Lys

<210> SEQ ID NO 260
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 260

Glu Pro Val Xaa Ala Ser Met Thr Asn Met Glu Leu Met Lys
1               5                   10

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 261

Lys Pro Leu Arg Ala Ser Met Thr Asn Met Glu Leu Met Lys
1               5                   10

<210> SEQ ID NO 262
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Citrulline
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 262

Ser Leu Val Arg Ala Ser Met Thr Asn Met Glu Leu Met Ser Leu Val
1               5                   10                  15

Xaa Lys

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 263

Arg Leu Val Ser Ala Ser Met Thr Asn Met Glu Leu Met Lys
1               5                   10

<210> SEQ ID NO 264
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 264

Ser Leu Val Arg Ala Ser Met Thr Asn Met Glu Leu Met Ser Leu Val
1               5                   10                  15

Leu Lys

<210> SEQ ID NO 265
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 265

Ser Leu Val Arg Ala Ser Met Thr Asn Met Glu Leu Met Glu Leu Val
1               5                   10                  15

Arg Lys

<210> SEQ ID NO 266
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 266

Ser Leu Val Xaa Ala Ser Met Thr Asn Met Glu Leu Met Lys
1               5                   10

<210> SEQ ID NO 267
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Citrulline
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 267

Ser Leu Val Arg Ala Ser Met Thr Asn Met Glu Leu Met Glu Pro Val
1               5                   10                  15

Xaa Lys

<210> SEQ ID NO 268
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 268

Ser Pro Val Xaa Ala Ser Met Thr Asn Met Glu Leu Met Lys
1               5                   10

<210> SEQ ID NO 269
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Citrulline
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 269

Ser Leu Val Arg Ala Ser Met Thr Asn Met Glu Leu Met Gly Gly Ser
1               5                   10                  15

Leu Val Xaa Lys
            20

<210> SEQ ID NO 270
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 270

Ser Leu Val Arg Ala Ser Met Thr Asn Met Glu Leu Met Gly Gly Gly
1               5                  10                  15

Gly Lys

<210> SEQ ID NO 271
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Citrulline
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 271

Ser Leu Val Arg Ala Ser Met Thr Asn Met Glu Leu Met Glu Leu Val
1               5                  10                  15

Xaa Lys

<210> SEQ ID NO 272
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 272

Ser Leu Val Leu Ala Ser Met Thr Asn Met Glu Leu Met Lys
1               5                  10

<210> SEQ ID NO 273
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 273

Ser Leu Val Arg Ala Ser Met Thr Asn Met Glu Leu Met Gly Gly Ser
1               5                  10                  15

Leu Val Arg Lys
            20
```

<210> SEQ ID NO 274
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Azido-Lys attached to a hydrophobic molecule on
      the sidechain

<400> SEQUENCE: 274

Gly Gly Gly Gly Ala Ser Met Thr Asn Met Glu Leu Met Lys
1               5                   10

<210> SEQ ID NO 275
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 275

Ser Leu Val Arg Ala Ser Met Thr Asn Met Glu Leu Met Glu Leu Val
1               5                   10                  15

Leu Lys

<210> SEQ ID NO 276
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (18)..(18)
<223> OTHER INFORMATION: Azido-Lys attached to a hydrophobic molecule on
      the sidechain

<400> SEQUENCE: 276

Ser Leu Val Arg Ala Ser Met Thr Asn Met Glu Leu Met Ser Leu Val
1               5                   10                  15

Arg Lys

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES

```
<222> LOCATION: (14)..(14)
<223> OTHER INFORMATION: Azido-Lys attached to a hydrophobic molecule on
      the sidechain

<400> SEQUENCE: 277

Ser Leu Val Arg Ala Ser Met Thr Asn Met Glu Leu Met Lys
1               5                   10

<210> SEQ ID NO 278
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 278

Glu Glu Glu Glu Leu Val Leu Lys Asn His Arg Asn Arg Gln Val Ile
1               5                   10                  15

Gly Gly Glu Ser Glu Leu Val Leu Lys
            20                  25

<210> SEQ ID NO 279
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 279

Glu Glu Glu Glu Leu Val Leu Lys Asn His Arg Asn Arg Gln Val Ile
1               5                   10                  15

Gly Gly Glu Leu Val Leu Lys
            20

<210> SEQ ID NO 280
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 280

Ser Leu Val Leu Lys Asn His Arg Asn Arg Gln Val Ile Gly Gly Glu
1               5                   10                  15

Leu Val Leu Lys
            20

<210> SEQ ID NO 281
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 281

Ser Leu Val Arg Lys Asn His Arg Asn Arg Gln Val Ile Gly Gly Glu
1               5                   10                  15

Ser Glu Leu Val Leu Lys
            20

<210> SEQ ID NO 282
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 282

Ser Leu Val Leu Lys Asn His Arg Asn Arg Gln Val Ile Gly Gly Ser
1               5                   10                  15

Leu Val Leu Lys
            20

<210> SEQ ID NO 283
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 283

Ser Leu Val Leu Lys Asn His Arg Asn Arg Gln Val Ile Gly Gly Glu
1               5                   10                  15

Leu Val Arg Lys
            20

<210> SEQ ID NO 284
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 284

Ser Leu Val Leu Lys Asn His Arg Asn Arg Gln Val Ile Gly Gly Ser
```

```
1               5                   10                  15

Leu Val Arg Lys
            20

<210> SEQ ID NO 285
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 285

Ser Leu Val Arg Lys Asn His Arg Asn Arg Gln Val Ile Gly Gly Ser
1               5                   10                  15

Leu Val Leu Lys
            20

<210> SEQ ID NO 286
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 286

Glu Lys Ser Leu Val Leu Lys Asn His Arg Asn Arg Gln Val Ile Gly
1               5                   10                  15

Gly Ser Leu Val Arg Lys
            20

<210> SEQ ID NO 287
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 287

Lys Leu Val Arg Lys Asn His Arg Asn Arg Gln Val Ile Gly Gly Glu
1               5                   10                  15

Leu Val Leu Lys
            20

<210> SEQ ID NO 288
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 288

Ser Leu Val Leu Lys Asn His Arg Asn Arg Gln Val Ile Gly Gly Lys
1               5                   10                  15

Leu Val Arg Lys
            20

<210> SEQ ID NO 289
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 289

Ser Leu Val Arg Lys Asn His Arg Asn Arg Gln Val Ile Gly Gly Ser
1               5                   10                  15

Leu Val Arg Lys
            20

<210> SEQ ID NO 290
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 290

Lys Leu Val Arg Lys Asn His Arg Asn Arg Gln Val Ile Gly Gly Glu
1               5                   10                  15

Leu Val Arg Lys
            20

<210> SEQ ID NO 291
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 291

Ser Leu Val Arg Lys Asn His Arg Asn Arg Gln Val Ile Gly Gly Lys
1               5                   10                  15

Leu Val Arg Lys
            20
```

```
<210> SEQ ID NO 292
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 292

Lys Ser Lys Leu Val Arg Lys Asn His Arg Asn Arg Gln Val Ile Gly
1               5                   10                  15

Gly Ser Leu Val Leu Lys
            20

<210> SEQ ID NO 293
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 293

Lys Glu Lys Leu Val Arg Lys Asn His Arg Asn Arg Gln Val Ile Gly
1               5                   10                  15

Gly Ser Leu Val Arg Lys
            20

<210> SEQ ID NO 294
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 294

Glu Ser Glu Ser Glu Leu Val Leu Ser Pro Glu Arg Asn Asp Trp Glu
1               5                   10                  15

Pro Leu Gly Gly Ser Leu Val Leu Lys
            20                  25

<210> SEQ ID NO 295
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Azido-Lys attached to a hydrophobic molecule on
``` the sidechain

<400> SEQUENCE: 295

Glu Ser Glu Leu Val Leu Ser Pro Glu Arg Asn Asp Trp Glu Pro Leu
1               5                   10                  15

Gly Gly Ser Leu Val Leu Lys
            20

<210> SEQ ID NO 296
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 296

Glu Ser Leu Val Leu Ser Pro Glu Arg Asn Asp Trp Glu Pro Leu Gly
1               5                   10                  15

Gly Ser Leu Val Leu Lys
            20

<210> SEQ ID NO 297
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 297

Glu Lys Glu Leu Val Leu Ser Pro Glu Arg Asn Asp Trp Glu Pro Leu
1               5                   10                  15

Gly Gly Ser Leu Val Leu Lys
            20

<210> SEQ ID NO 298
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 298

Ser Leu Val Leu Ser Pro Glu Arg Asn Asp Trp Glu Pro Leu Gly Gly
1               5                   10                  15

Ser Leu Val Leu Lys
            20

<210> SEQ ID NO 299
<211> LENGTH: 23

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 299

Glu Lys Ser Leu Val Leu Ser Pro Glu Arg Asn Asp Trp Glu Pro Leu
1               5                   10                  15

Gly Gly Ser Leu Val Leu Lys
            20

<210> SEQ ID NO 300
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 300

Lys Leu Val Arg Ser Pro Glu Arg Asn Asp Trp Glu Pro Leu Gly Gly
1               5                   10                  15

Lys Leu Val Arg Lys
            20

<210> SEQ ID NO 301
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 301

Lys Ser Lys Ser Lys Leu Val Arg Ser Pro Glu Arg Asn Asp Trp Glu
1               5                   10                  15

Pro Leu Gly Gly Ser Leu Val Leu Lys
            20                  25

<210> SEQ ID NO 302
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 302
```

```
Lys Ser Lys Leu Val Arg Ser Pro Glu Arg Asn Asp Trp Glu Pro Leu
1               5                   10                  15

Gly Gly Lys Leu Val Arg Lys
            20
```

<210> SEQ ID NO 303
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 303

```
Lys Ser Lys Ser Lys Leu Val Arg Ser Pro Glu Arg Asn Asp Trp Glu
1               5                   10                  15

Pro Leu Gly Gly Ser Leu Val Arg Lys
            20                  25
```

<210> SEQ ID NO 304
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 304

```
Lys Ser Lys Ser Lys Leu Val Arg Ser Pro Glu Arg Asn Asp Trp Glu
1               5                   10                  15

Pro Leu Gly Gly Lys Leu Val Arg Lys
            20                  25
```

<210> SEQ ID NO 305
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 305

```
Glu Glu Glu Glu Leu Val Leu Lys Asn His Arg Asn Arg Gln Val Ile
1               5                   10                  15

Gly Gly Glu Ser Glu Leu Val Leu Lys
            20                  25
```

<210> SEQ ID NO 306
<211> LENGTH: 23
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 306

Glu Glu Glu Glu Leu Val Leu Lys Asn His Arg Asn Arg Gln Val Ile
1               5                   10                  15

Gly Gly Glu Leu Val Leu Lys
            20

<210> SEQ ID NO 307
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 307

Ser Leu Val Leu Lys Asn His Arg Asn Arg Gln Val Ile Gly Gly Glu
1               5                   10                  15

Leu Val Leu Lys
            20

<210> SEQ ID NO 308
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 308

Ser Leu Val Arg Lys Asn His Arg Asn Arg Gln Val Ile Gly Gly Glu
1               5                   10                  15

Ser Glu Leu Val Leu Lys
            20

<210> SEQ ID NO 309
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 309

Ser Leu Val Leu Lys Asn His Arg Asn Arg Gln Val Ile Gly Gly Ser
1               5                   10                  15

Leu Val Leu Lys
```

20

<210> SEQ ID NO 310
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 310

Ser Leu Val Leu Lys Asn His Arg Asn Arg Gln Val Ile Gly Gly Glu
1               5                   10                  15

Leu Val Arg Lys
            20

<210> SEQ ID NO 311
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 311

Ser Leu Val Leu Lys Asn His Arg Asn Arg Gln Val Ile Gly Gly Ser
1               5                   10                  15

Leu Val Arg Lys
            20

<210> SEQ ID NO 312
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 312

Ser Leu Val Arg Lys Asn His Arg Asn Arg Gln Val Ile Gly Gly Ser
1               5                   10                  15

Leu Val Leu Lys
            20

<210> SEQ ID NO 313
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)

<223> OTHER INFORMATION: Azido-Lys attached to a hydrophobic molecule on
      the sidechain

<400> SEQUENCE: 313

Glu Lys Ser Leu Val Leu Lys Asn His Arg Asn Arg Gln Val Ile Gly
1               5                   10                  15

Gly Ser Leu Val Arg Lys
            20

<210> SEQ ID NO 314
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 314

Lys Leu Val Arg Lys Asn His Arg Asn Arg Gln Val Ile Gly Gly Glu
1               5                   10                  15

Leu Val Leu Lys
            20

<210> SEQ ID NO 315
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 315

Ser Leu Val Leu Lys Asn His Arg Asn Arg Gln Val Ile Gly Gly Lys
1               5                   10                  15

Leu Val Arg Lys
            20

<210> SEQ ID NO 316
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 316

Ser Leu Val Arg Lys Asn His Arg Asn Arg Gln Val Ile Gly Gly Ser
1               5                   10                  15

Leu Val Arg Lys
            20

<210> SEQ ID NO 317

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 317

Lys Leu Val Arg Lys Asn His Arg Asn Arg Gln Val Ile Gly Gly Glu
1               5                   10                  15

Leu Val Arg Lys
            20

<210> SEQ ID NO 318
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 318

Ser Leu Val Arg Lys Asn His Arg Asn Arg Gln Val Ile Gly Gly Lys
1               5                   10                  15

Leu Val Arg Lys
            20

<210> SEQ ID NO 319
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 319

Lys Ser Lys Leu Val Arg Lys Asn His Arg Asn Arg Gln Val Ile Gly
1               5                   10                  15

Gly Ser Leu Val Leu Lys
            20

<210> SEQ ID NO 320
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 320
```

Lys Glu Lys Leu Val Arg Lys Asn His Arg Asn Arg Gln Val Ile Gly
1               5                   10                  15

Gly Ser Leu Val Arg Lys
            20

<210> SEQ ID NO 321
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 321

Glu Ser Glu Ser Glu Leu Val Leu Ser Pro Glu Arg Asn Asp Trp Glu
1               5                   10                  15

Pro Leu Gly Gly Ser Leu Val Leu Lys
            20                  25

<210> SEQ ID NO 322
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 322

Glu Ser Glu Leu Val Leu Ser Pro Glu Arg Asn Asp Trp Glu Pro Leu
1               5                   10                  15

Gly Gly Ser Leu Val Leu Lys
            20

<210> SEQ ID NO 323
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 323

Glu Ser Leu Val Leu Ser Pro Glu Arg Asn Asp Trp Glu Pro Leu Gly
1               5                   10                  15

Gly Ser Leu Val Leu Lys
            20

<210> SEQ ID NO 324
<211> LENGTH: 23
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 324

Glu Lys Glu Leu Val Leu Ser Pro Glu Arg Asn Asp Trp Glu Pro Leu
1               5                   10                  15

Gly Gly Ser Leu Val Leu Lys
            20

<210> SEQ ID NO 325
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 325

Ser Leu Val Leu Ser Pro Glu Arg Asn Asp Trp Glu Pro Leu Gly Gly
1               5                   10                  15

Ser Leu Val Leu Lys
            20

<210> SEQ ID NO 326
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 326

Glu Lys Ser Leu Val Leu Ser Pro Glu Arg Asn Asp Trp Glu Pro Leu
1               5                   10                  15

Gly Gly Ser Leu Val Leu Lys
            20

<210> SEQ ID NO 327
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 327

Lys Leu Val Arg Ser Pro Glu Arg Asn Asp Trp Glu Pro Leu Gly Gly
1               5                   10                  15

```
<210> SEQ ID NO 328
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 328

Lys Ser Lys Ser Lys Leu Val Arg Ser Pro Glu Arg Asn Asp Trp Glu
1               5                   10                  15

Pro Leu Gly Gly Ser Leu Val Leu Lys
            20                  25

<210> SEQ ID NO 329
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 329

Lys Ser Lys Leu Val Arg Ser Pro Glu Arg Asn Asp Trp Glu Pro Leu
1               5                   10                  15

Gly Gly Lys Leu Val Arg Lys
            20

<210> SEQ ID NO 330
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 330

Lys Ser Lys Ser Lys Leu Val Arg Ser Pro Glu Arg Asn Asp Trp Glu
1               5                   10                  15

Pro Leu Gly Gly Ser Leu Val Arg Lys
            20                  25

<210> SEQ ID NO 331
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (25)..(25)
<223> OTHER INFORMATION: Azido-Lys attached to a hydrophobic molecule on
      the sidechain

<400> SEQUENCE: 331

Lys Ser Lys Ser Lys Leu Val Arg Ser Pro Glu Arg Asn Asp Trp Glu
1               5                   10                  15

Pro Leu Gly Gly Lys Leu Val Arg Lys
            20                  25

<210> SEQ ID NO 332
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 332

Lys Ser Lys Leu Val Arg Val Val Ile Ala Ile Phe Ile Ile Leu Gly
1               5                   10                  15

Gly Glu Leu Val Arg Lys
            20

<210> SEQ ID NO 333
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 333

Lys Ser Lys Ser Lys Leu Val Arg Val Val Ile Ala Ile Phe Ile Ile
1               5                   10                  15

Leu Gly Gly Glu Leu Val Arg Lys
            20

<210> SEQ ID NO 334
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 334

Lys Ser Lys Ser Lys Leu Val Arg Val Val Ile Ala Ile Phe Ile Ile
1               5                   10                  15

Leu Gly Gly Ser Leu Val Arg Lys
            20
```

```
<210> SEQ ID NO 335
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 335

Lys Ser Lys Ser Lys Leu Val Arg Val Val Ile Ala Ile Phe Ile Ile
1               5                   10                  15

Leu Gly Gly Lys Leu Val Arg Lys
            20

<210> SEQ ID NO 336
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 336

Glu Lys Glu Lys Leu Val Leu Ala Ser Met Thr Asn Met Glu Leu Met
1               5                   10                  15

Ser Ser Gly Gly Ser Leu Val Leu Lys
            20                  25

<210> SEQ ID NO 337
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 337

Glu Lys Ser Leu Val Arg Ala Ser Met Thr Asn Met Glu Leu Met Ser
1               5                   10                  15

Ser Gly Gly Glu Leu Val Arg Lys
            20

<210> SEQ ID NO 338
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain
```

```
<400> SEQUENCE: 338

Lys Glu Lys Leu Val Arg Ala Ser Met Thr Asn Met Glu Leu Met Ser
1               5                   10                  15

Ser Gly Gly Ser Leu Val Leu Lys
            20

<210> SEQ ID NO 339
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 339

Lys Glu Lys Leu Val Arg Ala Ser Met Thr Asn Met Glu Leu Met Ser
1               5                   10                  15

Ser Gly Gly Glu Leu Val Arg Lys
            20

<210> SEQ ID NO 340
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 340

Lys Ser Lys Leu Val Arg Ala Ser Met Thr Asn Met Glu Leu Met Ser
1               5                   10                  15

Ser Gly Gly Ser Leu Val Leu Lys
            20

<210> SEQ ID NO 341
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 341

Lys Ser Lys Ser Lys Leu Val Arg Ala Ser Met Thr Asn Met Glu Leu
1               5                   10                  15

Met Ser Ser Gly Gly Glu Leu Val Leu Lys
            20                  25

<210> SEQ ID NO 342
<211> LENGTH: 26
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 342

Lys Ser Lys Ser Lys Leu Val Arg Ala Ser Met Thr Asn Met Glu Leu
1               5                   10                  15

Met Ser Ser Gly Gly Ser Leu Val Leu Lys
            20                  25

<210> SEQ ID NO 343
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 343

Lys Ser Lys Ser Lys Leu Val Arg Ala Ser Met Thr Asn Met Glu Leu
1               5                   10                  15

Met Ser Ser Gly Gly Glu Leu Val Arg Lys
            20                  25

<210> SEQ ID NO 344
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 344

Lys Ser Lys Ser Lys Leu Val Arg Ala Ser Met Thr Asn Met Glu Leu
1               5                   10                  15

Met Ser Ser Gly Gly Ser Leu Val Arg Lys
            20                  25

<210> SEQ ID NO 345
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 345

Lys Ser Lys Ser Lys Leu Val Arg Ala Ser Met Thr Asn Met Glu Leu
1               5                   10                  15
```

```
Met Ser Ser Gly Gly Lys Leu Val Arg Lys
            20                  25

<210> SEQ ID NO 346
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 346

Glu Ser Glu Ser Glu Ser Glu Leu Val Leu Ala Lys Phe Val Ala Ala
1               5                   10                  15

Trp Thr Leu Lys Ala Ala Ala Gly Gly Glu Ser Glu Leu Val Leu Lys
            20                  25                  30

<210> SEQ ID NO 347
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 347

Glu Lys Glu Lys Leu Val Leu Ala Lys Phe Val Ala Ala Trp Thr Leu
1               5                   10                  15

Lys Ala Ala Ala Gly Gly Ser Leu Val Leu Lys
            20                  25

<210> SEQ ID NO 348
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 348

Glu Lys Glu Leu Val Leu Ala Lys Phe Val Ala Ala Trp Thr Leu Lys
1               5                   10                  15

Ala Ala Ala Gly Gly Lys Leu Val Arg Lys
            20                  25

<210> SEQ ID NO 349
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 349

Glu Lys Glu Lys Leu Val Leu Ala Lys Phe Val Ala Ala Trp Thr Leu
1               5                   10                  15

Lys Ala Ala Ala Gly Gly Lys Leu Val Arg Lys
            20                  25

<210> SEQ ID NO 350
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 350

Lys Glu Lys Leu Val Arg Ala Lys Phe Val Ala Ala Trp Thr Leu Lys
1               5                   10                  15

Ala Ala Ala Gly Gly Ser Leu Val Leu Lys
            20                  25

<210> SEQ ID NO 351
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 351

Lys Ser Lys Leu Val Arg Val Val Ile Ala Ile Phe Leu Ile Leu Gly
1               5                   10                  15

Gly Glu Leu Val Arg Lys
            20

<210> SEQ ID NO 352
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 352

Lys Ser Lys Ser Lys Leu Val Arg Val Val Ile Ala Ile Phe Leu Ile
1               5                   10                  15

Leu Gly Gly Glu Leu Val Arg Lys
            20
```

```
<210> SEQ ID NO 353
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 353

Lys Ser Lys Ser Lys Leu Val Arg Val Val Ile Ala Ile Phe Leu Ile
1               5                   10                  15

Leu Gly Gly Ser Leu Val Arg Lys
            20

<210> SEQ ID NO 354
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 354

Lys Ser Lys Ser Lys Leu Val Arg Val Val Ile Ala Ile Phe Leu Ile
1               5                   10                  15

Leu Gly Gly Lys Leu Val Arg Lys
            20

<210> SEQ ID NO 355
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 355

Glu Lys Glu Lys Leu Val Leu Ala Ser Met Thr Asn Met Glu Leu Met
1               5                   10                  15

Ser Ser Gly Gly Ser Leu Val Leu Lys
            20                  25

<210> SEQ ID NO 356
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain
```

<400> SEQUENCE: 356

Glu Lys Ser Leu Val Arg Ala Ser Met Thr Asn Met Glu Leu Met Ser
1               5                   10                  15

Ser Gly Gly Glu Leu Val Arg Lys
            20

<210> SEQ ID NO 357
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 357

Lys Glu Lys Leu Val Arg Ala Ser Met Thr Asn Met Glu Leu Met Ser
1               5                   10                  15

Ser Gly Gly Ser Leu Val Leu Lys
            20

<210> SEQ ID NO 358
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 358

Lys Glu Lys Leu Val Arg Ala Ser Met Thr Asn Met Glu Leu Met Ser
1               5                   10                  15

Ser Gly Gly Glu Leu Val Arg Lys
            20

<210> SEQ ID NO 359
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 359

Lys Ser Lys Leu Val Arg Ala Ser Met Thr Asn Met Glu Leu Met Ser
1               5                   10                  15

Ser Gly Gly Ser Leu Val Leu Lys
            20

<210> SEQ ID NO 360
<211> LENGTH: 26
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 360

Lys Ser Lys Ser Lys Leu Val Arg Ala Ser Met Thr Asn Met Glu Leu
1               5                   10                  15

Met Ser Ser Gly Gly Glu Leu Val Leu Lys
            20                  25

<210> SEQ ID NO 361
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 361

Lys Ser Lys Ser Lys Leu Val Arg Ala Ser Met Thr Asn Met Glu Leu
1               5                   10                  15

Met Ser Ser Gly Gly Ser Leu Val Leu Lys
            20                  25

<210> SEQ ID NO 362
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 362

Lys Ser Lys Ser Lys Leu Val Arg Ala Ser Met Thr Asn Met Glu Leu
1               5                   10                  15

Met Ser Ser Gly Gly Glu Leu Val Arg Lys
            20                  25

<210> SEQ ID NO 363
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 363

Lys Ser Lys Ser Lys Leu Val Arg Ala Ser Met Thr Asn Met Glu Leu
```

```
                1               5                  10                  15
Met Ser Ser Gly Gly Ser Leu Val Arg Lys
            20                  25

<210> SEQ ID NO 364
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 364

Lys Ser Lys Ser Lys Leu Val Arg Ala Ser Met Thr Asn Met Glu Leu
1               5                  10                  15
Met Ser Ser Gly Gly Lys Leu Val Arg Lys
            20                  25

<210> SEQ ID NO 365
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 365

Glu Ser Glu Ser Glu Ser Glu Leu Val Leu Ala Lys Phe Val Ala Ala
1               5                  10                  15
Trp Thr Leu Lys Ala Ala Ala Gly Gly Glu Ser Glu Leu Val Leu Lys
            20                  25                  30

<210> SEQ ID NO 366
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 366

Glu Lys Glu Lys Leu Val Leu Ala Lys Phe Val Ala Ala Trp Thr Leu
1               5                  10                  15
Lys Ala Ala Ala Gly Gly Ser Leu Val Leu Lys
            20                  25

<210> SEQ ID NO 367
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 367

Glu Lys Glu Leu Val Leu Ala Lys Phe Val Ala Ala Trp Thr Leu Lys
1               5                   10                  15

Ala Ala Ala Gly Gly Lys Leu Val Arg Lys
            20                  25

<210> SEQ ID NO 368
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 368

Glu Lys Glu Lys Leu Val Leu Ala Lys Phe Val Ala Ala Trp Thr Leu
1               5                   10                  15

Lys Ala Ala Ala Gly Gly Lys Leu Val Arg Lys
            20                  25

<210> SEQ ID NO 369
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 369

Lys Glu Lys Leu Val Arg Ala Lys Phe Val Ala Ala Trp Thr Leu Lys
1               5                   10                  15

Ala Ala Ala Gly Gly Ser Leu Val Leu Lys
            20                  25

<210> SEQ ID NO 370
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Azido-Lys attached to a hydrophobic molecule on
      the sidechain

<400> SEQUENCE: 370

Glu Ser Gly Ser Gly Ser Gly Ser Ser Leu Val Arg Gly Arg Val Leu
1               5                   10                  15

Glu Leu Phe Arg Ala Ala Gln Leu Ala Asn Asp Val Val Leu Gln Ile
            20                  25                  30
```

```
Met Glu Leu Cys Gly Ala Thr Arg Lys
        35                  40
```

<210> SEQ ID NO 371
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (46)..(46)
<223> OTHER INFORMATION: Azido-Lys attached to a hydrophobic molecule on
      the sidechain

<400> SEQUENCE: 371

```
Glu Ser Gly Ser Gly Ser Gly Ser Ser Leu Val Arg Gly Arg Val Leu
1               5                   10                  15

Glu Leu Phe Arg Ala Ala Gln Leu Ala Asn Asp Val Val Leu Gln Ile
            20                  25                  30

Met Glu Leu Cys Gly Ala Thr Arg Ser Gly Ser Gly Ser Lys
        35                  40                  45
```

<210> SEQ ID NO 372
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (46)..(46)
<223> OTHER INFORMATION: Azido-Lys attached to a hydrophobic molecule on
      the sidechain

<400> SEQUENCE: 372

```
Glu Ser Gly Ser Gly Ser Gly Ser Ser Leu Val Arg Gly Arg Val Leu
1               5                   10                  15

Glu Leu Phe Arg Ala Ala Gln Leu Ala Asn Asp Val Val Leu Gln Ile
            20                  25                  30

Met Glu Leu Cys Gly Ala Thr Arg Leu Leu Leu Leu Leu Lys
        35                  40                  45
```

<210> SEQ ID NO 373
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 373

```
Glu Glu Glu Glu Glu Glu Glu Glu Ser Leu Val Arg Val Leu Glu Leu
1               5                   10                  15

Phe Arg Ala Ala Gln Leu Ala Asn Asp Val Val Leu Gln Ile Met Glu
            20                  25                  30

Leu Cys Gly Ala Thr Arg Lys
        35
```

<210> SEQ ID NO 374
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Azido-Lys attached to a hydrophobic molecule on
      the sidechain

<400> SEQUENCE: 374

Arg Arg Arg Arg Arg Lys Pro Leu Arg Gly Arg Val Leu Glu Leu Phe
1               5                   10                  15

Arg Ala Ala Gln Leu Ala Asn Asp Val Val Leu Gln Ile Met Glu Leu
            20                  25                  30

Cys Gly Ala Thr Arg Leu Leu Leu Leu Lys
        35                  40

<210> SEQ ID NO 375
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (46)..(46)
<223> OTHER INFORMATION: Azido-Lys attached to a hydrophobic molecule on
      the sidechain

<400> SEQUENCE: 375

Glu Glu Glu Glu Glu Glu Glu Glu Ser Leu Val Arg Gly Arg Val Leu
1               5                   10                  15

Glu Leu Phe Arg Ala Ala Gln Leu Ala Asn Asp Val Val Leu Gln Ile
            20                  25                  30

Met Glu Leu Cys Gly Ala Thr Arg Leu Leu Leu Leu Leu Lys
        35                  40                  45

<210> SEQ ID NO 376
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 376

Glu Lys Glu Lys Leu Val Leu Ala Ser Met Thr Asn Met Glu Leu Met
1               5                   10                  15

Ser Ser Gly Gly Ser Leu Val Leu Lys
            20                  25

<210> SEQ ID NO 377
<211> LENGTH: 24
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 377

Glu Lys Ser Leu Val Arg Ala Ser Met Thr Asn Met Glu Leu Met Ser
1               5                   10                  15

Ser Gly Gly Glu Leu Val Arg Lys
            20

<210> SEQ ID NO 378
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 378

Lys Glu Lys Leu Val Arg Ala Ser Met Thr Asn Met Glu Leu Met Ser
1               5                   10                  15

Ser Gly Gly Ser Leu Val Leu Lys
            20

<210> SEQ ID NO 379
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 379

Lys Glu Lys Leu Val Arg Ala Ser Met Thr Asn Met Glu Leu Met Ser
1               5                   10                  15

Ser Gly Gly Glu Leu Val Arg Lys
            20

<210> SEQ ID NO 380
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 380

Lys Ser Lys Leu Val Arg Ala Ser Met Thr Asn Met Glu Leu Met Ser
1               5                   10                  15

Ser Gly Gly Ser Leu Val Leu Lys
```

<210> SEQ ID NO 381
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 381

Lys Ser Lys Ser Lys Leu Val Arg Ala Ser Met Thr Asn Met Glu Leu
1               5                   10                  15

Met Ser Ser Gly Gly Glu Leu Val Leu Lys
            20                  25

<210> SEQ ID NO 382
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 382

Lys Ser Lys Ser Lys Leu Val Arg Ala Ser Met Thr Asn Met Glu Leu
1               5                   10                  15

Met Ser Ser Gly Gly Ser Leu Val Leu Lys
            20                  25

<210> SEQ ID NO 383
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 383

Lys Ser Lys Ser Lys Leu Val Arg Ala Ser Met Thr Asn Met Glu Leu
1               5                   10                  15

Met Ser Ser Gly Gly Glu Leu Val Arg Lys
            20                  25

<210> SEQ ID NO 384
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)

```
<223> OTHER INFORMATION: Azido-Lys attached to a hydrophobic molecule on
      the sidechain

<400> SEQUENCE: 384

Lys Ser Lys Ser Lys Leu Val Arg Ala Ser Met Thr Asn Met Glu Leu
1               5                   10                  15

Met Ser Ser Gly Gly Ser Leu Val Arg Lys
            20                  25

<210> SEQ ID NO 385
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 385

Lys Ser Lys Ser Lys Leu Val Arg Ala Ser Met Thr Asn Met Glu Leu
1               5                   10                  15

Met Ser Ser Gly Gly Lys Leu Val Arg Lys
            20                  25

<210> SEQ ID NO 386
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 386

Glu Lys Glu Lys Leu Val Leu Ala Ser Met Thr Asn Met Glu Leu Met
1               5                   10                  15

Ser Ser Gly Gly Ser Leu Val Leu Lys
            20                  25

<210> SEQ ID NO 387
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 387

Glu Lys Ser Leu Val Arg Ala Ser Met Thr Asn Met Glu Leu Met Ser
1               5                   10                  15

Ser Gly Gly Glu Leu Val Arg Lys
            20

<210> SEQ ID NO 388
```

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 388

Lys Glu Lys Leu Val Arg Ala Ser Met Thr Asn Met Glu Leu Met Ser
1               5                   10                  15

Ser Gly Gly Ser Leu Val Leu Lys
            20

<210> SEQ ID NO 389
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 389

Lys Glu Lys Leu Val Arg Ala Ser Met Thr Asn Met Glu Leu Met Ser
1               5                   10                  15

Ser Gly Gly Glu Leu Val Arg Lys
            20

<210> SEQ ID NO 390
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 390

Lys Ser Lys Leu Val Arg Ala Ser Met Thr Asn Met Glu Leu Met Ser
1               5                   10                  15

Ser Gly Gly Ser Leu Val Leu Lys
            20

<210> SEQ ID NO 391
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 391
```

Lys Ser Lys Ser Lys Leu Val Arg Ala Ser Met Thr Asn Met Glu Leu
1               5                   10                  15

Met Ser Ser Gly Gly Glu Leu Val Leu Lys
            20                  25

<210> SEQ ID NO 392
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 392

Lys Ser Lys Ser Lys Leu Val Arg Ala Ser Met Thr Asn Met Glu Leu
1               5                   10                  15

Met Ser Ser Gly Gly Ser Leu Val Leu Lys
            20                  25

<210> SEQ ID NO 393
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 393

Lys Ser Lys Ser Lys Leu Val Arg Ala Ser Met Thr Asn Met Glu Leu
1               5                   10                  15

Met Ser Ser Gly Gly Glu Leu Val Arg Lys
            20                  25

<210> SEQ ID NO 394
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 394

Lys Ser Lys Ser Lys Leu Val Arg Ala Ser Met Thr Asn Met Glu Leu
1               5                   10                  15

Met Ser Ser Gly Gly Ser Leu Val Arg Lys
            20                  25

<210> SEQ ID NO 395
<211> LENGTH: 26
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 395

Lys Ser Lys Ser Lys Leu Val Arg Ala Ser Met Thr Asn Met Glu Leu
1               5                   10                  15

Met Ser Ser Gly Gly Lys Leu Val Arg Lys
            20                  25

<210> SEQ ID NO 396
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 396

Lys Lys Lys Lys Val Arg Arg Cys Ser Asp Ser Asp Gly Leu Ala Pro
1               5                   10                  15

Pro Gln Arg Leu Ile Arg Val Glu Gly Asn Leu Arg Val Glu Tyr Ser
            20                  25                  30

Pro Val Xaa Lys
        35

<210> SEQ ID NO 397
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 397

Lys Lys Lys Lys Lys Val Arg Met Cys Asn Ser Ser Cys Met Gly Gly
1               5                   10                  15

Met Asn Arg Ser Pro Ile Leu Thr Ile Ile Thr Leu Glu Asp Ser Ser
            20                  25                  30

Ser Pro Val Xaa Lys
        35

<210> SEQ ID NO 398
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 398

Lys Lys Lys Lys Lys Lys Val Arg Pro Pro Glu Val Gly Ser Asp Cys
1               5                   10                  15

Thr Thr Ile His Cys Asn Tyr Met Cys Asn Ser Ser Cys Met Gly Gly
            20                  25                  30

Met Ser Pro Val Xaa Lys
            35

<210> SEQ ID NO 399
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 399

Lys Lys Lys Lys Val Arg Pro Gly Glu Thr Val Arg His Cys Ser Ala
1               5                   10                  15

Pro Glu Asn Pro Ile Phe Arg Phe Ser Ser Leu His Ser Tyr Leu Ser
            20                  25                  30

Pro Val Xaa Lys
            35

<210> SEQ ID NO 400
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 400

Lys Lys Lys Val Arg Val Gly Ser Asp Cys Thr Thr Ile His Tyr Asn
1               5                   10                  15

Val Ile Cys Asn Ser Ser Cys Met Gly Gly Met Asn Arg Arg Ser Pro
            20                  25                  30
```

```
Val Xaa Lys
        35

<210> SEQ ID NO 401
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Citrulline
<220> FEATURE:
<221> NAME/KEY: MOD_RES
<222> LOCATION: (33)..(33)
<223> OTHER INFORMATION: Azido-Lys attached to a hydrophobic molecule on
      the sidechain

<400> SEQUENCE: 401

Lys Val Arg Leu Lys Lys Met Trp Lys Ser Pro Asn Gly Thr Ile Gln
1               5                   10                  15

Asn Ile Leu Gly Gly Thr Val Phe Arg Glu Pro Ile Ser Pro Val Xaa
            20                  25                  30

Lys

<210> SEQ ID NO 402
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 402

Lys Lys Lys Lys Lys Val Arg Ser Tyr Leu Asp Ser Gly Ile His Ser
1               5                   10                  15

Gly Ala Thr Ala Thr Ala Pro Ser Leu Ser Gly Lys Gly Asn Pro Glu
            20                  25                  30

Ser Pro Val Xaa Lys
        35

<210> SEQ ID NO 403
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 403
```

```
Lys Lys Lys Lys Lys Val Arg Thr Cys Leu Leu Ile Ser Tyr Thr
1               5                   10                  15

Thr Asn Ala Phe Ser Gly Glu Tyr Ile Pro Thr Val Phe Asp Asn Tyr
            20                  25                  30

Ser Ser Pro Val Xaa Lys
            35

<210> SEQ ID NO 404
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 404

Lys Lys Lys Lys Val Arg Ile Asp Gly Pro His Cys Val Lys Thr Cys
1               5                   10                  15

Pro Ala Val Val Met Gly Glu Asn Asn Thr Leu Val Trp Lys Tyr Ser
            20                  25                  30

Pro Val Xaa Lys
        35

<210> SEQ ID NO 405
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Citrulline
<220> FEATURE:
<221> NAME/KEY: MOD_RES
<222> LOCATION: (41)..(41)
<223> OTHER INFORMATION: Azido-Lys attached to a hydrophobic molecule on
      the sidechain

<400> SEQUENCE: 405

Lys Lys Lys Lys Lys Lys Lys Lys Val Arg Glu Glu Asp Val Glu
1               5                   10                  15

Asp Gly Gly Asp Arg Trp Ser Thr Pro Tyr Val Ala Thr Leu Ser Leu
            20                  25                  30

His Ser Leu Phe Ser Pro Val Xaa Lys
            35                  40

<210> SEQ ID NO 406
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
```

```
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 406

Lys Lys Lys Lys Val Arg Lys Met Gln Ile Thr Pro Glu Thr Pro Gly
1               5                   10                  15

Arg Ile Arg Val Leu Asn Pro Phe Glu Ser Pro Ser Asp Tyr Ser Ser
            20                  25                  30

Pro Val Xaa Lys
        35

<210> SEQ ID NO 407
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 407

Lys Lys Val Arg Arg Ser Gly Pro Asp Leu Arg Pro Pro Thr Pro
1               5                   10                  15

Val Pro Trp Pro Ser Thr Ser Leu Gly Thr Pro Leu Thr Ser Pro Val
            20                  25                  30

Xaa Lys

<210> SEQ ID NO 408
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 408

Lys Lys Lys Lys Lys Lys Lys Val Arg Tyr Glu Asp Asn Asp Glu
1               5                   10                  15

Val His Ile Glu Val His Thr Pro Arg Asn Thr Glu Ala Val Thr Leu
            20                  25                  30

Asn Phe Arg Ser Pro Val Xaa Lys
        35                  40

<210> SEQ ID NO 409
<211> LENGTH: 37
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 409

Lys Lys Lys Lys Lys Val Arg Ile Asn Cys Ser Leu Asp Trp Leu Met
1               5                   10                  15

Val Ser Val Ser Pro Leu Ala Glu Ser Arg Asn Leu Tyr Ile Phe Ala
            20                  25                  30

Ser Pro Val Xaa Lys
        35

<210> SEQ ID NO 410
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Citrulline
<220> FEATURE:
<221> NAME/KEY: MOD_RES
<222> LOCATION: (33)..(33)
<223> OTHER INFORMATION: Azido-Lys attached to a hydrophobic molecule on
      the sidechain

<400> SEQUENCE: 410

Lys Val Arg Ala Leu Tyr Thr Lys Met Val Pro Ala Ala Val Ser Arg
1               5                   10                  15

Ser Glu Phe Trp His Arg Tyr Phe Tyr Lys Val His Ser Pro Val Xaa
            20                  25                  30

Lys

<210> SEQ ID NO 411
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 411

Lys Lys Val Arg Val Cys Pro Gln Ser Leu Pro Tyr Phe Ala Ala Lys
1               5                   10                  15

Leu Asn Leu Ser Val Thr Asp Ala Ser Arg Arg Leu Cys Ser Pro Val
            20                  25                  30
```

Xaa Lys

```
<210> SEQ ID NO 412
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 412
```

Lys Lys Lys Val Arg Glu Ala Gly Lys Val Tyr Leu Lys Ala Pro Met
1               5                   10                  15

Ile Met Asn Gly Val Cys Val Ile Trp Lys Gly Trp Ile Asp Ser Pro
            20                  25                  30

Val Xaa Lys
        35

```
<210> SEQ ID NO 413
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 413
```

Lys Lys Lys Lys Val Arg Ser Arg Ser Ala Ser His Arg Ser Thr Arg
1               5                   10                  15

Phe Ala Glu Thr Phe Tyr Asp Ile Glu Thr Leu Lys Val Ile Asp Ser
            20                  25                  30

Pro Val Xaa Lys
            35

```
<210> SEQ ID NO 414
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Citrulline
<220> FEATURE:
<221> NAME/KEY: MOD_RES
<222> LOCATION: (33)..(33)
<223> OTHER INFORMATION: Azido-Lys attached to a hydrophobic molecule on
      the sidechain

<400> SEQUENCE: 414
```

```
Lys Val Arg Ala Ile Tyr His Tyr Arg Thr Ala Leu Lys Leu Tyr Ser
1               5                   10                  15

Arg His Ala Ser Ala Leu Asn Asn Leu Gly Thr Leu Ser Pro Val Xaa
                20                  25                  30

Lys
```

<210> SEQ ID NO 415
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 415

```
Lys Lys Lys Lys Lys Val Arg Thr Ser Leu Thr Ala Cys Leu Val
1               5                   10                  15

Asp Gln Ser Leu Leu Leu Asp Cys Arg His Glu Asn Thr Thr Ser Ser
                20                  25                  30

Pro Ser Pro Val Xaa Lys
        35
```

<210> SEQ ID NO 416
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 416

```
Lys Lys Lys Lys Lys Lys Lys Val Arg Gly Phe Gln Ala Leu Ser Glu
1               5                   10                  15

Gly Cys Thr Pro Tyr Asp Ile Asn Gln Met Leu Asn Cys Val Gly Asp
                20                  25                  30

His Gln Ser Pro Val Xaa Lys
        35
```

<210> SEQ ID NO 417
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline

```
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 417

Lys Lys Lys Lys Val Arg Met Ala Glu Ala Leu Lys Glu Ala Leu Ala
1               5                   10                  15

Pro Val Pro Ile Pro Phe Ala Ala Ala Gln Gln Arg Gly Pro Ser Pro
            20                  25                  30

Val Xaa Lys
        35

<210> SEQ ID NO 418
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 418

Lys Lys Lys Lys Val Arg Arg Cys Ser Asp Ser Asp Gly Leu Ala Pro
1               5                   10                  15

Pro Gln Arg Leu Ile Arg Val Glu Gly Asn Leu Arg Val Glu Tyr Ser
            20                  25                  30

Pro Val Xaa Lys
        35

<210> SEQ ID NO 419
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 419

Lys Lys Lys Lys Lys Val Arg Met Cys Asn Ser Ser Cys Met Gly Gly
1               5                   10                  15

Met Asn Arg Ser Pro Ile Leu Thr Ile Ile Thr Leu Glu Asp Ser Ser
            20                  25                  30

Ser Pro Val Xaa Lys
            35

<210> SEQ ID NO 420
<211> LENGTH: 38
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 420

Lys Lys Lys Lys Lys Lys Val Arg Pro Pro Glu Val Gly Ser Asp Cys
1               5                   10                  15

Thr Thr Ile His Cys Asn Tyr Met Cys Asn Ser Ser Cys Met Gly Gly
            20                  25                  30

Met Ser Pro Val Xaa Lys
        35

<210> SEQ ID NO 421
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 421

Lys Lys Lys Lys Val Arg Pro Gly Glu Thr Val Arg His Cys Ser Ala
1               5                   10                  15

Pro Glu Asn Pro Ile Phe Arg Phe Ser Ser Leu His Tyr Leu Ser
            20                  25                  30

Pro Val Xaa Lys
        35

<210> SEQ ID NO 422
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 422

Lys Lys Lys Val Arg Val Gly Ser Asp Cys Thr Thr Ile His Tyr Asn
1               5                   10                  15

Tyr Ile Cys Asn Ser Ser Cys Met Gly Gly Met Asn Arg Arg Ser Pro
            20                  25                  30
```

Val Xaa Lys
        35

<210> SEQ ID NO 423
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Citrulline
<220> FEATURE:
<221> NAME/KEY: MOD_RES
<222> LOCATION: (33)..(33)
<223> OTHER INFORMATION: Azido-Lys attached to a hydrophobic molecule on
      the sidechain

<400> SEQUENCE: 423

Lys Val Arg Leu Lys Lys Met Trp Lys Ser Pro Asn Gly Thr Ile Gln
1               5                   10                  15

Asn Ile Leu Gly Gly Thr Val Phe Arg Glu Pro Ile Ser Pro Val Xaa
            20                  25                  30

Lys

<210> SEQ ID NO 424
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 424

Lys Lys Lys Lys Lys Val Arg Ser Tyr Leu Asp Ser Gly Ile His Ser
1               5                   10                  15

Gly Ala Thr Ala Thr Ala Pro Ser Leu Ser Gly Lys Gly Asn Pro Glu
            20                  25                  30

Ser Pro Val Xaa Lys
        35

<210> SEQ ID NO 425
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain -continued

```
<400> SEQUENCE: 425

Lys Lys Lys Lys Lys Val Arg Thr Cys Leu Leu Ile Ser Tyr Thr
1               5                   10                  15

Thr Asn Ala Phe Ser Gly Glu Tyr Ile Pro Thr Val Phe Asp Asn Tyr
            20                  25                  30

Ser Ser Pro Val Xaa Lys
        35

<210> SEQ ID NO 426
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 426

Lys Lys Lys Lys Val Arg Ile Asp Gly Pro His Cys Val Lys Thr Cys
1               5                   10                  15

Pro Ala Val Val Met Gly Glu Asn Asn Thr Leu Val Trp Lys Tyr Ser
            20                  25                  30

Pro Val Xaa Lys
        35

<210> SEQ ID NO 427
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Citrulline
<220> FEATURE:
<221> NAME/KEY: MOD_RES
<222> LOCATION: (41)..(41)
<223> OTHER INFORMATION: Azido-Lys attached to a hydrophobic molecule on
      the sidechain

<400> SEQUENCE: 427

Lys Lys Lys Lys Lys Lys Lys Lys Lys Val Arg Glu Glu Asp Val Glu
1               5                   10                  15

Asp Gly Gly Asp Arg Trp Ser Thr Pro Tyr Val Ala Thr Leu Ser Leu
            20                  25                  30

His Ser Leu Phe Ser Pro Val Xaa Lys
        35                  40

<210> SEQ ID NO 428
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 428

Lys Lys Lys Lys Val Arg Lys Met Gln Ile Thr Pro Glu Thr Pro Gly
1               5                   10                  15

Arg Ile Arg Val Leu Asn Pro Phe Glu Ser Pro Ser Asp Tyr Ser Ser
                20                  25                  30

Pro Val Xaa Lys
        35

<210> SEQ ID NO 429
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 429

Lys Lys Val Arg Arg Ser Gly Pro Asp Leu Arg Arg Pro Pro Thr Pro
1               5                   10                  15

Val Pro Trp Pro Ser Thr Ser Leu Gly Thr Pro Leu Thr Ser Pro Val
                20                  25                  30

Xaa Lys

<210> SEQ ID NO 430
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 430

Lys Lys Lys Lys Lys Lys Lys Val Arg Tyr Glu Asp Asn Asp Glu
1               5                   10                  15

Val His Ile Glu Val His Thr Pro Arg Asn Thr Glu Ala Val Thr Leu
                20                  25                  30

Asn Phe Arg Ser Pro Val Xaa Lys
        35                  40

<210> SEQ ID NO 431
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 431

Lys Lys Lys Lys Lys Val Arg Ile Asn Cys Ser Leu Asp Trp Leu Met
1               5                   10                  15

Val Ser Val Ser Pro Leu Ala Glu Ser Arg Asn Leu Tyr Ile Phe Ala
            20                  25                  30

Ser Pro Val Xaa Lys
        35

<210> SEQ ID NO 432
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Citrulline
<220> FEATURE:
<221> NAME/KEY: MOD_RES
<222> LOCATION: (33)..(33)
<223> OTHER INFORMATION: Azido-Lys attached to a hydrophobic molecule on
      the sidechain

<400> SEQUENCE: 432

Lys Val Arg Ala Leu Tyr Thr Lys Met Val Pro Ala Ala Val Ser Arg
1               5                   10                  15

Ser Glu Phe Trp His Arg Tyr Phe Tyr Lys Val His Ser Pro Val Xaa
            20                  25                  30

Lys

<210> SEQ ID NO 433
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 433

Lys Lys Val Arg Val Cys Pro Gln Ser Leu Pro Tyr Phe Ala Ala Lys
1               5                   10                  15

Leu Asn Leu Ser Val Thr Asp Ala Ser Arg Arg Leu Cys Ser Pro Val
            20                  25                  30
```

Xaa Lys

<210> SEQ ID NO 434
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 434

Lys Lys Lys Val Arg Glu Ala Gly Lys Val Tyr Leu Lys Ala Pro Met
1               5                   10                  15

Ile Met Asn Gly Val Cys Val Ile Trp Lys Gly Trp Ile Asp Ser Pro
            20                  25                  30

Val Xaa Lys
        35

<210> SEQ ID NO 435
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 435

Lys Lys Lys Lys Val Arg Ser Arg Ser Ala Ser His Arg Ser Thr Arg
1               5                   10                  15

Phe Ala Glu Thr Phe Tyr Asp Ile Glu Thr Leu Lys Val Ile Asp Ser
            20                  25                  30

Pro Val Xaa Lys
        35

<210> SEQ ID NO 436
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Citrulline
<220> FEATURE:
<221> NAME/KEY: MOD_RES
<222> LOCATION: (33)..(33)
<223> OTHER INFORMATION: Azido-Lys attached to a hydrophobic molecule on
      the sidechain

<400> SEQUENCE: 436

Lys Val Arg Ala Ile Tyr His Tyr Arg Thr Ala Leu Lys Leu Tyr Ser
1               5                   10                  15

Arg His Ala Ser Ala Leu Asn Asn Leu Gly Thr Leu Ser Pro Val Xaa
            20                  25                  30

Lys

<210> SEQ ID NO 437
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 437

Lys Lys Lys Lys Lys Lys Val Arg Thr Ser Leu Thr Ala Cys Leu Val
1               5                   10                  15

Asp Gln Ser Leu Leu Leu Asp Cys Arg His Glu Asn Thr Thr Ser Ser
            20                  25                  30

Pro Ser Pro Val Xaa Lys
        35

<210> SEQ ID NO 438
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 438

Lys Lys Lys Lys Lys Lys Lys Val Arg Gly Phe Gln Ala Leu Ser Glu
1               5                   10                  15

Gly Cys Thr Pro Tyr Asp Ile Asn Gln Met Leu Asn Cys Val Gly Asp
            20                  25                  30

His Gln Ser Pro Val Xaa Lys
        35

<210> SEQ ID NO 439
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)

```
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 439

Lys Lys Lys Lys Val Arg Met Ala Glu Ala Leu Lys Glu Ala Leu Ala
1               5                   10                  15

Pro Val Pro Ile Pro Phe Ala Ala Ala Gln Gln Arg Gly Pro Ser Pro
            20                  25                  30

Val Xaa Lys
        35

<210> SEQ ID NO 440
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 440

Lys Lys Lys Lys Val Arg Gly Arg Val Leu Glu Leu Phe Arg Ala Ala
1               5                   10                  15

Gln Leu Ala Asn Asp Val Val Leu Gln Ile Met Glu Leu Cys Gly Ala
            20                  25                  30

Thr Arg Gly Ser Gly Val Xaa Lys
        35                  40

<210> SEQ ID NO 441
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys attached to a hydrophobic molecule on
      the sidechain

<400> SEQUENCE: 441

Lys Lys Lys Lys Lys Lys Val Arg Gly Ile Pro Val His Leu Glu Leu
1               5                   10                  15

Ala Ser Met Thr Asn Met Glu Leu Met Ser Ser Ile Val His Gln Gln
            20                  25                  30

Val Phe Pro Thr Gly Ser Gly Val Xaa Lys
        35                  40

<210> SEQ ID NO 442
<211> LENGTH: 40
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 442

Lys Lys Lys Lys Lys Lys Lys Val Arg Glu Ala Gly Gln Ser Leu Val
1               5                   10                  15

Ile Ser Ala Ser Ile Ile Val Phe Asn Leu Leu Glu Leu Glu Gly Asp
            20                  25                  30

Tyr Arg Gly Ser Gly Val Xaa Lys
        35                  40

<210> SEQ ID NO 443
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 443

Lys Lys Lys Lys Lys Val Arg Ser Lys Leu Leu Ser Phe Met Ala Pro
1               5                   10                  15

Ile Asp His Thr Thr Met Ser Asp Asp Ala Arg Thr Glu Leu Phe Arg
            20                  25                  30

Ser Gly Ser Gly Val Xaa Lys
        35

<210> SEQ ID NO 444
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Citrulline
<220> FEATURE:
<221> NAME/KEY: MOD_RES
<222> LOCATION: (41)..(41)
<223> OTHER INFORMATION: Azido-Lys attached to a hydrophobic molecule on
      the sidechain

<400> SEQUENCE: 444

Lys Lys Lys Lys Lys Lys Lys Val Arg Asp Phe Thr Gly Ser Asn Gly
1               5                   10                  15

Asp Pro Ser Ser Pro Tyr Ser Leu His Tyr Leu Ser Pro Thr Gly Val
```

-continued

```
                    20                  25                  30

Asn Glu Tyr Gly Ser Gly Val Xaa Lys
            35                  40

<210> SEQ ID NO 445
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 445

Lys Lys Lys Lys Lys Val Arg Lys Ala Arg Asp Glu Thr Ala Ala Leu
1               5                   10                  15

Leu Asn Ser Ala Val Leu Gly Ala Ala Pro Leu Phe Val Pro Pro Ala
            20                  25                  30

Asp Gly Ser Gly Val Xaa Lys
        35

<210> SEQ ID NO 446
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 446

Lys Lys Lys Lys Lys Lys Lys Val Arg Asp Ile Asp Pro Ser Ser
1               5                   10                  15

Ser Val Leu Phe Glu Tyr Met Glu Lys Pro Asp Phe Ser Leu Phe Ser
            20                  25                  30

Pro Ser Pro Val Xaa Lys
        35

<210> SEQ ID NO 447
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
``` the sidechain

<400> SEQUENCE: 447

Lys Lys Lys Lys Lys Lys Lys Val Arg Ser Lys Leu Leu Ser Phe Met
1               5                   10                  15

Ala Pro Ile Asp His Thr Thr Met Ser Asp Asp Ala Arg Thr Glu Leu
            20                  25                  30

Phe Arg Ser Ser Pro Val Xaa Lys
        35                  40

<210> SEQ ID NO 448
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Citrulline
<220> FEATURE:
<221> NAME/KEY: MOD_RES
<222> LOCATION: (43)..(43)
<223> OTHER INFORMATION: Azido-Lys attached to a hydrophobic molecule on
      the sidechain

<400> SEQUENCE: 448

Lys Lys Lys Lys Lys Lys Lys Lys Val Arg Gly Ile Pro Val His Leu
1               5                   10                  15

Glu Leu Ala Ser Met Thr Asn Met Gly Leu Met Ser Ser Ile Val His
            20                  25                  30

Gln Gln Val Phe Pro Thr Ser Pro Val Xaa Lys
        35                  40

<210> SEQ ID NO 449
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys attached to a hydrophobic molecule on
      the sidechain

<400> SEQUENCE: 449

Lys Lys Lys Lys Lys Lys Lys Lys Val Arg Asp Phe Thr Gly Ser
1               5                   10                  15

Asn Gly Asp Pro Ser Ser Pro Tyr Ser Leu His Tyr Leu Ser Pro Thr
            20                  25                  30

Gly Val Asn Glu Tyr Ser Pro Val Xaa Lys
        35                  40

<210> SEQ ID NO 450
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide -continued

```
<220> FEATURE:
<221> NAME/KEY: MOD_RES
<222> LOCATION: (40)..(40)
<223> OTHER INFORMATION: Citrulline
<220> FEATURE:
<221> NAME/KEY: MOD_RES
<222> LOCATION: (41)..(41)
<223> OTHER INFORMATION: Azido-Lys attached to a hydrophobic molecule on
      the sidechain

<400> SEQUENCE: 450

Lys Lys Lys Lys Lys Lys Lys Lys Val Arg Glu Ala Gly Gln Ser
1               5                   10                  15

Leu Val Ile Ser Ala Ser Ile Ile Val Phe Asn Leu Leu Glu Leu Glu
            20                  25                  30

Gly Asp Tyr Arg Ser Pro Val Xaa Lys
        35                  40

<210> SEQ ID NO 451
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 451

Lys Lys Lys Lys Lys Lys Lys Val Arg Lys Ala Arg Asp Glu Thr Ala
1               5                   10                  15

Ala Leu Leu Asn Ser Ala Val Leu Gly Ala Ala Pro Leu Phe Val Pro
            20                  25                  30

Pro Ala Asp Ser Pro Val Xaa Lys
        35                  40

<210> SEQ ID NO 452
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 452

Lys Lys Lys Lys Lys Lys Lys Lys Lys Lys Val Arg Asp Ile Asp Pro
1               5                   10                  15

Ser Ser Ser Val Leu Phe Glu Tyr Met Glu Lys Pro Asp Phe Ser Leu
            20                  25                  30

Phe Ser Pro Ser Pro Val Xaa Lys
        35                  40
```

<210> SEQ ID NO 453
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Citrulline
<220> FEATURE:
<221> NAME/KEY: MOD_RES
<222> LOCATION: (41)..(41)
<223> OTHER INFORMATION: Azido-Lys attached to a hydrophobic molecule on
      the sidechain

<400> SEQUENCE: 453

Lys Lys Lys Lys Lys Lys Val Arg Gly Arg Val Leu Glu Leu Phe Arg
1               5                   10                  15

Ala Ala Gln Leu Ala Asn Asp Val Val Leu Gln Ile Met Glu Leu Cys
            20                  25                  30

Gly Ala Thr Arg Ser Pro Val Xaa Lys
        35                  40

<210> SEQ ID NO 454
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys attached to a hydrophobic molecule on
      the sidechain

<400> SEQUENCE: 454

Lys Lys Lys Lys Lys Lys Lys Lys Lys Val Arg Glu Thr Leu Gly
1               5                   10                  15

Glu Ile Ser Phe Leu Leu Ser Leu Asp Leu His Phe Thr Asp Gly Asp
            20                  25                  30

Tyr Ser Ala Gly Asp Ser Pro Val Xaa Lys
        35                  40

<210> SEQ ID NO 455
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 455

Lys Lys Lys Lys Lys Lys Lys Lys Val Arg Asp Asp Glu Gly Asp Tyr

-continued

```
                1               5                    10                  15
Thr Cys Gln Phe Thr His Val Glu Asn Gly Thr Asn Tyr Ile Val Thr
                    20                  25                  30
Ala Thr Arg Ser Pro Val Xaa Lys
            35                  40
```

<210> SEQ ID NO 456
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Citrulline
<220> FEATURE:
<221> NAME/KEY: MOD_RES
<222> LOCATION: (41)..(41)
<223> OTHER INFORMATION: Azido-Lys attached to a hydrophobic molecule on
      the sidechain

<400> SEQUENCE: 456

```
Lys Lys Lys Lys Lys Lys Val Arg Gly Ile Pro Val His Leu Glu Leu
1               5                   10                  15
Ala Ser Met Thr Asn Met Glu Leu Met Ser Ser Ile Val His Gln Gln
                    20                  25                  30
Val Phe Pro Thr Ser Pro Val Xaa Lys
            35                  40
```

<210> SEQ ID NO 457
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 457

```
Lys Lys Lys Lys Val Arg Val Val Asp Arg Asn Pro Gln Phe Leu Asp
1               5                   10                  15
Pro Val Leu Ala Tyr Leu Met Lys Gly Leu Cys Glu Lys Pro Leu Ala
                    20                  25                  30
Ser Ser Pro Val Xaa Lys
            35
```

<210> SEQ ID NO 458
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:

```
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 458

Lys Lys Val Arg Asn Ile Glu Gly Ile Asp Lys Leu Thr Gln Leu Lys
1               5                   10                  15

Lys Pro Phe Leu Val Asn Asn Lys Ile Asn Lys Ile Glu Asn Ile Ser
            20                  25                  30

Pro Val Xaa Lys
        35

<210> SEQ ID NO 459
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Citrulline
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 459

Val Arg Met Ala Ala Ala Leu Thr Phe Arg Arg Leu Leu Thr Leu Pro
1               5                   10                  15

Arg Ala Ala Arg Gly Phe Gly Val Gln Val Ser Ser Pro Val Xaa Lys
            20                  25                  30

<210> SEQ ID NO 460
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 460

Val Arg Gly Arg Gly His Leu Leu Gly Arg Leu Ala Ala Ile Val Gly
1               5                   10                  15

Lys Gln Val Leu Leu Gly Arg Lys Val Val Val Arg Ser Pro Val
            20                  25                  30

Xaa Lys

<210> SEQ ID NO 461
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 461

Lys Lys Lys Val Arg Leu Lys Ser Ser Pro Glu Arg Asn Asp Trp Glu
1               5                   10                  15

Pro Leu Asp Lys Lys Val Asp Thr Arg Lys Tyr Arg Ala Glu Ser Pro
            20                  25                  30

Val Xaa Lys
        35

<210> SEQ ID NO 462
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Citrulline
<220> FEATURE:
<221> NAME/KEY: MOD_RES
<222> LOCATION: (44)..(44)
<223> OTHER INFORMATION: Azido-Lys attached to a hydrophobic molecule on
      the sidechain

<400> SEQUENCE: 462

Lys Lys Lys Lys Lys Lys Lys Lys Lys Lys Lys Lys Val Arg Glu Thr
1               5                   10                  15

Leu Gly Glu Ile Ser Phe Leu Leu Ser Leu Asp Leu His Phe Thr Asp
            20                  25                  30

Gly Asp Tyr Ser Ala Gly Asp Ser Pro Val Xaa Lys
            35                  40

<210> SEQ ID NO 463
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys attached to a hydrophobic molecule on
      the sidechain

<400> SEQUENCE: 463

Lys Lys Lys Lys Lys Lys Lys Lys Lys Val Arg Asp Asp Glu Gly
1               5                   10                  15

Asp Tyr Thr Cys Gln Phe Thr His Val Glu Asn Gly Thr Asn Tyr Ile
            20                  25                  30

Val Thr Ala Thr Arg Ser Pro Val Xaa Lys
            35                  40
```

```
<210> SEQ ID NO 464
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 464

Lys Lys Lys Lys Lys Lys Val Arg Val Val Asp Arg Asn Pro Gln Phe
1               5                   10                  15

Leu Asp Pro Val Leu Ala Tyr Leu Met Lys Gly Leu Cys Glu Lys Pro
            20                  25                  30

Leu Ala Ser Ser Pro Val Xaa Lys
        35                  40

<210> SEQ ID NO 465
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 465

Lys Lys Lys Lys Val Arg Asn Ile Glu Gly Ile Asp Lys Leu Thr Gln
1               5                   10                  15

Leu Lys Lys Pro Phe Leu Val Asn Asn Lys Ile Asn Lys Ile Glu Asn
            20                  25                  30

Ile Ser Pro Val Xaa Lys
        35

<210> SEQ ID NO 466
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 466

Lys Lys Val Arg Met Ala Ala Ala Leu Thr Phe Arg Arg Leu Leu Thr
1               5                   10                  15
```

```
Leu Pro Arg Ala Ala Arg Gly Phe Gly Val Gln Val Ser Ser Pro Val
            20                  25                  30

Xaa Lys

<210> SEQ ID NO 467
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 467

Lys Lys Lys Lys Val Arg Leu Lys Ser Ser Pro Glu Arg Asn Asp Trp
1               5                   10                  15

Glu Pro Leu Asp Lys Lys Val Asp Thr Arg Lys Tyr Arg Ala Glu Ser
            20                  25                  30

Pro Val Xaa Lys
        35

<210> SEQ ID NO 468
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 468

Lys Lys Lys Lys Lys Lys Lys Val Arg Gln Gly Thr Asp Val Val
1               5                   10                  15

Ile Ala Ile Phe Ile Ile Leu Ala Met Ser Phe Val Pro Ala Ser Glu
            20                  25                  30

Val Val Phe Ser Pro Val Xaa Lys
        35                  40

<210> SEQ ID NO 469
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
```

<223> OTHER INFORMATION: Azido-Lys attached to a hydrophobic molecule on
      the sidechain

<400> SEQUENCE: 469

Lys Asp Val Arg Met Ala Ala Ala Leu Thr Phe Arg Arg Leu Leu Thr
1               5                   10                  15

Leu Pro Arg Ala Ala Arg Gly Phe Gly Val Gln Val Ser Ser Pro Val
            20                  25                  30

Xaa Lys

<210> SEQ ID NO 470
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 470

Lys Lys Lys Lys Lys Val Arg Leu Cys Ser Glu Pro Met Phe Thr Phe
1               5                   10                  15

Val Tyr Pro Thr Ile Phe Pro Leu Arg Glu Thr Pro Met Ala Gly Leu
            20                  25                  30

Ser Pro Val Xaa Lys
        35

<210> SEQ ID NO 471
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 471

Lys Asp Val Arg Ala Trp His Thr Asn Leu Ser Arg Lys Ile Leu Arg
1               5                   10                  15

Met Ser Pro Leu Leu Ala Lys Phe His Gln Phe Leu Val Ser Pro Val
            20                  25                  30

Xaa Lys

<210> SEQ ID NO 472
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 472

Lys Lys Lys Lys Lys Val Arg Lys Gly Phe Glu Leu Leu Tyr Gln Pro
1               5                   10                  15

Glu Val Val Tyr His Leu Tyr Leu Ser Leu Leu Thr Glu Ser Arg Asn
                20                  25                  30

Phe Ser Pro Val Xaa Lys
                35

<210> SEQ ID NO 473
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 473

Lys Lys Lys Val Arg Ser Phe Val Arg Gln Leu Asn Met Tyr Gly Phe
1               5                   10                  15

Arg Asn Val Val His Ile Glu Ser Gly Ile Ile Lys Gln Glu Ser Pro
                20                  25                  30

Val Xaa Lys
        35

<210> SEQ ID NO 474
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 474

Lys Lys Val Arg Met Ala Ala Ala Leu Thr Phe Arg Arg Leu Leu Thr
1               5                   10                  15

Leu Pro Arg Ala Ala Arg Gly Phe Gly Val Gln Val Ser Ser Pro Val
                20                  25                  30

Xaa Lys

<210> SEQ ID NO 475
```

```
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 475

Lys Lys Lys Lys Lys Lys Lys Val Arg Leu Cys Ser Glu Pro Met Phe
1               5                   10                  15

Thr Phe Val Tyr Pro Thr Ile Phe Pro Leu Arg Glu Thr Pro Met Ala
            20                  25                  30

Gly Leu Ser Pro Val Xaa Lys
        35

<210> SEQ ID NO 476
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 476

Lys Lys Val Arg Ala Trp His Thr Asn Leu Ser Arg Lys Ile Leu Arg
1               5                   10                  15

Met Ser Pro Leu Leu Ala Lys Phe His Gln Phe Leu Val Ser Pro Val
            20                  25                  30

Xaa Lys

<210> SEQ ID NO 477
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 477

Lys Lys Lys Lys Lys Lys Lys Val Arg Lys Gly Phe Glu Leu Leu Tyr
1               5                   10                  15

Gln Pro Glu Val Val His Leu Tyr Leu Ser Leu Leu Thr Glu Ser Arg
```

-continued

```
                    20                  25                  30

Asn Phe Ser Pro Val Xaa Lys
            35

<210> SEQ ID NO 478
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 478

Lys Lys Lys Lys Lys Val Arg Ser Phe Val Arg Gln Leu Asn Met Tyr
1               5                   10                  15

Gly Phe Arg Asn Val Val His Ile Glu Ser Gly Ile Ile Lys Gln Glu
            20                  25                  30

Ser Pro Val Xaa Lys
        35

<210> SEQ ID NO 479
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Citrulline
<220> FEATURE:
<221> NAME/KEY: MOD_RES
<222> LOCATION: (30)..(30)
<223> OTHER INFORMATION: Azido-Lys attached to a hydrophobic molecule on
      the sidechain

<400> SEQUENCE: 479

Lys Lys Lys Val Arg Leu Gln Gly Asp Val Ala Phe Gly His Ser Asn
1               5                   10                  15

Leu Phe Ile Arg Ser Pro Arg Thr Leu Ser Pro Val Xaa Lys
            20                  25                  30

<210> SEQ ID NO 480
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Citrulline
<220> FEATURE:
<221> NAME/KEY: MOD_RES
<222> LOCATION: (31)..(31)
<223> OTHER INFORMATION: Azido-Lys attached to a hydrophobic molecule on
      the sidechain

<400> SEQUENCE: 480
```

```
Lys Lys Lys Lys Val Arg Ala Leu Glu Lys Ile Ala Phe Leu Pro Phe
1               5                   10                  15

Ala Tyr Leu Val Asp Gln Trp Arg Trp Gly Ser Pro Val Xaa Lys
            20                  25                  30

<210> SEQ ID NO 481
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Citrulline
<220> FEATURE:
<221> NAME/KEY: MOD_RES
<222> LOCATION: (33)..(33)
<223> OTHER INFORMATION: Azido-Lys attached to a hydrophobic molecule on
      the sidechain

<400> SEQUENCE: 481

Lys Lys Lys Lys Lys Lys Val Arg Gly Ser Ser Ala Glu Glu Ser His
1               5                   10                  15

Leu Ser Cys Leu Asn Trp Ser Thr Leu Val Pro Leu Ser Pro Val Xaa
            20                  25                  30

Lys

<210> SEQ ID NO 482
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Citrulline
<220> FEATURE:
<221> NAME/KEY: MOD_RES
<222> LOCATION: (31)..(31)
<223> OTHER INFORMATION: Azido-Lys attached to a hydrophobic molecule on
      the sidechain

<400> SEQUENCE: 482

Lys Lys Lys Lys Val Arg Met Leu Trp Leu Ala Leu Gly Pro Phe Cys
1               5                   10                  15

Gly Met Glu Asn Gln Val Leu Val Ile Arg Ser Pro Val Xaa Lys
            20                  25                  30

<210> SEQ ID NO 483
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Citrulline
<220> FEATURE:
<221> NAME/KEY: MOD_RES
<222> LOCATION: (31)..(31)
<223> OTHER INFORMATION: Azido-Lys attached to a hydrophobic molecule on
      the sidechain
```

```
<400> SEQUENCE: 483

Lys Lys Lys Lys Val Arg Thr Glu Arg Ile Tyr Ser Leu Phe Asn Leu
1               5                   10                  15

Ser Met Gly Lys Leu Glu Lys Met Gln Glu Ser Pro Val Xaa Lys
            20                  25                  30

<210> SEQ ID NO 484
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Citrulline
<220> FEATURE:
<221> NAME/KEY: MOD_RES
<222> LOCATION: (30)..(30)
<223> OTHER INFORMATION: Azido-Lys attached to a hydrophobic molecule on
      the sidechain

<400> SEQUENCE: 484

Lys Lys Lys Val Arg Ala Leu Gly Leu Arg His Leu Val Val Val Gly
1               5                   10                  15

Asn His Asn Gln Val Val Gly Leu Val Ser Pro Val Xaa Lys
            20                  25                  30

<210> SEQ ID NO 485
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 485

Lys Lys Lys Lys Lys Lys Lys Val Arg Ala Glu Leu Ile Asn Cys Gln
1               5                   10                  15

Ala Asp Val Ser Ala Val Asp Asp His Gly Lys Ser Ala Ser Pro Val
            20                  25                  30

Xaa Lys

<210> SEQ ID NO 486
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Citrulline
<220> FEATURE:
<221> NAME/KEY: MOD_RES
<222> LOCATION: (30)..(30)
<223> OTHER INFORMATION: Azido-Lys attached to a hydrophobic molecule on
      the sidechain
```

```
<400> SEQUENCE: 486

Lys Lys Lys Lys Asp Lys Val Arg Met Ala Ala Ala Leu Leu Pro
1               5                   10                  15

Leu Ala Phe Thr Leu Leu Ser Gly Gln Ser Pro Val Xaa Lys
            20                  25                  30

<210> SEQ ID NO 487
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Citrulline
<220> FEATURE:
<221> NAME/KEY: MOD_RES
<222> LOCATION: (29)..(29)
<223> OTHER INFORMATION: Azido-Lys attached to a hydrophobic molecule on
      the sidechain

<400> SEQUENCE: 487

Lys Asp Val Arg Leu Ser Gly Trp Trp Leu Leu Trp Lys Arg Cys Asn
1               5                   10                  15

Pro Leu Ala Thr Lys Val Lys Val Ser Pro Val Xaa Lys
            20                  25

<210> SEQ ID NO 488
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Citrulline
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 488

Lys Lys Lys Lys Lys Val Arg Ser His Arg Asn Ser Leu Asp Thr Asn
1               5                   10                  15

Leu Ile Ser Met Leu Phe Gln Asn Leu Ser Glu Ser Pro Val Xaa Lys
            20                  25                  30

<210> SEQ ID NO 489
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Citrulline
<220> FEATURE:
<221> NAME/KEY: MOD_RES
<222> LOCATION: (29)..(29)
<223> OTHER INFORMATION: Azido-Lys attached to a hydrophobic molecule on
      the sidechain
```

<400> SEQUENCE: 489

Lys Lys Val Arg Lys Val Gly Thr Ala Trp Lys Gln Val Tyr Leu Phe
1               5                   10                  15

Leu Gly Val Pro Tyr Ala Ala Pro Ser Pro Val Xaa Lys
            20                  25

<210> SEQ ID NO 490
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Citrulline
<220> FEATURE:
<221> NAME/KEY: MOD_RES
<222> LOCATION: (29)..(29)
<223> OTHER INFORMATION: Azido-Lys attached to a hydrophobic molecule on
      the sidechain

<400> SEQUENCE: 490

Lys Lys Val Arg Ile Lys Ile Val Arg Leu Thr Thr Gly Ser Ala Tyr
1               5                   10                  15

Gln Phe Arg Val Cys Ala Glu Asn Ser Pro Val Xaa Lys
            20                  25

<210> SEQ ID NO 491
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Citrulline
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 491

Lys Lys Lys Lys Lys Val Arg Leu Gln Gly Asp Val Ala Phe Gly His
1               5                   10                  15

Ser Asn Leu Phe Ile Arg Ser Pro Arg Thr Leu Ser Pro Val Xaa Lys
            20                  25                  30

<210> SEQ ID NO 492
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 492

```
Lys Lys Lys Lys Lys Lys Lys Val Arg Ala Leu Glu Lys Ile Ala Phe
1               5                   10                  15

Leu Pro Phe Ala Tyr Leu Val Asp Gln Trp Arg Trp Gly Ser Pro Val
            20                  25                  30

Xaa Lys

<210> SEQ ID NO 493
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 493

Lys Lys Lys Lys Lys Lys Lys Val Arg Gly Ser Ser Ala Glu Glu
1               5                   10                  15

Ser His Leu Ser Cys Leu Asn Trp Ser Thr Leu Val Pro Leu Ser Pro
            20                  25                  30

Val Xaa Lys
        35

<210> SEQ ID NO 494
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 494

Lys Lys Lys Lys Lys Lys Lys Val Arg Met Leu Trp Leu Ala Leu
1               5                   10                  15

Gly Pro Phe Cys Gly Met Glu Asn Gln Val Leu Val Ile Arg Ser Pro
            20                  25                  30

Val Xaa Lys
        35

<210> SEQ ID NO 495
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Citrulline
```

```
<220> FEATURE:
<221> NAME/KEY: MOD_RES
<222> LOCATION: (33)..(33)
<223> OTHER INFORMATION: Azido-Lys attached to a hydrophobic molecule on
      the sidechain

<400> SEQUENCE: 495

Lys Lys Lys Lys Lys Lys Val Arg Thr Glu Arg Ile Tyr Ser Leu Phe
1               5                   10                  15

Asn Leu Ser Met Gly Lys Leu Glu Lys Met Gln Glu Ser Pro Val Xaa
            20                  25                  30

Lys

<210> SEQ ID NO 496
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 496

Lys Lys Lys Lys Lys Lys Val Arg Ala Leu Gly Leu Arg His Leu
1               5                   10                  15

Val Val Val Gly Asn His Asn Gln Val Val Gly Leu Val Ser Pro Val
            20                  25                  30

Xaa Lys

<210> SEQ ID NO 497
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 497

Lys Lys Lys Lys Lys Lys Lys Lys Val Arg Ala Glu Leu Ile Asn
1               5                   10                  15

Cys Gln Ala Asp Val Ser Ala Val Asp Asp His Gly Lys Ser Ala Ser
            20                  25                  30

Pro Val Xaa Lys
        35

<210> SEQ ID NO 498
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Citrulline
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 498

Lys Lys Lys Lys Lys Lys Lys Val Arg Met Ala Ala Ala Leu Leu
1               5                   10                  15

Leu Pro Leu Ala Phe Thr Leu Leu Ser Gly Gln Ser Pro Val Xaa Lys
            20                  25                  30

<210> SEQ ID NO 499
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Citrulline
<220> FEATURE:
<221> NAME/KEY: MOD_RES
<222> LOCATION: (29)..(29)
<223> OTHER INFORMATION: Azido-Lys attached to a hydrophobic molecule on
      the sidechain

<400> SEQUENCE: 499

Lys Lys Val Arg Leu Ser Gly Trp Trp Leu Leu Trp Lys Arg Cys Asn
1               5                   10                  15

Pro Leu Ala Thr Lys Val Lys Val Ser Pro Val Xaa Lys
            20                  25

<210> SEQ ID NO 500
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 500

Lys Lys Lys Lys Lys Lys Lys Val Arg Ser His Arg Asn Ser Leu Asp
1               5                   10                  15

Thr Asn Leu Ile Ser Met Leu Phe Gln Asn Leu Ser Glu Ser Pro Val
            20                  25                  30

Xaa Lys

<210> SEQ ID NO 501
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Citrulline
<220> FEATURE:
<221> NAME/KEY: MOD_RES
<222> LOCATION: (32)..(32)
<223> OTHER INFORMATION: Azido-Lys attached to a hydrophobic molecule on
      the sidechain

<400> SEQUENCE: 501

Lys Lys Lys Lys Lys Val Arg Lys Val Gly Thr Ala Trp Lys Gln Val
1               5                   10                  15

Tyr Leu Phe Leu Gly Val Pro Tyr Ala Ala Pro Ser Pro Val Xaa Lys
            20                  25                  30

<210> SEQ ID NO 502
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Citrulline
<220> FEATURE:
<221> NAME/KEY: MOD_RES
<222> LOCATION: (31)..(31)
<223> OTHER INFORMATION: Azido-Lys attached to a hydrophobic molecule on
      the sidechain

<400> SEQUENCE: 502

Lys Lys Lys Lys Val Arg Ile Lys Ile Val Arg Leu Thr Thr Gly Ser
1               5                   10                  15

Ala Tyr Gln Phe Arg Val Cys Ala Glu Asn Ser Pro Val Xaa Lys
            20                  25                  30

<210> SEQ ID NO 503
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 503

Lys Lys Lys Lys Val Arg Phe Val Val Lys Ala Tyr Leu Pro Val Asn
1               5                   10                  15

Glu Ser Phe Ala Phe Thr Ala Asp Leu Arg Ser Asn Thr Gly Gly Gln
            20                  25                  30

Ala Gly Ser Leu Val Xaa Lys
        35

<210> SEQ ID NO 504
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 504

Lys Lys Val Arg Thr Ala Lys Ser Val Met Cys Thr Tyr Ser Pro Pro
1               5                   10                  15

Leu Asp Lys Leu Phe Cys Gln Leu Ala Lys Thr Cys Pro Val Gln Gly
            20                  25                  30

Ser Leu Val Xaa Lys
        35

<210> SEQ ID NO 505
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 505

Lys Lys Val Arg Ala Asn Phe Glu Ser Gly Lys His Lys Tyr Arg Gln
1               5                   10                  15

Thr Ala Met Phe Thr Ala Thr Met Pro Pro Ala Val Glu Arg Leu Gly
            20                  25                  30

Ser Leu Val Xaa Lys
        35

<210> SEQ ID NO 506
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 506

Lys Lys Lys Lys Val Arg Val Val Asp Arg Asn Pro Gln Phe Leu Asp
1               5                   10                  15

Pro Val Leu Ala Tyr Leu Met Lys Gly Leu Cys Glu Lys Pro Leu Ala
```

```
                    20                  25                  30

Ser Gly Ser Leu Val Xaa Lys
            35

<210> SEQ ID NO 507
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys attached to a hydrophobic molecule on
      the sidechain

<400> SEQUENCE: 507

Lys Lys Lys Lys Lys Lys Lys Val Arg Asn Glu Val Ala Pro Leu Glu
1               5                   10                  15

Trp Leu Arg Tyr Phe Asp Lys Lys Glu Leu Glu Leu Met Leu Cys Gly
            20                  25                  30

Met Gln Glu Ile Gly Ser Leu Val Xaa Lys
            35                  40

<210> SEQ ID NO 508
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Citrulline
<220> FEATURE:
<221> NAME/KEY: MOD_RES
<222> LOCATION: (41)..(41)
<223> OTHER INFORMATION: Azido-Lys attached to a hydrophobic molecule on
      the sidechain

<400> SEQUENCE: 508

Lys Lys Lys Lys Lys Lys Val Arg Ser Ser Pro Asp Glu Val Ala Leu
1               5                   10                  15

Val Glu Gly Val Gln Ser Leu Gly Phe Thr Tyr Leu Arg Leu Lys Asp
            20                  25                  30

Asn Tyr Met Gly Ser Leu Val Xaa Lys
            35                  40

<210> SEQ ID NO 509
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
``` the sidechain

<400> SEQUENCE: 509

Lys Lys Val Arg Pro Lys Pro Asp Phe Ser Gln Leu Gln Arg Asn Ile
1               5                   10                  15

Leu Pro Ser Asn Pro Arg Val Thr Arg Phe His Ile Asn Trp Asp Gly
            20                  25                  30

Ser Leu Val Xaa Lys
        35

<210> SEQ ID NO 510
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 510

Lys Lys Lys Lys Val Arg Leu Ile Leu Ile Ser Thr Asn Gly Ser Phe
1               5                   10                  15

Ile Arg Leu Leu Asp Ala Phe Lys Gly Val Val Met His Thr Phe Gly
            20                  25                  30

Gly Gly Ser Leu Val Xaa Lys
        35

<210> SEQ ID NO 511
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Citrulline
<220> FEATURE:
<221> NAME/KEY: MOD_RES
<222> LOCATION: (41)..(41)
<223> OTHER INFORMATION: Azido-Lys attached to a hydrophobic molecule on
      the sidechain

<400> SEQUENCE: 511

Lys Lys Lys Lys Lys Lys Val Arg Ser Thr Ala Asn Tyr Asn Thr Ser
1               5                   10                  15

His Leu Asn Asn Asp Val Trp Gln Ile Phe Glu Asn Pro Val Asp Trp
            20                  25                  30

Lys Glu Lys Gly Ser Leu Val Xaa Lys
        35                  40

<210> SEQ ID NO 512
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 512

Lys Lys Val Arg Arg Val Asp Gln Lys Thr Leu His Asn Leu Leu Arg
1               5                   10                  15

Lys Val Val Pro Ser Phe Ser Ala Glu Ile Glu Arg Leu Asn Gln Gly
            20                  25                  30

Ser Leu Val Xaa Lys
        35

<210> SEQ ID NO 513
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 513

Lys Lys Lys Lys Val Arg Ile Pro Ser Gly Thr Thr Ile Leu Asn Cys
1               5                   10                  15

Phe His Asp Val Leu Ser Gly Lys Leu Ser Gly Gly Ser Pro Gly Val
            20                  25                  30

Pro Gly Ser Leu Val Xaa Lys
        35

<210> SEQ ID NO 514
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 514

Lys Lys Lys Val Arg Asp Ser Gly Ser Pro Phe Pro Ala Ala Val Ile
1               5                   10                  15

Leu Arg Asp Ala Leu His Met Ala Arg Gly Leu Lys Tyr Leu His Gln
            20                  25                  30

Gly Ser Leu Val Xaa Lys
        35
```

```
<210> SEQ ID NO 515
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 515

Lys Lys Val Arg His Leu Thr Gln Gln Leu Asp Thr Tyr Ile Leu Lys
1               5                   10                  15

Asn Val Val Ala Phe Ser Arg Thr Asp Lys Tyr Arg Gln Leu Pro Gly
            20                  25                  30

Ser Leu Val Xaa Lys
        35

<210> SEQ ID NO 516
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 516

Lys Lys Lys Lys Val Arg Cys Gly Thr Ala Phe Phe Ile Asn Phe Ile
1               5                   10                  15

Ala Ile Tyr His His Ala Ser Arg Ala Ile Pro Phe Gly Thr Met Val
            20                  25                  30

Ala Gly Ser Leu Val Xaa Lys
        35

<210> SEQ ID NO 517
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 517

Lys Lys Lys Lys Val Arg Gly Pro Asp Gly Leu Ala Leu Pro Asn Asn
```

```
                1               5                  10                 15
Tyr Cys Asp Val Cys Leu Gly Asp Ser Lys Ile Asn Lys Lys Thr Gly
                        20                  25                 30
Gln Gly Ser Leu Val Xaa Lys
            35
```

<210> SEQ ID NO 518
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 518

```
Lys Lys Val Arg Glu Leu Ile Asn Phe Lys Arg Lys Arg Val Ala Ala
1               5                   10                  15
Phe Gln Lys Asn Leu Ile Glu Met Ser Glu Leu Glu Ile Lys His Gly
            20                  25                  30
Ser Leu Val Xaa Lys
            35
```

<210> SEQ ID NO 519
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 519

```
Lys Lys Lys Val Arg Asn Arg Glu Lys Met Lys Gly Glu Leu Gly Met
1               5                   10                  15
Met Leu Ile Leu Gln Asn Val Ile Gln Lys Thr Thr Thr Pro Gly Glu
            20                  25                  30
Gly Ser Leu Val Xaa Lys
            35
```

<210> SEQ ID NO 520
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:

```
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 520
```

Lys Lys Lys Val Arg Glu Phe Lys His Ile Lys Ala Phe Asp Arg Thr
1               5                   10                  15

Phe Ala Asn Asn Pro Gly Pro Met Val Val Phe Ala Thr Pro Gly Met
            20                  25                  30

Gly Ser Leu Val Xaa Lys
        35

```
<210> SEQ ID NO 521
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Citrulline
<220> FEATURE:
<221> NAME/KEY: MOD_RES
<222> LOCATION: (43)..(43)
<223> OTHER INFORMATION: Azido-Lys attached to a hydrophobic molecule on
      the sidechain

<400> SEQUENCE: 521
```

Lys Lys Lys Lys Lys Lys Lys Val Arg Asn His Ser Gly Leu Val
1               5                   10                  15

Thr Phe Gln Ala Phe Ile Asp Val Met Ser Arg Glu Thr Thr Asp Thr
            20                  25                  30

Asp Thr Ala Asp Gln Gly Ser Leu Val Xaa Lys
        35                  40

```
<210> SEQ ID NO 522
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 522
```

Asp Val Arg Gly Arg Gly His Leu Leu Gly Arg Leu Ala Ala Ile Val
1               5                   10                  15

Gly Lys Gln Val Leu Leu Gly Arg Lys Val Val Val Arg Gly Ser
            20                  25                  30

Leu Val Xaa Lys
        35

```
<210> SEQ ID NO 523
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 523

Lys Lys Lys Val Arg Glu Lys Phe Ser Met Asp His Lys Thr Gly Thr
1               5                   10                  15

Ile Ala Met Gln Asn Thr Thr Gln Leu Arg Ser Arg Tyr Glu Leu Thr
            20                  25                  30

Gly Ser Leu Val Xaa Lys
        35

<210> SEQ ID NO 524
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 524

Lys Lys Lys Lys Lys Val Arg Ser Gly Cys Tyr Phe Met Val Ala Val
1               5                   10                  15

Ala His Val Ala Ala Phe Leu Leu Glu Asp Arg Ala Val Cys Val Glu
            20                  25                  30

Arg Phe Gly Ser Leu Val Xaa Lys
        35                  40

<210> SEQ ID NO 525
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 525

Lys Lys Lys Lys Val Arg Arg Glu Gly Val Glu Leu Cys Pro Gly Asn
1               5                   10                  15

Lys Tyr Glu Met Arg Arg His Gly Thr Thr His Ser Leu Val Ile His
            20                  25                  30
```

```
Asp Ser Pro Val Xaa Lys
        35
```

<210> SEQ ID NO 526
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Citrulline
<220> FEATURE:
<221> NAME/KEY: MOD_RES
<222> LOCATION: (44)..(44)
<223> OTHER INFORMATION: Azido-Lys attached to a hydrophobic molecule on
      the sidechain

<400> SEQUENCE: 526

```
Lys Lys Lys Lys Lys Lys Lys Lys Lys Lys Val Arg Pro Ser Lys Pro
1               5                   10                  15

Ser Phe Gln Glu Phe Val Asp Trp Glu Asn Val Ser Pro Glu Leu Asn
                20                  25                  30

Ser Thr Asp Gln Pro Phe Leu Ser Pro Val Xaa Lys
        35                  40
```

<210> SEQ ID NO 527
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 527

```
Lys Lys Lys Lys Val Arg Thr Ala Lys Ser Val Met Cys Thr Tyr Ser
1               5                   10                  15

Pro Pro Leu Asp Lys Leu Phe Cys Gln Leu Ala Lys Thr Cys Pro Val
                20                  25                  30

Gln Ser Pro Val Xaa Lys
        35
```

<210> SEQ ID NO 528
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys attached to a hydrophobic molecule on
      the sidechain

```
<400> SEQUENCE: 528

Lys Lys Lys Lys Lys Lys Lys Val Arg Ser Ser Pro Asp Glu Val
1               5                   10                  15

Ala Leu Val Glu Gly Val Gln Ser Leu Gly Phe Thr Tyr Leu Arg Leu
            20                  25                  30

Lys Asp Asn Tyr Met Ser Pro Val Xaa Lys
            35                  40

<210> SEQ ID NO 529
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 529

Lys Lys Lys Lys Lys Lys Val Arg Ile Pro Ser Gly Thr Thr Ile Leu
1               5                   10                  15

Asn Cys Phe His Asp Val Leu Ser Gly Lys Leu Ser Gly Gly Ser Pro
            20                  25                  30

Gly Val Pro Ser Pro Val Xaa Lys
            35                  40

<210> SEQ ID NO 530
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 530

Lys Lys Lys Lys Lys Val Arg Asp Ser Gly Ser Pro Phe Pro Ala Ala
1               5                   10                  15

Val Ile Leu Arg Asp Ala Leu His Met Ala Arg Gly Leu Lys Tyr Leu
            20                  25                  30

His Gln Ser Pro Val Xaa Lys
            35

<210> SEQ ID NO 531
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 531

Lys Lys Lys Lys Lys Val Arg Asn Arg Glu Lys Met Lys Gly Glu Leu
1               5                   10                  15

Gly Met Met Leu Ile Leu Gln Asn Val Ile Gln Lys Thr Thr Thr Pro
            20                  25                  30

Gly Glu Ser Pro Val Xaa Lys
        35

<210> SEQ ID NO 532
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 532

Lys Lys Lys Lys Lys Val Arg Glu Lys Phe Ser Met Asp His Lys Thr
1               5                   10                  15

Gly Thr Ile Ala Met Gln Asn Thr Thr Gln Leu Arg Ser Arg Tyr Glu
            20                  25                  30

Leu Thr Ser Pro Val Xaa Lys
        35

<210> SEQ ID NO 533
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 533

Lys Lys Lys Lys Lys Lys Val Arg Arg Glu Gly Val Glu Leu Cys Pro
1               5                   10                  15

Gly Asn Lys Tyr Glu Met Arg Arg His Gly Thr Thr His Ser Leu Val
            20                  25                  30

Ile His Asp Ser Pro Val Xaa Lys
        35                  40

<210> SEQ ID NO 534
```

```
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 534

Lys Lys Lys Lys Lys Lys Lys Val Arg Tyr Met Arg Thr Gly Glu Gly
1               5                   10                  15

Phe Leu Cys Val Phe Ala Ile Asn Asn Thr Lys Ser Phe Glu Asp Ile
            20                  25                  30

His His Ser Pro Val Xaa Lys
        35

<210> SEQ ID NO 535
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 535

Lys Lys Lys Lys Lys Val Arg Asp Thr Lys Gln Ala Gln Glu Leu Ala
1               5                   10                  15

Arg Ser Tyr Gly Ile Pro Phe Ile Glu Thr Ser Ala Lys Thr Arg Gln
            20                  25                  30

Ser Pro Val Xaa Lys
        35

<210> SEQ ID NO 536
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 536

Lys Lys Lys Val Arg Gln Arg Val Glu Asp Ala Phe Tyr Thr Leu Val
1               5                   10                  15
```

-continued

```
Arg Glu Ile Arg Gln Tyr Arg Leu Lys Lys Ile Ser Lys Glu Ser Pro
            20                  25                  30

Val Xaa Lys
        35

<210> SEQ ID NO 537
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 537

Lys Lys Lys Lys Lys Lys Lys Val Arg Met Thr Glu Tyr Lys Leu Val
1               5                   10                  15

Val Val Gly Ala Asp Gly Val Gly Lys Ser Ala Leu Thr Ile Gln Leu
            20                  25                  30

Ile Gln Ser Pro Val Xaa Lys
        35

<210> SEQ ID NO 538
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 538

Lys Lys Lys Lys Val Arg Gln Ala Cys Ala His Phe Phe Ser Leu Ile
1               5                   10                  15

Ser Lys Ala Asn Val Asp Val Leu Pro Arg Arg Ser Leu Glu Arg Ser
            20                  25                  30

Pro Val Xaa Lys
        35

<210> SEQ ID NO 539
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
```

```
<223> OTHER INFORMATION: Azido-Lys attached to a hydrophobic molecule on
      the sidechain

<400> SEQUENCE: 539

Lys Lys Lys Lys Lys Val Arg Tyr Gln Lys Ala Cys Ser Ala Phe Gln
1               5                   10                  15

Asn Val Ser Gly Leu Glu Tyr Phe Glu Lys Ile Lys Thr Phe Leu Gly
            20                  25                  30

Ser Pro Val Xaa Lys
        35

<210> SEQ ID NO 540
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 540

Lys Lys Lys Lys Lys Lys Val Arg Leu Ala Arg Gln Met Asp Leu Val
1               5                   10                  15

Asn Glu Ile Pro Phe Thr Tyr Glu Gln Leu Ser Ile Phe Lys His Lys
            20                  25                  30

Leu Ser Pro Val Xaa Lys
        35

<210> SEQ ID NO 541
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 541

Lys Lys Lys Lys Lys Lys Val Arg Arg Leu Gly Leu Gly Leu Gln Gly
1               5                   10                  15

Gly Ile Pro Asn Gly Tyr Leu Val Leu Asp Phe Asn Val Arg Glu Ala
            20                  25                  30

Ser Pro Val Xaa Lys
        35

<210> SEQ ID NO 542
<211> LENGTH: 34
<212> TYPE: PRT
<213> ORGANISM: Artificial Sequence
<220> FEATURE:
<223> OTHER INFORMATION: Description of Artificial Sequence: Synthetic
```

```
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain

<400> SEQUENCE: 542

Lys Lys Val Arg Leu Lys Val Ser Lys Gly Gln Lys Met Asn Ala Gln
1               5                   10                  15

Ala Ile Ala Leu Val Ala Cys Tyr Leu Arg Gly Gly Gly Ser Pro Val
            20                  25                  30

Xaa Lys

<210> SEQ ID NO 543
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 543

Lys Lys Lys Lys Lys Val Arg Leu Arg Ala Leu Ser Gln His Asn Val
1               5                   10                  15

Ser Met Asp Ile Ala Thr Phe Lys Arg Leu Gln Val Asp Ser Leu Val
            20                  25                  30

Ser Pro Val Xaa Lys
        35

<210> SEQ ID NO 544
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Citrulline
<220> FEATURE:
<221> NAME/KEY: MOD_RES
<222> LOCATION: (38)..(38)
<223> OTHER INFORMATION: Azido-Lys attached to a hydrophobic molecule on
      the sidechain

<400> SEQUENCE: 544

Lys Lys Lys Lys Lys Lys Val Arg Leu Gly Ser Cys Gly Ser Pro Ile
1               5                   10                  15

Cys Ser Arg Ser Phe Leu Leu Leu Leu Ser Leu Gly Trp Ile Pro
            20                  25                  30

Arg Ser Pro Val Xaa Lys
        35
```

<210> SEQ ID NO 545
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys attached to a hydrophobic molecule on
      the sidechain

<400> SEQUENCE: 545

Lys Lys Lys Lys Lys Lys Lys Lys Val Arg Leu Ser Glu Asp Val Lys
1               5                   10                  15

Ser Tyr Tyr Thr Val His Leu Leu Gln Leu Glu Asn Ile Asn Thr Gly
            20                  25                  30

Glu Thr Arg Thr Ile Ser Pro Val Xaa Lys
        35                  40

<210> SEQ ID NO 546
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 546

Lys Lys Lys Lys Lys Lys Lys Val Arg Gly Val Pro Glu Ser Pro Ala
1               5                   10                  15

Ser Phe Leu Asn Phe Leu Phe Lys Val Arg Glu Ser Gly Cys Leu Thr
            20                  25                  30

Pro Asp Ser Pro Val Xaa Lys
        35

<210> SEQ ID NO 547
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 547

Lys Lys Lys Lys Lys Lys Lys Lys Lys Val Arg Asn Asp Tyr Ile Asn

```
                1               5                  10                 15
Ala Ser Leu Val Asp Ile Glu Glu Ala Gln Arg Ser Tyr Ile Leu Thr
                20                 25                 30

Gln Gly Pro Ser Pro Val Xaa Lys
        35                  40
```

<210> SEQ ID NO 548
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Citrulline
<220> FEATURE:
<221> NAME/KEY: MOD_RES
<222> LOCATION: (36)..(36)
<223> OTHER INFORMATION: Azido-Lys attached to a hydrophobic molecule on
      the sidechain

<400> SEQUENCE: 548

```
Lys Lys Lys Lys Val Arg Asp Val Asn Val Lys Gln Leu Leu Leu Asn
1               5                   10                  15

Met Arg Lys Tyr Arg Met Gly Leu Ile Gln Thr Pro Asp Gln Leu Ser
                20                  25                  30

Pro Val Xaa Lys
        35
```

<210> SEQ ID NO 549
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 549

```
Lys Lys Lys Ser Leu Val Arg Ala Ser Met Thr Asn Met Glu Leu Met
1               5                   10                  15

Ser Leu Val Arg Lys
            20
```

<210> SEQ ID NO 550
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 550

```
Lys Lys Lys Ser Leu Val Arg Ala Ser Met Thr Asn Met Glu Leu Met
1               5                   10                  15

Ser Leu Val Arg Lys
```

<210> SEQ ID NO 551
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 551

Arg Arg Arg Ser Leu Val Arg Ala Ser Met Thr Asn Met Glu Leu Met
1               5                   10                  15

Ser Leu Val Arg Lys
            20

<210> SEQ ID NO 552
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 552

Lys Lys Lys Ser Leu Val Arg Ala Ser Met Thr Asn Met Glu Leu Met
1               5                   10                  15

Ser Leu Val Arg Lys
            20

<210> SEQ ID NO 553
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 553

Asp Asp Asp Asp Asp Asp Asp Asp Asp Ser Leu Val Arg Ala Ser Met
1               5                   10                  15

Thr Asn Met Glu Leu Met Ser Leu Val Arg Lys
            20                  25

<210> SEQ ID NO 554
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)

<223> OTHER INFORMATION: Azido-Lys attached to a hydrophobic molecule on
      the sidechain

<400> SEQUENCE: 554

Lys Lys Lys Lys Ser Leu Val Arg Ala Ser Met Thr Asn Met Glu Leu
1               5                   10                  15

Met Ser Leu Val Arg Lys
            20

<210> SEQ ID NO 555
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (45)..(45)
<223> OTHER INFORMATION: Citrulline
<220> FEATURE:
<221> NAME/KEY: MOD_RES
<222> LOCATION: (46)..(46)
<223> OTHER INFORMATION: Azido-Lys attached to a hydrophobic molecule on
      the sidechain

<400> SEQUENCE: 555

Asp Asp Asp Asp Asp Asp Asp Asp Asp Asp Asp Asp Gly Ile Pro
1               5                   10                  15

Val His Leu Glu Leu Ala Ser Met Thr Asn Met Glu Leu Met Ser Ser
                20                  25                  30

Ile Val His Gln Gln Val Phe Pro Thr Ser Pro Val Xaa Lys
            35                  40                  45

<210> SEQ ID NO 556
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Citrulline
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 556

Ala Ser Met Thr Asn Met Glu Leu Met Gly Ser Pro Val Xaa Lys
1               5                   10                  15

<210> SEQ ID NO 557
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 557

Glu Lys Ser Leu Val Arg Ala Ser Met Thr Asn Met Glu Leu Met Ser
1               5                   10                  15

Ser Gly Gly Glu Leu Val Arg Lys
            20

<210> SEQ ID NO 558
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 558

Glu Lys Ser Leu Val Arg Ala Ser Met Thr Asn Met Glu Leu Met Ser
1               5                   10                  15

Ser Gly Gly Glu Leu Val Arg Lys
            20

<210> SEQ ID NO 559
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Azido-Lys attached to a hydrophobic molecule on
      the sidechain

<400> SEQUENCE: 559

Glu Lys Ser Leu Val Arg Ala Ser Met Thr Asn Met Glu Leu Met Ser
1               5                   10                  15

Ser Gly Gly Glu Leu Val Arg Lys
            20

<210> SEQ ID NO 560
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 560

Lys Ser Lys Ser Lys Leu Val Arg Ala Ser Met Thr Asn Met Glu Leu
1               5                   10                  15

Met Ser Ser Gly Gly Glu Leu Val Arg Lys
            20                  25

<210> SEQ ID NO 561
<211> LENGTH: 26
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 561

Lys Ser Lys Ser Lys Leu Val Arg Ala Ser Met Thr Asn Met Glu Leu
1               5                   10                  15

Met Ser Ser Gly Gly Glu Leu Val Arg Lys
            20                  25

<210> SEQ ID NO 562
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Azido-Lys attached to a hydrophobic molecule on
      the sidechain

<400> SEQUENCE: 562

Lys Ser Lys Ser Lys Leu Val Arg Ala Ser Met Thr Asn Met Glu Leu
1               5                   10                  15

Met Ser Ser Gly Gly Glu Leu Val Arg Lys
            20                  25

<210> SEQ ID NO 563
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: Azido-Lys attached to a hydrophobic molecule on
      the sidechain

<400> SEQUENCE: 563

Gly Ile Pro Val His Leu Glu Leu Ala Ser Met Thr Asn Met Glu Leu
1               5                   10                  15

Met Ser Ser Ile Val His Gln Gln Val Phe Pro Thr Lys
            20                  25

<210> SEQ ID NO 564
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 564

Asp Phe Thr Gly Ser Asn Gly Asp Pro Ser Ser Pro Tyr Ser Leu His
1               5                   10                  15

Tyr Leu Ser Pro Thr Gly Val Asn Glu Tyr Lys
```

```
                    20                  25

<210> SEQ ID NO 565
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 565

Lys Ala Arg Asp Glu Thr Ala Ala Leu Leu Asn Ser Ala Val Leu Gly
1               5                   10                  15

Ala Ala Pro Leu Phe Val Pro Pro Ala Asp Lys
            20                  25

<210> SEQ ID NO 566
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Citrulline
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 566

Lys Lys Lys Lys Ser Leu Val Arg Met Ala Pro Ile Asp His Thr Thr
1               5                   10                  15

Met Ser Pro Val Xaa Lys
            20

<210> SEQ ID NO 567
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Citrulline
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 567

Lys Lys Lys Lys Lys Ser Leu Val Arg Ala Ser Met Thr Asn Met Glu
1               5                   10                  15

Leu Met Ser Pro Val Xaa Lys
            20

<210> SEQ ID NO 568
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Citrulline
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 568

Lys Lys Lys Lys Ser Leu Val Arg Ser Ser Pro Tyr Ser Leu His Tyr
1               5                   10                  15

Leu Ser Pro Val Xaa Lys
            20

<210> SEQ ID NO 569
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Citrulline
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 569

Lys Lys Lys Lys Ser Leu Val Arg Ser Ile Ile Val Phe Asn Leu Leu
1               5                   10                  15

Ser Pro Val Xaa Lys
            20

<210> SEQ ID NO 570
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Citrulline
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 570

Lys Lys Lys Lys Ser Leu Val Arg Ala Ala Leu Leu Asn Ser Ala Val
1               5                   10                  15

Leu Ser Pro Val Xaa Lys
            20

<210> SEQ ID NO 571
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Citrulline
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 571

Lys Lys Lys Ser Leu Val Arg Ser Ser Val Leu Phe Glu Tyr Met Ser
1               5                   10                  15

Pro Val Xaa Lys
            20

<210> SEQ ID NO 572
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Citrulline
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 572

Lys Lys Lys Lys Lys Ser Leu Val Arg Ala Gln Leu Ala Asn Asp Val
1               5                   10                  15

Val Leu Ser Pro Val Xaa Lys
            20

<210> SEQ ID NO 573
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 573

Lys Lys Lys Lys Lys Lys Lys Lys Lys Val Arg Asp Ile Asp Pro
1               5                   10                  15

Ser Ser Ser Val Leu Phe Glu Tyr Met Glu Lys Pro Asp Phe Ser Leu
            20                  25                  30

Phe Ser Pro Ser Pro Val Xaa Lys
        35                  40

<210> SEQ ID NO 574
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Azido-Lys attached to a hydrophobic molecule on
      the sidechain

<400> SEQUENCE: 574

Lys Lys Pro Leu Arg Thr Ala Pro Asp Asn Leu Gly Tyr Met Ser Leu
1               5                   10                  15

Val Arg Lys

<210> SEQ ID NO 575
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Citrulline
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 575

Lys Lys Lys Ser Leu Val Arg Arg Ala His Tyr Asn Ile Val Thr Phe
1               5                   10                  15

Ser Pro Val Xaa Lys
            20

<210> SEQ ID NO 576
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Citrulline
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 576

Lys Lys Lys Arg Arg Ala His Tyr Asn Ile Val Thr Phe Xaa Lys
1               5                   10                  15

<210> SEQ ID NO 577
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
```

```
<223> OTHER INFORMATION: Citrulline
<220> FEATURE:
<221> NAME/KEY: MOD_RES
<222> LOCATION: (37)..(37)
<223> OTHER INFORMATION: Azido-Lys attached to a hydrophobic molecule on
      the sidechain

<400> SEQUENCE: 577

Lys Lys Lys Lys Lys Val Arg Cys Lys Gln Gln Leu Leu Arg Arg Glu
1               5                   10                  15

Val Tyr Asp Phe Ala Phe Arg Asp Leu Cys Ile Val Tyr Arg Asp Gly
            20                  25                  30

Ser Pro Val Xaa Lys
        35

<210> SEQ ID NO 578
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Citrulline
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 578

Lys Lys Lys Lys Lys Lys Ser Leu Val Arg Glu Val Tyr Asp Phe Ala
1               5                   10                  15

Phe Arg Asp Leu Ser Pro Val Xaa Lys
            20                  25

<210> SEQ ID NO 579
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 579

Lys Lys Lys Lys Lys Lys Lys Lys Val Arg Gln Gly Thr Asp Val Val
1               5                   10                  15

Ile Ala Ile Phe Ile Ile Leu Ala Met Ser Phe Val Pro Ala Ser Phe
            20                  25                  30

Val Val Phe Ser Pro Val Xaa Lys
        35                  40

<210> SEQ ID NO 580
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 580

Lys Lys Lys Lys Lys Lys Lys Val Arg Gly Phe Gln Ala Leu Ser Glu
1               5                   10                  15

Gly Cys Thr Pro Tyr Asp Ile Asn Gln Met Leu Asn Cys Val Gly Asp
            20                  25                  30

His Gln Ser Pro Val Xaa Lys
        35

<210> SEQ ID NO 581
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Azido-Lys attached to a hydrophobic molecule on
      the sidechain

<400> SEQUENCE: 581

Lys Lys Pro Leu Arg Thr Ala Pro Asp Asn Leu Gly Tyr Met Ser Leu
1               5                   10                  15

Val Arg Lys

<210> SEQ ID NO 582
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Azido-Lys attached to a hydrophobic molecule on
      the sidechain

<400> SEQUENCE: 582

Lys Ser Lys Lys Pro Leu Arg Ser Val Tyr Asp Phe Phe Val Trp Leu
1               5                   10                  15

Ser Leu Val Arg Lys
            20

<210> SEQ ID NO 583
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: Azido-Lys attached to a hydrophobic molecule on
      the sidechain
```

```
<400> SEQUENCE: 583

Lys Pro Leu Arg Ala Val Gly Ala Leu Glu Gly Pro Arg Asn Gln Asp
1               5                   10                  15

Trp Leu Gly Val Pro Arg Gln Leu Ser Leu Val Arg Lys
            20                  25

<210> SEQ ID NO 584
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Citrulline
<220> FEATURE:
<221> NAME/KEY: MOD_RES
<222> LOCATION: (39)..(39)
<223> OTHER INFORMATION: Azido-Lys attached to a hydrophobic molecule on
      the sidechain

<400> SEQUENCE: 584

Lys Lys Lys Lys Lys Lys Lys Val Arg Tyr Met Arg Thr Gly Glu Gly
1               5                   10                  15

Phe Leu Cys Val Phe Ala Ile Asn Asn Thr Lys Ser Phe Glu Asp Ile
            20                  25                  30

His His Ser Pro Val Xaa Lys
        35

<210> SEQ ID NO 585
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Citrulline
<220> FEATURE:
<221> NAME/KEY: MOD_RES
<222> LOCATION: (40)..(40)
<223> OTHER INFORMATION: Azido-Lys attached to a hydrophobic molecule on
      the sidechain

<400> SEQUENCE: 585

Lys Lys Lys Lys Lys Lys Lys Lys Lys Val Arg Val Ser Gly Leu Glu
1               5                   10                  15

Gln Leu Glu Ser Ile Ile Asn Phe Glu Lys Leu Thr Glu Trp Thr Ser
            20                  25                  30

Ser Asn Val Ser Pro Val Xaa Lys
        35                  40

<210> SEQ ID NO 586
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
``` the sidechain

<400> SEQUENCE: 586

Ala Gln Leu Ala Asn Asp Val Val Leu Gln Ser Leu Val Arg Lys
1               5                   10                  15

<210> SEQ ID NO 587
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (6-N,6-N,6-N)trimethyllysine
<220> FEATURE:
<221> NAME/KEY: MOD_RES
<222> LOCATION: (2)..(2)
<223> OTHER INFORMATION: (6-N,6-N,6-N)trimethyllysine
<220> FEATURE:
<221> NAME/KEY: MOD_RES
<222> LOCATION: (3)..(3)
<223> OTHER INFORMATION: (6-N,6-N,6-N)trimethyllysine
<220> FEATURE:
<221> NAME/KEY: MOD_RES
<222> LOCATION: (4)..(4)
<223> OTHER INFORMATION: (6-N,6-N,6-N)trimethyllysine
<220> FEATURE:
<221> NAME/KEY: MOD_RES
<222> LOCATION: (19)..(19)
<223> OTHER INFORMATION: Citrulline
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 587

Lys Lys Lys Lys Val Arg Ala Gln Leu Ala Asn Asp Val Val Leu Ser
1               5                   10                  15

Pro Val Xaa Lys
            20

<210> SEQ ID NO 588
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 588

Ser Pro Glu Arg Asn Asp Trp Glu Pro Leu Ser Leu Val Arg Lys
1               5                   10                  15

<210> SEQ ID NO 589
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: Phosphoserine
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (21)..(21)
<223> OTHER INFORMATION: Citrulline
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 589

Ser Ser Pro Leu Xaa Ser Pro Glu Arg Asn Asp Trp Glu Pro Leu Gly
1               5                   10                  15

Gly Ser Pro Leu Xaa Lys
            20

<210> SEQ ID NO 590
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phosphoserine
<220> FEATURE:
<221> NAME/KEY: MOD_RES
<222> LOCATION: (2)..(2)
<223> OTHER INFORMATION: Phosphoserine
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (21)..(21)
<223> OTHER INFORMATION: Citrulline
<220> FEATURE:
<221> NAME/KEY: MOD_RES
<222> LOCATION: (22)..(22)
<223> OTHER INFORMATION: Azido-Lys attached to a hydrophobic molecule on
      the sidechain

<400> SEQUENCE: 590

Ser Ser Pro Leu Xaa Ser Pro Glu Arg Asn Asp Trp Glu Pro Leu Gly
1               5                   10                  15

Gly Ser Pro Leu Xaa Lys
            20

<210> SEQ ID NO 591
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phosphoserine
<220> FEATURE:
<221> NAME/KEY: MOD_RES
<222> LOCATION: (2)..(2)
<223> OTHER INFORMATION: Phosphoserine
<220> FEATURE:
<221> NAME/KEY: MOD_RES
```

```
<222> LOCATION: (3)..(3)
<223> OTHER INFORMATION: Phosphoserine
<220> FEATURE:
<221> NAME/KEY: MOD_RES
<222> LOCATION: (6)..(6)
<223> OTHER INFORMATION: Citrulline
<220> FEATURE:
<221> NAME/KEY: MOD_RES
<222> LOCATION: (22)..(22)
<223> OTHER INFORMATION: Citrulline
<220> FEATURE:
<221> NAME/KEY: MOD_RES
<222> LOCATION: (23)..(23)
<223> OTHER INFORMATION: Azido-Lys attached to a hydrophobic molecule on
      the sidechain

<400> SEQUENCE: 591

Ser Ser Ser Pro Leu Xaa Ser Pro Glu Arg Asn Asp Trp Glu Pro Leu
1               5                   10                  15

Gly Gly Ser Pro Leu Xaa Lys
            20

<210> SEQ ID NO 592
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 592

Ala Ser Met Thr Asn Met Glu Leu Met Ser Ser Leu Val Arg Lys
1               5                   10                  15

<210> SEQ ID NO 593
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Azido-Lys attached to a hydrophobic molecule on
      the sidechain

<400> SEQUENCE: 593

Ala Ser Met Thr Asn Met Glu Leu Met Ser Ser Leu Val Arg Lys
1               5                   10                  15

<210> SEQ ID NO 594
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Citrulline
<220> FEATURE:
<221> NAME/KEY: MOD_RES
<222> LOCATION: (34)..(34)
<223> OTHER INFORMATION: Azido-Lys attached to a hydrophobic molecule on
      the sidechain
```

<400> SEQUENCE: 594

Gly Ile Pro Val His Leu Glu Leu Ala Ser Met Thr Asn Met Glu Leu
1               5                   10                  15

Met Ser Ser Ile Val His Gln Gln Val Phe Pro Thr Gly Ser Pro Val
            20                  25                  30

Xaa Lys

<210> SEQ ID NO 595
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys attached to a hydrophobic molecule on
      the sidechain

<400> SEQUENCE: 595

Lys Lys Lys Lys Lys Lys Val Arg Gly Ile Pro Val His Leu Glu Leu
1               5                   10                  15

Ala Ser Met Thr Asn Met Glu Leu Met Ser Ser Ile Val His Gln Gln
            20                  25                  30

Val Phe Pro Thr Gly Ser Gly Val Xaa Lys
            35                  40

<210> SEQ ID NO 596
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Citrulline
<220> FEATURE:
<221> NAME/KEY: MOD_RES
<222> LOCATION: (44)..(44)
<223> OTHER INFORMATION: Azido-Lys attached to a hydrophobic molecule on
      the sidechain

<400> SEQUENCE: 596

Lys Lys Lys Lys Lys Lys Lys Lys Val Arg Gly Ile Pro Val His
1               5                   10                  15

Leu Glu Leu Ala Ser Met Thr Asn Met Glu Leu Met Ser Ser Ile Val
            20                  25                  30

His Gln Gln Val Phe Pro Thr Ser Pro Val Xaa Lys
            35                  40

<210> SEQ ID NO 597
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: Tetra-alkyl ammonium Lys
<220> FEATURE:
<221> NAME/KEY: MOD_RES
<222> LOCATION: (2)..(2)
<223> OTHER INFORMATION: Tetra-alkyl ammonium Lys
<220> FEATURE:
<221> NAME/KEY: MOD_RES
<222> LOCATION: (3)..(3)
<223> OTHER INFORMATION: Tetra-alkyl ammonium Lys
<220> FEATURE:
<221> NAME/KEY: MOD_RES
<222> LOCATION: (4)..(4)
<223> OTHER INFORMATION: Tetra-alkyl ammonium Lys
<220> FEATURE:
<221> NAME/KEY: MOD_RES
<222> LOCATION: (19)..(19)
<223> OTHER INFORMATION: Citrulline
<220> FEATURE:
<221> NAME/KEY: MOD_RES
<222> LOCATION: (20)..(20)
<223> OTHER INFORMATION: Azido-Lys attached to a hydrophobic molecule on
      the sidechain

<400> SEQUENCE: 597

Lys Lys Lys Lys Val Arg Ala Gln Leu Ala Asn Asp Val Val Leu Ser
1               5                   10                  15

Pro Val Xaa Lys
            20

<210> SEQ ID NO 598
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phosphoserine
<220> FEATURE:
<221> NAME/KEY: MOD_RES
<222> LOCATION: (2)..(2)
<223> OTHER INFORMATION: Phosphoserine
<220> FEATURE:
<221> NAME/KEY: MOD_RES
<222> LOCATION: (3)..(3)
<223> OTHER INFORMATION: Phosphoserine
<220> FEATURE:
<221> NAME/KEY: MOD_RES
<222> LOCATION: (5)..(5)
<223> OTHER INFORMATION: Citrulline
<220> FEATURE:
<221> NAME/KEY: MOD_RES
<222> LOCATION: (18)..(18)
<223> OTHER INFORMATION: Citrulline
<220> FEATURE:
<221> NAME/KEY: MOD_RES
<222> LOCATION: (19)..(19)
<223> OTHER INFORMATION: Azido-Lys attached to a hydrophobic molecule on
      the sidechain

<400> SEQUENCE: 598

Ser Ser Ser Val Xaa Ala Gln Leu Ala Asn Asp Val Val Leu Ser Pro
1               5                   10                  15

Val Xaa Lys

<210> SEQ ID NO 599
<211> LENGTH: 44
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Citrulline
<220> FEATURE:
<221> NAME/KEY: MOD_RES
<222> LOCATION: (44)..(44)
<223> OTHER INFORMATION: Azido-Lys attached to a hydrophobic molecule on
      the sidechain

<400> SEQUENCE: 599

Lys Lys Lys Lys Lys Lys Lys Lys Lys Val Arg Gly Ile Pro Val His
1               5                   10                  15

Leu Glu Leu Ala Ser Met Thr Asn Met Glu Leu Met Ser Ser Ile Val
            20                  25                  30

His Gln Gln Val Phe Pro Thr Ser Pro Val Xaa Lys
            35                  40

<210> SEQ ID NO 600
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (4)..(4)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (7)..(7)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (10)..(10)
<223> OTHER INFORMATION: 1-(4-aminobutyl)-2-butyl-1H-imidazo[4,5-
      c]quinolin-4-amine Glu
<220> FEATURE:
<221> NAME/KEY: MOD_RES
<222> LOCATION: (13)..(13)
<223> OTHER INFORMATION: 1-(4-aminobutyl)-2-butyl-1H-imidazo[4,5-
      c]quinolin-4-amine Glu

<400> SEQUENCE: 600

Glu Gly Gly Glu Gly Gly Glu Gly Gly Glu Gly Gly Glu Gly Gly
1               5                   10                  15

<210> SEQ ID NO 601
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Citrulline
<220> FEATURE:
<221> NAME/KEY: MOD_RES
<222> LOCATION: (44)..(44)
<223> OTHER INFORMATION: Azido-Lys attached to a hydrophobic molecule on
      the sidechain
```

```
<400> SEQUENCE: 601

Lys Lys Lys Lys Lys Lys Lys Lys Val Arg Gly Ile Pro Val His
1               5                   10                  15

Leu Glu Leu Ala Ser Met Thr Asn Met Glu Leu Met Ser Ser Ile Val
            20                  25                  30

His Gln Gln Val Phe Pro Thr Ser Pro Val Xaa Lys
        35                  40

<210> SEQ ID NO 602
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 1-(4-aminobutyl)-2-butyl-1H-imidazo[4,5-
      c]quinolin-4-amine Lys
<220> FEATURE:
<221> NAME/KEY: MOD_RES
<222> LOCATION: (7)..(7)
<223> OTHER INFORMATION: 1-(4-aminobutyl)-2-butyl-1H-imidazo[4,5-
      c]quinolin-4-amine Lys
<220> FEATURE:
<221> NAME/KEY: MOD_RES
<222> LOCATION: (13)..(13)
<223> OTHER INFORMATION: 1-(4-aminobutyl)-2-butyl-1H-imidazo[4,5-
      c]quinolin-4-amine Lys
<220> FEATURE:
<221> NAME/KEY: MOD_RES
<222> LOCATION: (19)..(19)
<223> OTHER INFORMATION: 1-(4-aminobutyl)-2-butyl-1H-imidazo[4,5-
      c]quinolin-4-amine Lys
<220> FEATURE:
<221> NAME/KEY: MOD_RES
<222> LOCATION: (25)..(25)
<223> OTHER INFORMATION: 1-(4-aminobutyl)-2-butyl-1H-imidazo[4,5-
      c]quinolin-4-amine Lys

<400> SEQUENCE: 602

Lys Gly Trp Gly Trp Gly Lys Gly Trp Gly Trp Gly Lys Gly Trp Gly
1               5                   10                  15

Trp Gly Lys Gly Trp Gly Trp Gly Lys Gly Trp Gly Trp Gly
            20                  25                  30

<210> SEQ ID NO 603
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: Azido-Lys

<400> SEQUENCE: 603

Gly Ile Pro Val His Leu Glu Leu Ala Ser Met Thr Asn Met Glu Leu
1               5                   10                  15

Met Ser Ser Ile Val His Gln Gln Val Phe Pro Thr Lys
            20                  25

<210> SEQ ID NO 604
<211> LENGTH: 42
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Citrulline
<220> FEATURE:
<221> NAME/KEY: MOD_RES
<222> LOCATION: (42)..(42)
<223> OTHER INFORMATION: Azido-Lys

<400> SEQUENCE: 604

Lys Lys Lys Lys Lys Lys Val Arg Gly Ile Pro Val His Leu Glu Leu
1               5                   10                  15

Ala Ser Met Thr Asn Met Glu Leu Met Ser Ser Ile Val His Gln Gln
            20                  25                  30

Val Phe Pro Thr Gly Ser Gly Val Xaa Lys
            35                  40

<210> SEQ ID NO 605
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Citrulline
<220> FEATURE:
<221> NAME/KEY: MOD_RES
<222> LOCATION: (44)..(44)
<223> OTHER INFORMATION: Azido-Lys

<400> SEQUENCE: 605

Lys Lys Lys Lys Lys Lys Lys Lys Val Arg Gly Ile Pro Val His
1               5                   10                  15

Leu Glu Leu Ala Ser Met Thr Asn Met Glu Leu Met Ser Ser Ile Val
            20                  25                  30

His Gln Gln Val Phe Pro Thr Ser Pro Val Xaa Lys
            35                  40

<210> SEQ ID NO 606
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Citrulline
<220> FEATURE:
<221> NAME/KEY: MOD_RES
<222> LOCATION: (21)..(21)
<223> OTHER INFORMATION: Lys attached to a linker and a hydrophobic
      molecule on the sidechain

<400> SEQUENCE: 606

Arg Arg Arg Arg Arg Val Arg Ser Ser Pro Tyr Ser Leu His Tyr Leu
1               5                   10                  15

Ser Pro Val Xaa Lys Gly
            20
```

```
<210> SEQ ID NO 607
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg attached to a linker and a hydrophobic
      molecule on the sidechain
<220> FEATURE:
<221> NAME/KEY: MOD_RES
<222> LOCATION: (20)..(20)
<223> OTHER INFORMATION: Citrulline

<400> SEQUENCE: 607

Arg Arg Arg Arg Arg Val Arg Ser Ser Pro Tyr Ser Leu His Tyr Leu
1               5                   10                  15
Ser Pro Val Xaa
            20

<210> SEQ ID NO 608
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val attached to a linker and a hydrophobic
      molecule on the sidechain
<220> FEATURE:
<221> NAME/KEY: MOD_RES
<222> LOCATION: (2)..(2)
<223> OTHER INFORMATION: Citrulline

<400> SEQUENCE: 608

Val Xaa Ser Ser Pro Tyr Ser Leu His Tyr Leu Ser Pro Val Arg Arg
1               5                   10                  15
Arg Arg Arg Arg
            20

<210> SEQ ID NO 609
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Citrulline
<220> FEATURE:
<221> NAME/KEY: MOD_RES
<222> LOCATION: (21)..(21)
<223> OTHER INFORMATION: Cys attached to a linker and a hydrophobic
      molecule on the sidechain

<400> SEQUENCE: 609

Lys Lys Lys Lys Lys Val Arg Ser Ser Pro Tyr Ser Leu His Tyr Leu
1               5                   10                  15
Ser Pro Val Xaa Cys Gly
            20

<210> SEQ ID NO 610
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys attached to a linker and a hydrophobic
      molecule on the sidechain
<220> FEATURE:
<221> NAME/KEY: MOD_RES
<222> LOCATION: (23)..(23)
<223> OTHER INFORMATION: Citrulline

<400> SEQUENCE: 610

Cys Gly Gly Gly Arg Arg Arg Arg Val Arg Ser Ser Pro Tyr Ser Leu
1               5                   10                  15

His Tyr Leu Ser Pro Val Xaa
            20

<210> SEQ ID NO 611
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Citrulline
<220> FEATURE:
<221> NAME/KEY: MOD_RES
<222> LOCATION: (35)..(35)
<223> OTHER INFORMATION: Azido-Lys attached to a hydrophobic molecule on
      the sidechain

<400> SEQUENCE: 611

Lys Lys Lys Val Arg Met Ala Ala Ala Leu Thr Phe Arg Arg Leu Leu
1               5                   10                  15

Thr Leu Pro Arg Ala Ala Arg Gly Phe Gly Val Gln Val Ser Ser Pro
            20                  25                  30

Val Xaa Lys
        35

<210> SEQ ID NO 612
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: Azido-Lys

<400> SEQUENCE: 612

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg Lys
            20                  25

<210> SEQ ID NO 613
<211> LENGTH: 41
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Citrulline
<220> FEATURE:
<221> NAME/KEY: MOD_RES
<222> LOCATION: (41)..(41)
<223> OTHER INFORMATION: Azido-Lys

<400> SEQUENCE: 613

Lys Lys Lys Lys Lys Lys Val Arg Gly Arg Val Leu Glu Leu Phe Arg
1               5                   10                  15

Ala Ala Gln Leu Ala Asn Asp Val Val Leu Gln Ile Met Glu Leu Cys
            20                  25                  30

Gly Ala Thr Arg Ser Pro Val Xaa Lys
        35                  40

<210> SEQ ID NO 614
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Citrulline
<220> FEATURE:
<221> NAME/KEY: MOD_RES
<222> LOCATION: (15)..(15)
<223> OTHER INFORMATION: Azido-Lys

<400> SEQUENCE: 614

Ala Ser Met Thr Asn Met Glu Leu Met Gly Ser Pro Val Xaa Lys
1               5                   10                  15

<210> SEQ ID NO 615
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Citrulline
<220> FEATURE:
<221> NAME/KEY: MOD_RES
<222> LOCATION: (25)..(25)
<223> OTHER INFORMATION: Citrulline
<220> FEATURE:
<221> NAME/KEY: MOD_RES
<222> LOCATION: (26)..(26)
<223> OTHER INFORMATION: Azido-Lys

<400> SEQUENCE: 615

Asp Asp Asp Asp Asp Asp Asp Asp Ser Pro Val Xaa Ala Ser Met Thr
1               5                   10                  15

Asn Met Glu Leu Met Ser Pro Val Xaa Lys
            20                  25

<210> SEQ ID NO 616
<211> LENGTH: 31
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Citrulline
<220> FEATURE:
<221> NAME/KEY: MOD_RES
<222> LOCATION: (31)..(31)
<223> OTHER INFORMATION: Azido-Lys attached to a hydrophobic molecule on
      the sidechain

<400> SEQUENCE: 616

Lys Lys Lys Val Arg Met Glu Val Gly Trp Tyr Arg Ser Pro Phe Ser
1               5                   10                  15

Arg Val Val His Leu Tyr Arg Asn Gly Lys Ser Pro Val Xaa Lys
            20                  25                  30

<210> SEQ ID NO 617
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (46)..(46)
<223> OTHER INFORMATION: Citrulline
<220> FEATURE:
<221> NAME/KEY: MOD_RES
<222> LOCATION: (47)..(47)
<223> OTHER INFORMATION: Azido-Lys attached to a hydrophobic molecule on
      the sidechain

<400> SEQUENCE: 617

Lys Lys Lys Lys Lys Lys Val Arg Gly Pro Leu Gly Pro Lys Gly Gln
1               5                   10                  15

Ala Gly Glu Pro Gly Ile Ala Gly Phe Lys Gly Asp Gln Gly Pro Lys
            20                  25                  30

Gly Glu Thr Gly Pro Ala Gly Pro Gln Gly Ser Pro Val Xaa Lys
        35                  40                  45

<210> SEQ ID NO 618
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Citrulline
<220> FEATURE:
<221> NAME/KEY: MOD_RES
<222> LOCATION: (33)..(33)
<223> OTHER INFORMATION: Azido-Lys attached to a hydrophobic molecule on
      the sidechain

<400> SEQUENCE: 618

Lys Lys Lys Lys Lys Lys Lys Val Arg Gly Glu Pro Gly Ile Ala Gly
1               5                   10                  15

Phe Lys Gly Asp Gln Gly Pro Lys Gly Glu Thr Gly Ser Pro Val Xaa
            20                  25                  30

Lys
```

```
<210> SEQ ID NO 619
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)..(29)
<223> OTHER INFORMATION: Azido-Lys attached to a hydrophobic molecule on
      the sidechain

<400> SEQUENCE: 619

Gly Ile Pro Val His Leu Glu Leu Ala Ser Met Thr Asn Met Glu Leu
1               5                   10                  15

Met Ser Ser Ile Val His Gln Gln Val Phe Pro Thr Lys
            20                  25

<210> SEQ ID NO 620
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Citrulline
<220> FEATURE:
<221> NAME/KEY: MOD_RES
<222> LOCATION: (25)..(25)
<223> OTHER INFORMATION: Azido-Lys attached to a hydrophobic molecule on
      the sidechain

<400> SEQUENCE: 620

Lys Lys Lys Ser Leu Val Arg Ala Lys Phe Val Ala Ala Trp Thr Leu
1               5                   10                  15

Lys Ala Ala Ala Ser Pro Val Xaa Lys
            20                  25

<210> SEQ ID NO 621
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Azido-Lys attached to a hydrophobic molecule on
      the sidechain

<400> SEQUENCE: 621

Lys Lys Lys Lys Lys Lys Lys Lys Lys Lys Lys
1               5                   10

<210> SEQ ID NO 622
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala attached to a hydrophobic molecule on the
      sidechain
```

```
<220> FEATURE:
<221> NAME/KEY: MOD_RES
<222> LOCATION: (15)..(15)
<223> OTHER INFORMATION: Azido-Lys

<400> SEQUENCE: 622

Ala Ser Met Thr Asn Met Glu Leu Met Ser Ser Leu Val Arg Lys
1               5                   10                  15

<210> SEQ ID NO 623
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Azido-Lys attached to a hydrophobic molecule on
      the sidechain

<400> SEQUENCE: 623

Asp Phe Thr Gly Ser Asn Gly Asp Pro Ser Ser Pro Tyr Ser Leu His
1               5                   10                  15

Tyr Leu Ser Pro Thr Gly Val Asn Glu Tyr Lys
            20                  25
```